United States Patent
Morin et al.

(10) Patent No.: US 11,173,219 B2
(45) Date of Patent: Nov. 16, 2021

(54) PD-L1 BINDING POLYPEPTIDES FOR IMAGING

(71) Applicant: BRISTOL-MYERS SQUIBB COMPANY, Princeton, NJ (US)

(72) Inventors: Paul E. Morin, Pennington, NJ (US); David Donnelly, Doylestown, PA (US); Dasa Lipovsek, Pepperell, MA (US); Jochem Gokemeijer, Wayland, MA (US); Maria Jure-Kunkel, Plainsboro, NJ (US); David Fabrizio, South Hamilton, MA (US); Martin C. Wright, Belmont, MA (US); Douglas Dischino, Middlefield, CT (US); Samuel J. Bonacorsi, Jr., Flemington, NJ (US); Ralph Adam Smith, Yardley, PA (US); Virginie LaFont, Lawrence Township, NJ (US); Daniel Cohen, New York, NY (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 94 days.

(21) Appl. No.: 16/520,965

(22) Filed: Jul. 24, 2019

(65) Prior Publication Data
US 2019/0343972 A1    Nov. 14, 2019

Related U.S. Application Data

(62) Division of application No. 15/529,260, filed as application No. PCT/US2015/062485 on Nov. 24, 2015, now Pat. No. 10,406,251.

(60) Provisional application No. 62/084,298, filed on Nov. 25, 2014.

(51) Int. Cl.
| | |
|---|---|
| *A61K 51/08* | (2006.01) |
| *C07K 14/78* | (2006.01) |
| *G01N 33/574* | (2006.01) |
| *C12N 5/00* | (2006.01) |
| *C12N 15/09* | (2006.01) |
| *G01N 33/60* | (2006.01) |
| *G01N 33/68* | (2006.01) |

(52) U.S. Cl.
CPC ............ *A61K 51/08* (2013.01); *A61K 51/088* (2013.01); *C07K 14/78* (2013.01); *C12N 5/00* (2013.01); *C12N 15/09* (2013.01); *G01N 33/57492* (2013.01); *G01N 33/60* (2013.01); *G01N 33/6872* (2013.01); *C07K 2319/60* (2013.01); *C12N 2330/50* (2013.01); *G01N 2333/70532* (2013.01); *G01N 2333/78* (2013.01)

(58) Field of Classification Search
CPC ...... A61K 51/08; A61K 51/088; C12N 15/09; C12N 2330/50; G01N 33/6872; G01N 2333/78; C07K 14/78; C07K 2319/60
See application file for complete search history.

(56) References Cited

U.S. PATENT DOCUMENTS

| | | |
|---|---|---|
| 6,989,452 B2 | 1/2006 | Ng et al. |
| 7,087,600 B2 | 8/2006 | Ng et al. |
| 7,129,261 B2 | 10/2006 | Ng et al. |
| 7,556,925 B2 | 7/2009 | Koide et al. |
| 7,943,743 B2 | 5/2011 | Korman et al. |
| 8,008,449 B2 | 8/2011 | Korman et al. |
| 8,221,765 B2 | 7/2012 | Camphausen et al. |
| 8,324,362 B2 | 12/2012 | Chen et al. |
| 8,343,501 B2 | 1/2013 | Emanuel et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 | 5/2014 | Camphausen et al. |
| 8,808,665 B2 | 8/2014 | McBride et al. |
| 8,853,154 B2 | 10/2014 | Cload et al. |
| 8,933,199 B2 | 1/2015 | Cload et al. |
| 8,969,289 B2 | 3/2015 | Gosselin et al. |
| 8,993,265 B2 | 3/2015 | Cload et al. |
| 9,017,655 B2 | 4/2015 | Emanuel et al. |
| 9,234,028 B2 | 1/2016 | Camphausen et al. |
| 9,328,157 B2 | 5/2016 | Chen et al. |
| 9,469,676 B2 | 10/2016 | Camphausen et al. |
| 9,493,546 B2 | 11/2016 | Cload et al. |
| 9,522,951 B2 | 12/2016 | Davis et al. |
| 9,540,424 B2 | 1/2017 | Gosselin et al. |
| 9,562,089 B2 | 2/2017 | Camphausen et al. |
| 9,605,039 B2 | 3/2017 | Lipovsek et al. |
| 9,662,373 B2 | 5/2017 | Cload et al. |
| 9,771,411 B2 | 9/2017 | Emanuel et al. |
| 9,862,758 B2 | 1/2018 | Chen et al. |
| 9,902,762 B2 | 2/2018 | Camphausen et al. |

(Continued)

FOREIGN PATENT DOCUMENTS

| | | |
|---|---|---|
| WO | 02/096910 A1 | 12/2002 |
| WO | 2005056764 A2 | 6/2005 |

(Continued)

OTHER PUBLICATIONS

Abstracts DEGRO 2016, Strahlentherapie und Onkologie, vol. 192(1): 1-161 (2016), XP035803487, ISSN: 0179-7158, DOI:10.1007/S00066-016-0974-Z [retrieved on May 11, 2016].

(Continued)

*Primary Examiner* — Paul J Holland
(74) *Attorney, Agent, or Firm* — Nelson Mullins Riley & Scarborough LLP; Jane E. Remillard, Esq.; Cynthia L. Kanik

(57) ABSTRACT

Provided herein are novel [10]Fn3 domains which specifically bind to PD-L1, as well as imaging agents based on the same for diagnostics.

21 Claims, 12 Drawing Sheets
Specification includes a Sequence Listing.

(56) References Cited

U.S. PATENT DOCUMENTS

| | | |
|---|---|---|
| 9,920,108 B2 | 3/2018 | Camphausen et al. |
| 10,406,251 B2 | 9/2019 | Morin et al. |
| 2006/0004081 A1 | 1/2006 | Chen et al. |
| 2006/0024317 A1 | 2/2006 | Boyd et al. |
| 2006/0246059 A1 | 11/2006 | Lipovsek et al. |
| 2006/0247295 A1 | 11/2006 | Gangwar et al. |
| 2009/0208410 A1 | 8/2009 | Berndorff et al. |
| 2012/0309250 A1 | 12/2012 | Velev et al. |
| 2013/0309250 A1 | 11/2013 | Cogswell et al. |
| 2013/0310317 A1 | 11/2013 | Camphausen et al. |
| 2013/0323249 A1 | 12/2013 | Zhou et al. |
| 2014/0271467 A1 | 9/2014 | Hackel et al. |
| 2015/0252097 A1 | 9/2015 | Camphausen et al. |
| 2015/0361159 A1 | 12/2015 | Lipovsek et al. |
| 2015/0368319 A1 | 12/2015 | Yamniuk et al. |
| 2016/0287734 A1 | 10/2016 | Rashidian et al. |
| 2016/0376346 A1 | 12/2016 | Camphausen et al. |
| 2017/0088602 A1 | 3/2017 | Cload et al. |
| 2017/0114042 A1 | 4/2017 | Koike et al. |
| 2017/0137494 A1 | 5/2017 | Davis et al. |
| 2017/0145464 A1 | 5/2017 | Gosselin et al. |
| 2017/0166627 A1 | 6/2017 | Camphausen et al. |
| 2017/0174748 A1 | 6/2017 | Mitchell et al. |
| 2017/0183393 A1 | 6/2017 | Lipovsek |
| 2017/0190761 A1 | 7/2017 | Camphausen et al. |
| 2017/0258948 A1 | 9/2017 | Morin et al. |
| 2017/0275342 A1 | 9/2017 | Lipovsek et al. |
| 2017/0354718 A1 | 12/2017 | Cload et al. |
| 2018/0037631 A1 | 2/2018 | Emanuel et al. |
| 2018/0326098 A1 | 11/2018 | Donnelly |
| 2019/0015532 A1 | 1/2019 | Kjaer et al. |
| 2019/0184042 A1 | 6/2019 | Morin et al. |
| 2019/0184043 A1 | 6/2019 | Donnelly et al. |

FOREIGN PATENT DOCUMENTS

| | | |
|---|---|---|
| WO | 07/038658 A2 | 4/2007 |
| WO | 07/059404 A2 | 5/2007 |
| WO | 2007/051081 A1 | 5/2007 |
| WO | 2008073458 A2 | 6/2008 |
| WO | 08/083312 A2 | 7/2008 |
| WO | 08/103693 A2 | 8/2008 |
| WO | 2009080810 A1 | 7/2009 |
| WO | 2009142773 A2 | 11/2009 |
| WO | 2013/010573 A1 | 1/2013 |
| WO | 2013/173223 A1 | 11/2013 |
| WO | 2013181634 A2 | 12/2013 |
| WO | 2014/086364 A1 | 6/2014 |
| WO | 2014/126902 A1 | 8/2014 |
| WO | 2015/143199 A1 | 9/2015 |
| WO | 2016/022994 A2 | 2/2016 |
| WO | 2016/077518 A1 | 5/2016 |
| WO | 2016/086021 A1 | 6/2016 |
| WO | 2016/086036 A2 | 6/2016 |
| WO | 2016/162368 A1 | 10/2016 |
| WO | 2017/053617 A1 | 3/2017 |
| WO | 2017/053619 A1 | 3/2017 |
| WO | 2017/072273 A1 | 5/2017 |
| WO | 2017/072280 A1 | 5/2017 |
| WO | 2017/210302 A1 | 12/2017 |
| WO | 2017/210335 A1 | 12/2017 |

OTHER PUBLICATIONS

Berndt, M. et al., "Labeling of low-density lipoproteins using the 18F-labeled thiol-reactive reagent N-[6-(4-[18F] fluorobenzylidene)aminooxyhexyl]maleimide," Nuclear Medicine and Biology, vol. 34:5-15 (2007).

Campbell-Verduyn, S. et al., "Strain-Promoted Copper-Free "Click" Chemistry for 18F Radiolabeling of Bombesin," Angewandte Chemie International Edition, vol. 50 (47): 11117-11120 (2011)XP55250606.

Chatterjee, S. et al., "A humanized antibody for imaging immune checkpoint ligand PD-L1 expression in tumors," Oncotarget, vol. 7(9):10215-10227 (2016), XP055389519, Retrieved from the Internet: URL:http://www.impactjournals.com/oncotarget/index.php?Journal=oncotarget&page=article&op=download&path[]=7143&path[]=20347[retrieved on Jul. 10, 2017].

Chatterjee, S. et al., "Rapid PD-L1 detection in tumors with PET using a highly specific peptide," Biochemical and Biophysical Research Communications, vol. 483(1):258-263, (2016) XP029887248.

Chow, P. "Radiosynthesis and Preclinical PET Evaluation of 89Zr-Nivolumab (BMS-936558) in Healthy Non-Human Primates," Proceedings of the World Molecular Imaging Congress 2015, Honolulu, Hawaii, Sep. 2-5, 2015: Late-Breaking Abstracts Molecular Imaging and Biology, vol. 18, No. Suppl.1, p. 1669, (May 2016) XP002773214, ISSN: 1536-1632,Retrieved from the Internet: <URL:https://rd.springer.com/content/pdf/10.1007%2Fs11307-016-0968-3.pdf> Abstract, control ID: 2324486 [retrieved on Aug. 24, 2017].

Donnelly, D. et al., "Discovery of a novel 18F prosthetic group that enables radiolabeling of anti-human PD-L1 Adnectins," The Journal of Nuclear Medicine: Annual Meeting of the Society of Nuclear Medicine and Molecular Imaging, vol. 58, No. Suppl. 1 p. 68 (2017) XP008185772, Society of Nuclear Medicine, US, Denver, Colorado, ISSN: 0161-5505, Retrieved from the Internet: URL:http://jnm.snmjournals.org/content/58/supplement 1/68 [retrieved an Aug. 24, 2017].

Gill, H-S., et al., "Preparation of 18F-labeled peptides using the copper(I)-catalyzed azide-alkyne 1,3-dipolar cycloaddition.," Nature Protocols, vol. 6:1718-1725 (2011).

Hackel, B. et al., "Use of 64 cu-labeled Fibronectin Domain with egFr-Overexpressing Tumor Xenograft: Molecular Imaging 1", Radiology, vol. 263(1): 179-188 (2012)XP055255254.

Heskamp S. et al., "SPECT/CT imaging of tumor PD-L1 expression using radiolabeled anti-PD-L1 antibodies," (Abstract 116), Journal of Nuclear Medicine, vol. 56 (Suppl 3) 1 page (May 2015)XP002773040, & Annual Meeting of the Society of Nuclear Medicine—and Molecular Imaging, Jun. 6-10, 2015 Retrieved from the Internet URL:http://jnm.snmjournals.org/content/56/supplement 3/116.short [retrieved on Aug. 18, 2017].

Heskamp, S. et al., "Noninvasive Imaging of Tumor PD-L1 Expression Using Radiolabele Anti-PD-L1 Antibodies," Cancer Research, vol. 75 (14):2928-2936 (2015) XP055255277.

Inkster, J. et al., "2-Fluoropyridine prosthetic compounds for the 18F labeling of bombesin analogues," Bioorganic & Medicinal Chemistry Letters, vol. 23:3920-3926 (2013).

Inkster, J. et al., "Radiosynthesis and bioconjugation of [18F]FPy5yne, a prosthetic group for the 18F labeling of bioactive peptides," J. Label Compd. Radiopharm, vol. 51:444-452. (2008).

International Preliminary Report on Patentability, PCT/US2015/062485, dated May 30, 2017, 7 pages.

International Search Report and Written Opinion, PCT/US2015/062485, dated Mar. 17, 2016, 11 pages.

Josefsson, A. et al., "Imaging, Biodistribution, and Dosimetry of Radionuclide-Labeled PD-L1 Antibody in an Immunocompetent Mouse Model of Breast Cancer," Cancer Research, vol. 76 (2):472-479 (2016) XP055398622, ISSN: 0008-5472, DOI: 10.1158/0008-5472 [retrieved on May 11, 2016].

Koide S. et al., "Target-binding proteins based on the 10th human fibronectin type III domain(10Fn3)," Methods in Enzymology, Academ. Press, USA, vol. 503: 135-156 (2012).

Kuhnast, B. et al., "[ 18 F]FPyKYNE, a fluoropyridine-based alkyne reagent designed for the fluorine-18 labelling of macromolecules using click chemistry," Journal of Labelled Compounds and Radiopharmaceuticals, vol. 51 (9):336-342(2008)XP55250465.

Kuhnast, B. et al., "PEG-[18F]FPyZIDE and PEG-[18F]FPyKYNE, Two New Fluoropyridine-Based Reagents for the Fluorine-18 Labeling of Macromolecules Using Click Chemistry," Journal of Labelled Compounds and Radiopharmaceuticals, p. S184, Jun. 17, 2009, XP055250504.

Lesniak, W. et al., "PD-L1 Detection in Tumors Using [ 64 Cu]Atezolizumab with PET," Bioconjugate Chemistry, vol. 27(9):2103-2110 (2016).

Maute R. et al., "Engineering high-affinity PD-1 variants for optimized immunotherapy and immuno-PET imaging," PNAS, vol. 112 (47):E6506-E6514 (2015)XP002772779, ISSN: 0027-8424.

(56) References Cited

OTHER PUBLICATIONS

Maxwell, B. et al.,"The synthesis of a carbon-14 labeled pegylated Adnectin(TM) for placental transfer studies in guinea pigs," Journal of Labellled Compounds and Radiopharmaceuticals, vol. 56(9-10):492-494 (2013) XP055255267.
McCabe, K. et al., "Positive progress in immunoPET—not just a coincidence," Cancer Biotherapy and Radiopharmacueticals, vol. 25(3):253-261 (2010) XP009150571.
Michel, K. et al., Development and evaluation of endothelin-A receptor (radio)ligands for positron emission tomography, J Med Chem., vol. 54(4):939-48 (2011).
Natarajan, A. et al., "A Novel Engineered Anti-CD20 Tracer Enables Early Time PET Imaging in a Humanized Transgenic Mouse Model of B-cell Non-Hodgkins Lymphoma," Clinical Cancer Research, vol. 19 (24):6820-6829 (2013), XP055398629, ISSN: 1078-0432, DOI: 10.1158/1078-0432.CCR-13-0626.
Niemeijer, Anna-Larissa N. et al.: "Whole body PD-1 and PD-L1 PET with 89Zr-nivolumab and 18F-BMS-986192 in pts with NSCLC," Journal of Clinical Oncology, Abstract Only, May 2017, XP002773215, Retrieved from the Internet: <URL:http://ascopubs.org/author/Poot%2C+Alex+J> [retrieved on Aug. 24, 2017].
Patterson, C. et al., "Development of a New Positron Emission Tomography Tracer for Targeting Tumor Angiogenesis: Synthesis, Small Animal Imaging, and Radiation Dosimetry," Molecules, vol. 18(5):5594-5610 (2013) XP055255261.
Price, E. et al., "Matching chelators to radiometals for radiopharmaceuticals," Chem Soc Rev., vol. 43:260-290 (2014).
Proceedings of the World Molecular Imaging Congress 2015, Honolulu, Hawaii, Sep. 2-5, 2015 Late-Breaking Abstracts, Molecular Imaging & Biology, vol. 18(1):S1554-S1859 (2016)XP035974151, ISSN: 1536-1632, DOI:10.1007/S11307-016-0968-3 [retrieved on May 24, 2016].
Sachin, K et al., "F-18 Labeling Protocol of Peptides Based on Chemically Orthogonal Strain-Promoted Cycloaddition under Physiologically Friendly Reaction Conditions," Bioconjugate Chemistry, vol. 23 (8): 1680-1686 (2012) XP55043362.
Salsano, et al., "PET imaging using radiolabelled antibodies: future direction in tumor diagnosis and correlate applications," Research and Reports in Nuclear Medicine,p. 9(2013) XP055255276.
Schrama, D. et al., "Antibody targeted drugs as cancer therapeutics," Nature Rev. Drug Disc., vol. 5: 147-159 (2006).
Schrigten, D. et al., "A New Generation of Radiofluorinated Pyrimidine-2,4,6-triones as MMP-Targeted Radiotracers for Positron Emission Tomography," Med. Chem., vol. 55(1): 223-232 (2012).
Valdivia, A. et al., "A fast, simple, and reproducible automated synthesis of [18F]FPyKYNE-c RGDyK) for alpha v beta 3 receptor positron emission tomography imaging," Journal of Labelled Compounds and Radiopharmaceuticals, vol. 55(2):57-60 (2011) XP55250449.
Wang H. et al., "Development of a Carbon-14 Labeling Approach to Support Disposition Studies with a Pegylated Biologic," Drug Metabolism and Disposition, vol. 40(9): 1677-1685 (2012)XP055255270.
Yampolsky, L. et al., "The Exchangeability of Amino Acids in Proteins," Genetics, vol. 170:1459-1472 (2005).
U.S. Appl. No. 15/526,584, filed Sep. 10, 2020, J. Lamberski.
U.S. Appl. No. 15/526,584, filed May 1, 2020, J. Lamberski.
U.S. Appl. No. 16/305,284, filed Jul. 24, 2020, D. Jones.
U.S. Appl. No. 16/305,284, filed Mar. 23, 2020, D. Jones.
U.S. Appl. No. 16/305,286, filed Jul. 16, 2020, M. Taningco.
U.S. Appl. No. 16/305,286, filed Feb. 28, 2020, M. Taningco.

```
Core sequences

WT       VSDVPRDLEVVAATPTSLLISWRAPAVTVRYYRITYGETGSMSPVQEFTVPGSKSTATISGLKPGVDYTITVVAVTGRGDSPASSKPISIMYRT
ATI-968  VSDVPRDLEVVAATPTSLLISWIAPFINVLYVRITYGETGGMSPVQEFTVPGTGYTATISGLKPGVDYTITVVAVTDGASIASYAPISIMYRT
ATI-964  VSDVPRDLEVVAATPTSLLISWSYDGSIERYYRITYGETGGMSPVQEFTVPDQKTATISGLKPGVDYTITVVAVLEEAHYYRESPISIMYRT
ATI-967  VSDVPRDLEVVAATPTSLLISWGGQLSPSFYYRITYGETGSMSPVQEFTVPVASGTATISGLKPGVDYTITVVAVTSHGIYFYAPISIMYRT
402      VSDVPRDLEVVAATPTSLLISWSYDGPIDRYYRITYGETGGMSPVQEFTVPPQKETATISGLKPGVDYTITVVAVLEEAHYM

› # PD-L1 BINDING POLYPEPTIDES FOR IMAGING

REFERENCE TO RELATED APPLICATIONS

This application is a divisional of U.S. patent application Ser. No. 15/529,260 (Allowed), filed May 24, 2017, which is a 35 U.S.C. 371 national stage filing of International Application No. PCT/US2015/062485, filed Nov. 24, 2015, which claims priority to U.S. Provisional Application No. 62/084,298, entitled "Novel PD-L1 Binding Polypeptides for Imaging", filed Nov. 25, 2014. The contents of the aforementioned applications are hereby incorporated by reference.

SEQUENCE LISTING

The instant application contains a Sequence Listing which has been submitted in ASCII format via EFS-Web, and is hereby incorporated by reference in its entirety. Said ASCII copy, created on Jul. 22, 2019, is named MXI-537USDV_Sequence_Listing.txt and is 464,413 bytes in size.

BACKGROUND

Programmed Death Ligand-1 (PD-L1) is a surface glycoprotein ligand for PD-1, a key immune checkpoint receptor expressed by activated T and B cells and mediates immunosuppression, which is found on both antigen-presenting cells and human cancers and downregulates T cell activation and cytokine secretion by binding to PD-1 (Freeman et al., 2000; Latchman et al, 2001). Inhibition of the PD-L1/PD-1 interaction allows for potent anti-tumor activity in preclinical models, and antibodies that disrupt this interaction have entered clinical trials for the treatment of cancer (U.S. Pat. Nos. 8,008,449 and 7,943,743; Brahmer et al., 2010; Topalian et al., 2012b; Brahmer et al., 2012; Flies et al., 2011; Pardoll, 2012; Hamid and Carvajal, 2013).

PET, or Positron Emission Tomography, is a non-invasive, nuclear medicine technique that produces a three-dimensional image of various molecular processes within the body, or the location of proteins associated with disease pathology. The methodology detects pairs of gamma rays emitted indirectly by a positron-emitting radionuclide (tracer) introduced into the body on a biologically active molecule. PET imaging tools have a wide variety of uses for drug development and have a unique translational medicine advantage, in that the same tool could be used both pre-clinically and clinically. Examples include direct visualization of in vivo saturation of targets; monitoring uptake in normal tissues to anticipate toxicity or patient to patient variation; quantifying diseased tissue; tumor metastasis; monitoring drug efficacy over time, or resistance over time, and more.

Described herein are novel anti-PD-L1 Adnectins suitable for use as diagnostic/imaging agents, for example, for use in positron emission tomography.

SUMMARY

The present invention is based, at least in part, on the discovery of new anti-human PD-L1 Adnectins which are useful as diagnostic/imaging agents, for example, for use in positron emission tomography. These agents are useful in, e.g., the differentiation of PD-L1 expressing cells from non-PD-L1 expressing cells, e.g., tumor cells, and the differentiation of PD-L1 expressing tissue from non-PD-L1 expressing tissue, e.g., cancer tissue.

In one aspect, provided herein is a polypeptide comprising a fibronectin type III tenth domain ($^{10}$Fn3), wherein (a) the $^{10}$Fn3 domain comprises AB, BC, CD, DE, EF, and FG loops, (b) the $^{10}$Fn3 has at least one loop selected from loop BC, DE, and FG with an altered amino acid sequence relative to the sequence of the corresponding loop of the human $^{10}$Fn3 domain (SEQ ID NO: 1), and (c) the polypeptide specifically binds to PD-L1. In certain embodiments, the polypeptide binds to PD-L1 with a $K_D$ of 500 mM or less, for example, 100 mM or less.

In certain embodiments, the $^{10}$Fn3 domain comprises BC, DE, and FG loops comprising the amino acid sequences of:
(1) SEQ ID NOs: 6, 7, and 8, respectively;
(2) SEQ ID NOs: 21, 22, and 23, respectively;
(3) SEQ ID NOs: 36, 37, and 38, respectively;
(4) SEQ ID NOs: 51, 52, and 53, respectively;
(5) SEQ ID NOs: 66, 67, and 68, respectively;
(6) SEQ ID NOs: 81, 82, and 83, respectively;
(7) SEQ ID NOs: 97, 98, and 99, respectively;
(8) SEQ ID NOs: 113, 114, and 115, respectively;
(9) SEQ ID NOs: 124, 125 and 126, respectively;
(10) SEQ ID NOs: 135, 136 and 137, respectively;
(11) SEQ ID NOs: 146, 147 and 148, respectively;
(12) SEQ ID NOs: 157, 158 and 159, respectively;
(13) SEQ ID NOs: 168, 169 and 170, respectively;
(14) SEQ ID NOs: 179, 180 and 181, respectively;
(15) SEQ ID NOs: 190, 191 and 192, respectively;
(16) SEQ ID NOs: 201, 202 and 203, respectively;
(17) SEQ ID NOs: 212, 213 and 214, respectively;
(18) SEQ ID NOs: 223, 224 and 225, respectively;
(19) SEQ ID NOs: 234, 235, and 236, respectively;
(20) SEQ ID NOs: 245, 246 and 247, respectively;
(21) SEQ ID NOs: 256, 257 and 258, respectively;
(22) SEQ ID NOs: 267, 268 and 269, respectively;
(23) SEQ ID NOs: 278, 279 and 280, respectively;
(24) SEQ ID NOs: 289, 290 and 291, respectively;
(25) SEQ ID NOs: 300, 301 and 302, respectively;
(26) SEQ ID NOs: 311, 312 and 313, respectively;
(27) SEQ ID NOs: 322, 323 and 324, respectively;
(28) SEQ ID NOs: 333, 334 and 335, respectively;
(29) SEQ ID NOs: 344, 345 and 346, respectively;
(30) SEQ ID NOs: 355, 356 and 357, respectively;
(31) SEQ ID NOs: 366, 367 and 368, respectively;
(32) SEQ ID NOs: 377, 378 and 379, respectively;
(33) SEQ ID NOs: 388, 389 and 390 respectively;
(34) SEQ ID NOs: 399, 400 and 401, respectively;
(35) SEQ ID NOs: 410, 411 and 412, respectively;
(36) SEQ ID NOs: 421, 422 and 423, respectively;
(37) SEQ ID NOs: 432, 433 and 434 respectively;
(38) SEQ ID NOs: 443, 444 and 445, respectively;
(39) SEQ ID NOs: 454, 455 and 456, respectively;
(40) SEQ ID NOs: 465, 466 and 467, respectively;
(41) SEQ ID NOs: 476, 477 and 478, respectively;
(42) SEQ ID NOs: 487, 488 and 489, respectively;
(43) SEQ ID NOs: 498, 499 and 500, respectively;
(44) SEQ ID NOs: 509, 510 and 511, respectively;
(45) SEQ ID NOs: 520, 521 and 522, respectively;
(46) SEQ ID NOs: 531, 530 and 531, respectively;
(47) SEQ ID NOs: 542, 543 and 544, respectively;
(48) SEQ ID NOs: 553, 554 and 555, respectively; or
(49) SEQ ID NOs: 564, 565 and 566, respectively.

In certain embodiments, the polypeptide comprises an amino acid sequence at least 80%, 85%, 90%, 95%, 98%, 99% or 100% identical to a sequence set forth in Table 3, e.g., any one of SEQ ID NO: 5, 20, 35, 50, 65, 80, 96, 112, 123, 134, 145, 156, 167, 178, 189, 200, 211, 222. 233, 244, 255, 266, 277, 288, 299, 310, 321, 332, 343, 354, 365, 376, 387, 398, 409, 420, 431, 442, 453, 464, 475, 486, 497, 508, 519, 530, 541, 552 and 563. In certain embodiments, the polypeptide comprises an amino acid sequence at least 80%, 85%, 90%, 95%, 98%, 99% or 100% identical to the non-BC, DE, and FG loop regions of SEQ ID NO: 5, 20, 35, 50, 65, 80, 96, 112, 123, 134, 145, 156, 167, 178, 189, 200, 211, 222. 233, 244, 255, 266, 277, 288, 299, 310, 321, 332, 343, 354, 365, 376, 387, 398, 409, 420, 431, 442, 453, 464, 475, 486, 497, 508, 519, 530, 541, 552 or 563. In certain embodiments, the polypeptide comprises an amino acid sequence at least 80%, 85%, 90%, 95%, 98%, 99% or 100% identical to an amino acid sequence selected from the group consisting of: SEQ ID NOs: 9-15, 24-30, 39-45, 54-60, 69-75, 84-91, 100-107, 116-122, 127-133, 138-144, 150-155, 160-166, 171-177, 182-188, 193-199, 204-210, 215-221, 227-232, 237-243, 248-254, 259-265, 271-276, 291-287, 292-298, 303-309, 314-320, 325-331, 337-342, 347-353, 358-364, 369-375, 380-386, 391-397, 402-408, 413-419, 424-430, 435-441, 446-452, 457-463, 468-474, 479-485, 490-496, 501-507, 512-518, 523-529, 534-540, 545-551, and 556-562. In certain embodiments, the polypeptide comprises an amino acid sequence at least 80%, 85%, 90%, 95%, 98%, 99% or 100% identical to the non-BC, DE, and FG loop regions of an amino acid sequence selected from the group consisting of: SEQ ID NOs: 9-15, 24-30, 39-45, 54-60, 69-75, 84-91, 100-107, 116-122, 127-133, 138-144, 150-155, 160-166, 171-177, 182-188, 193-199, 204-210, 215-221, 227-232, 237-243, 248-254, 259-265, 271-276, 291-287, 292-298, 303-309, 314-320, 325-331, 337-342, 347-353, 358-364, 369-375, 380-386, 391-397, 402-408, 413-419, 424-430, 435-441, 446-452, 457-463, 468-474, 479-485, 490-496, 501-507, 512-518, 523-529, 534-540, 545-551, and 556-562.

In certain embodiments, the polypeptide comprises an N-terminal leader selected from the group consisting of SEQ ID NOs: 574-583, and/or a C-terminal tail selected from the group consisting of SEQ ID NOs: 584-618 or PmCn, wherein P is proline, and wherein m is an integer that is at least 0 (e.g., 0, 1 or 2) and n is an integer of at least 1 (e.g., 1 or 2).

In certain embodiments, the polypeptide comprises one or more pharmacokinetic (PK) moieties selected from the group consisting of polyethylene glycol, sialic acid, Fc, Fc fragment, transferrin, serum albumin, a serum albumin binding protein, and a serum immunoglobulin binding protein. In certain embodiments, the PK moiety and the polypeptide are linked via at least one disulfide bond, a peptide bond, a polypeptide, a polymeric sugar or a polyethylene glycol moiety. In certain embodiments, the PK moiety and the polypeptide are linked via a linker with an amino acid sequence selected from the group consisting of SEQ ID NOs: 629-678.

Provided herein are nucleic acids encoding the polypeptides, as well as vectors and cells comprising the nucleic acids, described herein. In certain embodiments, the nucleic acid comprises a nucleotide sequence selected from the group consisting of SEQ ID NOs: 16-19, 31-34, 46-49, 61-64, 76-79, 92-95, and 108-111.

Provided herein are compositions comprising the polypeptides described herein, and a carrier. For example, the compositions described herein comprise a polypeptide comprising an amino acid sequence selected from the group consisting of SEQ ID NOs: 5, 9-15, 20, 24-30, 35, 39-45, 50, 54-60, 65, 69-75, 80, 84-91, 96, 100-107, 112, 116-122, 123, 127-133, 134, 138-144, 145, 150-155, 156, 160-166, 167, 171-177, 178, 182-188, 189, 193-199, 200, 204-210, 211, 215-221, 222, 227-232, 233, 237-243, 244, 248-254, 255, 259-265, 266, 271-276, 277, 291-287, 288, 292-298, 299, 303-309, 310, 314-320, 321, 325-331, 332, 337-342, 343, 347-353, 354, 358-364, 365, 369-375, 376, 380-386, 387, 391-397, 398, 402-408, 409, 413-419, 420, 424-430, 431, 435-441, 442, 446-452, 453, 457-463, 464, 468-474, 475, 479-485, 486, 490-496, 497, 501-507, 508, 512-518, 519, 523-529, 530, 534-540, 541, 545-551, 552, and 556-562, and a carrier.

Provided herein are imaging agents comprising the polypeptide disclosed herein. In certain embodiments, the imaging agent comprises a polypeptide comprising an amino acid sequence selected from the group consisting of SEQ ID NOs: 5, 9-15, 20, 24-30, 35, 39-45, 50, 54-60, 65, 69-75, 80, 84-91, 96, 100-107, 112, 116-122, 123, 127-133, 134, 138-144, 145, 150-155, 156, 160-166, 167, 171-177, 178, 182-188, 189, 193-199, 200, 204-210, 211, 215-221, 222, 227-232, 233, 237-243, 244, 248-254, 255, 259-265, 266, 271-276, 277, 291-287, 288, 292-298, 299, 303-309, 310, 314-320, 321, 325-331, 332, 337-342, 343, 347-353, 354, 358-364, 365, 369-375, 376, 380-386, 387, 391-397, 398, 402-408, 409, 413-419, 420, 424-430, 431, 435-441, 442, 446-452, 453, 457-463, 464, 468-474, 475, 479-485, 486, 490-496, 497, 501-507, 508, 512-518, 519, 523-529, 530, 534-540, 541, 545-551, 552, and 556-562.

In certain embodiments, the imaging agent comprises a detectable label. In certain embodiments, the imaging agent comprises a polypeptide disclosed herein, a chelating agent, and a detectable label. In certain embodiments, the imaging agent comprises a polypeptide disclosed herein, a bifunctional chelator or conjugating (BFC) moiety and a detectable label. In certain embodiments, the detectable label is a prosthetic group containing a radionuclide. In certain embodiments, the detectable label is detectable by positron emission tomography.

In certain embodiments, the chelating agent and/or bifunctional chelator or conjugating (BFC) moiety is selected from the group consisting of DFO, DOTA, CB-DO2A, 3p-C-DEPA, TCMC, DBCO, DIBO, BARAC, DIMAC, Oxo-DO3A, TE2A, CB-TE2A, CB-TE1A1P, CB-TE2P, MM-TE2A, DM-TE2A, diamsar, NODASA, NODAGA, NOTA, NETA, TACN-TM, DTPA, 1B4M-DTPA, CHX-A"-DTPA, TRAP, NOPO, AAZTA, DATA, $H_2$dedpa, $H_4$octapa, $H_2$azapa, $H_5$decapa, $H_6$phospa, HBED, SHBED, BPCA, CP256, PCTA, HEHA, PEPA, EDTA, TETA, and TRITA.

In certain embodiments, the detectable label is a radionuclide, for example, $^{64}$Cu, $^{124}$I, $^{76/77}$Br, $^{86}$Y, $^{89}$Zr, $^{68}$Ga, $^{18}$F, $^{11}$C, $^{125}$I, $^{124}$I, $^{131}$I, $^{123}$I, $^{131}$I, $^{123}$I, $^{32}$Cl, $^{33}$Cl, $^{34}$Cl, $^{68}$Ga, $^{74}$Br, $^{75}$Br, $^{76}$Br, $^{77}$Br, $^{78}$Br, $^{89}$Zr, $^{186}$Re, $^{188}$Re, $^{90}$Y, $^{177}$Lu, $^{99}$Tc, or $^{153}$Sm.

In certain embodiments, the chelating agent is NODAGA and the radionuclide is $^{64}$Cu. In certain embodiments, the imaging agent comprises an anti-PD-L1 polypeptide (e.g., an anti-PD-L1 Adnectin described herein, e.g., an anti-PD-L1 Adnectin comprising the amino acid sequence set forth in SEQ ID NO: 80 or 96), the chelating agent NODAGA, and the radionuclide $^{64}$Cu.

In certain embodiments, the imaging agent comprises an anti-PD-L1 polypeptide (e.g., an anti-PD-L1 Adnectin described herein, e.g., an anti-PD-L1 Adnectin comprising the amino acid sequence set forth in SEQ ID NO: 80 or 96), a bifunctional chelator or conjugating (BFC) moiety, and a prosthetic group comprising the radionuclide $^{18}$F. In certain embodiments, the imaging agent has the following structure:

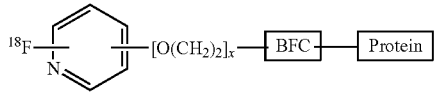

or a pharmaceutically acceptable salt thereof.

In certain embodiments, the imaging agent has the following structure:

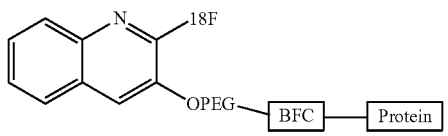

In some embodiments, the BFC is a cyclooctyne comprising a reactive group that forms a covalent bond with an amine, carboxyl, carbonyl or thiol functional group on the protein. In some embodiments, the cyclooctyne is selected from the group consisting of dibenzocyclooctyne (DIBO), biarylazacyclooctynone (BARAC), dimethoxyazacyclooctyne (DIMAC) and dibenzocyclooctyne (DBCO). In some embodiments, the cyclooctyne is DBCO.

In some embodiments, the BFC is DBCO-PEG4-NHS-Ester, DBCO-Sulfo-NHS-Ester, DBCO-PEG4-Acid, DBCO-PEG4-Amine or DBCO-PEG4-Maleimide. In some embodiments, the BFC is DBCO-PEG4-Maleimide.

In certain embodiments, the imaging agent has the structure:

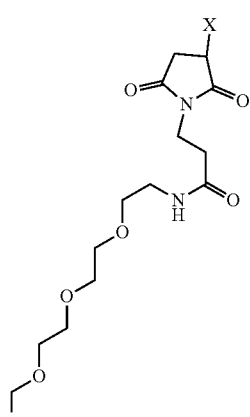

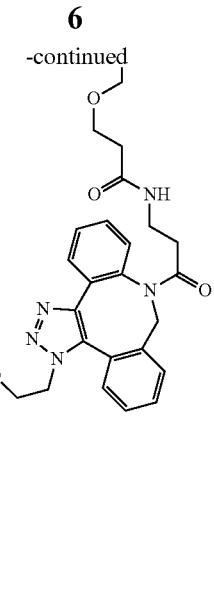

wherein X is a polypeptide comprising the amino acid sequence of any one of SEQ ID NOs: 13, 28, 43, 58, 73, 88, 104, 120, 131, 142, 153, 164, 175, 186, 197, 208, 219, 230, 241, 252, 263, 274, 285, 296, 307, 318, 329, 340, 351, 362, 373, 384, 395, 406, 417, 428, 439, 450, 461, 472, 483, 494, 505, 516, 527, 538, 549, 560 and 571. In certain embodiments, the polypeptide comprises the amino acid sequence set forth in SEQ ID NO: 88. In certain embodiments, the polypeptide comprises the amino acid sequence set forth in SEQ ID NO: 104.

Provided herein are kits comprising an anti-PD-L1 Adnectin composition and/or imaging agent described herein, and instructions for use.

Provided herein is a method of detecting PD-L1 in a sample, the method comprising contacting the sample with an anti-PD-L1 Adnectin, and detecting PD-L1.

Provided herein is a method of detecting PD-L1 positive cells in a subject comprising administering to the subject an imaging agent comprising an anti-PD-L1 Adnectin, and detecting the imaging agent, the detected imaging agent defining the location of the PD-L1 positive cells in the subject.

Provided herein is a method of detecting PD-L1-expressing tumors in a subject comprising administering to the subject an imaging agent comprising an anti-PD-L1 Adnectin, and detecting the imaging agent, the detected imaging agent defining the location of the tumor in the subject. In certain embodiments, the imaging agent is detected by positron emission tomography.

Provided herein is a method of obtaining an image of an imaging agent comprising an anti-PD-L1 Adnectin, the method comprising,
 a) administering the imaging agent to a subject; and
 b) imaging in vivo the distribution of the imaging agent by positron emission tomography.

Provided herein is a method of obtaining a quantitative image of tissues or cells expressing PD-L1, the method comprising contacting the cells or tissue with an imaging agent comprising an anti-PD-L1 Adnectin, and detecting or quantifying the tissue expressing PD-L1 using positron emission tomography.

Provided herein is a method for detecting a PD-L1-expressing tumor comprising administering an imaging-effective amount of an imaging agent comprising an anti- PD-L1 Adnectin to a subject having a PD-L1-expressing tumor, and detecting the radioactive emissions of said imaging agent in the tumor using positron emission tomography, wherein the radioactive emissions are detected in the tumor.

Provided herein is a method of diagnosing the presence of a PD-L1-expressing tumor in a subject, the method comprising
(a) administering to a subject in need thereof an imaging agent comprising an anti-PD-L1 Adnectin; and
(b) obtaining an radio-image of at least a portion of the subject to detect the presence or absence of the imaging agent;
wherein the presence and location of the imaging agent above background is indicative of the presence and location of the disease.

Provided herein is a method of monitoring the progress of an anti-tumor therapy against PD-L1-expressing tumors in a subject, the method comprising
(a) administering to a subject in need thereof an imaging agent comprising an anti-PD-L1 Adnectin at a first time point and obtaining an image of at least a portion of the subject to determine the size of the tumor;
(b) administering an anti-tumor therapy to the subject;
(c) administering to the subject the imaging agent at one or more subsequent time points and obtaining an image of at least a portion of the subject at each time point; wherein the dimension and location of the tumor at each time point is indicative of the progress of the disease.

BRIEF DESCRIPTION OF THE DRAWINGS

FIG. 1 is a schematic of the core amino acid sequences of exemplary anti-PD-L1 Adnectins described herein. The BC, DE, and FG loops are underlined. Wildtype (WT) (SEQ ID NO: 2), ATI-968 (SEQ ID NO: 5), ATI-964 (SEQ ID NO: 20), ATI-967 (SEQ ID NO: 65), A02 (SEQ ID NO: 80), E01 (SEQ ID NO: 96), ATI-965 (SEQ ID NO: 35), and ATI-966 (SEQ ID NO: 50).

DETAILED DESCRIPTION

Definitions

Figure 2:
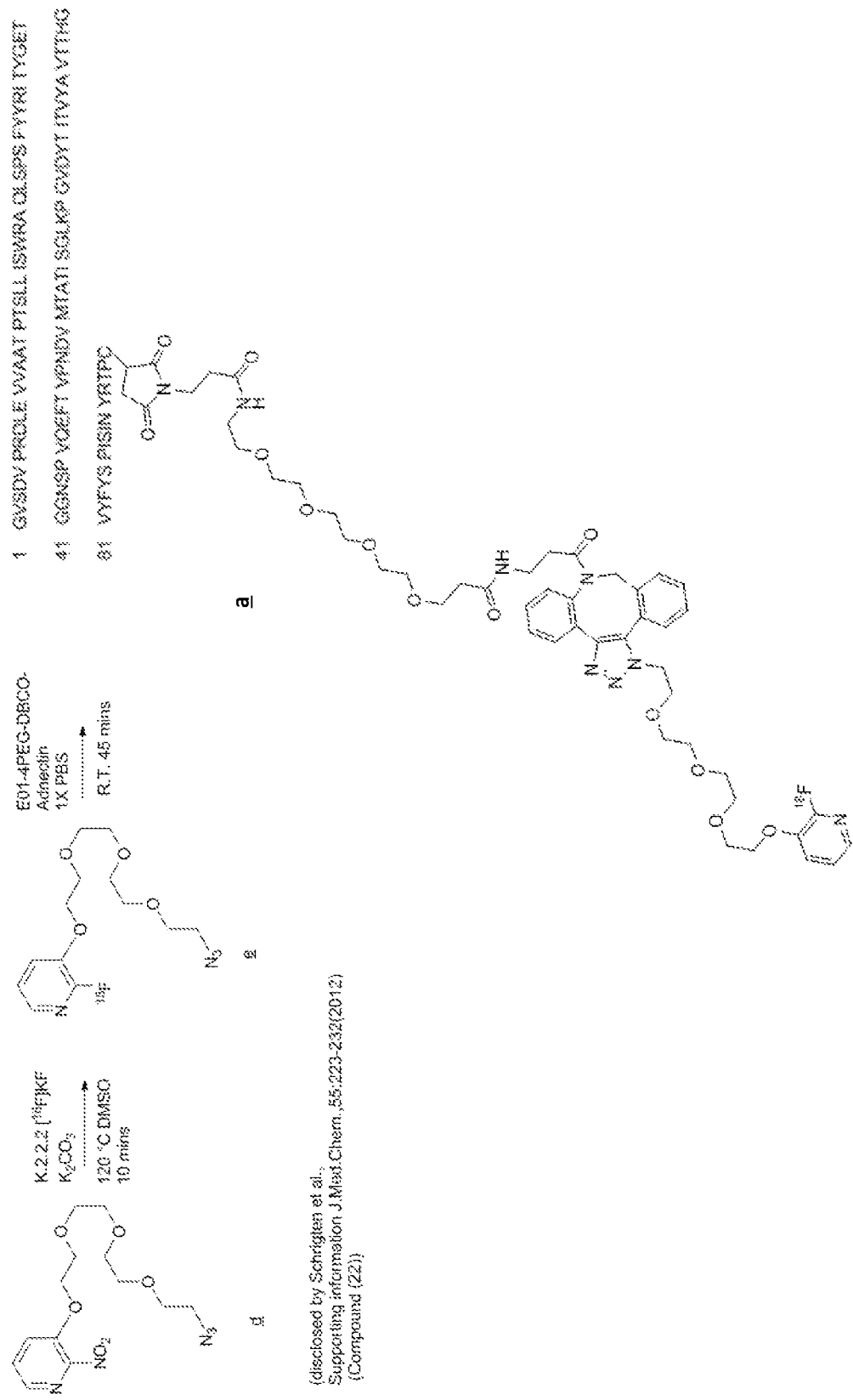
FIG. 2 is a schematic for the chemical synthesis of [$^{18}$F]-E01-4PEG-DBCO-FPPEGA. The E01 portion of the molecule has the sequence set forth in SEQ ID NO: 104.

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

"Programmed Death Ligand-1 (PD-L1)" is one of two cell surface glycoprotein ligands for PD-L1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No, Q9NZQ7. PD-L1 is also referred to as CD274, B7-H, B7H1, PDCD1L1, and PDCD1LG1.

"Polypeptide" as used herein refers to any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D). The peptides described herein are proteins derived from the tenth type III domain of fibronectin that have been modified to bind specifically to PD-L1 and are referred to herein as, "anti-PD-L1 Adnectin" or "PD-L1 Adnectin."

A "polypeptide chain," as used herein, refers to a polypeptide wherein each of the domains thereof is joined to other domain(s) by peptide bond(s), as opposed to non-covalent interactions or disulfide bonds.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "region" of a $^{10}$Fn3 domain as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-94 of SEQ ID NO: 1) of the human $^{10}$Fn3 domain.

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO: 1) and the C-terminal region (amino acids corresponding to residues 93-94 of SEQ ID NO: 1 and optionally comprising the 7 amino acids constituting the natural linker between the $10^{th}$ and the $11^{th}$ repeat of the Fn3 domain in human fibronectin).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR™) software. Those skilled in the art can readily determine appropriate parameters for measuring alignment, including any algorithms needed to achieve maximal alignment over the full-length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, the term "Adnectin binding site" refers to the site or portion of a protein (e.g., PD-L1) that interacts or binds to a particular Adnectin. Adnectin binding sites can be formed from contiguous amino acids or noncontiguous amino acids juxtaposed by tertiary folding of a protein. Adnectin binding sites formed by contiguous amino acids are typically retained on exposure to denaturing solvents, whereas Adnectin binding sites formed by tertiary folding are typically lost on treatment of denaturing solvents.

An Adnectin binding site for an anti-PD-L1 Adnectin described herein may be determined by application of standard techniques typically used for epitope mapping of antibodies including, but not limited to protease mapping and mutational analysis. Alternatively, an Adnectin binding site can be determined by competition assay using a reference Adnectin or antibody which binds to the same polypeptide, e.g., PD-L1 (as further described infra in the section "Cross-Competing Adnectins and/or Adnectins that Bind to the Same Adnectin Binding Site." If the test Adnectin and reference molecule (e.g., another Adnectin or antibody) compete, then they bind to the same Adnectin binding site or to Adnectin binding sites sufficiently proximal such that binding of one molecule interferes with the other.

The terms "specifically binds," "specific binding," "selective binding," and "selectively binds," as used interchangeably herein in the context of Adnectins binding to PD-L1 refers to an Adnectin that exhibits affinity for PD-L1, but does not significantly bind (e.g., less than about 10% binding) to a different polypeptides as measured by a technique available in the art such as, but not limited to, Scatchard analysis and/or competitive binding assays (e.g., competition ELISA, BIACORE assay). The term is also applicable where e.g., a binding domain of an Adnectin described herein is specific for PD-L1.

The term "preferentially binds" as used herein in the context of Adnectins binding to PD-L1 refers to the situation in which an Adnectin described herein binds PD-L1 at least about 20% greater than it binds a different polypeptide as measured by a technique available in the art such as, but not limited to, Scatchard analysis and/or competitive binding assays (e.g., competition ELISA, BIACORE assay).

As used herein in the context of Adnectins, the term "cross-reactivity" refers to an Adnectin which binds to more than one distinct protein having identical or very similar Adnectin binding sites.

The term "$K_D$," as used herein in the context of Adnectins binding to PD-L1, is intended to refer to the dissociation equilibrium constant of a particular Adnectin-protein (e.g., PD-L1) interaction or the affinity of an Adnectin for a protein (e.g., PD-L1), as measured using a surface plasmon resonance assay or a cell binding assay. A "desired $K_D$," as used herein, refers to a $K_D$ of an Adnectin that is sufficient for the purposes contemplated. For example, a desired $K_D$ may refer to the $K_D$ of an Adnectin required to elicit a functional effect in an in vitro assay, e.g., a cell-based luciferase assay.

The term "$k_a$", as used herein in the context of Adnectins binding to a protein, is intended to refer to the association rate constant for the association of an Adnectin into the Adnectin/protein complex.

The term "$k_d$", as used herein in the context of Adnectins binding to a protein, is intended to refer to the dissociation rate constant for the dissociation of an Adnectin from the Adnectin/protein complex.

The term "$IC_{50}$", as used herein in the context of Adnectins, refers to the concentration of an Adnectin that inhibits a response, either in an in vitro or an in vivo assay, to a level that is 50% of the maximal inhibitory response, i.e., halfway between the maximal inhibitory response and the untreated response.

The term "PK" is an acronym for "pharmacokinetic" and encompasses properties of a compound including, by way of example, absorption, distribution, metabolism, and elimination by a subject. A "PK modulation protein" or "PK moiety" as used herein refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549, PCT Publication Nos. WO 2009/083804 and WO 2009/133208), human serum albumin and variants thereof, transferrin and variants thereof, Fc or Fc fragments and variants thereof, and sugars (e.g., sialic acid).

The "serum half-life" of a protein or compound is the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to a subject a suitable dose of the amino acid sequence or compound described herein; collecting blood samples or other samples from the subject at regular intervals; determining the level or concentration of the amino acid sequence or compound described herein in said blood sample; and calculating, from (a plot of) the data thus obtained, the time until the level or concentration of the amino acid sequence or compound described herein has been reduced by 50% compared to the initial level upon dosing. Reference is, for example, made to the standard handbooks, such as Kenneth, A. et al., Chemical Stability of Pharmaceuticals: A Handbook for Pharmacists and in Peters et al., Pharmacokinete Analysis: A Practical Approach (1996). Reference is also made to Gibaldi, M. et al., Pharmacokinetics, 2nd Rev. Edition, Marcel Dekker (1982).

Half-life can be expressed using parameters such as the $t_{1/2}$-alpha, $t_{1/2}$-beta, HL_Lambda_z, and the area under the curve (AUC). In the present specification, an "increase in half-life" refers to an increase in any one of these parameters, any two of these parameters, any three of these parameters or all four of these parameters. An "increase in half-life" in particular refers to an increase in the $t_{1/2}$-beta, and/or HL_Lambda_z, either with or without an increase in the $t_{1/2}$-alpha and/or the AUC or both.

The term "detectable" refers to the ability to detect a signal over the background signal. The term "detectable signal" is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

A "detectably effective amount" of a composition comprising an imaging agent described herein is defined as an amount sufficient to yield an acceptable image using equipment that is available for clinical use. A detectably effective amount of an imaging agent provided herein may be administered in more than one injection. The detectably effective amount can vary according to factors such as the degree of susceptibility of the individual, the age, sex, and weight of the individual, idiosyncratic responses of the individual, and the like. Detectably effective amounts of imaging compositions can also vary according to instrument and methodologies used. Optimization of such factors is well within the level of skill in the art. In certain embodiments, a PD-L1 imaging agent, e.g., those described herein, provides a differentiation factor (i.e., specific signal to background signal) of 2 or more, e.g., 3, 4, 5 or more.

The term "bioorthogonal chemistry" refers to any chemical reaction that can occur inside of living systems without interfering with native biochemical processes. The term includes chemical reactions that are chemical reactions that occur in vitro at physiological pH in, or in the presence of water. To be considered bioorthogonol, the reactions are selective and avoid side-reactions with other functional groups found in the starting compounds. In addition, the resulting covalent bond between the reaction partners should be strong and chemically inert to biological reactions and should not affect the biological activity of the desired molecule.

The term "click chemistry" refers to a set of reliable and selective bioorthogonal reactions for the rapid synthesis of new compounds and combinatorial libraries. Properties of for click reactions include modularity, wideness in scope, high yielding, stereospecificity and simple product isolation (separation from inert by-products by non-chromatographic methods) to produce compounds that are stable under physiological conditions. In radiochemistry and radiopharmacy, click chemistry is a generic term for a set of labeling reactions which make use of selective and modular building blocks and enable chemoselective ligations to radiolabel biologically relevant compounds in the absence of catalysts. A "click reaction" can be with copper, or it can be a copper-free click reaction.

The term "prosthetic group" or "bifunctional labeling agent" refers to a small organic molecule containing a radionuclide (e.g., $^{18}F$) that is capable of being linked to peptides or proteins.

The term "chelator ligand" as used herein with respect to radiopharmaceutical chemistry refers to a bifunctional chelator or conjugating (BFC) moiety, which are used interchangeably herein, that covalently links a radiolabeled prosthetic group to a biologically active targeting molecule (e.g., peptide or protein). BFCs utilize functional groups such as carboxylic acids or activated esters for amide couplings, isothiocyanates for thiourea couplings and maleimides for thiol couplings.

The terms "individual," "subject," and "patient," used interchangeably herein, refer to an animal, preferably a mammal (including a nonprimate and a primate), e.g., a human. In certain embodiments, a subject has a disease or disorder or condition that would benefit from a decreased level or decreased bioactivity of PD-L1. In certain embodiments, a subject is at risk of developing a disorder, disease or condition that would benefit from a decreased level of PD-L1 or a decreased bioactivity of PD-L1.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Administration" or "administering," as used herein in the context of anti-PD-L1 Adnectins, refers to introducing a PD-L1 Adnectin or PD-L1 Adnectin-based probe or a labeled probe (also referred to as the "imaging agent") described herein into a subject. Any, route of administration is suitable, such as intravenous, oral, topical, subcutaneous, peritoneal, intra-arterial, inhalation, vaginal, rectal, nasal, introduction into the cerebrospinal fluid, or instillation into body compartments can be used.

The term "therapeutically effective amount" refers to at least the minimal dose, but less than a toxic dose, of an agent which is necessary to impart a therapeutic benefit to a subject.

As used herein, an "effective amount" refers to at least an amount effective, at dosages and for periods of time necessary, to achieve the desired result.

As used herein, a "sufficient amount" refers to an amount sufficient to achieve the desired result.

As used herein, "positron emission tomography" or "PET" refers to a non-invasive, nuclear medicine technique that produces a three-dimensional image of tracer location in the body. The method detects pairs of gamma rays emitted indirectly by a positron-emitting radionuclide (tracer), which is introduced into the body on a biologically active molecule. PET imaging tools have a wide variety of uses and aid in drug development both preclinically and clinically. Exemplary applications include direct visualization of in vivo saturation of targets; monitoring uptake in normal tissues to anticipate toxicity or patient to patient variation; quantifying diseased tissue; tumor metastasis; and monitoring drug efficacy over time, or resistance over time.

Overview

Provided herein are polypeptides that bind to human PD-L1 and can be coupled to heterologous molecule(s), such as a radiolabel. Such polypeptides are useful, for example, for detecting PD-L1 in a sample or tissue (e.g., a tissue, such as a cancer tissue that selectively expresses PD-L1) for diagnostic assays.

The invention is based on the development of a non-invasive clinical imaging agent that allows for whole body visualization of a patient's PD-L1 expression. In certain embodiments, single day "virtual biopsies" of a patient's whole body are performed to monitor and localize PD-L1 expression levels. PD-L1 imaging agents described herein may be used to provide a high contrast whole-body virtual biopsy in a single day.

I. Fibronectin-Based Scaffolds

Fn3 refers to a type III domain from fibronectin. An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). There are at least 15 different Fn3 modules in human Fibronectin, and while the sequence homology between the modules is low, they all share a high similarity in tertiary structure.

Described herein are anti-PD-L1 Adnectins comprising an Fn3 domain in which one or more of the solvent accessible loops has been randomized or mutated. In certain embodiments, the Fn3 domain is an Fn3 domain derived from the wild-type tenth module of the human fibronectin type III domain ($^{10}$Fn3):

(SEQ ID NO: 1)
VSDVPRDLEVVAA<u>TPTSLLISW</u>DAPAVTVRYYRIT<u>YGETGGNSPVQEFTV</u>

PGSKSTATISGL<u>KPGVD</u>YTITVYAVTGRGDSPASSKPISINYRT (94 amino acids; AB, CD, and EF loops are underlined; the core $^{10}$Fn3 domain begins with amino acid 9 ("E") and ends with amino acid 94 ("T") and corresponds to an 86 amino acid polypeptide). The core wild-type human $^{10}$Fn3 domain is set forth in SEQ ID NO: 2.

In certain embodiments, the non-ligand binding sequences of $^{10}$Fn3, i.e., the "$^{10}$Fn3 scaffold", may be altered provided that the $^{10}$Fn3 retains ligand binding function and/or structural stability. A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). A variety of additional alterations in the $^{10}$Fn3 scaffold that are either beneficial or neutral have been disclosed. See, for example, Batori et al., Protein Eng., 15(12):1015-1020 (December 2002); Koide et al., Biochemistry, 40(34):10326-10333 (Aug. 28, 2001).

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO: 1, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 76-87.

Accordingly, in certain embodiments, the anti-PD-L1 Adnectin described herein is an $^{10}$Fn3 polypeptide that is at least 40%, 50%, 60%, 65%, 70%, 75%, 80%, 85%, or 90% identical to the human $^{10}$Fn3 domain, shown in SEQ ID NO: 1, or its core sequence, as shown in SEQ ID NO: 2. Much of the variability will generally occur in one or more of the loops or one or more of the beta strands or N- or C-terminal regions. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 1 or 2, provided that such variation does not disrupt the stability of the polypeptide in physiological conditions.

In certain embodiments, the invention provides an anti-human PD-L1 Adnectin comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. In some embodiments, the anti-PD-L1 Adnectins described herein comprise a $^{10}$Fn3 domain comprising an amino acid sequence at least 80%, 85%, 90%, 95%, 98%, 99% or 100% identical to the non-loop regions of SEQ ID NO: 1 or 2, wherein at least one loop selected from BC, DE, and FG is altered. In certain embodiments, the BC and FG loops are altered, in certain embodiments, the BC and DE loops are altered, in certain embodiments, the DE and FG loops are altered, and in certain embodiments, the BC, DE, and FG loops are altered, i.e., the $^{10}$Fn3 domains comprise non-naturally occurring loops. In certain embodiments, the AB, CD and/or the EF loops are altered. By "altered" is meant one or more amino acid sequence alterations relative to a template sequence (corresponding human fibronectin domain) and includes amino acid additions, deletions, substitutions or a combination thereof. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In certain embodiments, one or more loops selected from BC, DE, and FG may be extended or shortened in length relative to the corresponding human fibronectin loop. In some embodiments, the length of the loop may be extended by 2-25 amino acids. In some embodiments, the length of the loop may be decreased by 1-11 amino acids. To optimize antigen binding, therefore, the length of a loop of $^{10}$Fn3 may be altered in length as well as in sequence to obtain the greatest possible flexibility and affinity in antigen binding.

In certain embodiments, the polypeptide comprises a Fn3 domain that comprises an amino acid sequence of the non-loop regions that is at least 80, 85, 90, 95, 98, 99, or 100% identical to the non-loop regions of SEQ ID NO: 1 or 2, wherein at least one loop selected from BC, DE, and FG is altered. In some embodiments, the altered BC loop has up to 1, 2, 3, 4, 5, 6, 7, 8, 9, or 10 amino acid substitutions, up to 1, 2, 3, or 4 amino acid deletions, up to 1, 2, 3, 4, 5, 6, 7, 8, 9, or 10 amino acid insertions, or a combination thereof.

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In some embodiments, the RGD sequence is replaced with SGE. In one embodiment, the RGD sequence is replaced with RGE.

In certain embodiments, the fibronectin based scaffold protein comprises a $^{10}$Fn3 domain that is defined generally by following the sequence:

(SEQ ID NO: 3)
EVVAA(Z)$_a$LLISW(Z)$_x$YRITY(Z)$_b$FTV(Z)$_y$ATISGL(Z)$_c$

YTITVYA(Z)$_z$ISINYRT wherein the AB loop is represented by $(Z)_a$, the CD loop is represented by $(Z)_b$, the EF loop is represented by $(Z)_c$, the BC loop is represented by $(Z)_x$, the DE loop is represented by $(Z)_y$, and the FG loop is represented by $(Z)_z$. Z represents any amino acid and the subscript following the Z represents an integer of the number of amino acids. In particular, a may be anywhere from 1-15, 2-15, 1-10, 2-10, 1-8, 2-8, 1-5, 2-5, 1-4, 2-4, 1-3, 2-3, or 1-2 amino acids; and b, c, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1 or 2. In certain embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1 or 2. In certain embodiments, the core amino acid residues are fixed and any substitutions, conservative substitutions, deletions or additions occur at residues other than the core amino acid residues.

In certain embodiments, the anti-PD-L1 Adnectins described herein are based on a $^{10}$Fn3 scaffold and are defined generally by the sequence:

(SEQ ID NO: 4)
EVVAATPTSLLISW(Z)$_x$YRITYGETGGNSPVQEFTV(Z)$_y$

ATISGLKPGVDYTITVYA(Z)$_z$ISINYRT.

wherein the BC loop is represented by $(Z)_x$, the DE loop is represented by $(Z)_y$, and the FG loop is represented by $(Z)_z$. Z represents any amino acid and the subscript following the Z represents an integer of the number of amino acids. In particular, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, x is 11 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1 or 2. In certain embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1 or 2. In certain embodiments, the core amino acid residues, e.g., outside one or more loops, are fixed and any substitutions, conservative substitutions, deletions or additions occur at residues other than the core amino acid residues.

In certain embodiments, an anti-PD-L1 Adnectin may comprise the sequence as set forth in SEQ ID NO: 3 or 4, wherein at least one of BC, DE, and FG loops as represented by $(Z)_x$, $(Z)_y$, and $(Z)_z$, respectively, are altered. As described above, amino acid residues corresponding to residues 23-31, 51-56, and 76-87 of SEQ ID NO: 1 define the BC, DE, and FG loops, respectively. However, it should be understood that not every residue within the loop region needs to be modified in order to achieve a $^{10}$Fn3 binder having strong affinity for a desired target (e.g., PD-L1).

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 21, 22, and 23, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 21, 22, and 23, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 36, 37, and 38, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 36, 37, and 38, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 51, 52, and 53, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 51, 52, and 53, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 66, 67, and 68, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 66, 67, and 68, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 6, 7, and 8, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 6, 7, and 8, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 81, 82, and 83, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 81, 82, and 83, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, have amino acid sequences at least 75%, 80%, 85%, 90%, 95%, 97%, 98%, or 99% identical to the BC, DE or FG loop sequences set forth in SEQ ID NOs: 97, 98, and 99, respectively. In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 97, 98, and 99, respectively.

In certain embodiments, an anti-PD-L1 Adnectin comprises the sequence set forth in SEQ ID NO: 3 or 4, wherein BC, DE and FG loops as represented by $(Z)_x$, $(Z)_y$, and $(Z)_z$, respectively, comprise BC, DE, and FG loops having the amino acid sequences of SEQ ID NOs: 113, 114, and 115, respectively; SEQ ID NOs: 124, 125 and 126, respectively; SEQ ID NOs: 135, 136 and 137, respectively; SEQ ID NOs: 146, 147 and 148, respectively; SEQ ID NOs: 157, 158 and 159, respectively; SEQ ID NOs: 168, 169 and 170, respectively; SEQ ID NOs: 179, 180 and 181, respectively; SEQ ID NOs: 190, 191 and 192, respectively; SEQ ID NOs: 201, 202 and 203, respectively; SEQ ID NOs: 212, 213 and 214, respectively; SEQ ID NOs: 223, 224 and 225, respectively; SEQ ID NOs: 234, 235, and 236, respectively; SEQ ID NOs: 245, 246 and 247, respectively; SEQ ID NOs: 256, 257 and 258, respectively; SEQ ID NOs: 267, 268 and 269, respectively; SEQ ID NOs: 278, 279 and 280, respectively; SEQ ID NOs: 289, 290 and 291, respectively; SEQ ID NOs: 300, 301 and 302, respectively; SEQ ID NOs: 311, 312 and 313, respectively; SEQ ID NOs: 322, 323 and 324, respectively; SEQ ID NOs: 333, 334 and 335, respectively; SEQ ID NOs: 344, 345 and 346, respectively; SEQ ID NOs: 355, 356 and 357, respectively; SEQ ID NOs: 366, 367 and 368, respectively; SEQ ID NOs: 377, 378 and 379, respectively; SEQ ID NOs: 388, 389 and 390 respectively; SEQ ID NOs: 399, 400 and 401, respectively; SEQ ID NOs: 410, 411 and 412, respectively; SEQ ID NOs: 421, 422 and 423, respectively; SEQ ID NOs: 432, 433 and 434 respectively; SEQ ID NOs: 443, 444 and 445, respectively; SEQ ID NOs: 454, 455 and 456, respectively; SEQ ID NOs: 465, 466 and 467, respectively; SEQ ID NOs: 476, 477 and 478, respectively; SEQ ID NOs: 487, 488 and 489, respectively; SEQ ID NOs: 498, 499 and 500, respectively; SEQ ID NOs: 509, 510 and 511, respectively; SEQ ID NOs: 520, 521 and 522, respectively; SEQ ID NOs: 531, 530 and 531, respectively; SEQ ID NOs: 542, 543 and 544, respectively; SEQ ID NOs: 553, 554 and 555, respectively; or SEQ ID NOs: 564, 565 and 566, respectively. The scaffold regions of such anti-PD-L1 Adnectins may comprise anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 4. Such scaffold modifications may be made, so long as the anti-PD-L1 Adnectin is capable of binding PD-L1 with a desired KID.

In certain embodiments, the BC loop of the anti-PD-L1 Adnectin comprises an amino acid sequence selected from the group consisting of: 6, 21, 36, 51, 66, 81, and 97.

In certain embodiments, the DE loop of the anti-PD-L1 Adnectin comprises an amino acid sequence selected from the group consisting of: 7, 22, 37, 52, 67, 82, and 98.

In certain embodiments, the FG loop of the anti-PD-L1 Adnectin comprises an amino acid sequence selected from the group consisting of: 8, 23, 38, 53, 68, 83, and 99.

In certain embodiments, the anti-PD-L1 Adnectin comprises a BC, DE and FG loop amino acid sequence at least 70%, 75%, 80%, 85%, 90%, 95%, 98%, 99% or 100% identical to any one of SEQ ID NOs: 6, 21, 36, 51, 66, 81, and 97; 7, 22, 37, 52, 67, 82, and 98; and 8, 23, 38, 53, 68, 83, and 99, respectively.

In certain embodiments, the anti-PD-L1 Adnectin comprises an amino acid sequence at least 70%, 75%, 80%, 85%, 90%, 95%, 98%, 99%, or 100% identical to any one of SEQ ID NOs: 5, 20, 35, 50, 65, 80, 96, 112, 123, 134, 145, 156, 167, 178, 189, 200, 211, 222, 233, 244, 255, 266, 277, 288, 299, 310, 321, 332, 343, 354, 365, 376, 387, 398, 409, 420, 431, 442, 453, 464, 475, 486, 497, 508, 519, 530, 541, 552 and 563.

In certain embodiments, the anti-PD-L1 Adnectins described herein comprise an amino acid sequence at least 80%, 85%, 90%, 95%, 98%, 99% or 100% identical to the non-BC, DE, and FG loop regions of SEQ ID NOs: 5, 20, 35, 50, 65, 80, or 96.

In certain embodiments, the anti-PD-L1 Adnectin comprises an amino acid sequence at least 70%, 75%, 80%, 85%, 90%, 95%, 98%, 99% or 100% identical to any one of SEQ ID NOs: 9-15, 24-30, 39-45, 54-60, 6975, 84-91, 100-107, 116-122, 127-133, 138-144, 150-155, 160-166, 171-177, 182-188, 193-199, 204-210, 215-221, 227-232, 237-243, 248-254, 259-265, 271-276, 291-287, 292-298, 303-309, 314-320, 325-331, 337-342, 347-353, 358-364, 369-375, 380-386, 391-397, 402-408, 413-419, 424-430, 435-441, 446-452, 457-463, 468-474, 479-485, 490-496, 501-507, 512-518, 523-529, 534-540, 545-551, and 556-562. In certain embodiments, the anti-PD-L1 Adnectins described herein comprise an amino acid sequence at least 80%, 85%, 90%, 95%, 98%, 99% or 100% identical to the non-BC, DE, and FG loop regions of any one of SEQ ID NOs: 9-15, 24-30, 39-45, 54-60, 6975, 84-91, and 100-107.

In certain embodiments, the anti-PD-L1 Adnectin comprises BC, DE, and FG loops as set forth in SEQ ID NOs: 6, 7, and 8, respectively.

In certain embodiments, the anti-PD-L1 Adnectin comprises BC, DE, and FG loops as set forth in SEQ ID NOs: 21, 22, and 23, respectively.

In certain embodiments, the anti-PD-L1 Adnectin comprises BC, DE, and FG loops as set forth in SEQ ID NOs: 36, 37, and 38, respectively.

In certain embodiments, the anti-PD-L1 Adnectin comprises BC, DE, and FG loops as set forth in SEQ ID NOs: 51, 52, and 53, respectively.

In certain embodiments, the anti-PD-L1 Adnectin comprises BC, DE, and FG loops as set forth in SEQ ID NOs: 66, 67, and 68, respectively.

In certain embodiments, the anti-PD-L1 Adnectin comprises BC, DE, and FG loops as set forth in SEQ ID NOs: 81, 82, and 83, respectively.

In certain embodiments, the anti-PD-L1 Adnectin comprises BC, DE, and FG loops as set forth in SEQ ID NOs: 97, 98, and 99, respectively.

In certain embodiments, BC, DE and/or FG loop amino acid sequences described herein (e.g., SEQ ID NOs: 6, 21, 36, 51, 66, 81, and 97; 7, 22, 37, 52, 67, 82, and 98; and 8, 23, 38, 53, 68, 83, and 99, respectively) are grafted into non-$^{10}$Fn3 domain protein scaffolds. For instance, one or more loop amino acid sequences is exchanged for or inserted into one or more CDR loops of an antibody heavy or light chain or fragment thereof. In some embodiments, the protein domain into which one or more amino acid loop sequences are exchanged or inserted includes, but is not limited to, consensus Fn3 domains (Centocor, US), ankyrin repeat proteins (Molecular Partners AG, Zurich Switzerland), domain antibodies (Domantis, Ltd, Cambridge, Mass.), single domain camelid nanobodies (Ablynx, Belgium), lipocalins (e.g., anticalins; Pieris Proteolab AG, Freising, Germany), Avimers (Amgen, CA), affibodies (Affibody AG, Sweden), ubiquitin (e.g., affilins; Scil Proteins GmbH, Halle, Germany), protein epitope mimetics (Polyphor Ltd, Allschwil, Switzerland), helical bundle scaffolds (e.g. alphabodies, Complix, Belgium), Fyn SH3 domains (Covagen AG, Switzerland), or atrimers (Anaphor, Inc., CA).

In certain embodiments, the amino acid sequences of the N-terminal and/or C-terminal regions of the polypeptides provided herein may be modified by deletion, substitution or insertion relative to the amino acid sequences of the corresponding regions of the wild-type human $^{10}$Fn3 domain (SEQ ID NO: 1 or 2). The $^{10}$Fn3 domains generally begin with amino acid number 1 of SEQ ID NO: 1. However, domains with amino acid deletions are also encompassed by the invention. Additional sequences may also be added to the N- or C-terminus of a $^{10}$Fn3 domain having the amino acid sequence of SEQ ID NO: 1 or 2. For example, in some embodiments, the N-terminal extension consists of an amino acid sequence selected from the group consisting of: M, MG, and G. In certain embodiments, an MG sequence may be placed at the N-terminus of the $^{10}$Fn3 defined by SEQ ID NO: 1. The M will usually be cleaved off, leaving a G at the N-terminus. In addition, an M, G or MG may also be placed N-terminal to any of the N-terminal extensions shown in Table 3.

In exemplary embodiments, an alternative N-terminal region having from 1-20, 1-15, 1-10, 1-8, 1-5, 1-4, 1-3, 1-2, or 1 amino acids in length can be added to the N-terminal region of SEQ ID NO: 1 or 2 or any adnectin set forth in Table 3. Exemplary alternative N-terminal regions include (represented by the single letter amino acid code) M, MG, G, MGVSDVPRDL (SEQ ID NO: 574) and GVSDVPRDL (SEQ ID NO: 575). Other suitable alternative N-terminal regions, which may be linked, e.g., to the N-terminus of an adnectin core sequence, include, for example, X$_n$SDVPRDL (SEQ ID NO: 576), X$_n$DVPRDL (SEQ ID NO: 577), X$_n$VPRDL (SEQ ID NO: 578), X$_n$PRDL (SEQ ID NO: 579) X$_n$RDL (SEQ ID NO: 580), X$_n$DL (SEQ ID NO: 581), or XI, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In some embodiments, the alternative N-terminal region comprises the amino acid sequence MASTSG (SEQ ID NO: 582).

In exemplary embodiments, an alternative C-terminal region having from 1-20, 1-15, 1-10, 1-8, 1-5, 1-4, 1-3, 1-2, or 1 amino acids in length can be added to the C-terminal region of SEQ ID NO: 1 or 2 or any adnectin set forth in Table 3. Specific examples of alternative C-terminal region sequences include, for example, polypeptides comprising, consisting essentially of, or consisting of, EIEK (SEQ ID NO: 584), EGSGC (SEQ ID NO: 585), EIEKPCQ (SEQ ID NO: 586), EIEKPSQ (SEQ ID NO: 587), EIEKP (SEQ ID NO: 588), EIEKPS (SEQ ID NO: 589), or EIEKPC (SEQ ID NO: 590). In some embodiments, the alternative C-terminal region comprises EIDK (SEQ ID NO: 591), and in particular embodiments, the alternative C-terminal region is either EIDKPCQ (SEQ ID NO: 592) or EIDKPSQ (SEQ ID NO: 593). Additional suitable alternative C-terminal regions are set forth in SEQ ID NOs: 594-618.

In certain embodiments, an Adnectin is linked to a C-terminal extension sequence that comprises E and D residues, and may be between 8 and 50, 10 and 30, 10 and 20, 5 and 10, and 2 and 4 amino acids in length. In some embodiments, tail sequences include ED-based linkers in which the sequence comprises tandem repeats of ED. In exemplary embodiments, the tail sequence comprises 2-10, 2-7, 2-5, 3-10, 3-7, 3-5, 3, 4 or 5 ED repeats. In certain embodiments, the ED-based tail sequences may also include additional amino acid residues, such as, for example: EI, EID, ES, EC, EGS, and EGC. Such sequences are based, in part, on known Adnectin tail sequences, such as EIDKPSQ (SEQ ID NO: 593), in which residues D and K have been removed. In exemplary embodiments, the ED-based tail comprises an E, I or EI residues before the ED repeats.

In certain embodiments, the N- or C-terminal extension sequences are linked to the anti-PD-L1 Adnectin sequences with known linker sequences (e.g., SEQ ID NOs: 629-678 in Table 3). In some embodiments, sequences may be placed at the C-terminus of the $^{10}$Fn3 domain to facilitate attachment of a pharmacokinetic moiety. For example, a cysteine containing linker such as GSGC (SEQ ID NO: 638) may be added to the C-terminus to facilitate site directed PEGylation on the cysteine residue.

In certain embodiments, an alternative C-terminal moiety, which can be linked to the C-terminal amino acids RT (i.e., amino acid 94) comprises the amino acids P$_m$X$_n$, wherein P is proline, X is any amino acid, m is an integer that is at least 1 and n is 0 or an integer that is at least 1. In certain embodiments, the alternative C-terminal moiety comprises the amino acids PC. In certain embodiments, the alternative C-terminal moiety comprises the amino acids PI, PC, PID, PIE, PIDK (SEQ ID NO: 605), PIEK (SEQ ID NO: 606), PIDKP (SEQ ID NO: 607), PIEKP (SEQ ID NO: 608), PIDKPS (SEQ ID NO: 609), PIEKPS (SEQ ID NO: 610), PIDKPC (SEQ ID NO: 611), PIEKPC (SEQ ID NO: 612), PIDKPSQ (SEQ ID NO: 613), PIEKPSQ (SEQ ID NO: 614), PIDKPCQ (SEQ ID NO: 615), PIEKPCQ (SEQ ID NO: 616), PHHHHHH (SEQ ID NO: 617), and PCH-HHHHH (SEQ ID NO: 618). Exemplary anti-PD-L1 Adnectins having PC at their C-terminus are provided in the Examples and Table 3.

In certain embodiments, the Adnectins described herein have a 6× his tail (SEQ ID NO: 619).

In certain embodiments, the fibronectin based scaffold proteins comprise a $^{10}$Fn3 domain having both an alternative N-terminal region sequence and an alternative C-terminal region sequence, and optionally a 6× his tail.

II. Biological Properties of Anti-PD-L1 Adnectins

Provided herein are adnectins that bind to human PD-L1 with a KD of 10 nM, 1 nM, 0.5 nM, 0.1 nM or less, as determined, e.g., by SPR (Biacore) and exhibit one or more of the following properties:

1. Inhibition of the interaction between human PD-L1 and human PD-1 by at least 50%, 70%, 80%, 90% or more, as determined, e.g., by flow cytometry, e.g., using a human PD-1Fc protein and human PD-L1 positive cells, such as L2987 cells;
2. Inhibition of the binding of human CD80 (B7-1) to human PD-L1 by at least 50%, 70%, 80%, 90% or more, as determined, e.g., in an ELISA assay or by SPR (Biacore);
3. Inhibition of the binding of the anti-PD-L1 antibody 12A4 (described, e.g., in U.S. Pat. No. 7,943,743) to human PD-L1 by at least 50%, 70%, 80%, 90% or more, as determined, e.g., in an ELISA assay or by SPR (Biacore); and
4. Inhibit cell proliferation in a mixed lymphocyte reaction (MLR).

In certain embodiments, an anti-PD-L1 adnectin binds to human PD-L1 with a KD of 1 nM or less and exhibits each one of properties 1-4. In certain embodiments, an anti-PD-L1 adnectin binds to human PD-L1 with a KD of 0.1 nM or less and exhibits each one of properties 1-4.

Provided herein are adnectins that comprise an amino acid sequence that is at least 70%, 80%, 90%, 95%, 97%, 98% or 99% identical to an anti-PD-L1 adnectin described herein or a portion thereof (e.g., the BC, DE and FG loops), bind to human PD-L1 with a KD of 10 nM, 1 nM, 0.5 nM, 0.1 nM or less, as determined, e.g., by SPR (Biacore) and exhibit one or more of the following properties:

1. Inhibition of the interaction between human PD-L1 and human PD-1 by at least 50%, 70%, 80%, 90% or more, as determined, e.g., by flow cytometry, e.g., using a human PD-1Fc protein and human PD-L1 positive cells, such as L2987 cells;
2. Inhibition of the binding of human CD80 (B7-1) to human PD-L1 by at least 50%, 70%, 80%, 90% or more, as determined, e.g., in an ELISA assay or by SPR (Biacore);
3. Inhibition of the binding of the anti-PD-L1 antibody 12A4 to human PD-L1 by at least 50%, 70%, 80%, 90% or more, as determined, e.g., in an ELISA assay or by SPR (Biacore); and
4. Inhibit cell proliferation in a mixed lymphocyte reaction (MLR).

In certain embodiments, an anti-PD-L1 adnectin comprises an amino acid sequence that is at least 70%, 80%, 90%, 95%, 97%, 98% or 99% identical to an anti-PD-L1 adnectin described herein or a portion thereof (e.g., the BC, DE and FG loops), binds to human PD-L1 with a KD of 1 nM or less and exhibits each one of properties 1-4. In certain embodiments, an anti-PD-L1 adnectin comprises an amino acid sequence that is at least 70%, 80%, 90%, 95%, 97%, 98% or 99% identical to an anti-PD-L1 adnectin described herein or a portion thereof (e.g., the BC, DE and FG loops), binds to human PD-L1 with a KD of 0.1 nM or less and exhibits each one of properties 1-4.

In certain embodiments, the anti-PD-L1 Adnectins compete (e.g., cross-compete) for binding to PD-L1 with the particular anti-PD-L1 Adnectins described herein. Such competing Adnectins can be identified based on their ability to competitively inhibit binding to PD-L1 of Adnectins described herein in standard PD-L1 binding assays. For example, standard ELISA assays can be used in which a recombinant PD-L1 protein is immobilized on the plate, one of the Adnectins is fluorescently labeled and the ability of non-labeled Adnectins to compete off the binding of the labeled Adnectin is evaluated.

In certain embodiments, a competitive ELISA format can be performed to determine whether two anti-PD-L1 Adnectins bind overlapping Adnectin binding sites on PD-L1. In one format, Adnectin #1 is coated on a plate, which is then blocked and washed. To this plate is added either PD-L1 alone, or PD-L1 pre-incubated with a saturating concentration of Adnectin #2. After a suitable incubation period, the plate is washed and probed with a polyclonal anti-PD-L1 antibody, such as a biotinylated anti-PD-L1 polyclonal antibody, followed by detection with streptavidin-HRP conjugate and standard tetramethylbenzidine development procedures. If the OD signal is the same with or without preincubation with Adnectin #2, then the two Adnectins bind independently of one another, and their Adnectin binding sites do not overlap. If, however, the OD signal for wells that received PD-L1/Adnectin #2 mixtures is lower than for those that received PD-L1 alone, then binding of Adnectin #2 is confirmed to block binding of Adnectin #1 to PD-L1.

Alternatively, a similar experiment is conducted by surface plasmon resonance (SPR, e.g., BIAcore). Adnectin #1 is immobilized on an SPR chip surface, followed by injections of either PD-L1 alone or PD-L1 pre-incubated with a saturating concentration of Adnectin #2. If the binding signal for PD-L1/Adnectin #2 mixtures is the same or higher than that of PD-L1 alone, then the two Adnectins bind independently of one another, and their Adnectin binding sites do not overlap. If, however, the binding signal for PD-L1/Adnectin #2 mixtures is lower than the binding signal for PD-L1 alone, then binding of Adnectin #2 is confirmed to block binding of Adnectin #1 to PD-L1. A feature of these experiments is the use of saturating concentrations of Adnectin #2. If PD-L1 is not saturated with Adnectin #2, then the conclusions above do not hold. Similar experiments can be used to determine if any two PD-L1 binding proteins bind to overlapping Adnectin binding sites.

Both assays exemplified above may also be performed in the reverse order where Adnectin #2 is immobilized and PD-L1-Adnectin #1 are added to the plate. Alternatively, Adnectin #1 and/or #2 can be replaced with a monoclonal antibody and/or soluble receptor-Fc fusion protein.

In certain embodiments, competition can be determined using a HTRF sandwich assay.

In certain embodiments, the competing Adnectin is an Adnectin that binds to the same Adnectin binding site on PD-L1 as a particular anti-PD-L1 Adnectin described herein. Standard mapping techniques, such as protease mapping, mutational analysis, HDX-MS, x-ray crystallography and 2-dimensional nuclear magnetic resonance, can be used to determine whether an Adnectin binds to the same Adnectin binding site or epitope as a reference Adnectin (see, e.g., *Epitope Mapping Protocols in Methods in Molecular Biology*, Vol. 66, G. E. Morris, Ed. (1996)). An epitope is defined by the method used to locate it. For example, in certain embodiments, a PD-L1 adnectin or antibody binds to the same epitope as that of one of the PD-L1 adnectins described herein, as determined by HDX-MS or as determined by X-ray crystallography.

Candidate competing anti-PD-L1 Adnectins can inhibit the binding of anti-PD-L1 Adnectins described herein to PD-L1 by at least 50%, at least 55%, at least 60%, at least 65%, at least 70%, at least 75%, at least 80%, at least 85%, at least 90%, at least 95%, at least 97%, at least 98%, or at least 99% and/or their binding is inhibited by at least 50%, at least 55%, at least 60%, at least 65%, at least 70%, at least 75%, at least 80%, at least 85%, at least 90%, at least 95%, at least 97%, at least 98%, or at least 99% by anti-PD-L1 Adnectins. The % competition can be determined using the methods described above.

Provided herein are adnectins that bind to human PD-L1 with a KD of 10 nM, 1 nM, 0.5 nM, 0.1 nM or less, as determined, e.g., by SPR (Biacore) and exhibit one or more of the following properties:
1. Inhibition of the interaction between human PD-L1 and human PD-1 by at least 50%, 70%, 80%, 90% or more, as determined, e.g., by flow cytometry, e.g., using a human PD-1Fc protein and human PD-L1 positive cells, such as L2987 cells;
2. Inhibition of the binding of human CD80 (B7-1) to human PD-L1 by at least 50%, 70%, 80%, 90% or more, as determined, e.g., in an ELISA assay or by SPR (Biacore);
3. Inhibition of the binding of the anti-PD-L1 antibody 12A4 to human PD-L1 by at least 50%, 70%, 80%, 90% or more, as determined, e.g., in an ELISA assay or by SPR (Biacore);
4. Inhibit cell proliferation in a mixed lymphocyte reaction (MLR); and
5. Compete with an anti-PD-L1 antibody described herein for binding to human PD-L1.

In certain embodiments, an anti-PD-L1 adnectin binds to human PD-L1 with a KD of 1 nM or less and exhibits each one of properties 1-5. In certain embodiments, an anti-PD-L1 adnectin binds to human PD-L1 with a KD of 0.1 nM or less and exhibits each one of properties 1-5.

Provided herein are adnectins that comprise an amino acid sequence that is at least 70%, 80%, 90%, 95%, 97%, 98% or 99% identical to an anti-PD-L1 adnectin described herein or a portion thereof (e.g., the BC, DE and FG loops), bind to human PD-L1 with a KD of 10 nM, 1 nM, 0.5 nM, 0.1 nM or less, as determined, e.g., by SPR (Biacore) and exhibit one or more of the following properties:
1. Inhibition of the interaction between human PD-L1 and human PD-1 by at least 50%, 70%, 80%, 90% or more, as determined, e.g., by flow cytometry, e.g., using a human PD-1Fc protein and human PD-L1 positive cells, such as L2987 cells;
2. Inhibition of the binding of human CD80 (B7-1) to human PD-L1 by at least 50%, 70%, 80%, 90% or more, as determined, e.g., in an ELISA assay or by SPR (Biacore);
3. Inhibition of the binding of the anti-PD-L1 antibody 12A4 to human PD-L1 by at least 50%, 70%, 80%, 90% or more, as determined, e.g., in an ELISA assay or by SPR (Biacore);
4. Inhibit cell proliferation in a mixed lymphocyte reaction (MLR); and
5. Compete with an anti-PD-L1 antibody described herein for binding to human PD-L1.

In certain embodiments, an anti-PD-L1 adnectin comprises an amino acid sequence that is at least 70%, 80%, 90%, 95%, 97%, 98% or 99% identical to an anti-PD-L1 adnectin described herein or a portion thereof (e.g., the BC, DE and FG loops), binds to human PD-L1 with a KD of 1 nM or less and exhibits each one of properties 1-5. In certain embodiments, an anti-PD-L1 adnectin comprises an amino acid sequence that is at least 70%, 80%, 90%, 95%, 97%, 98% or 99% identical to an anti-PD-L1 adnectin described herein or a portion thereof (e.g., the BC, DE and FG loops), binds to human PD-L1 with a KD of 0.1 nM or less and exhibits each one of properties 1-5.

III. Fusions, Including Pharmacokinetic Moieties

In certain embodiments, the anti-PD-L1 Adnectins desirably have a short half-life, for example, when used in diagnostic imaging.

Alternatively, e.g., for therapeutic purposes, the anti-PD-L1 Adnectins described herein further comprise a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The anti-PD-L1 Adnectin may be attached to a moiety that reduces the clearance rate of the polypeptide in a mammal (e.g., mouse, rat, or human) by greater than two-fold, greater than three-fold, greater than four-fold or greater than five-fold relative to the unmodified anti-PD-L1 Adnectin. Other measures of improved pharmacokinetics may include serum half-life, which is often divided into an alpha phase and a beta phase. Either or both phases may be improved significantly by addition of an appropriate moiety. For example, the PK moiety may increase the serum half-life of the polypeptide by more than 5, 10, 20, 30, 40, 50, 60, 70, 80, 90, 100, 120, 150, 200, 400, 600, 800, 1000% or more relative to the Fn3 domain alone.

Moieties that slow clearance of a protein from the blood, herein referred to as "PK moieties", include polyoxyalkylene moieties (e.g., polyethylene glycol), sugars (e.g., sialic acid), and well-tolerated protein moieties (e.g., Fc and fragments and variants thereof, transferrin, or serum albumin). The anti-PD-L1 Adnectin may also be fused to albumin or a fragment (portion) or variant of albumin as described in U.S. Publication No. 2007/0048282, or may be fused to one or more serum albumin binding Adnectin, as described herein.

Other PK moieties that can be used in the invention include those described in Kontermann et al., (*Current Opinion in Biotechnology* 2011; 22:868-76), herein incorporated by reference. Such PK moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the invention provides an anti-PD-L1 Adnectin fused to a PK moiety that is a polymeric sugar. In some embodiments, the PK moiety is a polyethylene glycol moiety or an Fc region. In some embodiments the PK moiety is a serum albumin binding protein such as those described in U.S. Publication Nos. 2007/0178082 and 2007/0269422. In some embodiments the PK moiety is human serum albumin. In some embodiments, the PK moiety is transferrin.

In some embodiments, the PK moiety is linked to the anti-PD-L1 Adnectin via a polypeptide linker. Exemplary polypeptide linkers include polypeptides having from 1-20, 1-15, 1-10, 1-8, 1-5, 1-4, 1-3, or 1-2 amino acids. Suitable linkers for joining the Fn3 domains are those which allow the separate domains to fold independently of each other forming a three dimensional structure that permits high affinity binding to a target molecule. Specific examples of suitable linkers include glycine-serine based linkers, glycine-proline based linkers, proline-alanine based linkers as well as any other linkers described herein. In some embodiments, the linker is a glycine-proline based linker. These linkers comprise glycine and proline residues and may be between 3 and 30, 10 and 30, and 3 and 20 amino acids in length. Examples of such linkers include GPG, GPGPGPG (SEQ ID NO: 672) and GPGPGPGPGPG (SEQ ID NO: 673). In some embodiments, the linker is a proline-alanine based linker. These linkers comprise proline and alanine residues and may be between 3 and 30, 10 and 30, 3 and 20 and 6 and 18 amino acids in length. Examples of such linkers include PAPAPA (SEQ ID NO: 674), PAPAPAPAPAPA (SEQ ID NO: 675) and PAPAPAPAPAPAPAPA (SEQ ID NO: 676). In some embodiments, the linker is a glycine-serine based linker. These linkers comprise glycine and serine residues and may be between 8 and 50, 10 and 30, and 10 and 20 amino acids in length. Examples of such linkers include GSGSGSGSGS ($(GS)_5$; SEQ ID NO: 662), GSGSGSGSGSGS ($(GS)_6$; SEQ ID NO: 663), GSGSGSGSGSGSGSGSGSGS ($(GS)_{10}$; SEQ ID NO: 677), GGGGSGGGGSGGGGSGGGGS ($(G_4S)_4$; SEQ ID NO: 678), GGGGSGGGGSGGGGSGGGGSGGGGS ($(G_4S)_5$; SEQ ID NO: 670), and GGGGSGGGGSGGGSG (SEQ ID NO: 671). In exemplary embodiments, the linker does not contain any Asp-Lys (DK) pairs. A list of suitable linkers is provided in Table 3.

Optimal linker length and amino acid composition may be determined by routine experimentation in view of the teachings provided herein. In some embodiments, an anti-PD-L1 Adnectin is linked, for example, to an anti-HSA Adnectin via a polypeptide linker having a protease site that is cleavable by a protease in the blood or target tissue. Such embodiments can be used to release an anti-PD-L1 Adnectin for better delivery or therapeutic properties or more efficient production.

Additional linkers or spacers, may be introduced at the N-terminus or C-terminus of a Fn3 domain between the Fn3 domain and the polypeptide linker.

Polyethylene Glycol

In some embodiments, the anti-PD-L1 Adnectin comprises polyethylene glycol (PEG). PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_{n-1}CH_2CH_2OH$, where n is 20 to 2300 and X is H or a terminal modification, e.g., a $C_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Published Application No. 473084A and U.S. Pat. No. 5,932,462.

One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

PEGylation may be achieved by site-directed PEGylation, wherein a suitable reactive group is introduced into the protein to create a site where PEGylation preferentially occurs. In some embodiments, the protein is modified to introduce a cysteine residue at a desired position, permitting site-directed PEGylation on the cysteine. Mutations may be introduced into a protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework, based on which binding polypeptides are designed and evolved, has been solved (see Himanen et al., *Nature* 2001; 414:933-8) and thus the surface-exposed residues identified. PEGylation of cysteine residues may be carried out using, for example, PEG-maleimide, PEG-vinylsulfone, PEG-iodoacetamide, or PEG-orthopyridyl disulfide. In certain embodiments, a PEG is linked to a C-terminal cysteine, e.g., a cysteine that has been added to an anti-PD-L1 Adnectin, such as in the form of a "PC" extension, as further described herein.

The PEG is typically activated with a suitable activating group appropriate for coupling to a desired site on the polypeptide. PEGylation methods are well-known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) *Advanced Drug Reviews* 16: 157-182.

PEG may vary widely in molecular weight and may be branched or linear. Typically, the weight-average molecular weight of PEG is from about 100 Daltons to about 150,000 Daltons. Exemplary weight-average molecular weights for PEG include about 5,000 Daltons, about 10,000 Daltons, about 20,000 Daltons, about 40,000 Daltons, about 60,000 Daltons and about 80,000 Daltons. In certain embodiments, the molecular weight of PEG is 40,000 Daltons. Branched versions of PEG having a total molecular weight of any of the foregoing can also be used. In some embodiments, the PEG has two branches. In some embodiments, the PEG has four branches. In some embodiments, the PEG is a bis-PEG (NOF Corporation, DE-200MA), in which two Adnectins are conjugated (see, e.g., Example 1 and ATI-1341 of Table 5).

Conventional separation and purification techniques known in the art can be used to purify PEGylated anti-PD-L1 Adnectins, such as size exclusion (e.g., gel filtration) and ion exchange chromatography. Products may also be separated using SDS-PAGE. Products that may be separated include mono-, di-, tri-, poly- and un-PEGylated Adnectins, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

In some embodiments, the PEGylated anti-PD-L1 Adnectins will preferably retain at least about 25%, 50%, 60%, 70%, 80%, 85%, 90%, 95% or 100% of the biological activity associated with the unmodified anti-PD-L1 Adnectin. In some embodiments, biological activity refers to its ability to bind to PD-L1, as assessed by $K_D$, $k_{on}$, or $k_{off}$. In some embodiments, the PEGylated anti-PD-L1 Adnectin shows an increase in binding to PD-L1 relative to unPEGylated anti-PD-L1 Adnectin.

Immunoglobulin Fc Domain (and Fragments)

In certain embodiments, the anti-PD-L1 Adnectin is fused to an immunoglobulin Fc domain, or a fragment or variant thereof. As used herein, a "functional Fc region" is an Fc domain or fragment thereof which retains the ability to bind FcRn. In some embodiments, a functional Fc region binds to FcRn, bud does not possess effector function. The ability of the Fc region or fragment thereof to bind to FcRn can be determined by standard binding assays known in the art. In some embodiments, the Fc region or fragment thereof binds to FcRn and possesses at least one "effector function" of a native Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an anti-PD-L1 Adnectin) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

In an exemplary embodiment, the Fc domain is derived from an IgG1 subclass, however, other subclasses (e.g., IgG2, IgG3, and IgG4) may also be used. Shown below is the sequence of a human IgG1 immunoglobulin Fc domain:

(SEQ ID NO: 620)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

-continued

GFYPSDIAVEWESNGQPENNYKTTPPVLDSDGSFFLYSKLTVDKSRWQQG

NVFSCSVMHEALHNHYTQKSLSLSPGK

The core hinge sequence is underlined, and the CH2 and CH3 regions are in regular text. It should be understood that the C-terminal lysine is optional. Allotypes and mutants of this sequence may also be used. As is known in the art, mutants can be designed to modulate a variety of properties of the Fc, e.g., ADCC, CDC or half-life.

In certain embodiments, the Fc region used in the anti-PD-L1 Adnectin fusion comprises a CH1 region. In certain embodiments, the Fc region used in the anti-PD-L1 Adnectin fusion comprises CH2 and CH3 regions. In certain embodiments, the Fc region used in the anti-PD-L1 Adnectin fusion comprises a CH2, CH3, and hinge region (e.g., as shown in SEQ ID NO: 620).

In certain embodiments, the "hinge" region comprises the core hinge residues spanning positions 1-16 of SEQ ID NO: 620 (DKTHTCPPCPAPELLG; SEQ ID NO: 621) of the IgG1 Fc region. In certain embodiments, the anti-PD-L1 Adnectin-Fc fusion adopts a multimeric structure (e.g., dimer) owing, in part, to the cysteine residues at positions 6 and 9 of SEQ ID NO: 620 within the hinge region. Other suitable exemplary hinge regions are set forth in SEQ ID NOs: 622-626.

Adnectins

In certain embodiments the PK moiety is another Adnectin specific, for example, to a serum protein (e.g., human serum albumin), as described in US 2012/0094909, herein incorporated by reference in its entirety. Other PK moieties that may be used with the Adnectins described herein are described in Kontermann et al. (*Current Opinion in Biotechnology* 2011; 22:868-76), as discussed supra.

In some embodiments, an anti-PD-L1 Adnectin may be directly or indirectly linked for example, to an anti-HSA Adnectin via a polymeric linker. Polymeric linkers can be used to optimally vary the distance between each component of the fusion to create a protein fusion with one or more of the following characteristics: 1) reduced or increased steric hindrance of binding of one or more protein domains when binding to a protein of interest, 2) increased protein stability or solubility, 3) decreased protein aggregation, and 4) increased overall avidity or affinity of the protein.

In some embodiments, an anti-PD-L1 Adnectin is linked, for example, to an anti-HSA Adnectin, via a biocompatible polymer such as a polymeric sugar. The polymeric sugar can include an enzymatic cleavage site that is cleavable by an enzyme in the blood or target tissue. Such embodiments can be used to release an anti-PD-L1 Adnectin for better delivery or therapeutic properties or more efficient production.

IV. Nucleic Acid-Protein Fusion Technology

In one aspect, the invention provides an Adnectin comprising fibronectin type III domains that binds PD-L1. One way to rapidly make and test Fn3 domains with specific binding properties is the nucleic acid-protein fusion technology of Adnexus, a Bristol-Myers Squibb R&D Company. This disclosure utilizes the in vitro expression and tagging technology, termed 'PROfusion' which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018 and 6,818,418; Roberts et al., *Proc. Natl. Acad. Sci.*, 1997; 94:12297-12302; and Kurz et al., *Molecules*, 2000; 5:1259-64, all of which are herein incorporated by reference.

V. Vectors and Polynucleotides

Also included in the present disclosure are nucleic acid sequences encoding any of the proteins described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a protein described herein may be modified slightly in sequence and yet still encode its respective gene product. Certain exemplary nucleic acids encoding the anti-PD-L1 Adnectins and their fusions described herein include nucleic acids having the sequences set forth in SEQ ID NOs: 16-19, 31-34, 46-49, 61-64, 76-79, 92-95, and 108-111.

Also contemplated are nucleic acid sequences that are at least 50%, such as at least 55%, at least 60%, at least 65%, at least 70%, at least 75%, at least 80%, at least 85%, at least 90%, at least 95%, at least 96%, at least 97%, at least 98%, or at least 99% identical to SEQ ID NOs: 16-19, 31-34, 46-49, 61-64, 76-79, 92-95, and 108-111, and encode a protein that binds to PD-L1. In some embodiments, nucleotide substitutions are introduced so as not to alter the resulting translated amino acid sequence.

Nucleic acids encoding any of the various proteins or polypeptides described herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100(2):438-442 (Jan. 21, 2003); Sinclair et al., *Protein Expr. Purif.*, 26(I):96-105 (October 2002); Connell, N. D., *Curr. Opin. Biotechnol.*, 12(5):446-449 (October 2001); Makrides et al., *Microbiol. Rev.*, 60(3):512-538 (September 1996); and Sharp et al., *Yeast*, 7(7):657-678 (October 1991).

General techniques for nucleic acid manipulation are described in, for example, Sambrook et al., Molecular Cloning: A Laboratory Manual, 2nd Edition, Vols. 1-3, Cold Spring Harbor Laboratory Press (1989), or Ausubel, F. et al., Current Protocols in Molecular Biology, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding site, and sequences that control the termination of transcription and translation. The ability to replicate in a host, usually conferred by an origin of replication, and a selection gene to facilitate recognition of transformants is additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An exemplary N-terminal leader sequence for production of polypeptides in a mammalian system is: METDTLLLWVLLLWVPG-STG (SEQ ID NO: 583), which is removed by the host cell following expression.

For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders.

For yeast secretion the native signal sequence may be substituted by, e.g., a yeast invertase leader, a factor leader (including Saccharomyces and Kluyveromyces alpha-factor leaders), or acid phosphatase leader, the C. albicans glucoamylase leader, or the signal sequence described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein described herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein described herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding protein described herein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein described herein. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include, but are not limited to, a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, E. coli or

*Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (Bio/Technology, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides described herein would make expression in *E. coli* as the preferred method for expression. The protein is then purified from culture media or cell extracts.

VI. Protein Production

Also described herein are cell lines that express an anti-PD-L1 Adnectin or fusion polypeptide thereof. Creation and isolation of cell lines producing an anti-PD-L1 Adnectin can be accomplished using standard techniques known in the art, such as those described herein.

Host cells are transformed with the herein-described expression or cloning vectors for protein production and cultured in conventional nutrient media modified as appropriate for inducing promoters, selecting transformants, or amplifying the genes encoding the desired sequences.

Adnectins of the present invention can also be obtained in aglycosylated form by producing the Adnectins in, e.g., prokaryotic cells (e.g., *E. coli*). Notably, aglycosylated forms of the Adnectins described herein exhibit the same affinity, potency, and mechanism of action as glycosylated Adnectins when tested in vitro.

The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma)) are suitable for culturing the host cells. In addition, many of the media described in Ham et al., Meth. Enzymol., 58:44 (1979), Barites et al., Anal. Biochem., 102:255 (1980), U.S. Pat. Nos. 4,767,704, 4,657,866, 4,927,762, 4,560,655, 5,122,469, 6,048,728, 5,672,502, or U.S. Pat. No. RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins described herein can also be produced using cell-free translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins described herein can also be produced by chemical synthesis (e.g., by the methods described in Solid Phase Peptide Synthesis, 2nd Edition, The Pierce Chemical Co., Rockford, Ill. (1984)). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, or preferably at least 95% pure, and most preferably at least 98% pure. Regardless of the exact numerical value of the purity, the polypeptide is sufficiently pure for use as a pharmaceutical product.

High Throughput Protein Production (HTPP)

Selected binders cloned into the PET9d vector upstream of a $HIS_6$tag and are transformed into *E. coli* BL21 DE3 plysS cells and inoculated in 5 ml LB medium containing 50 μg/mL kanamycin in a 24-well format and grown at 37° C. overnight. Fresh 5 ml LB medium (50 μg/mL kanamycin) cultures are prepared for inducible expression by aspiration of 200 μl from the overnight culture and dispensing it into the appropriate well. The cultures are grown at 37° C. until $A_{600}$ 0.6-0.9. After induction with 1 mM isopropyl-β-thio-galactoside (IPTG), the culture is expressed for 6 hours at 30° C. and harvested by centrifugation for 10 minutes at 2750 g at 4° C.

Cell pellets (in 24-well format) are lysed by resuspension in 450 μL of Lysis buffer (50 mM $NaH_2PO_4$, 0.5 M NaCl, 1× Complete™ Protease Inhibitor Cocktail-EDTA free (Roche), 1 mM PMSF, 10 mM CHAPS, 40 mM imidazole, 1 mg/ml lysozyme, 30 μg/ml DNAse, 2 μg/ml aprotonin, pH 8.0) and shaken at room temperature for 1-3 hours. Lysates are cleared and re-racked into a 96-well format by transfer into a 96-well Whatman GF/D Unifilter fitted with a 96-well, 1.2 ml catch plate and filtered by positive pressure. The cleared lysates are transferred to a 96-well Nickel or Cobalt-Chelating Plate that had been equilibrated with equilibration buffer (50 mM $NaH_2PO_4$, 0.5 M NaCl, 40 mM imidazole, pH 8.0) and are incubated for 5 min. Unbound material is removed by positive pressure. The resin is washed twice with 0.3 ml/well with Wash buffer #1 (50 mM $NaH_2PO_4$, 0.5 M NaCl, 5 mM CHAPS, 40 mM imidazole, pH 8.0). Each wash is removed by positive pressure. Prior to elution, each well is washed with 50 μl Elution buffer (PBS+20 mM EDTA), incubated for 5 min, and this wash is discarded by positive pressure. Protein is eluted by applying an additional 100 μl of Elution buffer to each well. After a 30 minute incubation at room temperature, the plate(s) are centrifuged for 5 minutes at 200 g and eluted protein collected in 96-well catch plates containing 5 μl of 0.5 M $MgCl_2$ added to the bottom of elution catch plate prior to elution. Eluted protein is quantified using a total protein assay with wild-type $^{10}Fn3$ domain as the protein standard.

Midscale Expression and Purification of Insoluble Fibronectin-Based Scaffold Protein Binders For expression of insoluble clones, the clone(s), followed by the $HIS_6$tag, are cloned into a pET9d (EMD Bioscience, San Diego, Calif.) vector and are expressed in *E. coli* HMS174 cells. Twenty ml of an inoculum culture (generated from a single plated colony) is used to inoculate 1 liter of LB medium containing 50 µg/ml carbenicillin and 34 µg/ml chloramphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at >10,000 g at 4° C. Cell pellets are frozen at −80° C. The cell pellet is resuspended in 25 ml of lysis buffer (20 mM a $H2P0_4$, 0.5 M NaCl, 1× Complete Protease Inhibitor Cocktail-EDTA free (Roche), ImM PMSF, pH 7.4) using an ULTRA-TURRAX® homogenizer (IKA works) on ice. Cell lysis is achieved by high pressure homogenization (>18,000 psi) using a Model M-1 10S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodiumphosphate/500 mM NaCl, pH 7.4. The pellet is resolubilized in 6.0M guanidine hydrochloride in 20 mM sodium phosphate/500M NaCl pH 7.4 with sonication followed by incubation at 37 degrees for 1-2 hours. The resolubilized pellet is filtered to 0.45 µm and loaded onto a Histrap column equilibrated with the 20 mM sodium phosphate/500 M NaCl/6.0 M guanidine pH 7.4 buffer. After loading, the column is washed for an additional 25 CV with the same buffer. Bound protein is eluted with 50 mM Imidazole in 20 mM sodium phosphate/500 mM NaCl/6.0 M guan-HCl pH 7.4. The purified protein is refolded by dialysis against 50 mM sodium acetate/150 mM NaCl pH 4.5.

Midscale Expression and Purification of Soluble Fibronectin-Base Scaffold Protein Binders For expression of soluble clones, the clone(s), followed by the $HIS_6$tag, are cloned into a pET9d (EMD Bioscience, San Diego, Calif.) vector and expressed in *E. coli* HMS174 cells. Twenty ml of an inoculum culture (generated from a single plated colony) is used to inoculate 1 liter of LB medium containing 50 µg/ml carbenicillin and 34 µg/ml chloramphenicol. The culture is grown at 37° C. until $A_{600}$ 0.6-1.0. After induction with 1 mM isopropyl-β-thiogalactoside (IPTG), the culture is grown for 4 hours at 30° C. and harvested by centrifugation for 30 minutes at >10,000 g at 4° C. Cell pellets are frozen at −80° C. The cell pellet is resuspended in 25 ml of lysis buffer (20 mM $NaH_2PO_4$, 0.5 M NaCl, 1× Complete Protease Inhibitor Cocktail-EDTA free (Roche), ImM PMSF, pH 7.4) using an ULTRA-TURRAX® homogenizer (IKA works) on ice. Cell lysis is achieved by high pressure homogenization (>18,000 psi) using a Model M-1 10S MICROFLUIDIZER® (Microfluidics). The soluble fraction is separated by centrifugation for 30 minutes at 23,300 g at 4° C. The supernatant is clarified via 0.45 µm filter. The clarified lysate is loaded onto a Histrap column (GE) pre-equilibrated with the 20 mM sodium phosphate/500M NaCl pH 7.4. The column is then washed with 25 column volumes of the same buffer, followed by 20 column volumes of 20 mM sodium phosphate/ 500 M NaCl/25 mM Imidazole, pH 7.4 and then 35 column volumes of 20 mM sodium phosphate/500 M NaCl/40 mM Imidazole, pH 7.4. Protein is eluted with 15 column volumes of 20 mM sodium phosphate/500 M NaCl/500 mM Imidazole, pH 7.4, fractions are pooled based on absorbance at $A_2SO$ and dialyzed against 1×PBS, 50 mM Tris, 150 mM NaCl; pH 8.5 or 50 mM NaOAc; 150 mM NaCl; pH 4.5. Any precipitate is removed by filtering at 0.22 µm.

VII. Compositions

The present invention further provides compositions, such as pharmaceutical compositions and radiopharmaceutical compositions, comprising an anti-PD-L1 Adnectin or fusion proteins thereof described herein, wherein the composition is essentially endotoxin free, or at least contain no more than acceptable levels of endotoxins as determined by the appropriate regulatory agency (e.g., FDA).

Compositions of the present invention can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making compositions are found, for example, in "Remington: The Science and Practice of Pharmacy" (20th ed., ed. A. R. Gennaro A R., 2000, Lippincott Williams & Wilkins, Philadelphia, Pa.). Compositions for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate compositions (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the composition varies depending upon a number of factors, including the dosage of the drug to be administered, the route of administration, and the purpose of the composition (e.g., prophylactic, therapeutic, diagnostic).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC™ or polyethylene glycol (PEG).

The polypeptides of the present invention may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the proteins described herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT' (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. While encapsulated proteins described herein may remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Compositions of the present invention for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Compositions for oral use may also be provided as chewable tablets, or as hard gelatin capsules wherein the active ingredient is mixed with an inert solid diluent, or as soft gelatin capsules wherein the active ingredient is mixed with water or an oil medium.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

The compositions herein may also contain more than one active compound as necessary for the particular indication being treated, preferably those with complementary activities that do not adversely affect each other. Such molecules are suitably present in combination in amounts that are effective for the purpose intended.

VIII. Biophysical and Biochemical Characterization

Binding of an anti-PD-L1 Adnectin described herein to PD-L1 may be assessed in terms of equilibrium constants (e.g., dissociation, $K_D$) and in terms of kinetic constants (e.g., on-rate constant, $k_{on}$ and off-rate constant, $k_{off}$). An Adnectin will generally bind to a target molecule with a $K_D$ of less than 500 nM, 100 nM, 10 nM, 1 nM, 500 pM, 200 pM, or 100 pM, although higher $K_D$ values may be tolerated where the $k_{off}$ is sufficiently low or the $k_{on}$, is sufficiently high.

In Vitro Assays for Binding Affinity

An Anti-PD-L1 Adnectin that binds to and antagonizes PD-L1 can be identified using various in vitro assays. In certain embodiments, the assays are high-throughput assays that allow for screening multiple candidate Adnectins simultaneously.

Exemplary assays for determining the binding affinity of an anti-PD-L1 Adnectin includes, but is not limited to, solution phase methods such as the kinetic exclusion assay (KinExA) (Blake et al., *JBC* 1996; 271:27677-85; Drake et al., *Anal Biochem* 2004; 328:35-43), surface plasmon resonance (SPR) with the Biacore system (Uppsala, Sweden) (Welford et al., *Opt. Quant. Elect* 1991; 23:1; Morton and Myszka, *Methods in Enzymology* 1998; 295:268) and homogeneous time resolved fluorescence (HTRF) assays (Newton et al., *J Biomol Screen* 2008; 13:674-82; Patel et al., *Assay Drug Technol* 2008; 6:55-68).

In certain embodiments, biomolecular interactions can be monitored in real time with the Biacore system, which uses SPR to detect changes in the resonance angle of light at the surface of a thin gold film on a glass support due to changes in the refractive index of the surface up to 300 nm away. Biacore analysis generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding, $K_D$'s are calculated from SPR measurements as $k_{off}/k_{on}$.

In some embodiments, the anti-PD-L1 Adnectins described herein exhibit a $K_D$ in the SPR affinity assay described in Example 2 of 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less; 10 nM or less, 5 nM or less, or 1 nM or less.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays)) can be used to assess the binding affinities of the anti-PD-L1 Adnectins described herein.

IX. In Vivo Imaging with Anti-PD-L1 Adnectins

Imaging Agents

The anti-PD-L1 Adnectins described herein also are useful in a variety of diagnostic and imaging applications. In certain embodiments, an anti-PD-L1 Adnectin is labelled with a moiety that is detectable in vivo and such labelled Adnectins may be used as in vivo imaging agents, e.g., for whole body imaging. For example, in one embodiment, a method for detecting a PD-L1 positive tumor in a subject comprises administering to the subject an anti-PD-L1 Adnectin linked to a detectable label, and following an appropriate time, detecting the label in the subject.

An anti-PD-L1 Adnectin imaging agent may be used to diagnose a disorder or disease associated with increased levels of PD-L1, for example, a cancer in which a tumor selectively overexpresses PD-L1. In a similar manner, an anti-PD-L1 Adnectin can be used to monitor PD-L1 levels in a subject, e.g., a subject that is being treated to reduce PD-L1 levels and/or PD-L1 positive cells (e.g., tumor cells). The anti-PD-L1 Adnectins may be used with or without modification, and may be labeled by covalent or non-covalent attachment of a detectable moiety.

Detectable moieties that may be used include radioactive agents, such as: radioactive heavy metals such as iron chelates, radioactive chelates of gadolinium or manganese, positron emitters of oxygen, nitrogen, iron, carbon, or gallium, $^{18}$F, $^{60}$Cu, $^{61}$Cu, $^{62}$Cu, $^{64}$Cu, $^{124}$I, $^{86}$Y, $^{89}$Zr, $^{66}$Ga, $^{67}$Ga, $^{68}$Ga, $^{44}$Sc, $^{47}$Sc, $^{11}$C, $^{111}$In, $^{114m}$In, $^{114}$In, $^{125}$I, $^{124}$I, $^{131}$I, $^{123}$I, $^{131}$I, $^{123}$I, $^{32}$Cl, $^{33}$Cl, $^{34}$Cl, $^{74}$Br, $^{75}$Br, $^{76}$Br, $^{77}$Br, $^{78}$Br, $^{89}$Zr, $^{186}$Re, $^{188}$Re, $^{86}$Y, $^{90}$Y, $^{177}$Lu, $^{99}$Tc, $^{212}$Bi, $^{213}$Bi, $^{212}$Pb, $^{225}$Ac, or $^{153}$Sm.

In certain embodiments, the radioactive agent is conjugated to the Adnectin at one or more amino acid residues. In certain embodiments, one or more, such as two or more, three or more, four or more, or a greater number of radionuclides can be present in the labelled probe. In certain embodiments, the radionuclide is attached directly to the Adnectin by a chelating agent (e.g., see U.S. Pat. No. 8,808,665). In certain embodiments, the radionuclide is present in a prosthetic group conjugated to the Adnectin by a bifunctional chelator or conjugating (BFC) moiety. In certain embodiments, the radionuclide chelating agent and/or conjugating moiety is DFO, DOTA and its derivatives (CB-DO2A, 3p-C-DEPA, TCMC, Oxo-DO3A), DBCO, TE2A, CB-TE2A, CB-TE1A1P, CB-TE2P, MM-TE2A, DM-TE2A, diamsar and derivatives, NODASA, NODAGA, NOTA, NETA, TACN-TM, DTPA, 1B4M-DTPA, CHX-A"-DTPA, TRAP (PRP9), NOPO, AAZTA and derivatives (DATA), H$_2$dedpa, H$_4$octapa, H$_2$azapa, H$_5$decapa, H$_6$phospa, HBED, SHBED, BPCA, CP256, PCTA, HEHA, PEPA, EDTA, TETA, and TRITA based chelating agents, and close analogs and derivatives thereof.

In certain embodiments, the radionuclide chelating or conjugating (BFC) moiety is maleamide-NODAGA or maleamide-DBCO, which can be attached covalently to a polypeptide via cysteine residues near the C-terminus of the polypeptide. In certain embodiments, an anti-PD-L1 Adnectin is modified at its C-terminus by the addition of a cysteine. For example, PxCy may be linked C-terminal to the amino acid residues NYRT, wherein P is proline, C is cysteine, and x and y are integers that are at least 1. Exemplary anti-PD-L1 Adnectins having the amino acid residues PC at their C-terminus are set forth in the Examples. Maleimide-NODAGA or maleimide-DBCO can be reacted with the cysteine, to yield Adnectin-NODAGA or Adnectin-DBCO, respectively.

In certain embodiments, the radionuclide chelating agent is DFO, which can be attached, e.g., at random surface lysines.

In certain embodiments, the chelator for $^{64}$Cu is DOTA, NOTA, EDTA, Df, DTPA, or TETA. Suitable combinations of chelating agents and radionuclides are extensively reviewed in Price et al., *Chem Soc Rev* 2014; 43:260-90.

In certain embodiments, an anti-PD-L1 Adnectin is labelled with the PET tracer $^{18}$F. $^{18}$F is an attractive PET radionuclide with a 1.8 hour radioactive half life, which provides a same day imaging tool, where the PET radionuclide better matches the Adnectin's biological half-life, resulting in excellent images with less radiation exposure to the patient. A PD-L1 Adnectin may be labelled with a prosthetic group, such as [$^{18}$F]-3-(2-(2-(2-(2-azidoethoxy)ethoxy)ethoxy)ethoxy)-2-fluoropyridine ([$^{18}$F]-FFPEGA), as further described in the Examples. As further shown in the Examples, an $^{18}$F-labelled anti-PD-L1 Adnectin specifically and efficiently labelled human PD-L1 positive tumors in mice and PD-L1 positive tumors in cynomolgus monkeys. Specific details on the labelling method is provided below and in the Examples.

In certain embodiments, a PD-L1 imaging agent is an anti-PD-L1 Adnectin that is labelled with $^{64}$Cu, e.g., as described in the Examples. $^{64}$Cu may be linked to an Adnectin with a chelating agent, such as NODAGA. As further shown in the Examples, a $^{64}$Cu-labelled anti-PD-L1 Adnectin specifically and efficiently labelled human PD-L1 positive tumors in mice and PD-L1 positive tumors in cyno.

Other art-recognized methods for labelling polypeptides with radionuclides such as $^{64}$Cu and $^{18}$F for synthesizing the anti-PD-L1 Adnectin-based imaging agents described herein may also be used. See, e.g., US2014/0271467; Gill et al., *Nature Protocols* 2011; 6:1718-25; Berndt et al. *Nuclear Medicine and Biology* 2007; 34:5-15, Inkster et al., *Bioorganic & Medicinal Chemistry Letters* 2013; 23:3920-6, the contents of which are herein incorporated by reference in their entirety.

In certain embodiments, a PD-L1 imaging agent comprises a PEG molecule (e.g., 5 KDa PEG, 6 KDa PEG, 7 KDa PEG, 8 KDa PEG, 9 KDa PEG, or 10 KDa PEG) to increase the blood PK of the imaging agent by small increments to enhance the imaging contrast or increase avidity of the anti-PD-L1 Adnectin based imaging agent.

Administration and Imaging

In certain embodiments, the labeled anti-PD-L1 Adnectins can be used to image PD-L1-positive cells or tissues, e.g., PD-L1 expressing tumors. For example, the labeled anti-PD-L1 Adnectin is administered to a subject in an amount sufficient to uptake the labeled Adnectin into the tissue of interest (e.g., the PD-L1-expressing tumor). The subject is then imaged using an imaging system such as PET for an amount of time appropriate for the particular radionuclide being used. The labeled anti-PD-L1 Adnectin-bound. PD-L1-expressing cells or tissues, e.g., PD-L1-expressing tumors, are then detected by the imaging system.

PET imaging with a PD-L1 imaging agent may be used to qualitatively or quantitatively detect PD-L1. A PD-L1 imaging agent may be used as a biomarker, and the presence or absence of a PD-L1 positive signal in a subject may be indicative that, e.g., the subject would be responsive to a given therapy, e.g., a cancer therapy, or that the subject is responding or not to a therapy.

In certain embodiments, the progression or regression of disease (e.g., tumor) can be imaged as a function of time or treatment. For instance, the size of the tumor can be monitored in a subject undergoing cancer therapy (e.g., chemotherapy, radiotherapy) and the extent of regression of the tumor can be monitored in real-time based on detection of the labeled anti-PD-L1 Adnectin.

The amount effective to result in uptake of the imaging agent (e.g., $^{18}$F-Adnectin imaging agent, $^{64}$Cu-Adnectin imaging agent) into the cells or tissue of interest (e.g., tumors) may depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; and other factors.

In certain embodiments, imaging of tissues expressing PD-L1 is effected before, during, and after administration of the labeled anti-PD-L1 Adnectin.

In certain embodiments, the subject is a mammal, for example, a human, dog, cat, ape, monkey, rat, or mouse.

In certain embodiments, the anti-PD-L1 Adnectins described herein are useful for PET imaging of lungs, heart, kidneys, liver, and skin, and other organs, or tumors associated with these organs which express PD-L1.

In certain embodiments, the anti-PD-L1 imaging agents provide a contrast of at least 50%, 75%, 2, 3, 4, 5 or more. The Examples show that all anti-PD-L1 Adnectins that were used provided a PET contrast of 2 or more, and that the affinity of the Adnectins was not important.

When used for imaging (e.g., PET) with short half-life radionuclides (e.g., $^{18}$F), the radiolabeled anti-PD-L1 Adnectins are preferably administered intravenously. Other routes of administration are also suitable and depend on the half-life of the radionuclides used.

In certain embodiments, the anti-PD-L1 imaging agents described herein are used to detect PD-L1 positive cells in a subject by administering to the subject an anti-PD-L1 imaging agent disclosed herein, and detecting the imaging agent, the detected imaging agent defining the location of the PD-L1 positive cells in the subject. In certain embodiments, the imaging agent is detected by positron emission tomography.

In certain embodiments, the anti-PD-L1 imaging agents described herein are used to detect PD-L1 expressing tumors in a subject by administering to the subject an anti-PD-L1 imaging agent disclosed herein, and detecting the imaging agent, the detected imaging agent defining the location of the tumor in the subject. In certain embodiments, the imaging agent is detected by positron emission tomography.

In certain embodiments, an image of an anti-PD-L1 imaging agent described herein is obtained by administering the imaging agent to a subject and imaging in vivo the distribution of the imaging agent by positron emission tomography.

Disclosed herein are methods of obtaining a quantitative image of tissues or cells expressing PD-L1, the method comprising contacting the cells or tissue with an anti-PD-L1 imaging agent described herein and detecting or quantifying the tissue expressing PD-L1 using positron emission tomography.

Also disclosed herein are methods of detecting a PD-L1-expressing tumor comprising administering an imaging-effective amount of an anti-PD-L1 imaging agent described herein to a subject having a PD-L1-expressing tumor, and detecting the radioactive emissions of said imaging agent in the tumor using positron emission tomography, wherein the radioactive emissions are detected in the tumor.

Also disclosed herein are methods of diagnosing the presence of a PD-L1-expressing tumor in a subject, the method comprising
(a) administering to a subject in need thereof an anti-PD-L1 imaging agent described herein; and
(b) obtaining an radio-image of at least a portion of the subject to detect the presence or absence of the imaging agent;
wherein the presence and location of the imaging agent above background is indicative of the presence and location of the disease.

Also disclosed herein are methods of monitoring the progress of an anti-tumor therapy against PD-L1-expressing tumors in a subject, the method comprising
(a) administering to a subject in need thereof an anti-PD-L1 imaging agent described herein at a first time point and obtaining an image of at least a portion of the subject to determine the size of the tumor;
(b) administering an anti-tumor therapy to the subject;
(c) administering to the subject the imaging agent at one or more subsequent time points and obtaining an image of at least a portion of the subject at each time point;
wherein the dimension and location of the tumor at each time point is indicative of the progress of the disease.

PET Imaging

Typically, for PET imaging purposes it is desirable to provide the recipient with a dosage of Adnectin that is in the range of from about 1 mg to 200 mg as a single intravenous infusion, although a lower or higher dosage also may be administered as circumstances dictate. Typically, it is desirable to provide the recipient with a dosage that is in the range of from about 1 mg to 10 mg per square meter of body surface area of the protein or peptide for the typical adult, although a lower or higher dosage also may be administered as circumstances dictate. Examples of dosages proteins or peptides that may be administered to a human subject for imaging purposes are about 1 to 200 mg, about 1 to 70 mg, about 1 to 20 mg, and about 1 to 10 mg, although higher or lower doses may be used.

In certain embodiments, administration occurs in an amount of radiolabeled Adnectin of between about 0.005 µg/kg of body weight to about 50 µg/kg of body weight per day, usually between 0.02 µg/kg of body weight to about 3 µg/kg of body weight. The mass associated with a PET tracer is in the form of the natural isotope (e.g., $^{19}$F for a $^{18}$F PET tracer). A particular analytical dosage for the instant composition includes from about 0.5 µg to about 100 µg of a radiolabeled protein. The dosage will usually be from about 1 µg to about 50 µg of a radiolabeled protein.

Dosage regimens are adjusted to provide the optimum detectable amount for obtaining a clear image of the tissue or cells which uptake the radiolabeled Adnectin. It is especially advantageous to formulate parenteral compositions in dosage unit form for ease of administration and uniformity of dosage. Dosage unit form as used herein refers to physically discrete units suited as unitary dosages for the subjects to which the radiolabeled Adnectin is to be administered. The specification for the dosage unit forms described herein are dictated by and directly dependent on (a) the unique characteristics of the targeting portion of the radiolabeled Adnectin; (b) the tissue or cells to be targeted; (c) the limitations inherent in the imaging technology used.

For administration of the radiolabeled Adnectin, the dosage used will depend upon the disease type, targeting compound used, the age, physical condition, and gender of the subject, the degree of the disease, the site to be examined, and others. In particular, sufficient care has to be taken about exposure doses to a subject. Preferably, a saturating dose of radiolabel (e.g., $^{18}$F or $^{64}$Cu) is administered to the patient. For example, the amount of radioactivity of $^{18}$F-labeled Adnectin usually ranges from 3.7 megabecquerels to 3.7 gigabecquerels, and preferably from 18 megabecquerels to 740 megabecquerels. Alternatively, the dosage may be measured by millicuries, for example. In some embodiments, the amount of $^{18}$F imaging administered for imaging studies is 5 to 10 mCi. In some embodiments, an effective amount will be the amount of compound sufficient to produce emissions in the range of from about 1-5 mCi.

Actual dosage levels of the active ingredients in the pharmaceutical compositions described herein may be varied so as to obtain an amount of the active ingredient which is effective to achieve the desired uptake of the radiolabeled Adnectin in the cells or tissues of a particular patient, composition, and mode of administration, without being toxic to the patient. It will be understood, however, that the total daily usage of the radiolabeled Adnectin of the present disclosure will be decided by the attending physician or other attending professional within the scope of sound medical judgment. The specific effective dose level for any particular subject will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; other drugs, compounds and/or materials used in combination with the particular compositions employed, the age, sex, weight, condition, general health and prior medical history of the patient being treated, and like factors well known in the medical arts. In certain embodiments, the amount of radiolabeled Adnectin administered into a human subject required for imaging will be determined by the prescribing physician with the dosage generally varying according to the quantity of emission from the radionuclide.

A composition described herein can be administered via one or more routes of administration using one or more of a variety of methods known in the art. As will be appreciated by the skilled artisan, the route and/or mode of administration will vary depending upon the desired results. Preferred routes of administration for radiolabeled Adnectin described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a radiolabeled Adnectin described herein can be administered via a non-parenteral route, such as a topical, epidermal or mucosal route of administration, for example, intranasally, orally, vaginally, rectally, sublingually or topically.

In certain embodiments, the radiolabeled Adnectin described herein can be formulated to ensure proper distribution in vivo. For example, the blood-brain barrier (BBB) excludes many highly hydrophilic compounds. Agents may cross the BBB by formulating them, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994).

Exemplary PET Procedure

The following illustrative procedure may be utilized when performing PET imaging studies on patients in the clinic. A 20 G two-inch venous catheter is inserted into the contralateral ulnar vein for radiotracer administration. Administration of the PET tracer is often timed to coincide with time of maximum (T max) or minimum (T min) of the anti-PD-L1 Adnectin concentration in the blood.

The patient is positioned in the PET camera and a tracer dose of the PET tracer of radiolabeled anti-PD-L1 Adnectin such as [$^{18}$F]-ADX_5417_E01 (<20 mCi) is administered via i.v. catheter. Either arterial or venous blood samples are taken at 15 appropriate time intervals throughout the PET scan in order to analyze and quantitate the fraction of unmetabolized PET tracer of [$^{18}$F]-ADX_5417_E01 in plasma. Images are acquired for up to 120 min. Within ten minutes of the injection of radiotracer and at the end of the imaging session, 1 ml blood samples are obtained for determining the plasma concentration of any unlabeled anti-PD-L1 Adnectin which may have been administered before the PET tracer.

Tomographic images are obtained through image reconstruction. For determining the distribution of radiotracer, regions of interest (ROIs) are drawn on the reconstructed image including, but not limited to, the lungs, liver, heart, kidney, skin, or other organs and tissue (e.g., cancer tissue). Radiotracer uptakes over time in these regions are used to generate time activity curves (TAC) obtained in the absence of any intervention or in the presence of the unlabeled anti-PD-L1 Adnectin at the various dosing paradigms examined. Data are expressed as radioactivity per unit time per unit volume (μci/cc/mCi injected dose).

X. Detection of PD-L1 with Anti-PD-L1 Adnectins

In addition to detecting PD-L1 in vivo, anti-PDL1 Adnectins, such as those described herein, may be used for detecting a target molecule in a sample. A method may comprise contacting the sample with an anti-PD-L1 Adnectins described herein, wherein said contacting is carried out under conditions that allow anti-PD-L1 Adnectin-target complex formation; and detecting said complex, thereby detecting said target in said sample. Detection may be carried out using any art-recognized technique, such as, e.g., radiography, immunological assay, fluorescence detection, mass spectroscopy, or surface plasmon resonance. The sample may be from a human or other mammal. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, biotin, luminescent markers, phosphorescent markers and the like, as well as enzyme labels that convert a given substrate to a detectable marker, and polynucleotide tags that are revealed following amplification such as by polymerase chain reaction. A biotinylated antibody would then be detectable by avidin or streptavidin binding. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium (III) and Europium (III). Other labels include those set forth above in the imaging section. The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In certain embodiments, conjugation methods result in linkages which are substantially (or nearly) non-immunogenic, e.g., peptide- (i.e. amide-), sulfide-, (sterically hindered), disulfide-, hydrazone-, and ether linkages. These linkages are nearly non-immunogenic and show reasonable stability within serum (see e.g. Senter, P. D., Curr. Opin. Chem. Biol. 13 (2009) 235-244; WO 2009/059278; WO 95/17886).

Depending on the biochemical nature of the moiety and Adnectin, different conjugation strategies can be employed. In case the moiety is naturally occurring or recombinant polypeptide of between 50 to 500 amino acids, there are standard procedures in textbooks describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the Adnectin or the moiety is used. Alternatively, coupling to the C-terminal end of the Adnectin is performed. C-terminal modification of a protein can be performed as described in, e.g., Sunbul, M. and Yin, J., Org. Biomol. Chem. 7 (2009) 3361-3371). When the moiety is a peptide or polypeptide, the Adnectin and moiety can be fused by standard genetic fusion, optionally with a linker disclosed herein.

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136. Protease-catalyzed formation of C—N bonds is described at Bordusa, F., Highlights in Bioorganic Chemistry (2004) 389-403.

Site specific reaction and covalent coupling can also be achieved by the selective reaction of terminal amino acids with appropriate modifying reagents. The reactivity of an N-terminal cysteine with benzonitrils (see Ren, H. et al., Angew. Chem. Int. Ed. Engl. 48 (2009) 9658-9662) can be used to achieve a site-specific covalent coupling. Native chemical ligation can also rely on C-terminal cysteine residues (Taylor, E. Vogel; Imperiali, B, Nucleic Acids and Molecular Biology (2009), 22 (Protein Engineering), 65-96). EP 1 074 563 describes a conjugation method which is based on the faster reaction of a cysteine within a stretch of negatively charged amino acids than a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see e.g. de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide the conjugate with 1:1 stoichiometry may be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

XI. Synthesis of $^{18}$F-Labeled Anti-PD-L1 Adnectins $^{18}$F-labeled anti-PD-L1 Adnectins may be synthesized by first preparing an $^{18}$F radiolabeled prosthetic group, linking an Adnectin to a bifunctional chelating agent, and then combining these two reagents (see, e.g., FIG. 9).

$^{18}$F Radiolabeled Prosthetic Groups

In one aspect, provided herein is an $^{18}$F-radiolabeled compound containing a prosthetic group for use in a bioorthogonal reaction involving 1,3-dipolar cycloaddition between an azide and a cyclooctyne which proceeds selectively under water tolerant conditions. The $^{18}$F-radiolabeled prosthetic groups disclosed herein are soluble in 100% aqueous, and there is no need for an organic phase to link the prosthetic groups to the anti-PD-L1 Adnectins disclosed herein. This feature is particularly advantageous as there is no need for an organic phase to link the prosthetic group to the anti-PD-L1 Adnectins, which cannot withstand even small amounts of organic solvents, given degradation and aggregation issues.

Additionally, unlike aliphatic prosthetic groups, the $^{18}$F fluorination reaction can be monitored with UV, and the $^{18}$F-radiolabeled prosthetic groups described herein are not volatile. Moreover, the $^{18}$F-radiolabeled prosthetic groups can be incorporated into the anti-PD-L1 Adnectins using a copper free click chemistry, e.g., as described in the Examples, thus avoiding the stability issues observed in some biologics when copper mediated click chemistry is used.

In one aspect, provided herein is a PEGylated $^{18}$F-pyridine covalently bound to an azide with the following structure,

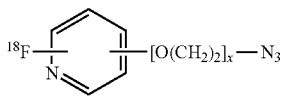

wherein x is an integer from 1 to 8. In certain embodiments, x is an integer from 2 to 6. In some embodiments x is an integer from 3 to 5. In certain embodiments, x is 4. In certain embodiments, $^{18}$F is attached to the pyridine ortho to the N atom. In certain embodiments, the $[O(CH_2)_2]_x$ moiety is present in the 1-3 configuration relative to the nitrogen on the pyridine ring. In certain embodiments, the $[O(CH_2)_2]_x$ moiety is present in the 1-2 configuration relative to the nitrogen on the pyridine ring. In certain embodiments, the $[O(CH_2)_2]_x$ moiety is present in the 1-4 configuration relative to the nitrogen on the pyridine ring.

In certain embodiments, the $^{18}$F-radiolabeled compound has the structure

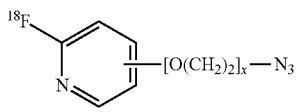

wherein x is an integer from 1 to 8. In certain embodiments, x is an integer from 2 to 6. In some embodiments x is an integer from 3 to 5. In certain embodiments, x is 4.

In certain embodiments, the $^{18}$F-radiolabeled compound has the structure

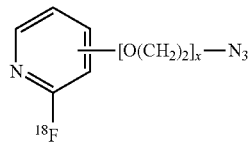

wherein x is an integer from 1 to 8. In certain embodiments, x is an integer from 2 to 6. In certain embodiments x is an integer from 3 to 5. In certain embodiments, x is 4.

In certain embodiments, the $^{18}$F-radiolabeled compound is [$^{18}$F]-3-(2-(2-(2-(2-azidoethoxy)ethoxy)ethoxy)ethoxy)-2-fluoropyridine ($^{18}$F-FPPEGA) and has the structure

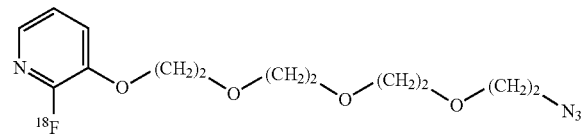

In certain embodiments, the $^{18}$F-radiolabeled prosthetic group may contain additional groups on the pyridine ring which do not interfere with the fluorination reaction. In certain embodiments, additions to the pyridine ring include $C_{1-6}$ alkyl groups, for example methyl, ethyl and propyl.

In certain embodiments, the $^{18}$F-radiolabeled prosthetic group is a fused ring system with the following structure:

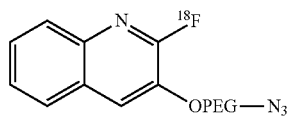

wherein "OPEG" is $[O(CH_2)_2]_x$, and x is an integer from 1 to 8. In certain embodiments, x is an integer from 2 to 6. In certain embodiments x is an integer from 3 to 5. In certain embodiments, x is 4.

The $^{18}$F-radiolabeled prosthetic groups described herein may be produced using chemical reactions described in the Examples herein.

Also provided herein is a method of preparing a PEGylated $^{18}$F-pyridine covalently bound to an azide with the following structure,

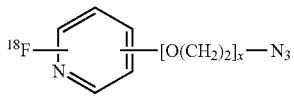

wherein x is an integer from 1 to 8, the method comprising the steps of (a) providing a solution of a compound a with the following structure:

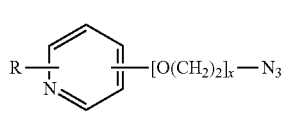

wherein x is an integer from 1 to 8, and R is $NO_2$, Br, F or

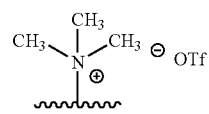

and is ortho to the N atom of the pyridine ring;

(b) providing a mixture of $^{18}$F in $^{18}$O water, 4,7,13,16,21,24-hexaoxa-1,10-diazabicyclo[8.8.8]hexacosane and a weak base;

c) drying the mixture from step b) to form a solid; and d) reacting the solution from step a) with the solid from step c) to form the $^{18}$F-labeled compound.

In certain embodiments, the method produces a $^{18}$F-pyridine prosthetic group with the following structure b according to the Scheme I shown below:

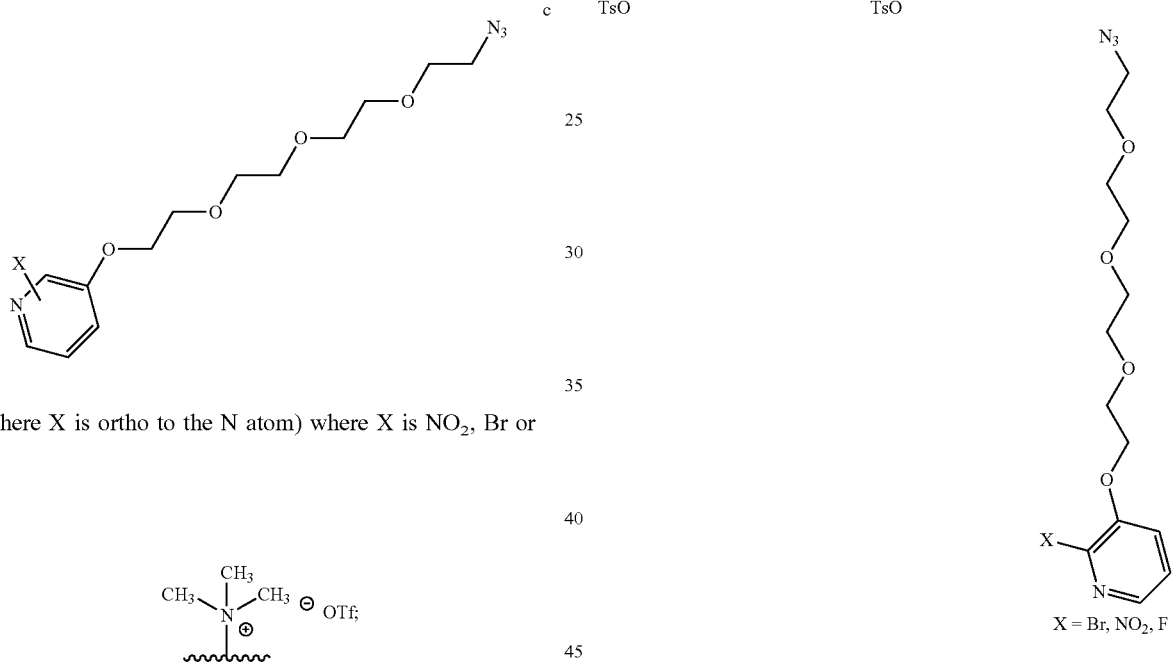

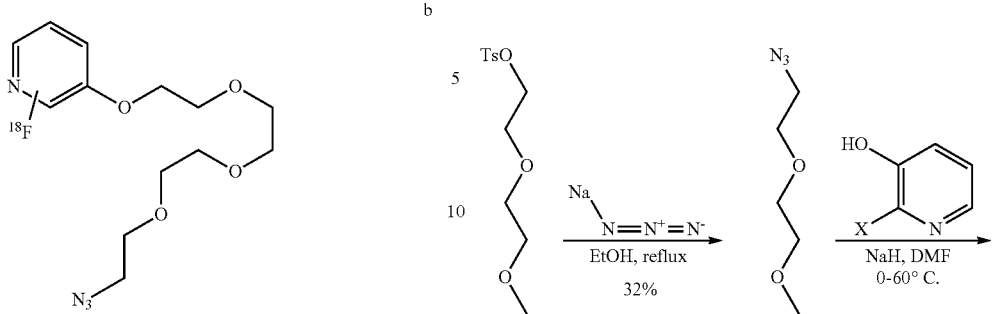

(where $^{18}F$ is ortho to the N atom), and includes the steps of a) providing a solution of the compound of the structure

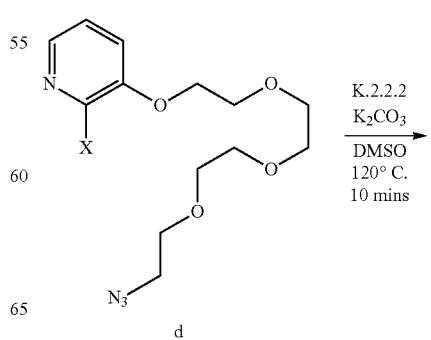

(where X is ortho to the N atom) where X is NO$_2$, Br or

b) providing a mixture of $^{18}F$ in $^{18}O$ water, 4,7,13,16,21,24-hexaoxa-1,10-diazabicyclo[8.8.8]hexacosane and weak base, such as K$_2$CO$_3$;

c) drying the mixture from step b) to form a solid; and d) reacting the solution from step a) with the solid from step c) to form the $^{18}F$-labeled compound.

In certain embodiments, the method further comprises the step of producing a compound with the following structure a R—[pyridine]—[O(CH$_2$)$_2$]$_x$—N$_3$ In certain embodiments, the method comprises producing $^{18}F$-pyridine prosthetic group is [$^{18}F$]-3-(2-(2-(2-(2-azido-ethoxy)ethoxy)ethoxy)ethoxy)-2-fluoropyridine ($^{18}F$-FPPEGA), e, from d according to the following reaction conditions:

-continued

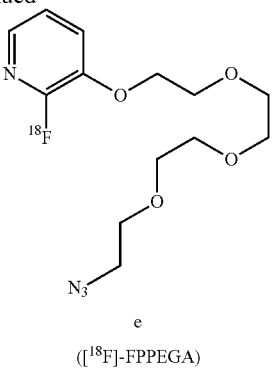

e
([$^{18}$F]-FPPEGA)

$^{18}$F-Radiolabeled PD-L1 Adnectins

In some aspects, provided herein are $^{18}$F-radiolabeled probes or agents with the following structure,

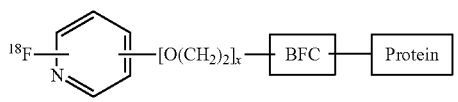

wherein the Protein is a PD-L1 Adnectin and x is an integer from 1 to 8. In certain embodiments, x is an integer from 2 to 6. In certain embodiments x is an integer from 3 to 5. In some embodiments, x is 4.

BFC

Bifunctional chelating or conjugating (BFC) moieties which can be used in the $^{18}$F-radiolabeled compositions disclosed herein are commercially available (e.g., Sigma Aldrich; Click Chemistry Tools), or may be synthesized according to well-known chemical reactions.

In certain embodiments, the BFC is selected from cyclooctyne based chelating agents (e.g., DBCO, DIBO), DFO, DOTA and its derivatives (CB-DO2A, 3p-C-DEPA, TCMC, Oxo-DO3A), TE2A, CB-TE2A, CB-TE1A1P, CB-TE2P, MM-TE2A, DM-TE2A, diamsar and derivatives, NODASA, NODAGA, NOTA, NETA, TACN-TM, DTPA, 1B4M-DTPA, CHX-A"-DTPA, TRAP (PRP9), NOPO, AAZTA and derivatives (DATA), H$_2$dedpa, H$_4$octapa, H$_2$azapa, H$_5$decapa, H$_6$phospa, HBED, SHBED, BPCA, CP256, PCTA, HEHA, PEPA, EDTA, TETA, and TRITA based chelating agents, and close analogs and derivatives thereof. Suitable combinations of chelating agents and radionuclides are extensively described in Price et al., *Chem Soc Rev* 2014; 43:260-90.

In certain embodiments, the BFC is a cyclooctyne comprising a reactive group that forms a covalent bond with an amine, carboxyl, carbonyl or thiol functional group on the targeting protein or peptide. Reactive groups on the cyclooctyne include esters, acids, hydroxyl groups, aminooxy groups, malaiemides, α-halogenketones and α-halogenacetamides.

In certain embodiments, the BFC is a cyclooctyne is dibenzocyclooctyne (DIBO), biarylazacyclooctynone (BARAC), dimethoxyazacyclooctyne (DIMAC) and dibenzocyclooctyne (DBCO). In certain embodiments, the cyclootyne is DBCO.

In certain embodiments, the cyclooctyne comprises a hydrophilic polyethylene glycol (PEG)$_y$ spacer arm, wherein y is an integer from 1 to 8. In certain embodiments, y is an integer from 2 to 6. In certain embodiments, y is 4 or 5.

In certain embodiments, the BFC is DBCO-PEG4-NHS-Ester or DBCO-Sulfo-NHS-Ester which react specifically and efficiently with a primary amine (e.g., side chain of lysine residues or aminosilane-coated surfaces). In certain embodiments, the BFC is DBCO-PEG4-Acid with terminal carboxylic acid (—COOH) that can be reacted with primary or secondary amine groups in the presence activators (e.g. EDC) forming a stable amide bond. In certain embodiments, the BFC is DBCO-PEG4-Amine which reacts with carboxyl groups in the presence of activators (e.g. EDC, or DCC) or with activated esters (e.g. NHS esters) forming stable amide bonds.

In certain embodiments, the BFC is DBCO-PEG4-Maleimide which reacts with sulfhydryl groups on cysteine residues, e.g., at or near the C-terminus of the polypeptide.

In certain embodiments, the polypeptide is modified at its C-terminus by the addition of a cysteine. For example, P$_m$C$_n$ may be linked to the C-terminal amino acid residue of the polypeptide, wherein P is proline, C is cysteine, m is an integer that at least 0 and n is an integer that is at least 1. Methods for making such modifications are well-known in the art.

In certain embodiments, the $^{18}$F-radiolabeled probe or agent has the following structure a,

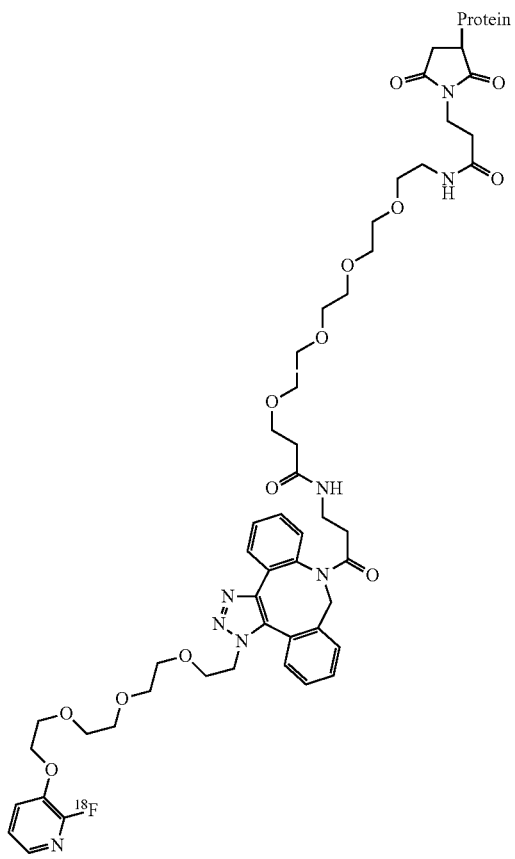

wherein the BFC is conjugated to the protein (e.g., an anti-PD-L1 Adnectin) at a cysteine residue.

The $^{18}$F-radiolabeled targeting agents described herein are produced using bioorthogonal, metal free click chemistry in medium suitable for direct use in vivo (e.g., saline) according to the procedures described herein.

XII. Therapeutic Methods

Immunotherapy of Cancer Patients Using an Anti-PD-L1 Adnectin

PD-L1 is the primary PD-1 ligand up-regulated within solid tumors, where it can inhibit cytokine production and the cytolytic activity of PD-1-positive, tumor-infiltrating $CD4^+$ and $CD8^+$ T-cells, respectively (Dong et al, 2002; Hino et al, 2010; Taube et al, 2012). These properties make PD-L1 a promising target for cancer immunotherapy. For example, clinical trials with anti-PD-L1 immunotherapy, as described in WO2013/173223, which is herein incorporated by reference in its entirety, demonstrate that mAb blockade of the immune inhibitory ligand, PD-L1, produces both durable tumor regression and prolonged (>24 weeks) disease stabilization in patients with metastatic NSCLC, MEL, RCC and OV, including those with extensive prior therapy. Accordingly, targeting PD-L1, e.g., using the PD-L1 Adnectins, are suitable for eliciting an anti-tumor response.

Based on the clinical data disclosed in WO2013/173223, described herein are methods for immunotherapy of a subject afflicted with cancer, which method comprises administering to the subject a composition comprising a therapeutically effective amount of a Adnectin described herein. The disclosure also provides a method of inhibiting growth of tumor cells in a subject, comprising administering to the subject a PD-L1 Adnectin described herein. In certain embodiments, the subject is a human.

Detailed methods for treating a subject with cancer by targeting PD-L1 are described in WO2013/173223.

In certain embodiments, the PD-L1 Adnectins described herein, which are suitable for use in the methods described herein, have one or more of the following features: high affinity for human PD-L1, increases T-cell proliferation, increases IL-2 secretion, e.g., from T cells, increases interferon-γ production, e.g., from T cells, inhibits the binding of PD-L1 to PD-1, and reverses the suppressive effect of T regulatory cells on T cell effector cells and/or dendritic cells.

Adnectin Drug Conjugates (Adnectin-DCs)

Adnectins described herein may be conjugated through a cysteine, e.g., a C-terminal cysteine, to a therapeutic agent to form an immunoconjugate such as an Adnectin-drug conjugate ("Adnectin-DC").

In an Adnectin-DC, the Adnectin is conjugated to a drug, with the Adnectin-DC functioning as a targeting agent for directing the Adnectin to a target cell expressing its antigen, such as a cancer cell. Preferably, the antigen is a tumor associated antigen, i.e., one that is uniquely expressed or over-expressed by the cancer cell. Once there, the drug is released, either inside the target cell or in its vicinity, to act as a therapeutic agent. For a review on the mechanism of action and use of drug conjugates as used with antibodies, e.g., in cancer therapy, see Schrama et al., Nature Rev. Drug Disc. 2006, 5, 147.

Suitable therapeutic agents for use in drug conjugates include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In an Adnectin-DC, the Adnectin and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO: 169), Ala-Asn-Val, Val-Leu-Lys, Ala-Ala-Asn, Cit-Cit, Val-Lys, Lys, Cit, Ser, or Glu. The Adnectin-DCs can be prepared according to methods similar to those described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference. A linker can itself be linked, e.g., covalently linked, e.g., using maleimide chemistry, to a cysteine of the polypeptide, e.g., a cysteine at or near the C-terminus of the polypeptide, e.g., a cysteine of a $P_mC_n$ moiety that is attached to the C-terminal amino acid residue of the polypeptide, wherein m is an integer that is at least 0 (e.g., 0, 1 or 2) and n is an integer that is at least 1 (e.g., 1 or 2). For example, a linker can be covalently linked to a cysteine, such as a cysteine in the C-terminal region of an Adnectin, e.g., a C-terminal cysteine in PC of an Adnectin-DC-$P_mC_n$, wherein m and n are independently an integer that is at least one. For example, a linker can be linked to an Adnectin-DC-PmCn, wherein P is a proline, C is a cysteine, and m and n are integers that are at least 1, e.g., 1-3. In certain embodiments, m is zero, i.e., the cysteine is not preceded by a proline. Ligation to a cysteine can be performed as known in the art using maleimide chemistry (e.g., Taylor, E. Vogel; Imperiali, B, Nucleic Acids and Molecular Biology (2009), 22 (Protein Engineering), 65-96). For attaching a linker to a cysteine on an Adnectin, the linker may, e.g. comprise a maleinimido moiety, which moiety then reacts with the cysteine to form a covalent bond. In certain embodiments, the amino acids surrounding the cysteine are optimized to facilitate the chemical reaction. For example, a cysteine may be surrounded by negatively charged amino acid for a faster reaction relative to a cysteine that is surrounded by a stretch of positively charged amino acids (EP 1 074 563).

For cancer treatment, the drug preferably is a cytotoxic drug that causes death of the targeted cancer cell. Cytotoxic drugs that can be used in Adnectin-DCs include the following types of compounds and their analogs and derivatives:

(a) enediynes such as calicheamicin (see, e.g., Lee et al., J. Am. Chem. Soc. 1987, 109, 3464 and 3466) and uncialamycin (see, e.g., Davies et al., WO 2007/038868 A2 (2007) and Chowdari et al., U.S. Pat. No. 8,709,431 B2 (2012));

(b) tubulysins (see, e.g., Domling et al., U.S. Pat. No. 7,778,814 B2 (2010); Cheng et al., U.S. Pat. No. 8,394,922 B2 (2013); and Cong et al., US 2014/0227295 A1;

(c) CC-1065 and duocarmycin (see, e.g., Boger, U.S. Pat. No. 6,5458,530 B1 (2003); Sufi et al., U.S. Pat. No. 8,461,117 B2 (2013); and Zhang et al., US 2012/0301490 A1 (2012));

(d) epothilones (see, e.g., Vite et al., US 2007/0275904 A1 (2007) and US RE42930 E (2011));

(e) auristatins (see, e.g., Senter et al., U.S. Pat. No. 6,844,869 B2 (2005) and Doronina et al., U.S. Pat. No. 7,498,298 B2 (2009));

(f) pyrrolobezodiazepine (PBD) dimers (see, e.g., Howard et al., US 2013/0059800 A1 (2013); US 2013/0028919 A1 (2013); and WO 2013/041606 A1 (2013)); and (g) maytansinoids such as DM1 and DM4 (see, e.g., Chari et al., U.S. Pat. No. 5,208,020 (1993) and Amphlett et al., U.S. Pat. No. 7,374,762 B2 (2008)).

Exemplary Cancers Treatable by PD-L1 Adnectins

The PD-L1 Adnectins described herein may be suitable for use in the treatment of a broad range of cancers, including treatment-refractory metastatic NSCLC, that are generally not considered to be immune-responsive. Exemplary cancers that may be treated using the PD-L1 Adnectins described herein include MEL (e.g., metastatic malignant melanoma). RCC, squamous NSCLC, non-squamous NSCLC, CRC, ovarian cancer (OV), gastric cancer (GC), breast cancer (BC), pancreatic carcinoma (PC), and carcinoma of the esophagus. Additionally, the PD-L1 Adnectins described herein are suitable for use in treating refractory or recurrent malignancies.

Non-limiting examples of cancers that may be treated using the PD-L1 Adnectins, based on the indications of very broad applicability of anti-PD-L1 immunotherapy disclosed in WO2013/173223, include bone cancer, skin cancer, cancer of the head or neck, breast cancer, lung cancer, cutaneous or intraocular malignant melanoma, renal cancer, uterine cancer, castration-resistant prostate cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, carcinomas of the ovary, gastrointestinal tract and breast, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, multiple myeloma, environmentally induced cancers including those induced by asbestos, metastatic cancers, and any combinations of said cancers. The PD-L1 Adnectins are also applicable to the treatment of metastatic cancers.

Combination Therapy with PD-L1 Adnectins

In certain embodiments, the PD-L1 Adnectins described herein may be combined with an immunogenic agent, for example a preparation of cancerous cells, purified tumor antigens (including recombinant proteins, peptides, and carbohydrate molecules), antigen-presenting cells such as dendritic cells bearing tumor-associated antigens, and cells transfected with genes encoding immune stimulating cytokines (He et ah, 2004). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF. PD-L1 blockade may also be effectively combined with standard cancer treatments, including chemotherapeutic regimes, radiation, surgery, hormone deprivation and angiogenesis inhibitors, as well as another immunotherapeutic antibody (e.g., an anti-PD-1, anti-CTLA-4, and anti-LAG-3 Ab).

Medicaments and Uses of Anti-PD-L1 Adnectins anti-PD-L1 Adnectin described herein may be used for the preparation of a medicament for inhibiting signaling from the PD-1/PD-L1 pathway so as to thereby potentiate an endogenous immune response in a subject afflicted with cancer. This disclosure also provides the use of any anti-PD-L1 Adnectin described herein for the preparation of a medicament for immunotherapy of a subject afflicted with cancer. The disclosure provides medical uses of any anti-PD-L1 Adnectin described herein corresponding to all the embodiments of the methods of treatment employing a PD-L1 Adnectin described herein.

Also described herein are anti-PD-L1 Adnectins for use in treating a subject afflicted with cancer comprising potentiating an endogenous immune response in a subject afflicted with cancer by inhibiting signaling from the PD-1/PD-L1 pathway. The disclosure further provides anti-PD-L1 Adnectins for use in immunotherapy of a subject afflicted with cancer comprising disrupting the interaction between PD-1 and PD-L1. These anti-PD-L1 Adnectins may be used in potentiating an endogenous immune response against, or in immunotherapy of, the full range of cancers described herein. In certain embodiments, the cancers include MEL (e.g., metastatic malignant MEL), RCC, squamous NSCLC, non-squamous NSCLC, CRC, ovarian cancer (OV), gastric cancer (GC), breast cancer (BC), pancreatic carcinoma (PC), and carcinoma of the esophagus.

Infectious Diseases

Also described herein are methods for treating patients that have been exposed to particular toxins or pathogens. For example, in certain aspects, this disclosure provides a method of treating an infectious disease in a subject comprising administering to the subject an anti-PD-L1 Adnectin described herein such that the subject is treated for the infectious disease.

Similar to its application to tumors as discussed above, Adnectin-mediated PD-L1 blockade can be used alone, or as an adjuvant, in combination with vaccines, to potentiate an immune response to pathogens, toxins, and/or self-antigens. Examples of pathogens for which this therapeutic approach may be particularly useful include pathogens for which there is currently no effective vaccine, or pathogens for which conventional vaccines are less than completely effective. These include, but are not limited to HIV, Hepatitis (A, B, and C), Influenza, Herpes, Giardia, Malaria, Leishmania, *Staphylococcus aureus, Pseudomonas aeruginosa*. PD-L1 blockade is particularly useful against established infections by agents such as HIV that present altered antigens over the course of an infection. Novel epitopes on these antigens are recognized as foreign at the time of anti-PD-L1 Adnectin administration, thus provoking a strong T cell response that is not dampened by negative signals through the PD-1/PD-L1 pathway.

In the above methods, PD-L1 blockade can be combined with other forms of immunotherapy known in the art, such as cytokine treatment (e.g., administration of interferons, GM-CSF, G-CSF or IL-2).

XIII. Kits and Articles of Manufacture

The anti-PD-L1 Adnectins described herein can be provided in a kit, a packaged combination of reagents in predetermined amounts with instructions for use in the therapeutic or diagnostic methods described herein.

For example, in certain embodiments, an article of manufacture containing materials useful for the treatment or prevention of the disorders or conditions described herein, or for use in the methods of detection described herein, are provided. The article of manufacture comprises a container and a label. Suitable containers include, for example, bottles, vials, syringes, and test tubes. The containers may be formed from a variety of materials such as glass or plastic. The container may hold a composition described herein for in vivo imaging, and may have a sterile access port (for example the container may be an intravenous solution bag or a vial having a stopper pierceable by a hypodermic injection needle). The active agent in the composition is an anti-PD-L1 Adnectin described herein. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

In certain embodiments, a kit comprises one or more reagents necessary for forming an $^{18}$F labelled anti-PD-L1 Adnectin in vivo imaging agent, such as a PD-L1 Adnectin-PEG4-DBCO-$^{18}$F, as further described herein. For example, a kit may comprise a first vial comprising anti-PD-L1 Adnectin-PEG-4-DBCO and a second vial comprising [$^{18}$F] FPPEGA. A kit may comprise a first vial comprising anti-PD-L1 Adnectin-PEG-4-DBCO, a second vial comprising 4-PEG-tosyl-azide and a third vial comprising $^{18}$F in O$^{18}$ water. The kits may further comprise vials, solutions and optionally additional reagents necessary for the manufacture of PD-L1 Adnectin-PEG4-DBCO-$^{18}$F. Similarly, kits may comprise the reagents necessary for forming a $^{64}$Cu labelled anti-PD-L1 Adnectin, such as the reagents described herein.

INCORPORATION BY REFERENCE

All documents and references, including patent documents and websites, described herein are individually incorporated by reference to into this document to the same extent as if there were written in this document in full or in part.

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

EXAMPLES

Example 1: Identification of PD-L1 Binding Adnectins

Anti-PD-L1 Adnectins were isolated from an Adnectin library screened with a human PD-L1 protein, or were affinity matured by PROfusion from clones identified in the library. The full length sequences, core sequences, BC, DE, and FG loop sequences of these Adnectins, as well as variants with a "PC" modified C-terminus, are presented in FIG. 1 and Table 3.

For example, the high-affinity, anti-PD-L1 Adnectin, ADX_5322_A02 ("A02"), was obtained by affinity-maturing the ATI-964 Adnectin. The gene encoding ATI-964 was re-diversified by introducing a small fraction of non-wild-type nucleotides at each nucleotide position that encoded a residue in loop BC, DE, or FG. The resulting library of Adnectin sequences related to ATI-964 was then subjected to in vitro selection by PROfusion (mRNA display) for binding to human PD-L1 under high-stringency conditions. The clones enriched after completed selection were sequenced, expressed in HTPP format, and screened for their ability to bind PD-L1 and for their fraction of monomericity. The clone with the best combination of affinity for PD-L1 and robust biophysical properties was mutated to include a C-terminal Cysteine, first with the C-terminal sequence NYRTPCH6 (SEQ ID NO: 686) (the form identified as ADX_5322_A02), and later with the C-terminal sequence NYRTPC (SEQ ID NO: 687).

The same process was followed to affinity-mature ATI-967, resulting in the Adnectin ADX_5417_E01. Similarly, affinity matured ATI_1760_C02, ATI_1760_E01 ("E01") and ATI_1760_F01 were obtained by affinity maturation of ATI_1422_G05.

Additional anti-human PD-L1 adnectins were isolated. Their sequences are set forth in Table 3.

Expression and Purification of His-Tagged Anti-PD-L1 Adnectins

All DNA constructs contained an N-terminal his tag followed by a TVMV recognition sequence. The expression plasmids (pET-28 NM vector) for the anti-PD-L1 Adnectins described supra were transformed into BL21(DE3) cells (New England Biolabs). Cells were grown in Overnight Express Autoinduction media (Novagen) in 1 L shake flasks at 37° C. for 6 hours followed by 20° C. for 16 hours at 220 RPM. Cells were harvested by centrifugation and suspended in PBS pH 7.2. Cells were lysed mechanically, then clarified by centrifugation. Soluble fractions were bound by gravity feed to Ni-NTA Agarose resin (Qiagen), washed in 20 mM Tris+10 mM Imidazole pH 8.0, followed by 20 mM Tris+40 mM Imidazole pH 8.0, and eluted with 20 mM Tris+400 mM Imidazole pH 8.0. Nickel eluates were spiked with TVMV protease at 1:23-fold molar excess of Adnectin. The TVMV-Adnectin eluate mixtures were dialyzed against 20 mM Tris pH 8.0 at 4° C. for 16 hours. To separate the TVMV protease and cleaved his tag fragments, samples were loaded onto a 10 mL HisTrap FF column (GE Healthcare) and flow through fractions were collected.

Example 2: Biophysical Assessment of PD-L1 Adnectins

The binding properties of ATI-1420D05, ATI-1420D05, AT1-1421E04 and ATI-1422G05, ATI_1760_C02, ATI_1760_E01 and ATI_1760_E01 were assessed.

TABLE 1

| Binding properties of anti-PD-L1 Adnectins | | |
|---|---|---|
| Sequence Name | SEQ ID | $K_D$ (nM) |
| ATI-1420B09 | | 2.5 |
| ATI-1420D05 | | 9.5 |
| AT1-1421E04 | | 5.6 |

Binding properties of the purified ATI-964, ATI-967, ATI-968, ADX_5322_A02, and ADX_5417_E01 Adnectins to human or cyno PD-L1, as determined by Biacore, are shown in Table 2. Cell binding was determined by measuring binding to human PD-L1 positive cells L2987.

TABLE 2

Biophysical properties of anti-PD-L1 Adnectins

| Sequence Name | SEQ ID | Binding Kinetics | | | $K_D$ (M) for cynoPD-L1 | Melting Transition Midpoint (Tm)° C. | Cell Binding $EC_{50}$ |
|---|---|---|---|---|---|---|---|
| | | $k_a$ (1/Ms) | $k_d$ (s) | $K_D$ (M) | | N.D. | N.D. |
| ATI-964 | 30 | $3.6 \times 10^5$ | $7.7 \times 10^{-5}$ | $2.1 \times 10^{-10}$ | $1.4 \times 10^{-10}$ | N.D. | 4.4 |
| ATI-965 | 45 | $4.6 \times 10^5$ | $3.3 \times 10^{-4}$ | $7.1 \times 10^{-10}$ | $8 \times 10^{-10}$ | N.D. | 4.9 |
| ATI-966 | 60 | $2.5 \times 10^6$ | $6.9 \times 10^{-5}$ | $2.8 \times 10^{-11}$ | $3.8 \times 10^{-11}$ | N.D. | 2.3 |
| ATI-967 | 75 | $2.1 \times 10^6$ | $6.7 \times 10^{-5}$ | $3.2 \times 10^{-11}$ | $6 \times 10^{-11}$ | N.D. | N.D. |
| ATI-968 | 15 | $7.5 \times 10^5$ | $1.2 \times 10^{-4}$ | $1.6 \times 10^{-10}$ | $1.1 \times 10^{-10}$ | 60 | 3.4 |
| ADX_5322_A02 | 91 | $2.5 \times 10^6$ | $5.7 \times 10^{-4}$ | $2.28 \times 10^{-10}$ | N.D. | 82 | 0.43 nM (Cys-Capped) |
| ADX_5417_E01 | 107 | $2.0 \times 10^7$ | $2.6 \times 10^{-4}$ | $1.3 \times 10^{-11}$ | N.D. | 73 | N.D. |

Figure 12:
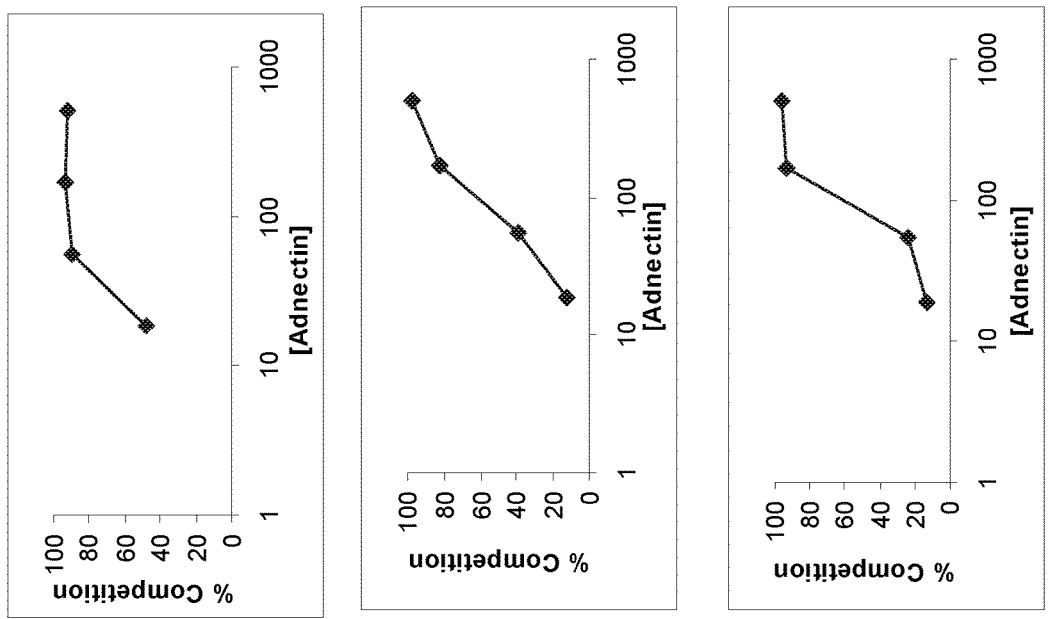
FIG. 12 depicts exemplary competition curves of anti-PD-L1 Adnectins.

The binding data indicates that the affinity matured anti-human PD-L1 adnectins bind to human PD-L1 with affinities that are less than 1 nM or even less than 0.1 nM. Exemplary inhibition curves are shown in FIG. 12.

Anti-PD-L1 adnectins have the following additional characteristics:

Inhibiting the binding of human PD-1 to human PD-L1, as determined by measuring inhibition of binding of human PD-1Fc to the PD-L1 positive cells L2987 by flow cytometry, and shown, e.g., for adnectins ATI-964, ATI-965, ATI-966, ATI-967, ATI-968, A02 and E01;

Inhibiting the binding of human CD80 (B7-1) to human PD-L1, as determined by ELISA. For example, ATI-964 inhibits binding with an EC50 of 41 pM; ATI-965 inhibits binding with an EC50 of 210 pM; ATI-966 inhibits binding with an EC50 of 28 pM; and ATI-968 inhibits binding with an EC50 of 56 pM;

Inhibiting the binding of the anti-PD-L1 antibody 12A4 to human PD-L1, as determined by ELISA.

Anti-PD-L1 antibodies were also tested in a mixed lymphocyte reaction (MLR): ATI-964, ATI-965, and ATI-968 were active in an MLR, whereas ATI-966 and ATI-967 were not active in an MLR.

The following examples relate to the labeling of anti-PD-L1 Adnectins with $^{18}F$ and $^{64}Cu$.

Example 3: Preparation of 2-(2-(2-(2-azidoethoxy)ethoxy)ethoxy)ethyl 4-methylbenzenesulfonate

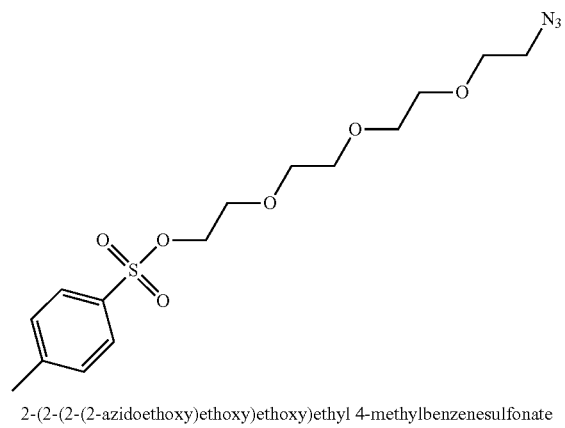

2-(2-(2-(2-azidoethoxy)ethoxy)ethoxy)ethyl 4-methylbenzenesulfonate

-continued

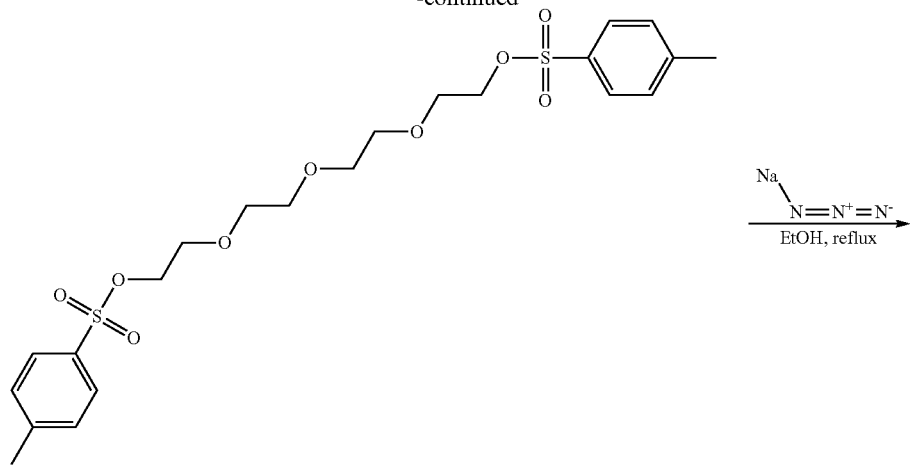

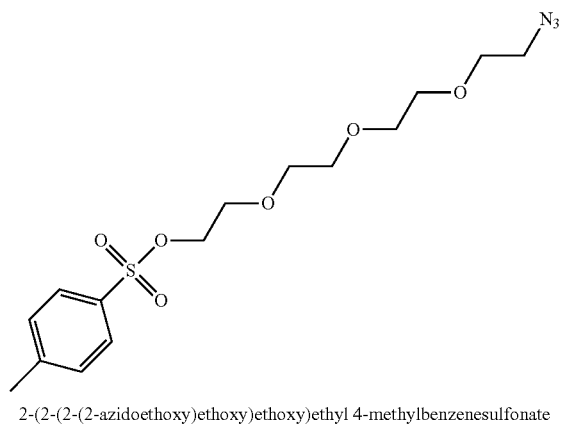

2-(2-(2-(2-azidoethoxy)ethoxy)ethoxy)ethyl 4-methylbenzenesulfonate

A mixture of ((oxybis(ethane-2,1-diyl))bis(oxy))bis(ethane-2,1-diyl) bis(4-methylbenzenesulfonate) (5 g, 9.95 mmol) and sodium azide (0.647 g, 9.95 mmol) were dissolved in ethanol (50 mL) and the reaction was refluxed at 90° C. over a 17 hour period. The solvent was removed using partial vacuum and then loaded onto a 40 gram silica cartridge and purified using flash chromatography (Isco-CombiFlash—eluted using a linear gradient method starting from 10% ethyl acetate in hexanes going to a 90% ethyl acetate in hexanes over a 45 minute period). The pooled fractions were checked by TLC and combined to give 2-(2-(2-(2-azidoethoxy)ethoxy)ethoxy)ethyl 4-methylbenzenesulfonate as a colorless oil. Due to the reactive nature of the 2-(2-(2-(2-azidoethoxy)ethoxy)ethoxy)ethyl 4-methylbenzenesulfonate product this material was used "as is" without any further characterizations.

Example 4: Preparation of 3-(2-(2-(2-(2-azidoethoxy)ethoxy)ethoxy)ethoxy)-2-fluoropyridine

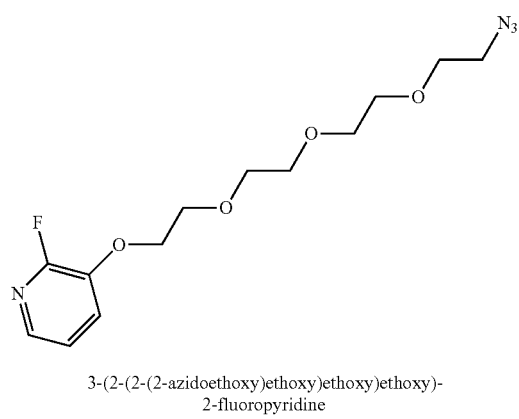

3-(2-(2-(2-(2-azidoethoxy)ethoxy)ethoxy)ethoxy)-2-fluoropyridine

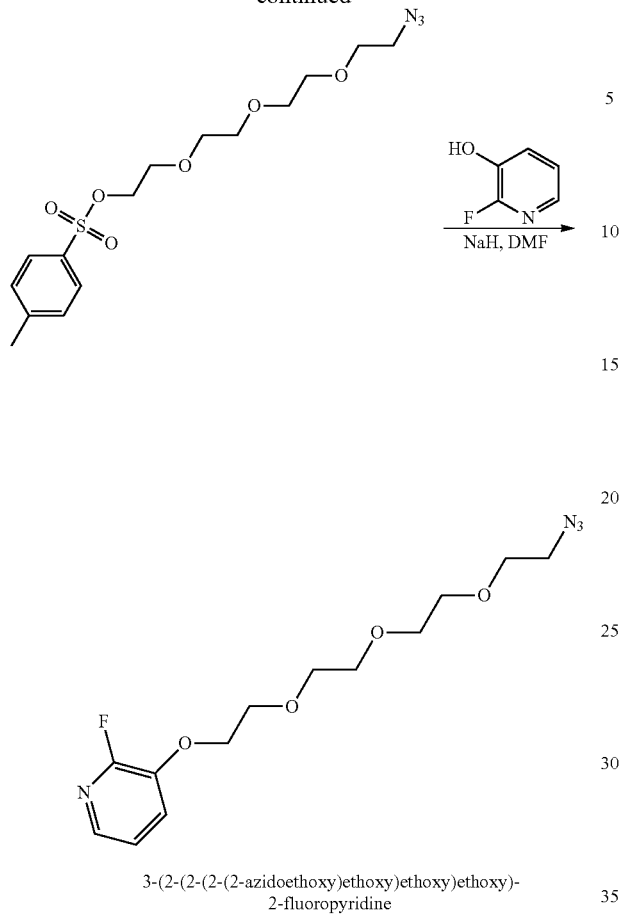

3-(2-(2-(2-(2-azidoethoxy)ethoxy)ethoxy)ethoxy)-
2-fluoropyridine

To a suspension of sodium hydride (0.129 g, 3.21 mmol) in DMF (10 mL) at 0° C. was dropwise added a stirring solution of 2-fluoropyridin-3-ol (0.363 g, 3.21 mmol) in DMF (5 mL), then followed by the dropwise addition of the solution of 2-(2-(2-(2-azidoethoxy)ethoxy)ethoxy)ethyl 4-methylbenzenesulfonate (1.00 g, 2.68 mmol) in DMF (5 mL). The suspension was held at 0° C. for 10 min, then brought to ambient temperature for 1 hour, followed by additional heating at 60° C. for 4 hours. The solvent was removed in vacuo. 100 ml of ethyl acetate was added followed by 3 separate wash extractions with concentrated brine solution. The organic layer was dried over sodium sulfate, filtered, and concentrated. The crude material was purified using flash chromatography (IscoCombiFlash— eluted with 10-50% EtOAc in Hex) to give a colorless oil. 3-(2-(2-(2-(2-azidoethoxy)ethoxy)ethoxy)ethoxy)-2-fluoro-pyridine (702 mg, 2.233 mmol, 83% yield) was isolated as a clear oil. $^1$H NMR (400 MHz, CHLOROFORM-d) δ 7.75 (dt, J=4.9, 1.6 Hz, 1H), 7.33 (ddd, J=10.0, 8.1, 1.5 Hz, 1H), 7.10 (ddd, J=7.9, 4.9, 0.7 Hz, 1H), 4.30-4.16 (m, 2H), 3.95-3.83 (m, 2H), 3.80-3.61 (m, 10H), 3.38 (t, J=5.1 Hz, 2H) 13C NMR (101 MHz, CHLOROFORM-d) d 142.3, 137.7, 137.5, 123.4, 123.4, 121.7, 121.6, 77.3, 76.7, 70.9, 70.7, 70.6, 70.0, 69.4, 69.0, 50.6 19F NMR (400 MHz, CHLOROFORM-d) δ −83.55. HRMS (ESI) Theory: C13H20FN4O4+ m/z 315.464; found 315.1463.

Example 5: Preparation of 3-(2-(2-(2-(2-azidoeth-oxy)ethoxy)ethoxy)ethoxy)-2-nitropyridine

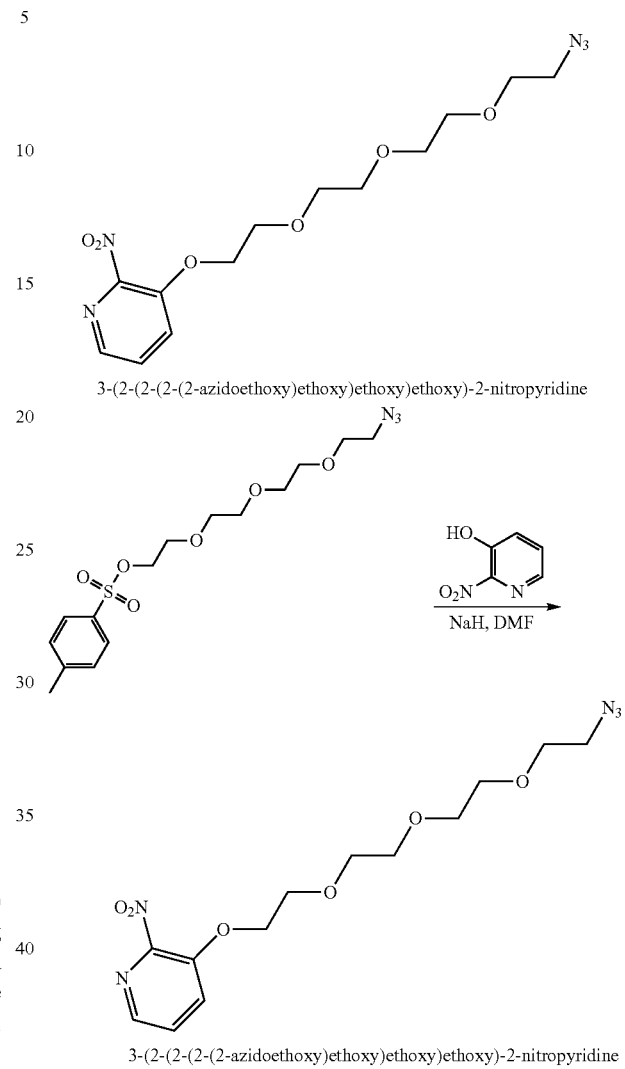

3-(2-(2-(2-(2-azidoethoxy)ethoxy)ethoxy)ethoxy)-2-nitropyridine

Sodium hydride (0.121 g, 3.01 mmol) (60% suspension in oil) was dissolved in DMF (7.0 mL) and the resulting suspension was cooled to 0° C. A solution of 2-nitropyridin-3-ol (0.384 g, 2.74 mmol) in DMF (1.5 mL) was added slowly, followed by the dropwise addition of 2-(2-(2-(2-azidoethoxy)ethoxy)ethoxy)ethyl 4-methylbenzene-sulfonate (1.023 g, 2.74 mmol) in DMF (1.5 mL). The suspension was held at 0° C. for 10 minutes, then brought to ambient temperature for 2 hours followed by heating 60° C. for a 72 hour period. The reaction was quenched with 10 ml of DI water, followed by ethyl acetate extraction (3×10 mL). Pooled EtOAc extracts were washed with a concentrated brine solution (10 mL), dried over sodium sulfate, filtered, and evaporated under reduced pressure to give a light yellow oil. The crude was purified by flash chromatography. 24 g silica cartridge, 25 mL/min, starting from 10% ethyl acetate in hexanes, followed by a linear change to 50% ethyl acetate in hexanes over a 25 minute period. After this time, the gradient was held at this solvent composition for 10 minutes then changed to 100% ethyl acetate over a 10 minute period. 3-(2-(2-(2-(2-azidoethoxy)ethoxy)ethoxy)ethoxy)-2-nitropyridine was eluted between the 30-40 minute portion of the chromatogram and the pooled fractions were evaporated under reduced pressure, then under vacuum for 2 hours to give 3-(2-(2-(2-(2-azidoethoxy)ethoxy)ethoxy)ethoxy)-2-nitropyridine (687 mg, 1.973 mmol, 72.0% yield) as a light yellow oil. $^1$H NMR (400 MHz, CHLOROFORM-d) δ 8.11 (dt, J=4.9, 1.6 Hz, 1H), 7.60 (ddd, J=10.0, 8.1, 1.5 Hz, 1H), 7.52 (ddd, J=7.9, 4.9, 0.7 Hz, 1H), 4.30-4.16 (m, 2H), 3.95-3.83 (m, 2H), 3.80-3.61 (m, 10H), 3.38 (t, J=5.1 Hz, 2H) 13C NMR (101 MHz, CHLOROFORM-d) d 147.3, 139.5, 128.4, 124.4. 71.1, 70.7, 70.6, 70.0, 69.9, 69.3, 50.7. HRMS (ESI) Theory: C13H20N5O6+ m/z 342.1408; found 342.1409

Example 6: Synthesis of 3-(2-(2-(2-(2-azidoethoxy)ethoxy)ethoxy)ethoxy)-2-bromopyridine

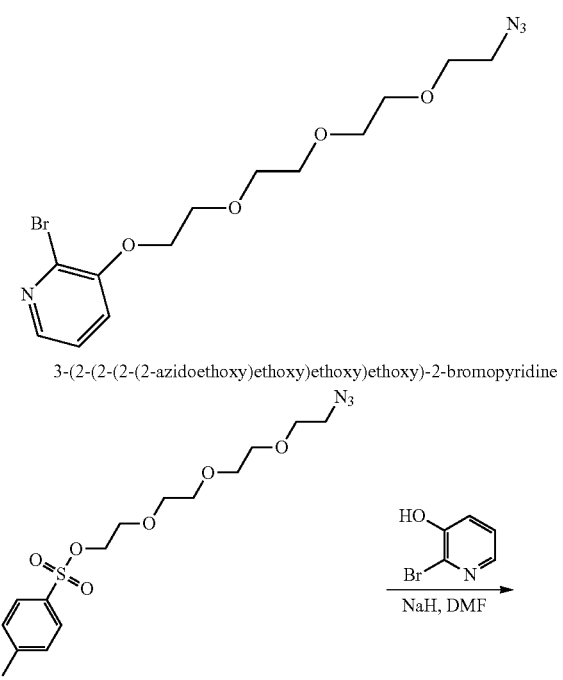

3-(2-(2-(2-(2-azidoethoxy)ethoxy)ethoxy)ethoxy)-2-bromopyridine

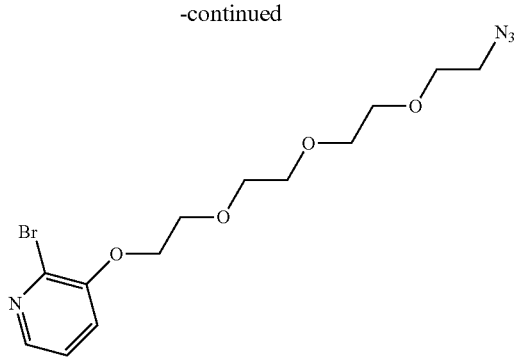

To the suspension of sodium hydride (NaH, 25.7 mg, 0.643 mmol) in dimethylformamide (DMF, 5 mL) at 0° C. was dropwise added a solution of 2-bromopyridin-3-ol (112 mg, 0.643 mmol) in DMF (1 mL), followed by the dropwise addition of the solution of 2-(2-(2-(2-azidoethoxy)ethoxy)ethoxy)ethyl 4-methylbenzenesulfonate (200 mg, 0.536 mmol) in DMF (1 mL). The suspension was held at 0° C. for 10 minutes, then brought to ambient temperature and held for 1 hour, followed by heating to 60° C. for 4 hours. Upon completion of heating, the solvent of the crude reaction mixture was removed in vacuo. The crude reaction was reconstituted in 50 mL of ethyl acetate, washed with 2×50 mL of a aqueous brine solution, and the organic layer was dried over magnesium sulfate, filtered, and concentrated in vacuo. The crude reaction was purified using reverse-phase HPLC to give 3-(2-(2-(2-(2-azidoethoxy)ethoxy)ethoxy)ethoxy)-2-bromopyridine, TFA (112 mg, 0.229 mmol, 42.7% yield) as a light yellow oil. HRMS ESI m/z (M+H), Theory C13H20BrN4O4 375.0664 found 375.0662; $^1$H NMR (400 MHz, DMSO-d$_6$) δ 7.97 (dd, J=4.6, 1.5 Hz, 1H), 7.54 (dd, J=8.2, 1.6 Hz, 1H), 7.40 (dd, J=8.1, 4.6 Hz, 1H), 4.24 (dd, J=5.3, 3.9 Hz, 2H), 3.85-3.78 (m, 2H), 3.68-3.62 (m, 2H), 3.62-3.52 (m, 8H), 3.42-3.34 (m, 2H).

Example 7: Scheme for Synthesis of Trimethylanilium Compound

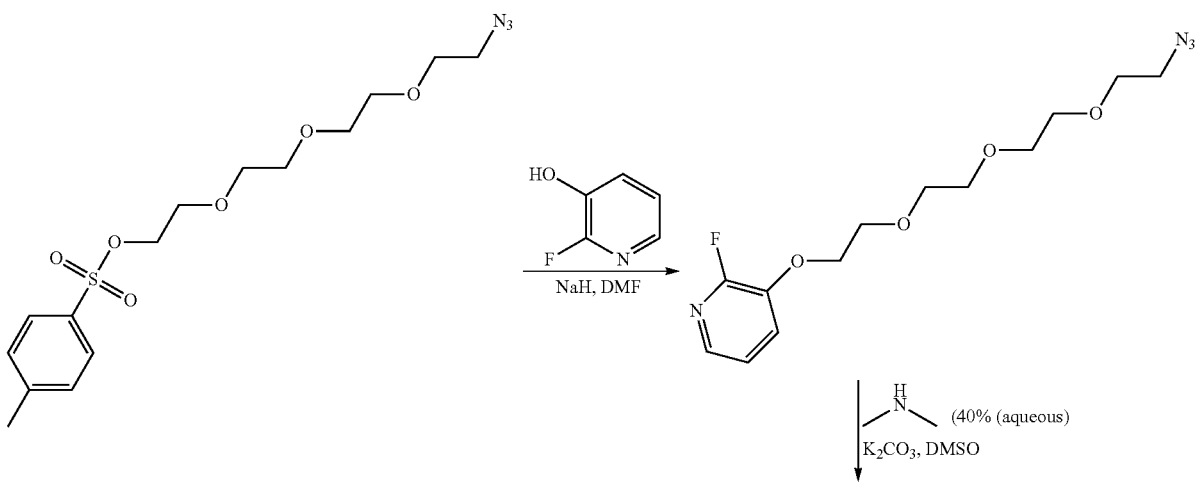

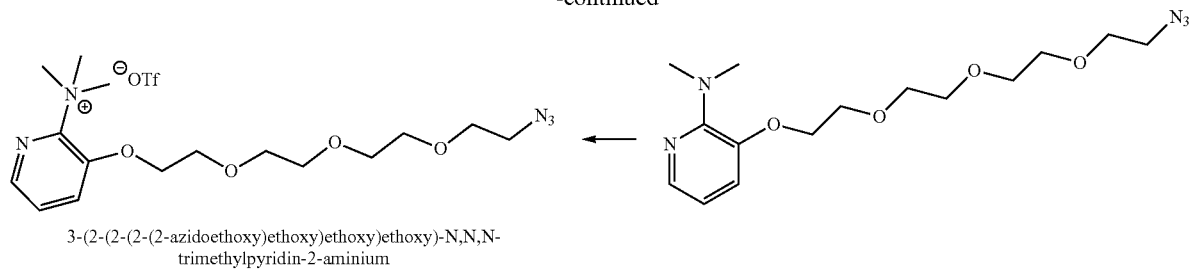

3-(2-(2-(2-(2-azidoethoxy)ethoxy)ethoxy)ethoxy)-N,N,N-trimethylpyridin-2-aminium

Example 8: Synthesis of 3-(2-(2-(2-(2-azidoethoxy)ethoxy)ethoxy)ethoxy)-N,N-dimethylpyridin-2-amine

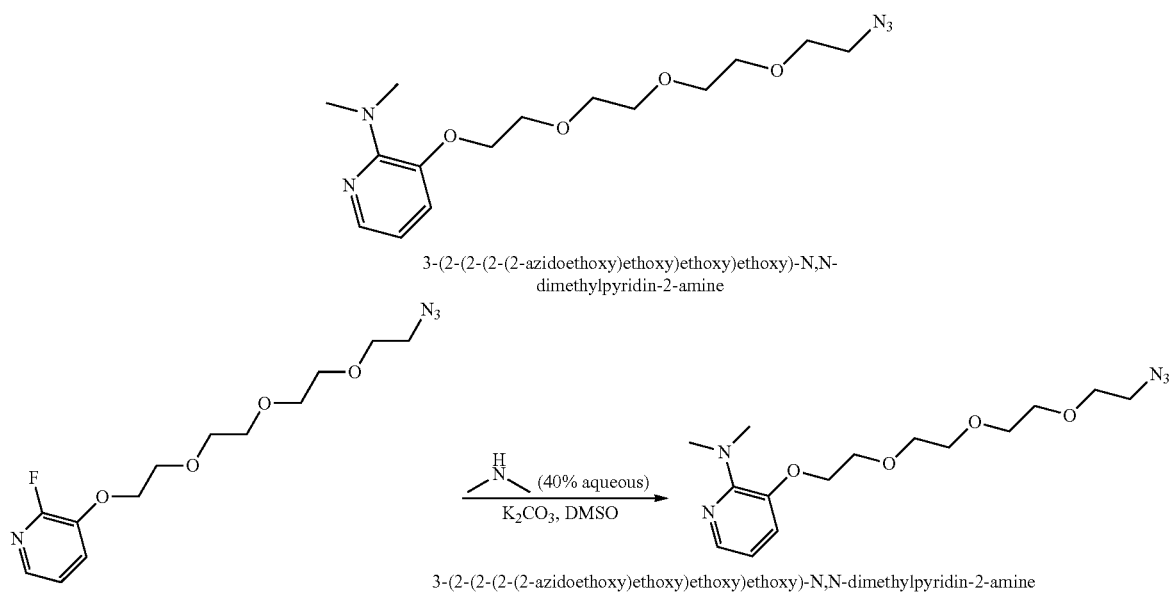

3-(2-(2-(2-(2-azidoethoxy)ethoxy)ethoxy)ethoxy)-N,N-dimethylpyridin-2-amine 3-(2-(2-(2-(2-azidoethoxy)ethoxy)ethoxy)ethoxy)-N,N-dimethylpyridin-2-amine A mixture of 3-(2-(2-(2-(2-azidoethoxy)ethoxy)ethoxy)ethoxy)-2-fluoropyridine (160 mg, 0.509 mmol), potassium carbonate ($K_2CO_3$, 84 mg, 0.611 mmol), and dimethylamine (40% in water, 0.097 mL, 0.764 mmol) in dimethylsulfoxide (DMSO, 2.5 mL) were heated in a sealed pressure-proof vessel at 110° C. for 14 hours. Upon completion of heating, the solvent of the crude reaction mixture was removed in vacuo. The crude reaction was reconstituted in 50 mL of ethyl acetate, washed with 2×50 mL of a aqueous brine solution, and the organic layer was dried over magnesium sulfate, filtered, and concentrated in vacuo. The crude reaction was purified using normal-phase chromatography to give 3-(2-(2-(2-(2-azidoethoxy)ethoxy)ethoxy)ethoxy)-N,N-dimethylpyridin-2-amine (140 mg, 0.413 mmol, 81% yield) as a colorless oil. $^1$H NMR (400 MHz, CHLOROFORM-d) δ 7.86 (dd, 1.5 Hz, 1H), 7.02 (dd, 1.5 Hz, 1H), 6.73 (dd, J=7.8, 4.9 Hz, 1H), 4.20-4.07 (m, 2H), 3.98-3.86 (m, 2H), 3.81-3.61 (m, 9H), 3.38 (t, J=5.1 Hz, 2H), 3.13-2.94 (m, 6H), 1.69 (s, 2H). HRMS (ESI) Theory: C15H26N5O4+ m/z 340.1980; found 340.1979.

Example 9: Synthesis of 3-(2-(2-(2-(2-azidoethoxy)ethoxy)ethoxy)ethoxy)-N,N,N-trimethylpyridin-2-aminium

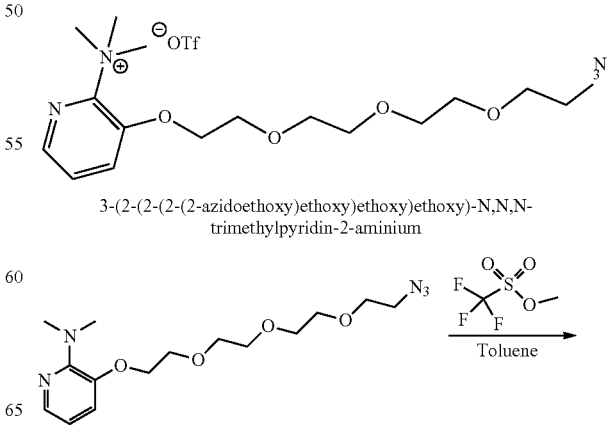

3-(2-(2-(2-(2-azidoethoxy)ethoxy)ethoxy)ethoxy)-N,N,N-trimethylpyridin-2-aminium

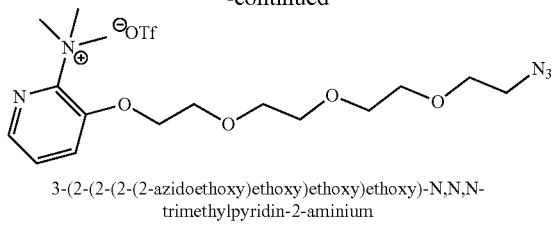

3-(2-(2-(2-(2-azidoethoxy)ethoxy)ethoxy)ethoxy)-N,N,N-trimethylpyridin-2-aminium Methyl trifluoromethanesufonate (0.065 mL, 0.589 mmol) was added to the solution of 3-(2-(2-(2-(2-azidoethoxy)ethoxy)ethoxy)ethoxy)-N,N-dimethylpyridin-2-amine (40 mg, 0.118 mmol) in toluene (1.5 mL) in a sealed container under a steady stream of nitrogen. The reaction mixture was stirred at room temperature over a 14 hour period. The solvent was removed and the resultant residue was washed with 2×10 ml of ether, azeotropically dried with 2×1 ml of dichloromethane, and dried under high-pressure vacuum overnight to give 3-(2-(2-(2-(2-azidoethoxy)ethoxy)ethoxy)ethoxy)-N,N,N-trimethylpyridin-2-aminium, trifluoromethanesulfonate salt in quantitative yield as a thick colorless oil. LCMS m/z 354.33; $^1$H NMR (400 MHz, DMSO-$d_6$) δ 8.24-8.17 (m, 1H), 7.98 (d, J=8.3 Hz, 1H), 7.75 (ddd, J=8.2, 4.6, 3.2 Hz, 1H), 4.44 (br. s., 2H), 3.88 (d, J=3.9 Hz, 2H), 3.69-3.45 (m, 21H).

Example 10: Synthesis of [$^{18F}$]-3-(2-(2-(2-(2-azidoethoxy)ethoxy)ethoxy)ethoxy)-2-fluoropyridine Using 3-(2-(2-(2-(2-azidoethoxy)ethoxy)ethoxy)ethoxy)-N,N,N-trimethylpyridin-2-aminium, Trifluoromethanesulfonate Salt

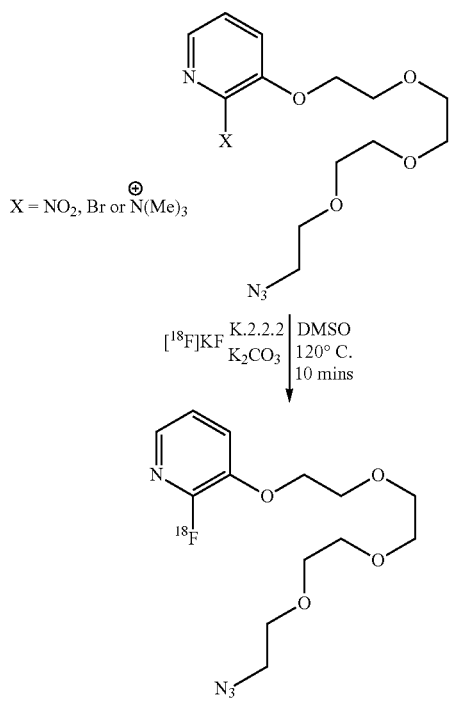

Synthesis of [$^{18}$F]-3-(2-(2-(2-(2-azidoethoxy)ethoxy)ethoxy)ethoxy)-2-fluoropyridine An aqueous [$^{18}$F]-Fluoride solution (2.0 ml, 33.3 GBq/900 mCi) was purchased from P.E.T. Net® Pharmaceuticals in West Point Pa. and directly transferred to a Sep-Pak light QMA [The Sep-Pak light QMA cartridge was pre-conditioned sequentially with 5 ml of 0.5 M potassium bicarbonate, 5 ml of deionized water, and 5 ml of MeCN before use.] Upon completion of this transfer, the aqueous [$^{18}$F] fluoride was released from the QMA Sep-Pak by the sequential addition of potassium carbonate (15 mg/ml; 0.1 ml) followed by a mixture of potassium carbonate (30 mg/ml, 0.1 ml), 4,7,13,16,21,24-hexaoxa-1,10-diazabicyclo[8.8.8]hexacosane (15 mg, 0.04 mmol) and 1.2 ml of MeCN. The solvent was evaporated under a gentle stream of nitrogen at 90° C. and vacuum. Azeotropic drying was repeated twice with 1 ml portions of acetonitrile to generate the anhydrous K.2.2.2/K[$^{18}$F]F complex. 3-(2-(2-(2-(2-azidoethoxy)ethoxy)ethoxy)ethoxy)-N,N,N-trimethylpyridin-2-aminium, trifluoromethanesulfonate salt (2 mg, 5.6 μmol) was dissolved in 500 microliters of DMSO and added to the dried cryptand. This solution was heated at 120° C. for 10 minutes. After this time, the crude reaction mixture was diluted with 3 ml of DI water. The entire contents of the crude reaction mixture was then transferred, loaded, and purified using reverse phase HPLC under the following conditions: HPLC Column: Luna C18 250×10 Solvent A: 0.1% TFA in DI water; solvent B: 0.1% TFA in acetonitrile at a flow rate of 4.6 ml/minute using isocratic method 32% B while the UV was monitored at 280 nm. [$^{18}$F]-3-(2-(2-(2-(2-azidoethoxy)ethoxy)ethoxy)ethoxy)-2-fluoropyridine was isolated at the 24 min mark of the chromatogram and collect over a 2 minute period. This product was collected into a 100 ml flask that contained 10 ml of DI water and the entire contents were delivered to a Sep-Pak Vac tC18 6 cc 1 g sep pack from Waters. 6.1 GBq/164 mCi of [$^{18}$F]-3-(2-(2-(2-(2-azidoethoxy)ethoxy)ethoxy)ethoxy)-2-fluoropyridine was isolated from this reaction. This was released from the sep-pak using 3 ml of ethanol and this solution was reduced with 98° C. heat source, a gentle stream of nitrogen, and vacuum over a 15 minute period until only a film remained in the vial. The final product was reconstituted in 100% 1×PBS buffer and was stable in this media for over 1 hour at 37° C.

The [$^{18}$F]-3-(2-(2-(2-(2-azidoethoxy)ethoxy)ethoxy)ethoxy)-2-fluoropyridine may be used to generate $^{18}$F-labeled biologic products (e.g., $^{18}$F-labeled anti-PD-L1 Adnectins, as described below) by taking advantage of "click" azide-alkyne reaction with the appropriate biologic containing an alkynes.

Example 11: Production of $^{18}$F-Radiolabeled Protein Using "Click Chemistry"

A. Fluorination of the 4-PEG-tosyl-azide Precursor to Form [$^{18}$F]-FPPEGA 900 mCi of $^{18}$F in $^{18}$O water (3 ml) activity (purchased from IBA Molecular) was transferred directly into a micro vial (no QMA) that contained 4,7,13,16,21,24-hexaoxa-1,10-diazabicyclo[8.8.8]hexacosane (2.8 mg, 7.44 μmol) and potassium carbonate (1.7 mg, 0.012 mmol). An additional 2.0 ml of acetonitrile was transferred into this crude reaction mixture and the entire mixture was azeotropically dried. This was completed by evaporating the solution using a 98° C. oil bath, and applying a gentle stream of N2 and partial vacuum. The solution's volume was reduced to about 2 ml. An additional 2 ml of acetonitrile was added and the process was repeated 3 times over a 40 minute period. When the volume of the liquid was reduced to less than 0.3 ml, a 0.7 ml aliquot of acetonitrile was added and the solution reduced by further azeotropic distillation until the volume was ~0.1 ml. An additional 0.9 ml of acetonitrile was added and this process was completed until a white solid was formed. This process took ~55 minutes. During the final procedure, the vial was removed from the oil bath before the solution had gone to dryness and the residue in the vial was placed under full vacuum (no N2 flow) at room temperature for 20 minutes. Total time for transfer and drying of [$^{18}$F]-FPPEGA cryptand mixture was 65 min.

To the dried [$^{18}$F]-FPPEGA cryptand mixture was added 3-(2-(2-(2-(2-azidoethoxy)ethoxy)ethoxy)ethoxy)-2-nitropyridine (2 mg, 5.86 μmol) dissolved in 500 microliters of DMSO and this mixture was heated at 120° C. for 10 minutes. After this time the crude reaction mixture was diluted with 3 ml of DI water and the entire contents were then transferred and loaded onto the following HPLC column and conditions: HPLC Column: Luna C18 250×10 mm; Solvent A: 0.1% TFA in DI water; Solvent B: 0.1% TFA in acetonitrile; flow rate 4.6 ml/min; pressure 1820 PSI; isocratic method 32% B; UV—280 nm. The [$^{18}$F]-3-(2-(2-(2-(2-azidoethoxy)ethoxy)ethoxy)-2-fluoropyridine ([$^{18}$F]-FPPEGA) product was isolated at the 24 minute mark of the chromatogram and was collect over a 2 minute period. This product was collected into a 100 ml flask that contained 15 ml of DI water and the entire contents were delivered to a Sep PakVac tC18 6 cc 1 g sep pack. PN WAT036795. The [$^{18}$F]-FPPEGA was released from the Sep Pak using 2.5 ml of ethanol and this solution was reduced with 98° C. N2 and vacuum over a 15 minute period until dryness. This compound was dissolved in 0.1 ml 1×PBS (phosphate buffered saline). This product was analyzed using a Varian HPLC HPLC Column Luna C18 (2) 4.6×150 mm Solvent A: 0.1% TFA in DI water; Solvent B: 0.1% TFA in acetonitrile; flow rate 1.0 ml/min; gradient method 0 min 90% A 10% B; 15 mins 30% A 70% B; 17 mins 30% A 70% B; 18 mins 90% A 10% B; 20 mins 90% A 10% B; UV—280 nm. 220 mCi of [$^{18}$F]-FPPEGA was isolated.

B. Preparation of E01-4PEG-DBCO

This Example describes the linking of the E01 anti-PD-L1 Adnectin to PEG4-DBCO.

As maleimide chemistry is used to link the Adnectin to PEG4-DBCO, the E01 Adnectin was first modified by adding a proline followed by a cysteine at its C-terminus. The amino acid sequence of this modified E01 Adnectin is provided in SEQ ID NO: 104. The cysteine is used to link the Adnectin to PEG4-DBCO.

A 4-fold molar excess of Maleimide-PEG4-DBCO (Click Chemistry Tools) was dissolved in DMSO and added to the purified modified E01 Adnectin in the presence of 1 mM TCEP. Final DMSO concentrations did not exceed 5% in the conjugation mixtures. The conjugation mixture was left at room temperature for one hour before mass spec analysis. After MS confirmation of conjugation, the sample was purified by size-exclusion chromatography using a HiLoad 26/60 Superdex 75 column (GE Healthcare) equilibrated in PBS pH 7.2.

C. Coupling of [$^{18}$F]-FPPEGA to Adnectin

Figure 9:
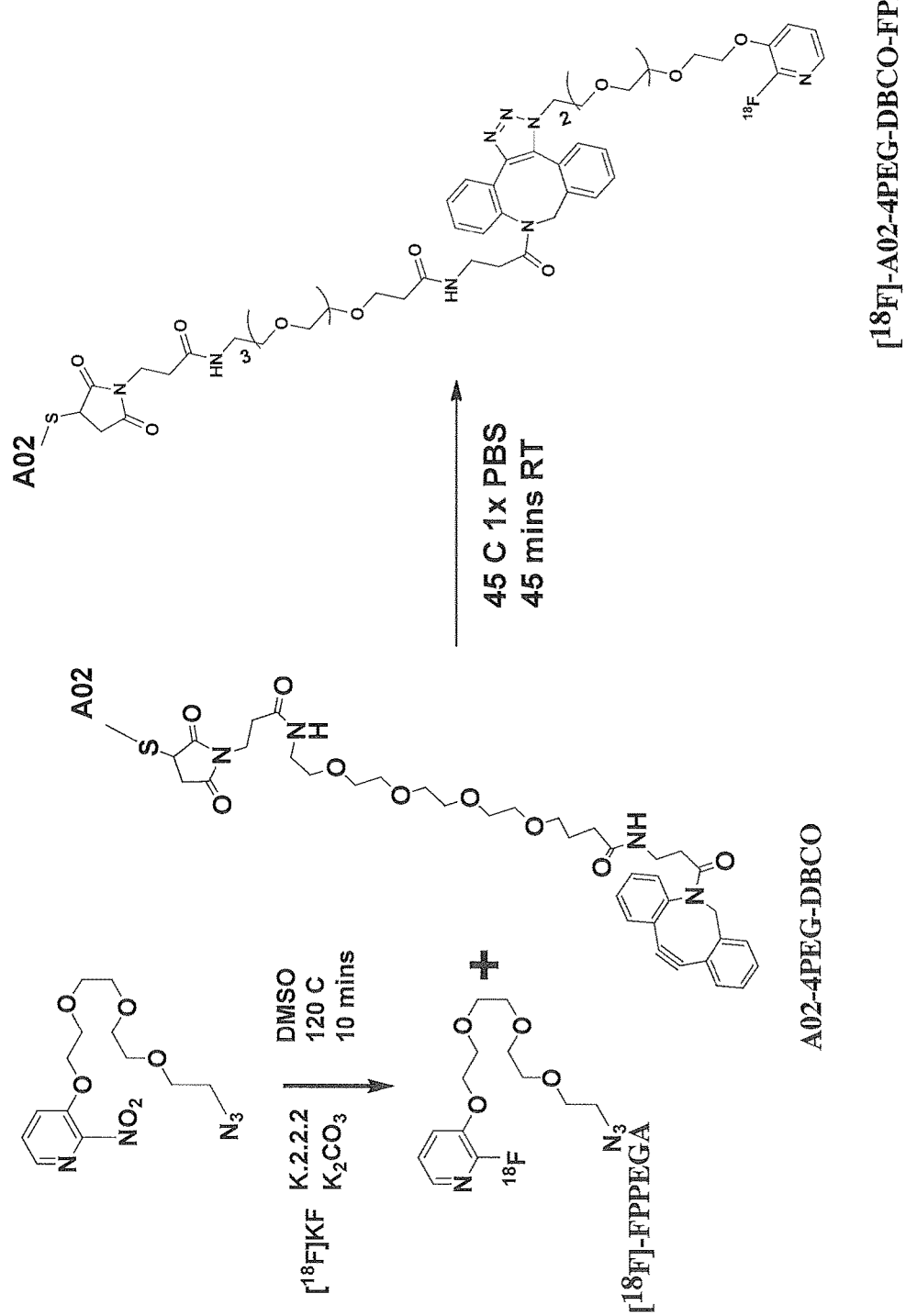
FIG. 9 shows a reaction scheme for synthesizing [$^{18}$F]-A02-4PEG-DBCO-FPPEGA. The same reaction scheme was used to label the E01 adnectin.
Figure 10:
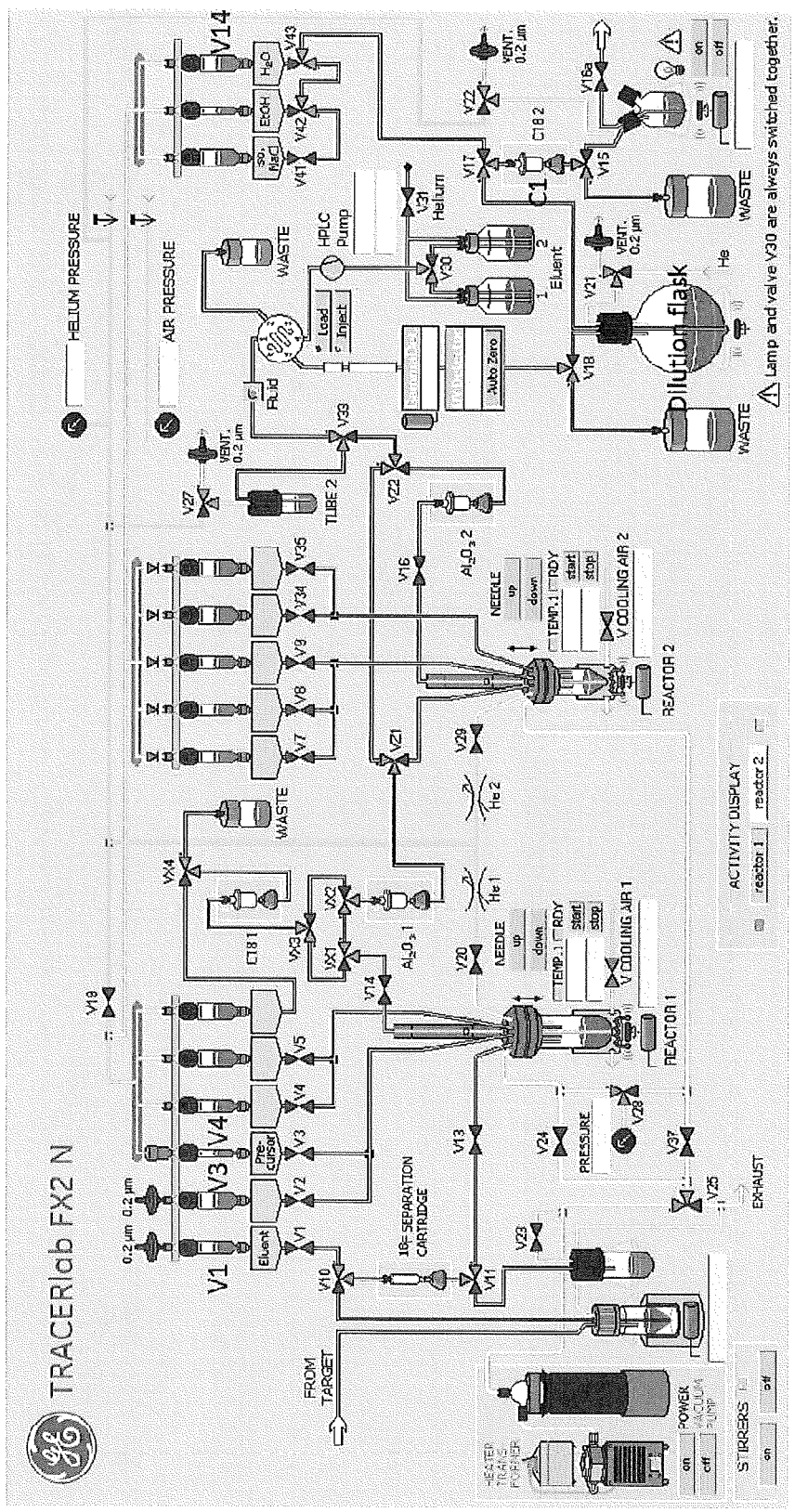
FIG. 10 is a schematic of the GE TRACERlab FX2 N Synthesis module for automated synthesis of [$^{18}$F]-FPPEGA.
Figure 11:
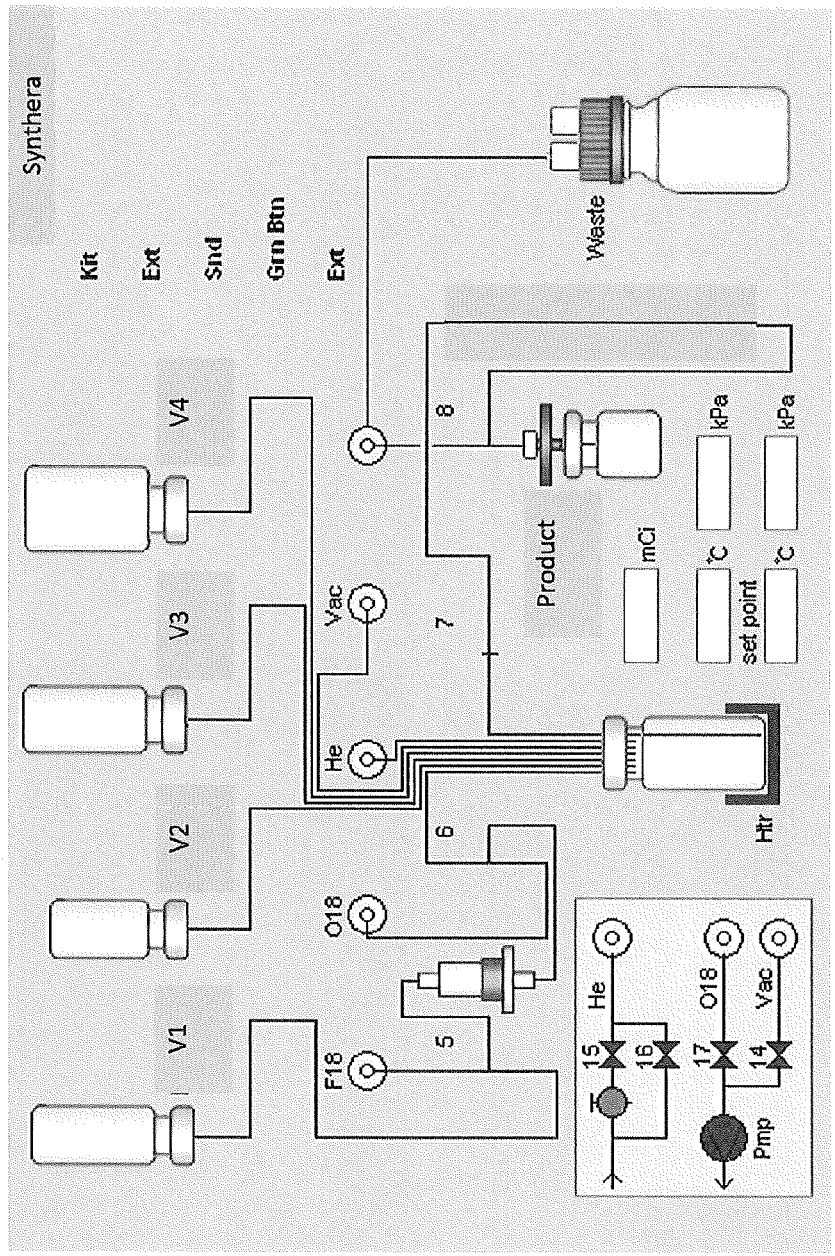
FIG. 11 is a schematic of the Synthera Synthesis module (IBA) for automated synthesis of [$^{18}$F]-FPPEGA.

A schematic for synthesizing [$^{18}$F]-E01-4PEG-DBCO-FPPEGA is shown in FIGS. 2 and 9.

0.2 ml of a 5.4 mg/ml solution of the E01-4PEG-DBCO Adnectin solution (prepared as described in Section B) was incubated with 200 mCi of 0.1 ml of [$^{18}$F]-FPPEGA (Example 4) in 1×PBS buffer. The solution was gently mixed by pipetting the crude reaction up and down several times and was incubated together for 45 minutes at 45° C. or room temperature. The contents of this crude reaction mixture were purified using a SEC column. Superdex 200 0.5 ml/min 1×PBS buffer and the [$^{18}$F]-E01-4PEG-DBCO-FPPEGA product was isolated at the 37 min mark of the chromatogram over a 2 minute period.

[$^{18}$F]-E01-4PEG-DBCO-FPPEGA was analyzed via SEC with co-injection of non-radioactive standard, RP HPLC using a PLRPS column and gel electrophoresis.

Size Exclusion Chromatography (SEC) was performed with the following parameters:
Superdex 200 column; Solvent 100% 1×PBS buffer; 0.5 ml/min 280 UV;
Reverse phase HPLC
Column: PLRPS 8 micron 1000 A 4.6×250 mm
Solvent A: 0.1% formic acid in DI water
Solvent B: Acetonitrile
Flow rate: 1 ml/min
Pressure: 1351 PSI
Gradient:
0 min 90% A 10% B
30 min 45% A 55% B
32 min 25% A 75% B
36 min 25% A 75% B
50 min 90% A 10% B 15 mCi [$^{18}$F]-E01-4PEG-DBCO-FPPEGA was isolated with a radiochemical purity (RCP) of >99% via both SEC and RP HPLC calculations, and with a specific activity of 0.6 mCi/nmol, when the reaction was conducted at 45° C. When conducting the reaction at room temperature, 5.72 mCi was obtained. Specific activity of the [$^{18}$F]-FPPEGA was 0.512 mCi/nmol and RCP of 85.7% 3 hours post the end of its synthesis, when conducting the reaction at 45° C. or at room temperature, respectively. Specific activity was measured via Nanodrop (see <www.nanodrop.com>). The product co-eluted with non-radioactive standard on both SEC and PLRPS. Gel electrophoresis confirmed an $^{18}$F product consistent with an 11 kDa molecular weight standard.

The $^{18}$F-radiolabeled E01-4PEG-DBCO can be used in a variety of in vitro and/or in vivo imaging applications, including diagnostic imaging, basic research, and radiotherapeutic applications. Specific examples of possible diagnostic imaging and radiotherapeutic applications, include determining the location, the relative activity and/or quantifying of PD-L1 positive tumors, radioimmunoassay of PD-L1 positive tumors, and autoradiography to determine the distribution of PD-L1 positive tumors in a mammal or an organ or tissue sample thereof.

In particular, the $^{18}$F-radiolabeled E01-4PEG-DBCO is useful for positron emission tomographic (PET) imaging of PD-L1 positive tumors in the lung, heart, kidneys, liver and skin and other organs of humans and experimental animals. PET imaging using the $^{18}$F-radiolabeled E01-4PEG-DBCO can be used to obtain the following information: relationship between level of tissue occupancy by candidate PD-L1 tumor-treating medicaments and clinical efficacy in patients; dose selection for clinical trials of PD-L1 tumor-treating medicaments prior to initiation of long term clinical studies; comparative potencies of structurally novel PD-L1 tumor-treating medicaments; investigating the influence of PD-L1 tumor-treating medicaments on in vivo transporter affinity and density during the treatment of clinical targets with PD-L1 tumor-treating medicaments; changes in the density and distribution of PD-L1 positive tumors during effective and ineffective treatment.

Example 12: Linking of PD-L1 Adnectins to NODAGA to Generate NODAGA-PD-L1 Adnectins This Example describes the linking of the E01 and A02 anti-PD-L1 Adnectins to NODAGA. As maleimide chemistry is used to link the Adnectins to NODAGA, both Adnectins used a proline followed by a cysteine at their C-terminus (as described for E01 above). The amino acid sequences of the modified E01 and A02 Adnectins are provided in SEQ ID NOs: 104 and 88, respectively. The cysteine will be used for linking the Adnectins to NODAGA. For $^{64}$Cu labeling of the Adnectins, a 50-fold molar excess of maleimide-NODAGA (CheMatech) was dissolved in PBS pH 7.4 and added to the purified Adnectins in the presence of 1 mM TCEP. Final DMSO concentrations did not exceed 5% in the conjugation mixtures. Conjugation mixtures were left at room temperature for one hour before mass spec analysis. After MS confirmation of conjugation, the samples were purified by size-exclusion chromatography using a HiLoad 26/60 Superdex 75 column (GE Healthcare) equilibrated in PBS pH 7.2.

Example 13: Synthesis of $^{64}$Cu-Based Anti-PD-L1 Adnectin Probes

Synthesis of $^{64}$Cu-A02-NODAGA

[$^{64}$Cu]-Copper chloride ($^{64}$CuCl$_2$) in 0.1N hydrochloric acid solution was neutralized with 0.8 mL of 0.1N sodium acetate (NaOAc) aqueous solution for 4 minutes at ambient temperature. 1 mL of the $^{64}$Cu/NaOAc solution was added to A02-NODAGA (30 µL of 1.6 mg/mL) and the crude reaction was gently pippetted to allow mixing followed by resting at ambient temperature for 30 minutes. The contents of crude reaction mixture were transferred to a PD-10 desalting column that was pre-activated with 20 mL of 1× phosphate buffered saline (PBS, pH 7.4) buffer prior to loading of sample. An additional 1.5 mL of 1×PBS was added to the column, followed by an additional 0.8 ml 1×PBS solution and these fractions were discarded. [$^{64}$Cu]-A02-NODAGA was then collected after a 1.2 mL elution of the PD-10 column to give 10.79 mCi as the desired product. Quality control was measured using a reverse phase HPLC system using an Agilent PLRP-S HPLC column Size: 250× 4.60 mm, 8 µm, 280 nm and a mobile phase of 0.1% Formic Acid in distilled water and acetonitrile. A gradient method was used where the percentage of acetonitrile was increased linearly from 10% to 45% over a 30 minute time frame. [$^{64}$Cu]-A02-NODAGA co-eluted with reference standard at the 22 minute mark of the HPLC chromatogram. Radiochemical purity was measured to be 96% using this method. [$^{64}$Cu]-A02-NODAGA also co-eluted with reference material at the 20 minute mark using a size exclusion chromatography, (SEC) Column: GE Superdex 200 GL Size: 10×300 mm, 280 nm. The calculated specific activity was 956.8 mCi/µmol based on Nanodrop protein concentration and isolated radioactivity of the purified sample.

Procedure for the Synthesis of $^{64}$Cu-E01-NODAGA

[$^{64}$Cu]-Copper chloride ([$^{64}$Cu]CuCl$_2$) in 0.1N hydrochloric acid solution (20 mCi in 0.25 mL) was pH adjusted with 1.10 mL of 0.1N ammonium acetate buffer, then mixed and incubated with E01-NODAGA Adnectin in a 1×PBS aqueous solution (40 µL of 1.2 mg/mL, 4.62 nmol) for 30 minutes at ambient temperature. After 30 minutes of incubation, the reaction mixture (~1250 µL) was transferred to the PD-10 desalting column (GE Healthcare Life Science, Sephadex G25 Medium, 14.5×50 mm—equilibrated with 40 mL of 1×PBS), and the sample was allowed to enter the column completely by gravity and followed with 1.1 mL of 1×PBS. After the liquid completely passed through the column, the product was collected via elution in 1 mL increments with 1×PBS per sample vial. The $^{64}$Cu-E01-NODAGA was isolated in the second 1 ml fraction and measured to be 9.26 mCi in 1 ml of 1×PBS. This sample was analyzed using an analytical size exclusion HPLC method using an Agilent HPLC system equipped with a UV/vis detector (λ=280 nm), a posi-ram detector and Superdex 200 10/300 GL size-exclusion column (GE Healthcare Life Science, pore size 13 µm.) The flow rate was 0.5 mL/min, and the aqueous mobile phase was isocratic with 1×PBS with 0.02% NaN$_3$ for 60 minutes. The radiochemical purity was 99% using this system, and the product co-eluted with non-radioactive reference standard. Specific activity was calculated based on the equation of the 3-points calibration curve (y=656978x). About 100 µL of the product solution from vial 3 was injected onto the Superdex −200 size exclusion column. Product peak was collected and measured to be 0.74 mCi, UV counts of product peak was 156367 unit, and specific activity was 3.1 mCi/nmol.

Figure 3:
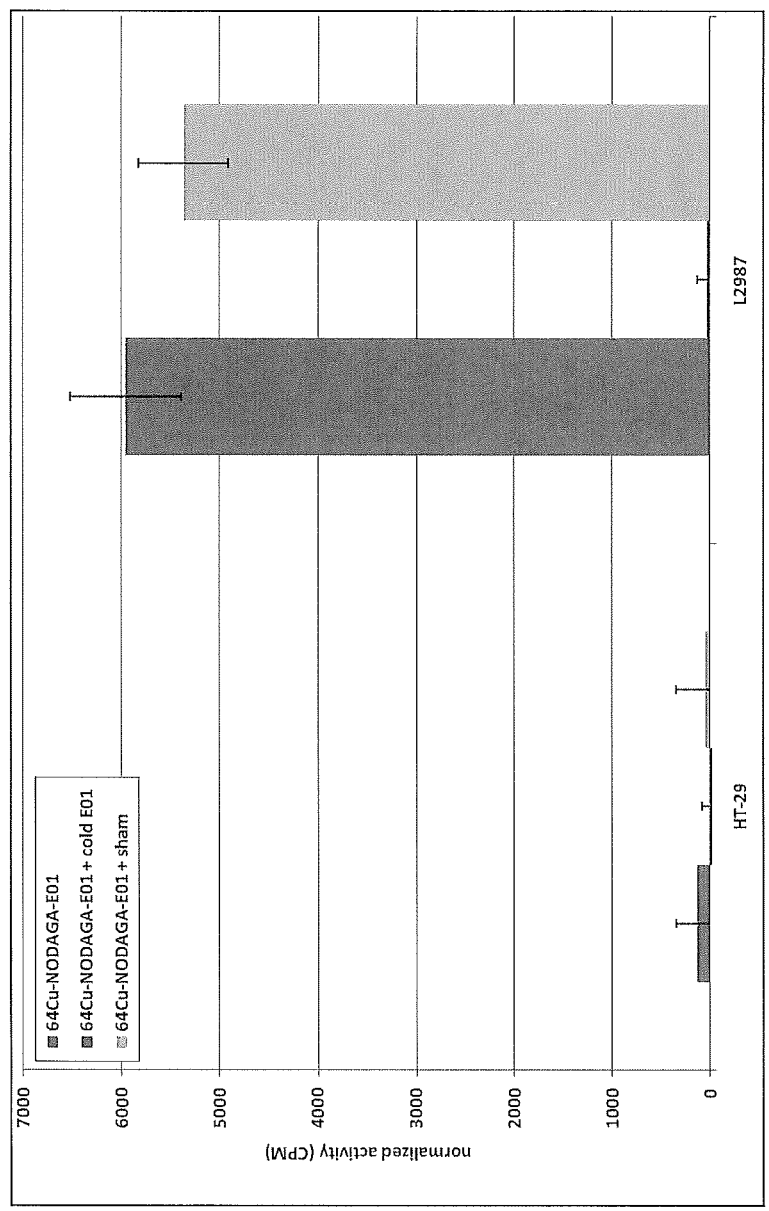
FIG. 3 is a graph demonstrating discrimination of hPD-L1-positive L2987 cells from hPD-L1-negative HT-29 cells with the $^{64}$Cu-E01 anti-PD-L1 Adnectin (with a NODAGA chelator). Specificity was confirmed by the reduction of cell-associated $^{64}$Cu-E01 when co-incubated with excess cold (unlabeled) E01 Adnectin.

Example 14: In Vitro Differentiation of PD-L1-Positive Cells from PD-L1-Negative Cells with an Anti-PD-L1 Adnectin Imaging Agent In this experiment, the $^{64}$Cu-E01 anti-PD-L1 Adnectin (NODAGA was used as a chelator) was tested for its ability to discriminate between hPD-L1-positive cells and hPD-L1-negative cells in vitro. Cell labeling was specific, as evidenced by differential association of $^{64}$Cu-E01 with hPD-L1-positive L2987 cells compared to hPD-L1-negative HT-29 cells (cell associated radioactivity was 44.6× higher in hPD-L1-positive L2987 cells). Specificity was further confirmed as evidenced by a marked reduction in cell-associated $^{64}$Cu-E01 when co-incubated with excess 450 nM cold (unlabeled) E01 Adnectin (99.6% reduction). Cell associated $^{18}$F-E01 was minimally reduced (9.9% reduction, not significant) when cells were co-incubated with 450 nM of a cold (unlabeled) non-PD-L1 binding Adnectin (FIG. 3).

1×10$^6$ hPD-L1-positive L2987 human lung carcinoma cells or hPD-L1-negative HT-29 human colorectal adenocarcinoma cells were placed into 5 mL culture tubes (n=3 tubes per condition). $^{64}$Cu-E01 Adnectin solution was prepared in PBS+0.5% BSA at a concentration of 300 nCi/200 µL. Portions of this solution were supplemented with either cold (unlabeled) E01 Adnectin or cold (unlabeled) non-PD-L1 binding Adnectin to a final concentration of 450 nM. Cell samples were centrifuged for 5 min at 200×g and then resuspended in 200 µL of the appropriate $^{64}$Cu-E01 Adnectin solution and incubated on ice for 1 hour. After the incubation period, cell samples were centrifuged at 200×g and the supernatant was discarded. Cell pellets were resuspended in 1 mL PBS+0.5% BSA and the wash procedure repeated for a total of 3 washes. Following the final wash, cells were again centrifuged at 200×g and the supernatant was discarded. The radioactivity of the remaining cell pellets was then measured by gamma counter.

Taken together, these results demonstrate the ability of the $^{64}$Cu-E01 Adnectin to differentiate PD-L1(+) vs. PD-L1(−) cells in vitro. Specificity was further demonstrated by a marked reduction in cell-associated radiotracer in samples co-incubated with 450 nM unlabeled anti-PD-L1 E01 Adnectin (and only a statistically insignificant reduction when co-incubated with 450 nM of a non-PD-L1 binding Adnectin). Similar experiments using different Adnectin variants as well as $^{18}$F as the radionuclide were conducted, with similar results.

Example 15: Distinguishing PD-L1-Positive Tumors from PD-L1-Negative Tumors with an Anti-PD-L1 Adnectin Imaging Agent For PET imaging, rapid blood clearance rates provide an advantage over more slowly clearing proteins, such as antibodies, by minimizing the amount of time needed for "background" probe signals to deplete from non-relevant tissue. In the clinic, long blood half-life antibody-based-PET tracers may require several days of waiting post injection before images can be collected. Rapid clearing probes open the door to high contrast images that can be collected on the same day the probe is injected, and very importantly, they can also serve to reduce overall radiation exposure to the animals studied or patients examined.

In this experiment, the $^{64}$Cu-A02 anti-PD-L1 Adnectin (NODAGA was used as the chelator), produced as described in the above Examples, was tested for its ability to discriminate between hPD-L1-positive tumors and hPD-L1-negative tumors in mice.

Mice bearing bilateral xenograft tumors were produced by introducing $1\times10^6$ hPD-L1(+) L2987 human lung carcinoma cells and $1.5\times10^6$ hPD-L1(−) HT-29 human colon carcinoma cells subcutaneously on opposite sides of the mouse. Once tumors reached approximately 300 mm$^3$ (approximately 2-3 weeks after cell implantation), animals were selected for imaging. For imaging, animals were placed under anesthesia with 2% isoflurane and tail vein catheters were installed. Mice were then placed into a custom animal holder with capacity for 4 animals, where they remained under anesthesia for the duration of the study. The animal holder was transferred to the microPET® F120™ scanner (Siemens Preclinical Solutions, Knoxville, Tenn.). The axial field of view of this instrument is 7.6 cm. With this limitation, animals were positioned such that the scanning region was from immediately in front of the eyes to approximately the base of the tail.

A 10-minute transmission image was first acquired using a $^{57}$Co point source for the purpose of attenuation correction of the final PET images. Following the transmission scan, radiotracer solutions were administered via the previously installed tail vein catheters and a 2 hour emission image was acquired. Injected radiotracer solutions consisted of either approximately 200 µCi $^{64}$Cu-A02 (with a NODAGA chelator) or 200 µCi $^{64}$Cu-A02 supplemented with 3 mg/kg final concentration of cold, unlabeled A02 Adnectin (based on individual animal weight). All injections were formulated in 200 µL saline prior to injection. Exact injected doses were calculated by taking direct measurements of the formulated dose and subtracting the radioactivity remaining in the syringe and the tail vein catheter.

Figure 4B:
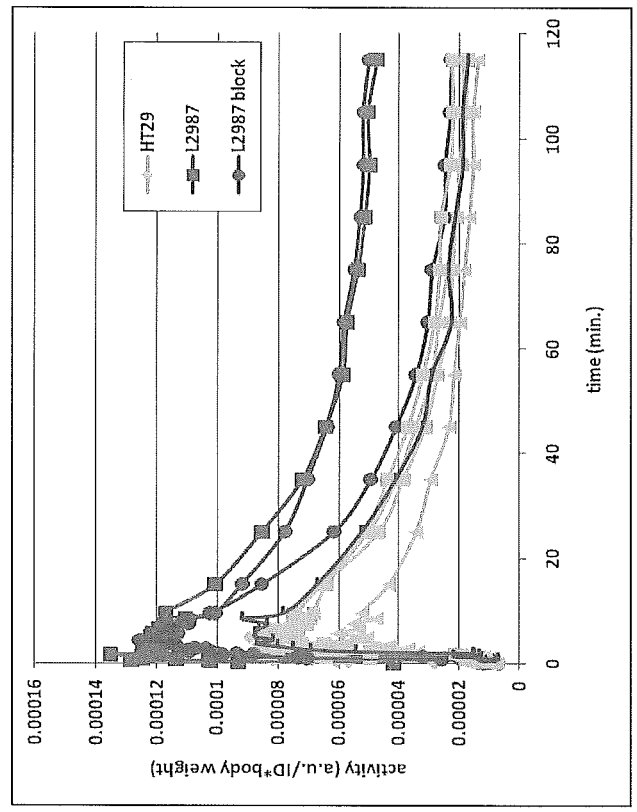
FIG. 4B is a graph depicting a time course of tumor labeling in hPD-L1 (+) [L2987] tumors. hPD-L1(−) [HT29] tumors and pulse chase experiment in hPD-L1(+) systems [L2987 block] show the specificity of the labelling.
Figure 4A:
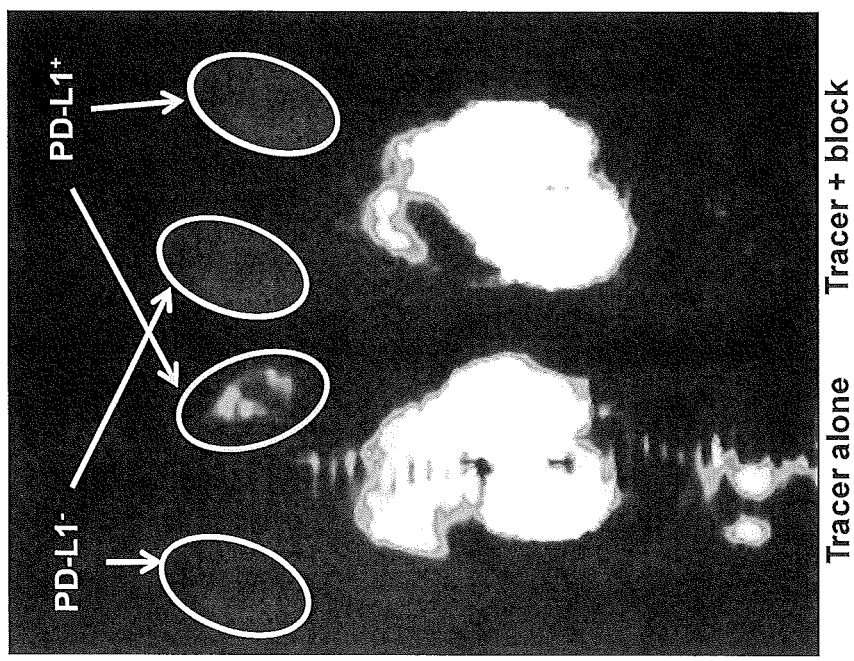
FIG. 4A is a PET image depicting the discrimination of hPD-L1 (+) from hPD-L1 (−) tumors in bilateral xenograft mice with a NODAGA-$^{64}$Cu-labeled A02 anti-PD-L1 Adnectin. Shown are summed 0 to 2 hour images showing areas of probe residence. Bright areas are tissues of greatest occupancy during exposure.

Images were reconstructed using a maximum a posteriori (MAP) algorithm with attenuation correction using the collected transmission images and corrected for radioisotope decay. In the final images, regions of interest (ROIs) were drawn around the tumor boundary using ASIPro software (Siemens Preclinical Solutions). Time-activity curves were calculated for each ROI to yield a quantitative view of radiotracer within the tumor volume over the course of the 2 hour emission image. For final comparison, individual time-activity curves were normalized based on the injected radiotracer dose for each specific animal. Radiotracer uptake was compared across tumors using the final 10 minutes of each time-activity curve (1 hour 50 minutes-2 h post-radiotracer injection). Using this methodology, radiotracer uptake in hPD-L1(+) L2987 xenografts was 3.05× that seen hPD-L1(−) HT-29 xenografts in animals receiving only the $^{64}$Cu-A02 radiotracer. In animals co-injected with the $^{64}$Cu-A02 radiotracer and 3 mg/kg unlabeled A02 Adnectin uptake in the hPD-L1(+) L2987 xenografts was only 1.04× that seen in hPD-L1(−) HT-29 xenografts (FIGS. 4A and 4B).

Figure 5:
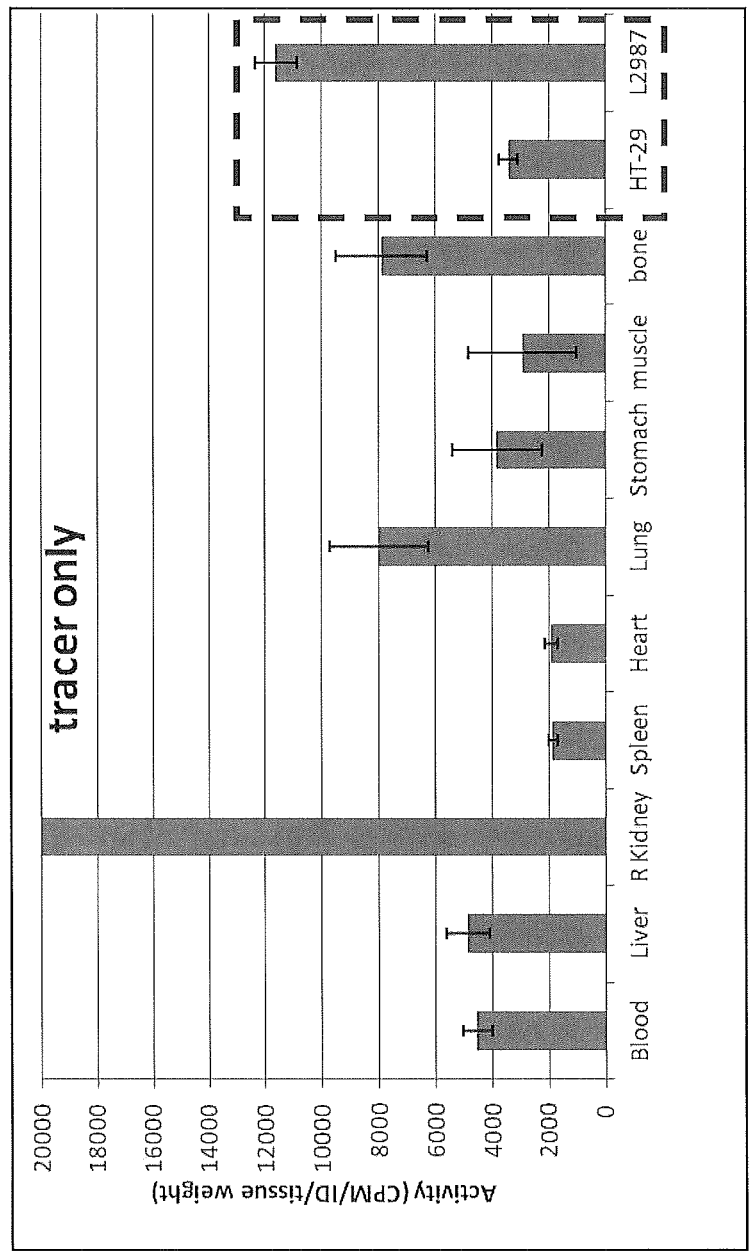
FIG. 5 is a graph depicting tissue distribution of the $^{18}$F-labeled A02 anti-PD-L1 Adnectin radiotracer in mice bearing bilateral hPD-L1(+) L2987 and hPD-L1(−) HT-29 xenografts as measured ex vivo by gamma counter.

For some studies, animals were sacrificed via cervical dislocation immediately following imaging. Necropsy was then performed on the animals, and individual tissues were collected (blood, heart, lung, liver, spleen, kidney, muscle, stomach, bone, L2987 tumor, and HT-29 tumor) into pre-weighed tubes. All tissues were then weighed again to determine the weight of each tissue. The radioactivity in each tissue was then directly measured ex vivo using a Perkin-Elmer Wizard3 gamma counter. For all tissues, measured values in counts per minute (CPM) were normalized to the injected radioactive dose for the individual animals and corrected for radioactive decay. These results were then plotted to show the biodistribution of the radiotracer. An example of this analysis for the $^{18}$F-A02 Adnectin radiotracer is shown in FIG. 5. These results demonstrate clear differential uptake of the radiotracer in hPD-L1(+) L2987 xenografts compared to hPD-L1(−) HT-29 xenografts. Furthermore, the only tissue with higher PD-L1 uptake was the kidney, which is expected as clearance of the $^{18}$F-A02 Adnectin is expected to be via kidney filtration based on the molecular weight of the molecule.

Taken together, these results provide direct visualization of differentiation of hPD-L1(+) versus hPD-L1(−) xenograft tumors in vivo. Specificity was further demonstrated by co-injection of 3 mg/kg unlabeled anti-PD-L1 A02 Adnectin, resulting in a reduction of radiotracer uptake in hPD-L1(+) tumors to the level of hPD-L1(−) xenografts. This further validates the use of anti-PD-L1 Adnectins for visualization of PD-L1 tissue expression using PET imaging. Similar experiments using $^{18}$F as the radionuclide were conducted in mice, and similar results were obtained, reaching a maximum radiotracer uptake ratio of 3.53:1 in hPD-L1(+) L2987 xenografts vs. hPD-L1(−) HT-29 xenografts using the $^{18}$F-A02 Adnectin radiotracer.

The anti-PD-L1 Adnectin-based imaging agents also showed similar results when performed in cynomolgus monkeys. In these studies, the $^{18}$F-E01 anti-PD-L1 Adnectin, produced as described in the above Examples, was tested for its ability to produce high-contrast images in cynomolgus monkeys. The anti-PD-L1 Adnectins described here maintain high affinity for cynomolgus PD-L1 (but have low affinity for rodent PD-L1). Furthermore, as cynomolgus monkeys do not contain PD-L1(+) tumors as in mouse models, imaging performance was assessed primarily on the background levels measured in the images in the context of endogenous PD-L1 expression (with low background enabling the potential for high-sensitivity detection of PD-L1(+) tissues). In these studies, background levels in the resulting PET images were very low, with notable radiotracer accumulation noted mainly in the kidneys, spleen, and bladder.

Cynomolgus male monkeys with a previously installed vascular access port (VAP) were anesthetized with 0.02 mg/kg atropine, 5 mg/kg Telazol and 0.01 mg/kg buprenorphine I.M. (all drawn into a single syringe). An i.v. catheter is then placed in the cephalic vessel for fluid administration during the imaging procedure to maintain hydration. Animals were intubated with an endotracheal tube—usually 3.0 mm and transferred to the imaging bed of a microPET® F220™ PET instrument (Siemens Preclinical Solutions, Knoxville, Tenn.). Anesthesia was maintained with isoflurane and oxygen and I.V. fluids (LRS) were administered at a rate of 6 ml/kg/hr during the imaging procedure. As the axial field of view of the microPET® F220™ instrument is only 7.6 cm, images over 5 distinct bed positions were acquired to create a composite image of the animals from just above the heart through approximately the pelvis.

For each field of view, a 10 minute transmission image was first acquired using a $^{57}$Co point source for the purpose of attenuation correction of the final PET images. Once transmission images were acquired for all bed positions, approximately 1.5 mCi (approximately 0.015 mg/kg) of the $^{18}$F-E01 Adnectin radiotracer was administered via the installed VAP. 5 minute duration emission scans were then sequentially acquired for each bed position, beginning at position 1 centered approximately at the heart and moving toward the pelvis of the animal. Once images were acquired at each position (1 through 5), the imaging bed was moved back to bed position 1 and the process was repeated. Using this procedure, a total of 5 distinct images were acquired for each bed position over the duration of the imaging study.

Figure 6:
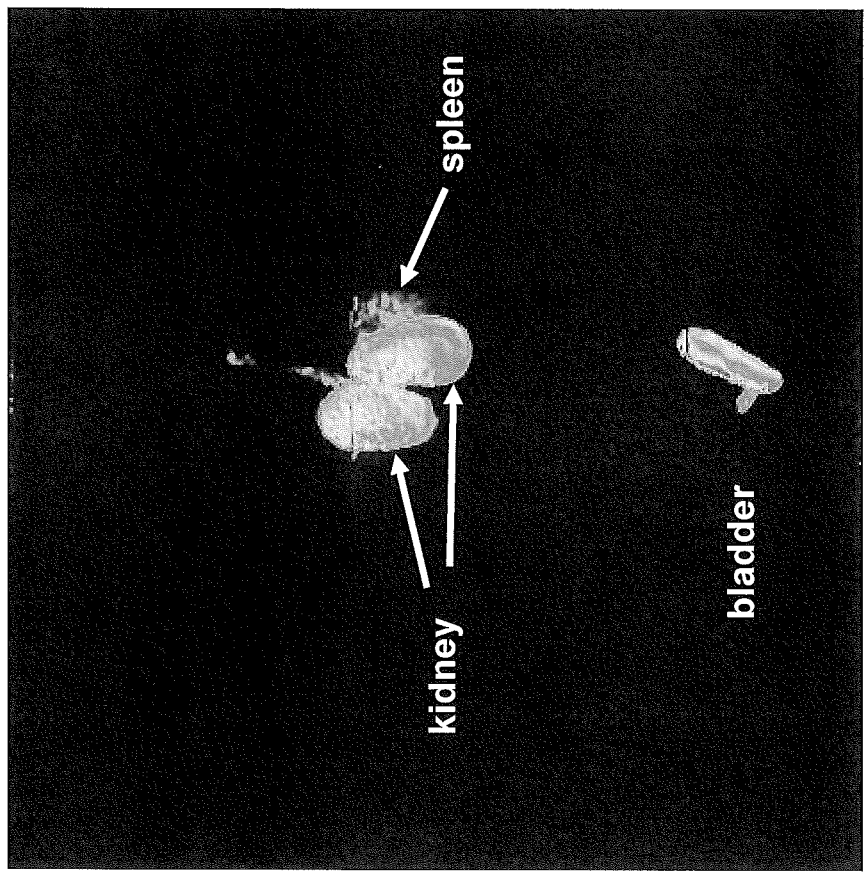
FIG. 6 is a composite image of $^{18}$F-labeled E01 anti-PD-L1 Adnectin distribution in cynomolgus monkey.

Individual images were reconstructed using a filtered back projection (FBP) algorithm with attenuation correction using the collected transmission images and corrected for radioisotope decay. Final composite images were then produced by aligning images from all 5 bed positions obtained from a single pass (i.e. a single composite image was produced from each set of sequential images from bed positions 1 through 5) covering the duration of the imaging study. Final images were visually inspected to note areas of visible radiotracer uptake (i.e. spleen, kidney, bladder) and background tissue (muscle) (FIG. 6). Background accumulation of $^{18}$F-E01 Adnectin was very low, with little signal visible in background tissues such as muscle. Additionally, uptake was verified in the spleen, which is believed to be PD-L1(+) based on mRNA expression. Thus, studies in cynomolgus monkeys demonstrate the potential for high-sensitivity PD-L1 imaging in the context of endogenous PD-L1.

In aggregate, PET studies in rodent and cynomolgus monkey show that $^{64}$Cu and $^{18}$F labeled anti-human PD-L1 Adnectins provide strong and specific probes for in vivo labeling of PD-L1 positive tissues with the potential for high-sensitivity detection of tissues with low level PD-L1 expression.

In vivo imaging experiments were also conducted with an anti-PD-L1 antibody, and the areas that this imaging agent detected were the same areas that were detected with the PD-L1 imaging agent, therefore confirming that anti-PD-L1 Adnectin imaging agents successfully detect PD-L1 positive cells in vivo.

Example 16: In Vitro Autoradiography of Human and Xenograft Tissue with [$^{18}$F]-E01 Anti-PD-L1 Adnectin Human lung tumor tissues were embedded in OCT and chilled in 2-methylbutane for 2-5 minutes until frozen. Samples were stored in −80° C. degree freezer until use. Human xenograft tissues were also included in the assay. Mice bearing bilateral xenografts were produced by introducing 4×10$^6$ hPD-L1(+) L2987 cells and 1.5×10$^6$ hPD-L1 (−) HT-29 t cells subcutaneously into opposite flanks of nu/nu mice. Once resulting xenograft tumors reached appropriate size (approx. 200-300 mm$^3$), mice were anesthetized with 2% isoflurane and sacrificed via cervical dislocation. Fresh tumor tissues were excised, immersed into OCT and chilled in 2-methylbutane for 2-5 minutes until frozen. The tissues were then wrapped in foil/ZIPLOC® bag and stored at −80° C. until use. For all tissues (human lung tumor and xenografts) sections of 5 µm thickness (collected as 2 sections/slide) were cut using a cryostat, thaw-mounted on glass microscope slides, and allowed to air dry for approximately 30 minutes.

Blocking studies with cold (unlabeled) A02 Adnectin at 0.025 nM, 0.25 nM, 2.5 nM and 25 nM respectively and 25 nM non-PD-L1 binding Adnectin were conducted using the following conditions. The individual slides, 1 slide per concentration, were placed in plastic slide cassettes and pre-incubated in Dako serum-free protein block solution for 30 minutes. Slides were then transferred to glass slide incubation chambers for further incubation. Separately, a stock solution of 0.25 nM $^{18}$F-A02 Adnectin was produced by diluting 10.6 µl of the original stock radioligand solution (7064 nM at the time of experiment) with 300 ml of PBS+0.5% BSA. From this stock solution, 40 ml was added to each incubation chamber. One of these chambers contained only the radioligand buffer solution, which is referred to as the total binding section. Other incubation chambers received 40 ml of this stock solution along with the relevant concentration of blocking compound (unlabeled A02 Adnectin at 0.025 nM, 0.25 nM, 2.5 nM, or 25 nM or unlabeled non-PD-L1 binding Adnectin at 25 nM). Slides were incubated in the individual buffer solutions for 1 hour at room temperature to reach maximum binding. After incubation, slides from each treatment group were removed from the incubation solutions and placed in an ice-cold wash buffer (PBS+0.5% BSA) for 3 minutes and rinsed 4 separate times. Slides were then dried under a stream of cold air for approximately 30 minutes. The air-dried slides were exposed by placing the slides onto an imaging plate (BAS-SR 3545S) overnight at room temperature. The imaging plate was scanned using the bioimaging analyzer (Fujifilm Fluorescent Image Analyzer, FLA-9000). The pixel size of the autoradiogram images was 100 µm. Image analysis was performed using the Multi-Gauge software. The regions of interest (ROIs) were drawn to surround the entire tumor tissue in all study groups. Autogradiography signal from tissue-associated radioactivity was quantified from these ROIs.

Figure 7:
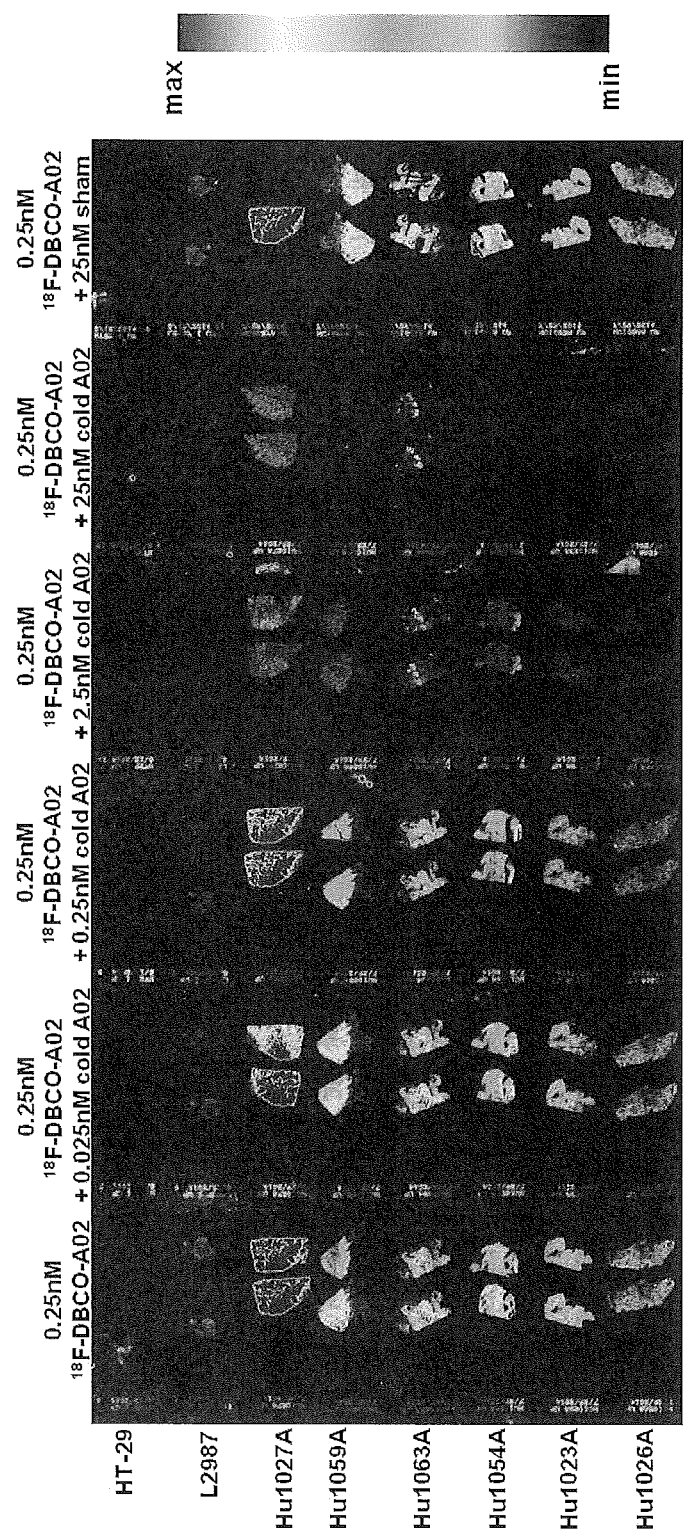
FIG. 7 is an image depicting in vitro autoradiography of xenograft and human lung tissues labelled with the 0.25 nM $^{18}$F-DBCO-A02 anti-PD-L1 Adnectin co-incubated with the indicated concentrations of cold A02 Adnectin.

The apparent displacement of the $^{18}$F-A02 Adnectin radioligand when compared to the total binding sections was determined for 4 different concentrations (0.025 nM, 0.25 nM, 2.5 nM and 25 nM) of unlabeled A02 Adnectin in both human lung tumor sections as well as human xenograft sections. A dose dependent displacement of $^{18}$F-A02 was seen in all tissue sections with the addition of unlabeled A02 Adnectin, while 25 nM non-PD-L1 binding Adnectin showed minimal blockade in all tissues compared to total binding (FIG. 7).

Figure 8:
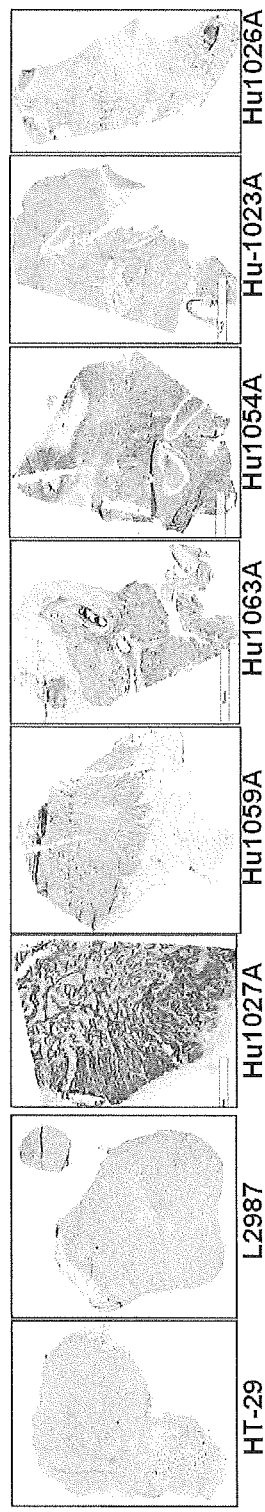
FIG. 8 depicts immunohistochemistry images of xenograft and human lung tumor specimens labelled with anti-PD-L1 Adnectins to demonstrate tumor expression of hPD-L1.

Serial 5 µm tissue sections from each tissue were subjected to an anti-human-PD-L1 immunohistochemical procedure to verify the level of PD-L1 antigen expression in the samples (FIG. 8).

Taken together, these results provide direct visualization of PD-L1 in both human lung tumor samples as well as human xenograft tissues. The level of radioligand binding in the individual tissues corresponds with the intensity of PD-L1 staining of frozen sections by IHC. In addition, the dose dependent blockade of the receptor with unlabeled anti-PD-L1 A02 Adnectin (and lack of blockade with unlabeled non-PD-L1 binding Adnectin), further validates the use of $^{18}$F-A02 for visualization of PD-L1 tissue expression using PET imaging.

Example 17: Automated Preparation of [$^{18}$F]-3-(2-(2-(2-(2-azidoethoxy)ethoxy)ethoxy)ethoxy)-2-fluoropyridine According to the General Procedure for Radiosynthesis Using Commercial GE TRACERlab FX2 N Synthesis Unit

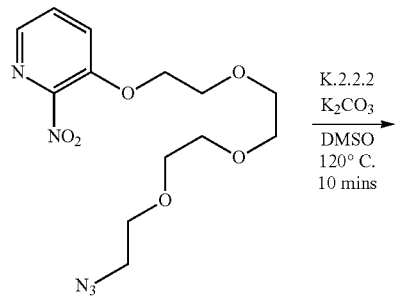

TABLE 4

| | |
|---|---|
| Vial 1 (V1) | 16 mg K.2.2.2, 3 mg Potassium carbonate, dissolved in 0.1 ml of distilled water and 1.4 ml of acetonitrile |
| Vial 3 (V3) | 2 mg 3-(2-(2-(2-(2-azidoethoxy)ethoxy)ethoxy)ethoxy)-2-nitropyridine in 0.5 ml DMSO |
| Vial 4 (V4) | 4 ml of distilled water |
| Vial 14 (V14) | 3 ml of 100% ethanol |
| Dilution Flask | 15 ml of distilled water |
| Cartridge 1 (C1) | tC18 6 cc 1 g sep pack |
| HPLC Column | Luna C18(2), 250 × 10 mm, 5 |m, Phenomenex |
| HPLC Solvent | 35% acetonitrile in an aqueous 0.1% trifluoroacetitic acid solution |
| HPLC flow | 4.6 ml/min |

Example 18 Automated Preparation of [$^{18}$F]-3-(2-(2-(2-(2-azidoethoxy)ethoxy)ethoxy)ethoxy)-2-fluoropyridine According to the General Procedure for Radiosynthesis on IBA Synthera Synthesis Unit

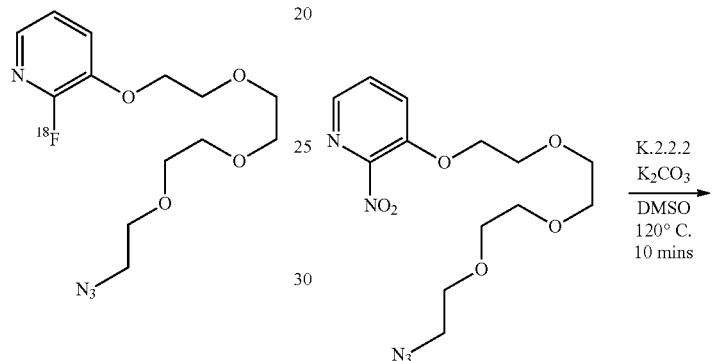

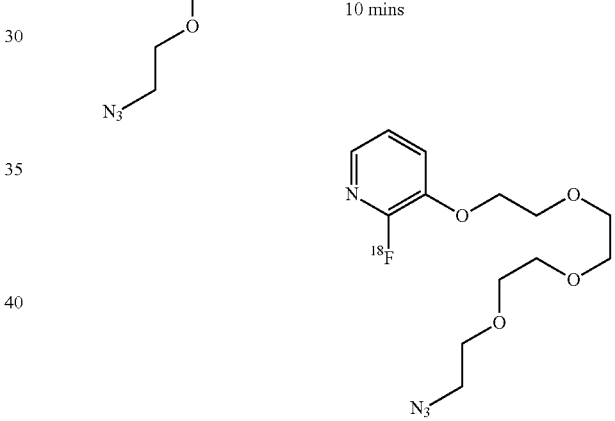

Procedure:

The automated synthesis of [$^{18}$F]-3-(2-(2-(2-(2-azidoethoxy)ethoxy)ethoxy)ethoxy)-2-fluoropyridine was carried out using a non-cassette type GE TRACERlab FX2 N Synthesis module. The setup of the synthesis unit is summarized in Table 4. The aqueous [$^{18}$F]-Fluoride solution (2.0 ml, 29.6 GBq/800 mCi) was delivered to a Sep-Pak light QMA [The Sep-Pak light QMA cartridge was pre-conditioned sequentially with 5 ml of 0.5 M potassium bicarbonate, 5 ml of deionized water, and 5 ml of acetonitrile before use.] Upon completion of this transfer, the aqueous [$^{18}$F] fluoride was released from the QMA Sep-Pak by the addition of the elution mixture (from "V1") into the reactor. The solvent was evaporated under a gentle stream of nitrogen and vacuum. The solution of precursor (from "V3") was added to the dried cryptand residue and this reaction mixture was heated 120° C. for 10 minutes. Then 4 ml of distilled water (from "V4") was added to the crude reaction mixture in the reactor and the mixture was transferred to the 5 ml sample injection loop of the semi-preparative HPLC via a liquid sensor which controls the end of the loading. The mixture was loaded onto the semi-preparative HPLC column (Luna C18(2), 250×10 mm, Phenomenex). A mixture of 35% acetonitrile in an aqueous 0.1% trifluoroacetic acid solution was flushed through the column at a rate of 4.6 ml per minute. The product was collected from this HPLC column into the dilution flask which contained 15 ml distilled water and its entire contents were transferred to a tC18 1 gram, solid phase extraction cartridge. 352 mCi (13 GBq) of [$^{18}$F]-3-(2-(2-(2-(2-azidoethoxy)ethoxy)ethoxy)ethoxy)-2-fluoropyridine was released from this cartridge (from "V14") with 3 ml of ethanol and may be used to generate $^{18}$F labeled biologic products by taking advantage of "click" azide-alkyne reaction with the appropriate biologic containing an alkynes.

Procedure:

The automated synthesis of [$^{18}$F]-3-(2-(2-(2-(2-azidoethoxy)ethoxy)ethoxy)ethoxy)-2-fluoropyridine was carried out using a cassette type IBA Synthera Synthesis module and an appropriately assembled integrator fluidic processor kit. The integrator fluidic processor (IFP) kit was loaded with appropriate precursors for this synthesis and is summarized in Table 5. The purification was performed on an Varian HPLC unit. The filling of the injection loop of the HPLC was controlled by a steady stream of nitrogen on the HPLC unit. The setup of both automates are summarized in Table 2. The aqueous [$^{18}$F]-Fluoride solution (2.0 ml, 29.6 GBq/800 mCi) was delivered to a Sep-Pak light QMA [The Sep-Pak light QMA cartridge was pre-conditioned sequentially with 5 ml of 0.5 M potassium bicarbonate, 5 ml of deionized water, and 5 ml of acetonitrile before use.] Upon completion of this transfer, the aqueous [$^{18}$F] fluoride was released from the QMA Sep-Pak by the addition of the elution mixture (from "V1") into the reactor. The solvent was evaporated under a gentle stream of nitrogen and vacuum. The solution of precursor (from "V2") was added to the dried cryptand residue and this reaction mixture was heated 120° C. for 10 minutes. Then 3 ml of distilled water (from "V4") was added to the crude reaction mixture in the reactor and the mixture is transferred to the 5 ml sample injection loop of the semi-preparative HPLC via a liquid sensor which controls the end of the loading. The mixture was loaded onto the semi-preparative HPLC column (Luna C18(2). 250×10 mm, Phenomenex). A mixture of 35% acetonitrile in an aqueous 0.1% trifluoroacetic acid solution was flushed through the column at a rate of 4.6 ml per minute. The product was collected from this HPLC column into the dilution flask which contained 15 ml distilled water and its entire contents were transferred to a tC18 1 gram, solid phase extraction cartridge. 325 mCi (12 GBq) of [$^{18}$F]-3-(2-(2-(2-(2-azidoethoxy)ethoxy)ethoxy)ethoxy)-2-fluoropyridine was released from this cartridge with 3 ml of ethanol and may be used to generate $^{18}$F labeled biologic products by taking advantage of "click" azide-alkyne reaction with the appropriate biologic containing an alkynes.

TABLE 5

| | |
|---|---|
| Vial 1 (V1) | 22 mg K.2.2.2, 4 mg Potassium carbonate, dissolved in 0.3 ml of distilled water and 0.3 ml of acetonitrile |
| Vial 2 (V2) | 2 mg 3-(2-(2-(2-(2-azidoethoxy)ethoxy)ethoxy)ethoxy)-2-nitropyridine in 0.5 ml DMSO |
| Vial 4 (V4) | 3 ml of distilled water |
| Dilution Flask | 15 ml of distilled water |
| Cartridge 1 (C1) | tC18 6 cc 1 g sep pack |
| HPLC Column | Luna C18(2), 250 × 10 mm, 5 l m, Phenomenex |
| HPLC Solvent | 35% acetonitrile in an aqueous 0.1% trifluoro-acetitic acid solution |
| HPLC flow | 4.6 ml/min |

Example 19: Synthesis of $^{68}$Ga-Based Anti-PD-L1 Adnectin Probes

Synthesis of $^{68}$Ga-E01-NODAGA

[$^{68}$Ga]-Gallium chloride in 0.1N hydrochloric acid solution was neutralized with 32 mg of sodium acetate (NaOAc) for 4 minutes at ambient temperature, the resultant solution was stirred to ensure the entire volume was properly mixed. This solution was then added to E01-NODAGA (15 μL of 1.3 mg/mL) solution and the crude reaction was gently pipetted to allow mixing followed by resting at ambient temperature for 15 minutes. The contents of crude reaction mixture were transferred to a PD-10 desalting column that was pre-activated with 20 mL of 1× phosphate buffered saline (PBS, pH 7.4) buffer prior to loading of sample. An additional 1.5 mL of 1×PBS was added to the column, followed by an additional 0.8 ml 1×PBS solution and these fractions were discarded. [$^{68}$Ga]-E01-NODAGA was then collected after a 1.4 mL elution of the PD-10 column to give 5.78 mCi (214 MBq) as the desired product. Quality control was measured using a reverse phase HPLC system using an Agilent PLRP-S HPLC column Size: 250×4.60 mm, 8 μm, 280 nm and a mobile phase of 0.1% Formic Acid in distilled water and acetonitrile. A gradient method was used where the percentage of acetonitrile was increased linearly from 10% to 45% over a 30 minute time frame. [$^{68}$Ga]-E01-NODAGA co-eluted with reference standard at the 22 minute mark of the HPLC chromatogram. Radiochemical purity was measured to be 98% using this method. [$^{68}$Ga]-E01-NODAGA also co-eluted with reference material at the 20 minute mark using a size exclusion chromatography, (SEC) Column: GE Superdex 200 GL Size: 10×300 mm, 280 nm.

```
  1 MGVSD VPRDL EVVAA TPTSL LISWR AQLSP SFYYR ITYGE

41 TGGNS PVQEF TVPND VMTAT ISGLK PGVDY TITVY AVTTH

81 GVYFY SPISI NYRTP CHHHH HH
```

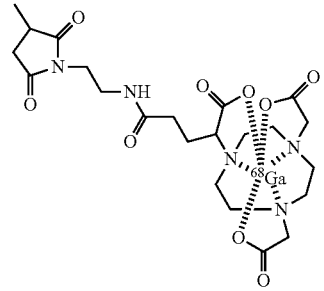

TABLE 3

| SEQUENCE LISTING | |
|---|---|
| SEQ ID DESCRIPTION | SEQUENCE |
| 1 Full length wild-type human $^{10}$Fn3 domain | VSDVPRDLEVVAATPTSLLISWDAPAVTVRYYRITYGETGGNSPVQEFTVPGSKSTATISGLKPGVDYTITVYAVTGRGDSPASSKPISINYRT |
| 2 Core wild-type human $^{10}$Fn3 domain | EVVAATPTSLLISWDAPAVTVRYYRITYGETGGNSPVQEFTVPGSKSTATISGLKPGVDYTITVYAVTGRGDSPASSKPISINYRT |
| 3 Corem $^{10}$Fn3-based scaffold with variable AB, BC, CD, DE, EF, and FG loops | EVVAA(Z)$_a$LLISW(Z)$_x$YRITY(Z)$_b$FTV(Z)$_y$ATISGL(Z)$_c$YTITVYA(Z)$_z$ISINYRT |
| 4 Core $^{10}$Fn3-based scaffold with variable BC, DE, and FG loops | EVVAATPTSLLISW(Z)$_x$YRITYGETGGNSPVQEFTV(Z)$_y$ATISGLKPGVDYTITVYA(Z)$_z$ISINYRT |
| 5 ATI-968 core (aka ADX_1760_C01) | EVVAATPTSLLISW<u>IAPFYNVI</u>YYRITYGETGGNSPVQEFTV<u>PGTGYT</u>ATISGLKPGVDYTITVYA<u>VTDGASIASYAFP</u>ISINYRT |
| 6 ATI-968 BC loop | IAPFYNVIY |
| 7 ATI-968 DE loop | PGTGYT |

TABLE 3-continued

SEQUENCE LISTING

| SEQ ID | DESCRIPTION | SEQUENCE |
|---|---|---|
| 8 | ATI-968 FG loop | VTDGASIASYAFP |
| 9 | ATI-968 w/N leader | GVSDVPRDLEVVAATPTSLLISW<u>IAPFYNVIY</u>YRITYGETGGNSPV<br>QEFTV<u>PGTGYT</u>ATISGLKPGVDYTITVYA<u>VTDGASIASYAFP</u>ISIN<br>YRT |
| 10 | ATI-968 w/N leader + his tag | GVSDVPRDLEVVAATPTSLLISW<u>IAPFYNVIY</u>YRITYGETGGNSPV<br>QEFTV<u>PGTGYT</u>ATISGLKPGVDYTITVYA<u>VTDGASIASYAFP</u>ISIN<br>YRTHHHHHH |
| 11 | ATI-968 w/N leader and C tail | GVSDVPRDLEVVAATPTSLLISW<u>IAPFYNVIY</u>YRITYGETGGNSPV<br>QEFTV<u>PGTGYT</u>ATISGLKPGVDYTITVYA<u>VTDGASIASYAFP</u>ISIN<br>YRTEIDKPSQ |
| 12 | ATI-968 w/N leader and C tail + his tag | GVSDVPRDLEVVAATPTSLLISW<u>IAPFYNVIY</u>YRITYGETGGNSPV<br>QEFTV<u>PGTGYT</u>ATISGLKPGVDYTITVYA<u>VTDGASIASYAFP</u>ISIN<br>YRTEIDKPSQHHHHHH |
| 13 | ATI-968 w/N leader and modified C-terminus including PC | GVSDVPRDLEVVAATPTSLLISW<u>IAPFYNVIY</u>YRITYGETGGNSPV<br>QEFTV<u>PGTGYT</u>ATISGLKPGVDYTITVYA<u>VTDGASIASYAFP</u>ISIN<br>YRTPC |
| 14 | ATI-968 w/N leader and modified C-terminus including PC + his tag | GVSDVPRDLEVVAATPTSLLISW<u>IAPFYNVIY</u>YRITYGETGGNSPV<br>QEFTV<u>PGTGYT</u>ATISGLKPGVDYTITVYA<u>VTDGASIASYAFP</u>ISIN<br>YRTPCHHHHHH |
| 15 | ATI-968 - full length | MGVSDVPRDLEVVAATPTSLLISWIAPFYNVIYYRITYGETGGNSP<br>VQEFTVPGTGYTATISGLKPGVDYTITVYAVTDGASIASYAFPISI<br>NYRTEIDKPSQHHHHHH |
| 16 | ATI-968 - core (nucleotide sequence) | GAAGTGGTTGCTGCCACCCCCACCAGCCTGCTGATCAGCTGGATCG<br>CTCCGTTCTACAATGTCATCTATTACCGCATCACTTACGGCGAAAC<br>AGGAGGCAATAGCCCTGTCCAGGAGTTCACTGTGCCTGGTACTGGT<br>TATACAGCTACAATCAGCGGCCTTAAACCTGGCGTTGATTATACCA<br>TCACTGTGTATGCTGTCACTGATGGAGCATCCATTGCTTCATACGC<br>GTTTCCAATTTCCATTAATTACCGCACA |
| 17 | ATI-968 w/N leader (nucleotide sequence with N-terminal methionine) | ATGGGAGTTTCTGATGTGCCGCGCGACCTGGAAGTGGTTGCTGCCA<br>CCCCCACCAGCCTGCTGATCAGCTGGATCGCTCCGTTCTACAATGT<br>CATCTATTACCGCATCACTTACGGCGAAACAGGAGGCAATAGCCCT<br>GTCCAGGAGTTCACTGTGCCTGGTACTGGTTATACAGCTACAATCA<br>GCGGCCTTAAACCTGGCGTTGATTATACCATCACTGTGTATGCTGT<br>CACTGATGGAGCATCCATTGCTTCATACGCGTTTCCAATTTCCATT<br>AATTACCGCACA |
| 18 | ATI-968 w/N leader and modified C-terminus including PC (nucleotide sequence with N-terminal methionine) | ATGGGAGTTTCTGATGTGCCGCGCGACCTGGAAGTGGTTGCTGCCA<br>CCCCCACCAGCCTGCTGATCAGCTGGATCGCTCCGTTCTACAATGT<br>CATCTATTACCGCATCACTTACGGCGAAACAGGAGGCAATAGCCCT<br>GTCCAGGAGTTCACTGTGCCTGGTACTGGTTATACAGCTACAATCA<br>GCGGCCTTAAACCTGGCGTTGATTATACCATCACTGTGTATGCTGT<br>CACTGATGGAGCATCCATTGCTTCATACGCGTTTCCAATTTCCATT<br>AATTACCGCACACCGTGC |
| 19 | ATI-968 w/N leader and C tail + his tag (nucleotide sequence with N-terminal methionine) | ATGGGAGTTTCTGATGTGCCGCGCGACCTGGAAGTGGTTGCTGCCA<br>CCCCCACCAGCCTGCTGATCAGCTGGATCGCTCCGTTCTACAATGT<br>CATCTATTACCGCATCACTTACGGCGAAACAGGAGGCAATAGCCCT<br>GTCCAGGAGTTCACTGTGCCTGGTACTGGTTATACAGCTACAATCA<br>GCGGCCTTAAACCTGGCGTTGATTATACCATCACTGTGTATGCTGT<br>CACTGATGGAGCATCCATTGCTTCATACGCGTTTCCAATTTCCATT<br>AATTACCGCACAGAAATTGACAAACCATCCCAGCACCATCACCACC<br>ACCACTGA |
| 20 | ATI-964 core (parent of ADX_5322_A02) | EVVAATPTSLLISW<u>SYDGSIERY</u>YRITYGETGGNSPVQEFTV<u>PPDQ<br>KT</u>ATISGLKPGVDYTITVYA<u>VRLEEAHYYRESP</u>ISINYRT |
| 21 | ATI-964 BC loop | SYDGSIERY |
| 22 | ATI-964 DE loop | PPDQKT |
| 23 | ATI-964 FG loop | VRLEEAHYYRESP |
| 24 | ATI-964 w/N leader | GVSDVPRDLEVVAATPTSLLISW<u>SYDGSIERY</u>YRITYGETGGNSPV<br>QEFTV<u>PPDQKT</u>ATISGLKPGVDYTITVYA<u>VRLEEAHYYRESP</u>ISIN<br>YRT |

TABLE 3-continued

SEQUENCE LISTING

| SEQ ID | DESCRIPTION | SEQUENCE |
|---|---|---|
| 25 | ATI-964 w/N leader + his tag | GVSDVPRDLEVVAATPTSLLISW<u>SYDGSIERY</u>YRITYGETGGNSPV QEFTV<u>PPDQKT</u>ATISGLKPGVDYTITVYA<u>VRLEEAHYYRESPI</u>SIN YRTHHHHHH |
| 26 | ATI-964 w/N leader and C tail | GVSDVPRDLEVVAATPTSLLISWSYDGSIERYYRITYGETGGNSPV QEFTVPPDQKTATISGLKPGVDYTITVYAVRLEEAHYYRESPISIN YRTEIDKPSQ |
| 27 | ATI-964 w/N leader and C tail + his tag | GVSDVPRDLEVVAATPTSLLISWSYDGSIERYYRITYGETGGNSPV QEFTVPPDQKTATISGLKPGVDYTITVYAVRLEEAHYYRESPISIN YRTEIDKPSQHHHHHH |
| 28 | ATI-964 w/N leader and modified C-terminus including PC | GVSDVPRDLEVVAATPTSLLISWSYDGSIERYYRITYGETGGNSPV QEFTVPPDQKTATISGLKPGVDYTITVYAVRLEEAHYYRESPISIN YRTPC |
| 29 | ATI-964 w/N leader and modified C-terminus including PC + his tag | GVSDVPRDLEVVAATPTSLLISWSYDGSIERYYRITYGETGGNSPV QEFTVPPDQKTATISGLKPGVDYTITVYAVRLEEAHYYRESPISIN YRTPCHHHHHH |
| 30 | ATI-964 - full length | MGVSDVPRDLEVVAATPTSLLISWSYDGSIERYYRITYGETGGNSP VQEFTVPPDQKTATISGLKPGVDYTITVYAVRLEEAHYYRESPISI NYRTEIDKPSQHHHHHH |
| 31 | ATI-964 - core (nucleotide sequence) | GAAGTGGTTGCTGCCACCCCCACCAGCCTGCTGATCAGCTGGTCTT ACGACGGTTCGATTGAACGTTATTACCGCATCACTTACGGCGAAAC AGGAGGCAATAGCCCTGTCCAGGAGTTCACTGTGCCTCCGGATCAG AAGACAGCTACCATCAGCGGCCTTAAACCTGGCGTTGATTATACCA TCACTGTGTATGCTGTCAGGCTGGAAGAAGCTCATTACTATCGAGA GTCTCCAATTTCCATTAATTACCGCACA |
| 32 | ATI-964 w/ N leader (nucleotide sequence with N-terminal methionine) | ATGGGAGTTTCTGATGTGCCGCGCGACCTGGAAGTGGTTGCTGCCA CCCCCACCAGCCTGCTGATCAGCTGGTCTTACGACGGTTCGATTGA ACGTTATTACCGCATCACTTACGGCGAAACAGGAGGCAATAGCCCT GTCCAGGAGTTCACTGTGCCTCCGGATCAGAAGACAGCTACCATCA GCGGCCTTAAACCTGGCGTTGATTATACCATCACTGTGTATGCTGT CAGGCTGGAAGAAGCTCATTACTATCGAGAGTCTCCAATTTCCATT AATTACCGCACA |
| 33 | ATI-964 w/N leader and modified C-terminus including PC (nucleotide sequence with N-terminal methionine) | ATGGGAGTTTCTGATGTGCCGCGCGACCTGGAAGTGGTTGCTGCCA CCCCCACCAGCCTGCTGATCAGCTGGTCTTACGACGGTTCGATTGA ACGTTATTACCGCATCACTTACGGCGAAACAGGAGGCAATAGCCCT GTCCAGGAGTTCACTGTGCCTCCGGATCAGAAGACAGCTACCATCA GCGGCCTTAAACCTGGCGTTGATTATACCATCACTGTGTATGCTGT CAGGCTGGAAGAAGCTCATTACTATCGAGAGTCTCCAATTTCCATT AATTACCGCACACCGTGC |
| 34 | ATI-964 w/N leader and C tail + his tag (nucleotide sequence with N-terminal methionine) | ATGGGAGTTTCTGATGTGCCGCGCGACCTGGAAGTGGTTGCTGCCA CCCCCACCAGCCTGCTGATCAGCTGGTCTTACGACGGTTCGATTGA ACGTTATTACCGCATCACTTACGGCGAAACAGGAGGCAATAGCCCT GTCCAGGAGTTCACTGTGCCTCCGGATCAGAAGACAGCTACCATCA GCGGCCTTAAACCTGGCGTTGATTATACCATCACTGTGTATGCTGT CAGGCTGGAAGAAGCTCATTACTATCGAGAGTCTCCAATTTCCATT AATTACCGCACAGAAATTGACAAACCATCCCAGCACCATCACCACC ACCACTGA |
| 35 | ATI-965 core | EVVAATPTSLLISWTAYDSVDKYYRITYGETGGNSPVQEFTVGPRH HTATISGLKPGVDYTITVYAVYHTEPGYHAHMPISINYRT |
| 36 | ATI-965 BC loop | TAYDSVDKY |
| 37 | ATI-965 DE loop | GPRHHT |
| 38 | ATI-965 FG loop | VYHTEPGYHAHMP |
| 39 | ATI-965 w/N leader | GVSDVPRDLEVVAATPTSLLISWTAYDSVDKYYRITYGETGGNSPV QEFTVGPRHHTATISGLKPGVDYTITVYAVYHTEPGYHAHMPISIN YRT |
| 40 | ATI-965 w/N leader + his tag | GVSDVPRDLEVVAATPTSLLISWTAYDSVDKYYRITYGETGGNSPV QEFTVGPRHHTATISGLKPGVDYTITVYAVYHTEPGYHAHMPISIN YRTHHHHHH |

TABLE 3-continued

SEQUENCE LISTING

| SEQ ID | DESCRIPTION | SEQUENCE |
|---|---|---|
| 41 | ATI-965 w/N leader and C tail | GVSDVPRDLEVVAATPTSLLISWTAYDSVDKYYRITYGETGGNSPV QEFTVGPRHHTATISGLKPGVDYTITVYAVYHTEPGYHAHMPISIN YRTEIDKPSQ |
| 42 | ATI-965 w/N leader and C tail + his tag | GVSDVPRDLEVVAATPTSLLISWTAYDSVDKYYRITYGETGGNSPV QEFTVGPRHHTATISGLKPGVDYTITVYAVYHTEPGYHAHMPISIN YRTEIDKPSQHHHHHH |
| 43 | ATI-965 w/N leader and modified C-terminus including PC | GVSDVPRDLEVVAATPTSLLISWTAYDSVDKYYRITYGETGGNSPV QEFTVGPRHHTATISGLKPGVDYTITVYAVYHTEPGYHAHMPISIN YRTPC |
| 44 | ATI-965 w/N leader and modified C-terminus including PC + his tag | GVSDVPRDLEVVAATPTSLLISWTAYDSVDKYYRITYGETGGNSPV QEFTVGPRHHTATISGLKPGVDYTITVYAVYHTEPGYHAHMPISIN YRTPCHHHHHH |
| 45 | ATI-965 - full length | MGVSDVPRDLEVVAATPTSLLISWTAYDSVDKYYRITYGE TGGNSPVQEFTVGPRHHTATISGLKPGVDYTITVYAVYHTEPGYHA HMPISINYRTEIDKPSQHHHHHH |
| 46 | ATI-965 - core (nucleotide sequence) | GAAGTGGTTGCTGCCACCCCCACCAGCCTGCTGATCAGCTGGACTG CATACGACTCTGTTGACAAATATTACCGCATCACTTACGGCGAAAC AGGAGGCAATAGCCCTGTCCAGGAGTTCACTGTGGGCCCTAGACAT CACACAGCTACCATCAGCGGCCTTAAACCTGGCGTTGATTATACCA TCACTGTGTATGCTGTCTATCACACTGAACCGGGCTATCATGCTCA TATGCCAATTTCCATTAATTACCGCACA |
| 47 | ATI-965 w/N leader (nucleotide sequence with N-terminal methionine) | ATGGGAGTTTCTGATGTGCCGCGCGACCTGGAAGTGGTTGCTGCCA CCCCCACCAGCCTGCTGATCAGCTGGACTGCATACGACTCTGTTGA CAAATATTACCGCATCACTTACGGCGAAACAGGAGGCAATAGCCCT GTCCAGGAGTTCACTGTGGGCCCTAGACATCACACAGCTACCATCA GCGGCCTTAAACCTGGCGTTGATTATACCATCACTGTGTATGCTGT CTATCACACTGAACCGGGCTATCATGCTCATATGCCAATTTCCATT AATTACCGCACA |
| 48 | ATI-965 w/N leader and modified C-terminus including PC (nucleotide sequence with N-terminal methionine) | ATGGGAGTTTCTGATGTGCCGCGCGACCTGGAAGTGGTTGCTGCCA CCCCCACCAGCCTGCTGATCAGCTGGACTGCATACGACTCTGTTGA CAAATATTACCGCATCACTTACGGCGAAACAGGAGGCAATAGCCCT GTCCAGGAGTTCACTGTGGGCCCTAGACATCACACAGCTACCATCA GCGGCCTTAAACCTGGCGTTGATTATACCATCACTGTGTATGCTGT CTATCACACTGAACCGGGCTATCATGCTCATATGCCAATTTCCATT AATTACCGCACACCGTGC |
| 49 | ATI-965 w/N leader and C tail + his tag (nucleotide sequence with N-terminal methionine) | ATGGGAGTTTCTGATGTGCCGCGCGACCTGGAAGTGGTTGCTGCCA CCCCCACCAGCCTGCTGATCAGCTGGACTGCATACGACTCTGTTGA CAAATATTACCGCATCACTTACGGCGAAACAGGAGGCAATAGCCCT GTCCAGGAGTTCACTGTGGGCCCTAGACATCACACAGCTACCATCA GCGGCCTTAAACCTGGCGTTGATTATACCATCACTGTGTATGCTGT CTATCACACTGAACCGGGCTATCATGCTCATATGCCAATTTCCATT AATTACCGCACAGAAATTGACAAACCATCCCAGCACCATCACCACC ACCACTGA |
| 50 | ATI-966 core | EVVAATPTSLLISWHRFSSIMAYYRITYGETGGNSPVQEFTVAGSV NTATISGLKPGVDYTITVYAVTIHNVSFPISINYRT |
| 51 | ATI-966 BC loop | HRFSSIMAY |
| 52 | ATI-966 DE loop | AGSVNT |
| 53 | ATI-966 FG loop | VTIHNVSFP |
| 54 | ATI-966 w/N leader | GVSDVPRDLEVVAATPTSLLISWHRFSSIMAYYRITYGETGGNSPV QEFTVAGSVNTATISGLKPGVDYTITVYAVTIHNVSFPISINYRT |
| 55 | ATI-966 w/N leader + his tag | GVSDVPRDLEVVAATPTSLLISWHRFSSIMAYYRITYGETGGNSPV QEFTVAGSVNTATISGLKPGVDYTITVYAVTIHNVSFPISINYRTH HHHHH |
| 56 | ATI-966 w/N leader and C tail | GVSDVPRDLEVVAATPTSLLISWHRFSSIMAYYRITYGETGGNSPV QEFTVAGSVNTATISGLKPGVDYTITVYAVTIHNVSFPISINYRTE IDKPSQ |

TABLE 3-continued

SEQUENCE LISTING

| SEQ ID | DESCRIPTION | SEQUENCE |
|---|---|---|
| 57 | ATI-966 w/N leader and C tail + his tag | GVSDVPRDLEVVAATPTSLLISWHRFSSIMAYYRITYGETGGNSPV QEFTVAGSVNTATISGLKPGVDYTITVYAVTIHNVSFPISINYRTE IDKPSQHHHHHH |
| 58 | ATI-966 w/N leader and modified C-terminus including PC | GVSDVPRDLEVVAATPTSLLISWHRFSSIMAYYRITYGETGGNSPV QEFTVAGSVNTATISGLKPGVDYTITVYAVTIHNVSFPISINYRTP C |
| 59 | ATI-966 w/N leader and modified C-terminus including PC + his tag | GVSDVPRDLEVVAATPTSLLISWHRFSSIMAYYRITYGETGGNSPV QEFTVAGSVNTATISGLKPGVDYTITVYAVTIHNVSFPISINYRTP CHHHHHH |
| 60 | ATI-966 - full length | MGVSDVPRDLEVVAATPTSLLISWHRFSSIMAYYRITYGETGGNSP VQEFTVAGSVNTATISGLKPGVDYTITVYAVTIHNVSFPISINYRT EIDKPSQHHHHHH |
| 61 | ATI-966 - core (nucleotide sequence) | GAAGTGGTTGCTGCCACCCCCACCAGCCTGCTGATCAGCTGGCATA GGTTCTCTTCTATCATGGCGTATTACCGCATCACTTACGGCGAAAC AGGAGGCAATAGCCCTGTCCAGGAGTTCACTGTGGCTGGCTCTGTT AACACAGCTACCATCAGCGGCCTTAAACCTGGCGTTGATTATACCA TCACTGTGTATGCTGTCACGATCCATAACGTTTCTTTCCCAATTTC CATTAATTACCGCACA |
| 62 | ATI-966w/N leader (nucleotide sequence with N-terminal methionine) | ATGGGAGTTTCTGATGTGCCGCGCGACCTGGAAGTGGTTGCTGCCA CCCCCACCAGCCTGCTGATCAGCTGGCATAGGTTCTCTTCTATCAT GGCGTATTACCGCATCACTTACGGCGAAACAGGAGGCAATAGCCCT GTCCAGGAGTTCACTGTGGCTGGCTCTGTTAACACAGCTACCATCA GCGGCCTTAAACCTGGCGTTGATTATACCATCACTGTGTATGCTGT CACGATCCATAACGTTTCTTTCCCAATTTCCATTAATTACCGCACA |
| 63 | ATI-966 w/N leader and modified C-terminus including PC (nucleotide sequence with N-terminal methionine) | ATGGGAGTTTCTGATGTGCCGCGCGACCTGGAAGTGGTTGCTGCCA CCCCCACCAGCCTGCTGATCAGCTGGCATAGGTTCTCTTCTATCAT GGCGTATTACCGCATCACTTACGGCGAAACAGGAGGCAATAGCCCT GTCCAGGAGTTCACTGTGGCTGGCTCTGTTAACACAGCTACCATCA GCGGCCTTAAACCTGGCGTTGATTATACCATCACTGTGTATGCTGT CACGATCCATAACGTTTCTTTCCCAATTTCCATTAATTACCGCACA CCGTGC |
| 64 | ATI-966 w/N leader and C tail + his tag (nucleotide sequence with N-terminal methionine) | ATGGGAGTTTCTGATGTGCCGCGCGACCTGGAAGTGGTTGCTGCCA CCCCCACCAGCCTGCTGATCAGCTGGCATAGGTTCTCTTCTATCAT GGCGTATTACCGCATCACTTACGGCGAAACAGGAGGCAATAGCCCT GTCCAGGAGTTCACTGTGGCTGGCTCTGTTAACACAGCTACCATCA GCGGCCTTAAACCTGGCGTTGATTATACCATCACTGTGTATGCTGT CACGATCCATAACGTTTCTTTCCCAATTTCCATTAATTACCGCACA GAAATTGACAAACCATCCCAGCACCATCACCACCACCACTGA |
| 65 | ATI-967 core (parent of ADX_5417_E01) | EVVAATPTSLLISW<u>QGQLSPSFY</u>YRITYGETGGNSPVQEFTV<u>PVAS GT</u>ATISGLKPGVDYTITVYA<u>VTSHGIYFYAP</u>ISINYRT |
| 66 | ATI-967 BC loop | QGQLSPSFY |
| 67 | ATI-967 DE loop | PVASGT |
| 68 | ATI-967 FG loop | VTSHGIYFYAP |
| 69 | ATI-967 w/N leader | GVSDVPRDLEVVAATPTSLLISWQGQLSPSFYYRITYGETGGNSPV QEFTVPVASGTATISGLKPGVDYTITVYAVTSHGIYFYAPISINYR T |
| 70 | ATI-967 w/N leader + his tag | GVSDVPRDLEVVAATPTSLLISWQGQLSPSFYYRITYGETGGNSPV QEFTVPVASGTATISGLKPGVDYTITVYAVTSHGIYFYAPISINYR THHHHHH |
| 71 | ATI-967 w/N leader and C tail | GVSDVPRDLEVVAATPTSLLISWQGQLSPSFYYRITYGETGGNSPV QEFTVPVASGTATISGLKPGVDYTITVYAVTSHGIYFYAPISINYR TEIDKPSQ |
| 72 | ATI-967 w/N leader and C tail + his tag | GVSDVPRDLEVVAATPTSLLISWQGQLSPSFYYRITYGETGGNSPV QEFTVPVASGTATISGLKPGVDYTITVYAVTSHGIYFYAPISINYR TEIDKPSQHHHHHH |
| 73 | ATI-967 w/N leader and modified C-terminus including PC | GVSDVPRDLEVVAATPTSLLISWQGQLSPSFYYRITYGETGGNSPV QEFTVPVASGTATISGLKPGVDYTITVYAVTSHGIYFYAPISINYR TPC |

TABLE 3-continued

SEQUENCE LISTING

| SEQ ID | DESCRIPTION | SEQUENCE |
|---|---|---|
| 74 | ATI-967 w/N leader and modified C-terminus including PC + his tag | GVSDVPRDLEVVAATPTSLLISWQGQLSPSFYYRITYGETGGNSPV QEFTVPVASGTATISGLKPGVDYTITVYAVTSHGIYFYAPISINYR TPCHHHHHH |
| 75 | ATI-967 - full length | MGVSDVPRDLEVVAATPTSLLISWQGQLSPSFYYRITYGETGGNSP VQEFTVPVASGTATISGLKPGVDYTITVYAVTSHGIYFYAPISINY RTEIDKPSQHHHHHH |
| 76 | ATI-967 - core (nucleotide sequence) | GAAGTGGTTGCTGCCACCCCCACCAGCCTGCTGATCAGCTGGCAGG GACAGCTGTCTCCGTCTTTCTATTACCGAATCACTTACGGCGAAAC AGGAGGCAATAGCCCTGTCCAGGAGTTCACTGTGCCTGTTGCTAGT GGGACAGCTACCATCAGCGGCCTTAAACCTGGCGTTGATTATACCA TCACTGTGTATGCTGTCACTTCTCATGGCATATACTTCTACGCTCC AATTTCCATTAATTACCGCACA |
| 77 | ATI-967 w/N leader (nucleotide sequence with N-terminal methionine) | ATGGGAGTTTCTGATGTGCCGCGCGACCTGGAAGTGGTTGCTGCCA CCCCCACCAGCCTGCTGATCAGCTGGCAGGGACAGCTGTCTCCGTC TTTCTATTACCGAATCACTTACGGCGAAACAGGAGGCAATAGCCCT GTCCAGGAGTTCACTGTGCCTGTTGCTAGTGGGACAGCTACCATCA GCGGCCTTAAACCTGGCGTTGATTATACCATCACTGTGTATGCTGT CACTTCTCATGGCATATACTTCTACGCTCCAATTTCCATTAATTAC CGCACA |
| 78 | ATI-967 w/N leader and modified C-terminus including PC (nucleotide sequence with N-terminal methionine) | ATGGGAGTTTCTGATGTGCCGCGCGACCTGGAAGTGGTTGCTGCCA CCCCCACCAGCCTGCTGATCAGCTGGCAGGGACAGCTGTCTCCGTC TTTCTATTACCGAATCACTTACGGCGAAACAGGAGGCAATAGCCCT GTCCAGGAGTTCACTGTGCCTGTTGCTAGTGGGACAGCTACCATCA GCGGCCTTAAACCTGGCGTTGATTATACCATCACTGTGTATGCTGT CACTTCTCATGGCATATACTTCTACGCTCCAATTTCCATTAATTAC CGCACACCGTGC |
| 79 | ATI-967 w/N leader and C tail + his tag (nucleotide sequence with N-terminal methionine) | ATGGGAGTTTCTGATGTGCCGCGCGACCTGGAAGTGGTTGCTGCCA CCCCCACCAGCCTGCTGATCAGCTGGCAGGGACAGCTGTCTCCGTC TTTCTATTACCGAATCACTTACGGCGAAACAGGAGGCAATAGCCCT GTCCAGGAGTTCACTGTGCCTGTTGCTAGTGGGACAGCTACCATCA GCGGCCTTAAACCTGGCGTTGATTATACCATCACTGTGTATGCTGT CACTTCTCATGGCATATACTTCTACGCTCCAATTTCCATTAATTAC CGCACAGAAATTGACAAACCATCCCAGCACCATCACCACCACCACT GAT |
| 80 | ADX_5322_A02 core | EVVAATPTSLLISW<u>SYDGPIDRY</u>YRITYGETGGNSPVQEFTV<u>PPDQ KT</u>ATISGLKPGVDYTITVYA<u>VRLEEAHYNREFP</u>ISINYRT |
| 81 | ADX_5322_A02 BC loop | SYDGPIDRY |
| 82 | ADX_5322_A02 DE loop | PPDQKT |
| 83 | ADX_5322_A02 FG loop | VRLEEAHYNREFP |
| 84 | ADX_5322_A02 w/N leader | GVSDVPRDLEVVAATPTSLLISWSYDGPIDRYYRITYGETGGNSPV QEFTVPPDQKTATISGLKPGVDYTITVYAVRLEEAHYNREFPISIN YRT |
| 85 | ADX_5322_A02 w/N leader + his tag | GVSDVPRDLEVVAATPTSLLISWSYDGPIDRYYRITYGETGGNSPV QEFTVPPDQKTATISGLKPGVDYTITVYAVRLEEAHYNREFPISIN YRTHHHHHH |
| 86 | ADX_5322_A02 w/N leader and C tail | GVSDVPRDLEVVAATPTSLLISWSYDGPIDRYYRITYGETGGNSPV QEFTVPPDQKTATISGLKPGVDYTITVYAVRLEEAHYNREFPISIN YRTEIDKPSQ |
| 87 | ADX_5322_A02 w/N leader and C tail + his tag | GVSDVPRDLEVVAATPTSLLISWSYDGPIDRYYRITYGETGGNSPV QEFTVPPDQKTATISGLKPGVDYTITVYAVRLEEAHYNREFPISIN YRTEIDKPSQHHHHHH |
| 88 | ADX_5322_A02 w/N leader and modified C-terminus including PC | GVSDVPRDLEVVAATPTSLLISWSYDGPIDRYYRITYGETGGNSPV QEFTVPPDQKTATISGLKPGVDYTITVYAVRLEEAHYNREFPISIN YRTPC |
| 89 | ADX_5322_A02 w/N leader and modified C-terminus including PC + his tag | GVSDVPRDLEVVAATPTSLLISWSYDGPIDRYYRITYGETGGNSPV QEFTVPPDQKTATISGLKPGVDYTITVYAVRLEEAHYNREFPISIN YRTPCHHHHHH |

TABLE 3-continued

SEQUENCE LISTING

| SEQ ID | DESCRIPTION | SEQUENCE |
|---|---|---|
| 90 | ADX_5322_A02-Mal-DBCO-FFPF18 | GVSDVPRDLEVVAATPTSLLISWSYDGPIDRYYRITYGETGGNSPV<br>QEFTVPPDQKTATISGLKPGVDYTITVYAVRLEEAHYNREFPISIN<br>YRTPC-[Maleamide-DBCO-FFP(18F)] |
| 91 | ADX_5322_A02 full length | MGVSDVPRDLEVVAATPTSLLISWSYDGPIDRYYRITYGETGGNSP<br>VQEFTVPPDQKTATISGLKPGVDYTITVYAVRLEEAHYNREFPISI<br>NYRTPCHHHHHH |
| 92 | ADX_5322_A02 - core (nucleotide sequence) | GAAGTGGTTGCTGCCACCCCCACCAGCCTGCTGATCAGCTGGTCTT<br>ACGATGGCCCAATTGACCGGTATTACCGCATCACTTACGGCGAAAC<br>AGGAGGCAATAGCCCTGTCCAGGAGTTCACTGTGCCTCCGGATCAG<br>AAGACAGCTACCATCAGCGGCCTTAAACCTGGCGTTGATTATACCA<br>TCACTGTGTATGCTGTCCGGCTGGAAGAAGCTCATTACAATCGAGA<br>GTTTCCAATTTCCATTAATTACCGCACA |
| 93 | ADX_5322_A02 w/N leader (nucleotide sequence with N-terminal methionine) | ATGGGAGTTTCTGATGTGCCGCGCGACCTGGAAGTGGTTGCTGCCA<br>CCCCCACCAGCCTGCTGATCAGCTGGTCTTACGATGGCCCAATTGA<br>CCGGTATTACCGCATCACTTACGGCGAAACAGGAGGCAATAGCCCT<br>GTCCAGGAGTTCACTGTGCCTCCGGATCAGAAGACAGCTACCATCA<br>GCGGCCTTAAACCTGGCGTTGATTATACCATCACTGTGTATGCTGT<br>CCGGCTGGAAGAAGCTCATTACAATCGAGAGTTTCCAATTTCCATT<br>AATTACCGCACA |
| 94 | ADX_5322_A02 w/N leader and modified C-terminus including PC (nucleotide sequence with N-terminal methionine) | ATGGGAGTTTCTGATGTGCCGCGCGACCTGGAAGTGGTTGCTGCCA<br>CCCCCACCAGCCTGCTGATCAGCTGGTCTTACGATGGCCCAATTGA<br>CCGGTATTACCGCATCACTTACGGCGAAACAGGAGGCAATAGCCCT<br>GTCCAGGAGTTCACTGTGCCTCCGGATCAGAAGACAGCTACCATCA<br>GCGGCCTTAAACCTGGCGTTGATTATACCATCACTGTGTATGCTGT<br>CCGGCTGGAAGAAGCTCATTACAATCGAGAGTTTCCAATTTCCATT<br>AATTACCGCACACCGTGC |
| 95 | ADX_5322_A02 w/N leader and C tail + his tag (nucleotide sequence with N-terminal methionine) | ATGGGAGTTTCTGATGTGCCGCGCGACCTGGAAGTGGTTGCTGCCA<br>CCCCCACCAGCCTGCTGATCAGCTGGTCTTACGATGGCCCAATTGA<br>CCGGTATTACCGCATCACTTACGGCGAAACAGGAGGCAATAGCCCT<br>GTCCAGGAGTTCACTGTGCCTCCGGATCAGAAGACAGCTACCATCA<br>GCGGCCTTAAACCTGGCGTTGATTATACCATCACTGTGTATGCTGT<br>CCGGCTGGAAGAAGCTCATTACAATCGAGAGTTTCCAATTTCCATT<br>AATTACCGCACACCGTGCCACCATCACCACCACCACTGA |
| 96 | ADX_5417_E01 core | EVVAATPTSLLISWRAQLSPSFYYRITYGETGGNSPVQEFTVPNDV<br>MTATISGLKPGVDYTITVYAVTTHGVYFYSPISINYRT |
| 97 | ADX_5417_E01 BC loop | RAQLSPSFY |
| 98 | ADX_5417_E01 DE loop | PNDVMT |
| 99 | ADX_5417_E01 FG loop | VTTHGVYFYSP |
| 100 | ADX_5417_E01 w/N leader | GVSDVPRDLEVVAATPTSLLISWRAQLSPSFYYRITYGETGGNSPV<br>QEFTVPNDVMTATISGLKPGVDYTITVYAVTTHGVYFYSPISINYR<br>T |
| 101 | ADX_5417_E01 w/N leader + his tag | GVSDVPRDLEVVAATPTSLLISWRAQLSPSFYYRITYGETGGNSPV<br>QEFTVPNDVMTATISGLKPGVDYTITVYAVTTHGVYFYSPISINYR<br>THHHHHH |
| 102 | ADX_5417_E01 w/N leader and C tail | GVSDVPRDLEVVAATPTSLLISWRAQLSPSFYYRITYGETGGNSPV<br>QEFTVPNDVMTATISGLKPGVDYTITVYAVTTHGVYFYSPISINYR<br>TEIDKPSQ |
| 103 | ADX_5417_E01 w/N leader and C tail + his tag | GVSDVPRDLEVVAATPTSLLISWRAQLSPSFYYRITYGETGGNSPV<br>QEFTVPNDVMTATISGLKPGVDYTITVYAVTTHGVYFYSPISINYR<br>TEIDKPSQHHHHHH |
| 104 | ADX_5417_E01 w/N leader and modified C-terminus including PC | GVSDVPRDLEVVAATPTSLLISWRAQLSPSFYYRITYGETGGNSPV<br>QEFTVPNDVMTATISGLKPGVDYTITVYAVTTHGVYFYSPISINYR<br>TPC |

TABLE 3-continued

SEQUENCE LISTING

| SEQ ID | DESCRIPTION | SEQUENCE |
|---|---|---|
| 105 | ADX_5417_E01 w/N leader and modified C-terminus including PC + his tag | GVSDVPRDLEVVAATPTSLLISWRAQLSPSFYYRITYGETGGNSPV QEFTVPNDVMTATISGLKPGVDYTITVYAVTTHGVYFYSPISINYR TPCHHHHHH |
| 106 | ADX-5417_E01 - Mal-DBCO-FFPF18 | GVSDVPRDLEVVAATPTSLLISWRAQLSPSFYYRITYGETGGNSPV QEFTVPNDVMTATISGLKPGVDYTITVYAVTTHGVYFYSPISINYR TPC-[Maleamide-DBCO-FFP(18F)] |
| 107 | ADX-5417_E01 full length | MGVSDVPRDLEVVAATPTSLLISWRAQLSPSFYYRITYGETGGNSP VQEFTVPNDVMTATISGLKPGVDYTITVYAVTTHGVYFYSPISINY RTPCHHHHHH |
| 108 | ADX-5417_E01 - core (nucleotide sequence) | GAAGTGGTTGCTGCCACCCCCACCAGCCTGCTGATCAGCTGGAGGG CTCAGCTGTCTCCGTCTTTCTATTACCGCATCACTTACGGCGAAAC AGGAGGCAATAGCCCTGTCCAGGAGTTCACTGTGCCTAATGATGTA ATGACAGCTACCATCAGCGGCCTTAAACCTGGCGTTGATTATACCA TCACTGTGTATGCTGTCACTACTCATGGTGTTTATTTCTACTCACC AATTTCCATTAATTACCGCACA |
| 109 | ADX_5417_E01 w/N leader (nucleotide sequence with N-terminal methionine) | ATGGGAGTTTCTGATGTGCCGCGCGACCTGGAAGTGGTTGCTGCCA CCCCCACCAGCCTGCTGATCAGCTGGAGGGCTCAGCTGTCTCCGTC TTTCTATTACCGCATCACTTACGGCGAAACAGGAGGCAATAGCCCT GTCCAGGAGTTCACTGTGCCTAATGATGTAATGACAGCTACCATCA GCGGCCTTAAACCTGGCGTTGATTATACCATCACTGTGTATGCTGT CACTACTCATGGTGTTTATTTCTACTCACCAATTTCCATTAATTAC CGCACA |
| 110 | ADX_5417_E01 w/N leader and modified C-terminus including PC (nucleotide sequence with N-terminal methionine) | ATGGGAGTTTCTGATGTGCCGCGCGACCTGGAAGTGGTTGCTGCCA CCCCCACCAGCCTGCTGATCAGCTGGAGGGCTCAGCTGTCTCCGTC TTTCTATTACCGCATCACTTACGGCGAAACAGGAGGCAATAGCCCT GTCCAGGAGTTCACTGTGCCTAATGATGTAATGACAGCTACCATCA GCGGCCTTAAACCTGGCGTTGATTATACCATCACTGTGTATGCTGT CACTACTCATGGTGTTTATTTCTACTCACCAATTTCCATTAATTAC CGCACACCGTGC |
| 111 | ADX_5417_E01 w/N leader and C tail + his tag (nucleotide sequence with N-terminal methionine) | ATGGGAGTTTCTGATGTGCCGCGCGACCTGGAAGTGGTTGCTGCCA CCCCCACCAGCCTGCTGATCAGCTGGAGGGCTCAGCTGTCTCCGTC TTTCTATTACCGCATCACTTACGGCGAAACAGGAGGCAATAGCCCT GTCCAGGAGTTCACTGTGCCTAATGATGTAATGACAGCTACCATCA GCGGCCTTAAACCTGGCGTTGATTATACCATCACTGTGTATGCTGT CACTACTCATGGTGTTTATTTCTACTCACCAATTTCCATTAATTAC CGCACACCGTGCCACCATCACCACCACCACTGA |
| 112 | ATI_1420_A10 core | EVVAATPTSLLISWPYPSYYIEYRITYGETGGNSPVQEFTVQSMKA TISGLKPGVDYTITVYAIRHPGMLEFGISINYRT |
| 113 | ATI_1420_A10 BC loop | PYPSYYIE |
| 114 | ATI_1420_A10 DE loop | QSMKA |
| 115 | ATI_1420_A10 FG loop | IRHPGMLEFG |
| 116 | ATI_1420_A10 w/N leader | GVSDVPRDLEVVAATPTSLLISWPYPSYYIEYRITYGETGGNSPVQ EFTVQSMKATISGLKPGVDYTITVYAIRHPGMLEFGISINYRT |
| 117 | ATI_1420_A10 w/N leader + his tag | GVSDVPRDLEVVAATPTSLLISWPYPSYYIEYRITYGETGGNSPVQ EFTVQSMKATISGLKPGVDYTITVYAIRHPGMLEFGISINYRTHHH HHH |
| 118 | ATI_1420_A10 w/N leader and C tail | GVSDVPRDLEVVAATPTSLLISWPYPSYYIEYRITYGETGGNSPVQ EFTVQSMKATISGLKPGVDYTITVYAIRHPGMLEFGISINYRTEID KPSQ |
| 119 | ATI_1420_A10 w/N leader and C tail + his tag | GVSDVPRDLEVVAATPTSLLISWPYPSYYIEYRITYGETGGNSPVQ EFTVQSMKATISGLKPGVDYTITVYAIRHPGMLEFGISINYRTEID KPSQHHHHHH |
| 120 | ATI_1420_A10 w/N leader and modified C-terminus including PC | GVSDVPRDLEVVAATPTSLLISWPYPSYYIEYRITYGETGGNSPVQ EFTVQSMKATISGLKPGVDYTITVYAIRHPGMLEFGISINYRTPC |

TABLE 3-continued

SEQUENCE LISTING

| SEQ ID | DESCRIPTION | SEQUENCE |
|---|---|---|
| 121 | ATI_1420_A10 w/N leader and modified C-terminus including PC + his tag | GVSDVPRDLEVVAATPTSLLISWPYPSYYIEYRITYGETGGNSPVQ EFTVQSMKATISGLKPGVDYTITVYAIRHPGMLEFGISINYRTPCH HHHHH |
| 122 | ATI_1420_A10 - full length | MGVSDVPRDLEVVAATPTSLLISWPYPSYYIEYRITYGETGGNSPV QEFTVQSMKATISGLKPGVDYTITVYAIRHPGMLEFGISINYRTEI DKPSQHHHHHH |
| 123 | ATI_1420_B09 core | EVVAATPTSLLISWHKFSSLMSYRITYGETGGNSPVQEFTVGSV NATISGLKPGVDYTITVYAIHNVGFISINYRT |
| 124 | ATI_1420_B09 BC loop | HKFSSLMS |
| 125 | ATI_1420_B09 DE loop | GSVN |
| 126 | ATI_1420_B09 FG loop | IHNVGF |
| 127 | ATI_1420_B09 w/N leader | GVSDVPRDLEVVAATPTSLLISWHKFSSLMSYRITYGETGGNSP VQEFTVGSVNATISGLKPGVDYTITVYAIHNVGFISINYRT |
| 128 | ATI_1420_B09 w/N leader + his tag | GVSDVPRDLEVVAATPTSLLISWHKFSSLMSYRITYGETGGNSP VQEFTVGSVNATISGLKPGVDYTITVYAIHNVGFISINYRTHHH HHH |
| 129 | AATI_1420_B09 w/N leader and C tail | GVSDVPRDLEVVAATPTSLLISWHKFSSLMSYRITYGETGGNSP VQEFTVGSVNATISGLKPGVDYTITVYAIHNVGFISINYRTEID KPSQ |
| 130 | ATI_1420_B09 w/N leader and C tail + his tag | GVSDVPRDLEVVAATPTSLLISWHKFSSLMSYRITYGETGGNSP VQEFTVGSVNATISGLKPGVDYTITVYAIHNVGFISINYRTEID KPSQHHHHHH |
| 131 | ATI_1420_B09 w/N leader and modified C-terminus including PC | GVSDVPRDLEVVAATPTSLLISWHKFSSLMSYRITYGETGGNSP VQEFTVGSVNATISGLKPGVDYTITVYAIHNVGFISINYRTPC |
| 132 | ATI_1420_B09 w/N leader and modified C-terminus including PC + his tag | GVSDVPRDLEVVAATPTSLLISWHKFSSLMSYRITYGETGGNSP VQEFTVGSVNATISGLKPGVDYTITVYAIHNVGFISINYRTPCH HHHHH |
| 133 | ATI_1420_B09 - full length | MGVSDVPRDLEVVAATPTSLLISWHKFSSLMSYRITYGETGGNS PVQEFTVGSVNATISGLKPGVDYTITVYAIHNVGFISINYRTEI DKPSQHHHHHH |
| 134 | ATI_1420_C02 core | EVVAATPTSLLISWRIKSYYAYRITYGETGGNSPVQEFTVRQHV ATISGLKPGVDYTITVYARLGDVELVYEISINYRT |
| 135 | ATI_1420_C02 BC loop | RIKSYYA |
| 136 | ATI_1420_C02 DE loop | RQHV |
| 137 | ATI_1420_C02 FG loop | RLGDVELVYE |
| 138 | ATI_1420_C02 w/N leader | GVSDVPRDLEVVAATPTSLLISWRIKSYYAYRITYGETGGNSPV QEFTVRQHVATISGLKPGVDYTITVYARLGDVELVYEISINYRT |
| 139 | ATI_1420_C02 w/N leader + his tag | GVSDVPRDLEVVAATPTSLLISWHKFSSLMSYRITYGETGGNSP VQEFTVGSVNATISGLKPGVDYTITVYAIHNVGFISINYRTHHH HHH |
| 140 | ATI_1420_C02 w/N leader and C tail | GVSDVPRDLEVVAATPTSLLISWRIKSYYAYRITYGETGGNSPV QEFTVRQHVATISGLKPGVDYTITVYARLGDVELVYEISINYRT EIDKPSQ |
| 141 | ATI_1420_C02 w/N leader and C tail + his tag | GVSDVPRDLEVVAATPTSLLISWRIKSYYAYRITYGETGGNSPV QEFTVRQHVATISGLKPGVDYTITVYARLGDVELVYEISINYRT EIDKPSQHHHHHH |
| 142 | ATI_1420_C02 w/N leader and modified C-terminus including PC | GVSDVPRDLEVVAATPTSLLISWRIKSYYAYRITYGETGGNSPV QEFTVRQHVATISGLKPGVDYTITVYARLGDVELVYEISINYRT PC |

TABLE 3-continued

SEQUENCE LISTING

| SEQ ID | DESCRIPTION | SEQUENCE |
|---|---|---|
| 143 | ATI_1420_C02 w/N leader and modified C-terminus including PC + his tag | GVSDVPRDLEVVAATPTSLLISWHKFSSLMSYRITYGETGGNSPVQEFTVGSVNATISGLKPGVDYTITVYAIHNVGFISINYRTPCHHHHHH |
| 144 | ATI_1420_C02 - full length | MGVSDVPRDLEVVAATPTSLLISWRIKSYYAYRITYGETGGNSPVQEFTVRQHVATISGLKPGVDYTITVYARLGDVELVYEISINYRTEIDKPSQHHHHHH |
| 145 | ATI_1420_C11 core | EVVAATPTSLLISWMYPLKSVPYRITYGETGGNSPVQEFTVYSSGATISGLKPGVDYTITVYAMSYSTYHAFMISINYRT |
| 146 | ATI_1420_C11 BC loop | MYPLKSVP |
| 147 | ATI_1420_C11 DE loop | YSSG |
| 148 | ATI_1420_C11 FG loop | MSYSTYHAFM |
| 149 | ATI_1420_C11 w/N leader | GVSDVPRDLEVVAATPTSLLISWMYPLKSVPYRITYGETGGNSPVQEFTVYSSGATISGLKPGVDYTITVYAMSYSTYHAFMISINYRT |
| 150 | ATI_1420_C11 w/N leader + his tag | GVSDVPRDLEVVAATPTSLLISWMYPLKSVPYRITYGETGGNSPVQEFTVYSSGATISGLKPGVDYTITVYAMSYSTYHAFMISINYRTHHHHHH |
| 151 | ATI_1420_C11 w/N leader and C tail | GVSDVPRDLEVVAATPTSLLISWMYPLKSVPYRITYGETGGNSPVQEFTVYSSGATISGLKPGVDYTITVYAMSYSTYHAFMISINYRTEIDKPSQ |
| 152 | ATI_1420_C11 w/N leader and C tail + his tag | GVSDVPRDLEVVAATPTSLLISWMYPLKSVPYRITYGETGGNSPVQEFTVYSSGATISGLKPGVDYTITVYAMSYSTYHAFMISINYRTEIDKPSQHHHHHH |
| 153 | ATI_1420_C11 w/N leader and modified C-terminus including PC | GVSDVPRDLEVVAATPTSLLISWMYPLKSVPYRITYGETGGNSPVQEFTVYSSGATISGLKPGVDYTITVYAMSYSTYHAFMISINYRTPC |
| 154 | ATI_1420_C11 w/N leader and modified C-terminus including PC + his tag | GVSDVPRDLEVVAATPTSLLISWMYPLKSVPYRITYGETGGNSPVQEFTVYSSGATISGLKPGVDYTITVYAMSYSTYHAFMISINYRTPCHHHHHH |
| 155 | AATI_1420_C11 - full length | MGVSDVPRDLEVVAATPTSLLISWMYPLKSVPYRITYGETGGNSPVQEFTVYSSGATISGLKPGVDYTITVYAMSYSTYHAFMISINYRTEIDKPSQHHHHHH |
| 156 | ATI_1420_D01 core | EVVAATPTSLLISWRTVPETDYRITYGETGGNSPVQEFTVPDNTATISGLKPGVDYTITVYALETAHYNRDYISINYRT |
| 157 | ATI_1420_D01 BC loop | RTVPETD |
| 158 | ATI_1420_D01 DE loop | PDNT |
| 159 | ATI_1420_D01 FG loop | LETAHYNRDY |
| 160 | ATI_1420_D01 w/N leader | GVSDVPRDLEVVAATPTSLLISWRTVPETDYRITYGETGGNSPVQEFTVPDNTATISGLKPGVDYTITVYALETAHYNRDYISINYRT |
| 161 | ATI_1420_D01 w/N leader + his tag | GVSDVPRDLEVVAATPTSLLISWRTVPETDYRITYGETGGNSPVQEFTVPDNTATISGLKPGVDYTITVYALETAHYNRDYISINYRTHHHHHH |
| 162 | ATI_1420_D01 w/N leader and C tail | GVSDVPRDLEVVAATPTSLLISWRTVPETDYRITYGETGGNSPVQEFTVPDNTATISGLKPGVDYTITVYALETAHYNRDYISINYRTEIDKPSQ |
| 163 | ATI_1420_D01 w/N leader and C tail + his tag | GVSDVPRDLEVVAATPTSLLISWRTVPETDYRITYGETGGNSPVQEFTVPDNTATISGLKPGVDYTITVYALETAHYNRDYISINYRTEIDKPSQHHHHHH |
| 164 | ATI_1420_D01 w/N leader and modified C-terminus including PC | GVSDVPRDLEVVAATPTSLLISWRTVPETDYRITYGETGGNSPVQEFTVPDNTATISGLKPGVDYTITVYALETAHYNRDYISINYRTPC |

TABLE 3-continued

SEQUENCE LISTING

| SEQ ID | DESCRIPTION | SEQUENCE |
|---|---|---|
| 165 | ATI_1420_D01 w/N leader and modified C-terminus including PC + his tag | GVSDVPRDLEVVAATPTSLLISWRTVPETDYRITYGETGGNSPV QEFTVPDNTATISGLKPGVDYTITVYALETAHYNRDYISINYRT PCHHHHHH |
| 166 | ATI_1420_D01 - full length | MGVSDVPRDLEVVAATPTSLLISWRTVPETDYRITYGETGGNSP VQEFTVPDNTATISGLKPGVDYTITVYALETAHYNRDYISINYR TEIDKPSQHHHHHH |
| 167 | ATI_1420_D05 core | EVVAATPTSLLISWTAYYSTIKYRITYGETGGNSPVQEFTVGPK HHATISGLKPGVDYTITVYAYNTKPGYHAHQISINYRT |
| 168 | ATI_1420_D05 BC loop | TAYYSTIK |
| 169 | ATI_1420_D05 DE loop | GPKHH |
| 170 | ATI_1420_D05 FG loop | YNTKPGYHAHQ |
| 171 | ATI_1420_D05 w/N leader | GVSDVPRDLEVVAATPTSLLISWTAYYSTIKYRITYGETGGNSP VQEFTVGPKHHATISGLKPGVDYTITVYAYNTKPGYHAHQISIN YRT |
| 172 | ATI_1420_D05 w/N leader + his tag | GVSDVPRDLEVVAATPTSLLISWTAYYSTIKYRITYGETGGNSP VQEFTVGPKHHATISGLKPGVDYTITVYAYNTKPGYHAHQISIN YRTHHHHHH |
| 173 | ATI_1420_D05 w/N leader and C tail | GVSDVPRDLEVVAATPTSLLISWTAYYSTIKYRITYGETGGNSP VQEFTVGPKHHATISGLKPGVDYTITVYAYNTKPGYHAHQISIN YRTEIDKPSQ |
| 174 | ATI_1420_D05 w/N leader and C tail + his tag | GVSDVPRDLEVVAATPTSLLISWTAYYSTIKYRITYGETGGNSP VQEFTVGPKHHATISGLKPGVDYTITVYAYNTKPGYHAHQISIN YRTEIDKPSQHHHHHH |
| 175 | ATI_1420_D05 w/N leader and modified C-terminus including PC | GVSDVPRDLEVVAATPTSLLISWTAYYSTIKYRITYGETGGNSP VQEFTVGPKHHATISGLKPGVDYTITVYAYNTKPGYHAHQISIN YRTPC |
| 176 | ATI_1420_D05 w/N leader and modified C-terminus including PC + his tag | GVSDVPRDLEVVAATPTSLLISWTAYYSTIKYRITYGETGGNSP VQEFTVGPKHHATISGLKPGVDYTITVYAYNTKPGYHAHQISIN YRTPCHHHHHH |
| 177 | ATI_1420_D05 - full length | MGVSDVPRDLEVVAATPTSLLISWTAYYSTIKYRITYGETGGNS PVQEFTVGPKHHATISGLKPGVDYTITVYAYNTKPGYHAHQISI NYRTEIDKPSQHHHHHH |
| 178 | ATI_1420_D10 core | EVVAATPTSLLISWRIPSYHIQYRITYGETGGNSPVQEFTVYQK YATISGLKPGVDYTITVYAVSPPKQLRFGISINYRT |
| 179 | ATI_1420_D10 BC loop | RIPSYHIQ |
| 180 | ATI_1420_D10 DE loop | YQKY |
| 181 | ATI_1420_D10 FG loop | VSPPKQLRFG |
| 182 | ATI_1420_D10 w/N leader | GVSDVPRDLEVVAATPTSLLISWRIPSYHIQYRITYGETGGNSP VQEFTVYQKYATISGLKPGVDYTITVYAVSPPKQLRFGISINYR T |
| 183 | ATI_1420_D10 w/N leader + his tag | GVSDVPRDLEVVAATPTSLLISWRIPSYHIQYRITYGETGGNSP VQEFTVYQKYATISGLKPGVDYTITVYAVSPPKQLRFGISINYR THHHHHH |
| 184 | ATI_1420_D10 w/N leader and C tail | GVSDVPRDLEVVAATPTSLLISWRIPSYHIQYRITYGETGGNSP VQEFTVYQKYATISGLKPGVDYTITVYAVSPPKQLRFGISINYR TEIDKPSQ |
| 185 | ATI_1420_D10 w/N leader and C tail + his tag | GVSDVPRDLEVVAATPTSLLISWRIPSYHIQYRITYGETGGNSP VQEFTVYQKYATISGLKPGVDYTITVYAVSPPKQLRFGISINYR TEIDKPSQHHHHHH |

TABLE 3-continued

SEQUENCE LISTING

| SEQ ID | DESCRIPTION | SEQUENCE |
|---|---|---|
| 186 | ATI_1420_D10 w/N leader and modified C-terminus including PC | GVSDVPRDLEVVAATPTSLLISWRIPSYHIQYRITYGETGGNSPVQEFTVYQKYATISGLKPGVDYTITVYAVSPPKQLRFGISINYRTPC |
| 187 | ATI_1420_D10 w/N leader and modified C-terminus including PC + his tag | GVSDVPRDLEVVAATPTSLLISWRIPSYHIQYRITYGETGGNSPVQEFTVYQKYATISGLKPGVDYTITVYAVSPPKQLRFGISINYRTPCHHHHHH |
| 188 | ATI_1420_D010 - full length | MGVSDVPRDLEVVAATPTSLLISWRIPSYHIQYRITYGETGGNSPVQEFTVYQKYATISGLKPGVDYTITVYAVSPPKQLRFGISINYRTEIDKPSQHHHHHH |
| 189 | ATI_1420_F10_core | EVVAATPTSLLISWPAPPSYVFYRITYGETGGNSPVQEFTVYPYMATISGLKPGVDYTITVYAYTSGFSISINYRT |
| 190 | ATI_1420_F10 BC loop | PAPPSVF |
| 191 | ATI_1420_F10 DE loop | YPYM |
| 192 | ATI_1420_F10 FG loop | YTSGFS |
| 193 | ATI_1420_F10 w/N leader | GVSDVPRDLEVVAATPTSLLISWPAPPSYVFYRITYGETGGNSPVQEFTVYPYMATISGLKPGVDYTITVYAYTSGFSISINYRT |
| 194 | ATI_1420_F10 w/N leader + his tag | GVSDVPRDLEVVAATPTSLLISWPAPPSYVFYRITYGETGGNSPVQEFTVYPYMATISGLKPGVDYTITVYAYTSGFSISINYRTHHHHHH |
| 195 | ATI_1420_F10 w/N leader and C tail | GVSDVPRDLEVVAATPTSLLISWPAPPSYVFYRITYGETGGNSPVQEFTVYPYMATISGLKPGVDYTITVYAYTSGFSISINYRTEIDKPSQ |
| 196 | ATI_1420_F10 w/N leader and C tail + his tag | GVSDVPRDLEVVAATPTSLLISWPAPPSYVFYRITYGETGGNSPVQEFTVYPYMATISGLKPGVDYTITVYAYTSGFSISINYRTEIDKPSQHHHHHH |
| 197 | ATI_1420_F10 w/N leader and modified C-terminus including PC | GVSDVPRDLEVVAATPTSLLISWPAPPSYVFYRITYGETGGNSPVQEFTVYPYMATISGLKPGVDYTITVYAYTSGFSISINYRTPC |
| 198 | ATI_1420_F10 w/N leader and modified C-terminus including PC + his tag | GVSDVPRDLEVVAATPTSLLISWPAPPSYVFYRITYGETGGNSPVQEFTVYPYMATISGLKPGVDYTITVYAYTSGFSISINYRTPCHHHHHH |
| 199 | ATI_1420_F10 - full length | MGVSDVPRDLEVVAATPTSLLISWPAPPSYVFYRITYGETGGNSPVQEFTVYPYMATISGLKPGVDYTITVYAYTSGFSISINYRTEIDKPSQHHHHHH |
| 200 | ATI_1421_C05_core | EVVAATPTSLLISWYMDHKSKYRITYGETGGNSPVQEFTVPDQRATISGLKPGVDYTITVYALSEAHYLRDKISINYRT |
| 201 | ATI_1421_C05 BC loop | YMDHKSK |
| 202 | ATI_1421_C05 DE loop | PDQR |
| 203 | ATI_1421_C05 FG loop | LSEAHYLRDK |
| 204 | ATI_1421_C05 w/N leader | GVSDVPRDLEVVAATPTSLLISWYMDHKSKYRITYGETGGNSPVQEFTVPDQRATISGLKPGVDYTITVYALSEAHYLRDKISINYRT |
| 205 | ATI_1421_C05 w/N leader + his tag | GVSDVPRDLEVVAATPTSLLISWYMDHKSKYRITYGETGGNSPVQEFTVPDQRATISGLKPGVDYTITVYALSEAHYLRDKISINYRTHHHHHH |
| 206 | ATI_1421_C05 w/N leader and C tail | GVSDVPRDLEVVAATPTSLLISWYMDHKSKYRITYGETGGNSPVQEFTVPDQRATISGLKPGVDYTITVYALSEAHYLRDKISINYRTEIDKPSQ |
| 207 | ATI_1421_C05 w/N leader and C tail + his tag | GVSDVPRDLEVVAATPTSLLISWYMDHKSKYRITYGETGGNSPVQEFTVPDQRATISGLKPGVDYTITVYALSEAHYLRDKISINYRTEIDKPSQHHHHHH |

TABLE 3-continued

SEQUENCE LISTING

| SEQ ID | DESCRIPTION | SEQUENCE |
|---|---|---|
| 208 | ATI_1421_C05 w/N leader and modified C-terminus including PC | GVSDVPRDLEVVAATPTSLLISWYMDHKSKYRITYGETGGNSPV QEFTVPDQRATISGLKPGVDYTITVYALSEAHYLRDKISINYRT PC |
| 209 | ATI_1421_C05 w/N leader and modified C-terminus including PC + his tag | GVSDVPRDLEVVAATPTSLLISWYMDHKSKYRITYGETGGNSPV QEFTVPDQRATISGLKPGVDYTITVYALSEAHYLRDKISINYRT PCHHHHHH |
| 210 | ATI_1421_C05 - full length | MGVSDVPRDLEVVAATPTSLLISWYMDHKSKYRITYGETGGNSP VQEFTVPDQRATISGLKPGVDYTITVYALSEAHYLRDKISINYR TEIDKPSQHHHHHH |
| 211 | ATI_1421_C06 core | EVVAATPTSLLISWENLASYQYRITYGETGGNSPVQEFTVPDQA ATISGLKPGVDYTITVYALQTAHYYRQHISINYRT |
| 212 | ATI_1421_C06 BC loop | ENLASYQ |
| 213 | ATI_1421_C06 DE loop | PDQA |
| 214 | ATI_1421_C06 FG loop | LQTAHYYRQH |
| 215 | ATI_1421_C06 w/N leader | GVSDVPRDLEVVAATPTSLLISWENLASYQYRITYGETGGNSPV QEFTVPDQAATISGLKPGVDYTITVYALQTAHYYRQHISINYRT |
| 216 | ATI_1421_C06 w/N leader + his tag | GVSDVPRDLEVVAATPTSLLISWENLASYQYRITYGETGGNSPV QEFTVPDQAATISGLKPGVDYTITVYALQTAHYYRQHISINYRT HHHHHH |
| 217 | ATI_1421_C06 w/N leader and C tail | GVSDVPRDLEVVAATPTSLLISWENLASYQYRITYGETGGNSPV QEFTVPDQAATISGLKPGVDYTITVYALQTAHYYRQHISINYRT EIDKPSQ |
| 218 | ATI_1421_C06 w/N leader and C tail + his tag | GVSDVPRDLEVVAATPTSLLISWENLASYQYRITYGETGGNSPV QEFTVPDQAATISGLKPGVDYTITVYALQTAHYYRQHISINYRT EIDKPSQHHHHHH |
| 219 | ATI_1421_C06 w/N leader and modified C-terminus including PC | GVSDVPRDLEVVAATPTSLLISWENLASYQYRITYGETGGNSPV QEFTVPDQAATISGLKPGVDYTITVYALQTAHYYRQHISINYRT PC |
| 220 | ATI_1421_C06 w/N leader and modified C-terminus including PC + his tag | GVSDVPRDLEVVAATPTSLLISWENLASYQYRITYGETGGNSPV QEFTVPDQAATISGLKPGVDYTITVYALQTAHYYRQHISINYRT PCHHHHHH |
| 221 | ATI_1421_C06 - full length | MGVSDVPRDLEVVAATPTSLLISWENLASYQYRITYGETGGNSP VQEFTVPDQAATISGLKPGVDYTITVYALQTAHYYRQHISINYR TEIDKPSQHHHHHH |
| 222 | ATI 1421_D05 core | EVVAATPTSLLISWYYVQYNDYRITYGETGGNSPVQEFTVPDQS ATISGLKPGVDYTITVYALEKAHYYRQNISINYRT |
| 223 | ATI 1421_D05 BC loop | YYVQYND |
| 224 | ATI 1421_D05 DE loop | PDQS |
| 225 | ATI 1421_D05 FG loop | LEKAHYYRQN |
| 226 | ATI 1421_D05 w/N leader | GVSDVPRDLEVVAATPTSLLISWYYVQYNDYRITYGETGGNSPV QEFTVPDQSATISGLKPGVDYTITVYALEKAHYYRQNISINYRT |
| 227 | ATI 1421_D05 w/N leader + his tag | GVSDVPRDLEVVAATPTSLLISWYYVQYNDYRITYGETGGNSPV QEFTVPDQSATISGLKPGVDYTITVYALEKAHYYRQNISINYRT HHHHHH |
| 228 | ATI 1421_D05 w/N leader and C tail | GVSDVPRDLEVVAATPTSLLISWYYVQYNDYRITYGETGGNSPV QEFTVPDQSATISGLKPGVDYTITVYALEKAHYYRQNISINYRT EIDKPSQ |
| 229 | ATI 1421_D05 w/N leader and C tail + his tag | GVSDVPRDLEVVAATPTSLLISWYYVQYNDYRITYGETGGNSPV QEFTVPDQSATISGLKPGVDYTITVYALEKAHYYRQNISINYRT EIDKPSQHHHHHH |

TABLE 3-continued

SEQUENCE LISTING

| SEQ ID | DESCRIPTION | SEQUENCE |
|---|---|---|
| 230 | ATI_1421_D05 w/N leader and modified C-terminus including PC | GVSDVPRDLEVVAATPTSLLISWYYVQYNDYRITYGETGGNSPV QEFTVPDQSATISGLKPGVDYTITVYALEKAHYYRQNISINYRT PC |
| 231 | ATI_1421_D05 w/ N leader and modified C-terminus including PC + his tag | GVSDVPRDLEVVAATPTSLLISWYYVQYNDYRITYGETGGNSPV QEFTVPDQSATISGLKPGVDYTITVYALEKAHYYRQNISINYRT PCHHHHHH |
| 232 | ATI_1421_D05 - full length | MGVSDVPRDLEVVAATPTSLLISWYYVQYNDYRITYGETGGNSP VQEFTVPDQSATISGLKPGVDYTITVYALEKAHYYRQNISINYR TEIDKPSQHHHHHH |
| 233 | ATI_1421_D06 core | EVVAATPTSLLISWGHNYDDEYRITYGETGGNSPVQEFTVPDQY ATISGLKPGVDYTITVYALAEAHVRKNHISINYRT |
| 234 | ATI_1421_D06 BC loop | GHNYDDE |
| 235 | ATI_1421_D06 DE loop | PDQY |
| 236 | ATI_1421_D06 FG loop | LAEAHVRKNH |
| 237 | ATI_1421_D06 w/N leader | GVSDVPRDLEVVAATPTSLLISWGHNYDDEYRITYGETGGNSPV QEFTVPDQYATISGLKPGVDYTITVYALAEAHVRKNHISINYRT |
| 238 | ATI_1421_D06 w/N leader + his tag | GVSDVPRDLEVVAATPTSLLISWGHNYDDEYRITYGETGGNSPV QEFTVPDQYATISGLKPGVDYTITVYALAEAHVRKNHISINYRT HHHHHH |
| 239 | ATI_1421_D06 w/N leader and C tail | GVSDVPRDLEVVAATPTSLLISWGHNYDDEYRITYGETGGNSPV QEFTVPDQYATISGLKPGVDYTITVYALAEAHVRKNHISINYRT EIDKPSQ |
| 240 | ATI_1421_D06 w/N leader and C tail + his tag | GVSDVPRDLEVVAATPTSLLISWGHNYDDEYRITYGETGGNSPV QEFTVPDQYATISGLKPGVDYTITVYALAEAHVRKNHISINYRT EIDKPSQHHHHHH |
| 241 | ATI_1421_D06 w/N leader and modified C-terminus including PC | GVSDVPRDLEVVAATPTSLLISWGHNYDDEYRITYGETGGNSPV QEFTVPDQYATISGLKPGVDYTITVYALAEAHVRKNHISINYRT PC |
| 242 | ATI_1421_D06 w/N leader and modified C-terminus including PC + his tag | GVSDVPRDLEVVAATPTSLLISWGHNYDDEYRITYGETGGNSPV QEFTVPDQYATISGLKPGVDYTITVYALAEAHVRKNHISINYRT PCHHHHHH |
| 243 | ATI_1421_D06 - full length | MGVSDVPRDLEVVAATPTSLLISWGHNYDDEYRITYGETGGNSP VQEFTVPDQYATISGLKPGVDYTITVYALAEAHVRKNHISINYR TEIDKPSQHHHHHH |
| 244 | ATI_1421_E03 core | EVVAATPTSLLISWVYHYDAQYRITYGETGGNSPVQEFTVPDQK ATISGLKPGVDYTITVYALSEAHHKRDSISINYRT |
| 245 | ATI_1421_E03 BC loop | VYHYDAQ |
| 246 | ATI_1421_E03 DE loop | PDQK |
| 247 | ATI_1421_E03 FG loop | LSEAHHKRDS |
| 248 | ATI_1421_E03 w/N leader | GVSDVPRDLEVVAATPTSLLISWVYHYDAQYRITYGETGGNSPV QEFTVPDQKATISGLKPGVDYTITVYALSEAHHKRDSISINYRT HHHHHH |
| 249 | ATI_1421_E03 w/N leader + his tag | GVSDVPRDLEVVAATPTSLLISWVYHYDAQYRITYGETGGNSPV QEFTVPDQKATISGLKPGVDYTITVYALSEAHHKRDSISINYRT EIDKPSQ |
| 250 | ATI_1421_E03 w/N leader and C tail | GVSDVPRDLEVVAATPTSLLISWVYHYDAQYRITYGETGGNSPV QEFTVPDQKATISGLKPGVDYTITVYALSEAHHKRDSISINYRT EIDKPSQHHHHHH |
| 251 | ATI_1421_E03 w/N leader and C tail + his tag | GVSDVPRDLEVVAATPTSLLISWVYHYDAQYRITYGETGGNSPV QEFTVPDQKATISGLKPGVDYTITVYALSEAHHKRDSISINYRT PC |

TABLE 3-continued

SEQUENCE LISTING

| SEQ ID | DESCRIPTION | SEQUENCE |
|---|---|---|
| 252 | ATI_1421_E03 w/N leader and modified C-terminus including PC | GVSDVPRDLEVVAATPTSLLISWVYHDAQYRITYGETGGNSPV QEFTVPDQKATISGLKPGVDYTITVYALSEAHHKRDSISINYRT PCHHHHHH |
| 253 | ATI_1421_E03 w/N leader and modified C-terminus including PC + his tag | GVSDVPRDLEVVAATPTSLLISWVYHDAQYRITYGETGGNSPV QEFTVPDQKATISGLKPGVDYTITVYALSEAHHKRDSISINYRT |
| 254 | ATI_1421_E03 - full length | MGVSDVPRDLEVVAATPTSLLISWVYHDAQYRITYGETGGNSP VQEFTVPDQKATISGLKPGVDYTITVYALSEAHHKRDSISINYR TEIDKPSQHHHHHH |
| 255 | ATI_1421_E04 core | EVVAATPTSLLISWSYNGPIEYRITYGETGGNSPVQEFTVPDQQ ATISGLKPGVDYTITVYALEEAHYSRQSISINYRT |
| 256 | ATI_1421_E04 BC loop | SYNGPIE |
| 257 | ATI_1421_E04 DE loop | PDQQ |
| 258 | ATI_1421_E04 FG loop | LEEAHYSRQS |
| 259 | ATI_1421_E04 w/N leader | GVSDVPRDLEVVAATPTSLLISWSYNGPIEYRITYGETGGNSPV QEFTVPDQQATISGLKPGVDYTITVYALEEAHYSRQSISINYRT |
| 260 | ATI_1421_E04 w/N leader + his tag | GVSDVPRDLEVVAATPTSLLISWSYNGPIEYRITYGETGGNSPV QEFTVPDQQATISGLKPGVDYTITVYALEEAHYSRQSISINYRT HHHHHH |
| 261 | ATI_1421_E04 w/N leader and C tail | GVSDVPRDLEVVAATPTSLLISWSYNGPIEYRITYGETGGNSPV QEFTVPDQQATISGLKPGVDYTITVYALEEAHYSRQSISINYRT EIDKPSQ |
| 262 | ATI_1421_E04 w/N leader and C tail + his tag | GVSDVPRDLEVVAATPTSLLISWSYNGPIEYRITYGETGGNSPV QEFTVPDQQATISGLKPGVDYTITVYALEEAHYSRQSISINYRT EIDKPSQHHHHHH |
| 263 | ATI_1421_E04 w/N leader and modified C-terminus including PC | GVSDVPRDLEVVAATPTSLLISWSYNGPIEYRITYGETGGNSPV QEFTVPDQQATISGLKPGVDYTITVYALEEAHYSRQSISINYRT PC |
| 264 | ATI_1421_E04 w/N leader and modified C-terminus including PC + his tag | GVSDVPRDLEVVAATPTSLLISWSYNGPIEYRITYGETGGNSPV QEFTVPDQQATISGLKPGVDYTITVYALEEAHYSRQSISINYRT PCHHHHHH |
| 265 | ATI_1421_E04 - full length | MGVSDVPRDLEVVAATPTSLLISWSYNGPIEYRITYGETGGNSP VQEFTVPDQQATISGLKPGVDYTITVYALEEAHYSRQSISINYR TEIDKPSQHHHHHH |
| 266 | ATI_1421_F03 core | EVVAATPTSLLISWISVQTYDRITYGETGGNSPVQEFTVPDQS ATISGLKPGVDYTITVYALEKAHYYRQNISINYRT |
| 267 | ATI_1421_F03 BC loop | ISVQTYD |
| 268 | ATI_1421_F03 DE loop | PDQS |
| 269 | ATI_1421_F03 FG loop | LEKAHYYRQN |
| 270 | ATI_1421_F03 w/N leader | GVSDVPRDLEVVAATPTSLLISWISVQTYDRITYGETGGNSPV QEFTVPDQSATISGLKPGVDYTITVYALEKAHYYRQNISINYRT |
| 271 | ATI_1421_F03 w/N leader + his tag | GVSDVPRDLEVVAATPTSLLISWISVQTYDRITYGETGGNSPV QEFTVPDQSATISGLKPGVDYTITVYALEKAHYYRQNISINYRT HHHHHH |
| 272 | ATI_1421_F03 w/N leader and C tail | GVSDVPRDLEVVAATPTSLLISWISVQTYDRITYGETGGNSPV QEFTVPDQSATISGLKPGVDYTITVYALEKAHYYRQNISINYRT EIDKPSQ |
| 273 | ATI_1421_F03 w/N leader and C tail + his tag | GVSDVPRDLEVVAATPTSLLISWISVQTYDRITYGETGGNSPV QEFTVPDQSATISGLKPGVDYTITVYALEKAHYYRQNISINYRT EIDKPSQHHHHHH |
| 274 | ATI_1421_F03 w/N leader and modified C-terminus including PC | GVSDVPRDLEVVAATPTSLLISWISVQTYDRITYGETGGNSPV QEFTVPDQSATISGLKPGVDYTITVYALEKAHYYRQNISINYRT PC |

TABLE 3-continued

SEQUENCE LISTING

| SEQ ID | DESCRIPTION | SEQUENCE |
|---|---|---|
| 275 | ATI_1421_F03 w/N leader and modified C-terminus including PC + his tag | GVSDVPRDLEVVAATPTSLLISWISVQTYDYRITYGETGGNSPV QEFTVPDQSATISGLKPGVDYTITVYALEKAHYYRQNISINYRT PCHHHHHH |
| 276 | ATI_1421_F03 - full length | MGVSDVPRDLEVVAATPTSLLISWISVQTYDYRITYGETGGNSP VQEFTVPDQSATISGLKPGVDYTITVYALEKAHYYRQNISINYR TEIDKPSQHHHHHH |
| 277 | ATI_1421_F05 core | EVVAATPTSLLISWLARHDARYRITYGETGGNSPVQEFTVPDRM ATISGLKPGVDYTITVYALEQAHYYRLYISINYRT |
| 278 | ATI_1421_F05 BC loop | LARHDAR |
| 279 | ATI_1421_F05 DE loop | PDRM |
| 280 | ATI_1421_F05 FG loop | LEQAHYYRLY |
| 281 | ATI_1421_F05 w/N leader | GVSDVPRDLEVVAATPTSLLISWLARHDARYRITYGETGGNSPV QEFTVPDRMATISGLKPGVDYTITVYALEQAHYYRLYISINYRT |
| 282 | ATI_1421_F05 w/N leader + his tag | GVSDVPRDLEVVAATPTSLLISWLARHDARYRITYGETGGNSPV QEFTVPDRMATISGLKPGVDYTITVYALEQAHYYRLYISINYRT HHHHHH |
| 283 | ATI_1421_F05 w/N leader and C tail | GVSDVPRDLEVVAATPTSLLISWLARHDARYRITYGETGGNSPV QEFTVPDRMATISGLKPGVDYTITVYALEQAHYYRLYISINYRT EIDKPSQ |
| 284 | ATI_1421_F05 w/N leader and C tail + his tag | GVSDVPRDLEVVAATPTSLLISWLARHDARYRITYGETGGNSPV QEFTVPDRMATISGLKPGVDYTITVYALEQAHYYRLYISINYRT EIDKPSQHHHHHH |
| 285 | ATI_1421_F05 w/N leader and modified C-terminus including PC | GVSDVPRDLEVVAATPTSLLISWLARHDARYRITYGETGGNSPV QEFTVPDRMATISGLKPGVDYTITVYALEQAHYYRLYISINYRT PC |
| 286 | ATI_1421_F05 w/N leader and modified C-terminus including PC + his tag | GVSDVPRDLEVVAATPTSLLISWLARHDARYRITYGETGGNSPV QEFTVPDRMATISGLKPGVDYTITVYALEQAHYYRLYISINYRT PCHHHHHH |
| 287 | ATI_1421_F05 - full length | MGVSDVPRDLEVVAATPTSLLISWLARHDARYRITYGETGGNSP VQEFTVPDRMATISGLKPGVDYTITVYALEQAHYYRLYISINYR TEIDKPSQHHHHHH |
| 288 | ATI_1421_G07 core | EVVAATPTSLLISWHSPTSGITYRITYGETGGNSPVQEFTVPYD PSATISGLKPGVDYTITVYAPYGSQYYPGYHISINYRT |
| 289 | ATI_1421_G07 BC loop | HSPTSGIT |
| 290 | ATI_1421_G07 DE loop | PYDPS |
| 291 | ATI_1421_G07 FG loop | PYGSQYYPGYH |
| 292 | ATI_1421_G07 w/N leader | GVSDVPRDLEVVAATPTSLLISWHSPTSGITYRITYGETGGNSP VQEFTVPYDPSATISGLKPGVDYTITVYAPYGSQYYPGYHISIN YRT |
| 293 | ATI_1421_G07 w/N leader + his tag | GVSDVPRDLEVVAATPTSLLISWHSPTSGITYRITYGETGGNSP VQEFTVPYDPSATISGLKPGVDYTITVYAPYGSQYYPGYHISIN YRTHHHHHH |
| 294 | ATI_1421_G07 w/N leader and C tail | GVSDVPRDLEVVAATPTSLLISWHSPTSGITYRITYGETGGNSP VQEFTVPYDPSATISGLKPGVDYTITVYAPYGSQYYPGYHISIN YRTEIDKPSQ |
| 295 | ATI_1421_G07 w/N leader and C tail + his tag | GVSDVPRDLEVVAATPTSLLISWHSPTSGITYRITYGETGGNSP VQEFTVPYDPSATISGLKPGVDYTITVYAPYGSQYYPGYHISIN YRTEIDKPSQHHHHHH |
| 296 | ATI_1421_G07 w/N leader and modified C-terminus including PC | GVSDVPRDLEVVAATPTSLLISWHSPTSGITYRITYGETGGNSP VQEFTVPYDPSATISGLKPGVDYTITVYAPYGSQYYPGYHISIN YRTPC |

TABLE 3-continued

SEQUENCE LISTING

| SEQ ID | DESCRIPTION | SEQUENCE |
|---|---|---|
| 297 | ATI_1421_G07 w/N leader and modified C-terminus including PC + his tag | GVSDVPRDLEVVAATPTSLLISWHSPTSGITYRITYGETGGNSP VQEFTVPYDPSATISGLKPGVDYTITVYAPYGSQYYPGYHISIN YRTPCHHHHHH |
| 298 | ATI_1421_G07 - full length | MGVSDVPRDLEVVAATPTSLLISWHSPTSGITYRITYGETGGNS PVQEFTVPYDPSATISGLKPGVDYTITVYAPYGSQYYPGYHISI NYRTEIDKPSQHHHHHH |
| 299 | ATI_1421_H03 core | EVVAATPTSLLISWVYHYDAQYRITYGETGGNSPVQEFTVPDSS ATISGLKPGVDYTITVYALEQAHIDRTTISINYRT |
| 300 | ATI_1421_H03 BC loop | VYHYDAQ |
| 301 | ATI_1421_H03 DE loop | PDSS |
| 302 | ATI_1421_H03 FG loop | LEQAHIDRTT |
| 303 | ATI_1421_H03 w/N leader | GVSDVPRDLEVVAATPTSLLISWVYHYDAQYRITYGETGGNSPV QEFTVPDSSATISGLKPGVDYTITVYALEQAHIDRTTISINYRT |
| 304 | ATI_142_H03 w/N leader + his tag | GVSDVPRDLEVVAATPTSLLISWVYHYDAQYRITYGETGGNSPV QEFTVPDSSATISGLKPGVDYTITVYALEQAHIDRTTISINYRT HHHHHH |
| 305 | ATI_1421_H03 w/N leader and C tail | GVSDVPRDLEVVAATPTSLLISWVYHYDAQYRITYGETGGNSPV QEFTVPDSSATISGLKPGVDYTITVYALEQAHIDRTTISINYRT EIDKPSQ |
| 306 | ATI_1421_H03 w/N leader and C tail + his tag | GVSDVPRDLEVVAATPTSLLISWVYHYDAQYRITYGETGGNSPV QEFTVPDSSATISGLKPGVDYTITVYALEQAHIDRTTISINYRT EIDKPSQHHHHHH |
| 307 | ATI_1421_H03 w/N leader and modified C-terminus including PC | GVSDVPRDLEVVAATPTSLLISWVYHYDAQYRITYGETGGNSPV QEFTVPDSSATISGLKPGVDYTITVYALEQAHIDRTTISINYRT PC |
| 308 | ATI_1421_H03 w/N leader and modified C-terminus including PC + his tag | GVSDVPRDLEVVAATPTSLLISWVYHYDAQYRITYGETGGNSPV QEFTVPDSSATISGLKPGVDYTITVYALEQAHIDRTTISINYRT PCHHHHHH |
| 309 | ATI_1421_H03 - full length | MGVSDVPRDLEVVAATPTSLLISWVYHYDAQYRITYGETGGNSP VQEFTVPDSSATISGLKPGVDYTITVYALEQAHIDRTTISINYR TEIDKPSQHHHHHH |
| 310 | ATI_1421_H05 core | EVVAATPTSLLISWTSVLLKDYRITYGETGGNSPVQEFTVPDQH ATISGLKPGVDYTITVYALQNAHHERLYISINYRT |
| 311 | ATI_1421_H05 BC loop | TSVLLKD |
| 312 | ATI_1421_H05 DE loop | PDQH |
| 313 | ATI_1421_H05 FG loop | LQNAHHERLY |
| 314 | ATI_1421_H05 w/N leader | GVSDVPRDLEVVAATPTSLLISWTSVLLKDYRITYGETGGNSPV QEFTVPDQHATISGLKPGVDYTITVYALQNAHHERLYISINYRT |
| 315 | ATI_1421_H05 w/N leader + his tag | GVSDVPRDLEVVAATPTSLLISWTSVLLKDYRITYGETGGNSPV QEFTVPDQHATISGLKPGVDYTITVYALQNAHHERLYISINYRT HHHHHH |
| 316 | ATI_1421_H05 w/N leader and C tail | GVSDVPRDLEVVAATPTSLLISWTSVLLKDYRITYGETGGNSPV QEFTVPDQHATISGLKPGVDYTITVYALQNAHHERLYISINYRT EIDKPSQ |
| 317 | ATI_1421_H05 w/N leader and C tail + his tag | GVSDVPRDLEVVAATPTSLLISWTSVLLKDYRITYGETGGNSPV QEFTVPDQHATISGLKPGVDYTITVYALQNAHHERLYISINYRT EIDKPSQHHHHHH |
| 318 | ATI_1421_H05 w/N leader and modified C-terminus including PC | GVSDVPRDLEVVAATPTSLLISWTSVLLKDYRITYGETGGNSPV QEFTVPDQHATISGLKPGVDYTITVYALQNAHHERLYISINYRT PC |

TABLE 3-continued

SEQUENCE LISTING

| SEQ ID | DESCRIPTION | SEQUENCE |
|---|---|---|
| 319 | ATI_1421_H05 w/N leader and modified C-terminus including PC + his tag | GVSDVPRDLEVVAATPTSLLISWTSVLLKDYRITYGETGGNSPV QEFTVPDQHATISGLKPGVDYTITVYALQNAHHERLYISINYRT PCHHHHHH |
| 320 | ATI_1421_H05 - full length | MGVSDVPRDLEVVAATPTSLLISWTSVLLKDYRITYGETGGNSP VQEFTVPDQHATISGLKPGVDYTITVYALQNAHHERLYISINYR TEIDKPSQHHHHHH |
| 321 | ATI_1422_E06 core | EVVAATPTSLLISWLPSYYITYRITYGETGGNSPVQEFTVSKDL ATISGLKPGVDYTITVYAFNGSSYYTFGISINYRT |
| 322 | ATI_1422_E06 BC loop | LPSYYIT |
| 323 | ATI_1422_E06 DE loop | SKDL |
| 324 | ATI_1422_E06 FG loop | FNGSSYYTFG |
| 325 | ATI_1422_E06 w/N leader | GVSDVPRDLEVVAATPTSLLISWLPSYYITYRITYGETGGNSPV QEFTVSKDLATISGLKPGVDYTITVYAFNGSSYYTFGISINYRT |
| 326 | ATI_1422_E06 w/N leader + his tag | GVSDVPRDLEVVAATPTSLLISWLPSYYITYRITYGETGGNSPV QEFTVSKDLATISGLKPGVDYTITVYAFNGSSYYTFGISINYRT EIDKPSQHHHHHH |
| 327 | ATI_1422_E06 w/N leader and C tail | GVSDVPRDLEVVAATPTSLLISWLPSYYITYRITYGETGGNSPV QEFTVSKDLATISGLKPGVDYTITVYAFNGSSYYTFGISINYRT EIDKPSQHHHHHH |
| 328 | ATI_1422_E06 w/N leader and C tail + his tag | GVSDVPRDLEVVAATPTSLLISWLPSYYITYRITYGETGGNSPV QEFTVSKDLATISGLKPGVDYTITVYAFNGSSYYTFGISINYRT PC |
| 329 | ATI_1422_E06 w/N leader and modified C-terminus including PC | GVSDVPRDLEVVAATPTSLLISWLPSYYITYRITYGETGGNSPV QEFTVSKDLATISGLKPGVDYTITVYAFNGSSYYTFGISINYRT PCHHHHHH |
| 330 | ATI_1422_E06 w/N leader and modified C-terminus including PC + his tag | GVSDVPRDLEVVAATPTSLLISWLPSYYITYRITYGETGGNSPV QEFTVSKDLATISGLKPGVDYTITVYAFNGSSYYTFGISINYRT EIDKPSQHHHHHH |
| 331 | ATI_1422_E06 - full length | MGVSDVPRDLEVVAATPTSLLISWLPSYYITYRITYGETGGNSP VQEFTVSKDLATISGLKPGVDYTITVYAFNGSSYYTFGISINYR T |
| 332 | ATI_1422_F04 core | EVVAATPTSLLISWSIPSYFISYRITYGETGGNSPVQEFTVYKN YATISGLKPGVDYTITVYASEGIMFYNISINYRT |
| 333 | ATI_1422_F04 BC loop | SIPSYFIS |
| 334 | ATI_1422_F04 DE loop | YKNY |
| 335 | ATI_1422_F04 FG loop | SEGIMFYN |
| 336 | ATI_1422_F04 w/N leader | GVSDVPRDLEVVAATPTSLLISWSIPSYFISYRITYGETGGNSP VQEFTVYKNYATISGLKPGVDYTITVYASEGIMFYNISINYRT |
| 337 | ATI_1422_F04 w/N leader + his tag | GVSDVPRDLEVVAATPTSLLISWSIPSYFISYRITYGETGGNSP VQEFTVYKNYATISGLKPGVDYTITVYASEGIMFYNISINYRTH HHHHH |
| 338 | ATI_1422_F04 w/N leader and C tail | GVSDVPRDLEVVAATPTSLLISWSIPSYFISYRITYGETGGNSP VQEFTVYKNYATISGLKPGVDYTITVYASEGIMFYNISINYRTE IDKPSQ |
| 339 | ATI_1422_F04 w/N leader and C tail + his tag | GVSDVPRDLEVVAATPTSLLISWSIPSYFISYRITYGETGGNSP VQEFTVYKNYATISGLKPGVDYTITVYASEGIMFYNISINYRTE IDKPSQHHHHHH |
| 340 | ATI_1422_F04 w/N leader and modified C-terminus including PC | GVSDVPRDLEVVAATPTSLLISWSIPSYFISYRITYGETGGNSP VQEFTVYKNYATISGLKPGVDYTITVYASEGIMFYNISINYRTP C |

TABLE 3-continued

SEQUENCE LISTING

| SEQ ID | DESCRIPTION | SEQUENCE |
|---|---|---|
| 341 | ATI_1422_F04 w/N leader and modified C-terminus including PC + his tag | GVSDVPRDLEVVAATPTSLLISWSIPSYFISYRITYGETGGNSP VQEFTVYKNYATISGLKPGVDYTITVYASEGIMFYNISINYRTP CHHHHHH |
| 342 | ATI_1422_F04 - full length | MGVSDVPRDLEVVAATPTSLLISWSIPSYFISYRITYGETGGNS PVQEFTVYKNYATISGLKPGVDYTITVYASEGIMFYNISINYRT EIDKPSQHHHHHH |
| 343 | ATI_1422_F05 core | EVVAATPTSLLISWPYPRGPYVFYRITYGETGGNSPVQEFTVYP GQATISGLKPGVDYTITVYAYTSGYVISINYRT |
| 344 | ATI_1422_F05 BC loop | PYPRGPYVF |
| 345 | ATI_1422_F05 DE loop | YPGQ |
| 346 | ATI_1422_F05 FG loop | YTSGYV |
| 347 | ATI_1422_F05 w/N leader | GVSDVPRDLEVVAATPTSLLISWPYPRGPYVFYRITYGETGGNS PVQEFTVYPGQATISGLKPGVDYTITVYAYTSGYVISINYRT |
| 348 | ATI_1422_F05 w/N leader + his tag | GVSDVPRDLEVVAATPTSLLISWPYPRGPYVFYRITYGETGGNS PVQEFTVYPGQATISGLKPGVDYTITVYAYTSGYVISINYRTEI DKPSQHHHHHH |
| 349 | ATI_1422_F05 w/N leader and C tail | GVSDVPRDLEVVAATPTSLLISWPYPRGPYVFYRITYGETGGNS PVQEFTVYPGQATISGLKPGVDYTITVYAYTSGYVISINYRTEI DKPSQ |
| 350 | ATI_1422_F05 w/N leader and C tail + his tag | GVSDVPRDLEVVAATPTSLLISWPYPRGPYVFYRITYGETGGNS PVQEFTVYPGQATISGLKPGVDYTITVYAYTSGYVISINYRTEI DKPSQHHHHHH |
| 351 | ATI_1422_F05 w/N leader and modified C-terminus including PC | GVSDVPRDLEVVAATPTSLLISWPYPRGPYVFYRITYGETGGNS PVQEFTVYPGQATISGLKPGVDYTITVYAYTSGYVISINYRTPC |
| 352 | ATI_1422_F05 w/N leader and modified C-terminus including PC + his tag | GVSDVPRDLEVVAATPTSLLISWPYPRGPYVFYRITYGETGGNS PVQEFTVYPGQATISGLKPGVDYTITVYAYTSGYVISINYRTPC HHHHHH |
| 353 | ATI_1422_F05 - full length | MGVSDVPRDLEVVAATPTSLLISWPYPRGPYVFYRITYGETGGN SPVQEFTVYPGQATISGLKPGVDYTITVYAYTSGYVISINYRTE IDKPSQHHHHHH |
| 354 | ATI_1422_H04 core | EVVAATPTSLLISWYLPSYYVQYRITYGETGGNSPVQEFTVKSY NATISGLKPGVDYTITVYARMGVYYLSYSISINYRT |
| 355 | ATI_1422_H04 BC loop | YLPSYYVQ |
| 356 | ATI_1422_H04 DE loop | KSYN |
| 357 | ATI_1422_H04 FG loop | RMGVYYLSYS |
| 358 | ATI_1422_H04 w/N leader | GVSDVPRDLEVVAATPTSLLISWYLPSYYVQYRITYGETGGNSP VQEFTVKSYNATISGLKPGVDYTITVYARMGVYYLSYSISINYR T |
| 359 | ATI_1422_H04 w/N leader + his tag | GVSDVPRDLEVVAATPTSLLISWYLPSYYVQYRITYGETGGNSP VQEFTVKSYNATISGLKPGVDYTITVYARMGVYYLSYSISINYR THHHHHH |
| 360 | ATI_1422_H04 w/N leader and C tail | GVSDVPRDLEVVAATPTSLLISWYLPSYYVQYRITYGETGGNSP VQEFTVKSYNATISGLKPGVDYTITVYARMGVYYLSYSISINYR TEIDKPSQ |
| 361 | ATI_1422_H04 w/N leader and C tail + his tag | GVSDVPRDLEVVAATPTSLLISWYLPSYYVQYRITYGETGGNSP VQEFTVKSYNATISGLKPGVDYTITVYARMGVYYLSYSISINYR TEIDKPSQHHHHHH |
| 362 | ATI_1422_H04 w/N leader and modified C-terminus including PC | GVSDVPRDLEVVAATPTSLLISWYLPSYYVQYRITYGETGGNSP VQEFTVKSYNATISGLKPGVDYTITVYARMGVYYLSYSISINYR TPC |

TABLE 3-continued

SEQUENCE LISTING

| SEQ ID | DESCRIPTION | SEQUENCE |
|---|---|---|
| 363 | ATI_1422_H04 w/N leader and modified C-terminus including PC + his tag | GVSDVPRDLEVVAATPTSLLISWYLPSYYVQYRITYGETGGNSPVQEFTVKSYNATISGLKPGVDYTITVYARMGVYYLSYSISINYRTPCHHHHHH |
| 364 | ATI_1422_H04 - full length | MGVSDVPRDLEVVAATPTSLLISWYLPSYYVQYRITYGETGGNSPVQEFTVKSYNATISGLKPGVDYTITVYARMGVYYLSYSISINYRTEIDKPSQHHHHHH |
| 365 | ATI_1422_H05 core | EVVAATPTSLLISWQGQLSPSFYRITYGETGGNSPVQEFTVVAGMATISGLKPGVDYTITVYATSDVYFYSISINYRT |
| 366 | ATI_1422_H05 BC loop | QGQLSPSF |
| 367 | ATI_1422_H05 DE loop | VAGM |
| 368 | ATI_1422_H05 FG loop | TSDVYFYS |
| 369 | ATI_1422_H05 w/N leader | GVSDVPRDLEVVAATPTSLLISWQGQLSPSFYRITYGETGGNSPVQEFTVVAGMATISGLKPGVDYTITVYATSDVYFYSISINYRT |
| 370 | ATI_1422_H05 w/N leader + his tag | GVSDVPRDLEVVAATPTSLLISWQGQLSPSFYRITYGETGGNSPVQEFTVVAGMATISGLKPGVDYTITVYATSDVYFYSISINYRTHHHHHH |
| 371 | ATI_1422_H05 w/N leader and C tail | GVSDVPRDLEVVAATPTSLLISWQGQLSPSFYRITYGETGGNSPVQEFTVVAGMATISGLKPGVDYTITVYATSDVYFYSISINYRTEIDKPSQ |
| 372 | ATI_1422_H05 w/N leader and C tail + his tag | GVSDVPRDLEVVAATPTSLLISWQGQLSPSFYRITYGETGGNSPVQEFTVVAGMATISGLKPGVDYTITVYATSDVYFYSISINYRTEIDKPSQHHHHHH |
| 373 | ATI_1422_H05 w/N leader and modified C-terminus including PC | GVSDVPRDLEVVAATPTSLLISWQGQLSPSFYRITYGETGGNSPVQEFTVVAGMATISGLKPGVDYTITVYATSDVYFYSISINYRTPC |
| 374 | ATI_1422_H05 w/N leader and modified C-terminus including PC + his tag | GVSDVPRDLEVVAATPTSLLISWQGQLSPSFYRITYGETGGNSPVQEFTVVAGMATISGLKPGVDYTITVYATSDVYFYSISINYRTPCHHHHHH |
| 375 | - full length | MGVSDVPRDLEVVAATPTSLLISWQGQLSPSFYRITYGETGGNSPVQEFTVVAGMATISGLKPGVDYTITVYATSDVYFYSISINYRTEIDKPSQHHHHHH |
| 376 | ATI_1422_G05 core | EVVAATPTSLLISWIAPYYSVIYRITYGETGGNSPVQEFTVTGSGYATISGLKPGVDYTITVYATYCASVASYAFISINYRT |
| 377 | ATI_1422_G05 BC loop | IAPYYSVI |
| 378 | ATI_1422_G05 DE loop | TGSGY |
| 379 | ATI_1422_G05 FG loop | TYCASVASYAF |
| 380 | ATI_1422_G05 w/N leader | GVSDVPRDLEVVAATPTSLLISWIAPYYSVIYRITYGETGGNSPVQEFTVTGSGYATISGLKPGVDYTITVYATYCASVASYAFISINYRT |
| 381 | ATI_1422_G05 w/N leader + his tag | GVSDVPRDLEVVAATPTSLLISWIAPYYSVIYRITYGETGGNSPVQEFTVTGSGYATISGLKPGVDYTITVYATYCASVASYAFISINYRTHHHHHH |
| 382 | ATI_1422_G05 w/N leader and C tail | GVSDVPRDLEVVAATPTSLLISWIAPYYSVIYRITYGETGGNSPVQEFTVTGSGYATISGLKPGVDYTITVYATYCASVASYAFISINYRTEIDKPSQ |
| 383 | ATI_1422_G05 w/N leader and C tail + his tag | GVSDVPRDLEVVAATPTSLLISWIAPYYSVIYRITYGETGGNSPVQEFTVTGSGYATISGLKPGVDYTITVYATYCASVASYAFISINYRTEIDKPSQHHHHHH |
| 384 | ATI_1422_G05 w/N leader and modified C-terminus including PC | GVSDVPRDLEVVAATPTSLLISWIAPYYSVIYRITYGETGGNSPVQEFTVTGSGYATISGLKPGVDYTITVYATYCASVASYAFISINYRTPC |

TABLE 3-continued

SEQUENCE LISTING

| SEQ ID | DESCRIPTION | SEQUENCE |
|---|---|---|
| 385 | ATI_1422_G05 w/N leader and modified C-terminus including PC + his tag | GVSDVPRDLEVVAATPTSLLISWIAPYYSVIYRITYGETGGNSPVQEFTVTGSGYATISGLKPGVDYTITVYATYCASVASYAFISINYRTPCHHHHHH |
| 386 | ATI_1422_G05 - full length | MGVSDVPRDLEVVAATPTSLLISWIAPYYSVIYRITYGETGGNSPVQEFTVTGSGYATISGLKPGVDYTITVYATYCASVASYAFISINYRTEIDKPSQHHHHHH |
| 387 | ATI_1760_C02 core | EVVAATPTSLLISWIAPYYSVIYRITYGETGGNSPVQEFTVPGSAYATISGLKPGVDYTITVYASSGASIAAYAFISINYRT |
| 388 | ATI_1760_C02 BC loop | IAPYYSVI |
| 389 | ATI_1760_C02 DE loop | PGSAY |
| 390 | ATI_1760_C02 FG loop | sSGASIAAYAF |
| 391 | ATI_1760_C02 w/N leader | GVSDVPRDLEVVAATPTSLLISWIAPYYSVIYRITYGETGGNSPVQEFTVPGSAYATISGLKPGVDYTITVYASSGASIAAYAFISINYRT |
| 392 | ATI_1760_C02 w/N leader + his tag | GVSDVPRDLEVVAATPTSLLISWIAPYYSVIYRITYGETGGNSPVQEFTVPGSAYATISGLKPGVDYTITVYASSGASIAAYAFISINYRTHHHHHH |
| 393 | ATI_1760_C02 w/N leader and C tail | GVSDVPRDLEVVAATPTSLLISWIAPYYSVIYRITYGETGGNSPVQEFTVPGSAYATISGLKPGVDYTITVYASSGASIAAYAFISINYRTEIDKPSQ |
| 394 | ATI_1760_C02 w/N leader and C tail + his tag | GVSDVPRDLEVVAATPTSLLISWIAPYYSVIYRITYGETGGNSPVQEFTVPGSAYATISGLKPGVDYTITVYASSGASIAAYAFISINYRTEIDKPSQHHHHHH |
| 395 | ATI_1760_C02 w/N leader and modified C-terminus including PC | GVSDVPRDLEVVAATPTSLLISWIAPYYSVIYRITYGETGGNSPVQEFTVPGSAYATISGLKPGVDYTITVYASSGASIAAYAFISINYRTPC |
| 396 | ATI_1760_C02 w/N leader and modified C-terminus including PC + his tag | GVSDVPRDLEVVAATPTSLLISWIAPYYSVIYRITYGETGGNSPVQEFTVPGSAYATISGLKPGVDYTITVYASSGASIAAYAFISINYRTPCHHHHHH |
| 397 | ATI_1760_C02 - full length | MGVSDVPRDLEVVAATPTSLLISWIAPYYSVIYRITYGETGGNSPVQEFTVPGSAYATISGLKPGVDYTITVYASSGASIAAYAFISINYRTEIDKPSQHHHHHH |
| 398 | ATI_1760_E01 core | EVVAATPTSLLISWIAPYYSVKYRITYGETGGNSPVQEFTVAGADYATISGLKPGVDYTITVYATYGASIASYAFISINYRT |
| 399 | ATI_1760_E01 BC loop | IAPYYSVK |
| 400 | ATI_1760_E01 DE loop | AGADY |
| 401 | ATI_1760_E01 FG loop | TYGASIASYAF |
| 402 | ATI_1760_E01 w/N leader | GVSDVPRDLEVVAATPTSLLISWIAPYYSVKYRITYGETGGNSPVQEFTVAGADYATISGLKPGVDYTITVYATYGASIASYAFISINYRT |
| 403 | ATI_1760_E01 w/N leader + his tag | GVSDVPRDLEVVAATPTSLLISWIAPYYSVKYRITYGETGGNSPVQEFTVAGADYATISGLKPGVDYTITVYATYGASIASYAFISINYRTHHHHHH |
| 404 | ATI_1760_E01 w/N leader and C tail | GVSDVPRDLEVVAATPTSLLISWIAPYYSVKYRITYGETGGNSPVQEFTVAGADYATISGLKPGVDYTITVYATYGASIASYAFISINYRTEIDKPSQ |
| 405 | ATI_1760_E01 w/N leader and C tail + his tag | GVSDVPRDLEVVAATPTSLLISWIAPYYSVKYRITYGETGGNSPVQEFTVAGADYATISGLKPGVDYTITVYATYGASIASYAFISINYRTEIDKPSQHHHHHH |

TABLE 3-continued

SEQUENCE LISTING

| SEQ ID | DESCRIPTION | SEQUENCE |
|---|---|---|
| 406 | ATI_1760_E01 w/N leader and modified C-terminus including PC | GVSDVPRDLEVVAATPTSLLISWIAPYYSVKYRITYGETGGNSPVQEFTVAGADYATISGLKPGVDYTITVYATYGASIASYAFISINYRTPC |
| 407 | ATI_1760_E01 w/N leader and modified C-terminus including PC + his tag | GVSDVPRDLEVVAATPTSLLISWIAPYYSVKYRITYGETGGNSPVQEFTVAGADYATISGLKPGVDYTITVYATYGASIASYAFISINYRTPCHHHHHH |
| 408 | ATI_1760_E01 - full length | MGVSDVPRDLEVVAATPTSLLISWIAPYYSVKYRITYGETGGNSPVQEFTVAGADYATISGLKPGVDYTITVYATYGASIASYAFISINYRTEIDKPSQHHHHHH |
| 409 | ATI_1760_F01 core | EVVAATPTSLLISWIAPYYAVMYRITYGETGGNSPVQEFTVPGGGYATISGLKPGVDYTITVYATGGASIAAYAFISINYRT |
| 410 | ATI_1760_F01 BC loop | IAPYYAVM |
| 411 | ATI_1760_F01 DE loop | PGGGY |
| 412 | ATI_1760_F01 FG loop | TGGASIAAYAF |
| 413 | ATI_1760_F01 w/N leader | GVSDVPRDLEVVAATPTSLLISWIAPYYAVMYRITYGETGGNSPVQEFTVPGGGYATISGLKPGVDYTITVYATGGASIAAYAFISINYRT |
| 414 | ATI_1760_F01 w/N leader + his tag | GVSDVPRDLEVVAATPTSLLISWIAPYYAVMYRITYGETGGNSPVQEFTVPGGGYATISGLKPGVDYTITVYATGGASIAAYAFISINYRTHHHHHH |
| 415 | ATI_1760_F01 w/N leader and C tail | GVSDVPRDLEVVAATPTSLLISWIAPYYAVMYRITYGETGGNSPVQEFTVPGGGYATISGLKPGVDYTITVYATGGASIAAYAFISINYRTEIDKPSQ |
| 416 | ATI_1760_F01 w/N leader and C tail + his tag | GVSDVPRDLEVVAATPTSLLISWIAPYYAVMYRITYGETGGNSPVQEFTVPGGGYATISGLKPGVDYTITVYATGGASIAAYAFISINYRTEIDKPSQHHHHHH |
| 417 | ATI_1760_F01 w/N leader and modified C-terminus including PC | GVSDVPRDLEVVAATPTSLLISWIAPYYAVMYRITYGETGGNSPVQEFTVPGGGYATISGLKPGVDYTITVYATGGASIAAYAFISINYRTPC |
| 418 | ATI_1760_F01 w/N leader and modified C-terminus including PC + his tag | GVSDVPRDLEVVAATPTSLLISWIAPYYAVMYRITYGETGGNSPVQEFTVPGGGYATISGLKPGVDYTITVYATGGASIAAYAFISINYRTPCHHHHHH |
| 419 | ATI_1760_F01 - full length | MGVSDVPRDLEVVAATPTSLLISWIAPYYAVMYRITYGETGGNSPVQEFTVPGGGYATISGLKPGVDYTITVYATGGASIAAYAFISINYRTEIDKPSQHHHHHH |
| 420 | ATI_1494_D03 core | EVVAATPTSLLISWSYPSYHLYRITYGETGGNSPVQEFTVHIDYATISGLKPGVDYTITVYAQSPPYDIYYEISINYRT |
| 421 | ATI_1494_D03 BC loop | SYPSYHL |
| 422 | ATI_1494_D03 DE loop | HIDY |
| 423 | ATI_1494_D03 FG loop | QSPPYDIYYE |
| 424 | ATI_1494_D03 w/N leader | GVSDVPRDLEVVAATPTSLLISWSYPSYHLYRITYGETGGNSPVQEFTVHIDYATISGLKPGVDYTITVYAQSPPYDIYYEISINYRT |
| 425 | ATI_1494_D03 w/N leader + his tag | GVSDVPRDLEVVAATPTSLLISWSYPSYHLYRITYGETGGNSPVQEFTVHIDYATISGLKPGVDYTITVYAQSPPYDIYYEISINYRTHHHHHH |
| 426 | ATI_1494_D03 w/N leader and C tail | GVSDVPRDLEVVAATPTSLLISWSYPSYHLYRITYGETGGNSPVQEFTVHIDYATISGLKPGVDYTITVYAQSPPYDIYYEISINYRTEIDKPSQ |
| 427 | ATI_1494_D03 w/N leader and C tail + his tag | GVSDVPRDLEVVAATPTSLLISWSYPSYHLYRITYGETGGNSPVQEFTVHIDYATISGLKPGVDYTITVYAQSPPYDIYYEISINYRTEIDKPSQHHHHHH |

TABLE 3-continued

SEQUENCE LISTING

| SEQ ID | DESCRIPTION | SEQUENCE |
|---|---|---|
| 428 | ATI_1494_D03 w/N leader and modified C-terminus including PC | GVSDVPRDLEVVAATPTSLLISWSYPSYHLYRITYGETGGNSPVQEFTVHIDYATISGLKPGVDYTITVYAQSPPYDIYYEISINYRTPC |
| 429 | ATI_1494_D03 w/N leader and modified C-terminus including PC + his tag | GVSDVPRDLEVVAATPTSLLISWSYPSYHLYRITYGETGGNSPVQEFTVHIDYATISGLKPGVDYTITVYAQSPPYDIYYEISINYRTPCHHHHHH |
| 430 | ATI_1494_D03 - full length | MGVSDVPRDLEVVAATPTSLLISWSYPSYHLYRITYGETGGNSPVQEFTVHIDYATISGLKPGVDYTITVYAQSPPYDIYYEISINYRTEIDKPSQHHHHHH |
| 431 | ATI_1494_D04 core | EVVAATPTSLLISWMESSSNSYRITYGETGGNSPVQEFTVPDQLATISGLKPGVDYTITVYALANAHYMRVGISINYRT |
| 432 | ATI_1494_D04 BC loop | MESSSNS |
| 433 | ATI_1494_D04 DE loop | PDQL |
| 434 | ATI_1494_D04 FG loop | LANAHYMRVG |
| 435 | ATI_1494_D04 w/N leader | GVSDVPRDLEVVAATPTSLLISWMESSSNSYRITYGETGGNSPVQEFTVPDQLATISGLKPGVDYTITVYALANAHYMRVGISINYRT |
| 436 | ATI_1494_D04 w/N leader + his tag | GVSDVPRDLEVVAATPTSLLISWMESSSNSYRITYGETGGNSPVQEFTVPDQLATISGLKPGVDYTITVYALANAHYMRVGISINYRTHHHHHH |
| 437 | ATI_1494_D04 w/N leader and C tail | GVSDVPRDLEVVAATPTSLLISWMESSSNSYRITYGETGGNSPVQEFTVPDQLATISGLKPGVDYTITVYALANAHYMRVGISINYRTEIDKPSQ |
| 438 | ATI_1494_D04 w/N leader and C tail + his tag | GVSDVPRDLEVVAATPTSLLISWMESSSNSYRITYGETGGNSPVQEFTVPDQLATISGLKPGVDYTITVYALANAHYMRVGISINYRTEIDKPSQHHHHHH |
| 439 | ATI_1494_D04 w/N leader and modified C-terminus including PC | GVSDVPRDLEVVAATPTSLLISWMESSSNSYRITYGETGGNSPVQEFTVPDQLATISGLKPGVDYTITVYALANAHYMRVGISINYRTPC |
| 440 | ATI_1494_D04 w/N leader and modified C-terminus including PC + his tag | GVSDVPRDLEVVAATPTSLLISWMESSSNSYRITYGETGGNSPVQEFTVPDQLATISGLKPGVDYTITVYALANAHYMRVGISINYRTPCHHHHHH |
| 441 | ATI_1494_D04 - full length | MGVSDVPRDLEVVAATPTSLLISWMESSSNSYRITYGETGGNSPVQEFTVPDQLATISGLKPGVDYTITVYALANAHYMRVGISINYRTEIDKPSQHHHHHH |
| 442 | ATI_1523_A08 core | EVVAATPTSLLISWISVQTYXYRITYGETGGNSPVQEFTVPDQSATISGLKPGVDYTITVYALEKAHYYRQNISINYRT |
| 443 | ATI_1523_A08 BC loop | ISVQTYX |
| 444 | ATI_1523_A08 DE loop | PDQS |
| 445 | ATI_1523_A08 FG loop | LEKAHYYRQN |
| 446 | ATI_1523_A08 w/N leader | GVSDVPRDLEVVAATPTSLLISWISVQTYXYRITYGETGGNSPVQEFTVPDQSATISGLKPGVDYTITVYALEKAHYYRQNISINYRT |
| 447 | ATI_1523_A08 w/N leader + his tag | GVSDVPRDLEVVAATPTSLLISWISVQTYXYRITYGETGGNSPVQEFTVPDQSATISGLKPGVDYTITVYALEKAHYYRQNISINYRTHHHHHH |
| 448 | ATI_1523_A08 w/N leader and C tail | GVSDVPRDLEVVAATPTSLLISWISVQTYXYRITYGETGGNSPVQEFTVPDQSATISGLKPGVDYTITVYALEKAHYYRQNISINYRTEIDKPSQ |
| 449 | ATI_1523_A08 w/N leader and C tail + his tag | GVSDVPRDLEVVAATPTSLLISWISVQTYXYRITYGETGGNSPVQEFTVPDQSATISGLKPGVDYTITVYALEKAHYYRQNISINYRTEIDKPSQHHHHHH |

TABLE 3-continued

SEQUENCE LISTING

| SEQ ID | DESCRIPTION | SEQUENCE |
|---|---|---|
| 450 | ATI_1523_A08 w/N leader and modified C-terminus including PC | GVSDVPRDLEVVAATPTSLLISWISVQTYXYRITYGETGGNSPV QEFTVPDQSATISGLKPGVDYTITVYALEKAHYYRQNISINYRT PC |
| 451 | ATI_1523_A08 w/N leader and modified C-terminus including PC + his tag | GVSDVPRDLEVVAATPTSLLISWISVQTYXYRITYGETGGNSPV QEFTVPDQSATISGLKPGVDYTITVYALEKAHYYRQNISINYRT PCHHHHHH |
| 452 | ATI_1523_A08 - full length | MGVSDVPRDLEVVAATPTSLLISWISVQTYXYRITYGETGGNSP VQEFTVPDQSATISGLKPGVDYTITVYALEKAHYYRQNISINYR TEIDKPSQHHHHHH |
| 453 | ATI_1523_B10 core | EVVAATPTSLLISWVYHYDXQYRITYGETGGNSPVQEFTVPDQK ATISGLKPGVDYTITVYALSEAHHKRDSISINYRT |
| 454 | ATI_1523_B10 BC loop | VYHYDXQ |
| 455 | ATI_1523_B10 DE loop | PDQK |
| 456 | ATI_1523_B10 FG loop | LSEAHHKRDS |
| 457 | ATI_1523_B10 w/N leader | GVSDVPRDLEVVAATPTSLLISWVYHYDXQYRITYGETGGNSPV QEFTVPDQKATISGLKPGVDYTITVYALSEAHHKRDSISINYRT |
| 458 | ATI_1523_B10 w/N leader + his tag | GVSDVPRDLEVVAATPTSLLISWVYHYDXQYRITYGETGGNSPV QEFTVPDQKATISGLKPGVDYTITVYALSEAHHKRDSISINYRT HHHHHH |
| 459 | ATI_1523_B10 w/N leader and C tail | GVSDVPRDLEVVAATPTSLLISWVYHYDXQYRITYGETGGNSPV QEFTVPDQKATISGLKPGVDYTITVYALSEAHHKRDSISINYRT EIDKPSQ |
| 460 | ATI_1523_B10 w/N leader and C tail + his tag | GVSDVPRDLEVVAATPTSLLISWVYHYDXQYRITYGETGGNSPV QEFTVPDQKATISGLKPGVDYTITVYALSEAHHKRDSISINYRT EIDKPSQHHHHHH |
| 461 | ATI_1523_B10 w/N leader and modified C-terminus including PC | GVSDVPRDLEVVAATPTSLLISWVYHYDXQYRITYGETGGNSPV QEFTVPDQKATISGLKPGVDYTITVYALSEAHHKRDSISINYRT PC |
| 462 | ATI_1523_B10 w/N leader and modified C-terminus including PC + his tag | GVSDVPRDLEVVAATPTSLLISWVYHYDXQYRITYGETGGNSPV QEFTVPDQKATISGLKPGVDYTITVYALSEAHHKRDSISINYRT PCHHHHHH |
| 463 | ATI_1523_B10 - full length | MGVSDVPRDLEVVAATPTSLLISWVYHYDXQYRITYGETGGNSP VQEFTVPDQKATISGLKPGVDYTITVYALSEAHHKRDSISINYR TEIDKPSQHHHHHH |
| 464 | ATI_1523_C07 core | EVVAATPTSLLISWRMHTDPDYRITYGETGGNSPVQEFTVPDQE ATISGLKPGVDYTITVYAIQTAHYYRINISINYRT |
| 465 | ATI_1523_C07 BC loop | RMHTDPD |
| 466 | ATI_1523_C07 DE loop | PDQE |
| 467 | ATI_1523_C07 FG loop | IQTAHYYRIN |
| 468 | ATI_1523_C07 w/N leader | GVSDVPRDLEVVAATPTSLLISWRMHTDPDYRITYGETGGNSPV QEFTVPDQEATISGLKPGVDYTITVYAIQTAHYYRINISINYRT |
| 469 | ATI_1523_C07 w/N leader + his tag | GVSDVPRDLEVVAATPTSLLISWRMHTDPDYRITYGETGGNSPV QEFTVPDQEATISGLKPGVDYTITVYAIQTAHYYRINISINYRT HHHHHH |
| 470 | ATI_1523_C07 w/N leader and C tail | GVSDVPRDLEVVAATPTSLLISWRMHTDPDYRITYGETGGNSPV QEFTVPDQEATISGLKPGVDYTITVYAIQTAHYYRINISINYRT EIDKPSQ |
| 471 | ATI_1523_C07 w/N leader and C tail + his tag | GVSDVPRDLEVVAATPTSLLISWRMHTDPDYRITYGETGGNSPV QEFTVPDQEATISGLKPGVDYTITVYAIQTAHYYRINISINYRT EIDKPSQHHHHHH |

TABLE 3-continued

SEQUENCE LISTING

| SEQ ID | DESCRIPTION | SEQUENCE |
|---|---|---|
| 472 | ATI_1523_C07 w/N leader and modified C-terminus including PC | GVSDVPRDLEVVAATPTSLLISWRMHTDPDYRITYGETGGNSPVQEFTVPDQEATISGLKPGVDYTITVYAIQTAHYYRINISINYRTPC |
| 473 | ATI_1523_C07 w/N leader and modified C-terminus including PC + his tag | GVSDVPRDLEVVAATPTSLLISWRMHTDPDYRITYGETGGNSPVQEFTVPDQEATISGLKPGVDYTITVYAIQTAHYYRINISINYRTPCHHHHHH |
| 474 | ATI_1523_C07 - full length | MGVSDVPRDLEVVAATPTSLLISWRMHTDPDYRITYGETGGNSPVQEFTVPDQEATISGLKPGVDYTITVYAIQTAHYYRINISINYRTEIDKPSQHHHHHH |
| 475 | ATI_1523_D07 core | EVVAATPTSLLISWENLASYQYRITYGETGGNSPVQEFTVPDVQATISGLKPGVDYTITVYALPYIHMKQRVISINYRT |
| 476 | ATI_1523_D07 BC loop | ENLASYQ |
| 477 | ATI_1523_D07 DE loop | PDVQ |
| 478 | ATI_1523_D07 FG loop | LPYIHMKQRV |
| 479 | ATI_1523_D07 w/N leader | GVSDVPRDLEVVAATPTSLLISWENLASYQYRITYGETGGNSPVQEFTVPDVQATISGLKPGVDYTITVYALPYIHMKQRVISINYRT |
| 480 | ATI_1523_D07 w/N leader + his tag | GVSDVPRDLEVVAATPTSLLISWENLASYQYRITYGETGGNSPVQEFTVPDVQATISGLKPGVDYTITVYALPYIHMKQRVISINYRTHHHHHH |
| 481 | ATI_1523_D07 w/N leader and C tail | GVSDVPRDLEVVAATPTSLLISWENLASYQYRITYGETGGNSPVQEFTVPDVQATISGLKPGVDYTITVYALPYIHMKQRVISINYRTEIDKPSQ |
| 482 | ATI_1523_D07 w/N leader and C tail + his tag | GVSDVPRDLEVVAATPTSLLISWENLASYQYRITYGETGGNSPVQEFTVPDVQATISGLKPGVDYTITVYALPYIHMKQRVISINYRTEIDKPSQHHHHHH |
| 483 | ATI_1523_D07 w/N leader and modified C-terminus including PC | GVSDVPRDLEVVAATPTSLLISWENLASYQYRITYGETGGNSPVQEFTVPDVQATISGLKPGVDYTITVYALPYIHMKQRVISINYRTPC |
| 484 | ATI_1523_D07 w/N leader and modified C-terminus including PC + his tag | GVSDVPRDLEVVAATPTSLLISWENLASYQYRITYGETGGNSPVQEFTVPDVQATISGLKPGVDYTITVYALPYIHMKQRVISINYRTPCHHHHHH |
| 485 | ATI_1523_D07 - full length | MGVSDVPRDLEVVAATPTSLLISWENLASYQYRITYGETGGNSPVQEFTVPDVQATISGLKPGVDYTITVYALPYIHMKQRVISINYRTEIDKPSQHHHHHH |
| 486 | ATI_1523_D08 core | EVVAATPTSLLISWMRYYDAYYRITYGETGGNSPVQEFTVPDQSATISGLKPGVDYTITVYALEKAHYYRQNISINYRT |
| 487 | ATI_1523_D08 BC loop | MRYYDAY |
| 488 | ATI_1523_D08 DE loop | PDQS |
| 489 | ATI_1523_D08 FG loop | LEKAHYYRQN |
| 490 | ATI_1523_D08 w/N leader | GVSDVPRDLEVVAATPTSLLISWMRYYDAYYRITYGETGGNSPVQEFTVPDQSATISGLKPGVDYTITVYALEKAHYYRQNISINYRT |
| 491 | ATI_1523_D08 w/N leader + his tag | GVSDVPRDLEVVAATPTSLLISWMRYYDAYYRITYGETGGNSPVQEFTVPDQSATISGLKPGVDYTITVYALEKAHYYRQNISINYRTHHHHHH |
| 492 | ATI_1523_D08 w/N leader and C tail | GVSDVPRDLEVVAATPTSLLISWMRYYDAYYRITYGETGGNSPVQEFTVPDQSATISGLKPGVDYTITVYALEKAHYYRQNISINYRTEIDKPSQ |
| 493 | ATI_1523_D08 w/N leader and C tail + his tag | GVSDVPRDLEVVAATPTSLLISWMRYYDAYYRITYGETGGNSPVQEFTVPDQSATISGLKPGVDYTITVYALEKAHYYRQNISINYRTEIDKPSQHHHHHH |

TABLE 3-continued

SEQUENCE LISTING

| SEQ ID | DESCRIPTION | SEQUENCE |
|---|---|---|
| 494 | ATI_1523_D08 w/N leader and modified C-terminus including PC | GVSDVPRDLEVVAATPTSLLISWMRYYDAYYRITYGETGGNSPV QEFTVPDQSATISGLKPGVDYTITVYALEKAHYYRQNISINYRT PC |
| 495 | ATI_1523_D08 w/N leader and modified C-terminus including PC + his tag | GVSDVPRDLEVVAATPTSLLISWMRYYDAYYRITYGETGGNSPV QEFTVPDQSATISGLKPGVDYTITVYALEKAHYYRQNISINYRT PCHHHHHH |
| 496 | ATI_1523_D08 - full length | MGVSDVPRDLEVVAATPTSLLISWMRYYDAYYRITYGETGGNSP VQEFTVPDQSATISGLKPGVDYTITVYALEKAHYYRQNISINYR TEIDKPSQHHHHHH |
| 497 | ATI_1523_E08 core | EVVAATPTSLLISWHHYQHYEYRITYGETGGNSPVQEFTVPDMG ATISGLKPGVDYTITVYALEEAHSDRSSISINYRT |
| 498 | ATI_1523_E08 BC loop | HHYQHYE |
| 499 | ATI_1523_E08 DE loop | PDMG |
| 500 | ATI_1523_E08 FG loop | LEEAHSDRSS |
| 501 | ATI_1523_E08 w/N leader | GVSDVPRDLEVVAATPTSLLISWHHYQHYEYRITYGETGGNSPV QEFTVPDMGATISGLKPGVDYTITVYALEEAHSDRSSISINYRT |
| 502 | ATI_1523_E08 w/N leader + his tag | GVSDVPRDLEVVAATPTSLLISWHHYQHYEYRITYGETGGNSPV QEFTVPDMGATISGLKPGVDYTITVYALEEAHSDRSSISINYRT HHHHHH |
| 503 | ATI_1523_E08 w/N leader and C tail | GVSDVPRDLEVVAATPTSLLISWHHYQHYEYRITYGETGGNSPV QEFTVPDMGATISGLKPGVDYTITVYALEEAHSDRSSISINYRT EIDKPSQ |
| 504 | ATI_1523_E08 w/N leader and C tail + his tag | GVSDVPRDLEVVAATPTSLLISWHHYQHYEYRITYGETGGNSPV QEFTVPDMGATISGLKPGVDYTITVYALEEAHSDRSSISINYRT EIDKPSQHHHHHH |
| 505 | ATI_1523_E08 w/N leader and modified C-terminus including PC | GVSDVPRDLEVVAATPTSLLISWHHYQHYEYRITYGETGGNSPV QEFTVPDMGATISGLKPGVDYTITVYALEEAHSDRSSISINYRT PC |
| 506 | ATI_1523_E08 w/N leader and modified C-terminus including PC + his tag | GVSDVPRDLEVVAATPTSLLISWHHYQHYEYRITYGETGGNSPV QEFTVPDMGATISGLKPGVDYTITVYALEEAHSDRSSISINYRT PCHHHHHH |
| 507 | ATI_1523_E08 - full length | MGVSDVPRDLEVVAATPTSLLISWHHYQHYEYRITYGETGGNSP VQEFTVPDMGATISGLKPGVDYTITVYALEEAHSDRSSISINYR TEIDKPSQHHHHHH |
| 508 | ATI_1523_F01 core | EVVAATPTSLLISWYKPSTIVTYRITYGETGGNSPVQEFTVYGY NATISGLKPGVDYTITVYAVHGVRFISINYRT |
| 509 | ATI_1523_F01 BC loop | YKPSTIVT |
| 510 | ATI_1523_F01 DE loop | YGYN |
| 511 | ATI_1523_F01 FG loop | VHGVRF |
| 512 | ATI_1523_F01 w/N leader | GVSDVPRDLEVVAATPTSLLISWYKPSTIVTYRITYGETGGNSP VQEFTVYGYNATISGLKPGVDYTITVYAVHGVRFISINYRT |
| 513 | ATI_1523_F01 w/N leader + his tag | GVSDVPRDLEVVAATPTSLLISWYKPSTIVTYRITYGETGGNSP VQEFTVYGYNATISGLKPGVDYTITVYAVHGVRFISINYRTHHH HHH |
| 514 | ATI_1523_F01 w/N leader and C tail | GVSDVPRDLEVVAATPTSLLISWYKPSTIVTYRITYGETGGNSP VQEFTVYGYNATISGLKPGVDYTITVYAVHGVRFISINYRTEID KPSQ |
| 515 | ATI_1523_F01 w/N leader and C tail + his tag | GVSDVPRDLEVVAATPTSLLISWYKPSTIVTYRITYGETGGNSP VQEFTVYGYNATISGLKPGVDYTITVYAVHGVRFISINYRTEID KPSQHHHHHH |

TABLE 3-continued

SEQUENCE LISTING

| SEQ ID | DESCRIPTION | SEQUENCE |
|---|---|---|
| 516 | ATI_1523_F01 w/N leader and modified C-terminus including PC | GVSDVPRDLEVVAATPTSLLISWYKPSTIVTYRITYGETGGNSPVQEFTVYGYNATISGLKPGVDYTITVYAVHGVRFISINYRTPC |
| 517 | ATI_1523_F01 w/N leader and modified C-terminus including PC + his tag | GVSDVPRDLEVVAATPTSLLISWYKPSTIVTYRITYGETGGNSPVQEFTVYGYNATISGLKPGVDYTITVYAVHGVRFISINYRTPCHHHHHH |
| 518 | ATI_1523_F01 - full length | MGVSDVPRDLEVVAATPTSLLISWYKPSTIVTYRITYGETGGNSPVQEFTVYGYNATISGLKPGVDYTITVYAVHGVRFISINYRTEIDKPSQHHHHHH |
| 519 | ATI_1523_F04 core | EVVAATPTSLLISWGGSLSPTFYRITYGETGGNSPVQEFTVTYQGATISGLKPGVDYTITVYATEGIVYYQISINYRT |
| 520 | ATI_1523_F04 BC loop | GGSLSPTF |
| 521 | ATI_1523_F04 DE loop | TYQG |
| 522 | ATI_1523_F04 FG loop | TEGIVYYQ |
| 523 | ATI_1523_F04 w/N leader | GVSDVPRDLEVVAATPTSLLISWGGSLSPTFYRITYGETGGNSPVQEFTVTYQGATISGLKPGVDYTITVYATEGIVYYQISINYRT |
| 524 | ATI_1523_F04 w/N leader + his tag | GVSDVPRDLEVVAATPTSLLISWGGSLSPTFYRITYGETGGNSPVQEFTVTYQGATISGLKPGVDYTITVYATEGIVYYQISINYRTHHHHHH |
| 525 | ATI_1523_F04 w/N leader and C tail | GVSDVPRDLEVVAATPTSLLISWGGSLSPTFYRITYGETGGNSPVQEFTVTYQGATISGLKPGVDYTITVYATEGIVYYQISINYRTEIDKPSQ |
| 526 | ATI_1523_F04 w/N leader and C tail + his tag | GVSDVPRDLEVVAATPTSLLISWGGSLSPTFYRITYGETGGNSPVQEFTVTYQGATISGLKPGVDYTITVYATEGIVYYQISINYRTEIDKPSQHHHHHH |
| 527 | ATI_1523_F04 w/N leader and modified C-terminus including PC | GVSDVPRDLEVVAATPTSLLISWGGSLSPTFYRITYGETGGNSPVQEFTVTYQGATISGLKPGVDYTITVYATEGIVYYQISINYRTPC |
| 528 | ATI_1523_F04 w/N leader and modified C-terminus including PC + his tag | GVSDVPRDLEVVAATPTSLLISWGGSLSPTFYRITYGETGGNSPVQEFTVTYQGATISGLKPGVDYTITVYATEGIVYYQISINYRTPCHHHHHH |
| 529 | ATI_1523_F04 - full length | MGVSDVPRDLEVVAATPTSLLISWGGSLSPTFYRITYGETGGNSPVQEFTVTYQGATISGLKPGVDYTITVYATEGIVYYQISINYRTEIDKPSQHHHHHH |
| 530 | ATI_1523_F08 core | EVVAATPTSLLISWVYHYDAQYRITYGETGGNSPVQEFTVPDQKATISGLKPGVDYTITVYALPRAHMDRSHISINYRT |
| 531 | ATI_1523_F08 BC loop | VYHYDAQ |
| 532 | ATI_1523_F08 DE loop | PDQK |
| 533 | ATI_1523_F08 FG loop | LPRAHMDRSH |
| 534 | ATI_1523_F08 w/N leader | GVSDVPRDLEVVAATPTSLLISWVYHYDAQYRITYGETGGNSPVQEFTVPDQKATISGLKPGVDYTITVYALPRAHMDRSHISINYRT |
| 535 | ATI_1523_F08 w/N leader + his tag | GVSDVPRDLEVVAATPTSLLISWVYHYDAQYRITYGETGGNSPVQEFTVPDQKATISGLKPGVDYTITVYALPRAHMDRSHISINYRTHHHHHH |
| 536 | ATI_1523_F08 w/N leader and C tail | GVSDVPRDLEVVAATPTSLLISWVYHYDAQYRITYGETGGNSPVQEFTVPDQKATISGLKPGVDYTITVYALPRAHMDRSHISINYRTEIDKPSQ |
| 537 | ATI_1523_F08 w/N leader and C tail + his tag | GVSDVPRDLEVVAATPTSLLISWVYHYDAQYRITYGETGGNSPVQEFTVPDQKATISGLKPGVDYTITVYALPRAHMDRSHISINYRTEIDKPSQHHHHHH |

TABLE 3-continued

SEQUENCE LISTING

| SEQ ID | DESCRIPTION | SEQUENCE |
|---|---|---|
| 538 | ATI_1523_F08 w/N leader and modified C-terminus including PC | GVSDVPRDLEVVAATPTSLLISWVYHYDAQYRITYGETGGNSPV QEFTVPDQKATISGLKPGVDYTITVYALPRAHMDRSHISINYRT PC |
| 539 | ATI_1523_F08 w/N leader and modified C-terminus including PC + his tag | GVSDVPRDLEVVAATPTSLLISWVYHYDAQYRITYGETGGNSPV QEFTVPDQKATISGLKPGVDYTITVYALPRAHMDRSHISINYRT PCHHHHHH |
| 540 | ATI_1523_F08 - full length | MGVSDVPRDLEVVAATPTSLLISWVYHYDAQYRITYGETGGNSP VQEFTVPDQKATISGLKPGVDYTITVYALPRAHMDRSHISINYR TEIDKPSQHHHHHH |
| 541 | ATI_1523_G06 core | EVVAATPTSLLISWRIKSYHKYRITYGETGGNSPVQEFTVRSYA ATISGLKPGVDYTITVYAIMEETHLAYAISINYRT |
| 542 | ATI_1523_G06 BC loop | RIKSYHK |
| 543 | ATI_1523_G06 DE loop | RSYA |
| 544 | ATI_1523_G06 FG loop | IMEETHLAYA |
| 545 | ATI_1523_G06 w/N leader | GVSDVPRDLEVVAATPTSLLISWRIKSYHKYRITYGETGGNSPV QEFTVRSYAATISGLKPGVDYTITVYAIMEETHLAYAISINYRT |
| 546 | ATI_1523_G06 w/N leader + his tag | GVSDVPRDLEVVAATPTSLLISWRIKSYHKYRITYGETGGNSPV QEFTVRSYAATISGLKPGVDYTITVYAIMEETHLAYAISINYRT HHHHHH |
| 547 | ATI_1523_G06 w/N leader and C tail | GVSDVPRDLEVVAATPTSLLISWRIKSYHKYRITYGETGGNSPV QEFTVRSYAATISGLKPGVDYTITVYAIMEETHLAYAISINYRT EIDKPSQ |
| 548 | ATI_1523_G06 w/N leader and C tail + his tag | GVSDVPRDLEVVAATPTSLLISWRIKSYHKYRITYGETGGNSPV QEFTVRSYAATISGLKPGVDYTITVYAIMEETHLAYAISINYRT EIDKPSQHHHHHH |
| 549 | ATI_1523_G06 w/N leader and modified C-terminus including PC | GVSDVPRDLEVVAATPTSLLISWRIKSYHKYRITYGETGGNSPV QEFTVRSYAATISGLKPGVDYTITVYAIMEETHLAYAISINYRT PC |
| 550 | ATI_1523_G06 w/N leader and modified C-terminus including PC + his tag | GVSDVPRDLEVVAATPTSLLISWRIKSYHKYRITYGETGGNSPV QEFTVRSYAATISGLKPGVDYTITVYAIMEETHLAYAISINYRT PCHHHHHH |
| 551 | ATI_1523_G06 - full length | MGVSDVPRDLEVVAATPTSLLISWRIKSYHKYRITYGETGGNSP VQEFTVRSYAATISGLKPGVDYTITVYAIMEETHLAYAISINYR TEIDKPSQHHHHHH |
| 552 | ATI_1523_G07 core | EVVAATPTSLLISWVYPQADDYRITYGETGGNSPVQEFTVPDQN ATISGLKPGVDYTITVYALAEAHLVRIYISINYRT |
| 553 | ATI_1523_G07 BC loop | VYPQADD |
| 554 | ATI_1523_G07 DE loop | PDQN |
| 555 | ATI_1523_G07 FG loop | LAEAHLVRIY |
| 556 | ATI_1523_G07 w/N leader | GVSDVPRDLEVVAATPTSLLISWVYPQADDYRITYGETGGNSPV QEFTVPDQNATISGLKPGVDYTITVYALAEAHLVRIYISINYRT |
| 557 | ATI_1523_G07 w/N leader + his tag | GVSDVPRDLEVVAATPTSLLISWVYPQADDYRITYGETGGNSPV QEFTVPDQNATISGLKPGVDYTITVYALAEAHLVRIYISINYRT HHHHHH |
| 558 | ATI_1523_G07 w/N leader and C tail | GVSDVPRDLEVVAATPTSLLISWVYPQADDYRITYGETGGNSPV QEFTVPDQNATISGLKPGVDYTITVYALAEAHLVRIYISINYRT EIDKPSQ |
| 559 | ATI_1523_G07 w/N leader and C tail + his tag | GVSDVPRDLEVVAATPTSLLISWVYPQADDYRITYGETGGNSPV QEFTVPDQNATISGLKPGVDYTITVYALAEAHLVRIYISINYRT EIDKPSQHHHHHH |

TABLE 3-continued

SEQUENCE LISTING

| SEQ ID | DESCRIPTION | SEQUENCE |
|---|---|---|
| 560 | ATI_1523_G07 w/N leader and modified C-terminus including PC | GVSDVPRDLEVVAATPTSLLISWVYPQADDYRITYGETGGNSPVQEFTVPDQNATISGLKPGVDYTITVYALAEAHLVRIYISINYRTPC |
| 561 | ATI_1523_G07 w/N leader and modified C-terminus including PC + his tag | GVSDVPRDLEVVAATPTSLLISWVYPQADDYRITYGETGGNSPVQEFTVPDQNATISGLKPGVDYTITVYALAEAHLVRIYISINYRTPCHHHHHH |
| 562 | ATI_1523_G07 - full length | MGVSDVPRDLEVVAATPTSLLISWVYPQADDYRITYGETGGNSPVQEFTVPDQNATISGLKPGVDYTITVYALAEAHLVRIYISINYRTEIDKPSQHHHHHH |
| 563 | ATI_1523_H07 core | EVVAATPTSLLISWVYHYDAXYRITYGETGGNSPVQEFTVPDQKATISGLKPGVDYTITVYALSEAHHKRDSISINYRT |
| 564 | ATI_1523_H07 BC loop | VYHYDAX |
| 565 | ATI_1523_H07 DE loop | PDQK |
| 566 | ATI_1523_H07 FG loop | LSEAHHKRDS |
| 567 | ATI_1523_H07 w/N leader | GVSDVPRDLEVVAATPTSLLISWVYHYDAXYRITYGETGGNSPVQEFTVPDQKATISGLKPGVDYTITVYALSEAHHKRDSISINYRT |
| 568 | ATI_1523_H07 w/N leader + his tag | GVSDVPRDLEVVAATPTSLLISWVYHYDAXYRITYGETGGNSPVQEFTVPDQKATISGLKPGVDYTITVYALSEAHHKRDSISINYRTHHHHHH |
| 569 | ATI_1523_H07 w/N leader and C tail | GVSDVPRDLEVVAATPTSLLISWVYHYDAXYRITYGETGGNSPVQEFTVPDQKATISGLKPGVDYTITVYALSEAHHKRDSISINYRTEIDKPSQ |
| 570 | ATI_1523_H07 w/N leader and C tail + his tag | GVSDVPRDLEVVAATPTSLLISWVYHYDAXYRITYGETGGNSPVQEFTVPDQKATISGLKPGVDYTITVYALSEAHHKRDSISINYRTEIDKPSQHHHHHH |
| 571 | ATI_1523_H07 w/N leader and modified C-terminus including PC | GVSDVPRDLEVVAATPTSLLISWVYHYDAXYRITYGETGGNSPVQEFTVPDQKATISGLKPGVDYTITVYALSEAHHKRDSISINYRTPC |
| 572 | ATI_1523_H07 w/N leader and modified C-terminus including PC + his tag | GVSDVPRDLEVVAATPTSLLISWVYHYDAXYRITYGETGGNSPVQEFTVPDQKATISGLKPGVDYTITVYALSEAHHKRDSISINYRTPCHHHHHH |
| 573 | ATI_1523_H07 - full length | GVSDVPRDLEVVAATPTSLLISWVYHYDAXYRITYGETGGNSPVQEFTVPDQKATISGLKPGVDYTITVYALSEAHHKRDSISINYRTEIDKPSQHHHHHH |
| 574 | N-terminal leader | MGVSDVPRDL |
| 575 | N-terminal leader | GVSDVPRDL |
| 576 | N-terminal leader | $X_n$SDVPRDL |
| 577 | N-terminal leader | $X_n$DVPRDL |
| 578 | N-terminal leader | $X_n$VPRDL |
| 579 | N-terminal leader | $X_n$PRDL |
| 580 | N-terminal leader | $X_n$RDL |
| 581 | N-terminal leader | $X_n$DL |
| 582 | N-terminal leader | MASTSG |
| 583 | N-terminal leader | METDTLLLWVLLLWVPGSTG |
| 584 | C-terminal tail | EIEK |
| 585 | C-terminal tail | EGSGC |

TABLE 3-continued

SEQUENCE LISTING

| SEQ ID | DESCRIPTION | SEQUENCE |
|---|---|---|
| 586 | C-terminal tail | EIEKPCQ |
| 587 | C-terminal tail | EIEKPSQ |
| 588 | C-terminal tail | EIEKP |
| 589 | C-terminal tail | EIEKPS |
| 590 | C-terminal tail | EIEKPC |
| 591 | C-terminal tail | EIDK |
| 592 | C-terminal tail | EIDKPCQ |
| 593 | C-terminal tail | EIDKPSQ |
| 594 | C-terminal tail | EIEPKSS |
| 595 | C-terminal tail | EIDKPC |
| 596 | C-terminal tail | EIDKP |
| 597 | C-terminal tail | EIDKPS |
| 598 | C-terminal tail | EIDKPSQLE |
| 599 | C-terminal tail | EIEDEDEDED |
| 600 | C-terminal tail | EGSGS |
| 601 | C-terminal tail | EIDKPCQLE |
| 602 | C-terminal tail | EIDKPSQHHHHHH |
| 603 | C-terminal tail | GSGCHHHHHH |
| 604 | C-terminal tail | EGSGCHHHHHH |
| 605 | C-terminal tail | PIDK |
| 606 | C-terminal tail | PIEK |
| 607 | C-terminal tail | PIDKP |
| 608 | C-terminal tail | PIEKP |
| 609 | C-terminal tail | PIDKPS |
| 610 | C-terminal tail | PIEKPS |
| 611 | C-terminal tail | PIDKPC |
| 612 | C-terminal tail | PIEKPC |
| 613 | C-terminal tail | PIDKPSQ |
| 614 | C-terminal tail | PIEKPSQ |
| 615 | C-terminal tail | PIDKPCQ |
| 616 | C-terminal tail | PIEKPCQ |
| 617 | C-terminal tail | PHHHHHH |
| 618 | C-terminal tail | PCHHHHHH |
| 619 | 6X-His tag | HHHHHH |
| 620 | Human IgG1 Fc domain | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |

TABLE 3-continued

SEQUENCE LISTING

| SEQ ID | DESCRIPTION | SEQUENCE |
|---|---|---|
| 621 | Core hinge region of Fc | DKTHTCPPCPAPELLG |
| 622 | Exemplary hinge sequence | EPKSSDKTHTCPPCPAPELLGGPS |
| 623 | Exemplary hinge sequence | EPKSSDKTHTCPPCPAPELLGGSS |
| 624 | Exemplary hinge sequence | EPKSSGSTHTCPPCPAPELLGGSS |
| 625 | Exemplary hinge sequence | DKTHTCPPCPAPELLGGPS |
| 626 | Exemplary hinge sequence | DKTHTCPPCPAPELLGGSS |
| 627 | Fc with CH2 and CH3 regions of IgG1 for Adnectin-hinge-Fc construct | VFLEPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSRDELTKNQVSLTCLVKGFYPSDI AVEWESNGQPENNYKTTPPVLDSDGSFFLYSKLTVDKSRWQQGNVF SCSVMHEALHNHYTQKSLSLSPGK |
| 628 | Fc with CH2 and CH3 regions of IgG1 for Fc-hinge-Adnectin construct | VFLEPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSRDELTKNQVSLTCLVKGFYPSDI AVEWESNGQPENNYKTTPPVLDSDGSFFLYSKLTVDKSRWQQGNVF SCSVMHEALHNHYTQKSLSLSP |
| 629 | Linker 1 | GAGGGGSG |
| 630 | Linker 2 | EPKSSD |
| 631 | Linker 3 | PVGVV |
| 632 | Linker 4 | ESPKAQASSVPTAQPQAEGLA |
| 633 | Linker 5 | ELQLEESAAEAQDGELD |
| 634 | Linker 6 | GQPDEPGGS |
| 635 | Linker 7 | GGSGSGSGSGSGS |
| 636 | Linker 8 | ELQLEESAAEAQEGELE |
| 637 | Linker 9 | GSGSG |
| 638 | Linker 10 | GSGC |
| 639 | Linker 11 | AGGGGSG |
| 640 | Linker 12 | GSGS |
| 641 | Linker 13 | QPDEPGGS |
| 642 | Linker 14 | GSGSGS |
| 643 | Linker 15 | TVAAPS |
| 644 | Linker 16 | KAGGGGSG |
| 645 | Linker 17 | KGSGSGSGSGSGS |
| 646 | Linker 18 | KQPDEPGGS |
| 647 | Linker 19 | KELQLEESAAEAQDGELD |
| 648 | Linker 20 | KTVAAPS |
| 649 | Linker 21 | KAGGGGSGG |
| 650 | Linker 22 | KGSGSGSGSGSGSG |
| 651 | Linker 23 | KQPDEPGGSG |
| 652 | Linker 24 | KELQLEESAAEAQDGELDG |
| 653 | Linker 25 | KTVAAPSG |

TABLE 3-continued

SEQUENCE LISTING

| SEQ ID | DESCRIPTION | SEQUENCE |
|---|---|---|
| 654 | Linker 26 | AGGGGSGG |
| 655 | Linker 27 | AGGGGSG |
| 656 | Linker 28 | GSGSGSGSGSGSG |
| 657 | Linker 29 | QPDEPGGSG |
| 658 | Linker 30 | TVAAPSG |
| 659 | Linker 31 | PSTSTST |
| 660 | Linker 32 | EIDKPSQ |
| 661 | Linker 33 | GSGSGSGS |
| 662 | Linker 34 | GSGSGSGSGS |
| 663 | Linker 35 | GSGSGSGSGSGS |
| 664 | Linker 36 | GSGSGSGSGSGSGS |
| 665 | Linker 37 | GGSGSGSGSGSGS |
| 666 | Linker 38 | GGSGSGSGSGSGSG |
| 667 | Linker 39 | GSEGSEGSEGSEGSE |
| 668 | Linker 40 | GGSEGGSE |
| 669 | Linker 41 | GGGGSGGGGSGGGGSGGGGSGGGGSGGGGSGGGGS |
| 670 | Linker 42 | GGGGSGGGGSGGGGSGGGGSGGGGS |
| 671 | Linker 43 | GGGGSGGGGSGGGGSG |
| 672 | Linker 44 | GPGPGPG |
| 673 | Linker 45 | GPGPGPGPGPG |
| 674 | Linker 46 | PAPAPA |
| 675 | Linker 47 | PAPAPAPAPAPA |
| 676 | Linker 48 | PAPAPAPAPAPAPAPA |
| 677 | Linker 49 | GSGSGSGSGSGSGSGSGS |
| 678 | Linker 50 | GGGGSGGGGSGGGGSGGGGS |

EQUIVALENTS

Those skilled in the art will recognize, or be able to ascertain using no more than routine experimentation, many equivalents of the specific embodiments described herein. Such equivalents are intended to be encompassed by the following claims.

SEQUENCE LISTING

```
<160> NUMBER OF SEQ ID NOS: 687

<210> SEQ ID NO 1
<211> LENGTH: 94
<212> TYPE: PRT
<213> ORGANISM: Homo sapiens
<220> FEATURE:
<221> NAME/KEY: misc_feature
<223> OTHER INFORMATION: Full length wild-type human 10Fn3 domain
```

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 86
<212> TYPE: PRT
<213> ORGANISM: Homo sapiens
<220> FEATURE:
<221> NAME/KEY: misc_feature
<223> OTHER INFORMATION: Core wild-type human 10Fn3 domain

<400> SEQUENCE: 2

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Glu Thr Gly
                20                  25                  30

Gly Asn Ser Pro Val Gln Glu Phe Thr Val Pro Gly Ser Lys Ser Thr
            35                  40                  45

Ala Thr Ile Ser Gly Leu Lys Pro Gly Val Asp Tyr Thr Ile Thr Val
    50                  55                  60

Tyr Ala Val Thr Gly Arg Gly Asp Ser Pro Ala Ser Ser Lys Pro Ile
65                  70                  75                  80

Ser Ile Asn Tyr Arg Thr
                85

<210> SEQ ID NO 3
<211> LENGTH: 128
<212> TYPE: PRT
<213> ORGANISM: Artificial Sequence
<220> FEATURE:
<223> OTHER INFORMATION: Synthetic: Core 10Fn3-based scaffold with
      variable AB, BC, CD, DE, EF, and FG loops
<220> FEATURE:
<221> NAME/KEY: misc_feature
<222> LOCATION: (6)..(20)
<223> OTHER INFORMATION: Xaa can be any naturally occurring amino acid;
      at least one amino acid must be present, the rest may be present
      or absent
<220> FEATURE:
<221> NAME/KEY: misc_feature
<222> LOCATION: (26)..(40)
<223> OTHER INFORMATION: Xaa can be any naturally occurring amino acid;
      at least two amino acids must be present, the rest may be present
      or absent
<220> FEATURE:
<221> NAME/KEY: misc_feature
<222> LOCATION: (46)..(60)
<223> OTHER INFORMATION: Xaa can be any naturally occurring amino acid;
      at least two amino acids must be present, the rest may be present
      or absent
<220> FEATURE:
<221> NAME/KEY: misc_feature
<222> LOCATION: (64)..(78)

-continued

```
<223> OTHER INFORMATION: Xaa can be any naturally occurring amino acid;
      at least two amino acids must be present, the rest may be present
      or absent
<220> FEATURE:
<221> NAME/KEY: misc_feature
<222> LOCATION: (85)..(99)
<223> OTHER INFORMATION: Xaa can be any naturally occurring amino acid;
      at least two amino acids must be present, the rest may be present
      or absent
<220> FEATURE:
<221> NAME/KEY: misc_feature
<222> LOCATION: (107)..(121)
<223> OTHER INFORMATION: Xaa can be any naturally occurring amino acid;
      at least two amino acids must be present, the rest may be present
      or absent

<400> SEQUENCE: 3

Glu Val Val Ala Ala Xaa Xaa Xaa Xaa Xaa Xaa Xaa Xaa Xaa Xaa
1               5                   10                  15

Xaa Xaa Xaa Xaa Leu Leu Ile Ser Trp Xaa Xaa Xaa Xaa Xaa Xaa
            20                  25                  30

Xaa Xaa Xaa Xaa Xaa Xaa Xaa Xaa Tyr Arg Ile Thr Tyr Xaa Xaa
        35                  40                  45

Xaa Xaa Xaa Xaa Xaa Xaa Xaa Xaa Xaa Xaa Xaa Phe Thr Val Xaa
    50                  55                  60

Xaa Xaa Xaa Xaa Xaa Xaa Xaa Xaa Xaa Xaa Xaa Xaa Xaa Ala Thr
65                  70                  75                  80

Ile Ser Gly Leu Xaa Xaa Xaa Xaa Xaa Xaa Xaa Xaa Xaa Xaa Xaa
                85                  90                  95

Xaa Xaa Xaa Tyr Thr Ile Thr Val Tyr Ala Xaa Xaa Xaa Xaa Xaa
            100                 105                 110

Xaa Xaa Xaa Xaa Xaa Xaa Xaa Xaa Xaa Ile Ser Ile Asn Tyr Arg Thr
        115                 120                 125

<210> SEQ ID NO 4
<211> LENGTH: 103
<212> TYPE: PRT
<213> ORGANISM: Artificial Sequence
<220> FEATURE:
<223> OTHER INFORMATION: Synthetic: Core 10Fn3-based scaffold with
      variable BC, DE, and FG loops
<220> FEATURE:
<221> NAME/KEY: misc_feature
<222> LOCATION: (15)..(29)
<223> OTHER INFORMATION: Xaa can be any naturally occurring amino acid;
      at least two amino acids must be present, the rest may be present
      or absent
<220> FEATURE:
<221> NAME/KEY: misc_feature
<222> LOCATION: (49)..(63)
<223> OTHER INFORMATION: Xaa can be any naturally occurring amino acid;
      at least two amino acids must be present, the rest may be present
      or absent
<220> FEATURE:
<221> NAME/KEY: misc_feature
<222> LOCATION: (82)..(96)
<223> OTHER INFORMATION: Xaa can be any naturally occurring amino acid;
      at least two amino acids must be present, the rest may be present
      or absent

<400> SEQUENCE: 4

Glu Val Val Ala Ala Thr Pro Thr Ser Leu Leu Ile Ser Trp Xaa Xaa
1               5                   10                  15

Xaa Xaa Xaa Xaa Xaa Xaa Xaa Xaa Xaa Xaa Xaa Xaa Xaa Tyr Arg Ile
            20                  25                  30

Thr Tyr Gly Glu Thr Gly Gly Asn Ser Pro Val Gln Glu Phe Thr Val
            35                  40                  45
```

```
Xaa Xaa Xaa Xaa Xaa Xaa Xaa Xaa Xaa Xaa Xaa Xaa Xaa Ala
    50                  55                  60

Thr Ile Ser Gly Leu Lys Pro Gly Val Asp Tyr Thr Ile Thr Val Tyr
65                  70                  75                  80

Ala Xaa Xaa Xaa Xaa Xaa Xaa Xaa Xaa Xaa Xaa Xaa Xaa Xaa Xaa Xaa
                85                  90                  95

Ile Ser Ile Asn Tyr Arg Thr
            100

<210> SEQ ID NO 5
<211> LENGTH: 86
<212> TYPE: PRT
<213> ORGANISM: Artificial Sequence
<220> FEATURE:
<223> OTHER INFORMATION: Synthetic: ATI-968 core (aka ADX_1760_C01)

<400> SEQUENCE: 5

Glu Val Val Ala Ala Thr Pro Thr Ser Leu Leu Ile Ser Trp Ile Ala
1               5                   10                  15

Pro Phe Tyr Asn Val Ile Tyr Tyr Arg Ile Thr Tyr Gly Glu Thr Gly
            20                  25                  30

Gly Asn Ser Pro Val Gln Glu Phe Thr Val Pro Gly Thr Gly Tyr Thr
        35                  40                  45

Ala Thr Ile Ser Gly Leu Lys Pro Gly Val Asp Tyr Thr Ile Thr Val
    50                  55                  60

Tyr Ala Val Thr Asp Gly Ala Ser Ile Ala Ser Tyr Ala Phe Pro Ile
65                  70                  75                  80

Ser Ile Asn Tyr Arg Thr
            85

<210> SEQ ID NO 6
<211> LENGTH: 9
<212> TYPE: PRT
<213> ORGANISM: Artificial Sequence
<220> FEATURE:
<223> OTHER INFORMATION: Synthetic: ATI-968 BC loop

<400> SEQUENCE: 6

Ile Ala Pro Phe Tyr Asn Val Ile Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic: ATI-968 DE loop

<400> SEQUENCE: 7

Pro Gly Thr Gly Tyr Thr
1               5

<210> SEQ ID NO 8
<211> LENGTH: 13
<212> TYPE: PRT
<213> ORGANISM: Artificial Sequence
<220> FEATURE:
<223> OTHER INFORMATION: Synthetic: ATI-968 FG loop

<400> SEQUENCE: 8

Val Thr Asp Gly Ala Ser Ile Ala Ser Tyr Ala Phe Pro
1               5                   10
```

```
<210> SEQ ID NO 9
<211> LENGTH: 95
<212> TYPE: PRT
<213> ORGANISM: Artificial Sequence
<220> FEATURE:
<223> OTHER INFORMATION: Synthetic: ATI-968 w/ N leader

<400> SEQUENCE: 9

Gly Val Ser Asp Val Pro Arg Asp Leu Glu Val Val Ala Ala Thr Pro
1               5                   10                  15

Thr Ser Leu Leu Ile Ser Trp Ile Ala Pro Phe Tyr Asn Val Ile Tyr
            20                  25                  30

Tyr Arg Ile Thr Tyr Gly Glu Thr Gly Gly Asn Ser Pro Val Gln Glu
        35                  40                  45

Phe Thr Val Pro Gly Thr Gly Tyr Thr Ala Thr Ile Ser Gly Leu Lys
    50                  55                  60

Pro Gly Val Asp Tyr Thr Ile Thr Val Tyr Ala Val Thr Asp Gly Ala
65                  70                  75                  80

Ser Ile Ala Ser Tyr Ala Phe Pro Ile Ser Ile Asn Tyr Arg Thr
                85                  90                  95

<210> SEQ ID NO 10
<211> LENGTH: 101
<212> TYPE: PRT
<213> ORGANISM: Artificial Sequence
<220> FEATURE:
<223> OTHER INFORMATION: Synthetic: ATI-968 w/ N leader + his tag

<400> SEQUENCE: 10

Gly Val Ser Asp Val Pro Arg Asp Leu Glu Val Val Ala Ala Thr Pro
1               5                   10                  15

Thr Ser Leu Leu Ile Ser Trp Ile Ala Pro Phe Tyr Asn Val Ile Tyr
            20                  25                  30

Tyr Arg Ile Thr Tyr Gly Glu Thr Gly Gly Asn Ser Pro Val Gln Glu
        35                  40                  45

Phe Thr Val Pro Gly Thr Gly Tyr Thr Ala Thr Ile Ser Gly Leu Lys
    50                  55                  60

Pro Gly Val Asp Tyr Thr Ile Thr Val Tyr Ala Val Thr Asp Gly Ala
65                  70                  75                  80

Ser Ile Ala Ser Tyr Ala Phe Pro Ile Ser Ile Asn Tyr Arg Thr His
                85                  90                  95

His His His His His
            100

<210> SEQ ID NO 11
<211> LENGTH: 102
<212> TYPE: PRT
<213> ORGANISM: Artificial Sequence
<220> FEATURE:
<223> OTHER INFORMATION: Synthetic: ATI-968 w/ N leader and C tail

<400> SEQUENCE: 11

Gly Val Ser Asp Val Pro Arg Asp Leu Glu Val Val Ala Ala Thr Pro
1               5                   10                  15

Thr Ser Leu Leu Ile Ser Trp Ile Ala Pro Phe Tyr Asn Val Ile Tyr
            20                  25                  30

Tyr Arg Ile Thr Tyr Gly Glu Thr Gly Gly Asn Ser Pro Val Gln Glu
        35                  40                  45
```

```
Phe Thr Val Pro Gly Thr Gly Tyr Thr Ala Thr Ile Ser Gly Leu Lys
 50                  55                  60

Pro Gly Val Asp Tyr Thr Ile Thr Val Tyr Ala Val Thr Asp Gly Ala
 65                  70                  75                  80

Ser Ile Ala Ser Tyr Ala Phe Pro Ile Ser Ile Asn Tyr Arg Thr Glu
                 85                  90                  95

Ile Asp Lys Pro Ser Gln
            100

<210> SEQ ID NO 12
<211> LENGTH: 108
<212> TYPE: PRT
<213> ORGANISM: Artificial Sequence
<220> FEATURE:
<223> OTHER INFORMATION: Synthetic: ATI-968 w/ N leader and C tail + his
      tag

<400> SEQUENCE: 12

Gly Val Ser Asp Val Pro Arg Asp Leu Glu Val Val Ala Ala Thr Pro
 1               5                  10                  15

Thr Ser Leu Leu Ile Ser Trp Ile Ala Pro Phe Tyr Asn Val Ile Tyr
                 20                  25                  30

Tyr Arg Ile Thr Tyr Gly Glu Thr Gly Gly Asn Ser Pro Val Gln Glu
             35                  40                  45

Phe Thr Val Pro Gly Thr Gly Tyr Thr Ala Thr Ile Ser Gly Leu Lys
 50                  55                  60

Pro Gly Val Asp Tyr Thr Ile Thr Val Tyr Ala Val Thr Asp Gly Ala
 65                  70                  75                  80

Ser Ile Ala Ser Tyr Ala Phe Pro Ile Ser Ile Asn Tyr Arg Thr Glu
                 85                  90                  95

Ile Asp Lys Pro Ser Gln His His His His His His
            100                 105

<210> SEQ ID NO 13
<211> LENGTH: 97
<212> TYPE: PRT
<213> ORGANISM: Artificial Sequence
<220> FEATURE:
<223> OTHER INFORMATION: Synthetic: ATI-968 w/ N leader and modified
      C-terminus including PC

<400> SEQUENCE: 13

Gly Val Ser Asp Val Pro Arg Asp Leu Glu Val Val Ala Ala Thr Pro
 1               5                  10                  15

Thr Ser Leu Leu Ile Ser Trp Ile Ala Pro Phe Tyr Asn Val Ile Tyr
                 20                  25                  30

Tyr Arg Ile Thr Tyr Gly Glu Thr Gly Gly Asn Ser Pro Val Gln Glu
             35                  40                  45

Phe Thr Val Pro Gly Thr Gly Tyr Thr Ala Thr Ile Ser Gly Leu Lys
 50                  55                  60

Pro Gly Val Asp Tyr Thr Ile Thr Val Tyr Ala Val Thr Asp Gly Ala
 65                  70                  75                  80

Ser Ile Ala Ser Tyr Ala Phe Pro Ile Ser Ile Asn Tyr Arg Thr Pro
                 85                  90                  95

Cys

<210> SEQ ID NO 14
<211> LENGTH: 103
<212> TYPE: PRT
```

<213> ORGANISM: Artificial Sequence
<220> FEATURE:
<223> OTHER INFORMATION: Synthetic: ATI-968 w/ N leader and modified
      C-terminus including PC + his tag

<400> SEQUENCE: 14

Gly Val Ser Asp Val Pro Arg Asp Leu Glu Val Val Ala Ala Thr Pro
1               5                   10                  15

Thr Ser Leu Leu Ile Ser Trp Ile Ala Pro Phe Tyr Asn Val Ile Tyr
            20                  25                  30

Tyr Arg Ile Thr Tyr Gly Glu Thr Gly Gly Asn Ser Pro Val Gln Glu
        35                  40                  45

Phe Thr Val Pro Gly Thr Gly Tyr Thr Ala Thr Ile Ser Gly Leu Lys
50                  55                  60

Pro Gly Val Asp Tyr Thr Ile Thr Val Tyr Ala Val Thr Asp Gly Ala
65                  70                  75                  80

Ser Ile Ala Ser Tyr Ala Phe Pro Ile Ser Ile Asn Tyr Arg Thr Pro
                85                  90                  95

Cys His His His His His His
            100

<210> SEQ ID NO 15
<211> LENGTH: 109
<212> TYPE: PRT
<213> ORGANISM: Artificial Sequence
<220> FEATURE:
<223> OTHER INFORMATION: Synthetic: ATI-968  full length

<400> SEQUENCE: 15

Met Gly Val Ser Asp Val Pro Arg Asp Leu Glu Val Val Ala Ala Thr
1               5                   10                  15

Pro Thr Ser Leu Leu Ile Ser Trp Ile Ala Pro Phe Tyr Asn Val Ile
            20                  25                  30

Tyr Tyr Arg Ile Thr Tyr Gly Glu Thr Gly Gly Asn Ser Pro Val Gln
        35                  40                  45

Glu Phe Thr Val Pro Gly Thr Gly Tyr Thr Ala Thr Ile Ser Gly Leu
50                  55                  60

Lys Pro Gly Val Asp Tyr Thr Ile Thr Val Tyr Ala Val Thr Asp Gly
65                  70                  75                  80

Ala Ser Ile Ala Ser Tyr Ala Phe Pro Ile Ser Ile Asn Tyr Arg Thr
                85                  90                  95

Glu Ile Asp Lys Pro Ser Gln His His His His His
            100                 105

<210> SEQ ID NO 16
<211> LENGTH: 258
<212> TYPE: DNA
<213> ORGANISM: Artificial Sequence
<220> FEATURE:
<223> OTHER INFORMATION: Synthetic: ATI-968  core (nucleotide sequence)

<400> SEQUENCE: 16
gaagtggttg ctgccacccc caccagcctg ctgatcagct ggatcgctcc gttctacaat      60
gtcatctatt accgcatcac ttacggcgaa acaggaggca atagccctgt ccaggagttc     120
actgtgcctg gtactggtta tacagctaca atcagcggcc ttaaacctgg cgttgattat     180
accatcactg tgtatgctgt cactgatgga gcatccattg cttcatacgc gtttccaatt     240
tccattaatt accgcaca                                                    258

-continued

<210> SEQ ID NO 17
<211> LENGTH: 288
<212> TYPE: DNA
<213> ORGANISM: Artificial Sequence
<220> FEATURE:
<223> OTHER INFORMATION: Synthetic: ATI-968 w/ N leader (nucleotide
      sequence with N-terminal methionine)

<400> SEQUENCE: 17

```
atgggagttt ctgatgtgcc gcgcgacctg gaagtggttg ctgccacccc caccagcctg      60
ctgatcagct ggatcgctcc gttctacaat gtcatctatt accgcatcac ttacggcgaa     120
acaggaggca atagccctgt ccaggagttc actgtgcctg gtactggtta tacagctaca     180
atcagcggcc ttaaacctgg cgttgattat accatcactg tgtatgctgt cactgatgga     240
gcatccattg cttcatacgc gtttccaatt tccattaatt accgcaca                   288
```

<210> SEQ ID NO 18
<211> LENGTH: 294
<212> TYPE: DNA
<213> ORGANISM: Artificial Sequence
<220> FEATURE:
<223> OTHER INFORMATION: Synthetic: ATI-968 w/ N leader and modified
      C-terminus including PC (nucleotide sequence with N-terminal
      methionine)

<400> SEQUENCE: 18

```
atgggagttt ctgatgtgcc gcgcgacctg gaagtggttg ctgccacccc caccagcctg      60
ctgatcagct ggatcgctcc gttctacaat gtcatctatt accgcatcac ttacggcgaa     120
acaggaggca atagccctgt ccaggagttc actgtgcctg gtactggtta tacagctaca     180
atcagcggcc ttaaacctgg cgttgattat accatcactg tgtatgctgt cactgatgga     240
gcatccattg cttcatacgc gtttccaatt tccattaatt accgcacacc gtgc           294
```

<210> SEQ ID NO 19
<211> LENGTH: 330
<212> TYPE: DNA
<213> ORGANISM: Artificial Sequence
<220> FEATURE:
<223> OTHER INFORMATION: Synthetic: ATI-968 w/ N leader and C tail + his
      tag (nucleotide sequence with N-terminal methionine)

<400> SEQUENCE: 19

```
atgggagttt ctgatgtgcc gcgcgacctg gaagtggttg ctgccacccc caccagcctg      60
ctgatcagct ggatcgctcc gttctacaat gtcatctatt accgcatcac ttacggcgaa     120
acaggaggca atagccctgt ccaggagttc actgtgcctg gtactggtta tacagctaca     180
atcagcggcc ttaaacctgg cgttgattat accatcactg tgtatgctgt cactgatgga     240
gcatccattg cttcatacgc gtttccaatt tccattaatt accgcacaga aattgacaaa     300
ccatcccagc accatcacca ccaccactga                                       330
```

<210> SEQ ID NO 20
<211> LENGTH: 86
<212> TYPE: PRT
<213> ORGANISM: Artificial Sequence
<220> FEATURE:
<223> OTHER INFORMATION: Synthetic: ATI-964 core (parent of
      ADX_5322_A02)

<400> SEQUENCE: 20

```
Glu Val Val Ala Ala Thr Pro Thr Ser Leu Leu Ile Ser Trp Ser Tyr
1               5                   10                  15
```

Asp Gly Ser Ile Glu Arg Tyr Tyr Arg Ile Thr Tyr Gly Glu Thr Gly
            20                  25                  30

Gly Asn Ser Pro Val Gln Glu Phe Thr Val Pro Pro Asp Gln Lys Thr
        35                  40                  45

Ala Thr Ile Ser Gly Leu Lys Pro Gly Val Asp Tyr Thr Ile Thr Val
 50                  55                  60

Tyr Ala Val Arg Leu Glu Glu Ala His Tyr Tyr Arg Glu Ser Pro Ile
 65                  70                  75                  80

Ser Ile Asn Tyr Arg Thr
                 85

<210> SEQ ID NO 21
<211> LENGTH: 9
<212> TYPE: PRT
<213> ORGANISM: Artificial Sequence
<220> FEATURE:
<223> OTHER INFORMATION: Synthetic: ATI-964 BC loop

<400> SEQUENCE: 21

Ser Tyr Asp Gly Ser Ile Glu Arg Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic: ATI-964 DE loop

<400> SEQUENCE: 22

Pro Pro Asp Gln Lys Thr
1               5

<210> SEQ ID NO 23
<211> LENGTH: 13
<212> TYPE: PRT
<213> ORGANISM: Artificial Sequence
<220> FEATURE:
<223> OTHER INFORMATION: Synthetic: ATI-964 FG loop

<400> SEQUENCE: 23

Val Arg Leu Glu Glu Ala His Tyr Tyr Arg Glu Ser Pro
1               5                   10

<210> SEQ ID NO 24
<211> LENGTH: 95
<212> TYPE: PRT
<213> ORGANISM: Artificial Sequence
<220> FEATURE:
<223> OTHER INFORMATION: Synthetic: ATI-964 w/ N leader

<400> SEQUENCE: 24

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Ser Ile Glu Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Tyr Arg Glu Ser Pro Ile Ser Ile Asn Tyr Arg Thr
            85                  90                  95

<210> SEQ ID NO 25
<211> LENGTH: 101
<212> TYPE: PRT
<213> ORGANISM: Artificial Sequence
<220> FEATURE:
<223> OTHER INFORMATION: Synthetic: ATI-964 w/ N leader + his tag

<400> SEQUENCE: 25

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Ser Ile Glu Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Tyr Arg Glu Ser Pro Ile Ser Ile Asn Tyr Arg Thr His
            85                  90                  95

His His His His
        100

<210> SEQ ID NO 26
<211> LENGTH: 102
<212> TYPE: PRT
<213> ORGANISM: Artificial Sequence
<220> FEATURE:
<223> OTHER INFORMATION: Synthetic: ATI-964 w/ N leader and C tail

<400> SEQUENCE: 26

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Ser Ile Glu Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Tyr Arg Glu Ser Pro Ile Ser Ile Asn Tyr Arg Thr Glu
            85                  90                  95

Ile Asp Lys Pro Ser Gln
        100

<210> SEQ ID NO 27
<211> LENGTH: 108
<212> TYPE: PRT
<213> ORGANISM: Artificial Sequence
<220> FEATURE:
<223> OTHER INFORMATION: Synthetic: ATI-964 w/ N leader and C tail + his
      tag

<400> SEQUENCE: 27

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Ser Ile Glu Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
 50                  55                  60

Pro Gly Val Asp Tyr Thr Ile Thr Val Tyr Ala Val Arg Leu Glu Glu
65                  70                  75                  80

Ala His Tyr Tyr Arg Glu Ser Pro Ile Ser Ile Asn Tyr Arg Thr Glu
            85                  90                  95

Ile Asp Lys Pro Ser Gln His His His His His
            100                 105

<210> SEQ ID NO 28
<211> LENGTH: 97
<212> TYPE: PRT
<213> ORGANISM: Artificial Sequence
<220> FEATURE:
<223> OTHER INFORMATION: Synthetic: ATI-964 w/ N leader and modified
      C-terminus including PC

<400> SEQUENCE: 28

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Ser Ile Glu Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
 50                  55                  60

Pro Gly Val Asp Tyr Thr Ile Thr Val Tyr Ala Val Arg Leu Glu Glu
65                  70                  75                  80

Ala His Tyr Tyr Arg Glu Ser Pro Ile Ser Ile Asn Tyr Arg Thr Pro
            85                  90                  95

Cys

<210> SEQ ID NO 29
<211> LENGTH: 103
<212> TYPE: PRT
<213> ORGANISM: Artificial Sequence
<220> FEATURE:
<223> OTHER INFORMATION: Synthetic: ATI-964 w/ N leader and modified
      C-terminus including PC + his tag

<400> SEQUENCE: 29

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Ser Ile Glu Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
 50                  55                  60

Pro Gly Val Asp Tyr Thr Ile Thr Val Tyr Ala Val Arg Leu Glu Glu
65                  70                  75                  80

Ala His Tyr Tyr Arg Glu Ser Pro Ile Ser Ile Asn Tyr Arg Thr Pro
            85                  90                  95

-continued

Cys His His His His His
                100

<210> SEQ ID NO 30
<211> LENGTH: 109
<212> TYPE: PRT
<213> ORGANISM: Artificial Sequence
<220> FEATURE:
<223> OTHER INFORMATION: Synthetic: ATI-964  full length

<400> SEQUENCE: 30

Met Gly Val Ser Asp Val Pro Arg Asp Leu Glu Val Val Ala Ala Thr
1               5                   10                  15

Pro Thr Ser Leu Leu Ile Ser Trp Ser Tyr Asp Gly Ser Ile Glu Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro Asp Gln Lys Thr Ala Thr Ile Ser Gly Leu
    50                  55                  60

Lys Pro Gly Val Asp Tyr Thr Ile Thr Val Tyr Ala Val Arg Leu Glu
65                  70                  75                  80

Glu Ala His Tyr Tyr Arg Glu Ser Pro Ile Ser Ile Asn Tyr Arg Thr
                85                  90                  95

Glu Ile Asp Lys Pro Ser Gln His His His His His
                100                 105

<210> SEQ ID NO 31
<211> LENGTH: 258
<212> TYPE: DNA
<213> ORGANISM: Artificial Sequence
<220> FEATURE:
<223> OTHER INFORMATION: Synthetic: ATI-964  core (nucleotide sequence)

<400> SEQUENCE: 31
gaagtggttg ctgccacccc caccagcctg ctgatcagct ggtcttacga cggttcgatt      60
gaacgttatt accgcatcac ttacggcgaa acaggaggca atagccctgt ccaggagttc     120
actgtgcctc cggatcagaa gacagctacc atcagcggcc ttaaacctgg cgttgattat     180
accatcactg tgtatgctgt caggctggaa gaagctcatt actatcgaga gtctccaatt     240
tccattaatt accgcaca                                                    258

<210> SEQ ID NO 32
<211> LENGTH: 288
<212> TYPE: DNA
<213> ORGANISM: Artificial Sequence
<220> FEATURE:
<223> OTHER INFORMATION: Synthetic: ATI-964 w/ N leader (nucleotide
      sequence with N-terminal methionine)

<400> SEQUENCE: 32
atgggagttt ctgatgtgcc gcgcgacctg gaagtggttg ctgccacccc caccagcctg      60
ctgatcagct ggtcttacga cggttcgatt gaacgttatt accgcatcac ttacggcgaa     120
acaggaggca atagccctgt ccaggagttc actgtgcctc cggatcagaa gacagctacc     180
atcagcggcc ttaaacctgg cgttgattat accatcactg tgtatgctgt caggctggaa     240
gaagctcatt actatcgaga gtctccaatt tccattaatt accgcaca                  288

<210> SEQ ID NO 33
<211> LENGTH: 294
<212> TYPE: DNA

-continued

<213> ORGANISM: Artificial Sequence
<220> FEATURE:
<223> OTHER INFORMATION: Synthetic: ATI-964 w/ N leader and modified
      C-terminus including PC (nucleotide sequence with N-terminal
      methionine)

<400> SEQUENCE: 33
atgggagttt ctgatgtgcc gcgcgacctg gaagtggttg ctgccacccc caccagcctg    60
ctgatcagct ggtcttacga cggttcgatt gaacgttatt accgcatcac ttacggcgaa   120
acaggaggca atagccctgt ccaggagttc actgtgcctc cggatcagaa gacagctacc   180
atcagcggcc ttaaacctgg cgttgattat accatcactg tgtatgctgt caggctggaa   240
gaagctcatt actatcgaga gtctccaatt tccattaatt accgcacacc gtgc          294

<210> SEQ ID NO 34
<211> LENGTH: 330
<212> TYPE: DNA
<213> ORGANISM: Artificial Sequence
<220> FEATURE:
<223> OTHER INFORMATION: Synthetic: ATI-964 w/ N leader and C tail + his
      tag (nucleotide sequence with N-terminal methionine)

<400> SEQUENCE: 34
atgggagttt ctgatgtgcc gcgcgacctg gaagtggttg ctgccacccc caccagcctg    60
ctgatcagct ggtcttacga cggttcgatt gaacgttatt accgcatcac ttacggcgaa   120
acaggaggca atagccctgt ccaggagttc actgtgcctc cggatcagaa gacagctacc   180
atcagcggcc ttaaacctgg cgttgattat accatcactg tgtatgctgt caggctggaa   240
gaagctcatt actatcgaga gtctccaatt tccattaatt accgcacaga aattgacaaa   300
ccatcccagc accatcacca ccaccactga                                     330

<210> SEQ ID NO 35
<211> LENGTH: 86
<212> TYPE: PRT
<213> ORGANISM: Artificial Sequence
<220> FEATURE:
<223> OTHER INFORMATION: Synthetic: ATI-965 core

<400> SEQUENCE: 35

Glu Val Val Ala Ala Thr Pro Thr Ser Leu Leu Ile Ser Trp Thr Ala
1               5                   10                  15

Tyr Asp Ser Val Asp Lys Tyr Tyr Arg Ile Thr Tyr Gly Glu Thr Gly
                20                  25                  30

Gly Asn Ser Pro Val Gln Glu Phe Thr Val Gly Pro Arg His His Thr
            35                  40                  45

Ala Thr Ile Ser Gly Leu Lys Pro Gly Val Asp Tyr Thr Ile Thr Val
        50                  55                  60

Tyr Ala Val Tyr His Thr Glu Pro Gly Tyr His Ala His Met Pro Ile
65                  70                  75                  80

Ser Ile Asn Tyr Arg Thr
                85

<210> SEQ ID NO 36
<211> LENGTH: 9
<212> TYPE: PRT
<213> ORGANISM: Artificial Sequence
<220> FEATURE:
<223> OTHER INFORMATION: Synthetic: ATI-965 BC loop

<400> SEQUENCE: 36

```
Thr Ala Tyr Asp Ser Val Asp Lys Tyr
1               5
```

```
<210> SEQ ID NO 37
<211> LENGTH: 6
<212> TYPE: PRT
<213> ORGANISM: Artificial Sequence
<220> FEATURE:
<223> OTHER INFORMATION: Synthetic: ATI-965 DE loop

<400> SEQUENCE: 37

Gly Pro Arg His His Thr
1               5
```

```
<210> SEQ ID NO 38
<211> LENGTH: 13
<212> TYPE: PRT
<213> ORGANISM: Artificial Sequence
<220> FEATURE:
<223> OTHER INFORMATION: Synthetic: ATI-965 FG loop

<400> SEQUENCE: 38

Val Tyr His Thr Glu Pro Gly Tyr His Ala His Met Pro
1               5                   10
```

```
<210> SEQ ID NO 39
<211> LENGTH: 95
<212> TYPE: PRT
<213> ORGANISM: Artificial Sequence
<220> FEATURE:
<223> OTHER INFORMATION: Synthetic: ATI-965 w/ N leader

<400> SEQUENCE: 39

Gly Val Ser Asp Val Pro Arg Asp Leu Glu Val Val Ala Ala Thr Pro
1               5                   10                  15

Thr Ser Leu Leu Ile Ser Trp Thr Ala Tyr Asp Ser Val Asp Lys Tyr
                20                  25                  30

Tyr Arg Ile Thr Tyr Gly Glu Thr Gly Gly Asn Ser Pro Val Gln Glu
            35                  40                  45

Phe Thr Val Gly Pro Arg His His Thr Ala Thr Ile Ser Gly Leu Lys
50                  55                  60

Pro Gly Val Asp Tyr Thr Ile Thr Val Tyr Ala Val Tyr His Thr Glu
65                  70                  75                  80

Pro Gly Tyr His Ala His Met Pro Ile Ser Ile Asn Tyr Arg Thr
                85                  90                  95
```

```
<210> SEQ ID NO 40
<211> LENGTH: 101
<212> TYPE: PRT
<213> ORGANISM: Artificial Sequence
<220> FEATURE:
<223> OTHER INFORMATION: Synthetic: ATI-965 w/ N leader + his tag

<400> SEQUENCE: 40

Gly Val Ser Asp Val Pro Arg Asp Leu Glu Val Val Ala Ala Thr Pro
1               5                   10                  15

Thr Ser Leu Leu Ile Ser Trp Thr Ala Tyr Asp Ser Val Asp Lys Tyr
                20                  25                  30

Tyr Arg Ile Thr Tyr Gly Glu Thr Gly Gly Asn Ser Pro Val Gln Glu
            35                  40                  45

Phe Thr Val Gly Pro Arg His His Thr Ala Thr Ile Ser Gly Leu Lys
50                  55                  60
```

```
Pro Gly Val Asp Tyr Thr Ile Thr Val Tyr Ala Val Tyr His Thr Glu
65                  70                  75                  80

Pro Gly Tyr His Ala His Met Pro Ile Ser Ile Asn Tyr Arg Thr His
                85                  90                  95

His His His His His
            100
```

<210> SEQ ID NO 41
<211> LENGTH: 102
<212> TYPE: PRT
<213> ORGANISM: Artificial Sequence
<220> FEATURE:
<223> OTHER INFORMATION: Synthetic: ATI-965 w/ N leader and C tail

<400> SEQUENCE: 41

```
Gly Val Ser Asp Val Pro Arg Asp Leu Glu Val Val Ala Ala Thr Pro
1               5                   10                  15

Thr Ser Leu Leu Ile Ser Trp Thr Ala Tyr Asp Ser Val Asp Lys Tyr
                20                  25                  30

Tyr Arg Ile Thr Tyr Gly Glu Thr Gly Gly Asn Ser Pro Val Gln Glu
            35                  40                  45

Phe Thr Val Gly Pro Arg His His Thr Ala Thr Ile Ser Gly Leu Lys
        50                  55                  60

Pro Gly Val Asp Tyr Thr Ile Thr Val Tyr Ala Val Tyr His Thr Glu
65                  70                  75                  80

Pro Gly Tyr His Ala His Met Pro Ile Ser Ile Asn Tyr Arg Thr Glu
                85                  90                  95

Ile Asp Lys Pro Ser Gln
            100
```

<210> SEQ ID NO 42
<211> LENGTH: 108
<212> TYPE: PRT
<213> ORGANISM: Artificial Sequence
<220> FEATURE:
<223> OTHER INFORMATION: Synthetic: ATI-965 w/ N leader and C tail + his
      tag

<400> SEQUENCE: 42

```
Gly Val Ser Asp Val Pro Arg Asp Leu Glu Val Val Ala Ala Thr Pro
1               5                   10                  15

Thr Ser Leu Leu Ile Ser Trp Thr Ala Tyr Asp Ser Val Asp Lys Tyr
                20                  25                  30

Tyr Arg Ile Thr Tyr Gly Glu Thr Gly Gly Asn Ser Pro Val Gln Glu
            35                  40                  45

Phe Thr Val Gly Pro Arg His His Thr Ala Thr Ile Ser Gly Leu Lys
        50                  55                  60

Pro Gly Val Asp Tyr Thr Ile Thr Val Tyr Ala Val Tyr His Thr Glu
65                  70                  75                  80

Pro Gly Tyr His Ala His Met Pro Ile Ser Ile Asn Tyr Arg Thr Glu
                85                  90                  95

Ile Asp Lys Pro Ser Gln His His His His His
            100                 105
```

<210> SEQ ID NO 43
<211> LENGTH: 97
<212> TYPE: PRT
<213> ORGANISM: Artificial Sequence
<220> FEATURE:
<223> OTHER INFORMATION: Synthetic: ATI-965 w/ N leader and modified C-terminus including PC

<400> SEQUENCE: 43

Gly Val Ser Asp Val Pro Arg Asp Leu Glu Val Val Ala Ala Thr Pro
1               5                   10                  15

Thr Ser Leu Leu Ile Ser Trp Thr Ala Tyr Asp Ser Val Asp Lys Tyr
            20                  25                  30

Tyr Arg Ile Thr Tyr Gly Glu Thr Gly Gly Asn Ser Pro Val Gln Glu
        35                  40                  45

Phe Thr Val Gly Pro Arg His His Thr Ala Thr Ile Ser Gly Leu Lys
    50                  55                  60

Pro Gly Val Asp Tyr Thr Ile Thr Val Tyr Ala Val Tyr His Thr Glu
65                  70                  75                  80

Pro Gly Tyr His Ala His Met Pro Ile Ser Ile Asn Tyr Arg Thr Pro
                85                  90                  95

Cys

<210> SEQ ID NO 44
<211> LENGTH: 103
<212> TYPE: PRT
<213> ORGANISM: Artificial Sequence
<220> FEATURE:
<223> OTHER INFORMATION: Synthetic: ATI-965 w/ N leader and modified
      C-terminus including PC + his tag

<400> SEQUENCE: 44

Gly Val Ser Asp Val Pro Arg Asp Leu Glu Val Val Ala Ala Thr Pro
1               5                   10                  15

Thr Ser Leu Leu Ile Ser Trp Thr Ala Tyr Asp Ser Val Asp Lys Tyr
            20                  25                  30

Tyr Arg Ile Thr Tyr Gly Glu Thr Gly Gly Asn Ser Pro Val Gln Glu
        35                  40                  45

Phe Thr Val Gly Pro Arg His His Thr Ala Thr Ile Ser Gly Leu Lys
    50                  55                  60

Pro Gly Val Asp Tyr Thr Ile Thr Val Tyr Ala Val Tyr His Thr Glu
65                  70                  75                  80

Pro Gly Tyr His Ala His Met Pro Ile Ser Ile Asn Tyr Arg Thr Pro
                85                  90                  95

Cys His His His His His
            100

<210> SEQ ID NO 45
<211> LENGTH: 109
<212> TYPE: PRT
<213> ORGANISM: Artificial Sequence
<220> FEATURE:
<223> OTHER INFORMATION: Synthetic: ATI-965  full length

<400> SEQUENCE: 45

Met Gly Val Ser Asp Val Pro Arg Asp Leu Glu Val Val Ala Ala Thr
1               5                   10                  15

Pro Thr Ser Leu Leu Ile Ser Trp Thr Ala Tyr Asp Ser Val Asp Lys
            20                  25                  30

Tyr Tyr Arg Ile Thr Tyr Gly Glu Thr Gly Gly Asn Ser Pro Val Gln
        35                  40                  45

Glu Phe Thr Val Gly Pro Arg His His Thr Ala Thr Ile Ser Gly Leu
    50                  55                  60

Lys Pro Gly Val Asp Tyr Thr Ile Thr Val Tyr Ala Val Tyr His Thr

```
                65                  70                  75                  80
Glu Pro Gly Tyr His Ala His Met Pro Ile Ser Ile Asn Tyr Arg Thr
                    85                  90                  95
Glu Ile Asp Lys Pro Ser Gln His His His His His
            100                 105
```

<210> SEQ ID NO 46
<211> LENGTH: 258
<212> TYPE: DNA
<213> ORGANISM: Artificial Sequence
<220> FEATURE:
<223> OTHER INFORMATION: Synthetic: ATI-965 core (nucleotide sequence)

<400> SEQUENCE: 46

```
gaagtggttg ctgccacccc caccagcctg ctgatcagct ggactgcata cgactctgtt      60
gacaaatatt accgcatcac ttacggcgaa acaggaggca atagccctgt ccaggagttc     120
actgtgggcc ctagacatca cacagctacc atcagcggcc ttaaacctgg cgttgattat     180
accatcactg tgtatgctgt ctatcacact gaaccgggct atcatgctca tatgccaatt     240
tccattaatt accgcaca                                                   258
```

<210> SEQ ID NO 47
<211> LENGTH: 288
<212> TYPE: DNA
<213> ORGANISM: Artificial Sequence
<220> FEATURE:
<223> OTHER INFORMATION: Synthetic: ATI-965 w/ N leader (nucleotide
      sequence with N-terminal methionine)

<400> SEQUENCE: 47

```
atgggagttt ctgatgtgcc gcgcgacctg gaagtggttg ctgccacccc caccagcctg      60
ctgatcagct ggactgcata cgactctgtt gacaaatatt accgcatcac ttacggcgaa     120
acaggaggca atagccctgt ccaggagttc actgtgggcc ctagacatca cacagctacc     180
atcagcggcc ttaaacctgg cgttgattat accatcactg tgtatgctgt ctatcacact     240
gaaccgggct atcatgctca tatgccaatt tccattaatt accgcaca                  288
```

<210> SEQ ID NO 48
<211> LENGTH: 294
<212> TYPE: DNA
<213> ORGANISM: Artificial Sequence
<220> FEATURE:
<223> OTHER INFORMATION: Synthetic: ATI-965 w/ N leader and modified
      C-terminus including PC (nucleotide sequence with N-terminal
      methionine)

<400> SEQUENCE: 48

```
atgggagttt ctgatgtgcc gcgcgacctg gaagtggttg ctgccacccc caccagcctg      60
ctgatcagct ggactgcata cgactctgtt gacaaatatt accgcatcac ttacggcgaa     120
acaggaggca atagccctgt ccaggagttc actgtgggcc ctagacatca cacagctacc     180
atcagcggcc ttaaacctgg cgttgattat accatcactg tgtatgctgt ctatcacact     240
gaaccgggct atcatgctca tatgccaatt tccattaatt accgcacacc gtgc           294
```

<210> SEQ ID NO 49
<211> LENGTH: 330
<212> TYPE: DNA
<213> ORGANISM: Artificial Sequence
<220> FEATURE:
<223> OTHER INFORMATION: Synthetic: ATI-965 w/ N leader and C tail + his
      tag (nucleotide sequence with N-terminal methionine)

<400> SEQUENCE: 49

```
atgggagttt ctgatgtgcc gcgcgacctg gaagtggttg ctgccacccc caccagcctg      60
ctgatcagct ggactgcata cgactctgtt gacaaatatt accgcatcac ttacggcgaa     120
acaggaggca atagccctgt ccaggagttc actgtgggcc tagacatca cacagctacc      180 atcagcggcc ttaaacctgg cgttgattat accatcactg tgtatgctgt ctatcacact     240
gaaccgggct atcatgctca tatgccaatt tccattaatt accgcacaga aattgacaaa     300
ccatcccagc accatcacca ccaccactga                                      330
```

<210> SEQ ID NO 50
<211> LENGTH: 82
<212> TYPE: PRT
<213> ORGANISM: Artificial Sequence
<220> FEATURE:
<223> OTHER INFORMATION: Synthetic: ATI-966 core

<400> SEQUENCE: 50

```
Glu Val Val Ala Ala Thr Pro Thr Ser Leu Leu Ile Ser Trp His Arg
1               5                   10                  15

Phe Ser Ser Ile Met Ala Tyr Tyr Arg Ile Thr Tyr Gly Glu Thr Gly
            20                  25                  30

Gly Asn Ser Pro Val Gln Glu Phe Thr Val Ala Gly Ser Val Asn Thr
        35                  40                  45

Ala Thr Ile Ser Gly Leu Lys Pro Gly Val Asp Tyr Thr Ile Thr Val
    50                  55                  60

Tyr Ala Val Thr Ile His Asn Val Ser Phe Pro Ile Ser Ile Asn Tyr
65                  70                  75                  80

Arg Thr
```

<210> SEQ ID NO 51
<211> LENGTH: 9
<212> TYPE: PRT
<213> ORGANISM: Artificial Sequence
<220> FEATURE:
<223> OTHER INFORMATION: Synthetic: ATI-966 BC loop

<400> SEQUENCE: 51

```
His Arg Phe Ser Ser Ile Met Ala Tyr
1               5
```

<210> SEQ ID NO 52
<211> LENGTH: 6
<212> TYPE: PRT
<213> ORGANISM: Artificial Sequence
<220> FEATURE:
<223> OTHER INFORMATION: Synthetic: ATI-966 DE loop

<400> SEQUENCE: 52

```
Ala Gly Ser Val Asn Thr
1               5
```

<210> SEQ ID NO 53
<211> LENGTH: 9
<212> TYPE: PRT
<213> ORGANISM: Artificial Sequence
<220> FEATURE:
<223> OTHER INFORMATION: Synthetic: ATI-966 FG loop

<400> SEQUENCE: 53

```
Val Thr Ile His Asn Val Ser Phe Pro
```

-continued

```
<210> SEQ ID NO 54
<211> LENGTH: 91
<212> TYPE: PRT
<213> ORGANISM: Artificial Sequence
<220> FEATURE:
<223> OTHER INFORMATION: Synthetic: ATI-966 w/ N leader

<400> SEQUENCE: 54

Gly Val Ser Asp Val Pro Arg Asp Leu Glu Val Val Ala Ala Thr Pro
1               5                   10                  15

Thr Ser Leu Leu Ile Ser Trp His Arg Phe Ser Ser Ile Met Ala Tyr
            20                  25                  30

Tyr Arg Ile Thr Tyr Gly Glu Thr Gly Gly Asn Ser Pro Val Gln Glu
        35                  40                  45

Phe Thr Val Ala Gly Ser Val Asn Thr Ala Thr Ile Ser Gly Leu Lys
    50                  55                  60

Pro Gly Val Asp Tyr Thr Ile Thr Val Tyr Ala Val Thr Ile His Asn
65                  70                  75                  80

Val Ser Phe Pro Ile Ser Ile Asn Tyr Arg Thr
                85                  90

<210> SEQ ID NO 55
<211> LENGTH: 97
<212> TYPE: PRT
<213> ORGANISM: Artificial Sequence
<220> FEATURE:
<223> OTHER INFORMATION: Synthetic: ATI-966 w/ N leader + his tag

<400> SEQUENCE: 55

Gly Val Ser Asp Val Pro Arg Asp Leu Glu Val Val Ala Ala Thr Pro
1               5                   10                  15

Thr Ser Leu Leu Ile Ser Trp His Arg Phe Ser Ser Ile Met Ala Tyr
            20                  25                  30

Tyr Arg Ile Thr Tyr Gly Glu Thr Gly Gly Asn Ser Pro Val Gln Glu
        35                  40                  45

Phe Thr Val Ala Gly Ser Val Asn Thr Ala Thr Ile Ser Gly Leu Lys
    50                  55                  60

Pro Gly Val Asp Tyr Thr Ile Thr Val Tyr Ala Val Thr Ile His Asn
65                  70                  75                  80

Val Ser Phe Pro Ile Ser Ile Asn Tyr Arg Thr His His His His
                85                  90                  95

His

<210> SEQ ID NO 56
<211> LENGTH: 98
<212> TYPE: PRT
<213> ORGANISM: Artificial Sequence
<220> FEATURE:
<223> OTHER INFORMATION: Synthetic: ATI-966 w/ N leader and C tail

<400> SEQUENCE: 56

Gly Val Ser Asp Val Pro Arg Asp Leu Glu Val Val Ala Ala Thr Pro
1               5                   10                  15

Thr Ser Leu Leu Ile Ser Trp His Arg Phe Ser Ser Ile Met Ala Tyr
            20                  25                  30

Tyr Arg Ile Thr Tyr Gly Glu Thr Gly Gly Asn Ser Pro Val Gln Glu
        35                  40                  45
```

```
Phe Thr Val Ala Gly Ser Val Asn Thr Ala Thr Ile Ser Gly Leu Lys
 50                  55                  60

Pro Gly Val Asp Tyr Thr Ile Thr Val Tyr Ala Val Thr Ile His Asn
 65                  70                  75                  80

Val Ser Phe Pro Ile Ser Ile Asn Tyr Arg Thr Glu Ile Asp Lys Pro
                 85                  90                  95

Ser Gln

<210> SEQ ID NO 57
<211> LENGTH: 104
<212> TYPE: PRT
<213> ORGANISM: Artificial Sequence
<220> FEATURE:
<223> OTHER INFORMATION: Synthetic: ATI-966 w/ N leader and C tail + his
      tag

<400> SEQUENCE: 57

Gly Val Ser Asp Val Pro Arg Asp Leu Glu Val Val Ala Ala Thr Pro
 1                5                  10                  15

Thr Ser Leu Leu Ile Ser Trp His Arg Phe Ser Ser Ile Met Ala Tyr
                 20                  25                  30

Tyr Arg Ile Thr Tyr Gly Glu Thr Gly Gly Asn Ser Pro Val Gln Glu
             35                  40                  45

Phe Thr Val Ala Gly Ser Val Asn Thr Ala Thr Ile Ser Gly Leu Lys
 50                  55                  60

Pro Gly Val Asp Tyr Thr Ile Thr Val Tyr Ala Val Thr Ile His Asn
 65                  70                  75                  80

Val Ser Phe Pro Ile Ser Ile Asn Tyr Arg Thr Glu Ile Asp Lys Pro
                 85                  90                  95

Ser Gln His His His His His His
            100

<210> SEQ ID NO 58
<211> LENGTH: 93
<212> TYPE: PRT
<213> ORGANISM: Artificial Sequence
<220> FEATURE:
<223> OTHER INFORMATION: Synthetic: ATI-966 w/ N leader and modified
      C-terminus including PC

<400> SEQUENCE: 58

Gly Val Ser Asp Val Pro Arg Asp Leu Glu Val Val Ala Ala Thr Pro
 1                5                  10                  15

Thr Ser Leu Leu Ile Ser Trp His Arg Phe Ser Ser Ile Met Ala Tyr
                 20                  25                  30

Tyr Arg Ile Thr Tyr Gly Glu Thr Gly Gly Asn Ser Pro Val Gln Glu
             35                  40                  45

Phe Thr Val Ala Gly Ser Val Asn Thr Ala Thr Ile Ser Gly Leu Lys
 50                  55                  60

Pro Gly Val Asp Tyr Thr Ile Thr Val Tyr Ala Val Thr Ile His Asn
 65                  70                  75                  80

Val Ser Phe Pro Ile Ser Ile Asn Tyr Arg Thr Pro Cys
                 85                  90

<210> SEQ ID NO 59
<211> LENGTH: 99
<212> TYPE: PRT
<213> ORGANISM: Artificial Sequence
<220> FEATURE:
<223> OTHER INFORMATION: Synthetic: ATI-966 w/ N leader and modified
```

C-terminus including PC + his tag

<400> SEQUENCE: 59

Gly Val Ser Asp Val Pro Arg Asp Leu Glu Val Val Ala Ala Thr Pro
1               5                   10                  15

Thr Ser Leu Leu Ile Ser Trp His Arg Phe Ser Ser Ile Met Ala Tyr
            20                  25                  30

Tyr Arg Ile Thr Tyr Gly Glu Thr Gly Gly Asn Ser Pro Val Gln Glu
        35                  40                  45

Phe Thr Val Ala Gly Ser Val Asn Thr Ala Thr Ile Ser Gly Leu Lys
    50                  55                  60

Pro Gly Val Asp Tyr Thr Ile Thr Val Tyr Ala Val Thr Ile His Asn
65                  70                  75                  80

Val Ser Phe Pro Ile Ser Ile Asn Tyr Arg Thr Pro Cys His His His
            85                  90                  95

His His His

<210> SEQ ID NO 60
<211> LENGTH: 105
<212> TYPE: PRT
<213> ORGANISM: Artificial Sequence
<220> FEATURE:
<223> OTHER INFORMATION: Synthetic: ATI-966  full length

<400> SEQUENCE: 60

Met Gly Val Ser Asp Val Pro Arg Asp Leu Glu Val Val Ala Ala Thr
1               5                   10                  15

Pro Thr Ser Leu Leu Ile Ser Trp His Arg Phe Ser Ser Ile Met Ala
            20                  25                  30

Tyr Tyr Arg Ile Thr Tyr Gly Glu Thr Gly Gly Asn Ser Pro Val Gln
        35                  40                  45

Glu Phe Thr Val Ala Gly Ser Val Asn Thr Ala Thr Ile Ser Gly Leu
    50                  55                  60

Lys Pro Gly Val Asp Tyr Thr Ile Thr Val Tyr Ala Val Thr Ile His
65                  70                  75                  80

Asn Val Ser Phe Pro Ile Ser Ile Asn Tyr Arg Thr Glu Ile Asp Lys
            85                  90                  95

Pro Ser Gln His His His His His His
            100                 105

<210> SEQ ID NO 61
<211> LENGTH: 246
<212> TYPE: DNA
<213> ORGANISM: Artificial Sequence
<220> FEATURE:
<223> OTHER INFORMATION: Synthetic: ATI-966  core (nucleotide sequence)

<400> SEQUENCE: 61
gaagtggttg ctgccacccc caccagcctg ctgatcagct ggcataggtt ctcttctatc      60
atggcgtatt accgcatcac ttacggcgaa acaggaggca atagccctgt ccaggagttc     120
actgtggctg gctctgttaa cacagctacc atcagcggcc ttaaacctgg cgttgattat     180
accatcactg tgtatgctgt cacgatccat aacgtttctt tcccaatttc cattaattac     240
cgcaca                                                                246

<210> SEQ ID NO 62
<211> LENGTH: 276
<212> TYPE: DNA

<213> ORGANISM: Artificial Sequence
<220> FEATURE:
<223> OTHER INFORMATION: Synthetic: ATI-966w/ N leader (nucleotide sequence with N-terminal methionine)

<400> SEQUENCE: 62

```
atgggagttt ctgatgtgcc gcgcgacctg gaagtggttg ctgccacccc caccagcctg      60
ctgatcagct ggcataggtt ctcttctatc atggcgtatt accgcatcac ttacggcgaa     120
acaggaggca atagccctgt ccaggagttc actgtggctg gctctgttaa cacagctacc     180
atcagcggcc ttaaacctgg cgttgattat accatcactg tgtatgctgt cacgatccat     240
aacgtttctt tcccaatttc cattaattac cgcaca                                276
```

<210> SEQ ID NO 63
<211> LENGTH: 282
<212> TYPE: DNA
<213> ORGANISM: Artificial Sequence
<220> FEATURE:
<223> OTHER INFORMATION: Synthetic: ATI-966 w/ N leader and modified C-terminus including PC (nucleotide sequence with N-terminal methionine)

<400> SEQUENCE: 63

```
atgggagttt ctgatgtgcc gcgcgacctg gaagtggttg ctgccacccc caccagcctg      60
ctgatcagct ggcataggtt ctcttctatc atggcgtatt accgcatcac ttacggcgaa     120
acaggaggca atagccctgt ccaggagttc actgtggctg gctctgttaa cacagctacc     180
atcagcggcc ttaaacctgg cgttgattat accatcactg tgtatgctgt cacgatccat     240
aacgtttctt tcccaatttc cattaattac cgcacaccgt gc                         282
```

<210> SEQ ID NO 64
<211> LENGTH: 318
<212> TYPE: DNA
<213> ORGANISM: Artificial Sequence
<220> FEATURE:
<223> OTHER INFORMATION: Synthetic: ATI-966 w/ N leader and C tail + his tag (nucleotide sequence with N-terminal methionine)

<400> SEQUENCE: 64

```
atgggagttt ctgatgtgcc gcgcgacctg gaagtggttg ctgccacccc caccagcctg      60
ctgatcagct ggcataggtt ctcttctatc atggcgtatt accgcatcac ttacggcgaa     120
acaggaggca atagccctgt ccaggagttc actgtggctg gctctgttaa cacagctacc     180
atcagcggcc ttaaacctgg cgttgattat accatcactg tgtatgctgt cacgatccat     240
aacgtttctt tcccaatttc cattaattac cgcacagaaa ttgacaaacc atcccagcac     300
catcaccacc accactga                                                    318
```

<210> SEQ ID NO 65
<211> LENGTH: 84
<212> TYPE: PRT
<213> ORGANISM: Artificial Sequence
<220> FEATURE:
<223> OTHER INFORMATION: Synthetic: ATI-967 core (parent of ADX_5417_E01)

<400> SEQUENCE: 65

```
Glu Val Val Ala Ala Thr Pro Thr Ser Leu Leu Ile Ser Trp Gln Gly
 1               5                  10                  15
Gln Leu Ser Pro Ser Phe Tyr Tyr Arg Ile Thr Tyr Gly Glu Thr Gly
            20                  25                  30
```

```
Gly Asn Ser Pro Val Gln Glu Phe Thr Val Pro Val Ala Ser Gly Thr
            35                  40                  45

Ala Thr Ile Ser Gly Leu Lys Pro Gly Val Asp Tyr Thr Ile Thr Val
 50                  55                  60

Tyr Ala Val Thr Ser His Gly Ile Tyr Phe Tyr Ala Pro Ile Ser Ile
 65                  70                  75                  80

Asn Tyr Arg Thr

<210> SEQ ID NO 66
<211> LENGTH: 9
<212> TYPE: PRT
<213> ORGANISM: Artificial Sequence
<220> FEATURE:
<223> OTHER INFORMATION: Synthetic: ATI-967 BC loop

<400> SEQUENCE: 66

Gln Gly Gln Leu Ser Pro Ser Phe Tyr
 1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic: ATI-967 DE loop

<400> SEQUENCE: 67

Pro Val Ala Ser Gly Thr
 1               5

<210> SEQ ID NO 68
<211> LENGTH: 11
<212> TYPE: PRT
<213> ORGANISM: Artificial Sequence
<220> FEATURE:
<223> OTHER INFORMATION: Synthetic: ATI-967 FG loop

<400> SEQUENCE: 68

Val Thr Ser His Gly Ile Tyr Phe Tyr Ala Pro
 1               5                  10

<210> SEQ ID NO 69
<211> LENGTH: 93
<212> TYPE: PRT
<213> ORGANISM: Artificial Sequence
<220> FEATURE:
<223> OTHER INFORMATION: Synthetic: ATI-967 w/ N leader

<400> SEQUENCE: 69

Gly Val Ser Asp Val Pro Arg Asp Leu Glu Val Val Ala Ala Thr Pro
 1               5                  10                  15

Thr Ser Leu Leu Ile Ser Trp Gln Gly Gln Leu Ser Pro Ser Phe Tyr
            20                  25                  30

Tyr Arg Ile Thr Tyr Gly Glu Thr Gly Gly Asn Ser Pro Val Gln Glu
            35                  40                  45

Phe Thr Val Pro Val Ala Ser Gly Thr Ala Thr Ile Ser Gly Leu Lys
 50                  55                  60

Pro Gly Val Asp Tyr Thr Ile Thr Val Tyr Ala Val Thr Ser His Gly
 65                  70                  75                  80

Ile Tyr Phe Tyr Ala Pro Ile Ser Ile Asn Tyr Arg Thr
                85                  90
```

-continued

```
<210> SEQ ID NO 70
<211> LENGTH: 99
<212> TYPE: PRT
<213> ORGANISM: Artificial Sequence
<220> FEATURE:
<223> OTHER INFORMATION: Synthetic: ATI-967 w/ N leader + his tag

<400> SEQUENCE: 70

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Val Ala Ser Gly Thr Ala Thr Ile Ser Gly Leu Lys
    50                  55                  60

Pro Gly Val Asp Tyr Thr Ile Thr Val Tyr Ala Val Thr Ser His Gly
65                  70                  75                  80

Ile Tyr Phe Tyr Ala Pro Ile Ser Ile Asn Tyr Arg Thr His His His
                85                  90                  95

His His His

<210> SEQ ID NO 71
<211> LENGTH: 100
<212> TYPE: PRT
<213> ORGANISM: Artificial Sequence
<220> FEATURE:
<223> OTHER INFORMATION: Synthetic: ATI-967 w/ N leader and C tail

<400> SEQUENCE: 71

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Val Ala Ser Gly Thr Ala Thr Ile Ser Gly Leu Lys
    50                  55                  60

Pro Gly Val Asp Tyr Thr Ile Thr Val Tyr Ala Val Thr Ser His Gly
65                  70                  75                  80

Ile Tyr Phe Tyr Ala Pro Ile Ser Ile Asn Tyr Arg Thr Glu Ile Asp
                85                  90                  95

Lys Pro Ser Gln
            100

<210> SEQ ID NO 72
<211> LENGTH: 106
<212> TYPE: PRT
<213> ORGANISM: Artificial Sequence
<220> FEATURE:
<223> OTHER INFORMATION: Synthetic: ATI-967 w/ N leader and C tail + his
      tag

<400> SEQUENCE: 72

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45
```

Phe Thr Val Pro Val Ala Ser Gly Thr Ala Thr Ile Ser Gly Leu Lys
    50                  55                  60

Pro Gly Val Asp Tyr Thr Ile Thr Val Tyr Ala Val Thr Ser His Gly
65                  70                  75                  80

Ile Tyr Phe Tyr Ala Pro Ile Ser Ile Asn Tyr Arg Thr Glu Ile Asp
                85                  90                  95

Lys Pro Ser Gln His His His His His His
                100                 105

<210> SEQ ID NO 73
<211> LENGTH: 95
<212> TYPE: PRT
<213> ORGANISM: Artificial Sequence
<220> FEATURE:
<223> OTHER INFORMATION: Synthetic: ATI-967 w/ N leader and modified
      C-terminus including PC

<400> SEQUENCE: 73

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
                20                  25                  30

Tyr Arg Ile Thr Tyr Gly Glu Thr Gly Gly Asn Ser Pro Val Gln Glu
            35                  40                  45

Phe Thr Val Pro Val Ala Ser Gly Thr Ala Thr Ile Ser Gly Leu Lys
    50                  55                  60

Pro Gly Val Asp Tyr Thr Ile Thr Val Tyr Ala Val Thr Ser His Gly
65                  70                  75                  80

Ile Tyr Phe Tyr Ala Pro Ile Ser Ile Asn Tyr Arg Thr Pro Cys
                85                  90                  95

<210> SEQ ID NO 74
<211> LENGTH: 101
<212> TYPE: PRT
<213> ORGANISM: Artificial Sequence
<220> FEATURE:
<223> OTHER INFORMATION: Synthetic: ATI-967 w/ N leader and modified
      C-terminus including PC + his tag

<400> SEQUENCE: 74

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
                20                  25                  30

Tyr Arg Ile Thr Tyr Gly Glu Thr Gly Gly Asn Ser Pro Val Gln Glu
            35                  40                  45

Phe Thr Val Pro Val Ala Ser Gly Thr Ala Thr Ile Ser Gly Leu Lys
    50                  55                  60

Pro Gly Val Asp Tyr Thr Ile Thr Val Tyr Ala Val Thr Ser His Gly
65                  70                  75                  80

Ile Tyr Phe Tyr Ala Pro Ile Ser Ile Asn Tyr Arg Thr Pro Cys His
                85                  90                  95

His His His His His
            100

<210> SEQ ID NO 75
<211> LENGTH: 107
<212> TYPE: PRT
<213> ORGANISM: Artificial Sequence
<220> FEATURE:
<223> OTHER INFORMATION: Synthetic: ATI-967  full length

<400> SEQUENCE: 75

Met Gly Val Ser Asp Val Pro Arg Asp Leu Glu Val Val Ala Ala Thr
1               5                   10                  15

Pro Thr Ser Leu Leu Ile Ser Trp Gln Gly Gln Leu Ser Pro Ser Phe
            20                  25                  30

Tyr Tyr Arg Ile Thr Tyr Gly Glu Thr Gly Gly Asn Ser Pro Val Gln
        35                  40                  45

Glu Phe Thr Val Pro Val Ala Ser Gly Thr Ala Thr Ile Ser Gly Leu
    50                  55                  60

Lys Pro Gly Val Asp Tyr Thr Ile Thr Val Tyr Ala Val Thr Ser His
65                  70                  75                  80

Gly Ile Tyr Phe Tyr Ala Pro Ile Ser Ile Asn Tyr Arg Thr Glu Ile
                85                  90                  95

Asp Lys Pro Ser Gln His His His His His
            100                 105

<210> SEQ ID NO 76
<211> LENGTH: 252
<212> TYPE: DNA
<213> ORGANISM: Artificial Sequence
<220> FEATURE:
<223> OTHER INFORMATION: Synthetic: ATI-967  core (nucleotide sequence)

<400> SEQUENCE: 76
gaagtggttg ctgccacccc caccagcctg ctgatcagct ggcagggaca gctgtctccg      60
tctttctatt accgaatcac ttacggcgaa acaggaggca atagccctgt ccaggagttc     120
actgtgcctg ttgctagtgg gacagctacc atcagcggcc ttaaacctgg cgttgattat     180
accatcactg tgtatgctgt cacttctcat ggcatatact tctacgctcc aatttccatt     240
aattaccgca ca                                                         252

<210> SEQ ID NO 77
<211> LENGTH: 282
<212> TYPE: DNA
<213> ORGANISM: Artificial Sequence
<220> FEATURE:
<223> OTHER INFORMATION: Synthetic: ATI-967 w/ N leader (nucleotide
      sequence with N-terminal methionine)

<400> SEQUENCE: 77
atgggagttt ctgatgtgcc gcgcgacctg gaagtggttg ctgccacccc caccagcctg      60
ctgatcagct ggcagggaca gctgtctccg tctttctatt accgaatcac ttacggcgaa     120
acaggaggca atagccctgt ccaggagttc actgtgcctg ttgctagtgg gacagctacc     180
atcagcggcc ttaaacctgg cgttgattat accatcactg tgtatgctgt cacttctcat     240
ggcatatact tctacgctcc aatttccatt aattaccgca ca                        282

<210> SEQ ID NO 78
<211> LENGTH: 288
<212> TYPE: DNA
<213> ORGANISM: Artificial Sequence
<220> FEATURE:
<223> OTHER INFORMATION: Synthetic: ATI-967 w/ N leader and modified
      C-terminus including PC (nucleotide sequence with N-terminal
      methionine)

<400> SEQUENCE: 78

```
atgggagttt ctgatgtgcc gcgcgacctg gaagtggttg ctgccacccc caccagcctg    60
ctgatcagct ggcagggaca gctgtctccg tctttctatt accgaatcac ttacggcgaa   120
acaggaggca atagccctgt ccaggagttc actgtgcctg ttgctagtgg gacagctacc   180
atcagcggcc ttaaacctgg cgttgattat accatcactg tgtatgctgt cacttctcat   240
ggcatatact tctacgctcc aatttccatt aattaccgca caccgtgc                288
```

<210> SEQ ID NO 79
<211> LENGTH: 325
<212> TYPE: DNA
<213> ORGANISM: Artificial Sequence
<220> FEATURE:
<223> OTHER INFORMATION: Synthetic: ATI-967 w/ N leader and C tail + his
    tag (nucleotide sequence with N-terminal methionine)

<400> SEQUENCE: 79

```
atgggagttt ctgatgtgcc gcgcgacctg gaagtggttg ctgccacccc caccagcctg    60
ctgatcagct ggcagggaca gctgtctccg tctttctatt accgaatcac ttacggcgaa   120
acaggaggca atagccctgt ccaggagttc actgtgcctg ttgctagtgg gacagctacc   180
atcagcggcc ttaaacctgg cgttgattat accatcactg tgtatgctgt cacttctcat   240
ggcatatact tctacgctcc aatttccatt aattaccgca cagaaattga caaaccatcc   300
cagcaccatc accaccacca ctgat                                         325
```

<210> SEQ ID NO 80
<211> LENGTH: 86
<212> TYPE: PRT
<213> ORGANISM: Artificial Sequence
<220> FEATURE:
<223> OTHER INFORMATION: Synthetic: ADX_5322_A02 core

<400> SEQUENCE: 80

Glu Val Val Ala Ala Thr Pro Thr Ser Leu Leu Ile Ser Trp Ser Tyr
1               5                   10                  15

Asp Gly Pro Ile Asp Arg Tyr Tyr Arg Ile Thr Tyr Gly Glu Thr Gly
            20                  25                  30

Gly Asn Ser Pro Val Gln Glu Phe Thr Val Pro Pro Asp Gln Lys Thr
        35                  40                  45

Ala Thr Ile Ser Gly Leu Lys Pro Gly Val Asp Tyr Thr Ile Thr Val
    50                  55                  60

Tyr Ala Val Arg Leu Glu Glu Ala His Tyr Asn Arg Glu Phe Pro Ile
65                  70                  75                  80

Ser Ile Asn Tyr Arg Thr
                85

<210> SEQ ID NO 81
<211> LENGTH: 9
<212> TYPE: PRT
<213> ORGANISM: Artificial Sequence
<220> FEATURE:
<223> OTHER INFORMATION: Synthetic: ADX_5322_A02  BC loop

<400> SEQUENCE: 81

Ser Tyr Asp Gly Pro Ile Asp Arg Tyr
1               5

<210> SEQ ID NO 82
<211> LENGTH: 6
<212> TYPE: PRT
<213> ORGANISM: Artificial Sequence

```
<220> FEATURE:
<223> OTHER INFORMATION: Synthetic: ADX_5322_A02  DE loop

<400> SEQUENCE: 82

Pro Pro Asp Gln Lys Thr
1               5

<210> SEQ ID NO 83
<211> LENGTH: 13
<212> TYPE: PRT
<213> ORGANISM: Artificial Sequence
<220> FEATURE:
<223> OTHER INFORMATION: Synthetic: ADX_5322_A02  FG loop

<400> SEQUENCE: 83

Val Arg Leu Glu Glu Ala His Tyr Asn Arg Glu Phe Pro
1               5                   10

<210> SEQ ID NO 84
<211> LENGTH: 95
<212> TYPE: PRT
<213> ORGANISM: Artificial Sequence
<220> FEATURE:
<223> OTHER INFORMATION: Synthetic: ADX_5322_A02  w/ N leader

<400> SEQUENCE: 84

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Pro Ile Asp Arg Tyr
                20                  25                  30

Tyr Arg Ile Thr Tyr Gly Glu Thr Gly Gly Asn Ser Pro Val Gln Glu
            35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Asn Arg Glu Phe Pro Ile Ser Ile Asn Tyr Arg Thr
                85                  90                  95

<210> SEQ ID NO 85
<211> LENGTH: 101
<212> TYPE: PRT
<213> ORGANISM: Artificial Sequence
<220> FEATURE:
<223> OTHER INFORMATION: Synthetic: ADX_5322_A02  w/ N leader + his tag

<400> SEQUENCE: 85

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Pro Ile Asp Arg Tyr
                20                  25                  30

Tyr Arg Ile Thr Tyr Gly Glu Thr Gly Gly Asn Ser Pro Val Gln Glu
            35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Asn Arg Glu Phe Pro Ile Ser Ile Asn Tyr Arg Thr His
                85                  90                  95

His His His His His
            100
```

```
<210> SEQ ID NO 86
<211> LENGTH: 102
<212> TYPE: PRT
<213> ORGANISM: Artificial Sequence
<220> FEATURE:
<223> OTHER INFORMATION: Synthetic: ADX_5322_A02  w/ N leader and C tail

<400> SEQUENCE: 86
```

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Pro Ile Asp Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Asn Arg Glu Phe Pro Ile Ser Ile Asn Tyr Arg Thr Glu
                85                  90                  95

Ile Asp Lys Pro Ser Gln
            100

```
<210> SEQ ID NO 87
<211> LENGTH: 108
<212> TYPE: PRT
<213> ORGANISM: Artificial Sequence
<220> FEATURE:
<223> OTHER INFORMATION: Synthetic: ADX_5322_A02  w/ N leader and C
      tail + his tag

<400> SEQUENCE: 87
```

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Pro Ile Asp Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Asp Gln Lys Thr Ala Thr Ile Ser Gly Leu Lys
    50                  55                  60

Pro Gly Val Asp Tyr Thr Ile Thr Val Tyr Ala Val Arg Leu Glu Glu
65                  70                  75                  80

Ala His Tyr Asn Arg Glu Phe Pro Ile Ser Ile Asn Tyr Arg Thr Glu
                85                  90                  95

Ile Asp Lys Pro Ser Gln His His His His His His
            100                 105

```
<210> SEQ ID NO 88
<211> LENGTH: 97
<212> TYPE: PRT
<213> ORGANISM: Artificial Sequence
<220> FEATURE:
<223> OTHER INFORMATION: Synthetic: ADX_5322_A02  w/ N leader and
      modified C-terminus including PC

<400> SEQUENCE: 88
```

Gly Val Ser Asp Val Pro Arg Asp Leu Glu Val Val Ala Ala Thr Pro
1               5                   10                  15

Thr Ser Leu Leu Ile Ser Trp Ser Tyr Asp Gly Pro Ile Asp Arg Tyr

```
                20                  25                  30

Tyr Arg Ile Thr Tyr Gly Glu Thr Gly Gly Asn Ser Pro Val Gln Glu
            35                  40                  45

Phe Thr Val Pro Pro Asp Gln Lys Thr Ala Thr Ile Ser Gly Leu Lys
 50                  55                  60

Pro Gly Val Asp Tyr Thr Ile Thr Val Tyr Ala Val Arg Leu Glu Glu
 65                  70                  75                  80

Ala His Tyr Asn Arg Glu Phe Pro Ile Ser Ile Asn Tyr Arg Thr Pro
                85                  90                  95

Cys

<210> SEQ ID NO 89
<211> LENGTH: 103
<212> TYPE: PRT
<213> ORGANISM: Artificial Sequence
<220> FEATURE:
<223> OTHER INFORMATION: Synthetic: ADX_5322_A02  w/ N leader and
      modified C-terminus including PC + his tag

<400> SEQUENCE: 89

Gly Val Ser Asp Val Pro Arg Asp Leu Glu Val Val Ala Ala Thr Pro
 1               5                  10                  15

Thr Ser Leu Leu Ile Ser Trp Ser Tyr Asp Gly Pro Ile Asp Arg Tyr
                20                  25                  30

Tyr Arg Ile Thr Tyr Gly Glu Thr Gly Gly Asn Ser Pro Val Gln Glu
            35                  40                  45

Phe Thr Val Pro Pro Asp Gln Lys Thr Ala Thr Ile Ser Gly Leu Lys
 50                  55                  60

Pro Gly Val Asp Tyr Thr Ile Thr Val Tyr Ala Val Arg Leu Glu Glu
 65                  70                  75                  80

Ala His Tyr Asn Arg Glu Phe Pro Ile Ser Ile Asn Tyr Arg Thr Pro
                85                  90                  95

Cys His His His His His His
            100

<210> SEQ ID NO 90
<211> LENGTH: 97
<212> TYPE: PRT
<213> ORGANISM: Artificial Sequence
<220> FEATURE:
<223> OTHER INFORMATION: Synthetic: ADX_5322_A02-Mal-DBCO-FFPF18

<400> SEQUENCE: 90

Gly Val Ser Asp Val Pro Arg Asp Leu Glu Val Val Ala Ala Thr Pro
 1               5                  10                  15

Thr Ser Leu Leu Ile Ser Trp Ser Tyr Asp Gly Pro Ile Asp Arg Tyr
                20                  25                  30

Tyr Arg Ile Thr Tyr Gly Glu Thr Gly Gly Asn Ser Pro Val Gln Glu
            35                  40                  45

Phe Thr Val Pro Pro Asp Gln Lys Thr Ala Thr Ile Ser Gly Leu Lys
 50                  55                  60

Pro Gly Val Asp Tyr Thr Ile Thr Val Tyr Ala Val Arg Leu Glu Glu
 65                  70                  75                  80

Ala His Tyr Asn Arg Glu Phe Pro Ile Ser Ile Asn Tyr Arg Thr Pro
                85                  90                  95

Cys
```

<210> SEQ ID NO 91
<211> LENGTH: 104
<212> TYPE: PRT
<213> ORGANISM: Artificial Sequence
<220> FEATURE:
<223> OTHER INFORMATION: Synthetic: ADX_5322_A02 full length

<400> SEQUENCE: 91

Met Gly Val Ser Asp Val Pro Arg Asp Leu Glu Val Val Ala Ala Thr
1               5                   10                  15

Pro Thr Ser Leu Leu Ile Ser Trp Ser Tyr Asp Gly Pro Ile Asp Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro Asp Gln Lys Thr Ala Thr Ile Ser Gly Leu
    50                  55                  60

Lys Pro Gly Val Asp Tyr Thr Ile Thr Val Tyr Ala Val Arg Leu Glu
65                  70                  75                  80

Glu Ala His Tyr Asn Arg Glu Phe Pro Ile Ser Ile Asn Tyr Arg Thr
                85                  90                  95

Pro Cys His His His His His His
            100

<210> SEQ ID NO 92
<211> LENGTH: 258
<212> TYPE: DNA
<213> ORGANISM: Artificial Sequence
<220> FEATURE:
<223> OTHER INFORMATION: Synthetic: ADX_5322_A02 core (nucleotide
      sequence)

<400> SEQUENCE: 92
gaagtggttg ctgccacccc caccagcctg ctgatcagct ggtcttacga tggcccaatt      60
gaccggtatt accgcatcac ttacggcgaa acaggaggca atagccctgt ccaggagttc     120
actgtgcctc cggatcagaa gacagctacc atcagcggcc ttaaacctgg cgttgattat     180
accatcactg tgtatgctgt ccggctggaa gaagctcatt acaatcgaga gtttccaatt     240
tccattaatt accgcaca                                                    258

<210> SEQ ID NO 93
<211> LENGTH: 288
<212> TYPE: DNA
<213> ORGANISM: Artificial Sequence
<220> FEATURE:
<223> OTHER INFORMATION: Synthetic: ADX_5322_A02 w/ N leader (nucleotide
      sequence with N-terminal methionine)

<400> SEQUENCE: 93
atgggagttt ctgatgtgcc gcgcgacctg gaagtggttg ctgccacccc caccagcctg      60
ctgatcagct ggtcttacga tggcccaatt gaccggtatt accgcatcac ttacggcgaa     120
acaggaggca atagccctgt ccaggagttc actgtgcctc cggatcagaa gacagctacc     180
atcagcggcc ttaaacctgg cgttgattat accatcactg tgtatgctgt ccggctggaa     240
gaagctcatt acaatcgaga gtttccaatt tccattaatt accgcaca                   288

<210> SEQ ID NO 94
<211> LENGTH: 294
<212> TYPE: DNA
<213> ORGANISM: Artificial Sequence
<220> FEATURE:
<223> OTHER INFORMATION: Synthetic: ADX_5322_A02 w/ N leader and modified C-terminus including PC (nucleotide sequence with
N-terminal methionine)

<400> SEQUENCE: 94

```
atgggagttt ctgatgtgcc gcgcgacctg gaagtggttg ctgccacccc caccagcctg      60
ctgatcagct ggtcttacga tgcccaatt gaccggtatt accgcatcac ttacggcgaa     120
acaggaggca atagccctgt ccaggagttc actgtgcctc cggatcagaa gacagctacc     180
atcagcggcc ttaaacctgg cgttgattat accatcactg tgtatgctgt ccggctggaa     240
gaagctcatt acaatcgaga gtttccaatt tccattaatt accgcacacc gtgc           294
```

<210> SEQ ID NO 95
<211> LENGTH: 315
<212> TYPE: DNA
<213> ORGANISM: Artificial Sequence
<220> FEATURE:
<223> OTHER INFORMATION: Synthetic: ADX_5322_A02 w/ N leader and C
      tail + his tag (nucleotide sequence with N-terminal methionine)

<400> SEQUENCE: 95

```
atgggagttt ctgatgtgcc gcgcgacctg gaagtggttg ctgccacccc caccagcctg      60
ctgatcagct ggtcttacga tgcccaatt gaccggtatt accgcatcac ttacggcgaa     120
acaggaggca atagccctgt ccaggagttc actgtgcctc cggatcagaa gacagctacc     180
atcagcggcc ttaaacctgg cgttgattat accatcactg tgtatgctgt ccggctggaa     240
gaagctcatt acaatcgaga gtttccaatt tccattaatt accgcacacc gtgccaccat     300
caccaccacc actga                                                      315
```

<210> SEQ ID NO 96
<211> LENGTH: 84
<212> TYPE: PRT
<213> ORGANISM: Artificial Sequence
<220> FEATURE:
<223> OTHER INFORMATION: Synthetic: ADX_5417_E01 core

<400> SEQUENCE: 96

```
Glu Val Val Ala Ala Thr Pro Thr Ser Leu Leu Ile Ser Trp Arg Ala
1               5                   10                  15

Gln Leu Ser Pro Ser Phe Tyr Tyr Arg Ile Thr Tyr Gly Glu Thr Gly
            20                  25                  30

Gly Asn Ser Pro Val Gln Glu Phe Thr Val Pro Asn Asp Val Met Thr
        35                  40                  45

Ala Thr Ile Ser Gly Leu Lys Pro Gly Val Asp Tyr Thr Ile Thr Val
    50                  55                  60

Tyr Ala Val Thr Thr His Gly Val Tyr Phe Tyr Ser Pro Ile Ser Ile
65                  70                  75                  80

Asn Tyr Arg Thr
```

<210> SEQ ID NO 97
<211> LENGTH: 9
<212> TYPE: PRT
<213> ORGANISM: Artificial Sequence
<220> FEATURE:
<223> OTHER INFORMATION: Synthetic: ADX_5417_E01 BC loop

<400> SEQUENCE: 97

```
Arg Ala Gln Leu Ser Pro Ser Phe Tyr
1               5
```

```
<210> SEQ ID NO 98
<211> LENGTH: 6
<212> TYPE: PRT
<213> ORGANISM: Artificial Sequence
<220> FEATURE:
<223> OTHER INFORMATION: Synthetic: ADX_5417_E01 DE loop

<400> SEQUENCE: 98

Pro Asn Asp Val Met Thr
1               5

<210> SEQ ID NO 99
<211> LENGTH: 11
<212> TYPE: PRT
<213> ORGANISM: Artificial Sequence
<220> FEATURE:
<223> OTHER INFORMATION: Synthetic: ADX_5417_E01 FG loop

<400> SEQUENCE: 99

Val Thr Thr His Gly Val Tyr Phe Tyr Ser Pro
1               5                   10

<210> SEQ ID NO 100
<211> LENGTH: 93
<212> TYPE: PRT
<213> ORGANISM: Artificial Sequence
<220> FEATURE:
<223> OTHER INFORMATION: Synthetic: ADX_5417_E01 w/ N leader

<400> SEQUENCE: 100

Gly Val Ser Asp Val Pro Arg Asp Leu Glu Val Val Ala Ala Thr Pro
1               5                   10                  15

Thr Ser Leu Leu Ile Ser Trp Arg Ala Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Asn Asp Val Met Thr Ala Thr Ile Ser Gly Leu Lys
    50                  55                  60

Pro Gly Val Asp Tyr Thr Ile Thr Val Tyr Ala Val Thr Thr His Gly
65                  70                  75                  80

Val Tyr Phe Tyr Ser Pro Ile Ser Ile Asn Tyr Arg Thr
                85                  90

<210> SEQ ID NO 101
<211> LENGTH: 99
<212> TYPE: PRT
<213> ORGANISM: Artificial Sequence
<220> FEATURE:
<223> OTHER INFORMATION: Synthetic: ADX_5417_E01 w/ N leader + his tag

<400> SEQUENCE: 101

Gly Val Ser Asp Val Pro Arg Asp Leu Glu Val Val Ala Ala Thr Pro
1               5                   10                  15

Thr Ser Leu Leu Ile Ser Trp Arg Ala Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Asn Asp Val Met Thr Ala Thr Ile Ser Gly Leu Lys
    50                  55                  60

Pro Gly Val Asp Tyr Thr Ile Thr Val Tyr Ala Val Thr Thr His Gly
65                  70                  75                  80

Val Tyr Phe Tyr Ser Pro Ile Ser Ile Asn Tyr Arg Thr His His His
```

His His His

<210> SEQ ID NO 102
<211> LENGTH: 100
<212> TYPE: PRT
<213> ORGANISM: Artificial Sequence
<220> FEATURE:
<223> OTHER INFORMATION: Synthetic: ADX_5417_E01 w/ N leader and C tail

<400> SEQUENCE: 102

```
Gly Val Ser Asp Val Pro Arg Asp Leu Glu Val Val Ala Ala Thr Pro
1               5                   10                  15

Thr Ser Leu Leu Ile Ser Trp Arg Ala Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Asn Asp Val Met Thr Ala Thr Ile Ser Gly Leu Lys
    50                  55                  60

Pro Gly Val Asp Tyr Thr Ile Thr Val Tyr Ala Val Thr Thr His Gly
65                  70                  75                  80

Val Tyr Phe Tyr Ser Pro Ile Ser Ile Asn Tyr Arg Thr Glu Ile Asp
                85                  90                  95

Lys Pro Ser Gln
            100
```

<210> SEQ ID NO 103
<211> LENGTH: 106
<212> TYPE: PRT
<213> ORGANISM: Artificial Sequence
<220> FEATURE:
<223> OTHER INFORMATION: Synthetic: ADX_5417_E01 w/ N leader and C
     tail + his tag

<400> SEQUENCE: 103

```
Gly Val Ser Asp Val Pro Arg Asp Leu Glu Val Val Ala Ala Thr Pro
1               5                   10                  15

Thr Ser Leu Leu Ile Ser Trp Arg Ala Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Asn Asp Val Met Thr Ala Thr Ile Ser Gly Leu Lys
    50                  55                  60

Pro Gly Val Asp Tyr Thr Ile Thr Val Tyr Ala Val Thr Thr His Gly
65                  70                  75                  80

Val Tyr Phe Tyr Ser Pro Ile Ser Ile Asn Tyr Arg Thr Glu Ile Asp
                85                  90                  95

Lys Pro Ser Gln His His His His His His
            100                 105
```

<210> SEQ ID NO 104
<211> LENGTH: 95
<212> TYPE: PRT
<213> ORGANISM: Artificial Sequence
<220> FEATURE:
<223> OTHER INFORMATION: Synthetic: ADX_5417_E01 w/ N leader and
     modified C-terminus including PC

<400> SEQUENCE: 104

```
Gly Val Ser Asp Val Pro Arg Asp Leu Glu Val Val Ala Ala Thr Pro
```

```
            1               5                  10                  15
          Thr Ser Leu Leu Ile Ser Trp Arg Ala Gln Leu Ser Pro Ser Phe Tyr
                          20                  25                  30

Tyr Arg Ile Thr Tyr Gly Glu Thr Gly Gly Asn Ser Pro Val Gln Glu
                          35                  40                  45

Phe Thr Val Pro Asn Asp Val Met Thr Ala Thr Ile Ser Gly Leu Lys
                  50                  55                  60

Pro Gly Val Asp Tyr Thr Ile Thr Val Tyr Ala Val Thr Thr His Gly
          65                  70                  75                  80

Val Tyr Phe Tyr Ser Pro Ile Ser Ile Asn Tyr Arg Thr Pro Cys
                          85                  90                  95

<210> SEQ ID NO 105
<211> LENGTH: 101
<212> TYPE: PRT
<213> ORGANISM: Artificial Sequence
<220> FEATURE:
<223> OTHER INFORMATION: Synthetic: ADX_5417_E01 w/ N leader and
      modified C-terminus including PC + his tag

<400> SEQUENCE: 105

Gly Val Ser Asp Val Pro Arg Asp Leu Glu Val Val Ala Ala Thr Pro
1               5                  10                  15

Thr Ser Leu Leu Ile Ser Trp Arg Ala Gln Leu Ser Pro Ser Phe Tyr
                20                  25                  30

Tyr Arg Ile Thr Tyr Gly Glu Thr Gly Gly Asn Ser Pro Val Gln Glu
            35                  40                  45

Phe Thr Val Pro Asn Asp Val Met Thr Ala Thr Ile Ser Gly Leu Lys
        50                  55                  60

Pro Gly Val Asp Tyr Thr Ile Thr Val Tyr Ala Val Thr Thr His Gly
65                  70                  75                  80

Val Tyr Phe Tyr Ser Pro Ile Ser Ile Asn Tyr Arg Thr Pro Cys His
                85                  90                  95

His His His His His
            100

<210> SEQ ID NO 106
<211> LENGTH: 95
<212> TYPE: PRT
<213> ORGANISM: Artificial Sequence
<220> FEATURE:
<223> OTHER INFORMATION: Synthetic: ADX-5417_E01 Mal-DBCO-FFPF18

<400> SEQUENCE: 106

Gly Val Ser Asp Val Pro Arg Asp Leu Glu Val Val Ala Ala Thr Pro
1               5                  10                  15

Thr Ser Leu Leu Ile Ser Trp Arg Ala Gln Leu Ser Pro Ser Phe Tyr
                20                  25                  30

Tyr Arg Ile Thr Tyr Gly Glu Thr Gly Gly Asn Ser Pro Val Gln Glu
            35                  40                  45

Phe Thr Val Pro Asn Asp Val Met Thr Ala Thr Ile Ser Gly Leu Lys
        50                  55                  60

Pro Gly Val Asp Tyr Thr Ile Thr Val Tyr Ala Val Thr Thr His Gly
65                  70                  75                  80

Val Tyr Phe Tyr Ser Pro Ile Ser Ile Asn Tyr Arg Thr Pro Cys
                85                  90                  95

<210> SEQ ID NO 107
```

<211> LENGTH: 102
<212> TYPE: PRT
<213> ORGANISM: Artificial Sequence
<220> FEATURE:
<223> OTHER INFORMATION: Synthetic: ADX-5417_E01 full length

<400> SEQUENCE: 107

```
Met Gly Val Ser Asp Val Pro Arg Asp Leu Glu Val Val Ala Ala Thr
1               5                   10                  15

Pro Thr Ser Leu Leu Ile Ser Trp Arg Ala Gln Leu Ser Pro Ser Phe
            20                  25                  30

Tyr Tyr Arg Ile Thr Tyr Gly Glu Thr Gly Gly Asn Ser Pro Val Gln
        35                  40                  45

Glu Phe Thr Val Pro Asn Asp Val Met Thr Ala Thr Ile Ser Gly Leu
    50                  55                  60

Lys Pro Gly Val Asp Tyr Thr Ile Thr Val Tyr Ala Val Thr Thr His
65                  70                  75                  80

Gly Val Tyr Phe Tyr Ser Pro Ile Ser Ile Asn Tyr Arg Thr Pro Cys
                85                  90                  95

His His His His His His
            100
```

<210> SEQ ID NO 108
<211> LENGTH: 252
<212> TYPE: DNA
<213> ORGANISM: Artificial Sequence
<220> FEATURE:
<223> OTHER INFORMATION: Synthetic: ADX-5417_E01 core (nucleotide sequence)

<400> SEQUENCE: 108

```
gaagtggttg ctgccacccc caccagcctg ctgatcagct ggagggctca gctgtctccg      60
tctttctatt accgcatcac ttacggcgaa acaggaggca atagccctgt ccaggagttc     120
actgtgccta atgatgtaat gacagctacc atcagcggcc ttaaacctgg cgttgattat     180
accatcactg tgtatgctgt cactactcat ggtgtttatt tctactcacc aatttccatt     240
aattaccgca ca                                                         252
```

<210> SEQ ID NO 109
<211> LENGTH: 282
<212> TYPE: DNA
<213> ORGANISM: Artificial Sequence
<220> FEATURE:
<223> OTHER INFORMATION: Synthetic: ADX_5417_E01 w/ N leader (nucleotide sequence with N-terminal methionine)

<400> SEQUENCE: 109

```
atgggagttt ctgatgtgcc gcgcgacctg gaagtggttg ctgccacccc caccagcctg      60
ctgatcagct ggagggctca gctgtctccg tctttctatt accgcatcac ttacggcgaa     120
acaggaggca atagccctgt ccaggagttc actgtgccta atgatgtaat gacagctacc     180
atcagcggcc ttaaacctgg cgttgattat accatcactg tgtatgctgt cactactcat     240
ggtgtttatt tctactcacc aatttccatt aattaccgca ca                        282
```

<210> SEQ ID NO 110
<211> LENGTH: 288
<212> TYPE: DNA
<213> ORGANISM: Artificial Sequence
<220> FEATURE:
<223> OTHER INFORMATION: Synthetic: ADX_5417_E01 w/ N leader and modified C-terminus including PC (nucleotide sequence with -continued N-terminal methionine)

<400> SEQUENCE: 110

```
atgggagttt ctgatgtgcc gcgcgacctg gaagtggttg ctgccacccc caccagcctg      60
ctgatcagct ggagggctca gctgtctccg tctttctatt accgcatcac ttacggcgaa     120
acaggaggca atagccctgt ccaggagttc actgtgccta atgatgtaat gacagctacc     180
atcagcggcc ttaaacctgg cgttgattat accatcactg tgtatgctgt cactactcat     240
ggtgtttatt tctactcacc aatttccatt aattaccgca caccgtgc                  288
```

<210> SEQ ID NO 111
<211> LENGTH: 309
<212> TYPE: DNA
<213> ORGANISM: Artificial Sequence
<220> FEATURE:
<223> OTHER INFORMATION: Synthetic: ADX_5417_E01 w/ N leader and C
      tail + his tag (nucleotide sequence with N-terminal methionine)

<400> SEQUENCE: 111

```
atgggagttt ctgatgtgcc gcgcgacctg gaagtggttg ctgccacccc caccagcctg      60
ctgatcagct ggagggctca gctgtctccg tctttctatt accgcatcac ttacggcgaa     120
acaggaggca atagccctgt ccaggagttc actgtgccta atgatgtaat gacagctacc     180
atcagcggcc ttaaacctgg cgttgattat accatcactg tgtatgctgt cactactcat     240
ggtgtttatt tctactcacc aatttccatt aattaccgca caccgtgcca ccatcaccac     300
caccactga                                                             309
```

<210> SEQ ID NO 112
<211> LENGTH: 80
<212> TYPE: PRT
<213> ORGANISM: Artificial Sequence
<220> FEATURE:
<223> OTHER INFORMATION: Synthetic: ATI_1420_A10 core

<400> SEQUENCE: 112

```
Glu Val Val Ala Ala Thr Pro Thr Ser Leu Leu Ile Ser Trp Pro Tyr
1               5                   10                  15

Pro Ser Tyr Tyr Ile Glu Tyr Arg Ile Thr Tyr Gly Glu Thr Gly Gly
                20                  25                  30

Asn Ser Pro Val Gln Glu Phe Thr Val Gln Ser Met Lys Ala Thr Ile
            35                  40                  45

Ser Gly Leu Lys Pro Gly Val Asp Tyr Thr Ile Thr Val Tyr Ala Ile
        50                  55                  60

Arg His Pro Gly Met Leu Glu Phe Gly Ile Ser Ile Asn Tyr Arg Thr
65                  70                  75                  80
```

<210> SEQ ID NO 113
<211> LENGTH: 8
<212> TYPE: PRT
<213> ORGANISM: Artificial Sequence
<220> FEATURE:
<223> OTHER INFORMATION: Synthetic: ATI_1420_A10 BC loop

<400> SEQUENCE: 113

```
Pro Tyr Pro Ser Tyr Tyr Ile Glu
1               5
```

<210> SEQ ID NO 114
<211> LENGTH: 5
<212> TYPE: PRT

```
<213> ORGANISM: Artificial Sequence
<220> FEATURE:
<223> OTHER INFORMATION: Synthetic: ATI_1420_A10 DE loop

<400> SEQUENCE: 114

Gln Ser Met Lys Ala
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic: ATI_1420_A10 FG loop

<400> SEQUENCE: 115

Ile Arg His Pro Gly Met Leu Glu Phe Gly
1               5                   10

<210> SEQ ID NO 116
<211> LENGTH: 89
<212> TYPE: PRT
<213> ORGANISM: Artificial Sequence
<220> FEATURE:
<223> OTHER INFORMATION: Synthetic: ATI_1420_A10 w/ N leader

<400> SEQUENCE: 116

Gly Val Ser Asp Val Pro Arg Asp Leu Glu Val Val Ala Ala Thr Pro
1               5                   10                  15

Thr Ser Leu Leu Ile Ser Trp Pro Tyr Pro Ser Tyr Tyr Ile Glu Tyr
            20                  25                  30

Arg Ile Thr Tyr Gly Glu Thr Gly Gly Asn Ser Pro Val Gln Glu Phe
        35                  40                  45

Thr Val Gln Ser Met Lys Ala Thr Ile Ser Gly Leu Lys Pro Gly Val
    50                  55                  60

Asp Tyr Thr Ile Thr Val Tyr Ala Ile Arg His Pro Gly Met Leu Glu
65                  70                  75                  80

Phe Gly Ile Ser Ile Asn Tyr Arg Thr
                85

<210> SEQ ID NO 117
<211> LENGTH: 95
<212> TYPE: PRT
<213> ORGANISM: Artificial Sequence
<220> FEATURE:
<223> OTHER INFORMATION: Synthetic: ATI_1420_A10 w/ N leader + his tag

<400> SEQUENCE: 117

Gly Val Ser Asp Val Pro Arg Asp Leu Glu Val Val Ala Ala Thr Pro
1               5                   10                  15

Thr Ser Leu Leu Ile Ser Trp Pro Tyr Pro Ser Tyr Tyr Ile Glu Tyr
            20                  25                  30

Arg Ile Thr Tyr Gly Glu Thr Gly Gly Asn Ser Pro Val Gln Glu Phe
        35                  40                  45

Thr Val Gln Ser Met Lys Ala Thr Ile Ser Gly Leu Lys Pro Gly Val
    50                  55                  60

Asp Tyr Thr Ile Thr Val Tyr Ala Ile Arg His Pro Gly Met Leu Glu
65                  70                  75                  80

Phe Gly Ile Ser Ile Asn Tyr Arg Thr His His His His His His
                85                  90                  95
```

<210> SEQ ID NO 118
<211> LENGTH: 96
<212> TYPE: PRT
<213> ORGANISM: Artificial Sequence
<220> FEATURE:
<223> OTHER INFORMATION: Synthetic: ATI_1420_A10 w/ N leader and C tail

<400> SEQUENCE: 118

```
Gly Val Ser Asp Val Pro Arg Asp Leu Glu Val Val Ala Ala Thr Pro
1               5                   10                  15

Thr Ser Leu Leu Ile Ser Trp Pro Tyr Pro Ser Tyr Tyr Ile Glu Tyr
            20                  25                  30

Arg Ile Thr Tyr Gly Glu Thr Gly Gly Asn Ser Pro Val Gln Glu Phe
        35                  40                  45

Thr Val Gln Ser Met Lys Ala Thr Ile Ser Gly Leu Lys Pro Gly Val
    50                  55                  60

Asp Tyr Thr Ile Thr Val Tyr Ala Ile Arg His Pro Gly Met Leu Glu
65                  70                  75                  80

Phe Gly Ile Ser Ile Asn Tyr Arg Thr Glu Ile Asp Lys Pro Ser Gln
                85                  90                  95
```

<210> SEQ ID NO 119
<211> LENGTH: 102
<212> TYPE: PRT
<213> ORGANISM: Artificial Sequence
<220> FEATURE:
<223> OTHER INFORMATION: Synthetic: ATI_1420_A10w/ N leader and C
      tail + his tag

<400> SEQUENCE: 119

```
Gly Val Ser Asp Val Pro Arg Asp Leu Glu Val Val Ala Ala Thr Pro
1               5                   10                  15

Thr Ser Leu Leu Ile Ser Trp Pro Tyr Pro Ser Tyr Tyr Ile Glu Tyr
            20                  25                  30

Arg Ile Thr Tyr Gly Glu Thr Gly Gly Asn Ser Pro Val Gln Glu Phe
        35                  40                  45

Thr Val Gln Ser Met Lys Ala Thr Ile Ser Gly Leu Lys Pro Gly Val
    50                  55                  60

Asp Tyr Thr Ile Thr Val Tyr Ala Ile Arg His Pro Gly Met Leu Glu
65                  70                  75                  80

Phe Gly Ile Ser Ile Asn Tyr Arg Thr Glu Ile Asp Lys Pro Ser Gln
                85                  90                  95

His His His His His His
            100
```

<210> SEQ ID NO 120
<211> LENGTH: 91
<212> TYPE: PRT
<213> ORGANISM: Artificial Sequence
<220> FEATURE:
<223> OTHER INFORMATION: Synthetic: ATI_1420_A10w/ N leader and modified
      C-terminus including PC

<400> SEQUENCE: 120

```
Gly Val Ser Asp Val Pro Arg Asp Leu Glu Val Val Ala Ala Thr Pro
1               5                   10                  15

Thr Ser Leu Leu Ile Ser Trp Pro Tyr Pro Ser Tyr Tyr Ile Glu Tyr
            20                  25                  30

Arg Ile Thr Tyr Gly Glu Thr Gly Gly Asn Ser Pro Val Gln Glu Phe
        35                  40                  45
```

Thr Val Gln Ser Met Lys Ala Thr Ile Ser Gly Leu Lys Pro Gly Val
            50                  55                  60

Asp Tyr Thr Ile Thr Val Tyr Ala Ile Arg His Pro Gly Met Leu Glu
65                  70                  75                  80

Phe Gly Ile Ser Ile Asn Tyr Arg Thr Pro Cys
                85                  90

<210> SEQ ID NO 121
<211> LENGTH: 97
<212> TYPE: PRT
<213> ORGANISM: Artificial Sequence
<220> FEATURE:
<223> OTHER INFORMATION: Synthetic: ATI_1420_A10 w/ N leader and
      modified C-terminus including PC + his tag

<400> SEQUENCE: 121

Gly Val Ser Asp Val Pro Arg Asp Leu Glu Val Val Ala Ala Thr Pro
1               5                   10                  15

Thr Ser Leu Leu Ile Ser Trp Pro Tyr Pro Ser Tyr Tyr Ile Glu Tyr
            20                  25                  30

Arg Ile Thr Tyr Gly Glu Thr Gly Gly Asn Ser Pro Val Gln Glu Phe
        35                  40                  45

Thr Val Gln Ser Met Lys Ala Thr Ile Ser Gly Leu Lys Pro Gly Val
    50                  55                  60

Asp Tyr Thr Ile Thr Val Tyr Ala Ile Arg His Pro Gly Met Leu Glu
65                  70                  75                  80

Phe Gly Ile Ser Ile Asn Tyr Arg Thr Pro Cys His His His His
                85                  90                  95

His

<210> SEQ ID NO 122
<211> LENGTH: 103
<212> TYPE: PRT
<213> ORGANISM: Artificial Sequence
<220> FEATURE:
<223> OTHER INFORMATION: Synthetic: ATI_1420_A10 full length

<400> SEQUENCE: 122

Met Gly Val Ser Asp Val Pro Arg Asp Leu Glu Val Val Ala Ala Thr
1               5                   10                  15

Pro Thr Ser Leu Leu Ile Ser Trp Pro Tyr Pro Ser Tyr Tyr Ile Glu
            20                  25                  30

Tyr Arg Ile Thr Tyr Gly Glu Thr Gly Gly Asn Ser Pro Val Gln Glu
        35                  40                  45

Phe Thr Val Gln Ser Met Lys Ala Thr Ile Ser Gly Leu Lys Pro Gly
    50                  55                  60

Val Asp Tyr Thr Ile Thr Val Tyr Ala Ile Arg His Pro Gly Met Leu
65                  70                  75                  80

Glu Phe Gly Ile Ser Ile Asn Tyr Arg Thr Glu Ile Asp Lys Pro Ser
                85                  90                  95

Gln His His His His His His
            100

<210> SEQ ID NO 123
<211> LENGTH: 76
<212> TYPE: PRT
<213> ORGANISM: Artificial Sequence
<220> FEATURE:
<223> OTHER INFORMATION: Synthetic: ATI_1420_B09 core

<400> SEQUENCE: 123

Glu Val Ala Ala Thr Pro Thr Ser Leu Leu Ile Ser Trp His Lys
1               5                   10                  15

Phe Ser Ser Leu Met Ser Tyr Arg Ile Thr Tyr Gly Glu Thr Gly Gly
            20                  25                  30

Asn Ser Pro Val Gln Glu Phe Thr Val Gly Ser Val Asn Ala Thr Ile
        35                  40                  45

Ser Gly Leu Lys Pro Gly Val Asp Tyr Thr Ile Thr Val Tyr Ala Ile
    50                  55                  60

His Asn Val Gly Phe Ile Ser Ile Asn Tyr Arg Thr
65                  70                  75

<210> SEQ ID NO 124
<211> LENGTH: 8
<212> TYPE: PRT
<213> ORGANISM: Artificial Sequence
<220> FEATURE:
<223> OTHER INFORMATION: Synthetic: ATI_1420_B09 BC loop

<400> SEQUENCE: 124

His Lys Phe Ser Ser Leu Met Ser
1               5

<210> SEQ ID NO 125
<211> LENGTH: 4
<212> TYPE: PRT
<213> ORGANISM: Artificial Sequence
<220> FEATURE:
<223> OTHER INFORMATION: Synthetic: ATI_1420_B09 DE loop

<400> SEQUENCE: 125

Gly Ser Val Asn
1

<210> SEQ ID NO 126
<211> LENGTH: 6
<212> TYPE: PRT
<213> ORGANISM: Artificial Sequence
<220> FEATURE:
<223> OTHER INFORMATION: Synthetic: ATI_1420_B09 FG loop

<400> SEQUENCE: 126

Ile His Asn Val Gly Phe
1               5

<210> SEQ ID NO 127
<211> LENGTH: 85
<212> TYPE: PRT
<213> ORGANISM: Artificial Sequence
<220> FEATURE:
<223> OTHER INFORMATION: Synthetic: ATI_1420_B09 w/ N leader

<400> SEQUENCE: 127

Gly Val Ser Asp Val Pro Arg Asp Leu Glu Val Ala Ala Thr Pro
1               5                   10                  15

Thr Ser Leu Leu Ile Ser Trp His Lys Phe Ser Ser Leu Met Ser Tyr
            20                  25                  30

Arg Ile Thr Tyr Gly Glu Thr Gly Gly Asn Ser Pro Val Gln Glu Phe
        35                  40                  45

Thr Val Gly Ser Val Asn Ala Thr Ile Ser Gly Leu Lys Pro Gly Val
    50                  55                  60

Asp Tyr Thr Ile Thr Val Tyr Ala Ile His Asn Val Gly Phe Ile Ser

Ile Asn Tyr Arg Thr
              85

<210> SEQ ID NO 128
<211> LENGTH: 91
<212> TYPE: PRT
<213> ORGANISM: Artificial Sequence
<220> FEATURE:
<223> OTHER INFORMATION: Synthetic: ATI_1420_B09 w/ N leader + his tag

<400> SEQUENCE: 128

Gly Val Ser Asp Val Pro Arg Asp Leu Glu Val Val Ala Ala Thr Pro
1               5                   10                  15

Thr Ser Leu Leu Ile Ser Trp His Lys Phe Ser Ser Leu Met Ser Tyr
            20                  25                  30

Arg Ile Thr Tyr Gly Glu Thr Gly Gly Asn Ser Pro Val Gln Glu Phe
        35                  40                  45

Thr Val Gly Ser Val Asn Ala Thr Ile Ser Gly Leu Lys Pro Gly Val
    50                  55                  60

Asp Tyr Thr Ile Thr Val Tyr Ala Ile His Asn Val Gly Phe Ile Ser
65                  70                  75                  80

Ile Asn Tyr Arg Thr His His His His His
            85                  90

<210> SEQ ID NO 129
<211> LENGTH: 92
<212> TYPE: PRT
<213> ORGANISM: Artificial Sequence
<220> FEATURE:
<223> OTHER INFORMATION: Synthetic: AATI_1420_B09 w/ N leader and C tail

<400> SEQUENCE: 129

Gly Val Ser Asp Val Pro Arg Asp Leu Glu Val Val Ala Ala Thr Pro
1               5                   10                  15

Thr Ser Leu Leu Ile Ser Trp His Lys Phe Ser Ser Leu Met Ser Tyr
            20                  25                  30

Arg Ile Thr Tyr Gly Glu Thr Gly Gly Asn Ser Pro Val Gln Glu Phe
        35                  40                  45

Thr Val Gly Ser Val Asn Ala Thr Ile Ser Gly Leu Lys Pro Gly Val
    50                  55                  60

Asp Tyr Thr Ile Thr Val Tyr Ala Ile His Asn Val Gly Phe Ile Ser
65                  70                  75                  80

Ile Asn Tyr Arg Thr Glu Ile Asp Lys Pro Ser Gln
            85                  90

<210> SEQ ID NO 130
<211> LENGTH: 98
<212> TYPE: PRT
<213> ORGANISM: Artificial Sequence
<220> FEATURE:
<223> OTHER INFORMATION: Synthetic: ATI_1420_B09 w/ N leader and C
      tail + his tag

<400> SEQUENCE: 130

Gly Val Ser Asp Val Pro Arg Asp Leu Glu Val Val Ala Ala Thr Pro
1               5                   10                  15

Thr Ser Leu Leu Ile Ser Trp His Lys Phe Ser Ser Leu Met Ser Tyr
            20                  25                  30

Arg Ile Thr Tyr Gly Glu Thr Gly Gly Asn Ser Pro Val Gln Glu Phe 35                  40                  45

Thr Val Gly Ser Val Asn Ala Thr Ile Ser Gly Leu Lys Pro Gly Val
         50                  55                  60

Asp Tyr Thr Ile Thr Val Tyr Ala Ile His Asn Val Gly Phe Ile Ser
 65                  70                  75                  80

Ile Asn Tyr Arg Thr Glu Ile Asp Lys Pro Ser Gln His His His His
                 85                  90                  95

His His

<210> SEQ ID NO 131
<211> LENGTH: 87
<212> TYPE: PRT
<213> ORGANISM: Artificial Sequence
<220> FEATURE:
<223> OTHER INFORMATION: Synthetic: ATI_1420_B09 w/ N leader and
      modified C-terminus including PC

<400> SEQUENCE: 131

Gly Val Ser Asp Val Pro Arg Asp Leu Glu Val Val Ala Ala Thr Pro
 1               5                  10                  15

Thr Ser Leu Leu Ile Ser Trp His Lys Phe Ser Ser Leu Met Ser Tyr
                 20                  25                  30

Arg Ile Thr Tyr Gly Glu Thr Gly Gly Asn Ser Pro Val Gln Glu Phe
             35                  40                  45

Thr Val Gly Ser Val Asn Ala Thr Ile Ser Gly Leu Lys Pro Gly Val
         50                  55                  60

Asp Tyr Thr Ile Thr Val Tyr Ala Ile His Asn Val Gly Phe Ile Ser
 65                  70                  75                  80

Ile Asn Tyr Arg Thr Pro Cys
                 85

<210> SEQ ID NO 132
<211> LENGTH: 93
<212> TYPE: PRT
<213> ORGANISM: Artificial Sequence
<220> FEATURE:
<223> OTHER INFORMATION: Synthetic: ATI_1420_B09 w/ N leader and
      modified C-terminus including PC + his tag

<400> SEQUENCE: 132

Gly Val Ser Asp Val Pro Arg Asp Leu Glu Val Val Ala Ala Thr Pro
 1               5                  10                  15

Thr Ser Leu Leu Ile Ser Trp His Lys Phe Ser Ser Leu Met Ser Tyr
                 20                  25                  30

Arg Ile Thr Tyr Gly Glu Thr Gly Gly Asn Ser Pro Val Gln Glu Phe
             35                  40                  45

Thr Val Gly Ser Val Asn Ala Thr Ile Ser Gly Leu Lys Pro Gly Val
         50                  55                  60

Asp Tyr Thr Ile Thr Val Tyr Ala Ile His Asn Val Gly Phe Ile Ser
 65                  70                  75                  80

Ile Asn Tyr Arg Thr Pro Cys His His His His His
                 85                  90

<210> SEQ ID NO 133
<211> LENGTH: 99
<212> TYPE: PRT
<213> ORGANISM: Artificial Sequence
<220> FEATURE:
<223> OTHER INFORMATION: Synthetic: ATI_1420_B09 full length

```
<400> SEQUENCE: 133

Met Gly Val Ser Asp Val Pro Arg Asp Leu Glu Val Val Ala Ala Thr
1               5                   10                  15

Pro Thr Ser Leu Leu Ile Ser Trp His Lys Phe Ser Ser Leu Met Ser
            20                  25                  30

Tyr Arg Ile Thr Tyr Gly Glu Thr Gly Gly Asn Ser Pro Val Gln Glu
        35                  40                  45

Phe Thr Val Gly Ser Val Asn Ala Thr Ile Ser Gly Leu Lys Pro Gly
    50                  55                  60

Val Asp Tyr Thr Ile Thr Val Tyr Ala Ile His Asn Val Gly Phe Ile
65                  70                  75                  80

Ser Ile Asn Tyr Arg Thr Glu Ile Asp Lys Pro Ser Gln His His His
                85                  90                  95

His His His

<210> SEQ ID NO 134
<211> LENGTH: 79
<212> TYPE: PRT
<213> ORGANISM: Artificial Sequence
<220> FEATURE:
<223> OTHER INFORMATION: Synthetic: ATI_1420_C02 core

<400> SEQUENCE: 134

Glu Val Val Ala Ala Thr Pro Thr Ser Leu Leu Ile Ser Trp Arg Ile
1               5                   10                  15

Lys Ser Tyr Tyr Ala Tyr Arg Ile Thr Tyr Gly Glu Thr Gly Gly Asn
            20                  25                  30

Ser Pro Val Gln Glu Phe Thr Val Arg Gln His Val Ala Thr Ile Ser
        35                  40                  45

Gly Leu Lys Pro Gly Val Asp Tyr Thr Ile Thr Val Tyr Ala Arg Leu
    50                  55                  60

Gly Asp Val Glu Leu Val Tyr Glu Ile Ser Ile Asn Tyr Arg Thr
65                  70                  75

<210> SEQ ID NO 135
<211> LENGTH: 7
<212> TYPE: PRT
<213> ORGANISM: Artificial Sequence
<220> FEATURE:
<223> OTHER INFORMATION: Synthetic: ATI_1420_C02 BC loop

<400> SEQUENCE: 135

Arg Ile Lys Ser Tyr Tyr Ala
1               5

<210> SEQ ID NO 136
<211> LENGTH: 4
<212> TYPE: PRT
<213> ORGANISM: Artificial Sequence
<220> FEATURE:
<223> OTHER INFORMATION: Synthetic: ATI_1420_C02 DE loop

<400> SEQUENCE: 136

Arg Gln His Val
1

<210> SEQ ID NO 137
<211> LENGTH: 10
<212> TYPE: PRT
<213> ORGANISM: Artificial Sequence
<220> FEATURE:
```

<223> OTHER INFORMATION: Synthetic: ATI_1420_C02 FG loop

<400> SEQUENCE: 137

Arg Leu Gly Asp Val Glu Leu Val Tyr Glu
1               5                   10

<210> SEQ ID NO 138
<211> LENGTH: 88
<212> TYPE: PRT
<213> ORGANISM: Artificial Sequence
<220> FEATURE:
<223> OTHER INFORMATION: Synthetic: ATI_1420_C02 w/ N leader

<400> SEQUENCE: 138

Gly Val Ser Asp Val Pro Arg Asp Leu Glu Val Val Ala Ala Thr Pro
1               5                   10                  15

Thr Ser Leu Leu Ile Ser Trp Arg Ile Lys Ser Tyr Tyr Ala Tyr Arg
            20                  25                  30

Ile Thr Tyr Gly Glu Thr Gly Gly Asn Ser Pro Val Gln Glu Phe Thr
        35                  40                  45

Val Arg Gln His Val Ala Thr Ile Ser Gly Leu Lys Pro Gly Val Asp
    50                  55                  60

Tyr Thr Ile Thr Val Tyr Ala Arg Leu Gly Asp Val Glu Leu Val Tyr
65                  70                  75                  80

Glu Ile Ser Ile Asn Tyr Arg Thr
                85

<210> SEQ ID NO 139
<211> LENGTH: 91
<212> TYPE: PRT
<213> ORGANISM: Artificial Sequence
<220> FEATURE:
<223> OTHER INFORMATION: Synthetic: ATI_1420_C02 w/ N leader + his tag

<400> SEQUENCE: 139

Gly Val Ser Asp Val Pro Arg Asp Leu Glu Val Val Ala Ala Thr Pro
1               5                   10                  15

Thr Ser Leu Leu Ile Ser Trp His Lys Phe Ser Ser Leu Met Ser Tyr
            20                  25                  30

Arg Ile Thr Tyr Gly Glu Thr Gly Gly Asn Ser Pro Val Gln Glu Phe
        35                  40                  45

Thr Val Gly Ser Val Asn Ala Thr Ile Ser Gly Leu Lys Pro Gly Val
    50                  55                  60

Asp Tyr Thr Ile Thr Val Tyr Ala Ile His Asn Val Gly Phe Ile Ser
65                  70                  75                  80

Ile Asn Tyr Arg Thr His His His His His
                85                  90

<210> SEQ ID NO 140
<211> LENGTH: 95
<212> TYPE: PRT
<213> ORGANISM: Artificial Sequence
<220> FEATURE:
<223> OTHER INFORMATION: Synthetic: ATI_1420_C02 w/ N leader and C tail

<400> SEQUENCE: 140

Gly Val Ser Asp Val Pro Arg Asp Leu Glu Val Val Ala Ala Thr Pro
1               5                   10                  15

Thr Ser Leu Leu Ile Ser Trp Arg Ile Lys Ser Tyr Tyr Ala Tyr Arg
            20                  25                  30

```
Ile Thr Tyr Gly Glu Thr Gly Asn Ser Pro Val Gln Glu Phe Thr
            35                  40                  45

Val Arg Gln His Val Ala Thr Ile Ser Gly Leu Lys Pro Gly Val Asp
 50                  55                  60

Tyr Thr Ile Thr Val Tyr Ala Arg Leu Gly Asp Val Glu Leu Val Tyr
 65                  70                  75                  80

Glu Ile Ser Ile Asn Tyr Arg Thr Gly Ile Asp Lys Pro Ser Gln
                85                  90                  95
```

<210> SEQ ID NO 141
<211> LENGTH: 101
<212> TYPE: PRT
<213> ORGANISM: Artificial Sequence
<220> FEATURE:
<223> OTHER INFORMATION: Synthetic: ATI_1420_C02 w/ N leader and C
      tail + his tag

<400> SEQUENCE: 141

```
Gly Val Ser Asp Val Pro Arg Asp Leu Glu Val Val Ala Ala Thr Pro
 1               5                  10                  15

Thr Ser Leu Leu Ile Ser Trp Arg Ile Lys Ser Tyr Tyr Ala Tyr Arg
                20                  25                  30

Ile Thr Tyr Gly Glu Thr Gly Asn Ser Pro Val Gln Glu Phe Thr
            35                  40                  45

Val Arg Gln His Val Ala Thr Ile Ser Gly Leu Lys Pro Gly Val Asp
 50                  55                  60

Tyr Thr Ile Thr Val Tyr Ala Arg Leu Gly Asp Val Glu Leu Val Tyr
 65                  70                  75                  80

Glu Ile Ser Ile Asn Tyr Arg Thr Gly Ile Asp Lys Pro Ser Gln His
                85                  90                  95

His His His His His
            100
```

<210> SEQ ID NO 142
<211> LENGTH: 90
<212> TYPE: PRT
<213> ORGANISM: Artificial Sequence
<220> FEATURE:
<223> OTHER INFORMATION: Synthetic: ATI_1420_C02 w/ N leader and
      modified C-terminus including PC

<400> SEQUENCE: 142

```
Gly Val Ser Asp Val Pro Arg Asp Leu Glu Val Val Ala Ala Thr Pro
 1               5                  10                  15

Thr Ser Leu Leu Ile Ser Trp Arg Ile Lys Ser Tyr Tyr Ala Tyr Arg
                20                  25                  30

Ile Thr Tyr Gly Glu Thr Gly Asn Ser Pro Val Gln Glu Phe Thr
            35                  40                  45

Val Arg Gln His Val Ala Thr Ile Ser Gly Leu Lys Pro Gly Val Asp
 50                  55                  60

Tyr Thr Ile Thr Val Tyr Ala Arg Leu Gly Asp Val Glu Leu Val Tyr
 65                  70                  75                  80

Glu Ile Ser Ile Asn Tyr Arg Thr Pro Cys
                85                  90
```

<210> SEQ ID NO 143
<211> LENGTH: 93
<212> TYPE: PRT
<213> ORGANISM: Artificial Sequence
<220> FEATURE:

<223> OTHER INFORMATION: Synthetic: ATI_1420_C02 w/ N leader and
modified C-terminus including PC + his tag

<400> SEQUENCE: 143

Gly Val Ser Asp Val Pro Arg Asp Leu Glu Val Val Ala Ala Thr Pro
1               5                   10                  15

Thr Ser Leu Leu Ile Ser Trp His Lys Phe Ser Ser Leu Met Ser Tyr
            20                  25                  30

Arg Ile Thr Tyr Gly Glu Thr Gly Asn Ser Pro Val Gln Glu Phe
        35                  40                  45

Thr Val Gly Ser Val Asn Ala Thr Ile Ser Gly Leu Lys Pro Gly Val
    50                  55                  60

Asp Tyr Thr Ile Thr Val Tyr Ala Ile His Asn Val Gly Phe Ile Ser
65                  70                  75                  80

Ile Asn Tyr Arg Thr Pro Cys His His His His His
            85                  90

<210> SEQ ID NO 144
<211> LENGTH: 102
<212> TYPE: PRT
<213> ORGANISM: Artificial Sequence
<220> FEATURE:
<223> OTHER INFORMATION: Synthetic: ATI_1420_C02 full length

<400> SEQUENCE: 144

Met Gly Val Ser Asp Val Pro Arg Asp Leu Glu Val Val Ala Ala Thr
1               5                   10                  15

Pro Thr Ser Leu Leu Ile Ser Trp Arg Ile Lys Ser Tyr Tyr Ala Tyr
            20                  25                  30

Arg Ile Thr Tyr Gly Glu Thr Gly Asn Ser Pro Val Gln Glu Phe
        35                  40                  45

Thr Val Arg Gln His Val Ala Thr Ile Ser Gly Leu Lys Pro Gly Val
    50                  55                  60

Asp Tyr Thr Ile Thr Val Tyr Ala Arg Leu Gly Asp Val Glu Leu Val
65                  70                  75                  80

Tyr Glu Ile Ser Ile Asn Tyr Arg Thr Glu Ile Asp Lys Pro Ser Gln
            85                  90                  95

His His His His His His
            100

<210> SEQ ID NO 145
<211> LENGTH: 80
<212> TYPE: PRT
<213> ORGANISM: Artificial Sequence
<220> FEATURE:
<223> OTHER INFORMATION: Synthetic: ATI_1420_C11 core

<400> SEQUENCE: 145

Glu Val Val Ala Ala Thr Pro Thr Ser Leu Leu Ile Ser Trp Met Tyr
1               5                   10                  15

Pro Leu Lys Ser Val Pro Tyr Arg Ile Thr Tyr Gly Glu Thr Gly Gly
            20                  25                  30

Asn Ser Pro Val Gln Glu Phe Thr Val Tyr Ser Ser Gly Ala Thr Ile
        35                  40                  45

Ser Gly Leu Lys Pro Gly Val Asp Tyr Thr Ile Thr Val Tyr Ala Met
    50                  55                  60

Ser Tyr Ser Thr Tyr His Ala Phe Met Ile Ser Ile Asn Tyr Arg Thr
65                  70                  75                  80

<210> SEQ ID NO 146
<211> LENGTH: 8
<212> TYPE: PRT
<213> ORGANISM: Artificial Sequence
<220> FEATURE:
<223> OTHER INFORMATION: Synthetic: ATI_1420_C11 BC loop

<400> SEQUENCE: 146

Met Tyr Pro Leu Lys Ser Val Pro
1               5

<210> SEQ ID NO 147
<211> LENGTH: 4
<212> TYPE: PRT
<213> ORGANISM: Artificial Sequence
<220> FEATURE:
<223> OTHER INFORMATION: Synthetic: ATI_1420_C11 DE loop

<400> SEQUENCE: 147

Tyr Ser Ser Gly
1

<210> SEQ ID NO 148
<211> LENGTH: 10
<212> TYPE: PRT
<213> ORGANISM: Artificial Sequence
<220> FEATURE:
<223> OTHER INFORMATION: Synthetic: ATI_1420_C11 FG loop

<400> SEQUENCE: 148

Met Ser Tyr Ser Thr Tyr His Ala Phe Met
1               5                   10

<210> SEQ ID NO 149
<211> LENGTH: 89
<212> TYPE: PRT
<213> ORGANISM: Artificial Sequence
<220> FEATURE:
<223> OTHER INFORMATION: Synthetic: ATI_1420_C11 w/ N leader

<400> SEQUENCE: 149

Gly Val Ser Asp Val Pro Arg Asp Leu Glu Val Val Ala Ala Thr Pro
1               5                   10                  15

Thr Ser Leu Leu Ile Ser Trp Met Tyr Pro Leu Lys Ser Val Pro Tyr
            20                  25                  30

Arg Ile Thr Tyr Gly Glu Thr Gly Gly Asn Ser Pro Val Gln Glu Phe
        35                  40                  45

Thr Val Tyr Ser Ser Gly Ala Thr Ile Ser Gly Leu Lys Pro Gly Val
    50                  55                  60

Asp Tyr Thr Ile Thr Val Tyr Ala Met Ser Tyr Ser Thr Tyr His Ala
65                  70                  75                  80

Phe Met Ile Ser Ile Asn Tyr Arg Thr
                85

<210> SEQ ID NO 150
<211> LENGTH: 95
<212> TYPE: PRT
<213> ORGANISM: Artificial Sequence
<220> FEATURE:
<223> OTHER INFORMATION: Synthetic: ATI_1420_C11 w/ N leader + his tag

<400> SEQUENCE: 150

Gly Val Ser Asp Val Pro Arg Asp Leu Glu Val Val Ala Ala Thr Pro
1               5                   10                  15

Thr Ser Leu Leu Ile Ser Trp Met Tyr Pro Leu Lys Ser Val Pro Tyr
            20                  25                  30

Arg Ile Thr Tyr Gly Glu Thr Gly Asn Ser Pro Val Gln Glu Phe
        35                  40                  45

Thr Val Tyr Ser Ser Gly Ala Thr Ile Ser Gly Leu Lys Pro Gly Val
    50                  55                  60

Asp Tyr Thr Ile Thr Val Tyr Ala Met Ser Tyr Ser Thr Tyr His Ala
65                  70                  75                  80

Phe Met Ile Ser Ile Asn Tyr Arg Thr His His His His His
            85                  90                  95

<210> SEQ ID NO 151
<211> LENGTH: 96
<212> TYPE: PRT
<213> ORGANISM: Artificial Sequence
<220> FEATURE:
<223> OTHER INFORMATION: Synthetic: ATI_1420_C11 w/ N leader and C tail

<400> SEQUENCE: 151

Gly Val Ser Asp Val Pro Arg Asp Leu Glu Val Val Ala Ala Thr Pro
1               5                   10                  15

Thr Ser Leu Leu Ile Ser Trp Met Tyr Pro Leu Lys Ser Val Pro Tyr
            20                  25                  30

Arg Ile Thr Tyr Gly Glu Thr Gly Gly Asn Ser Pro Val Gln Glu Phe
        35                  40                  45

Thr Val Tyr Ser Ser Gly Ala Thr Ile Ser Gly Leu Lys Pro Gly Val
    50                  55                  60

Asp Tyr Thr Ile Thr Val Tyr Ala Met Ser Tyr Ser Thr Tyr His Ala
65                  70                  75                  80

Phe Met Ile Ser Ile Asn Tyr Arg Thr Glu Ile Asp Lys Pro Ser Gln
            85                  90                  95

<210> SEQ ID NO 152
<211> LENGTH: 102
<212> TYPE: PRT
<213> ORGANISM: Artificial Sequence
<220> FEATURE:
<223> OTHER INFORMATION: Synthetic: ATI_1420_C11 w/ N leader and C
      tail + his tag

<400> SEQUENCE: 152

Gly Val Ser Asp Val Pro Arg Asp Leu Glu Val Val Ala Ala Thr Pro
1               5                   10                  15

Thr Ser Leu Leu Ile Ser Trp Met Tyr Pro Leu Lys Ser Val Pro Tyr
            20                  25                  30

Arg Ile Thr Tyr Gly Glu Thr Gly Gly Asn Ser Pro Val Gln Glu Phe
        35                  40                  45

Thr Val Tyr Ser Ser Gly Ala Thr Ile Ser Gly Leu Lys Pro Gly Val
    50                  55                  60

Asp Tyr Thr Ile Thr Val Tyr Ala Met Ser Tyr Ser Thr Tyr His Ala
65                  70                  75                  80

Phe Met Ile Ser Ile Asn Tyr Arg Thr Glu Ile Asp Lys Pro Ser Gln
            85                  90                  95

His His His His His His
            100

<210> SEQ ID NO 153
<211> LENGTH: 91

<212> TYPE: PRT
<213> ORGANISM: Artificial Sequence
<220> FEATURE:
<223> OTHER INFORMATION: Synthetic: ATI_1420_C11 w/ N leader and
      modified C-terminus including PC

<400> SEQUENCE: 153

Gly Val Ser Asp Val Pro Arg Asp Leu Glu Val Val Ala Ala Thr Pro
1               5                   10                  15

Thr Ser Leu Leu Ile Ser Trp Met Tyr Pro Leu Lys Ser Val Pro Tyr
            20                  25                  30

Arg Ile Thr Tyr Gly Glu Thr Gly Gly Asn Ser Pro Val Gln Glu Phe
        35                  40                  45

Thr Val Tyr Ser Ser Gly Ala Thr Ile Ser Gly Leu Lys Pro Gly Val
    50                  55                  60

Asp Tyr Thr Ile Thr Val Tyr Ala Met Ser Tyr Ser Tyr His Ala
65                  70                  75                  80

Phe Met Ile Ser Ile Asn Tyr Arg Thr Pro Cys
                85                  90

<210> SEQ ID NO 154
<211> LENGTH: 97
<212> TYPE: PRT
<213> ORGANISM: Artificial Sequence
<220> FEATURE:
<223> OTHER INFORMATION: Synthetic: ATI_1420_C11 w/ N leader and
      modified C-terminus including PC + his tag

<400> SEQUENCE: 154

Gly Val Ser Asp Val Pro Arg Asp Leu Glu Val Val Ala Ala Thr Pro
1               5                   10                  15

Thr Ser Leu Leu Ile Ser Trp Met Tyr Pro Leu Lys Ser Val Pro Tyr
            20                  25                  30

Arg Ile Thr Tyr Gly Glu Thr Gly Gly Asn Ser Pro Val Gln Glu Phe
        35                  40                  45

Thr Val Tyr Ser Ser Gly Ala Thr Ile Ser Gly Leu Lys Pro Gly Val
    50                  55                  60

Asp Tyr Thr Ile Thr Val Tyr Ala Met Ser Tyr Ser Tyr His Ala
65                  70                  75                  80

Phe Met Ile Ser Ile Asn Tyr Arg Thr Pro Cys His His His His
                85                  90                  95

His

<210> SEQ ID NO 155
<211> LENGTH: 103
<212> TYPE: PRT
<213> ORGANISM: Artificial Sequence
<220> FEATURE:
<223> OTHER INFORMATION: Synthetic: AATI_1420_C11 full length

<400> SEQUENCE: 155

Met Gly Val Ser Asp Val Pro Arg Asp Leu Glu Val Val Ala Ala Thr
1               5                   10                  15

Pro Thr Ser Leu Leu Ile Ser Trp Met Tyr Pro Leu Lys Ser Val Pro
            20                  25                  30

Tyr Arg Ile Thr Tyr Gly Glu Thr Gly Gly Asn Ser Pro Val Gln Glu
        35                  40                  45

Phe Thr Val Tyr Ser Ser Gly Ala Thr Ile Ser Gly Leu Lys Pro Gly
    50                  55                  60

Val Asp Tyr Thr Ile Thr Val Tyr Ala Met Ser Tyr Thr Tyr His
65                  70                  75                  80

Ala Phe Met Ile Ser Ile Asn Tyr Arg Thr Glu Ile Asp Lys Pro Ser
                85                  90                  95

Gln His His His His His His
            100

<210> SEQ ID NO 156
<211> LENGTH: 79
<212> TYPE: PRT
<213> ORGANISM: Artificial Sequence
<220> FEATURE:
<223> OTHER INFORMATION: Synthetic: ATI_1420_D01 core

<400> SEQUENCE: 156

Glu Val Val Ala Ala Thr Pro Thr Ser Leu Leu Ile Ser Trp Arg Thr
1               5                   10                  15

Val Pro Glu Thr Asp Tyr Arg Ile Thr Tyr Gly Glu Thr Gly Gly Asn
            20                  25                  30

Ser Pro Val Gln Glu Phe Thr Val Pro Asp Asn Thr Ala Thr Ile Ser
        35                  40                  45

Gly Leu Lys Pro Gly Val Asp Tyr Thr Ile Thr Val Tyr Ala Leu Glu
    50                  55                  60

Thr Ala His Tyr Asn Arg Asp Tyr Ile Ser Ile Asn Tyr Arg Thr
65                  70                  75

<210> SEQ ID NO 157
<211> LENGTH: 7
<212> TYPE: PRT
<213> ORGANISM: Artificial Sequence
<220> FEATURE:
<223> OTHER INFORMATION: Synthetic: ATI_1420_D01 BC loop

<400> SEQUENCE: 157

Arg Thr Val Pro Glu Thr Asp
1               5

<210> SEQ ID NO 158
<211> LENGTH: 4
<212> TYPE: PRT
<213> ORGANISM: Artificial Sequence
<220> FEATURE:
<223> OTHER INFORMATION: Synthetic: ATI_1420_D01 DE loop

<400> SEQUENCE: 158

Pro Asp Asn Thr
1

<210> SEQ ID NO 159
<211> LENGTH: 10
<212> TYPE: PRT
<213> ORGANISM: Artificial Sequence
<220> FEATURE:
<223> OTHER INFORMATION: Synthetic: ATI_1420_D01 FG loop

<400> SEQUENCE: 159

Leu Glu Thr Ala His Tyr Asn Arg Asp Tyr
1               5                   10

<210> SEQ ID NO 160
<211> LENGTH: 88
<212> TYPE: PRT
<213> ORGANISM: Artificial Sequence
<220> FEATURE:

<223> OTHER INFORMATION: Synthetic: ATI_1420_D01 w/ N leader

<400> SEQUENCE: 160

Gly Val Ser Asp Val Pro Arg Asp Leu Glu Val Val Ala Ala Thr Pro
1               5                   10                  15

Thr Ser Leu Leu Ile Ser Trp Arg Thr Val Pro Glu Thr Asp Tyr Arg
            20                  25                  30

Ile Thr Tyr Gly Glu Thr Gly Gly Asn Ser Pro Val Gln Glu Phe Thr
        35                  40                  45

Val Pro Asp Asn Thr Ala Thr Ile Ser Gly Leu Lys Pro Gly Val Asp
    50                  55                  60

Tyr Thr Ile Thr Val Tyr Ala Leu Glu Thr Ala His Tyr Asn Arg Asp
65                  70                  75                  80

Tyr Ile Ser Ile Asn Tyr Arg Thr
                85

<210> SEQ ID NO 161
<211> LENGTH: 94
<212> TYPE: PRT
<213> ORGANISM: Artificial Sequence
<220> FEATURE:
<223> OTHER INFORMATION: Synthetic: ATI_1420_D01 w/ N leader + his tag

<400> SEQUENCE: 161

Gly Val Ser Asp Val Pro Arg Asp Leu Glu Val Val Ala Ala Thr Pro
1               5                   10                  15

Thr Ser Leu Leu Ile Ser Trp Arg Thr Val Pro Glu Thr Asp Tyr Arg
            20                  25                  30

Ile Thr Tyr Gly Glu Thr Gly Gly Asn Ser Pro Val Gln Glu Phe Thr
        35                  40                  45

Val Pro Asp Asn Thr Ala Thr Ile Ser Gly Leu Lys Pro Gly Val Asp
    50                  55                  60

Tyr Thr Ile Thr Val Tyr Ala Leu Glu Thr Ala His Tyr Asn Arg Asp
65                  70                  75                  80

Tyr Ile Ser Ile Asn Tyr Arg Thr His His His His His His
                85                  90

<210> SEQ ID NO 162
<211> LENGTH: 95
<212> TYPE: PRT
<213> ORGANISM: Artificial Sequence
<220> FEATURE:
<223> OTHER INFORMATION: Synthetic: ATI_1420_D01 w/ N leader and C tail

<400> SEQUENCE: 162

Gly Val Ser Asp Val Pro Arg Asp Leu Glu Val Val Ala Ala Thr Pro
1               5                   10                  15

Thr Ser Leu Leu Ile Ser Trp Arg Thr Val Pro Glu Thr Asp Tyr Arg
            20                  25                  30

Ile Thr Tyr Gly Glu Thr Gly Gly Asn Ser Pro Val Gln Glu Phe Thr
        35                  40                  45

Val Pro Asp Asn Thr Ala Thr Ile Ser Gly Leu Lys Pro Gly Val Asp
    50                  55                  60

Tyr Thr Ile Thr Val Tyr Ala Leu Glu Thr Ala His Tyr Asn Arg Asp
65                  70                  75                  80

Tyr Ile Ser Ile Asn Tyr Arg Thr Glu Ile Asp Lys Pro Ser Gln
                85                  90                  95

<210> SEQ ID NO 163
<211> LENGTH: 101
<212> TYPE: PRT
<213> ORGANISM: Artificial Sequence
<220> FEATURE:
<223> OTHER INFORMATION: Synthetic: ATI_1420_D01 w/ N leader and C
      tail + his tag

<400> SEQUENCE: 163

Gly Val Ser Asp Val Pro Arg Asp Leu Glu Val Val Ala Ala Thr Pro
1               5                   10                  15

Thr Ser Leu Leu Ile Ser Trp Arg Thr Val Pro Glu Thr Asp Tyr Arg
            20                  25                  30

Ile Thr Tyr Gly Glu Thr Gly Gly Asn Ser Pro Val Gln Glu Phe Thr
        35                  40                  45

Val Pro Asp Asn Thr Ala Thr Ile Ser Gly Leu Lys Pro Gly Val Asp
    50                  55                  60

Tyr Thr Ile Thr Val Tyr Ala Leu Glu Thr Ala His Tyr Asn Arg Asp
65                  70                  75                  80

Tyr Ile Ser Ile Asn Tyr Arg Thr Glu Ile Asp Lys Pro Ser Gln His
                85                  90                  95

His His His His His
            100

<210> SEQ ID NO 164
<211> LENGTH: 90
<212> TYPE: PRT
<213> ORGANISM: Artificial Sequence
<220> FEATURE:
<223> OTHER INFORMATION: Synthetic: ATI_1420_D01 w/ N leader and
      modified C-terminus including PC

<400> SEQUENCE: 164

Gly Val Ser Asp Val Pro Arg Asp Leu Glu Val Val Ala Ala Thr Pro
1               5                   10                  15

Thr Ser Leu Leu Ile Ser Trp Arg Thr Val Pro Glu Thr Asp Tyr Arg
            20                  25                  30

Ile Thr Tyr Gly Glu Thr Gly Gly Asn Ser Pro Val Gln Glu Phe Thr
        35                  40                  45

Val Pro Asp Asn Thr Ala Thr Ile Ser Gly Leu Lys Pro Gly Val Asp
    50                  55                  60

Tyr Thr Ile Thr Val Tyr Ala Leu Glu Thr Ala His Tyr Asn Arg Asp
65                  70                  75                  80

Tyr Ile Ser Ile Asn Tyr Arg Thr Pro Cys
                85                  90

<210> SEQ ID NO 165
<211> LENGTH: 96
<212> TYPE: PRT
<213> ORGANISM: Artificial Sequence
<220> FEATURE:
<223> OTHER INFORMATION: Synthetic: ATI_1420_D01 w/ N leader and
      modified C-terminus including PC + his tag

<400> SEQUENCE: 165

Gly Val Ser Asp Val Pro Arg Asp Leu Glu Val Val Ala Ala Thr Pro
1               5                   10                  15

Thr Ser Leu Leu Ile Ser Trp Arg Thr Val Pro Glu Thr Asp Tyr Arg
            20                  25                  30

Ile Thr Tyr Gly Glu Thr Gly Gly Asn Ser Pro Val Gln Glu Phe Thr
        35                  40                  45

Val Pro Asp Asn Thr Ala Thr Ile Ser Gly Leu Lys Pro Gly Val Asp
    50                  55                  60

Tyr Thr Ile Thr Val Tyr Ala Leu Glu Thr Ala His Tyr Asn Arg Asp
65                  70                  75                  80

Tyr Ile Ser Ile Asn Tyr Arg Thr Pro Cys His His His His His
                85                  90                  95

<210> SEQ ID NO 166
<211> LENGTH: 102
<212> TYPE: PRT
<213> ORGANISM: Artificial Sequence
<220> FEATURE:
<223> OTHER INFORMATION: Synthetic: ATI_1420_D01 full length

<400> SEQUENCE: 166

Met Gly Val Ser Asp Val Pro Arg Asp Leu Glu Val Val Ala Ala Thr
1               5                   10                  15

Pro Thr Ser Leu Leu Ile Ser Trp Arg Thr Val Pro Glu Thr Asp Tyr
            20                  25                  30

Arg Ile Thr Tyr Gly Glu Thr Gly Gly Asn Ser Pro Val Gln Glu Phe
        35                  40                  45

Thr Val Pro Asp Asn Thr Ala Thr Ile Ser Gly Leu Lys Pro Gly Val
    50                  55                  60

Asp Tyr Thr Ile Thr Val Tyr Ala Leu Glu Thr Ala His Tyr Asn Arg
65                  70                  75                  80

Asp Tyr Ile Ser Ile Asn Tyr Arg Thr Glu Ile Asp Lys Pro Ser Gln
                85                  90                  95

His His His His His His
            100

<210> SEQ ID NO 167
<211> LENGTH: 82
<212> TYPE: PRT
<213> ORGANISM: Artificial Sequence
<220> FEATURE:
<223> OTHER INFORMATION: Synthetic: ATI_1420_D05 core

<400> SEQUENCE: 167

Glu Val Val Ala Ala Thr Pro Thr Ser Leu Leu Ile Ser Trp Thr Ala
1               5                   10                  15

Tyr Tyr Ser Thr Ile Lys Tyr Arg Ile Thr Tyr Gly Glu Thr Gly Gly
            20                  25                  30

Asn Ser Pro Val Gln Glu Phe Thr Val Gly Pro Lys His His Ala Thr
        35                  40                  45

Ile Ser Gly Leu Lys Pro Gly Val Asp Tyr Thr Ile Thr Val Tyr Ala
    50                  55                  60

Tyr Asn Thr Lys Pro Gly Tyr His Ala His Gln Ile Ser Ile Asn Tyr
65                  70                  75                  80

Arg Thr

<210> SEQ ID NO 168
<211> LENGTH: 8
<212> TYPE: PRT
<213> ORGANISM: Artificial Sequence
<220> FEATURE:
<223> OTHER INFORMATION: Synthetic: ATI_1420_D05 BC loop

<400> SEQUENCE: 168

Thr Ala Tyr Tyr Ser Thr Ile Lys

```
<210> SEQ ID NO 169
<211> LENGTH: 5
<212> TYPE: PRT
<213> ORGANISM: Artificial Sequence
<220> FEATURE:
<223> OTHER INFORMATION: Synthetic: ATI_1420_D05 DE loop

<400> SEQUENCE: 169

Gly Pro Lys His His
1               5

<210> SEQ ID NO 170
<211> LENGTH: 11
<212> TYPE: PRT
<213> ORGANISM: Artificial Sequence
<220> FEATURE:
<223> OTHER INFORMATION: Synthetic: ATI_1420_D05 FG loop

<400> SEQUENCE: 170

Tyr Asn Thr Lys Pro Gly Tyr His Ala His Gln
1               5                   10

<210> SEQ ID NO 171
<211> LENGTH: 91
<212> TYPE: PRT
<213> ORGANISM: Artificial Sequence
<220> FEATURE:
<223> OTHER INFORMATION: Synthetic: ATI_1420_D05 w/ N leader

<400> SEQUENCE: 171

Gly Val Ser Asp Val Pro Arg Asp Leu Glu Val Val Ala Ala Thr Pro
1               5                   10                  15

Thr Ser Leu Leu Ile Ser Trp Thr Ala Tyr Tyr Ser Thr Ile Lys Tyr
            20                  25                  30

Arg Ile Thr Tyr Gly Glu Thr Gly Gly Asn Ser Pro Val Gln Glu Phe
        35                  40                  45

Thr Val Gly Pro Lys His His Ala Thr Ile Ser Gly Leu Lys Pro Gly
    50                  55                  60

Val Asp Tyr Thr Ile Thr Val Tyr Ala Tyr Asn Thr Lys Pro Gly Tyr
65                  70                  75                  80

His Ala His Gln Ile Ser Ile Asn Tyr Arg Thr
                85                  90

<210> SEQ ID NO 172
<211> LENGTH: 97
<212> TYPE: PRT
<213> ORGANISM: Artificial Sequence
<220> FEATURE:
<223> OTHER INFORMATION: Synthetic: ATI_1420_D05 w/ N leader + his tag

<400> SEQUENCE: 172

Gly Val Ser Asp Val Pro Arg Asp Leu Glu Val Val Ala Ala Thr Pro
1               5                   10                  15

Thr Ser Leu Leu Ile Ser Trp Thr Ala Tyr Tyr Ser Thr Ile Lys Tyr
            20                  25                  30

Arg Ile Thr Tyr Gly Glu Thr Gly Gly Asn Ser Pro Val Gln Glu Phe
        35                  40                  45

Thr Val Gly Pro Lys His His Ala Thr Ile Ser Gly Leu Lys Pro Gly
    50                  55                  60

Val Asp Tyr Thr Ile Thr Val Tyr Ala Tyr Asn Thr Lys Pro Gly Tyr
```

His Ala His Gln Ile Ser Ile Asn Tyr Arg Thr His His His His
                85                  90                  95

His

<210> SEQ ID NO 173
<211> LENGTH: 98
<212> TYPE: PRT
<213> ORGANISM: Artificial Sequence
<220> FEATURE:
<223> OTHER INFORMATION: Synthetic: ATI_1420_D05 w/ N leader and C tail

<400> SEQUENCE: 173

Gly Val Ser Asp Val Pro Arg Asp Leu Glu Val Val Ala Ala Thr Pro
1               5                   10                  15

Thr Ser Leu Leu Ile Ser Trp Thr Ala Tyr Tyr Ser Thr Ile Lys Tyr
                20                  25                  30

Arg Ile Thr Tyr Gly Glu Thr Gly Gly Asn Ser Pro Val Gln Glu Phe
            35                  40                  45

Thr Val Gly Pro Lys His His Ala Thr Ile Ser Gly Leu Lys Pro Gly
        50                  55                  60

Val Asp Tyr Thr Ile Thr Val Tyr Ala Tyr Asn Thr Lys Pro Gly Tyr
65                  70                  75                  80

His Ala His Gln Ile Ser Ile Asn Tyr Arg Thr Glu Ile Asp Lys Pro
                85                  90                  95

Ser Gln

<210> SEQ ID NO 174
<211> LENGTH: 104
<212> TYPE: PRT
<213> ORGANISM: Artificial Sequence
<220> FEATURE:
<223> OTHER INFORMATION: Synthetic: ATI_1420_D05 w/ N leader and C
      tail + his tag

<400> SEQUENCE: 174

Gly Val Ser Asp Val Pro Arg Asp Leu Glu Val Val Ala Ala Thr Pro
1               5                   10                  15

Thr Ser Leu Leu Ile Ser Trp Thr Ala Tyr Tyr Ser Thr Ile Lys Tyr
                20                  25                  30

Arg Ile Thr Tyr Gly Glu Thr Gly Gly Asn Ser Pro Val Gln Glu Phe
            35                  40                  45

Thr Val Gly Pro Lys His His Ala Thr Ile Ser Gly Leu Lys Pro Gly
        50                  55                  60

Val Asp Tyr Thr Ile Thr Val Tyr Ala Tyr Asn Thr Lys Pro Gly Tyr
65                  70                  75                  80

His Ala His Gln Ile Ser Ile Asn Tyr Arg Thr Glu Ile Asp Lys Pro
                85                  90                  95

Ser Gln His His His His His His
            100

<210> SEQ ID NO 175
<211> LENGTH: 93
<212> TYPE: PRT
<213> ORGANISM: Artificial Sequence
<220> FEATURE:
<223> OTHER INFORMATION: Synthetic: ATI_1420_D05 w/ N leader and
      modified C-terminus including PC

<400> SEQUENCE: 175

Gly Val Ser Asp Val Pro Arg Asp Leu Glu Val Val Ala Ala Thr Pro
1               5                   10                  15

Thr Ser Leu Leu Ile Ser Trp Thr Ala Tyr Tyr Ser Thr Ile Lys Tyr
            20                  25                  30

Arg Ile Thr Tyr Gly Glu Thr Gly Gly Asn Ser Pro Val Gln Glu Phe
            35                  40                  45

Thr Val Gly Pro Lys His His Ala Thr Ile Ser Gly Leu Lys Pro Gly
        50                  55                  60

Val Asp Tyr Thr Ile Thr Val Tyr Ala Tyr Asn Thr Lys Pro Gly Tyr
65                  70                  75                  80

His Ala His Gln Ile Ser Ile Asn Tyr Arg Thr Pro Cys
            85                  90

<210> SEQ ID NO 176
<211> LENGTH: 99
<212> TYPE: PRT
<213> ORGANISM: Artificial Sequence
<220> FEATURE:
<223> OTHER INFORMATION: Synthetic: ATI_1420_D05 w/ N leader and
      modified C-terminus including PC + his tag

<400> SEQUENCE: 176

Gly Val Ser Asp Val Pro Arg Asp Leu Glu Val Val Ala Ala Thr Pro
1               5                   10                  15

Thr Ser Leu Leu Ile Ser Trp Thr Ala Tyr Tyr Ser Thr Ile Lys Tyr
            20                  25                  30

Arg Ile Thr Tyr Gly Glu Thr Gly Gly Asn Ser Pro Val Gln Glu Phe
            35                  40                  45

Thr Val Gly Pro Lys His His Ala Thr Ile Ser Gly Leu Lys Pro Gly
        50                  55                  60

Val Asp Tyr Thr Ile Thr Val Tyr Ala Tyr Asn Thr Lys Pro Gly Tyr
65                  70                  75                  80

His Ala His Gln Ile Ser Ile Asn Tyr Arg Thr Pro Cys His His His
            85                  90                  95

His His His

<210> SEQ ID NO 177
<211> LENGTH: 105
<212> TYPE: PRT
<213> ORGANISM: Artificial Sequence
<220> FEATURE:
<223> OTHER INFORMATION: Synthetic: ATI_1420_D05 full length

<400> SEQUENCE: 177

Met Gly Val Ser Asp Val Pro Arg Asp Leu Glu Val Val Ala Ala Thr
1               5                   10                  15

Pro Thr Ser Leu Leu Ile Ser Trp Thr Ala Tyr Tyr Ser Thr Ile Lys
            20                  25                  30

Tyr Arg Ile Thr Tyr Gly Glu Thr Gly Gly Asn Ser Pro Val Gln Glu
            35                  40                  45

Phe Thr Val Gly Pro Lys His His Ala Thr Ile Ser Gly Leu Lys Pro
        50                  55                  60

Gly Val Asp Tyr Thr Ile Thr Val Tyr Ala Tyr Asn Thr Lys Pro Gly
65                  70                  75                  80

Tyr His Ala His Gln Ile Ser Ile Asn Tyr Arg Thr Glu Ile Asp Lys
            85                  90                  95

Pro Ser Gln His His His His His His

```
<210> SEQ ID NO 178
<211> LENGTH: 80
<212> TYPE: PRT
<213> ORGANISM: Artificial Sequence
<220> FEATURE:
<223> OTHER INFORMATION: Synthetic: ATI_1420_D10  core

<400> SEQUENCE: 178
```

Glu Val Val Ala Ala Thr Pro Thr Ser Leu Leu Ile Ser Trp Arg Ile
1               5                   10                  15

Pro Ser Tyr His Ile Gln Tyr Arg Ile Thr Tyr Gly Glu Thr Gly Gly
            20                  25                  30

Asn Ser Pro Val Gln Glu Phe Thr Val Tyr Gln Lys Tyr Ala Thr Ile
        35                  40                  45

Ser Gly Leu Lys Pro Gly Val Asp Tyr Thr Ile Thr Val Tyr Ala Val
    50                  55                  60

Ser Pro Pro Lys Gln Leu Arg Phe Gly Ile Ser Ile Asn Tyr Arg Thr
65                  70                  75                  80

```
<210> SEQ ID NO 179
<211> LENGTH: 8
<212> TYPE: PRT
<213> ORGANISM: Artificial Sequence
<220> FEATURE:
<223> OTHER INFORMATION: Synthetic: ATI_1420_D10  BC loop

<400> SEQUENCE: 179
```

Arg Ile Pro Ser Tyr His Ile Gln
1               5

```
<210> SEQ ID NO 180
<211> LENGTH: 4
<212> TYPE: PRT
<213> ORGANISM: Artificial Sequence
<220> FEATURE:
<223> OTHER INFORMATION: Synthetic: ATI_1420_D10  DE loop

<400> SEQUENCE: 180
```

Tyr Gln Lys Tyr
1

```
<210> SEQ ID NO 181
<211> LENGTH: 10
<212> TYPE: PRT
<213> ORGANISM: Artificial Sequence
<220> FEATURE:
<223> OTHER INFORMATION: Synthetic: ATI_1420_D10  FG loop

<400> SEQUENCE: 181
```

Val Ser Pro Pro Lys Gln Leu Arg Phe Gly
1               5                   10

```
<210> SEQ ID NO 182
<211> LENGTH: 89
<212> TYPE: PRT
<213> ORGANISM: Artificial Sequence
<220> FEATURE:
<223> OTHER INFORMATION: Synthetic: ATI_1420_D10  w/ N leader

<400> SEQUENCE: 182
```

Gly Val Ser Asp Val Pro Arg Asp Leu Glu Val Val Ala Ala Thr Pro
1               5                   10                  15

Thr Ser Leu Leu Ile Ser Trp Arg Ile Pro Ser Tyr His Ile Gln Tyr
            20                  25                  30

Arg Ile Thr Tyr Gly Glu Thr Gly Asn Ser Pro Val Gln Glu Phe
        35                  40                  45

Thr Val Tyr Gln Lys Tyr Ala Thr Ile Ser Gly Leu Lys Pro Gly Val
    50                  55                  60

Asp Tyr Thr Ile Thr Val Tyr Ala Val Ser Pro Pro Lys Gln Leu Arg
65                  70                  75                  80

Phe Gly Ile Ser Ile Asn Tyr Arg Thr
                85

<210> SEQ ID NO 183
<211> LENGTH: 95
<212> TYPE: PRT
<213> ORGANISM: Artificial Sequence
<220> FEATURE:
<223> OTHER INFORMATION: Synthetic: ATI_1420_D10  w/ N leader + his tag

<400> SEQUENCE: 183

Gly Val Ser Asp Val Pro Arg Asp Leu Glu Val Val Ala Ala Thr Pro
1               5                   10                  15

Thr Ser Leu Leu Ile Ser Trp Arg Ile Pro Ser Tyr His Ile Gln Tyr
            20                  25                  30

Arg Ile Thr Tyr Gly Glu Thr Gly Asn Ser Pro Val Gln Glu Phe
        35                  40                  45

Thr Val Tyr Gln Lys Tyr Ala Thr Ile Ser Gly Leu Lys Pro Gly Val
    50                  55                  60

Asp Tyr Thr Ile Thr Val Tyr Ala Val Ser Pro Pro Lys Gln Leu Arg
65                  70                  75                  80

Phe Gly Ile Ser Ile Asn Tyr Arg Thr His His His His His His
                85                  90                  95

<210> SEQ ID NO 184
<211> LENGTH: 96
<212> TYPE: PRT
<213> ORGANISM: Artificial Sequence
<220> FEATURE:
<223> OTHER INFORMATION: Synthetic: ATI_1420_D10  w/ N leader and C tail

<400> SEQUENCE: 184

Gly Val Ser Asp Val Pro Arg Asp Leu Glu Val Val Ala Ala Thr Pro
1               5                   10                  15

Thr Ser Leu Leu Ile Ser Trp Arg Ile Pro Ser Tyr His Ile Gln Tyr
            20                  25                  30

Arg Ile Thr Tyr Gly Glu Thr Gly Asn Ser Pro Val Gln Glu Phe
        35                  40                  45

Thr Val Tyr Gln Lys Tyr Ala Thr Ile Ser Gly Leu Lys Pro Gly Val
    50                  55                  60

Asp Tyr Thr Ile Thr Val Tyr Ala Val Ser Pro Pro Lys Gln Leu Arg
65                  70                  75                  80

Phe Gly Ile Ser Ile Asn Tyr Arg Thr Glu Ile Asp Lys Pro Ser Gln
                85                  90                  95

<210> SEQ ID NO 185
<211> LENGTH: 102
<212> TYPE: PRT
<213> ORGANISM: Artificial Sequence
<220> FEATURE:
<223> OTHER INFORMATION: Synthetic: ATI_1420_D10  w/ N leader and C
      tail + his tag

<400> SEQUENCE: 185

Gly Val Ser Asp Val Pro Arg Asp Leu Glu Val Val Ala Ala Thr Pro
1               5                   10                  15

Thr Ser Leu Leu Ile Ser Trp Arg Ile Pro Ser Tyr His Ile Gln Tyr
            20                  25                  30

Arg Ile Thr Tyr Gly Glu Thr Gly Gly Asn Ser Pro Val Gln Glu Phe
        35                  40                  45

Thr Val Tyr Gln Lys Tyr Ala Thr Ile Ser Gly Leu Lys Pro Gly Val
    50                  55                  60

Asp Tyr Thr Ile Thr Val Tyr Ala Val Ser Pro Pro Lys Gln Leu Arg
65                  70                  75                  80

Phe Gly Ile Ser Ile Asn Tyr Arg Thr Glu Ile Asp Lys Pro Ser Gln
                85                  90                  95

His His His His His His
            100

<210> SEQ ID NO 186
<211> LENGTH: 91
<212> TYPE: PRT
<213> ORGANISM: Artificial Sequence
<220> FEATURE:
<223> OTHER INFORMATION: Synthetic: ATI_1420_D10  w/ N leader and
      modified C-terminus including PC

<400> SEQUENCE: 186

Gly Val Ser Asp Val Pro Arg Asp Leu Glu Val Val Ala Ala Thr Pro
1               5                   10                  15

Thr Ser Leu Leu Ile Ser Trp Arg Ile Pro Ser Tyr His Ile Gln Tyr
            20                  25                  30

Arg Ile Thr Tyr Gly Glu Thr Gly Gly Asn Ser Pro Val Gln Glu Phe
        35                  40                  45

Thr Val Tyr Gln Lys Tyr Ala Thr Ile Ser Gly Leu Lys Pro Gly Val
    50                  55                  60

Asp Tyr Thr Ile Thr Val Tyr Ala Val Ser Pro Pro Lys Gln Leu Arg
65                  70                  75                  80

Phe Gly Ile Ser Ile Asn Tyr Arg Thr Pro Cys
                85                  90

<210> SEQ ID NO 187
<211> LENGTH: 97
<212> TYPE: PRT
<213> ORGANISM: Artificial Sequence
<220> FEATURE:
<223> OTHER INFORMATION: Synthetic: ATI_1420_D10  w/ N leader and
      modified C-terminus including PC + his tag

<400> SEQUENCE: 187

Gly Val Ser Asp Val Pro Arg Asp Leu Glu Val Val Ala Ala Thr Pro
1               5                   10                  15

Thr Ser Leu Leu Ile Ser Trp Arg Ile Pro Ser Tyr His Ile Gln Tyr
            20                  25                  30

Arg Ile Thr Tyr Gly Glu Thr Gly Gly Asn Ser Pro Val Gln Glu Phe
        35                  40                  45

Thr Val Tyr Gln Lys Tyr Ala Thr Ile Ser Gly Leu Lys Pro Gly Val
    50                  55                  60

Asp Tyr Thr Ile Thr Val Tyr Ala Val Ser Pro Pro Lys Gln Leu Arg
65                  70                  75                  80

Phe Gly Ile Ser Ile Asn Tyr Arg Thr Pro Cys His His His His
                85                  90                  95

His

<210> SEQ ID NO 188
<211> LENGTH: 103
<212> TYPE: PRT
<213> ORGANISM: Artificial Sequence
<220> FEATURE:
<223> OTHER INFORMATION: Synthetic: ATI_1420_D010 full length

<400> SEQUENCE: 188

Met Gly Val Ser Asp Val Pro Arg Asp Leu Glu Val Val Ala Ala Thr
1               5                   10                  15

Pro Thr Ser Leu Leu Ile Ser Trp Arg Ile Pro Ser Tyr His Ile Gln
            20                  25                  30

Tyr Arg Ile Thr Tyr Gly Glu Thr Gly Gly Asn Ser Pro Val Gln Glu
        35                  40                  45

Phe Thr Val Tyr Gln Lys Tyr Ala Thr Ile Ser Gly Leu Lys Pro Gly
    50                  55                  60

Val Asp Tyr Thr Ile Thr Val Tyr Ala Val Ser Pro Pro Lys Gln Leu
65                  70                  75                  80

Arg Phe Gly Ile Ser Ile Asn Tyr Arg Thr Glu Ile Asp Lys Pro Ser
                85                  90                  95

Gln His His His His His His
            100

<210> SEQ ID NO 189
<211> LENGTH: 76
<212> TYPE: PRT
<213> ORGANISM: Artificial Sequence
<220> FEATURE:
<223> OTHER INFORMATION: Synthetic: ATI_1420_F10_core

<400> SEQUENCE: 189

Glu Val Val Ala Ala Thr Pro Thr Ser Leu Leu Ile Ser Trp Pro Ala
1               5                   10                  15

Pro Pro Ser Tyr Val Phe Tyr Arg Ile Thr Tyr Gly Glu Thr Gly Gly
            20                  25                  30

Asn Ser Pro Val Gln Glu Phe Thr Val Tyr Pro Tyr Met Ala Thr Ile
        35                  40                  45

Ser Gly Leu Lys Pro Gly Val Asp Tyr Thr Ile Thr Val Tyr Ala Tyr
    50                  55                  60

Thr Ser Gly Phe Ser Ile Ser Ile Asn Tyr Arg Thr
65                  70                  75

<210> SEQ ID NO 190
<211> LENGTH: 8
<212> TYPE: PRT
<213> ORGANISM: Artificial Sequence
<220> FEATURE:
<223> OTHER INFORMATION: Synthetic: ATI_1420_F10  BC loop

<400> SEQUENCE: 190

Pro Ala Pro Pro Ser Tyr Val Phe
1               5

<210> SEQ ID NO 191
<211> LENGTH: 4
<212> TYPE: PRT
<213> ORGANISM: Artificial Sequence

```
<220> FEATURE:
<223> OTHER INFORMATION: Synthetic: ATI_1420_F10 DE loop

<400> SEQUENCE: 191

Tyr Pro Tyr Met
1

<210> SEQ ID NO 192
<211> LENGTH: 6
<212> TYPE: PRT
<213> ORGANISM: Artificial Sequence
<220> FEATURE:
<223> OTHER INFORMATION: Synthetic: ATI_1420_F10 FG loop

<400> SEQUENCE: 192

Tyr Thr Ser Gly Phe Ser
1               5

<210> SEQ ID NO 193
<211> LENGTH: 85
<212> TYPE: PRT
<213> ORGANISM: Artificial Sequence
<220> FEATURE:
<223> OTHER INFORMATION: Synthetic: ATI_1420_F10 w/ N leader

<400> SEQUENCE: 193

Gly Val Ser Asp Val Pro Arg Asp Leu Glu Val Val Ala Ala Thr Pro
1               5                   10                  15

Thr Ser Leu Leu Ile Ser Trp Pro Ala Pro Pro Ser Tyr Val Phe Tyr
                20                  25                  30

Arg Ile Thr Tyr Gly Glu Thr Gly Gly Asn Ser Pro Val Gln Glu Phe
            35                  40                  45

Thr Val Tyr Pro Tyr Met Ala Thr Ile Ser Gly Leu Lys Pro Gly Val
        50                  55                  60

Asp Tyr Thr Ile Thr Val Tyr Ala Tyr Thr Ser Gly Phe Ser Ile Ser
65                  70                  75                  80

Ile Asn Tyr Arg Thr
                85

<210> SEQ ID NO 194
<211> LENGTH: 91
<212> TYPE: PRT
<213> ORGANISM: Artificial Sequence
<220> FEATURE:
<223> OTHER INFORMATION: Synthetic: ATI_1420_F10  w/ N leader + his tag

<400> SEQUENCE: 194

Gly Val Ser Asp Val Pro Arg Asp Leu Glu Val Val Ala Ala Thr Pro
1               5                   10                  15

Thr Ser Leu Leu Ile Ser Trp Pro Ala Pro Pro Ser Tyr Val Phe Tyr
                20                  25                  30

Arg Ile Thr Tyr Gly Glu Thr Gly Gly Asn Ser Pro Val Gln Glu Phe
            35                  40                  45

Thr Val Tyr Pro Tyr Met Ala Thr Ile Ser Gly Leu Lys Pro Gly Val
        50                  55                  60

Asp Tyr Thr Ile Thr Val Tyr Ala Tyr Thr Ser Gly Phe Ser Ile Ser
65                  70                  75                  80

Ile Asn Tyr Arg Thr His His His His His His
                85                  90

<210> SEQ ID NO 195
```

```
<211> LENGTH: 92
<212> TYPE: PRT
<213> ORGANISM: Artificial Sequence
<220> FEATURE:
<223> OTHER INFORMATION: Synthetic: ATI_1420_F10 w/ N leader and C tail

<400> SEQUENCE: 195

Gly Val Ser Asp Val Pro Arg Asp Leu Glu Val Val Ala Ala Thr Pro
1               5                   10                  15

Thr Ser Leu Leu Ile Ser Trp Pro Ala Pro Pro Ser Tyr Val Phe Tyr
            20                  25                  30

Arg Ile Thr Tyr Gly Glu Thr Gly Gly Asn Ser Pro Val Gln Glu Phe
        35                  40                  45

Thr Val Tyr Pro Tyr Met Ala Thr Ile Ser Gly Leu Lys Pro Gly Val
    50                  55                  60

Asp Tyr Thr Ile Thr Val Tyr Ala Tyr Thr Ser Gly Phe Ser Ile Ser
65                  70                  75                  80

Ile Asn Tyr Arg Thr Glu Ile Asp Lys Pro Ser Gln
                85                  90

<210> SEQ ID NO 196
<211> LENGTH: 98
<212> TYPE: PRT
<213> ORGANISM: Artificial Sequence
<220> FEATURE:
<223> OTHER INFORMATION: Synthetic: ATI_1420_F10  w/ N leader and C
      tail + his tag

<400> SEQUENCE: 196

Gly Val Ser Asp Val Pro Arg Asp Leu Glu Val Val Ala Ala Thr Pro
1               5                   10                  15

Thr Ser Leu Leu Ile Ser Trp Pro Ala Pro Pro Ser Tyr Val Phe Tyr
            20                  25                  30

Arg Ile Thr Tyr Gly Glu Thr Gly Gly Asn Ser Pro Val Gln Glu Phe
        35                  40                  45

Thr Val Tyr Pro Tyr Met Ala Thr Ile Ser Gly Leu Lys Pro Gly Val
    50                  55                  60

Asp Tyr Thr Ile Thr Val Tyr Ala Tyr Thr Ser Gly Phe Ser Ile Ser
65                  70                  75                  80

Ile Asn Tyr Arg Thr Glu Ile Asp Lys Pro Ser Gln His His His His
                85                  90                  95

His His

<210> SEQ ID NO 197
<211> LENGTH: 87
<212> TYPE: PRT
<213> ORGANISM: Artificial Sequence
<220> FEATURE:
<223> OTHER INFORMATION: Synthetic: ATI_1420_F10  w/ N leader and
      modified C-terminus including PC

<400> SEQUENCE: 197

Gly Val Ser Asp Val Pro Arg Asp Leu Glu Val Val Ala Ala Thr Pro
1               5                   10                  15

Thr Ser Leu Leu Ile Ser Trp Pro Ala Pro Pro Ser Tyr Val Phe Tyr
            20                  25                  30

Arg Ile Thr Tyr Gly Glu Thr Gly Gly Asn Ser Pro Val Gln Glu Phe
        35                  40                  45

Thr Val Tyr Pro Tyr Met Ala Thr Ile Ser Gly Leu Lys Pro Gly Val
    50                  55                  60
```

```
Asp Tyr Thr Ile Thr Val Tyr Ala Tyr Thr Ser Gly Phe Ser Ile Ser
 65                  70                  75                  80

Ile Asn Tyr Arg Thr Pro Cys
                85
```

<210> SEQ ID NO 198
<211> LENGTH: 93
<212> TYPE: PRT
<213> ORGANISM: Artificial Sequence
<220> FEATURE:
<223> OTHER INFORMATION: Synthetic: ATI_1420_F10  w/ N leader and
      modified C-terminus including PC + his tag

<400> SEQUENCE: 198

```
Gly Val Ser Asp Val Pro Arg Asp Leu Glu Val Val Ala Ala Thr Pro
 1               5                  10                  15

Thr Ser Leu Leu Ile Ser Trp Pro Ala Pro Ser Tyr Val Phe Tyr
                20                  25                  30

Arg Ile Thr Tyr Gly Glu Thr Gly Gly Asn Ser Pro Val Gln Glu Phe
                35                  40                  45

Thr Val Tyr Pro Tyr Met Ala Thr Ile Ser Gly Leu Lys Pro Gly Val
             50                  55                  60

Asp Tyr Thr Ile Thr Val Tyr Ala Tyr Thr Ser Gly Phe Ser Ile Ser
 65                  70                  75                  80

Ile Asn Tyr Arg Thr Pro Cys His His His His His
                85                  90
```

<210> SEQ ID NO 199
<211> LENGTH: 99
<212> TYPE: PRT
<213> ORGANISM: Artificial Sequence
<220> FEATURE:
<223> OTHER INFORMATION: Synthetic: ATI_1420_F10 full length

<400> SEQUENCE: 199

```
Met Gly Val Ser Asp Val Pro Arg Asp Leu Glu Val Val Ala Ala Thr
 1               5                  10                  15

Pro Thr Ser Leu Leu Ile Ser Trp Pro Ala Pro Ser Tyr Val Phe
                20                  25                  30

Tyr Arg Ile Thr Tyr Gly Glu Thr Gly Gly Asn Ser Pro Val Gln Glu
                35                  40                  45

Phe Thr Val Tyr Pro Tyr Met Ala Thr Ile Ser Gly Leu Lys Pro Gly
             50                  55                  60

Val Asp Tyr Thr Ile Thr Val Tyr Ala Tyr Thr Ser Gly Phe Ser Ile
 65                  70                  75                  80

Ser Ile Asn Tyr Arg Thr Glu Ile Asp Lys Pro Ser Gln His His His
                85                  90                  95

His His His
```

<210> SEQ ID NO 200
<211> LENGTH: 79
<212> TYPE: PRT
<213> ORGANISM: Artificial Sequence
<220> FEATURE:
<223> OTHER INFORMATION: Synthetic: ATI_1421_C05_core

<400> SEQUENCE: 200

```
Glu Val Val Ala Ala Thr Pro Thr Ser Leu Leu Ile Ser Trp Tyr Met
 1               5                  10                  15
```

```
Asp His Lys Ser Lys Tyr Arg Ile Thr Tyr Gly Glu Thr Gly Gly Asn
            20                  25                  30

Ser Pro Val Gln Glu Phe Thr Val Pro Asp Gln Arg Ala Thr Ile Ser
        35                  40                  45

Gly Leu Lys Pro Gly Val Asp Tyr Thr Ile Thr Val Tyr Ala Leu Ser
    50                  55                  60

Glu Ala His Tyr Leu Arg Asp Lys Ile Ser Ile Asn Tyr Arg Thr
65                  70                  75

<210> SEQ ID NO 201
<211> LENGTH: 7
<212> TYPE: PRT
<213> ORGANISM: Artificial Sequence
<220> FEATURE:
<223> OTHER INFORMATION: Synthetic: ATI_1421_C05  BC loop

<400> SEQUENCE: 201

Tyr Met Asp His Lys Ser Lys
1               5

<210> SEQ ID NO 202
<211> LENGTH: 4
<212> TYPE: PRT
<213> ORGANISM: Artificial Sequence
<220> FEATURE:
<223> OTHER INFORMATION: Synthetic: ATI_1421_C05 DE loop

<400> SEQUENCE: 202

Pro Asp Gln Arg
1

<210> SEQ ID NO 203
<211> LENGTH: 10
<212> TYPE: PRT
<213> ORGANISM: Artificial Sequence
<220> FEATURE:
<223> OTHER INFORMATION: Synthetic: ATI_1421_C05 FG loop

<400> SEQUENCE: 203

Leu Ser Glu Ala His Tyr Leu Arg Asp Lys
1               5                   10

<210> SEQ ID NO 204
<211> LENGTH: 88
<212> TYPE: PRT
<213> ORGANISM: Artificial Sequence
<220> FEATURE:
<223> OTHER INFORMATION: Synthetic: ATI_1421_C05 w/ N leader

<400> SEQUENCE: 204

Gly Val Ser Asp Val Pro Arg Asp Leu Glu Val Val Ala Ala Thr Pro
1               5                   10                  15

Thr Ser Leu Leu Ile Ser Trp Tyr Met Asp His Lys Ser Lys Tyr Arg
            20                  25                  30

Ile Thr Tyr Gly Glu Thr Gly Gly Asn Ser Pro Val Gln Glu Phe Thr
        35                  40                  45

Val Pro Asp Gln Arg Ala Thr Ile Ser Gly Leu Lys Pro Gly Val Asp
    50                  55                  60

Tyr Thr Ile Thr Val Tyr Ala Leu Ser Glu Ala His Tyr Leu Arg Asp
65                  70                  75                  80

Lys Ile Ser Ile Asn Tyr Arg Thr
                85
```

<210> SEQ ID NO 205
<211> LENGTH: 94
<212> TYPE: PRT
<213> ORGANISM: Artificial Sequence
<220> FEATURE:
<223> OTHER INFORMATION: Synthetic: ATI_1421_C05  w/ N leader + his tag

<400> SEQUENCE: 205

Gly Val Ser Asp Val Pro Arg Asp Leu Glu Val Val Ala Ala Thr Pro
1               5                   10                  15

Thr Ser Leu Leu Ile Ser Trp Tyr Met Asp His Lys Ser Lys Tyr Arg
            20                  25                  30

Ile Thr Tyr Gly Glu Thr Gly Gly Asn Ser Pro Val Gln Glu Phe Thr
        35                  40                  45

Val Pro Asp Gln Arg Ala Thr Ile Ser Gly Leu Lys Pro Gly Val Asp
    50                  55                  60

Tyr Thr Ile Thr Val Tyr Ala Leu Ser Glu Ala His Tyr Leu Arg Asp
65                  70                  75                  80

Lys Ile Ser Ile Asn Tyr Arg Thr His His His His His
                85                  90

<210> SEQ ID NO 206
<211> LENGTH: 95
<212> TYPE: PRT
<213> ORGANISM: Artificial Sequence
<220> FEATURE:
<223> OTHER INFORMATION: Synthetic: ATI_1421_C05 w/ N leader and C tail

<400> SEQUENCE: 206

Gly Val Ser Asp Val Pro Arg Asp Leu Glu Val Val Ala Ala Thr Pro
1               5                   10                  15

Thr Ser Leu Leu Ile Ser Trp Tyr Met Asp His Lys Ser Lys Tyr Arg
            20                  25                  30

Ile Thr Tyr Gly Glu Thr Gly Gly Asn Ser Pro Val Gln Glu Phe Thr
        35                  40                  45

Val Pro Asp Gln Arg Ala Thr Ile Ser Gly Leu Lys Pro Gly Val Asp
    50                  55                  60

Tyr Thr Ile Thr Val Tyr Ala Leu Ser Glu Ala His Tyr Leu Arg Asp
65                  70                  75                  80

Lys Ile Ser Ile Asn Tyr Arg Thr Glu Ile Asp Lys Pro Ser Gln
                85                  90                  95

<210> SEQ ID NO 207
<211> LENGTH: 101
<212> TYPE: PRT
<213> ORGANISM: Artificial Sequence
<220> FEATURE:
<223> OTHER INFORMATION: Synthetic: ATI_1421_C05  w/ N leader and C
      tail + his tag

<400> SEQUENCE: 207

Gly Val Ser Asp Val Pro Arg Asp Leu Glu Val Val Ala Ala Thr Pro
1               5                   10                  15

Thr Ser Leu Leu Ile Ser Trp Tyr Met Asp His Lys Ser Lys Tyr Arg
            20                  25                  30

Ile Thr Tyr Gly Glu Thr Gly Gly Asn Ser Pro Val Gln Glu Phe Thr
        35                  40                  45

Val Pro Asp Gln Arg Ala Thr Ile Ser Gly Leu Lys Pro Gly Val Asp
    50                  55                  60

Tyr Thr Ile Thr Val Tyr Ala Leu Ser Glu Ala His Tyr Leu Arg Asp
 65                  70                  75                  80

Lys Ile Ser Ile Asn Tyr Arg Thr Glu Ile Asp Lys Pro Ser Gln His
                 85                  90                  95

His His His His His
            100

<210> SEQ ID NO 208
<211> LENGTH: 90
<212> TYPE: PRT
<213> ORGANISM: Artificial Sequence
<220> FEATURE:
<223> OTHER INFORMATION: Synthetic: ATI_1421_C05  w/ N leader and
      modified C-terminus including PC

<400> SEQUENCE: 208

Gly Val Ser Asp Val Pro Arg Asp Leu Glu Val Val Ala Ala Thr Pro
  1               5                  10                  15

Thr Ser Leu Leu Ile Ser Trp Tyr Met Asp His Lys Ser Lys Tyr Arg
                 20                  25                  30

Ile Thr Tyr Gly Glu Thr Gly Gly Asn Ser Pro Val Gln Glu Phe Thr
             35                  40                  45

Val Pro Asp Gln Arg Ala Thr Ile Ser Gly Leu Lys Pro Gly Val Asp
 50                  55                  60

Tyr Thr Ile Thr Val Tyr Ala Leu Ser Glu Ala His Tyr Leu Arg Asp
 65                  70                  75                  80

Lys Ile Ser Ile Asn Tyr Arg Thr Pro Cys
                 85                  90

<210> SEQ ID NO 209
<211> LENGTH: 96
<212> TYPE: PRT
<213> ORGANISM: Artificial Sequence
<220> FEATURE:
<223> OTHER INFORMATION: Synthetic: ATI_1421_C05 w/ N leader and
      modified C-terminus including PC + his tag

<400> SEQUENCE: 209

Gly Val Ser Asp Val Pro Arg Asp Leu Glu Val Val Ala Ala Thr Pro
  1               5                  10                  15

Thr Ser Leu Leu Ile Ser Trp Tyr Met Asp His Lys Ser Lys Tyr Arg
                 20                  25                  30

Ile Thr Tyr Gly Glu Thr Gly Gly Asn Ser Pro Val Gln Glu Phe Thr
             35                  40                  45

Val Pro Asp Gln Arg Ala Thr Ile Ser Gly Leu Lys Pro Gly Val Asp
 50                  55                  60

Tyr Thr Ile Thr Val Tyr Ala Leu Ser Glu Ala His Tyr Leu Arg Asp
 65                  70                  75                  80

Lys Ile Ser Ile Asn Tyr Arg Thr Pro Cys His His His His His
                 85                  90                  95

<210> SEQ ID NO 210
<211> LENGTH: 102
<212> TYPE: PRT
<213> ORGANISM: Artificial Sequence
<220> FEATURE:
<223> OTHER INFORMATION: Synthetic: ATI_1421_C05 full length

<400> SEQUENCE: 210

Met Gly Val Ser Asp Val Pro Arg Asp Leu Glu Val Val Ala Ala Thr
  1               5                  10                  15

```
Pro Thr Ser Leu Leu Ile Ser Trp Tyr Met Asp His Lys Ser Lys Tyr
            20                  25                  30

Arg Ile Thr Tyr Gly Glu Thr Gly Gly Asn Ser Pro Val Gln Glu Phe
        35                  40                  45

Thr Val Pro Asp Gln Arg Ala Thr Ile Ser Gly Leu Lys Pro Gly Val
 50                  55                  60

Asp Tyr Thr Ile Thr Val Tyr Ala Leu Ser Glu Ala His Tyr Leu Arg
 65                  70                  75                  80

Asp Lys Ile Ser Ile Asn Tyr Arg Thr Glu Ile Asp Lys Pro Ser Gln
                85                  90                  95

His His His His His His
            100

<210> SEQ ID NO 211
<211> LENGTH: 79
<212> TYPE: PRT
<213> ORGANISM: Artificial Sequence
<220> FEATURE:
<223> OTHER INFORMATION: Synthetic: ATI_1421_C06 core

<400> SEQUENCE: 211

Glu Val Val Ala Ala Thr Pro Thr Ser Leu Leu Ile Ser Trp Glu Asn
1               5                   10                  15

Leu Ala Ser Tyr Gln Tyr Arg Ile Thr Tyr Gly Glu Thr Gly Gly Asn
            20                  25                  30

Ser Pro Val Gln Glu Phe Thr Val Pro Asp Gln Ala Ala Thr Ile Ser
        35                  40                  45

Gly Leu Lys Pro Gly Val Asp Tyr Thr Ile Thr Val Tyr Ala Leu Gln
    50                  55                  60

Thr Ala His Tyr Tyr Arg Gln His Ile Ser Ile Asn Tyr Arg Thr
65                  70                  75

<210> SEQ ID NO 212
<211> LENGTH: 7
<212> TYPE: PRT
<213> ORGANISM: Artificial Sequence
<220> FEATURE:
<223> OTHER INFORMATION: Synthetic: ATI_1421_C06 BC loop

<400> SEQUENCE: 212

Glu Asn Leu Ala Ser Tyr Gln
1               5

<210> SEQ ID NO 213
<211> LENGTH: 4
<212> TYPE: PRT
<213> ORGANISM: Artificial Sequence
<220> FEATURE:
<223> OTHER INFORMATION: Synthetic: ATI_1421_C06DE loop

<400> SEQUENCE: 213

Pro Asp Gln Ala
1

<210> SEQ ID NO 214
<211> LENGTH: 10
<212> TYPE: PRT
<213> ORGANISM: Artificial Sequence
<220> FEATURE:
<223> OTHER INFORMATION: Synthetic: ATI_1421_C06FG loop

<400> SEQUENCE: 214
```

```
<210> SEQ ID NO 215
<211> LENGTH: 88
<212> TYPE: PRT
<213> ORGANISM: Artificial Sequence
<220> FEATURE:
<223> OTHER INFORMATION: Synthetic: ATI_1421_C06 w/ N leader

<400> SEQUENCE: 215

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Ala Ala Thr Ile Ser Gly Leu Lys Pro Gly Val Asp
    50                  55                  60

Tyr Thr Ile Thr Val Tyr Ala Leu Gln Thr Ala His Tyr Tyr Arg Gln
65                  70                  75                  80

His Ile Ser Ile Asn Tyr Arg Thr
                85

<210> SEQ ID NO 216
<211> LENGTH: 94
<212> TYPE: PRT
<213> ORGANISM: Artificial Sequence
<220> FEATURE:
<223> OTHER INFORMATION: Synthetic: ATI_1421_C06 w/ N leader + his tag

<400> SEQUENCE: 216

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Ala Ala Thr Ile Ser Gly Leu Lys Pro Gly Val Asp
    50                  55                  60

Tyr Thr Ile Thr Val Tyr Ala Leu Gln Thr Ala His Tyr Tyr Arg Gln
65                  70                  75                  80

His Ile Ser Ile Asn Tyr Arg Thr His His His His His His
                85                  90

<210> SEQ ID NO 217
<211> LENGTH: 95
<212> TYPE: PRT
<213> ORGANISM: Artificial Sequence
<220> FEATURE:
<223> OTHER INFORMATION: Synthetic: ATI_1421_C06 w/ N leader and C tail

<400> SEQUENCE: 217

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Gly Asn Ser Pro Val Gln Glu Phe Thr
        35                  40                  45
```

(Leu Gln Thr Ala His Tyr Tyr Arg Gln His sequence at top of page — part of previous SEQ ID)

```
Leu Gln Thr Ala His Tyr Tyr Arg Gln His
1               5                   10
```

Val Pro Asp Gln Ala Ala Thr Ile Ser Gly Leu Lys Pro Gly Val Asp
    50                  55                  60

Tyr Thr Ile Thr Val Tyr Ala Leu Gln Thr Ala His Tyr Tyr Arg Gln
65                  70                  75                  80

His Ile Ser Ile Asn Tyr Arg Thr Glu Ile Asp Lys Pro Ser Gln
                85                  90                  95

<210> SEQ ID NO 218
<211> LENGTH: 101
<212> TYPE: PRT
<213> ORGANISM: Artificial Sequence
<220> FEATURE:
<223> OTHER INFORMATION: Synthetic: ATI_1421_C06 w/ N leader and C
      tail + his tag

<400> SEQUENCE: 218

Gly Val Ser Asp Val Pro Arg Asp Leu Glu Val Ala Ala Thr Pro
1               5                   10                  15

Thr Ser Leu Leu Ile Ser Trp Glu Asn Leu Ala Ser Tyr Gln Tyr Arg
                20                  25                  30

Ile Thr Tyr Gly Glu Thr Gly Gly Asn Ser Pro Val Gln Glu Phe Thr
                35                  40                  45

Val Pro Asp Gln Ala Ala Thr Ile Ser Gly Leu Lys Pro Gly Val Asp
    50                  55                  60

Tyr Thr Ile Thr Val Tyr Ala Leu Gln Thr Ala His Tyr Tyr Arg Gln
65                  70                  75                  80

His Ile Ser Ile Asn Tyr Arg Thr Glu Ile Asp Lys Pro Ser Gln His
                85                  90                  95

His His His His His
            100

<210> SEQ ID NO 219
<211> LENGTH: 90
<212> TYPE: PRT
<213> ORGANISM: Artificial Sequence
<220> FEATURE:
<223> OTHER INFORMATION: Synthetic: ATI_1421_C06 w/ N leader and
      modified C-terminus including PC

<400> SEQUENCE: 219

Gly Val Ser Asp Val Pro Arg Asp Leu Glu Val Ala Ala Thr Pro
1               5                   10                  15

Thr Ser Leu Leu Ile Ser Trp Glu Asn Leu Ala Ser Tyr Gln Tyr Arg
                20                  25                  30

Ile Thr Tyr Gly Glu Thr Gly Gly Asn Ser Pro Val Gln Glu Phe Thr
                35                  40                  45

Val Pro Asp Gln Ala Ala Thr Ile Ser Gly Leu Lys Pro Gly Val Asp
    50                  55                  60

Tyr Thr Ile Thr Val Tyr Ala Leu Gln Thr Ala His Tyr Tyr Arg Gln
65                  70                  75                  80

His Ile Ser Ile Asn Tyr Arg Thr Pro Cys
                85                  90

<210> SEQ ID NO 220
<211> LENGTH: 96
<212> TYPE: PRT
<213> ORGANISM: Artificial Sequence
<220> FEATURE:
<223> OTHER INFORMATION: Synthetic: ATI_1421_C06 w/ N leader and
      modified C-terminus including PC + his tag

```
<400> SEQUENCE: 220

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Asn Ser Pro Val Gln Glu Phe Thr
                35                  40                  45

Val Pro Asp Gln Ala Ala Thr Ile Ser Gly Leu Lys Pro Gly Val Asp
50                  55                  60

Tyr Thr Ile Thr Val Tyr Ala Leu Gln Thr Ala His Tyr Tyr Arg Gln
65                  70                  75                  80

His Ile Ser Ile Asn Tyr Arg Thr Pro Cys His His His His His
                85                  90                  95

<210> SEQ ID NO 221
<211> LENGTH: 102
<212> TYPE: PRT
<213> ORGANISM: Artificial Sequence
<220> FEATURE:
<223> OTHER INFORMATION: Synthetic: ATI_1421_C06 full length

<400> SEQUENCE: 221

Met Gly Val Ser Asp Val Pro Arg Asp Leu Glu Val Val Ala Ala Thr
1               5                   10                  15

Pro Thr Ser Leu Leu Ile Ser Trp Glu Asn Leu Ala Ser Tyr Gln Tyr
            20                  25                  30

Arg Ile Thr Tyr Gly Glu Thr Gly Gly Asn Ser Pro Val Gln Glu Phe
        35                  40                  45

Thr Val Pro Asp Gln Ala Ala Thr Ile Ser Gly Leu Lys Pro Gly Val
50                  55                  60

Asp Tyr Thr Ile Thr Val Tyr Ala Leu Gln Thr Ala His Tyr Tyr Arg
65                  70                  75                  80

Gln His Ile Ser Ile Asn Tyr Arg Thr Glu Ile Asp Lys Pro Ser Gln
                85                  90                  95

His His His His His His
            100

<210> SEQ ID NO 222
<211> LENGTH: 79
<212> TYPE: PRT
<213> ORGANISM: Artificial Sequence
<220> FEATURE:
<223> OTHER INFORMATION: Synthetic: ATI 1421_D05 core

<400> SEQUENCE: 222

Glu Val Val Ala Ala Thr Pro Thr Ser Leu Leu Ile Ser Trp Tyr Tyr
1               5                   10                  15

Val Gln Tyr Asn Asp Tyr Arg Ile Thr Tyr Gly Glu Thr Gly Gly Asn
            20                  25                  30

Ser Pro Val Gln Glu Phe Thr Val Pro Asp Gln Ser Ala Thr Ile Ser
        35                  40                  45

Gly Leu Lys Pro Gly Val Asp Tyr Thr Ile Thr Val Tyr Ala Leu Glu
50                  55                  60

Lys Ala His Tyr Tyr Arg Gln Asn Ile Ser Ile Asn Tyr Arg Thr
65                  70                  75

<210> SEQ ID NO 223
<211> LENGTH: 7
```

```
<212> TYPE: PRT
<213> ORGANISM: Artificial Sequence
<220> FEATURE:
<223> OTHER INFORMATION: Synthetic: ATI 1421_D05 BC loop

<400> SEQUENCE: 223

Tyr Tyr Val Gln Tyr Asn Asp
1               5

<210> SEQ ID NO 224
<211> LENGTH: 4
<212> TYPE: PRT
<213> ORGANISM: Artificial Sequence
<220> FEATURE:
<223> OTHER INFORMATION: Synthetic: ATI 1421_D05 DE loop

<400> SEQUENCE: 224

Pro Asp Gln Ser
1

<210> SEQ ID NO 225
<211> LENGTH: 10
<212> TYPE: PRT
<213> ORGANISM: Artificial Sequence
<220> FEATURE:
<223> OTHER INFORMATION: Synthetic: ATI 1421_D05 FG loop

<400> SEQUENCE: 225

Leu Glu Lys Ala His Tyr Tyr Arg Gln Asn
1               5                   10

<210> SEQ ID NO 226
<211> LENGTH: 88
<212> TYPE: PRT
<213> ORGANISM: Artificial Sequence
<220> FEATURE:
<223> OTHER INFORMATION: Synthetic: ATI 1421_D05 w/ N leader

<400> SEQUENCE: 226

Gly Val Ser Asp Val Pro Arg Asp Leu Glu Val Val Ala Ala Thr Pro
1               5                   10                  15

Thr Ser Leu Leu Ile Ser Trp Tyr Tyr Val Gln Tyr Asn Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr
                85

<210> SEQ ID NO 227
<211> LENGTH: 94
<212> TYPE: PRT
<213> ORGANISM: Artificial Sequence
<220> FEATURE:
<223> OTHER INFORMATION: Synthetic: ATI 1421_D05 w/ N leader + his tag

<400> SEQUENCE: 227

Gly Val Ser Asp Val Pro Arg Asp Leu Glu Val Val Ala Ala Thr Pro
1               5                   10                  15

Thr Ser Leu Leu Ile Ser Trp Tyr Tyr Val Gln Tyr Asn Asp Tyr Arg
            20                  25                  30
```

Ile Thr Tyr Gly Glu Thr Gly Gly Asn Ser Pro Val Gln Glu Phe Thr
            35                  40                  45

Val Pro Asp Gln Ser Ala Thr Ile Ser Gly Leu Lys Pro Gly Val Asp
        50                  55                  60

Tyr Thr Ile Thr Val Tyr Ala Leu Glu Lys Ala His Tyr Tyr Arg Gln
 65                  70                  75                  80

Asn Ile Ser Ile Asn Tyr Arg Thr His His His His His
                85                  90

<210> SEQ ID NO 228
<211> LENGTH: 95
<212> TYPE: PRT
<213> ORGANISM: Artificial Sequence
<220> FEATURE:
<223> OTHER INFORMATION: Synthetic: ATI 1421_D05 w/ N leader and C tail

<400> SEQUENCE: 228

Gly Val Ser Asp Val Pro Arg Asp Leu Glu Val Val Ala Ala Thr Pro
1               5                   10                  15

Thr Ser Leu Leu Ile Ser Trp Tyr Tyr Val Gln Tyr Asn Asp Tyr Arg
            20                  25                  30

Ile Thr Tyr Gly Glu Thr Gly Gly Asn Ser Pro Val Gln Glu Phe Thr
            35                  40                  45

Val Pro Asp Gln Ser Ala Thr Ile Ser Gly Leu Lys Pro Gly Val Asp
        50                  55                  60

Tyr Thr Ile Thr Val Tyr Ala Leu Glu Lys Ala His Tyr Tyr Arg Gln
 65                  70                  75                  80

Asn Ile Ser Ile Asn Tyr Arg Thr Glu Ile Asp Lys Pro Ser Gln
                85                  90                  95

<210> SEQ ID NO 229
<211> LENGTH: 101
<212> TYPE: PRT
<213> ORGANISM: Artificial Sequence
<220> FEATURE:
<223> OTHER INFORMATION: Synthetic: ATI 1421_D05 w/ N leader and C
      tail + his tag

<400> SEQUENCE: 229

Gly Val Ser Asp Val Pro Arg Asp Leu Glu Val Val Ala Ala Thr Pro
1               5                   10                  15

Thr Ser Leu Leu Ile Ser Trp Tyr Tyr Val Gln Tyr Asn Asp Tyr Arg
            20                  25                  30

Ile Thr Tyr Gly Glu Thr Gly Gly Asn Ser Pro Val Gln Glu Phe Thr
            35                  40                  45

Val Pro Asp Gln Ser Ala Thr Ile Ser Gly Leu Lys Pro Gly Val Asp
        50                  55                  60

Tyr Thr Ile Thr Val Tyr Ala Leu Glu Lys Ala His Tyr Tyr Arg Gln
 65                  70                  75                  80

Asn Ile Ser Ile Asn Tyr Arg Thr Glu Ile Asp Lys Pro Ser Gln His
                85                  90                  95

His His His His His
            100

<210> SEQ ID NO 230
<211> LENGTH: 90
<212> TYPE: PRT
<213> ORGANISM: Artificial Sequence
<220> FEATURE:

<223> OTHER INFORMATION: Synthetic: ATI 1421_D05 w/ N leader and
      modified C-terminus including PC

<400> SEQUENCE: 230

Gly Val Ser Asp Val Pro Arg Asp Leu Glu Val Val Ala Ala Thr Pro
1               5                   10                  15

Thr Ser Leu Leu Ile Ser Trp Tyr Tyr Val Gln Tyr Asn Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Pro Cys
                85                  90

<210> SEQ ID NO 231
<211> LENGTH: 96
<212> TYPE: PRT
<213> ORGANISM: Artificial Sequence
<220> FEATURE:
<223> OTHER INFORMATION: Synthetic: ATI 1421_D05 w/ N leader and
      modified C-terminus including PC + his tag

<400> SEQUENCE: 231

Gly Val Ser Asp Val Pro Arg Asp Leu Glu Val Val Ala Ala Thr Pro
1               5                   10                  15

Thr Ser Leu Leu Ile Ser Trp Tyr Tyr Val Gln Tyr Asn Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Pro Cys His His His His His His
                85                  90                  95

<210> SEQ ID NO 232
<211> LENGTH: 102
<212> TYPE: PRT
<213> ORGANISM: Artificial Sequence
<220> FEATURE:
<223> OTHER INFORMATION: Synthetic: ATI 1421_D05  full length

<400> SEQUENCE: 232

Met Gly Val Ser Asp Val Pro Arg Asp Leu Glu Val Val Ala Ala Thr
1               5                   10                  15

Pro Thr Ser Leu Leu Ile Ser Trp Tyr Tyr Val Gln Tyr Asn Asp Tyr
            20                  25                  30

Arg Ile Thr Tyr Gly Glu Thr Gly Gly Asn Ser Pro Val Gln Glu Phe
        35                  40                  45

Thr Val Pro Asp Gln Ser Ala Thr Ile Ser Gly Leu Lys Pro Gly Val
    50                  55                  60

Asp Tyr Thr Ile Thr Val Tyr Ala Leu Glu Lys Ala His Tyr Tyr Arg
65                  70                  75                  80

Gln Asn Ile Ser Ile Asn Tyr Arg Thr Glu Ile Asp Lys Pro Ser Gln
                85                  90                  95

His His His His His His
            100

<210> SEQ ID NO 233
<211> LENGTH: 79
<212> TYPE: PRT
<213> ORGANISM: Artificial Sequence
<220> FEATURE:
<223> OTHER INFORMATION: Synthetic: ATI_1421_D06 core

<400> SEQUENCE: 233

Glu Val Val Ala Ala Thr Pro Thr Ser Leu Leu Ile Ser Trp Gly His
1               5                   10                  15

Asn Tyr Asp Asp Glu Tyr Arg Ile Thr Tyr Gly Glu Thr Gly Gly Asn
            20                  25                  30

Ser Pro Val Gln Glu Phe Thr Val Pro Asp Gln Tyr Ala Thr Ile Ser
        35                  40                  45

Gly Leu Lys Pro Gly Val Asp Tyr Thr Ile Thr Val Tyr Ala Leu Ala
    50                  55                  60

Glu Ala His Val Arg Lys Asn His Ile Ser Ile Asn Tyr Arg Thr
65                  70                  75

<210> SEQ ID NO 234
<211> LENGTH: 7
<212> TYPE: PRT
<213> ORGANISM: Artificial Sequence
<220> FEATURE:
<223> OTHER INFORMATION: Synthetic: ATI_1421_D06 BC loop

<400> SEQUENCE: 234

Gly His Asn Tyr Asp Asp Glu
1               5

<210> SEQ ID NO 235
<211> LENGTH: 4
<212> TYPE: PRT
<213> ORGANISM: Artificial Sequence
<220> FEATURE:
<223> OTHER INFORMATION: Synthetic: ATI_1421_D06  DE loop

<400> SEQUENCE: 235

Pro Asp Gln Tyr
1

<210> SEQ ID NO 236
<211> LENGTH: 10
<212> TYPE: PRT
<213> ORGANISM: Artificial Sequence
<220> FEATURE:
<223> OTHER INFORMATION: Synthetic: ATI_1421_D06  FG loop

<400> SEQUENCE: 236

Leu Ala Glu Ala His Val Arg Lys Asn His
1               5                   10

<210> SEQ ID NO 237
<211> LENGTH: 88
<212> TYPE: PRT
<213> ORGANISM: Artificial Sequence
<220> FEATURE:
<223> OTHER INFORMATION: Synthetic: ATI_1421_D06 w/ N leader

<400> SEQUENCE: 237

Gly Val Ser Asp Val Pro Arg Asp Leu Glu Val Val Ala Ala Thr Pro

```
                1               5                  10                  15
            Thr Ser Leu Leu Ile Ser Trp Gly His Asn Tyr Asp Asp Glu Tyr Arg
                            20                  25                  30

Ile Thr Tyr Gly Glu Thr Gly Gly Asn Ser Pro Val Gln Glu Phe Thr
                            35                  40                  45

Val Pro Asp Gln Tyr Ala Thr Ile Ser Gly Leu Lys Pro Gly Val Asp
                50                  55                  60

Tyr Thr Ile Thr Val Tyr Ala Leu Ala Glu Ala His Val Arg Lys Asn
            65                  70                  75                  80

His Ile Ser Ile Asn Tyr Arg Thr
                            85

<210> SEQ ID NO 238
<211> LENGTH: 94
<212> TYPE: PRT
<213> ORGANISM: Artificial Sequence
<220> FEATURE:
<223> OTHER INFORMATION: Synthetic: ATI_1421_D06 w/ N leader + his tag

<400> SEQUENCE: 238

Gly Val Ser Asp Val Pro Arg Asp Leu Glu Val Val Ala Ala Thr Pro
            1               5                  10                  15

Thr Ser Leu Leu Ile Ser Trp Gly His Asn Tyr Asp Asp Glu Tyr Arg
                            20                  25                  30

Ile Thr Tyr Gly Glu Thr Gly Gly Asn Ser Pro Val Gln Glu Phe Thr
                            35                  40                  45

Val Pro Asp Gln Tyr Ala Thr Ile Ser Gly Leu Lys Pro Gly Val Asp
                50                  55                  60

Tyr Thr Ile Thr Val Tyr Ala Leu Ala Glu Ala His Val Arg Lys Asn
            65                  70                  75                  80

His Ile Ser Ile Asn Tyr Arg Thr His His His His His
                            85                  90

<210> SEQ ID NO 239
<211> LENGTH: 95
<212> TYPE: PRT
<213> ORGANISM: Artificial Sequence
<220> FEATURE:
<223> OTHER INFORMATION: Synthetic: ATI_1421_D06 w/ N leader and C tail

<400> SEQUENCE: 239

Gly Val Ser Asp Val Pro Arg Asp Leu Glu Val Val Ala Ala Thr Pro
            1               5                  10                  15

Thr Ser Leu Leu Ile Ser Trp Gly His Asn Tyr Asp Asp Glu Tyr Arg
                            20                  25                  30

Ile Thr Tyr Gly Glu Thr Gly Gly Asn Ser Pro Val Gln Glu Phe Thr
                            35                  40                  45

Val Pro Asp Gln Tyr Ala Thr Ile Ser Gly Leu Lys Pro Gly Val Asp
                50                  55                  60

Tyr Thr Ile Thr Val Tyr Ala Leu Ala Glu Ala His Val Arg Lys Asn
            65                  70                  75                  80

His Ile Ser Ile Asn Tyr Arg Thr Glu Ile Asp Lys Pro Ser Gln
                            85                  90                  95

<210> SEQ ID NO 240
<211> LENGTH: 101
<212> TYPE: PRT
<213> ORGANISM: Artificial Sequence
<220> FEATURE:
```

<223> OTHER INFORMATION: Synthetic: ATI_1421_D06 w/ N leader and C
      tail + his tag

<400> SEQUENCE: 240

Gly Val Ser Asp Val Pro Arg Asp Leu Glu Val Val Ala Ala Thr Pro
1               5                   10                  15

Thr Ser Leu Leu Ile Ser Trp Gly His Asn Tyr Asp Asp Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Tyr Ala Thr Ile Ser Gly Leu Lys Pro Gly Val Asp
    50                  55                  60

Tyr Thr Ile Thr Val Tyr Ala Leu Ala Glu Ala His Val Arg Lys Asn
65                  70                  75                  80

His Ile Ser Ile Asn Tyr Arg Thr Glu Ile Asp Lys Pro Ser Gln His
                85                  90                  95

His His His His His
            100

<210> SEQ ID NO 241
<211> LENGTH: 90
<212> TYPE: PRT
<213> ORGANISM: Artificial Sequence
<220> FEATURE:
<223> OTHER INFORMATION: Synthetic: ATI_1421_D06 w/ N leader and
      modified C-terminus including PC

<400> SEQUENCE: 241

Gly Val Ser Asp Val Pro Arg Asp Leu Glu Val Val Ala Ala Thr Pro
1               5                   10                  15

Thr Ser Leu Leu Ile Ser Trp Gly His Asn Tyr Asp Asp Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Tyr Ala Thr Ile Ser Gly Leu Lys Pro Gly Val Asp
    50                  55                  60

Tyr Thr Ile Thr Val Tyr Ala Leu Ala Glu Ala His Val Arg Lys Asn
65                  70                  75                  80

His Ile Ser Ile Asn Tyr Arg Thr Pro Cys
                85                  90

<210> SEQ ID NO 242
<211> LENGTH: 96
<212> TYPE: PRT
<213> ORGANISM: Artificial Sequence
<220> FEATURE:
<223> OTHER INFORMATION: Synthetic: ATI_1421_D06 w/ N leader and
      modified C-terminus including PC + his tag

<400> SEQUENCE: 242

Gly Val Ser Asp Val Pro Arg Asp Leu Glu Val Val Ala Ala Thr Pro
1               5                   10                  15

Thr Ser Leu Leu Ile Ser Trp Gly His Asn Tyr Asp Asp Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Tyr Ala Thr Ile Ser Gly Leu Lys Pro Gly Val Asp
    50                  55                  60

Tyr Thr Ile Thr Val Tyr Ala Leu Ala Glu Ala His Val Arg Lys Asn

```
                65                  70                  75                  80
His Ile Ser Ile Asn Tyr Arg Thr Pro Cys His His His His His
                    85                  90                  95

<210> SEQ ID NO 243
<211> LENGTH: 102
<212> TYPE: PRT
<213> ORGANISM: Artificial Sequence
<220> FEATURE:
<223> OTHER INFORMATION: Synthetic: ATI_1421_D06  full length

<400> SEQUENCE: 243

Met Gly Val Ser Asp Val Pro Arg Asp Leu Glu Val Val Ala Ala Thr
1               5                   10                  15

Pro Thr Ser Leu Leu Ile Ser Trp Gly His Asn Tyr Asp Asp Glu Tyr
                20                  25                  30

Arg Ile Thr Tyr Gly Glu Thr Gly Gly Asn Ser Pro Val Gln Glu Phe
            35                  40                  45

Thr Val Pro Asp Gln Tyr Ala Thr Ile Ser Gly Leu Lys Pro Gly Val
        50                  55                  60

Asp Tyr Thr Ile Thr Val Tyr Ala Leu Ala Glu Ala His Val Arg Lys
65                  70                  75                  80

Asn His Ile Ser Ile Asn Tyr Arg Thr Glu Ile Asp Lys Pro Ser Gln
                85                  90                  95

His His His His His His
            100

<210> SEQ ID NO 244
<211> LENGTH: 79
<212> TYPE: PRT
<213> ORGANISM: Artificial Sequence
<220> FEATURE:
<223> OTHER INFORMATION: Synthetic: ATI_1421_E03 core

<400> SEQUENCE: 244

Glu Val Val Ala Ala Thr Pro Thr Ser Leu Leu Ile Ser Trp Val Tyr
1               5                   10                  15

His Tyr Asp Ala Gln Tyr Arg Ile Thr Tyr Gly Glu Thr Gly Gly Asn
                20                  25                  30

Ser Pro Val Gln Glu Phe Thr Val Pro Asp Gln Lys Ala Thr Ile Ser
            35                  40                  45

Gly Leu Lys Pro Gly Val Asp Tyr Thr Ile Thr Val Tyr Ala Leu Ser
        50                  55                  60

Glu Ala His His Lys Arg Asp Ser Ile Ser Ile Asn Tyr Arg Thr
65                  70                  75

<210> SEQ ID NO 245
<211> LENGTH: 7
<212> TYPE: PRT
<213> ORGANISM: Artificial Sequence
<220> FEATURE:
<223> OTHER INFORMATION: Synthetic: ATI_1421_E03 BC loop

<400> SEQUENCE: 245

Val Tyr His Tyr Asp Ala Gln
1               5

<210> SEQ ID NO 246
<211> LENGTH: 4
<212> TYPE: PRT
<213> ORGANISM: Artificial Sequence
```

<220> FEATURE:
<223> OTHER INFORMATION: Synthetic: ATI_1421_E03 DE loop

<400> SEQUENCE: 246

Pro Asp Gln Lys
1

<210> SEQ ID NO 247
<211> LENGTH: 10
<212> TYPE: PRT
<213> ORGANISM: Artificial Sequence
<220> FEATURE:
<223> OTHER INFORMATION: Synthetic: ATI_1421_E03 FG loop

<400> SEQUENCE: 247

Leu Ser Glu Ala His His Lys Arg Asp Ser
1               5                   10

<210> SEQ ID NO 248
<211> LENGTH: 94
<212> TYPE: PRT
<213> ORGANISM: Artificial Sequence
<220> FEATURE:
<223> OTHER INFORMATION: Synthetic: ATI_1421_E03 w/ N leader

<400> SEQUENCE: 248

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr His His His His His
                85                  90

<210> SEQ ID NO 249
<211> LENGTH: 95
<212> TYPE: PRT
<213> ORGANISM: Artificial Sequence
<220> FEATURE:
<223> OTHER INFORMATION: Synthetic: ATI_1421_E03w/ N leader + his tag

<400> SEQUENCE: 249

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Glu Ile Asp Lys Pro Ser Gln
                85                  90                  95

<210> SEQ ID NO 250

```
<211> LENGTH: 101
<212> TYPE: PRT
<213> ORGANISM: Artificial Sequence
<220> FEATURE:
<223> OTHER INFORMATION: Synthetic: ATI_1421_E03w/ N leader and C tail

<400> SEQUENCE: 250

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Glu Ile Asp Lys Pro Ser Gln His
                85                  90                  95

His His His His His
            100

<210> SEQ ID NO 251
<211> LENGTH: 90
<212> TYPE: PRT
<213> ORGANISM: Artificial Sequence
<220> FEATURE:
<223> OTHER INFORMATION: Synthetic: ATI_1421_E03 w/ N leader and C
      tail + his tag

<400> SEQUENCE: 251

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Pro Cys
                85                  90

<210> SEQ ID NO 252
<211> LENGTH: 96
<212> TYPE: PRT
<213> ORGANISM: Artificial Sequence
<220> FEATURE:
<223> OTHER INFORMATION: Synthetic: ATI_1421_E03 w/ N leader and
      modified C-terminus including PC

<400> SEQUENCE: 252

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
```

```
                    50                  55                  60

Tyr Thr Ile Thr Val Tyr Ala Leu Ser Glu Ala His His Lys Arg Asp
 65                  70                  75                  80

Ser Ile Ser Ile Asn Tyr Arg Thr Pro Cys His His His His His
                     85                  90                  95
```

<210> SEQ ID NO 253
<211> LENGTH: 88
<212> TYPE: PRT
<213> ORGANISM: Artificial Sequence
<220> FEATURE:
<223> OTHER INFORMATION: Synthetic: ATI_1421_E03 w/ N leader and
      modified C-terminus including PC + his tag

<400> SEQUENCE: 253

```
Gly Val Ser Asp Val Pro Arg Asp Leu Glu Val Val Ala Ala Thr Pro
 1               5                   10                  15

Thr Ser Leu Leu Ile Ser Trp Val Tyr His Tyr Asp Ala Gln Tyr Arg
                 20                  25                  30

Ile Thr Tyr Gly Glu Thr Gly Gly Asn Ser Pro Val Gln Glu Phe Thr
             35                  40                  45

Val Pro Asp Gln Lys Ala Thr Ile Ser Gly Leu Lys Pro Gly Val Asp
     50                  55                  60

Tyr Thr Ile Thr Val Tyr Ala Leu Ser Glu Ala His His Lys Arg Asp
 65                  70                  75                  80

Ser Ile Ser Ile Asn Tyr Arg Thr
                 85
```

<210> SEQ ID NO 254
<211> LENGTH: 102
<212> TYPE: PRT
<213> ORGANISM: Artificial Sequence
<220> FEATURE:
<223> OTHER INFORMATION: Synthetic: ATI_1421_E03  full length

<400> SEQUENCE: 254

```
Met Gly Val Ser Asp Val Pro Arg Asp Leu Glu Val Val Ala Ala Thr
 1               5                   10                  15

Pro Thr Ser Leu Leu Ile Ser Trp Val Tyr His Tyr Asp Ala Gln Tyr
                 20                  25                  30

Arg Ile Thr Tyr Gly Glu Thr Gly Gly Asn Ser Pro Val Gln Glu Phe
             35                  40                  45

Thr Val Pro Asp Gln Lys Ala Thr Ile Ser Gly Leu Lys Pro Gly Val
     50                  55                  60

Asp Tyr Thr Ile Thr Val Tyr Ala Leu Ser Glu Ala His His Lys Arg
 65                  70                  75                  80

Asp Ser Ile Ser Ile Asn Tyr Arg Thr Glu Ile Asp Lys Pro Ser Gln
                 85                  90                  95

His His His His His His
            100
```

<210> SEQ ID NO 255
<211> LENGTH: 79
<212> TYPE: PRT
<213> ORGANISM: Artificial Sequence
<220> FEATURE:
<223> OTHER INFORMATION: Synthetic: ATI_1421_E04 core

<400> SEQUENCE: 255

```
Glu Val Val Ala Ala Thr Pro Thr Ser Leu Leu Ile Ser Trp Ser Tyr
```

```
             1               5                  10                 15
           Asn Gly Pro Ile Glu Tyr Arg Ile Thr Tyr Gly Glu Thr Gly Asn
                           20                  25                 30

Ser Pro Val Gln Glu Phe Thr Val Pro Asp Gln Gln Ala Thr Ile Ser
                       35                  40                  45

Gly Leu Lys Pro Gly Val Asp Tyr Thr Ile Thr Val Tyr Ala Leu Glu
               50                  55                  60

Glu Ala His Tyr Ser Arg Gln Ser Ile Ser Ile Asn Tyr Arg Thr
           65                  70                  75
```

<210> SEQ ID NO 256
<211> LENGTH: 7
<212> TYPE: PRT
<213> ORGANISM: Artificial Sequence
<220> FEATURE:
<223> OTHER INFORMATION: Synthetic: ATI_1421_E04 BC loop

<400> SEQUENCE: 256

```
Ser Tyr Asn Gly Pro Ile Glu
1               5
```

<210> SEQ ID NO 257
<211> LENGTH: 4
<212> TYPE: PRT
<213> ORGANISM: Artificial Sequence
<220> FEATURE:
<223> OTHER INFORMATION: Synthetic: ATI_1421_E04 DE loop

<400> SEQUENCE: 257

```
Pro Asp Gln Gln
1
```

<210> SEQ ID NO 258
<211> LENGTH: 10
<212> TYPE: PRT
<213> ORGANISM: Artificial Sequence
<220> FEATURE:
<223> OTHER INFORMATION: Synthetic: ATI_1421_E04 FG loop

<400> SEQUENCE: 258

```
Leu Glu Glu Ala His Tyr Ser Arg Gln Ser
1               5                  10
```

<210> SEQ ID NO 259
<211> LENGTH: 88
<212> TYPE: PRT
<213> ORGANISM: Artificial Sequence
<220> FEATURE:
<223> OTHER INFORMATION: Synthetic: ATI_1421_E04 w/ N leader

<400> SEQUENCE: 259

```
Gly Val Ser Asp Val Pro Arg Asp Leu Glu Val Val Ala Ala Thr Pro
1               5                  10                  15

Thr Ser Leu Leu Ile Ser Trp Ser Tyr Asn Gly Pro Ile Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Gln Ala Thr Ile Ser Gly Leu Lys Pro Gly Val Asp
    50                  55                  60

Tyr Thr Ile Thr Val Tyr Ala Leu Glu Glu Ala His Tyr Ser Arg Gln
65                  70                  75                  80

Ser Ile Ser Ile Asn Tyr Arg Thr
```

<210> SEQ ID NO 260
<211> LENGTH: 94
<212> TYPE: PRT
<213> ORGANISM: Artificial Sequence
<220> FEATURE:
<223> OTHER INFORMATION: Synthetic: ATI_1421_E04 w/ N leader + his tag

<400> SEQUENCE: 260

Gly Val Ser Asp Val Pro Arg Asp Leu Glu Val Val Ala Ala Thr Pro
1               5                   10                  15

Thr Ser Leu Leu Ile Ser Trp Ser Tyr Asn Gly Pro Ile Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Gln Ala Thr Ile Ser Gly Leu Lys Pro Gly Val Asp
    50                  55                  60

Tyr Thr Ile Thr Val Tyr Ala Leu Glu Glu Ala His Tyr Ser Arg Gln
65                  70                  75                  80

Ser Ile Ser Ile Asn Tyr Arg Thr His His His His His
                85                  90

<210> SEQ ID NO 261
<211> LENGTH: 95
<212> TYPE: PRT
<213> ORGANISM: Artificial Sequence
<220> FEATURE:
<223> OTHER INFORMATION: Synthetic: ATI_1421_E04 w/ N leader and C tail

<400> SEQUENCE: 261

Gly Val Ser Asp Val Pro Arg Asp Leu Glu Val Val Ala Ala Thr Pro
1               5                   10                  15

Thr Ser Leu Leu Ile Ser Trp Ser Tyr Asn Gly Pro Ile Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Gln Ala Thr Ile Ser Gly Leu Lys Pro Gly Val Asp
    50                  55                  60

Tyr Thr Ile Thr Val Tyr Ala Leu Glu Glu Ala His Tyr Ser Arg Gln
65                  70                  75                  80

Ser Ile Ser Ile Asn Tyr Arg Thr Glu Ile Asp Lys Pro Ser Gln
                85                  90                  95

<210> SEQ ID NO 262
<211> LENGTH: 101
<212> TYPE: PRT
<213> ORGANISM: Artificial Sequence
<220> FEATURE:
<223> OTHER INFORMATION: Synthetic: ATI_1421_E04 w/ N leader and C
      tail + his tag

<400> SEQUENCE: 262

Gly Val Ser Asp Val Pro Arg Asp Leu Glu Val Val Ala Ala Thr Pro
1               5                   10                  15

Thr Ser Leu Leu Ile Ser Trp Ser Tyr Asn Gly Pro Ile Glu Tyr Arg
            20                  25                  30

Ile Thr Tyr Gly Glu Thr Gly Gly Asn Ser Pro Val Gln Glu Phe Thr
        35                  40                  45

Val Pro Asp Gln Gln Ala Thr Ile Ser Gly Leu Lys Pro Gly Val Asp

-continued

```
                50                  55                  60

Tyr Thr Ile Thr Val Tyr Ala Leu Glu Glu Ala His Tyr Ser Arg Gln
 65                  70                  75                  80

Ser Ile Ser Ile Asn Tyr Arg Thr Glu Ile Asp Lys Pro Ser Gln His
                 85                  90                  95

His His His His His
            100

<210> SEQ ID NO 263
<211> LENGTH: 90
<212> TYPE: PRT
<213> ORGANISM: Artificial Sequence
<220> FEATURE:
<223> OTHER INFORMATION: Synthetic: ATI_1421_E04 w/ N leader and
      modified C-terminus including PC

<400> SEQUENCE: 263

Gly Val Ser Asp Val Pro Arg Asp Leu Glu Val Val Ala Ala Thr Pro
 1               5                  10                  15

Thr Ser Leu Leu Ile Ser Trp Ser Tyr Asn Gly Pro Ile Glu Tyr Arg
                20                  25                  30

Ile Thr Tyr Gly Glu Thr Gly Gly Asn Ser Pro Val Gln Glu Phe Thr
            35                  40                  45

Val Pro Asp Gln Gln Ala Thr Ile Ser Gly Leu Lys Pro Gly Val Asp
     50                  55                  60

Tyr Thr Ile Thr Val Tyr Ala Leu Glu Glu Ala His Tyr Ser Arg Gln
 65                  70                  75                  80

Ser Ile Ser Ile Asn Tyr Arg Thr Pro Cys
                 85                  90

<210> SEQ ID NO 264
<211> LENGTH: 96
<212> TYPE: PRT
<213> ORGANISM: Artificial Sequence
<220> FEATURE:
<223> OTHER INFORMATION: Synthetic: ATI_1421_E04 w/ N leader and
      modified C-terminus including PC + his tag

<400> SEQUENCE: 264

Gly Val Ser Asp Val Pro Arg Asp Leu Glu Val Val Ala Ala Thr Pro
 1               5                  10                  15

Thr Ser Leu Leu Ile Ser Trp Ser Tyr Asn Gly Pro Ile Glu Tyr Arg
                20                  25                  30

Ile Thr Tyr Gly Glu Thr Gly Gly Asn Ser Pro Val Gln Glu Phe Thr
            35                  40                  45

Val Pro Asp Gln Gln Ala Thr Ile Ser Gly Leu Lys Pro Gly Val Asp
     50                  55                  60

Tyr Thr Ile Thr Val Tyr Ala Leu Glu Glu Ala His Tyr Ser Arg Gln
 65                  70                  75                  80

Ser Ile Ser Ile Asn Tyr Arg Thr Pro Cys His His His His His
                 85                  90                  95

<210> SEQ ID NO 265
<211> LENGTH: 102
<212> TYPE: PRT
<213> ORGANISM: Artificial Sequence
<220> FEATURE:
<223> OTHER INFORMATION: Synthetic: ATI_1421_E04 full length

<400> SEQUENCE: 265
```

```
Met Gly Val Ser Asp Val Pro Arg Asp Leu Glu Val Val Ala Ala Thr
1               5                   10                  15

Pro Thr Ser Leu Leu Ile Ser Trp Ser Tyr Asn Gly Pro Ile Glu Tyr
            20                  25                  30

Arg Ile Thr Tyr Gly Glu Thr Gly Asn Ser Pro Val Gln Glu Phe
        35                  40                  45

Thr Val Pro Asp Gln Gln Ala Thr Ile Ser Gly Leu Lys Pro Gly Val
    50                  55                  60

Asp Tyr Thr Ile Thr Val Tyr Ala Leu Glu Ala His Tyr Ser Arg
65                  70                  75                  80

Gln Ser Ile Ser Ile Asn Tyr Arg Thr Glu Ile Asp Lys Pro Ser Gln
                85                  90                  95

His His His His His His
            100
```

<210> SEQ ID NO 266
<211> LENGTH: 79
<212> TYPE: PRT
<213> ORGANISM: Artificial Sequence
<220> FEATURE:
<223> OTHER INFORMATION: Synthetic: ATI_1421_F03 core

<400> SEQUENCE: 266

```
Glu Val Val Ala Ala Thr Pro Thr Ser Leu Leu Ile Ser Trp Ile Ser
1               5                   10                  15

Val Gln Thr Tyr Asp Tyr Arg Ile Thr Tyr Gly Glu Thr Gly Gly Asn
            20                  25                  30

Ser Pro Val Gln Glu Phe Thr Val Pro Asp Gln Ser Ala Thr Ile Ser
            35                  40                  45

Gly Leu Lys Pro Gly Val Asp Tyr Thr Ile Thr Val Tyr Ala Leu Glu
50                  55                  60

Lys Ala His Tyr Tyr Arg Gln Asn Ile Ser Ile Asn Tyr Arg Thr
65                  70                  75
```

<210> SEQ ID NO 267
<211> LENGTH: 7
<212> TYPE: PRT
<213> ORGANISM: Artificial Sequence
<220> FEATURE:
<223> OTHER INFORMATION: Synthetic: ATI_1421_F03 BC loop

<400> SEQUENCE: 267

```
Ile Ser Val Gln Thr Tyr Asp
1               5
```

<210> SEQ ID NO 268
<211> LENGTH: 4
<212> TYPE: PRT
<213> ORGANISM: Artificial Sequence
<220> FEATURE:
<223> OTHER INFORMATION: Synthetic: ATI_1421_F03 DE loop

<400> SEQUENCE: 268

```
Pro Asp Gln Ser
1
```

<210> SEQ ID NO 269
<211> LENGTH: 10
<212> TYPE: PRT
<213> ORGANISM: Artificial Sequence
<220> FEATURE:
<223> OTHER INFORMATION: Synthetic: ATI_1421_F03 FG loop

<400> SEQUENCE: 269

Leu Glu Lys Ala His Tyr Tyr Arg Gln Asn
1               5                   10

<210> SEQ ID NO 270
<211> LENGTH: 88
<212> TYPE: PRT
<213> ORGANISM: Artificial Sequence
<220> FEATURE:
<223> OTHER INFORMATION: Synthetic: ATI_1421_F03 w/ N leader

<400> SEQUENCE: 270

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr
                85

<210> SEQ ID NO 271
<211> LENGTH: 94
<212> TYPE: PRT
<213> ORGANISM: Artificial Sequence
<220> FEATURE:
<223> OTHER INFORMATION: Synthetic: ATI_1421_F03 w/ N leader + his tag

<400> SEQUENCE: 271

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr His His His His His His
                85                  90

<210> SEQ ID NO 272
<211> LENGTH: 95
<212> TYPE: PRT
<213> ORGANISM: Artificial Sequence
<220> FEATURE:
<223> OTHER INFORMATION: Synthetic: ATI_1421_F03 w/ N leader and C tail

<400> SEQUENCE: 272

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Asp Tyr Arg
            20                  25                  30

Ile Thr Tyr Gly Glu Thr Gly Gly Asn Ser Pro Val Gln Glu Phe Thr

```
            35                  40                  45

Val Pro Asp Gln Ser Ala Thr Ile Ser Gly Leu Lys Pro Gly Val Asp
 50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Glu Ile Asp Lys Pro Ser Gln
                85                  90                  95

<210> SEQ ID NO 273
<211> LENGTH: 101
<212> TYPE: PRT
<213> ORGANISM: Artificial Sequence
<220> FEATURE:
<223> OTHER INFORMATION: Synthetic: ATI_1421_F03 w/ N leader and C
      tail + his tag

<400> SEQUENCE: 273

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Asp Tyr Arg
                20                  25                  30

Ile Thr Tyr Gly Glu Thr Gly Gly Asn Ser Pro Val Gln Glu Phe Thr
            35                  40                  45

Val Pro Asp Gln Ser Ala Thr Ile Ser Gly Leu Lys Pro Gly Val Asp
 50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Glu Ile Asp Lys Pro Ser Gln His
                85                  90                  95

His His His His His
            100

<210> SEQ ID NO 274
<211> LENGTH: 90
<212> TYPE: PRT
<213> ORGANISM: Artificial Sequence
<220> FEATURE:
<223> OTHER INFORMATION: Synthetic: ATI_1421_F03 w/ N leader and
      modified C-terminus including PC

<400> SEQUENCE: 274

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Asp Tyr Arg
                20                  25                  30

Ile Thr Tyr Gly Glu Thr Gly Gly Asn Ser Pro Val Gln Glu Phe Thr
            35                  40                  45

Val Pro Asp Gln Ser Ala Thr Ile Ser Gly Leu Lys Pro Gly Val Asp
 50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Pro Cys
                85                  90

<210> SEQ ID NO 275
<211> LENGTH: 96
<212> TYPE: PRT
<213> ORGANISM: Artificial Sequence
<220> FEATURE:
<223> OTHER INFORMATION: Synthetic: ATI_1421_F03 w/ N leader and
``` modified C-terminus including PC + his tag

<400> SEQUENCE: 275

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Pro Cys His His His His His
                85                  90                  95

<210> SEQ ID NO 276
<211> LENGTH: 102
<212> TYPE: PRT
<213> ORGANISM: Artificial Sequence
<220> FEATURE:
<223> OTHER INFORMATION: Synthetic: ATI_1421_F03 full length

<400> SEQUENCE: 276

Met Gly Val Ser Asp Val Pro Arg Asp Leu Glu Val Val Ala Ala Thr
1               5                   10                  15

Pro Thr Ser Leu Leu Ile Ser Trp Ile Ser Val Gln Thr Tyr Asp Tyr
            20                  25                  30

Arg Ile Thr Tyr Gly Glu Thr Gly Gly Asn Ser Pro Val Gln Glu Phe
        35                  40                  45

Thr Val Pro Asp Gln Ser Ala Thr Ile Ser Gly Leu Lys Pro Gly Val
    50                  55                  60

Asp Tyr Thr Ile Thr Val Tyr Ala Leu Glu Lys Ala His Tyr Tyr Arg
65                  70                  75                  80

Gln Asn Ile Ser Ile Asn Tyr Arg Thr Glu Ile Asp Lys Pro Ser Gln
                85                  90                  95

His His His His His His
            100

<210> SEQ ID NO 277
<211> LENGTH: 79
<212> TYPE: PRT
<213> ORGANISM: Artificial Sequence
<220> FEATURE:
<223> OTHER INFORMATION: Synthetic: ATI_1421_F05 core

<400> SEQUENCE: 277

Glu Val Val Ala Ala Thr Pro Thr Ser Leu Leu Ile Ser Trp Leu Ala
1               5                   10                  15

Arg His Asp Ala Arg Tyr Arg Ile Thr Tyr Gly Glu Thr Gly Gly Asn
            20                  25                  30

Ser Pro Val Gln Glu Phe Thr Val Pro Asp Arg Met Ala Thr Ile Ser
        35                  40                  45

Gly Leu Lys Pro Gly Val Asp Tyr Thr Ile Thr Val Tyr Ala Leu Glu
    50                  55                  60

Gln Ala His Tyr Tyr Arg Leu Tyr Ile Ser Ile Asn Tyr Arg Thr
65                  70                  75

<210> SEQ ID NO 278
<211> LENGTH: 7
<212> TYPE: PRT
<213> ORGANISM: Artificial Sequence
<220> FEATURE:
<223> OTHER INFORMATION: Synthetic: ATI_1421_F05 BC loop

<400> SEQUENCE: 278

Leu Ala Arg His Asp Ala Arg
1               5

<210> SEQ ID NO 279
<211> LENGTH: 4
<212> TYPE: PRT
<213> ORGANISM: Artificial Sequence
<220> FEATURE:
<223> OTHER INFORMATION: Synthetic: ATI_1421_F05 DE loop

<400> SEQUENCE: 279

Pro Asp Arg Met
1

<210> SEQ ID NO 280
<211> LENGTH: 10
<212> TYPE: PRT
<213> ORGANISM: Artificial Sequence
<220> FEATURE:
<223> OTHER INFORMATION: Synthetic: ATI_1421_F05 FG loop

<400> SEQUENCE: 280

Leu Glu Gln Ala His Tyr Tyr Arg Leu Tyr
1               5                   10

<210> SEQ ID NO 281
<211> LENGTH: 88
<212> TYPE: PRT
<213> ORGANISM: Artificial Sequence
<220> FEATURE:
<223> OTHER INFORMATION: Synthetic: ATI_1421_F05 w/ N leader

<400> SEQUENCE: 281

Gly Val Ser Asp Val Pro Arg Asp Leu Glu Val Val Ala Ala Thr Pro
1               5                   10                  15

Thr Ser Leu Leu Ile Ser Trp Leu Ala Arg His Asp Ala Arg Tyr Arg
                20                  25                  30

Ile Thr Tyr Gly Glu Thr Gly Gly Asn Ser Pro Val Gln Glu Phe Thr
            35                  40                  45

Val Pro Asp Arg Met Ala Thr Ile Ser Gly Leu Lys Pro Gly Val Asp
        50                  55                  60

Tyr Thr Ile Thr Val Tyr Ala Leu Glu Gln Ala His Tyr Tyr Arg Leu
65                  70                  75                  80

Tyr Ile Ser Ile Asn Tyr Arg Thr
                85

<210> SEQ ID NO 282
<211> LENGTH: 94
<212> TYPE: PRT
<213> ORGANISM: Artificial Sequence
<220> FEATURE:
<223> OTHER INFORMATION: Synthetic: ATI_1421_F05 w/ N leader + his tag

<400> SEQUENCE: 282

Gly Val Ser Asp Val Pro Arg Asp Leu Glu Val Val Ala Ala Thr Pro
1               5                   10                  15

Thr Ser Leu Leu Ile Ser Trp Leu Ala Arg His Asp Ala Arg Tyr Arg
            20                  25                  30

Ile Thr Tyr Gly Glu Thr Gly Gly Asn Ser Pro Val Gln Glu Phe Thr
            35                  40                  45

Val Pro Asp Arg Met Ala Thr Ile Ser Gly Leu Lys Pro Gly Val Asp
    50                  55                  60

Tyr Thr Ile Thr Val Tyr Ala Leu Glu Gln Ala His Tyr Tyr Arg Leu
65                  70                  75                  80

Tyr Ile Ser Ile Asn Tyr Arg Thr His His His His His
            85                  90

<210> SEQ ID NO 283
<211> LENGTH: 95
<212> TYPE: PRT
<213> ORGANISM: Artificial Sequence
<220> FEATURE:
<223> OTHER INFORMATION: Synthetic: ATI_1421_F05 w/ N leader and C tail

<400> SEQUENCE: 283

Gly Val Ser Asp Val Pro Arg Asp Leu Glu Val Val Ala Ala Thr Pro
1               5                   10                  15

Thr Ser Leu Leu Ile Ser Trp Leu Ala Arg His Asp Ala Arg Tyr Arg
            20                  25                  30

Ile Thr Tyr Gly Glu Thr Gly Gly Asn Ser Pro Val Gln Glu Phe Thr
            35                  40                  45

Val Pro Asp Arg Met Ala Thr Ile Ser Gly Leu Lys Pro Gly Val Asp
    50                  55                  60

Tyr Thr Ile Thr Val Tyr Ala Leu Glu Gln Ala His Tyr Tyr Arg Leu
65                  70                  75                  80

Tyr Ile Ser Ile Asn Tyr Arg Thr Glu Ile Asp Lys Pro Ser Gln
            85                  90                  95

<210> SEQ ID NO 284
<211> LENGTH: 101
<212> TYPE: PRT
<213> ORGANISM: Artificial Sequence
<220> FEATURE:
<223> OTHER INFORMATION: Synthetic: ATI_1421_F05 w/ N leader and C
      tail + his tag

<400> SEQUENCE: 284

Gly Val Ser Asp Val Pro Arg Asp Leu Glu Val Val Ala Ala Thr Pro
1               5                   10                  15

Thr Ser Leu Leu Ile Ser Trp Leu Ala Arg His Asp Ala Arg Tyr Arg
            20                  25                  30

Ile Thr Tyr Gly Glu Thr Gly Gly Asn Ser Pro Val Gln Glu Phe Thr
            35                  40                  45

Val Pro Asp Arg Met Ala Thr Ile Ser Gly Leu Lys Pro Gly Val Asp
    50                  55                  60

Tyr Thr Ile Thr Val Tyr Ala Leu Glu Gln Ala His Tyr Tyr Arg Leu
65                  70                  75                  80

Tyr Ile Ser Ile Asn Tyr Arg Thr Glu Ile Asp Lys Pro Ser Gln His
            85                  90                  95

His His His His His
        100

<210> SEQ ID NO 285
<211> LENGTH: 90
<212> TYPE: PRT

<213> ORGANISM: Artificial Sequence
<220> FEATURE:
<223> OTHER INFORMATION: Synthetic: ATI_1421_F05 w/ N leader and
      modified C-terminus including PC

<400> SEQUENCE: 285

Gly Val Ser Asp Val Pro Arg Asp Leu Glu Val Val Ala Ala Thr Pro
1               5                   10                  15

Thr Ser Leu Leu Ile Ser Trp Leu Ala Arg His Asp Ala Arg Tyr Arg
            20                  25                  30

Ile Thr Tyr Gly Glu Thr Gly Gly Asn Ser Pro Val Gln Glu Phe Thr
        35                  40                  45

Val Pro Asp Arg Met Ala Thr Ile Ser Gly Leu Lys Pro Gly Val Asp
    50                  55                  60

Tyr Thr Ile Thr Val Tyr Ala Leu Glu Gln Ala His Tyr Tyr Arg Leu
65                  70                  75                  80

Tyr Ile Ser Ile Asn Tyr Arg Thr Pro Cys
                85                  90

<210> SEQ ID NO 286
<211> LENGTH: 96
<212> TYPE: PRT
<213> ORGANISM: Artificial Sequence
<220> FEATURE:
<223> OTHER INFORMATION: Synthetic: ATI_1421_F05 w/ N leader and
      modified C-terminus including PC + his tag

<400> SEQUENCE: 286

Gly Val Ser Asp Val Pro Arg Asp Leu Glu Val Val Ala Ala Thr Pro
1               5                   10                  15

Thr Ser Leu Leu Ile Ser Trp Leu Ala Arg His Asp Ala Arg Tyr Arg
            20                  25                  30

Ile Thr Tyr Gly Glu Thr Gly Gly Asn Ser Pro Val Gln Glu Phe Thr
        35                  40                  45

Val Pro Asp Arg Met Ala Thr Ile Ser Gly Leu Lys Pro Gly Val Asp
    50                  55                  60

Tyr Thr Ile Thr Val Tyr Ala Leu Glu Gln Ala His Tyr Tyr Arg Leu
65                  70                  75                  80

Tyr Ile Ser Ile Asn Tyr Arg Thr Pro Cys His His His His His His
                85                  90                  95

<210> SEQ ID NO 287
<211> LENGTH: 102
<212> TYPE: PRT
<213> ORGANISM: Artificial Sequence
<220> FEATURE:
<223> OTHER INFORMATION: Synthetic: ATI_1421_F05 full length

<400> SEQUENCE: 287

Met Gly Val Ser Asp Val Pro Arg Asp Leu Glu Val Val Ala Ala Thr
1               5                   10                  15

Pro Thr Ser Leu Leu Ile Ser Trp Leu Ala Arg His Asp Ala Arg Tyr
            20                  25                  30

Arg Ile Thr Tyr Gly Glu Thr Gly Gly Asn Ser Pro Val Gln Glu Phe
        35                  40                  45

Thr Val Pro Asp Arg Met Ala Thr Ile Ser Gly Leu Lys Pro Gly Val
    50                  55                  60

Asp Tyr Thr Ile Thr Val Tyr Ala Leu Glu Gln Ala His Tyr Tyr Arg
65                  70                  75                  80

Leu Tyr Ile Ser Ile Asn Tyr Arg Thr Glu Ile Asp Lys Pro Ser Gln
                85                  90                  95

His His His His His His
            100

<210> SEQ ID NO 288
<211> LENGTH: 82
<212> TYPE: PRT
<213> ORGANISM: Artificial Sequence
<220> FEATURE:
<223> OTHER INFORMATION: Synthetic: ATI_1421_G07 core

<400> SEQUENCE: 288

Glu Val Val Ala Ala Thr Pro Thr Ser Leu Leu Ile Ser Trp His Ser
1               5                   10                  15

Pro Thr Ser Gly Ile Thr Tyr Arg Ile Thr Tyr Gly Glu Thr Gly Gly
            20                  25                  30

Asn Ser Pro Val Gln Glu Phe Thr Val Pro Tyr Asp Pro Ser Ala Thr
        35                  40                  45

Ile Ser Gly Leu Lys Pro Gly Val Asp Tyr Thr Ile Thr Val Tyr Ala
50                  55                  60

Pro Tyr Gly Ser Gln Tyr Tyr Pro Gly Tyr His Ile Ser Ile Asn Tyr
65                  70                  75                  80

Arg Thr

<210> SEQ ID NO 289
<211> LENGTH: 8
<212> TYPE: PRT
<213> ORGANISM: Artificial Sequence
<220> FEATURE:
<223> OTHER INFORMATION: Synthetic: ATI_1421_G07 BC loop

<400> SEQUENCE: 289

His Ser Pro Thr Ser Gly Ile Thr
1               5

<210> SEQ ID NO 290
<211> LENGTH: 5
<212> TYPE: PRT
<213> ORGANISM: Artificial Sequence
<220> FEATURE:
<223> OTHER INFORMATION: Synthetic: ATI_1421_G07 DE loop

<400> SEQUENCE: 290

Pro Tyr Asp Pro Ser
1               5

<210> SEQ ID NO 291
<211> LENGTH: 11
<212> TYPE: PRT
<213> ORGANISM: Artificial Sequence
<220> FEATURE:
<223> OTHER INFORMATION: Synthetic: ATI_1421_G07 FG loop

<400> SEQUENCE: 291

Pro Tyr Gly Ser Gln Tyr Tyr Pro Gly Tyr His
1               5                   10

<210> SEQ ID NO 292
<211> LENGTH: 91
<212> TYPE: PRT
<213> ORGANISM: Artificial Sequence
<220> FEATURE:
<223> OTHER INFORMATION: Synthetic: ATI_1421_G07 w/ N leader

<400> SEQUENCE: 292

Gly Val Ser Asp Val Pro Arg Asp Leu Glu Val Val Ala Ala Thr Pro
1               5                   10                  15

Thr Ser Leu Leu Ile Ser Trp His Ser Pro Thr Ser Gly Ile Thr Tyr
            20                  25                  30

Arg Ile Thr Tyr Gly Glu Thr Gly Gly Asn Ser Pro Val Gln Glu Phe
        35                  40                  45

Thr Val Pro Tyr Asp Pro Ser Ala Thr Ile Ser Gly Leu Lys Pro Gly
    50                  55                  60

Val Asp Tyr Thr Ile Thr Val Tyr Ala Pro Tyr Gly Ser Gln Tyr Tyr
65                  70                  75                  80

Pro Gly Tyr His Ile Ser Ile Asn Tyr Arg Thr
                85                  90

<210> SEQ ID NO 293
<211> LENGTH: 97
<212> TYPE: PRT
<213> ORGANISM: Artificial Sequence
<220> FEATURE:
<223> OTHER INFORMATION: Synthetic: ATI_1421_G07 w/ N leader + his tag

<400> SEQUENCE: 293

Gly Val Ser Asp Val Pro Arg Asp Leu Glu Val Val Ala Ala Thr Pro
1               5                   10                  15

Thr Ser Leu Leu Ile Ser Trp His Ser Pro Thr Ser Gly Ile Thr Tyr
            20                  25                  30

Arg Ile Thr Tyr Gly Glu Thr Gly Gly Asn Ser Pro Val Gln Glu Phe
        35                  40                  45

Thr Val Pro Tyr Asp Pro Ser Ala Thr Ile Ser Gly Leu Lys Pro Gly
    50                  55                  60

Val Asp Tyr Thr Ile Thr Val Tyr Ala Pro Tyr Gly Ser Gln Tyr Tyr
65                  70                  75                  80

Pro Gly Tyr His Ile Ser Ile Asn Tyr Arg Thr His His His His
                85                  90                  95

His

<210> SEQ ID NO 294
<211> LENGTH: 98
<212> TYPE: PRT
<213> ORGANISM: Artificial Sequence
<220> FEATURE:
<223> OTHER INFORMATION: Synthetic: ATI_1421_G07 w/ N leader and C tail

<400> SEQUENCE: 294

Gly Val Ser Asp Val Pro Arg Asp Leu Glu Val Val Ala Ala Thr Pro
1               5                   10                  15

Thr Ser Leu Leu Ile Ser Trp His Ser Pro Thr Ser Gly Ile Thr Tyr
            20                  25                  30

Arg Ile Thr Tyr Gly Glu Thr Gly Gly Asn Ser Pro Val Gln Glu Phe
        35                  40                  45

Thr Val Pro Tyr Asp Pro Ser Ala Thr Ile Ser Gly Leu Lys Pro Gly
    50                  55                  60

Val Asp Tyr Thr Ile Thr Val Tyr Ala Pro Tyr Gly Ser Gln Tyr Tyr
65                  70                  75                  80

Pro Gly Tyr His Ile Ser Ile Asn Tyr Arg Thr Glu Ile Asp Lys Pro
                85                  90                  95

Ser Gln

<210> SEQ ID NO 295
<211> LENGTH: 104
<212> TYPE: PRT
<213> ORGANISM: Artificial Sequence
<220> FEATURE:
<223> OTHER INFORMATION: Synthetic: ATI_1421_G07 w/ N leader and C
      tail + his tag

<400> SEQUENCE: 295

Gly Val Ser Asp Val Pro Arg Asp Leu Glu Val Val Ala Ala Thr Pro
1               5                   10                  15

Thr Ser Leu Leu Ile Ser Trp His Ser Pro Thr Ser Gly Ile Thr Tyr
            20                  25                  30

Arg Ile Thr Tyr Gly Glu Thr Gly Gly Asn Ser Pro Val Gln Glu Phe
        35                  40                  45

Thr Val Pro Tyr Asp Pro Ser Ala Thr Ile Ser Gly Leu Lys Pro Gly
    50                  55                  60

Val Asp Tyr Thr Ile Thr Val Tyr Ala Pro Tyr Gly Ser Gln Tyr Tyr
65                  70                  75                  80

Pro Gly Tyr His Ile Ser Ile Asn Tyr Arg Thr Glu Ile Asp Lys Pro
                85                  90                  95

Ser Gln His His His His His His
            100

<210> SEQ ID NO 296
<211> LENGTH: 93
<212> TYPE: PRT
<213> ORGANISM: Artificial Sequence
<220> FEATURE:
<223> OTHER INFORMATION: Synthetic: ATI_1421_G07 w/ N leader and
      modified C-terminus including PC

<400> SEQUENCE: 296

Gly Val Ser Asp Val Pro Arg Asp Leu Glu Val Val Ala Ala Thr Pro
1               5                   10                  15

Thr Ser Leu Leu Ile Ser Trp His Ser Pro Thr Ser Gly Ile Thr Tyr
            20                  25                  30

Arg Ile Thr Tyr Gly Glu Thr Gly Gly Asn Ser Pro Val Gln Glu Phe
        35                  40                  45

Thr Val Pro Tyr Asp Pro Ser Ala Thr Ile Ser Gly Leu Lys Pro Gly
    50                  55                  60

Val Asp Tyr Thr Ile Thr Val Tyr Ala Pro Tyr Gly Ser Gln Tyr Tyr
65                  70                  75                  80

Pro Gly Tyr His Ile Ser Ile Asn Tyr Arg Thr Pro Cys
                85                  90

<210> SEQ ID NO 297
<211> LENGTH: 99
<212> TYPE: PRT
<213> ORGANISM: Artificial Sequence
<220> FEATURE:
<223> OTHER INFORMATION: Synthetic: ATI_1421_G07 w/ N leader and
      modified C-terminus including PC + his tag

<400> SEQUENCE: 297

Gly Val Ser Asp Val Pro Arg Asp Leu Glu Val Val Ala Ala Thr Pro
1               5                   10                  15

Thr Ser Leu Leu Ile Ser Trp His Ser Pro Thr Ser Gly Ile Thr Tyr
            20                  25                  30

```
Arg Ile Thr Tyr Gly Glu Thr Gly Gly Asn Ser Pro Val Gln Glu Phe
        35                  40                  45

Thr Val Pro Tyr Asp Pro Ser Ala Thr Ile Ser Gly Leu Lys Pro Gly
    50                  55                  60

Val Asp Tyr Thr Ile Thr Val Tyr Ala Pro Tyr Gly Ser Gln Tyr Tyr
65                  70                  75                  80

Pro Gly Tyr His Ile Ser Ile Asn Tyr Arg Thr Pro Cys His His His
                85                  90                  95

His His His
```

<210> SEQ ID NO 298
<211> LENGTH: 105
<212> TYPE: PRT
<213> ORGANISM: Artificial Sequence
<220> FEATURE:
<223> OTHER INFORMATION: Synthetic: ATI_1421_G07 full length

<400> SEQUENCE: 298

```
Met Gly Val Ser Asp Val Pro Arg Asp Leu Glu Val Val Ala Ala Thr
1               5                   10                  15

Pro Thr Ser Leu Leu Ile Ser Trp His Ser Pro Thr Gly Ile Thr
            20                  25                  30

Tyr Arg Ile Thr Tyr Gly Glu Thr Gly Gly Asn Ser Pro Val Gln Glu
            35                  40                  45

Phe Thr Val Pro Tyr Asp Pro Ser Ala Thr Ile Ser Gly Leu Lys Pro
        50                  55                  60

Gly Val Asp Tyr Thr Ile Thr Val Tyr Ala Pro Tyr Gly Ser Gln Tyr
65                  70                  75                  80

Tyr Pro Gly Tyr His Ile Ser Ile Asn Tyr Arg Thr Glu Ile Asp Lys
                85                  90                  95

Pro Ser Gln His His His His His His
            100                 105
```

<210> SEQ ID NO 299
<211> LENGTH: 79
<212> TYPE: PRT
<213> ORGANISM: Artificial Sequence
<220> FEATURE:
<223> OTHER INFORMATION: Synthetic: ATI_1421_H03 core

<400> SEQUENCE: 299

```
Glu Val Val Ala Ala Thr Pro Thr Ser Leu Leu Ile Ser Trp Val Tyr
1               5                   10                  15

His Tyr Asp Ala Gln Tyr Arg Ile Thr Tyr Gly Glu Thr Gly Gly Asn
            20                  25                  30

Ser Pro Val Gln Glu Phe Thr Val Pro Asp Ser Ser Ala Thr Ile Ser
            35                  40                  45

Gly Leu Lys Pro Gly Val Asp Tyr Thr Ile Thr Val Tyr Ala Leu Glu
        50                  55                  60

Gln Ala His Ile Asp Arg Thr Thr Ile Ser Ile Asn Tyr Arg Thr
65                  70                  75
```

<210> SEQ ID NO 300
<211> LENGTH: 7
<212> TYPE: PRT
<213> ORGANISM: Artificial Sequence
<220> FEATURE:
<223> OTHER INFORMATION: Synthetic: ATI_1421_H03 BC loop

```
<400> SEQUENCE: 300

Val Tyr His Tyr Asp Ala Gln
1               5

<210> SEQ ID NO 301
<211> LENGTH: 4
<212> TYPE: PRT
<213> ORGANISM: Artificial Sequence
<220> FEATURE:
<223> OTHER INFORMATION: Synthetic: ATI_1421_H03   DE loop

<400> SEQUENCE: 301

Pro Asp Ser Ser
1

<210> SEQ ID NO 302
<211> LENGTH: 10
<212> TYPE: PRT
<213> ORGANISM: Artificial Sequence
<220> FEATURE:
<223> OTHER INFORMATION: Synthetic: ATI_1421_H03   FG loop

<400> SEQUENCE: 302

Leu Glu Gln Ala His Ile Asp Arg Thr Thr
1               5                   10

<210> SEQ ID NO 303
<211> LENGTH: 88
<212> TYPE: PRT
<213> ORGANISM: Artificial Sequence
<220> FEATURE:
<223> OTHER INFORMATION: Synthetic: ATI_1421_H03   w/ N leader

<400> SEQUENCE: 303

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Ser Ser Ala Thr Ile Ser Gly Leu Lys Pro Gly Val Asp
    50                  55                  60

Tyr Thr Ile Thr Val Tyr Ala Leu Glu Gln Ala His Ile Asp Arg Thr
65                  70                  75                  80

Thr Ile Ser Ile Asn Tyr Arg Thr
                85

<210> SEQ ID NO 304
<211> LENGTH: 94
<212> TYPE: PRT
<213> ORGANISM: Artificial Sequence
<220> FEATURE:
<223> OTHER INFORMATION: Synthetic: ATI_1421_H03   w/ N leader + his tag

<400> SEQUENCE: 304

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Ser Ser Ala Thr Ile Ser Gly Leu Lys Pro Gly Val Asp
```

```
                50                   55                  60
Tyr Thr Ile Thr Val Tyr Ala Leu Glu Gln Ala His Ile Asp Arg Thr
 65                  70                  75                  80

Thr Ile Ser Ile Asn Tyr Arg Thr His His His His His
                 85                  90
```

<210> SEQ ID NO 305
<211> LENGTH: 95
<212> TYPE: PRT
<213> ORGANISM: Artificial Sequence
<220> FEATURE:
<223> OTHER INFORMATION: Synthetic: ATI_1421_H03 w/ N leader and C tail

<400> SEQUENCE: 305

```
Gly Val Ser Asp Val Pro Arg Asp Leu Glu Val Val Ala Ala Thr Pro
 1                   5                  10                  15

Thr Ser Leu Leu Ile Ser Trp Val Tyr His Tyr Asp Ala Gln Tyr Arg
                 20                  25                  30

Ile Thr Tyr Gly Glu Thr Gly Gly Asn Ser Pro Val Gln Glu Phe Thr
             35                  40                  45

Val Pro Asp Ser Ser Ala Thr Ile Ser Gly Leu Lys Pro Gly Val Asp
     50                  55                  60

Tyr Thr Ile Thr Val Tyr Ala Leu Glu Gln Ala His Ile Asp Arg Thr
 65                  70                  75                  80

Thr Ile Ser Ile Asn Tyr Arg Thr Glu Ile Asp Lys Pro Ser Gln
                 85                  90                  95
```

<210> SEQ ID NO 306
<211> LENGTH: 101
<212> TYPE: PRT
<213> ORGANISM: Artificial Sequence
<220> FEATURE:
<223> OTHER INFORMATION: Synthetic: ATI_1421_H03 w/ N leader and C
      tail + his tag

<400> SEQUENCE: 306

```
Gly Val Ser Asp Val Pro Arg Asp Leu Glu Val Val Ala Ala Thr Pro
 1                   5                  10                  15

Thr Ser Leu Leu Ile Ser Trp Val Tyr His Tyr Asp Ala Gln Tyr Arg
                 20                  25                  30

Ile Thr Tyr Gly Glu Thr Gly Gly Asn Ser Pro Val Gln Glu Phe Thr
             35                  40                  45

Val Pro Asp Ser Ser Ala Thr Ile Ser Gly Leu Lys Pro Gly Val Asp
     50                  55                  60

Tyr Thr Ile Thr Val Tyr Ala Leu Glu Gln Ala His Ile Asp Arg Thr
 65                  70                  75                  80

Thr Ile Ser Ile Asn Tyr Arg Thr Glu Ile Asp Lys Pro Ser Gln His
                 85                  90                  95

His His His His His
            100
```

<210> SEQ ID NO 307
<211> LENGTH: 90
<212> TYPE: PRT
<213> ORGANISM: Artificial Sequence
<220> FEATURE:
<223> OTHER INFORMATION: Synthetic: ATI_1421_H03 w/ N leader and
      modified C-terminus including PC

<400> SEQUENCE: 307

-continued

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
            35                  40                  45

Val Pro Asp Ser Ser Ala Thr Ile Ser Gly Leu Lys Pro Gly Val Asp
50                  55                  60

Tyr Thr Ile Thr Val Tyr Ala Leu Glu Gln Ala His Ile Asp Arg Thr
65                  70                  75                  80

Thr Ile Ser Ile Asn Tyr Arg Thr Pro Cys
            85                  90

<210> SEQ ID NO 308
<211> LENGTH: 96
<212> TYPE: PRT
<213> ORGANISM: Artificial Sequence
<220> FEATURE:
<223> OTHER INFORMATION: Synthetic: ATI_1421_H03 w/ N leader and
      modified C-terminus including PC + his tag

<400> SEQUENCE: 308

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
            35                  40                  45

Val Pro Asp Ser Ser Ala Thr Ile Ser Gly Leu Lys Pro Gly Val Asp
50                  55                  60

Tyr Thr Ile Thr Val Tyr Ala Leu Glu Gln Ala His Ile Asp Arg Thr
65                  70                  75                  80

Thr Ile Ser Ile Asn Tyr Arg Thr Pro Cys His His His His His
            85                  90                  95

<210> SEQ ID NO 309
<211> LENGTH: 102
<212> TYPE: PRT
<213> ORGANISM: Artificial Sequence
<220> FEATURE:
<223> OTHER INFORMATION: Synthetic: ATI_1421_H03 full length

<400> SEQUENCE: 309

Met Gly Val Ser Asp Val Pro Arg Asp Leu Glu Val Val Ala Ala Thr
1               5                   10                  15

Pro Thr Ser Leu Leu Ile Ser Trp Val Tyr His Tyr Asp Ala Gln Tyr
            20                  25                  30

Arg Ile Thr Tyr Gly Glu Thr Gly Gly Asn Ser Pro Val Gln Glu Phe
            35                  40                  45

Thr Val Pro Asp Ser Ser Ala Thr Ile Ser Gly Leu Lys Pro Gly Val
    50                  55                  60

Asp Tyr Thr Ile Thr Val Tyr Ala Leu Glu Gln Ala His Ile Asp Arg
65                  70                  75                  80

Thr Thr Ile Ser Ile Asn Tyr Arg Thr Glu Ile Asp Lys Pro Ser Gln
            85                  90                  95

His His His His His His
            100

-continued

```
<210> SEQ ID NO 310
<211> LENGTH: 79
<212> TYPE: PRT
<213> ORGANISM: Artificial Sequence
<220> FEATURE:
<223> OTHER INFORMATION: Synthetic: ATI_1421_H05 core

<400> SEQUENCE: 310

Glu Val Val Ala Ala Thr Pro Thr Ser Leu Leu Ile Ser Trp Thr Ser
1               5                   10                  15

Val Leu Leu Lys Asp Tyr Arg Ile Thr Tyr Gly Glu Thr Gly Gly Asn
            20                  25                  30

Ser Pro Val Gln Glu Phe Thr Val Pro Asp Gln His Ala Thr Ile Ser
        35                  40                  45

Gly Leu Lys Pro Gly Val Asp Tyr Thr Ile Thr Val Tyr Ala Leu Gln
    50                  55                  60

Asn Ala His His Glu Arg Leu Tyr Ile Ser Ile Asn Tyr Arg Thr
65                  70                  75

<210> SEQ ID NO 311
<211> LENGTH: 7
<212> TYPE: PRT
<213> ORGANISM: Artificial Sequence
<220> FEATURE:
<223> OTHER INFORMATION: Synthetic: ATI_1421_H05 BC loop

<400> SEQUENCE: 311

Thr Ser Val Leu Leu Lys Asp
1               5

<210> SEQ ID NO 312
<211> LENGTH: 4
<212> TYPE: PRT
<213> ORGANISM: Artificial Sequence
<220> FEATURE:
<223> OTHER INFORMATION: Synthetic: ATI_1421_H05 DE loop

<400> SEQUENCE: 312

Pro Asp Gln His
1

<210> SEQ ID NO 313
<211> LENGTH: 10
<212> TYPE: PRT
<213> ORGANISM: Artificial Sequence
<220> FEATURE:
<223> OTHER INFORMATION: Synthetic: ATI_1421_H05 FG loop

<400> SEQUENCE: 313

Leu Gln Asn Ala His His Glu Arg Leu Tyr
1               5                   10

<210> SEQ ID NO 314
<211> LENGTH: 88
<212> TYPE: PRT
<213> ORGANISM: Artificial Sequence
<220> FEATURE:
<223> OTHER INFORMATION: Synthetic: ATI_1421_H05 w/ N leader

<400> SEQUENCE: 314

Gly Val Ser Asp Val Pro Arg Asp Leu Glu Val Val Ala Ala Thr Pro
1               5                   10                  15

Thr Ser Leu Leu Ile Ser Trp Thr Ser Val Leu Leu Lys Asp Tyr Arg
            20                  25                  30
```

Ile Thr Tyr Gly Glu Thr Gly Asn Ser Pro Val Gln Glu Phe Thr
          35                  40                  45

Val Pro Asp Gln His Ala Thr Ile Ser Gly Leu Lys Pro Gly Val Asp
 50                      55                  60

Tyr Thr Ile Thr Val Tyr Ala Leu Gln Asn Ala His His Glu Arg Leu
 65                  70                  75                  80

Tyr Ile Ser Ile Asn Tyr Arg Thr
                85

<210> SEQ ID NO 315
<211> LENGTH: 94
<212> TYPE: PRT
<213> ORGANISM: Artificial Sequence
<220> FEATURE:
<223> OTHER INFORMATION: Synthetic: ATI_1421_H05 w/ N leader + his tag

<400> SEQUENCE: 315

Gly Val Ser Asp Val Pro Arg Asp Leu Glu Val Val Ala Ala Thr Pro
 1               5                  10                  15

Thr Ser Leu Leu Ile Ser Trp Thr Ser Val Leu Leu Lys Asp Tyr Arg
            20                  25                  30

Ile Thr Tyr Gly Glu Thr Gly Gly Asn Ser Pro Val Gln Glu Phe Thr
          35                  40                  45

Val Pro Asp Gln His Ala Thr Ile Ser Gly Leu Lys Pro Gly Val Asp
 50                      55                  60

Tyr Thr Ile Thr Val Tyr Ala Leu Gln Asn Ala His His Glu Arg Leu
 65                  70                  75                  80

Tyr Ile Ser Ile Asn Tyr Arg Thr His His His His His His
                85                      90

<210> SEQ ID NO 316
<211> LENGTH: 95
<212> TYPE: PRT
<213> ORGANISM: Artificial Sequence
<220> FEATURE:
<223> OTHER INFORMATION: Synthetic: ATI_1421_H05 w/ N leader and C tail

<400> SEQUENCE: 316

Gly Val Ser Asp Val Pro Arg Asp Leu Glu Val Val Ala Ala Thr Pro
 1               5                  10                  15

Thr Ser Leu Leu Ile Ser Trp Thr Ser Val Leu Leu Lys Asp Tyr Arg
            20                  25                  30

Ile Thr Tyr Gly Glu Thr Gly Gly Asn Ser Pro Val Gln Glu Phe Thr
          35                  40                  45

Val Pro Asp Gln His Ala Thr Ile Ser Gly Leu Lys Pro Gly Val Asp
 50                      55                  60

Tyr Thr Ile Thr Val Tyr Ala Leu Gln Asn Ala His His Glu Arg Leu
 65                  70                  75                  80

Tyr Ile Ser Ile Asn Tyr Arg Thr Glu Ile Asp Lys Pro Ser Gln
                85                      90                  95

<210> SEQ ID NO 317
<211> LENGTH: 101
<212> TYPE: PRT
<213> ORGANISM: Artificial Sequence
<220> FEATURE:
<223> OTHER INFORMATION: Synthetic: ATI_1421_H05 w/ N leader and C
      tail + his tag

<400> SEQUENCE: 317

```
Gly Val Ser Asp Val Pro Arg Asp Leu Glu Val Val Ala Ala Thr Pro
1               5                   10                  15

Thr Ser Leu Leu Ile Ser Trp Thr Ser Val Leu Leu Lys Asp Tyr Arg
            20                  25                  30

Ile Thr Tyr Gly Glu Thr Gly Gly Asn Ser Pro Val Gln Glu Phe Thr
        35                  40                  45

Val Pro Asp Gln His Ala Thr Ile Ser Gly Leu Lys Pro Gly Val Asp
    50                  55                  60

Tyr Thr Ile Thr Val Tyr Ala Leu Gln Asn Ala His His Glu Arg Leu
65                  70                  75                  80

Tyr Ile Ser Ile Asn Tyr Arg Thr Glu Ile Asp Lys Pro Ser Gln His
                85                  90                  95

His His His His His
            100
```

<210> SEQ ID NO 318
<211> LENGTH: 90
<212> TYPE: PRT
<213> ORGANISM: Artificial Sequence
<220> FEATURE:
<223> OTHER INFORMATION: Synthetic: ATI_1421_H05 w/ N leader and
      modified C-terminus including PC

<400> SEQUENCE: 318

```
Gly Val Ser Asp Val Pro Arg Asp Leu Glu Val Val Ala Ala Thr Pro
1               5                   10                  15

Thr Ser Leu Leu Ile Ser Trp Thr Ser Val Leu Leu Lys Asp Tyr Arg
            20                  25                  30

Ile Thr Tyr Gly Glu Thr Gly Gly Asn Ser Pro Val Gln Glu Phe Thr
        35                  40                  45

Val Pro Asp Gln His Ala Thr Ile Ser Gly Leu Lys Pro Gly Val Asp
    50                  55                  60

Tyr Thr Ile Thr Val Tyr Ala Leu Gln Asn Ala His His Glu Arg Leu
65                  70                  75                  80

Tyr Ile Ser Ile Asn Tyr Arg Thr Pro Cys
                85                  90
```

<210> SEQ ID NO 319
<211> LENGTH: 96
<212> TYPE: PRT
<213> ORGANISM: Artificial Sequence
<220> FEATURE:
<223> OTHER INFORMATION: Synthetic: ATI_1421_H05 w/ N leader and
      modified C-terminus including PC + his tag

<400> SEQUENCE: 319

```
Gly Val Ser Asp Val Pro Arg Asp Leu Glu Val Val Ala Ala Thr Pro
1               5                   10                  15

Thr Ser Leu Leu Ile Ser Trp Thr Ser Val Leu Leu Lys Asp Tyr Arg
            20                  25                  30

Ile Thr Tyr Gly Glu Thr Gly Gly Asn Ser Pro Val Gln Glu Phe Thr
        35                  40                  45

Val Pro Asp Gln His Ala Thr Ile Ser Gly Leu Lys Pro Gly Val Asp
    50                  55                  60

Tyr Thr Ile Thr Val Tyr Ala Leu Gln Asn Ala His His Glu Arg Leu
65                  70                  75                  80

Tyr Ile Ser Ile Asn Tyr Arg Thr Pro Cys His His His His His
                85                  90                  95
```

<210> SEQ ID NO 320
<211> LENGTH: 102
<212> TYPE: PRT
<213> ORGANISM: Artificial Sequence
<220> FEATURE:
<223> OTHER INFORMATION: Synthetic: ATI_1421_H05 full length

<400> SEQUENCE: 320

```
Met Gly Val Ser Asp Val Pro Arg Asp Leu Glu Val Val Ala Ala Thr
1               5                   10                  15

Pro Thr Ser Leu Leu Ile Ser Trp Thr Ser Val Leu Leu Lys Asp Tyr
            20                  25                  30

Arg Ile Thr Tyr Gly Glu Thr Gly Gly Asn Ser Pro Val Gln Glu Phe
        35                  40                  45

Thr Val Pro Asp Gln His Ala Thr Ile Ser Gly Leu Lys Pro Gly Val
    50                  55                  60

Asp Tyr Thr Ile Thr Val Tyr Ala Leu Gln Asn Ala His His Glu Arg
65                  70                  75                  80

Leu Tyr Ile Ser Ile Asn Tyr Arg Thr Glu Ile Asp Lys Pro Ser Gln
                85                  90                  95

His His His His His His
            100
```

<210> SEQ ID NO 321
<211> LENGTH: 79
<212> TYPE: PRT
<213> ORGANISM: Artificial Sequence
<220> FEATURE:
<223> OTHER INFORMATION: Synthetic: ATI_1422_E06 core

<400> SEQUENCE: 321

```
Glu Val Val Ala Ala Thr Pro Thr Ser Leu Leu Ile Ser Trp Leu Pro
1               5                   10                  15

Ser Tyr Tyr Ile Thr Tyr Arg Ile Thr Tyr Gly Glu Thr Gly Gly Asn
            20                  25                  30

Ser Pro Val Gln Glu Phe Thr Val Ser Lys Asp Leu Ala Thr Ile Ser
        35                  40                  45

Gly Leu Lys Pro Gly Val Asp Tyr Thr Ile Thr Val Tyr Ala Phe Asn
    50                  55                  60

Gly Ser Ser Tyr Tyr Thr Phe Gly Ile Ser Ile Asn Tyr Arg Thr
65                  70                  75
```

<210> SEQ ID NO 322
<211> LENGTH: 7
<212> TYPE: PRT
<213> ORGANISM: Artificial Sequence
<220> FEATURE:
<223> OTHER INFORMATION: Synthetic: ATI_1422_E06 BC loop

<400> SEQUENCE: 322

```
Leu Pro Ser Tyr Tyr Ile Thr
1               5
```

<210> SEQ ID NO 323
<211> LENGTH: 4
<212> TYPE: PRT
<213> ORGANISM: Artificial Sequence
<220> FEATURE:
<223> OTHER INFORMATION: Synthetic: ATI_1422_E06 DE loop

<400> SEQUENCE: 323

Ser Lys Asp Leu
1

<210> SEQ ID NO 324
<211> LENGTH: 10
<212> TYPE: PRT
<213> ORGANISM: Artificial Sequence
<220> FEATURE:
<223> OTHER INFORMATION: Synthetic: ATI_1422_E06 FG loop

<400> SEQUENCE: 324

Phe Asn Gly Ser Ser Tyr Tyr Thr Phe Gly
1               5                   10

<210> SEQ ID NO 325
<211> LENGTH: 88
<212> TYPE: PRT
<213> ORGANISM: Artificial Sequence
<220> FEATURE:
<223> OTHER INFORMATION: Synthetic: ATI_1422_E06 w/ N leader

<400> SEQUENCE: 325

Gly Val Ser Asp Val Pro Arg Asp Leu Glu Val Val Ala Ala Thr Pro
1               5                   10                  15

Thr Ser Leu Leu Ile Ser Trp Leu Pro Ser Tyr Tyr Ile Thr Tyr Arg
            20                  25                  30

Ile Thr Tyr Gly Glu Thr Gly Gly Asn Ser Pro Val Gln Glu Phe Thr
        35                  40                  45

Val Ser Lys Asp Leu Ala Thr Ile Ser Gly Leu Lys Pro Gly Val Asp
    50                  55                  60

Tyr Thr Ile Thr Val Tyr Ala Phe Asn Gly Ser Ser Tyr Tyr Thr Phe
65                  70                  75                  80

Gly Ile Ser Ile Asn Tyr Arg Thr
                85

<210> SEQ ID NO 326
<211> LENGTH: 101
<212> TYPE: PRT
<213> ORGANISM: Artificial Sequence
<220> FEATURE:
<223> OTHER INFORMATION: Synthetic: ATI_1422_E06 w/ N leader + his tag

<400> SEQUENCE: 326

Gly Val Ser Asp Val Pro Arg Asp Leu Glu Val Val Ala Ala Thr Pro
1               5                   10                  15

Thr Ser Leu Leu Ile Ser Trp Leu Pro Ser Tyr Tyr Ile Thr Tyr Arg
            20                  25                  30

Ile Thr Tyr Gly Glu Thr Gly Gly Asn Ser Pro Val Gln Glu Phe Thr
        35                  40                  45

Val Ser Lys Asp Leu Ala Thr Ile Ser Gly Leu Lys Pro Gly Val Asp
    50                  55                  60

Tyr Thr Ile Thr Val Tyr Ala Phe Asn Gly Ser Ser Tyr Tyr Thr Phe
65                  70                  75                  80

Gly Ile Ser Ile Asn Tyr Arg Thr Glu Ile Asp Lys Pro Ser Gln His
                85                  90                  95

His His His His His
            100

<210> SEQ ID NO 327
<211> LENGTH: 101
<212> TYPE: PRT

<213> ORGANISM: Artificial Sequence
<220> FEATURE:
<223> OTHER INFORMATION: Synthetic: ATI_1422_E06 w/ N leader and C tail

<400> SEQUENCE: 327

Gly Val Ser Asp Val Pro Arg Asp Leu Glu Val Val Ala Ala Thr Pro
1               5                   10                  15

Thr Ser Leu Leu Ile Ser Trp Leu Pro Ser Tyr Tyr Ile Thr Tyr Arg
            20                  25                  30

Ile Thr Tyr Gly Glu Thr Gly Gly Asn Ser Pro Val Gln Glu Phe Thr
        35                  40                  45

Val Ser Lys Asp Leu Ala Thr Ile Ser Gly Leu Lys Pro Gly Val Asp
    50                  55                  60

Tyr Thr Ile Thr Val Tyr Ala Phe Asn Gly Ser Ser Tyr Tyr Thr Phe
65                  70                  75                  80

Gly Ile Ser Ile Asn Tyr Arg Thr Glu Ile Asp Lys Pro Ser Gln His
                85                  90                  95

His His His His
        100

<210> SEQ ID NO 328
<211> LENGTH: 90
<212> TYPE: PRT
<213> ORGANISM: Artificial Sequence
<220> FEATURE:
<223> OTHER INFORMATION: Synthetic: ATI_1422_E06 w/ N leader and C
      tail + his tag

<400> SEQUENCE: 328

Gly Val Ser Asp Val Pro Arg Asp Leu Glu Val Val Ala Ala Thr Pro
1               5                   10                  15

Thr Ser Leu Leu Ile Ser Trp Leu Pro Ser Tyr Tyr Ile Thr Tyr Arg
            20                  25                  30

Ile Thr Tyr Gly Glu Thr Gly Gly Asn Ser Pro Val Gln Glu Phe Thr
        35                  40                  45

Val Ser Lys Asp Leu Ala Thr Ile Ser Gly Leu Lys Pro Gly Val Asp
    50                  55                  60

Tyr Thr Ile Thr Val Tyr Ala Phe Asn Gly Ser Ser Tyr Tyr Thr Phe
65                  70                  75                  80

Gly Ile Ser Ile Asn Tyr Arg Thr Pro Cys
                85                  90

<210> SEQ ID NO 329
<211> LENGTH: 96
<212> TYPE: PRT
<213> ORGANISM: Artificial Sequence
<220> FEATURE:
<223> OTHER INFORMATION: Synthetic: ATI_1422_E06 w/ N leader and
      modified C-terminus including PC

<400> SEQUENCE: 329

Gly Val Ser Asp Val Pro Arg Asp Leu Glu Val Val Ala Ala Thr Pro
1               5                   10                  15

Thr Ser Leu Leu Ile Ser Trp Leu Pro Ser Tyr Tyr Ile Thr Tyr Arg
            20                  25                  30

Ile Thr Tyr Gly Glu Thr Gly Gly Asn Ser Pro Val Gln Glu Phe Thr
        35                  40                  45

Val Ser Lys Asp Leu Ala Thr Ile Ser Gly Leu Lys Pro Gly Val Asp
    50                  55                  60

Tyr Thr Ile Thr Val Tyr Ala Phe Asn Gly Ser Ser Tyr Tyr Thr Phe
65                  70                  75                  80

Gly Ile Ser Ile Asn Tyr Arg Thr Pro Cys His His His His His
                85                  90                  95

<210> SEQ ID NO 330
<211> LENGTH: 101
<212> TYPE: PRT
<213> ORGANISM: Artificial Sequence
<220> FEATURE:
<223> OTHER INFORMATION: Synthetic: ATI_1422_E06 w/ N leader and
      modified C-terminus including PC + his tag

<400> SEQUENCE: 330

Gly Val Ser Asp Val Pro Arg Asp Leu Glu Val Val Ala Ala Thr Pro
1               5                   10                  15

Thr Ser Leu Leu Ile Ser Trp Leu Pro Ser Tyr Tyr Ile Thr Tyr Arg
                20                  25                  30

Ile Thr Tyr Gly Glu Thr Gly Gly Asn Ser Pro Val Gln Glu Phe Thr
            35                  40                  45

Val Ser Lys Asp Leu Ala Thr Ile Ser Gly Leu Lys Pro Gly Val Asp
    50                  55                  60

Tyr Thr Ile Thr Val Tyr Ala Phe Asn Gly Ser Ser Tyr Tyr Thr Phe
65                  70                  75                  80

Gly Ile Ser Ile Asn Tyr Arg Thr Glu Ile Asp Lys Pro Ser Gln His
                85                  90                  95

His His His His His
            100

<210> SEQ ID NO 331
<211> LENGTH: 89
<212> TYPE: PRT
<213> ORGANISM: Artificial Sequence
<220> FEATURE:
<223> OTHER INFORMATION: Synthetic: ATI_1422_E06 full length

<400> SEQUENCE: 331

Met Gly Val Ser Asp Val Pro Arg Asp Leu Glu Val Val Ala Ala Thr
1               5                   10                  15

Pro Thr Ser Leu Leu Ile Ser Trp Leu Pro Ser Tyr Tyr Ile Thr Tyr
                20                  25                  30

Arg Ile Thr Tyr Gly Glu Thr Gly Gly Asn Ser Pro Val Gln Glu Phe
            35                  40                  45

Thr Val Ser Lys Asp Leu Ala Thr Ile Ser Gly Leu Lys Pro Gly Val
    50                  55                  60

Asp Tyr Thr Ile Thr Val Tyr Ala Phe Asn Gly Ser Ser Tyr Tyr Thr
65                  70                  75                  80

Phe Gly Ile Ser Ile Asn Tyr Arg Thr
                85

<210> SEQ ID NO 332
<211> LENGTH: 78
<212> TYPE: PRT
<213> ORGANISM: Artificial Sequence
<220> FEATURE:
<223> OTHER INFORMATION: Synthetic: ATI_1422_F04 core

<400> SEQUENCE: 332

Glu Val Val Ala Ala Thr Pro Thr Ser Leu Leu Ile Ser Trp Ser Ile
1               5                   10                  15

```
Pro Ser Tyr Phe Ile Ser Tyr Arg Ile Thr Tyr Gly Glu Thr Gly Gly
                20                  25                  30

Asn Ser Pro Val Gln Glu Phe Thr Val Tyr Lys Asn Tyr Ala Thr Ile
        35                  40                  45

Ser Gly Leu Lys Pro Gly Val Asp Tyr Thr Ile Thr Val Tyr Ala Ser
50                  55                  60

Glu Gly Ile Met Phe Tyr Asn Ile Ser Ile Asn Tyr Arg Thr
65                  70                  75

<210> SEQ ID NO 333
<211> LENGTH: 8
<212> TYPE: PRT
<213> ORGANISM: Artificial Sequence
<220> FEATURE:
<223> OTHER INFORMATION: Synthetic: ATI_1422_F04 BC loop

<400> SEQUENCE: 333

Ser Ile Pro Ser Tyr Phe Ile Ser
1               5

<210> SEQ ID NO 334
<211> LENGTH: 4
<212> TYPE: PRT
<213> ORGANISM: Artificial Sequence
<220> FEATURE:
<223> OTHER INFORMATION: Synthetic: ATI_1422_F04 DE loop

<400> SEQUENCE: 334

Tyr Lys Asn Tyr
1

<210> SEQ ID NO 335
<211> LENGTH: 8
<212> TYPE: PRT
<213> ORGANISM: Artificial Sequence
<220> FEATURE:
<223> OTHER INFORMATION: Synthetic: ATI_1422_F04 FG loop

<400> SEQUENCE: 335

Ser Glu Gly Ile Met Phe Tyr Asn
1               5

<210> SEQ ID NO 336
<211> LENGTH: 87
<212> TYPE: PRT
<213> ORGANISM: Artificial Sequence
<220> FEATURE:
<223> OTHER INFORMATION: Synthetic: ATI_1422_F04w/ N leader

<400> SEQUENCE: 336

Gly Val Ser Asp Val Pro Arg Asp Leu Glu Val Val Ala Ala Thr Pro
1               5                   10                  15

Thr Ser Leu Leu Ile Ser Trp Ser Ile Pro Ser Tyr Phe Ile Ser Tyr
                20                  25                  30

Arg Ile Thr Tyr Gly Glu Thr Gly Gly Asn Ser Pro Val Gln Glu Phe
            35                  40                  45

Thr Val Tyr Lys Asn Tyr Ala Thr Ile Ser Gly Leu Lys Pro Gly Val
        50                  55                  60

Asp Tyr Thr Ile Thr Val Tyr Ala Ser Glu Gly Ile Met Phe Tyr Asn
65                  70                  75                  80

Ile Ser Ile Asn Tyr Arg Thr
                85
```

```
<210> SEQ ID NO 337
<211> LENGTH: 93
<212> TYPE: PRT
<213> ORGANISM: Artificial Sequence
<220> FEATURE:
<223> OTHER INFORMATION: Synthetic: ATI_1422_F04w/ N leader + his tag

<400> SEQUENCE: 337

Gly Val Ser Asp Val Pro Arg Asp Leu Glu Val Val Ala Ala Thr Pro
1               5                   10                  15

Thr Ser Leu Leu Ile Ser Trp Ser Ile Pro Ser Tyr Phe Ile Ser Tyr
            20                  25                  30

Arg Ile Thr Tyr Gly Glu Thr Gly Gly Asn Ser Pro Val Gln Glu Phe
        35                  40                  45

Thr Val Tyr Lys Asn Tyr Ala Thr Ile Ser Gly Leu Lys Pro Gly Val
    50                  55                  60

Asp Tyr Thr Ile Thr Val Tyr Ala Ser Glu Gly Ile Met Phe Tyr Asn
65                  70                  75                  80

Ile Ser Ile Asn Tyr Arg Thr His His His His His
                85                  90

<210> SEQ ID NO 338
<211> LENGTH: 94
<212> TYPE: PRT
<213> ORGANISM: Artificial Sequence
<220> FEATURE:
<223> OTHER INFORMATION: Synthetic: ATI_1422_F04 w/ N leader and C tail

<400> SEQUENCE: 338

Gly Val Ser Asp Val Pro Arg Asp Leu Glu Val Val Ala Ala Thr Pro
1               5                   10                  15

Thr Ser Leu Leu Ile Ser Trp Ser Ile Pro Ser Tyr Phe Ile Ser Tyr
            20                  25                  30

Arg Ile Thr Tyr Gly Glu Thr Gly Gly Asn Ser Pro Val Gln Glu Phe
        35                  40                  45

Thr Val Tyr Lys Asn Tyr Ala Thr Ile Ser Gly Leu Lys Pro Gly Val
    50                  55                  60

Asp Tyr Thr Ile Thr Val Tyr Ala Ser Glu Gly Ile Met Phe Tyr Asn
65                  70                  75                  80

Ile Ser Ile Asn Tyr Arg Thr Glu Ile Asp Lys Pro Ser Gln
                85                  90

<210> SEQ ID NO 339
<211> LENGTH: 100
<212> TYPE: PRT
<213> ORGANISM: Artificial Sequence
<220> FEATURE:
<223> OTHER INFORMATION: Synthetic: ATI_1422_F04 w/ N leader and C
      tail + his tag

<400> SEQUENCE: 339

Gly Val Ser Asp Val Pro Arg Asp Leu Glu Val Val Ala Ala Thr Pro
1               5                   10                  15

Thr Ser Leu Leu Ile Ser Trp Ser Ile Pro Ser Tyr Phe Ile Ser Tyr
            20                  25                  30

Arg Ile Thr Tyr Gly Glu Thr Gly Gly Asn Ser Pro Val Gln Glu Phe
        35                  40                  45

Thr Val Tyr Lys Asn Tyr Ala Thr Ile Ser Gly Leu Lys Pro Gly Val
    50                  55                  60
```

Asp Tyr Thr Ile Thr Val Tyr Ala Ser Glu Gly Ile Met Phe Tyr Asn
65                  70                  75                  80

Ile Ser Ile Asn Tyr Arg Thr Glu Ile Asp Lys Pro Ser Gln His His
                85                  90                  95

His His His His
            100

<210> SEQ ID NO 340
<211> LENGTH: 89
<212> TYPE: PRT
<213> ORGANISM: Artificial Sequence
<220> FEATURE:
<223> OTHER INFORMATION: Synthetic: ATI_1422_F04 w/ N leader and
      modified C-terminus including PC

<400> SEQUENCE: 340

Gly Val Ser Asp Val Pro Arg Asp Leu Glu Val Val Ala Ala Thr Pro
1               5                   10                  15

Thr Ser Leu Leu Ile Ser Trp Ser Ile Pro Ser Tyr Phe Ile Ser Tyr
                20                  25                  30

Arg Ile Thr Tyr Gly Glu Thr Gly Gly Asn Ser Pro Val Gln Glu Phe
            35                  40                  45

Thr Val Tyr Lys Asn Tyr Ala Thr Ile Ser Gly Leu Lys Pro Gly Val
        50                  55                  60

Asp Tyr Thr Ile Thr Val Tyr Ala Ser Glu Gly Ile Met Phe Tyr Asn
65                  70                  75                  80

Ile Ser Ile Asn Tyr Arg Thr Pro Cys
                85

<210> SEQ ID NO 341
<211> LENGTH: 95
<212> TYPE: PRT
<213> ORGANISM: Artificial Sequence
<220> FEATURE:
<223> OTHER INFORMATION: Synthetic: ATI_1422_F04 w/ N leader and
      modified C-terminus including PC + his tag

<400> SEQUENCE: 341

Gly Val Ser Asp Val Pro Arg Asp Leu Glu Val Val Ala Ala Thr Pro
1               5                   10                  15

Thr Ser Leu Leu Ile Ser Trp Ser Ile Pro Ser Tyr Phe Ile Ser Tyr
                20                  25                  30

Arg Ile Thr Tyr Gly Glu Thr Gly Gly Asn Ser Pro Val Gln Glu Phe
            35                  40                  45

Thr Val Tyr Lys Asn Tyr Ala Thr Ile Ser Gly Leu Lys Pro Gly Val
        50                  55                  60

Asp Tyr Thr Ile Thr Val Tyr Ala Ser Glu Gly Ile Met Phe Tyr Asn
65                  70                  75                  80

Ile Ser Ile Asn Tyr Arg Thr Pro Cys His His His His His
                85                  90                  95

<210> SEQ ID NO 342
<211> LENGTH: 101
<212> TYPE: PRT
<213> ORGANISM: Artificial Sequence
<220> FEATURE:
<223> OTHER INFORMATION: Synthetic: ATI_1422_F04 full length

<400> SEQUENCE: 342

Met Gly Val Ser Asp Val Pro Arg Asp Leu Glu Val Val Ala Ala Thr
1               5                   10                  15

```
Pro Thr Ser Leu Leu Ile Ser Trp Ser Ile Pro Ser Tyr Phe Ile Ser
            20                  25                  30

Tyr Arg Ile Thr Tyr Gly Glu Thr Gly Gly Asn Ser Pro Val Gln Glu
            35                  40                  45

Phe Thr Val Tyr Lys Asn Tyr Ala Thr Ile Ser Gly Leu Lys Pro Gly
 50                  55                  60

Val Asp Tyr Thr Ile Thr Val Tyr Ala Ser Glu Gly Ile Met Phe Tyr
 65                  70                  75                  80

Asn Ile Ser Ile Asn Tyr Arg Thr Glu Ile Asp Lys Pro Ser Gln His
                 85                  90                  95

His His His His His
            100

<210> SEQ ID NO 343
<211> LENGTH: 77
<212> TYPE: PRT
<213> ORGANISM: Artificial Sequence
<220> FEATURE:
<223> OTHER INFORMATION: Synthetic: ATI_1422_F05 core

<400> SEQUENCE: 343

Glu Val Val Ala Ala Thr Pro Thr Ser Leu Leu Ile Ser Trp Pro Tyr
  1               5                  10                  15

Pro Arg Gly Pro Tyr Val Phe Tyr Arg Ile Thr Tyr Gly Glu Thr Gly
            20                  25                  30

Gly Asn Ser Pro Val Gln Glu Phe Thr Val Tyr Pro Gly Gln Ala Thr
            35                  40                  45

Ile Ser Gly Leu Lys Pro Gly Val Asp Tyr Thr Ile Thr Val Tyr Ala
 50                  55                  60

Tyr Thr Ser Gly Tyr Val Ile Ser Ile Asn Tyr Arg Thr
 65                  70                  75

<210> SEQ ID NO 344
<211> LENGTH: 9
<212> TYPE: PRT
<213> ORGANISM: Artificial Sequence
<220> FEATURE:
<223> OTHER INFORMATION: Synthetic: ATI_1422_F05 BC loop

<400> SEQUENCE: 344

Pro Tyr Pro Arg Gly Pro Tyr Val Phe
  1               5

<210> SEQ ID NO 345
<211> LENGTH: 4
<212> TYPE: PRT
<213> ORGANISM: Artificial Sequence
<220> FEATURE:
<223> OTHER INFORMATION: Synthetic: ATI_1422_F05 DE loop

<400> SEQUENCE: 345

Tyr Pro Gly Gln
  1

<210> SEQ ID NO 346
<211> LENGTH: 6
<212> TYPE: PRT
<213> ORGANISM: Artificial Sequence
<220> FEATURE:
<223> OTHER INFORMATION: Synthetic: ATI_1422_F05 FG loop

<400> SEQUENCE: 346
```

Tyr Thr Ser Gly Tyr Val
1               5

<210> SEQ ID NO 347
<211> LENGTH: 86
<212> TYPE: PRT
<213> ORGANISM: Artificial Sequence
<220> FEATURE:
<223> OTHER INFORMATION: Synthetic: ATI_1422_F05 w/ N leader

<400> SEQUENCE: 347

Gly Val Ser Asp Val Pro Arg Asp Leu Glu Val Val Ala Ala Thr Pro
1               5                   10                  15

Thr Ser Leu Leu Ile Ser Trp Pro Tyr Pro Arg Gly Pro Tyr Val Phe
            20                  25                  30

Tyr Arg Ile Thr Tyr Gly Glu Thr Gly Gly Asn Ser Pro Val Gln Glu
        35                  40                  45

Phe Thr Val Tyr Pro Gly Gln Ala Thr Ile Ser Gly Leu Lys Pro Gly
    50                  55                  60

Val Asp Tyr Thr Ile Thr Val Tyr Ala Tyr Thr Ser Gly Tyr Val Ile
65                  70                  75                  80

Ser Ile Asn Tyr Arg Thr
                85

<210> SEQ ID NO 348
<211> LENGTH: 99
<212> TYPE: PRT
<213> ORGANISM: Artificial Sequence
<220> FEATURE:
<223> OTHER INFORMATION: Synthetic: ATI_1422_F05 w/ N leader + his tag

<400> SEQUENCE: 348

Gly Val Ser Asp Val Pro Arg Asp Leu Glu Val Val Ala Ala Thr Pro
1               5                   10                  15

Thr Ser Leu Leu Ile Ser Trp Pro Tyr Pro Arg Gly Pro Tyr Val Phe
            20                  25                  30

Tyr Arg Ile Thr Tyr Gly Glu Thr Gly Gly Asn Ser Pro Val Gln Glu
        35                  40                  45

Phe Thr Val Tyr Pro Gly Gln Ala Thr Ile Ser Gly Leu Lys Pro Gly
    50                  55                  60

Val Asp Tyr Thr Ile Thr Val Tyr Ala Tyr Thr Ser Gly Tyr Val Ile
65                  70                  75                  80

Ser Ile Asn Tyr Arg Thr Glu Ile Asp Lys Pro Ser Gln His His His
                85                  90                  95

His His His

<210> SEQ ID NO 349
<211> LENGTH: 93
<212> TYPE: PRT
<213> ORGANISM: Artificial Sequence
<220> FEATURE:
<223> OTHER INFORMATION: Synthetic: ATI_1422_F05 w/ N leader and C tail

<400> SEQUENCE: 349

Gly Val Ser Asp Val Pro Arg Asp Leu Glu Val Val Ala Ala Thr Pro
1               5                   10                  15

Thr Ser Leu Leu Ile Ser Trp Pro Tyr Pro Arg Gly Pro Tyr Val Phe
            20                  25                  30

Tyr Arg Ile Thr Tyr Gly Glu Thr Gly Gly Asn Ser Pro Val Gln Glu

```
                35                  40                  45
Phe Thr Val Tyr Pro Gly Gln Ala Thr Ile Ser Gly Leu Lys Pro Gly
    50                  55                  60

Val Asp Tyr Thr Ile Thr Val Tyr Ala Tyr Thr Ser Gly Tyr Val Ile
 65                  70                  75                  80

Ser Ile Asn Tyr Arg Thr Glu Ile Asp Lys Pro Ser Gln
                 85                  90

<210> SEQ ID NO 350
<211> LENGTH: 99
<212> TYPE: PRT
<213> ORGANISM: Artificial Sequence
<220> FEATURE:
<223> OTHER INFORMATION: Synthetic: ATI_1422_F05 w/ N leader and C
      tail + his tag

<400> SEQUENCE: 350

Gly Val Ser Asp Val Pro Arg Asp Leu Glu Val Val Ala Ala Thr Pro
 1               5                  10                  15

Thr Ser Leu Leu Ile Ser Trp Pro Tyr Pro Arg Gly Pro Tyr Val Phe
                20                  25                  30

Tyr Arg Ile Thr Tyr Gly Glu Thr Gly Gly Asn Ser Pro Val Gln Glu
            35                  40                  45

Phe Thr Val Tyr Pro Gly Gln Ala Thr Ile Ser Gly Leu Lys Pro Gly
    50                  55                  60

Val Asp Tyr Thr Ile Thr Val Tyr Ala Tyr Thr Ser Gly Tyr Val Ile
 65                  70                  75                  80

Ser Ile Asn Tyr Arg Thr Glu Ile Asp Lys Pro Ser Gln His His His
                 85                  90                  95

His His His

<210> SEQ ID NO 351
<211> LENGTH: 88
<212> TYPE: PRT
<213> ORGANISM: Artificial Sequence
<220> FEATURE:
<223> OTHER INFORMATION: Synthetic: ATI_1422_F05 w/ N leader and
      modified C-terminus including PC

<400> SEQUENCE: 351

Gly Val Ser Asp Val Pro Arg Asp Leu Glu Val Val Ala Ala Thr Pro
 1               5                  10                  15

Thr Ser Leu Leu Ile Ser Trp Pro Tyr Pro Arg Gly Pro Tyr Val Phe
                20                  25                  30

Tyr Arg Ile Thr Tyr Gly Glu Thr Gly Gly Asn Ser Pro Val Gln Glu
            35                  40                  45

Phe Thr Val Tyr Pro Gly Gln Ala Thr Ile Ser Gly Leu Lys Pro Gly
    50                  55                  60

Val Asp Tyr Thr Ile Thr Val Tyr Ala Tyr Thr Ser Gly Tyr Val Ile
 65                  70                  75                  80

Ser Ile Asn Tyr Arg Thr Pro Cys
                 85

<210> SEQ ID NO 352
<211> LENGTH: 94
<212> TYPE: PRT
<213> ORGANISM: Artificial Sequence
<220> FEATURE:
<223> OTHER INFORMATION: Synthetic: ATI_1422_F05 w/ N leader and
      modified C-terminus including PC + his tag
```

<400> SEQUENCE: 352

Gly Val Ser Asp Val Pro Arg Asp Leu Glu Val Val Ala Ala Thr Pro
1               5                   10                  15

Thr Ser Leu Leu Ile Ser Trp Pro Tyr Pro Arg Gly Pro Tyr Val Phe
            20                  25                  30

Tyr Arg Ile Thr Tyr Gly Glu Thr Gly Gly Asn Ser Pro Val Gln Glu
        35                  40                  45

Phe Thr Val Tyr Pro Gly Gln Ala Thr Ile Ser Gly Leu Lys Pro Gly
50                  55                  60

Val Asp Tyr Thr Ile Thr Val Tyr Ala Tyr Thr Ser Gly Tyr Val Ile
65                  70                  75                  80

Ser Ile Asn Tyr Arg Thr Pro Cys His His His His His His
            85                  90

<210> SEQ ID NO 353
<211> LENGTH: 100
<212> TYPE: PRT
<213> ORGANISM: Artificial Sequence
<220> FEATURE:
<223> OTHER INFORMATION: Synthetic: ATI_1422_F05 full length

<400> SEQUENCE: 353

Met Gly Val Ser Asp Val Pro Arg Asp Leu Glu Val Val Ala Ala Thr
1               5                   10                  15

Pro Thr Ser Leu Leu Ile Ser Trp Pro Tyr Pro Arg Gly Pro Tyr Val
            20                  25                  30

Phe Tyr Arg Ile Thr Tyr Gly Glu Thr Gly Gly Asn Ser Pro Val Gln
        35                  40                  45

Glu Phe Thr Val Tyr Pro Gly Gln Ala Thr Ile Ser Gly Leu Lys Pro
    50                  55                  60

Gly Val Asp Tyr Thr Ile Thr Val Tyr Ala Tyr Thr Ser Gly Tyr Val
65                  70                  75                  80

Ile Ser Ile Asn Tyr Arg Thr Glu Ile Asp Lys Pro Ser Gln His His
                85                  90                  95

His His His His
        100

<210> SEQ ID NO 354
<211> LENGTH: 80
<212> TYPE: PRT
<213> ORGANISM: Artificial Sequence
<220> FEATURE:
<223> OTHER INFORMATION: Synthetic: ATI_1422_H04 core

<400> SEQUENCE: 354

Glu Val Val Ala Ala Thr Pro Thr Ser Leu Leu Ile Ser Trp Tyr Leu
1               5                   10                  15

Pro Ser Tyr Tyr Val Gln Tyr Arg Ile Thr Tyr Gly Glu Thr Gly Gly
            20                  25                  30

Asn Ser Pro Val Gln Glu Phe Thr Val Lys Ser Tyr Asn Ala Thr Ile
        35                  40                  45

Ser Gly Leu Lys Pro Gly Val Asp Tyr Thr Ile Thr Val Tyr Ala Arg
    50                  55                  60

Met Gly Val Tyr Tyr Leu Ser Tyr Ser Ile Ser Ile Asn Tyr Arg Thr
65                  70                  75                  80

<210> SEQ ID NO 355

```
<211> LENGTH: 8
<212> TYPE: PRT
<213> ORGANISM: Artificial Sequence
<220> FEATURE:
<223> OTHER INFORMATION: Synthetic: ATI_1422_H04 BC loop

<400> SEQUENCE: 355

Tyr Leu Pro Ser Tyr Tyr Val Gln
1               5

<210> SEQ ID NO 356
<211> LENGTH: 4
<212> TYPE: PRT
<213> ORGANISM: Artificial Sequence
<220> FEATURE:
<223> OTHER INFORMATION: Synthetic: ATI_1422_H04 DE loop

<400> SEQUENCE: 356

Lys Ser Tyr Asn
1

<210> SEQ ID NO 357
<211> LENGTH: 10
<212> TYPE: PRT
<213> ORGANISM: Artificial Sequence
<220> FEATURE:
<223> OTHER INFORMATION: Synthetic: ATI_1422_H04 FG loop

<400> SEQUENCE: 357

Arg Met Gly Val Tyr Tyr Leu Ser Tyr Ser
1               5                   10

<210> SEQ ID NO 358
<211> LENGTH: 89
<212> TYPE: PRT
<213> ORGANISM: Artificial Sequence
<220> FEATURE:
<223> OTHER INFORMATION: Synthetic: ATI_1422_H04 w/ N leader

<400> SEQUENCE: 358

Gly Val Ser Asp Val Pro Arg Asp Leu Glu Val Val Ala Ala Thr Pro
1               5                   10                  15

Thr Ser Leu Leu Ile Ser Trp Tyr Leu Pro Ser Tyr Tyr Val Gln Tyr
            20                  25                  30

Arg Ile Thr Tyr Gly Glu Thr Gly Gly Asn Ser Pro Val Gln Glu Phe
        35                  40                  45

Thr Val Lys Ser Tyr Asn Ala Thr Ile Ser Gly Leu Lys Pro Gly Val
    50                  55                  60

Asp Tyr Thr Ile Thr Val Tyr Ala Arg Met Gly Val Tyr Tyr Leu Ser
65                  70                  75                  80

Tyr Ser Ile Ser Ile Asn Tyr Arg Thr
                85

<210> SEQ ID NO 359
<211> LENGTH: 95
<212> TYPE: PRT
<213> ORGANISM: Artificial Sequence
<220> FEATURE:
<223> OTHER INFORMATION: Synthetic: ATI_1422_H04 w/ N leader + his tag

<400> SEQUENCE: 359

Gly Val Ser Asp Val Pro Arg Asp Leu Glu Val Val Ala Ala Thr Pro
1               5                   10                  15

Thr Ser Leu Leu Ile Ser Trp Tyr Leu Pro Ser Tyr Tyr Val Gln Tyr
```

```
                    20                  25                  30

Arg Ile Thr Tyr Gly Glu Thr Gly Gly Asn Ser Pro Val Gln Glu Phe
            35                  40                  45

Thr Val Lys Ser Tyr Asn Ala Thr Ile Ser Gly Leu Lys Pro Gly Val
        50                  55                  60

Asp Tyr Thr Ile Thr Val Tyr Ala Arg Met Gly Val Tyr Tyr Leu Ser
65                  70                  75                  80

Tyr Ser Ile Ser Ile Asn Tyr Arg Thr His His His His His His
                85                  90                  95

<210> SEQ ID NO 360
<211> LENGTH: 96
<212> TYPE: PRT
<213> ORGANISM: Artificial Sequence
<220> FEATURE:
<223> OTHER INFORMATION: Synthetic: ATI_1422_H04 w/ N leader and C tail

<400> SEQUENCE: 360

Gly Val Ser Asp Val Pro Arg Asp Leu Glu Val Val Ala Ala Thr Pro
1               5                   10                  15

Thr Ser Leu Leu Ile Ser Trp Tyr Leu Pro Ser Tyr Tyr Val Gln Tyr
            20                  25                  30

Arg Ile Thr Tyr Gly Glu Thr Gly Gly Asn Ser Pro Val Gln Glu Phe
        35                  40                  45

Thr Val Lys Ser Tyr Asn Ala Thr Ile Ser Gly Leu Lys Pro Gly Val
    50                  55                  60

Asp Tyr Thr Ile Thr Val Tyr Ala Arg Met Gly Val Tyr Tyr Leu Ser
65                  70                  75                  80

Tyr Ser Ile Ser Ile Asn Tyr Arg Thr Glu Ile Asp Lys Pro Ser Gln
                85                  90                  95

<210> SEQ ID NO 361
<211> LENGTH: 102
<212> TYPE: PRT
<213> ORGANISM: Artificial Sequence
<220> FEATURE:
<223> OTHER INFORMATION: Synthetic: ATI_1422_H04 w/ N leader and C
      tail + his tag

<400> SEQUENCE: 361

Gly Val Ser Asp Val Pro Arg Asp Leu Glu Val Val Ala Ala Thr Pro
1               5                   10                  15

Thr Ser Leu Leu Ile Ser Trp Tyr Leu Pro Ser Tyr Tyr Val Gln Tyr
            20                  25                  30

Arg Ile Thr Tyr Gly Glu Thr Gly Gly Asn Ser Pro Val Gln Glu Phe
        35                  40                  45

Thr Val Lys Ser Tyr Asn Ala Thr Ile Ser Gly Leu Lys Pro Gly Val
    50                  55                  60

Asp Tyr Thr Ile Thr Val Tyr Ala Arg Met Gly Val Tyr Tyr Leu Ser
65                  70                  75                  80

Tyr Ser Ile Ser Ile Asn Tyr Arg Thr Glu Ile Asp Lys Pro Ser Gln
                85                  90                  95

His His His His His His
            100

<210> SEQ ID NO 362
<211> LENGTH: 91
<212> TYPE: PRT
<213> ORGANISM: Artificial Sequence
```

<220> FEATURE:
<223> OTHER INFORMATION: Synthetic: ATI_1422_H04 w/ N leader and
      modified C-terminus including PC

<400> SEQUENCE: 362

Gly Val Ser Asp Val Pro Arg Asp Leu Glu Val Val Ala Ala Thr Pro
1               5                   10                  15

Thr Ser Leu Leu Ile Ser Trp Tyr Leu Pro Ser Tyr Tyr Val Gln Tyr
            20                  25                  30

Arg Ile Thr Tyr Gly Glu Thr Gly Gly Asn Ser Pro Val Gln Glu Phe
        35                  40                  45

Thr Val Lys Ser Tyr Asn Ala Thr Ile Ser Gly Leu Lys Pro Gly Val
    50                  55                  60

Asp Tyr Thr Ile Thr Val Tyr Ala Arg Met Gly Val Tyr Tyr Leu Ser
65                  70                  75                  80

Tyr Ser Ile Ser Ile Asn Tyr Arg Thr Pro Cys
                85                  90

<210> SEQ ID NO 363
<211> LENGTH: 97
<212> TYPE: PRT
<213> ORGANISM: Artificial Sequence
<220> FEATURE:
<223> OTHER INFORMATION: Synthetic: ATI_1422_H04 w/ N leader and
      modified C-terminus including PC + his tag

<400> SEQUENCE: 363

Gly Val Ser Asp Val Pro Arg Asp Leu Glu Val Val Ala Ala Thr Pro
1               5                   10                  15

Thr Ser Leu Leu Ile Ser Trp Tyr Leu Pro Ser Tyr Tyr Val Gln Tyr
            20                  25                  30

Arg Ile Thr Tyr Gly Glu Thr Gly Gly Asn Ser Pro Val Gln Glu Phe
        35                  40                  45

Thr Val Lys Ser Tyr Asn Ala Thr Ile Ser Gly Leu Lys Pro Gly Val
    50                  55                  60

Asp Tyr Thr Ile Thr Val Tyr Ala Arg Met Gly Val Tyr Tyr Leu Ser
65                  70                  75                  80

Tyr Ser Ile Ser Ile Asn Tyr Arg Thr Pro Cys His His His His
                85                  90                  95

His

<210> SEQ ID NO 364
<211> LENGTH: 103
<212> TYPE: PRT
<213> ORGANISM: Artificial Sequence
<220> FEATURE:
<223> OTHER INFORMATION: Synthetic: ATI_1422_H04  full length

<400> SEQUENCE: 364

Met Gly Val Ser Asp Val Pro Arg Asp Leu Glu Val Val Ala Ala Thr
1               5                   10                  15

Pro Thr Ser Leu Leu Ile Ser Trp Tyr Leu Pro Ser Tyr Tyr Val Gln
            20                  25                  30

Tyr Arg Ile Thr Tyr Gly Glu Thr Gly Gly Asn Ser Pro Val Gln Glu
        35                  40                  45

Phe Thr Val Lys Ser Tyr Asn Ala Thr Ile Ser Gly Leu Lys Pro Gly
    50                  55                  60

Val Asp Tyr Thr Ile Thr Val Tyr Ala Arg Met Gly Val Tyr Tyr Leu
65                  70                  75                  80

Ser Tyr Ser Ile Ser Ile Asn Tyr Arg Thr Glu Ile Asp Lys Pro Ser
                85                  90                  95

Gln His His His His His
            100

<210> SEQ ID NO 365
<211> LENGTH: 78
<212> TYPE: PRT
<213> ORGANISM: Artificial Sequence
<220> FEATURE:
<223> OTHER INFORMATION: Synthetic: ATI_1422_H05 core

<400> SEQUENCE: 365

Glu Val Val Ala Ala Thr Pro Thr Ser Leu Leu Ile Ser Trp Gln Gly
1               5                   10                  15

Gln Leu Ser Pro Ser Phe Tyr Arg Ile Thr Tyr Gly Glu Thr Gly Gly
            20                  25                  30

Asn Ser Pro Val Gln Glu Phe Thr Val Ala Gly Met Ala Thr Ile
        35                  40                  45

Ser Gly Leu Lys Pro Gly Val Asp Tyr Thr Ile Thr Val Tyr Ala Thr
    50                  55                  60

Ser Asp Val Tyr Phe Tyr Ser Ile Ser Ile Asn Tyr Arg Thr
65                  70                  75

<210> SEQ ID NO 366
<211> LENGTH: 8
<212> TYPE: PRT
<213> ORGANISM: Artificial Sequence
<220> FEATURE:
<223> OTHER INFORMATION: Synthetic: ATI_1422_H05 BC loop

<400> SEQUENCE: 366

Gln Gly Gln Leu Ser Pro Ser Phe
1               5

<210> SEQ ID NO 367
<211> LENGTH: 4
<212> TYPE: PRT
<213> ORGANISM: Artificial Sequence
<220> FEATURE:
<223> OTHER INFORMATION: Synthetic: ATI_1422_H05 DE loop

<400> SEQUENCE: 367

Val Ala Gly Met
1

<210> SEQ ID NO 368
<211> LENGTH: 8
<212> TYPE: PRT
<213> ORGANISM: Artificial Sequence
<220> FEATURE:
<223> OTHER INFORMATION: Synthetic: ATI_1422_H05 FG loop

<400> SEQUENCE: 368

Thr Ser Asp Val Tyr Phe Tyr Ser
1               5

<210> SEQ ID NO 369
<211> LENGTH: 87
<212> TYPE: PRT
<213> ORGANISM: Artificial Sequence
<220> FEATURE:
<223> OTHER INFORMATION: Synthetic: ATI_1422_H05 w/ N leader

<400> SEQUENCE: 369

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Arg Ile Thr Tyr Gly Glu Thr Gly Gly Asn Ser Pro Val Gln Glu Phe
        35                  40                  45

Thr Val Val Ala Gly Met Ala Thr Ile Ser Gly Leu Lys Pro Gly Val
    50                  55                  60

Asp Tyr Thr Ile Thr Val Tyr Ala Thr Ser Asp Val Tyr Phe Tyr Ser
65                  70                  75                  80

Ile Ser Ile Asn Tyr Arg Thr
                85

<210> SEQ ID NO 370
<211> LENGTH: 93
<212> TYPE: PRT
<213> ORGANISM: Artificial Sequence
<220> FEATURE:
<223> OTHER INFORMATION: Synthetic: ATI_1422_H05 w/ N leader + his tag

<400> SEQUENCE: 370

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Arg Ile Thr Tyr Gly Glu Thr Gly Gly Asn Ser Pro Val Gln Glu Phe
        35                  40                  45

Thr Val Val Ala Gly Met Ala Thr Ile Ser Gly Leu Lys Pro Gly Val
    50                  55                  60

Asp Tyr Thr Ile Thr Val Tyr Ala Thr Ser Asp Val Tyr Phe Tyr Ser
65                  70                  75                  80

Ile Ser Ile Asn Tyr Arg Thr His His His His His His
                85                  90

<210> SEQ ID NO 371
<211> LENGTH: 94
<212> TYPE: PRT
<213> ORGANISM: Artificial Sequence
<220> FEATURE:
<223> OTHER INFORMATION: Synthetic: ATI_1422_H05 w/ N leader and C tail

<400> SEQUENCE: 371

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Arg Ile Thr Tyr Gly Glu Thr Gly Gly Asn Ser Pro Val Gln Glu Phe
        35                  40                  45

Thr Val Val Ala Gly Met Ala Thr Ile Ser Gly Leu Lys Pro Gly Val
    50                  55                  60

Asp Tyr Thr Ile Thr Val Tyr Ala Thr Ser Asp Val Tyr Phe Tyr Ser
65                  70                  75                  80

Ile Ser Ile Asn Tyr Arg Thr Glu Ile Asp Lys Pro Ser Gln
                85                  90

<210> SEQ ID NO 372
<211> LENGTH: 100

<212> TYPE: PRT
<213> ORGANISM: Artificial Sequence
<220> FEATURE:
<223> OTHER INFORMATION: Synthetic: ATI_1422_H05 w/ N leader and C
      tail + his tag

<400> SEQUENCE: 372

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Arg Ile Thr Tyr Gly Glu Thr Gly Gly Asn Ser Pro Val Gln Glu Phe
        35                  40                  45

Thr Val Val Ala Gly Met Ala Thr Ile Ser Gly Leu Lys Pro Gly Val
    50                  55                  60

Asp Tyr Thr Ile Thr Val Tyr Ala Thr Ser Asp Val Tyr Phe Tyr Ser
65                  70                  75                  80

Ile Ser Ile Asn Tyr Arg Thr Glu Ile Asp Lys Pro Ser Gln His His
                85                  90                  95

His His His His
        100

<210> SEQ ID NO 373
<211> LENGTH: 89
<212> TYPE: PRT
<213> ORGANISM: Artificial Sequence
<220> FEATURE:
<223> OTHER INFORMATION: Synthetic: ATI_1422_H05 w/ N leader and
      modified C-terminus including PC

<400> SEQUENCE: 373

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Arg Ile Thr Tyr Gly Glu Thr Gly Gly Asn Ser Pro Val Gln Glu Phe
        35                  40                  45

Thr Val Val Ala Gly Met Ala Thr Ile Ser Gly Leu Lys Pro Gly Val
    50                  55                  60

Asp Tyr Thr Ile Thr Val Tyr Ala Thr Ser Asp Val Tyr Phe Tyr Ser
65                  70                  75                  80

Ile Ser Ile Asn Tyr Arg Thr Pro Cys
                85

<210> SEQ ID NO 374
<211> LENGTH: 95
<212> TYPE: PRT
<213> ORGANISM: Artificial Sequence
<220> FEATURE:
<223> OTHER INFORMATION: Synthetic: ATI_1422_H05 w/ N leader and
      modified C-terminus including PC + his tag

<400> SEQUENCE: 374

Gly Val Ser Asp Val Pro Arg Asp Leu Glu Val Val Ala Ala Thr Pro
1               5                   10                  15

Thr Ser Leu Leu Ile Ser Trp Gln Gly Gln Leu Ser Pro Ser Phe Tyr
            20                  25                  30

Arg Ile Thr Tyr Gly Glu Thr Gly Gly Asn Ser Pro Val Gln Glu Phe
        35                  40                  45

Thr Val Val Ala Gly Met Ala Thr Ile Ser Gly Leu Lys Pro Gly Val

```
                50                    55                   60
Asp Tyr Thr Ile Thr Val Tyr Ala Thr Ser Asp Val Tyr Phe Tyr Ser
65                  70                  75                  80

Ile Ser Ile Asn Tyr Arg Thr Pro Cys His His His His His
                85                  90                  95

<210> SEQ ID NO 375
<211> LENGTH: 101
<212> TYPE: PRT
<213> ORGANISM: Artificial Sequence
<220> FEATURE:
<223> OTHER INFORMATION: Synthetic:  full length

<400> SEQUENCE: 375

Met Gly Val Ser Asp Val Pro Arg Asp Leu Glu Val Val Ala Ala Thr
1               5                   10                  15

Pro Thr Ser Leu Leu Ile Ser Trp Gln Gly Gln Leu Ser Pro Ser Phe
                20                  25                  30

Tyr Arg Ile Thr Tyr Gly Glu Thr Gly Gly Asn Ser Pro Val Gln Glu
            35                  40                  45

Phe Thr Val Val Ala Gly Met Ala Thr Ile Ser Gly Leu Lys Pro Gly
50                  55                  60

Val Asp Tyr Thr Ile Thr Val Tyr Ala Thr Ser Asp Val Tyr Phe Tyr
65                  70                  75                  80

Ser Ile Ser Ile Asn Tyr Arg Thr Glu Ile Asp Lys Pro Ser Gln His
                85                  90                  95

His His His His His
            100

<210> SEQ ID NO 376
<211> LENGTH: 82
<212> TYPE: PRT
<213> ORGANISM: Artificial Sequence
<220> FEATURE:
<223> OTHER INFORMATION: Synthetic: ATI_1422_G05 core

<400> SEQUENCE: 376

Glu Val Val Ala Ala Thr Pro Thr Ser Leu Leu Ile Ser Trp Ile Ala
1               5                   10                  15

Pro Tyr Tyr Ser Val Ile Tyr Arg Ile Thr Tyr Gly Glu Thr Gly Gly
                20                  25                  30

Asn Ser Pro Val Gln Glu Phe Thr Val Thr Gly Ser Gly Tyr Ala Thr
            35                  40                  45

Ile Ser Gly Leu Lys Pro Gly Val Asp Tyr Thr Ile Thr Val Tyr Ala
        50                  55                  60

Thr Tyr Cys Ala Ser Val Ala Ser Tyr Ala Phe Ile Ser Ile Asn Tyr
65                  70                  75                  80

Arg Thr

<210> SEQ ID NO 377
<211> LENGTH: 8
<212> TYPE: PRT
<213> ORGANISM: Artificial Sequence
<220> FEATURE:
<223> OTHER INFORMATION: Synthetic: ATI_1422_G05 BC loop

<400> SEQUENCE: 377

Ile Ala Pro Tyr Tyr Ser Val Ile
1               5
```

<210> SEQ ID NO 378
<211> LENGTH: 5
<212> TYPE: PRT
<213> ORGANISM: Artificial Sequence
<220> FEATURE:
<223> OTHER INFORMATION: Synthetic: ATI_1422_G05 DE loop

<400> SEQUENCE: 378

Thr Gly Ser Gly Tyr
1               5

<210> SEQ ID NO 379
<211> LENGTH: 11
<212> TYPE: PRT
<213> ORGANISM: Artificial Sequence
<220> FEATURE:
<223> OTHER INFORMATION: Synthetic: ATI_1422_G05 FG loop

<400> SEQUENCE: 379

Thr Tyr Cys Ala Ser Val Ala Ser Tyr Ala Phe
1               5                   10

<210> SEQ ID NO 380
<211> LENGTH: 91
<212> TYPE: PRT
<213> ORGANISM: Artificial Sequence
<220> FEATURE:
<223> OTHER INFORMATION: Synthetic: ATI_1422_G05 w/ N leader

<400> SEQUENCE: 380

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Thr Gly Ser Gly Tyr Ala Thr Ile Ser Gly Leu Lys Pro Gly
    50                  55                  60

Val Asp Tyr Thr Ile Thr Val Tyr Ala Thr Tyr Cys Ala Ser Val Ala
65                  70                  75                  80

Ser Tyr Ala Phe Ile Ser Ile Asn Tyr Arg Thr
                85                  90

<210> SEQ ID NO 381
<211> LENGTH: 97
<212> TYPE: PRT
<213> ORGANISM: Artificial Sequence
<220> FEATURE:
<223> OTHER INFORMATION: Synthetic: ATI_1422_G05 w/ N leader + his tag

<400> SEQUENCE: 381

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Thr Gly Ser Gly Tyr Ala Thr Ile Ser Gly Leu Lys Pro Gly
    50                  55                  60

Val Asp Tyr Thr Ile Thr Val Tyr Ala Thr Tyr Cys Ala Ser Val Ala
65                  70                  75                  80

Ser Tyr Ala Phe Ile Ser Ile Asn Tyr Arg Thr His His His His
                85                  90                  95

His

<210> SEQ ID NO 382
<211> LENGTH: 98
<212> TYPE: PRT
<213> ORGANISM: Artificial Sequence
<220> FEATURE:
<223> OTHER INFORMATION: Synthetic: ATI_1422_G05 w/ N leader and C tail

<400> SEQUENCE: 382

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Thr Gly Ser Gly Tyr Ala Thr Ile Ser Gly Leu Lys Pro Gly
    50                  55                  60

Val Asp Tyr Thr Ile Thr Val Tyr Ala Thr Tyr Cys Ala Ser Val Ala
65                  70                  75                  80

Ser Tyr Ala Phe Ile Ser Ile Asn Tyr Arg Thr Glu Ile Asp Lys Pro
                85                  90                  95

Ser Gln

<210> SEQ ID NO 383
<211> LENGTH: 104
<212> TYPE: PRT
<213> ORGANISM: Artificial Sequence
<220> FEATURE:
<223> OTHER INFORMATION: Synthetic: ATI_1422_G05 w/ N leader and C
      tail + his tag

<400> SEQUENCE: 383

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Thr Gly Ser Gly Tyr Ala Thr Ile Ser Gly Leu Lys Pro Gly
    50                  55                  60

Val Asp Tyr Thr Ile Thr Val Tyr Ala Thr Tyr Cys Ala Ser Val Ala
65                  70                  75                  80

Ser Tyr Ala Phe Ile Ser Ile Asn Tyr Arg Thr Glu Ile Asp Lys Pro
                85                  90                  95

Ser Gln His His His His His His
        100

<210> SEQ ID NO 384
<211> LENGTH: 93
<212> TYPE: PRT
<213> ORGANISM: Artificial Sequence
<220> FEATURE:
<223> OTHER INFORMATION: Synthetic: ATI_1422_G05 w/ N leader and
      modified C-terminus including PC

<400> SEQUENCE: 384

Gly Val Ser Asp Val Pro Arg Asp Leu Glu Val Val Ala Ala Thr Pro

```
                1               5                   10                  15
Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
            35                  40                  45

Thr Val Thr Gly Ser Gly Tyr Ala Thr Ile Ser Gly Leu Lys Pro Gly
            50                  55                  60

Val Asp Tyr Thr Ile Thr Val Tyr Ala Thr Tyr Cys Ala Ser Val Ala
 65                 70                  75                  80

Ser Tyr Ala Phe Ile Ser Ile Asn Tyr Arg Thr Pro Cys
                85                  90

<210> SEQ ID NO 385
<211> LENGTH: 99
<212> TYPE: PRT
<213> ORGANISM: Artificial Sequence
<220> FEATURE:
<223> OTHER INFORMATION: Synthetic: ATI_1422_G05 w/ N leader and
      modified C-terminus including PC + his tag

<400> SEQUENCE: 385

Gly Val Ser Asp Val Pro Arg Asp Leu Glu Val Val Ala Ala Thr Pro
 1               5                  10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
            35                  40                  45

Thr Val Thr Gly Ser Gly Tyr Ala Thr Ile Ser Gly Leu Lys Pro Gly
            50                  55                  60

Val Asp Tyr Thr Ile Thr Val Tyr Ala Thr Tyr Cys Ala Ser Val Ala
 65                 70                  75                  80

Ser Tyr Ala Phe Ile Ser Ile Asn Tyr Arg Thr Pro Cys His His His
                85                  90                  95

His His His

<210> SEQ ID NO 386
<211> LENGTH: 105
<212> TYPE: PRT
<213> ORGANISM: Artificial Sequence
<220> FEATURE:
<223> OTHER INFORMATION: Synthetic: ATI_1422_G05 full length

<400> SEQUENCE: 386

Met Gly Val Ser Asp Val Pro Arg Asp Leu Glu Val Val Ala Ala Thr
 1               5                  10                  15

Pro Thr Ser Leu Leu Ile Ser Trp Ile Ala Pro Tyr Tyr Ser Val Ile
            20                  25                  30

Tyr Arg Ile Thr Tyr Gly Glu Thr Gly Gly Asn Ser Pro Val Gln Glu
            35                  40                  45

Phe Thr Val Thr Gly Ser Gly Tyr Ala Thr Ile Ser Gly Leu Lys Pro
            50                  55                  60

Gly Val Asp Tyr Thr Ile Thr Val Tyr Ala Thr Tyr Cys Ala Ser Val
 65                 70                  75                  80

Ala Ser Tyr Ala Phe Ile Ser Ile Asn Tyr Arg Thr Glu Ile Asp Lys
                85                  90                  95

Pro Ser Gln His His His His His
            100                 105
```

<210> SEQ ID NO 387
<211> LENGTH: 82
<212> TYPE: PRT
<213> ORGANISM: Artificial Sequence
<220> FEATURE:
<223> OTHER INFORMATION: Synthetic: ATI_1760_C02 core

<400> SEQUENCE: 387

```
Glu Val Val Ala Ala Thr Pro Thr Ser Leu Leu Ile Ser Trp Ile Ala
1               5                   10                  15

Pro Tyr Tyr Ser Val Ile Tyr Arg Ile Thr Tyr Gly Glu Thr Gly Gly
            20                  25                  30

Asn Ser Pro Val Gln Glu Phe Thr Val Pro Gly Ser Ala Tyr Ala Thr
        35                  40                  45

Ile Ser Gly Leu Lys Pro Gly Val Asp Tyr Thr Ile Thr Val Tyr Ala
    50                  55                  60

Ser Ser Gly Ala Ser Ile Ala Ala Tyr Ala Phe Ile Ser Ile Asn Tyr
65                  70                  75                  80

Arg Thr
```

<210> SEQ ID NO 388
<211> LENGTH: 8
<212> TYPE: PRT
<213> ORGANISM: Artificial Sequence
<220> FEATURE:
<223> OTHER INFORMATION: Synthetic: ATI_1760_C02 BC loop

<400> SEQUENCE: 388

```
Ile Ala Pro Tyr Tyr Ser Val Ile
1               5
```

<210> SEQ ID NO 389
<211> LENGTH: 5
<212> TYPE: PRT
<213> ORGANISM: Artificial Sequence
<220> FEATURE:
<223> OTHER INFORMATION: Synthetic: ATI_1760_C02 DE loop

<400> SEQUENCE: 389

```
Pro Gly Ser Ala Tyr
1               5
```

<210> SEQ ID NO 390
<211> LENGTH: 11
<212> TYPE: PRT
<213> ORGANISM: Artificial Sequence
<220> FEATURE:
<223> OTHER INFORMATION: Synthetic: ATI_1760_C02 FG loop

<400> SEQUENCE: 390

```
Ser Ser Gly Ala Ser Ile Ala Ala Tyr Ala Phe
1               5                   10
```

<210> SEQ ID NO 391
<211> LENGTH: 91
<212> TYPE: PRT
<213> ORGANISM: Artificial Sequence
<220> FEATURE:
<223> OTHER INFORMATION: Synthetic: ATI_1760_C02 w/ N leader

<400> SEQUENCE: 391

```
Gly Val Ser Asp Val Pro Arg Asp Leu Glu Val Val Ala Ala Thr Pro
1               5                   10                  15
```

```
Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Tyr Ala Thr Ile Ser Gly Leu Lys Pro Gly
    50                  55                  60

Val Asp Tyr Thr Ile Thr Val Tyr Ala Ser Ser Gly Ala Ser Ile Ala
65                  70                  75                  80

Ala Tyr Ala Phe Ile Ser Ile Asn Tyr Arg Thr
                85                  90

<210> SEQ ID NO 392
<211> LENGTH: 97
<212> TYPE: PRT
<213> ORGANISM: Artificial Sequence
<220> FEATURE:
<223> OTHER INFORMATION: Synthetic: ATI_1760_C02 w/ N leader + his tag

<400> SEQUENCE: 392

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Tyr Ala Thr Ile Ser Gly Leu Lys Pro Gly
    50                  55                  60

Val Asp Tyr Thr Ile Thr Val Tyr Ala Ser Ser Gly Ala Ser Ile Ala
65                  70                  75                  80

Ala Tyr Ala Phe Ile Ser Ile Asn Tyr Arg Thr His His His His
                85                  90                  95

His

<210> SEQ ID NO 393
<211> LENGTH: 98
<212> TYPE: PRT
<213> ORGANISM: Artificial Sequence
<220> FEATURE:
<223> OTHER INFORMATION: Synthetic: ATI_1760_C02 w/ N leader and C tail

<400> SEQUENCE: 393

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Tyr Ala Thr Ile Ser Gly Leu Lys Pro Gly
    50                  55                  60

Val Asp Tyr Thr Ile Thr Val Tyr Ala Ser Ser Gly Ala Ser Ile Ala
65                  70                  75                  80

Ala Tyr Ala Phe Ile Ser Ile Asn Tyr Arg Thr Glu Ile Asp Lys Pro
                85                  90                  95

Ser Gln

<210> SEQ ID NO 394
<211> LENGTH: 104
<212> TYPE: PRT
```

-continued

```
<213> ORGANISM: Artificial Sequence
<220> FEATURE:
<223> OTHER INFORMATION: Synthetic: ATI_1760_C02 w/ N leader and C
      tail + his tag

<400> SEQUENCE: 394

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Tyr Ala Thr Ile Ser Gly Leu Lys Pro Gly
    50                  55                  60

Val Asp Tyr Thr Ile Thr Val Tyr Ala Ser Ser Gly Ala Ser Ile Ala
65                  70                  75                  80

Ala Tyr Ala Phe Ile Ser Ile Asn Tyr Arg Thr Glu Ile Asp Lys Pro
                85                  90                  95

Ser Gln His His His His His His
            100

<210> SEQ ID NO 395
<211> LENGTH: 93
<212> TYPE: PRT
<213> ORGANISM: Artificial Sequence
<220> FEATURE:
<223> OTHER INFORMATION: Synthetic: ATI_1760_C02 w/ N leader and
      modified C-terminus including PC

<400> SEQUENCE: 395

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Tyr Ala Thr Ile Ser Gly Leu Lys Pro Gly
    50                  55                  60

Val Asp Tyr Thr Ile Thr Val Tyr Ala Ser Ser Gly Ala Ser Ile Ala
65                  70                  75                  80

Ala Tyr Ala Phe Ile Ser Ile Asn Tyr Arg Thr Pro Cys
                85                  90

<210> SEQ ID NO 396
<211> LENGTH: 99
<212> TYPE: PRT
<213> ORGANISM: Artificial Sequence
<220> FEATURE:
<223> OTHER INFORMATION: Synthetic: ATI_1760_C02 w/ N leader and
      modified C-terminus including PC + his tag

<400> SEQUENCE: 396

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Ile Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Tyr Ala Thr Ile Ser Gly Leu Lys Pro Gly
    50                  55                  60
```

Val Asp Tyr Thr Ile Thr Val Tyr Ala Ser Ser Gly Ala Ser Ile Ala
65                  70                  75                  80

Ala Tyr Ala Phe Ile Ser Ile Asn Tyr Arg Thr Pro Cys His His His
                85                  90                  95

His His His

<210> SEQ ID NO 397
<211> LENGTH: 105
<212> TYPE: PRT
<213> ORGANISM: Artificial Sequence
<220> FEATURE:
<223> OTHER INFORMATION: Synthetic: ATI_1760_C02 full length

<400> SEQUENCE: 397

Met Gly Val Ser Asp Val Pro Arg Asp Leu Glu Val Val Ala Ala Thr
1               5                   10                  15

Pro Thr Ser Leu Leu Ile Ser Trp Ile Ala Pro Tyr Tyr Ser Val Ile
                20                  25                  30

Tyr Arg Ile Thr Tyr Gly Glu Thr Gly Gly Asn Ser Pro Val Gln Glu
            35                  40                  45

Phe Thr Val Pro Gly Ser Ala Tyr Ala Thr Ile Ser Gly Leu Lys Pro
    50                  55                  60

Gly Val Asp Tyr Thr Ile Thr Val Tyr Ala Ser Ser Gly Ala Ser Ile
65                  70                  75                  80

Ala Ala Tyr Ala Phe Ile Ser Ile Asn Tyr Arg Thr Glu Ile Asp Lys
                85                  90                  95

Pro Ser Gln His His His His His
            100                 105

<210> SEQ ID NO 398
<211> LENGTH: 82
<212> TYPE: PRT
<213> ORGANISM: Artificial Sequence
<220> FEATURE:
<223> OTHER INFORMATION: Synthetic: ATI_1760_E01 core

<400> SEQUENCE: 398

Glu Val Val Ala Ala Thr Pro Thr Ser Leu Leu Ile Ser Trp Ile Ala
1               5                   10                  15

Pro Tyr Tyr Ser Val Lys Tyr Arg Ile Thr Tyr Gly Glu Thr Gly Gly
                20                  25                  30

Asn Ser Pro Val Gln Glu Phe Thr Val Ala Gly Ala Asp Tyr Ala Thr
            35                  40                  45

Ile Ser Gly Leu Lys Pro Gly Val Asp Tyr Thr Ile Thr Val Tyr Ala
    50                  55                  60

Thr Tyr Gly Ala Ser Ile Ala Ser Tyr Ala Phe Ile Ser Ile Asn Tyr
65                  70                  75                  80

Arg Thr

<210> SEQ ID NO 399
<211> LENGTH: 8
<212> TYPE: PRT
<213> ORGANISM: Artificial Sequence
<220> FEATURE:
<223> OTHER INFORMATION: Synthetic: ATI_1760_E01 BC loop

<400> SEQUENCE: 399

Ile Ala Pro Tyr Tyr Ser Val Lys
1               5

-continued

<210> SEQ ID NO 400
<211> LENGTH: 5
<212> TYPE: PRT
<213> ORGANISM: Artificial Sequence
<220> FEATURE:
<223> OTHER INFORMATION: Synthetic: ATI_1760_E01 DE loop

<400> SEQUENCE: 400

Ala Gly Ala Asp Tyr
1               5

<210> SEQ ID NO 401
<211> LENGTH: 11
<212> TYPE: PRT
<213> ORGANISM: Artificial Sequence
<220> FEATURE:
<223> OTHER INFORMATION: Synthetic: ATI_1760_E01 FG loop

<400> SEQUENCE: 401

Thr Tyr Gly Ala Ser Ile Ala Ser Tyr Ala Phe
1               5                   10

<210> SEQ ID NO 402
<211> LENGTH: 91
<212> TYPE: PRT
<213> ORGANISM: Artificial Sequence
<220> FEATURE:
<223> OTHER INFORMATION: Synthetic: ATI_1760_E01 w/ N leader

<400> SEQUENCE: 402

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Lys Tyr
            20                  25                  30

Arg Ile Thr Tyr Gly Glu Thr Gly Gly Asn Ser Pro Val Gln Glu Phe
        35                  40                  45

Thr Val Ala Gly Ala Asp Tyr Ala Thr Ile Ser Gly Leu Lys Pro Gly
    50                  55                  60

Val Asp Tyr Thr Ile Thr Val Tyr Ala Thr Tyr Gly Ala Ser Ile Ala
65                  70                  75                  80

Ser Tyr Ala Phe Ile Ser Ile Asn Tyr Arg Thr
                85                  90

<210> SEQ ID NO 403
<211> LENGTH: 97
<212> TYPE: PRT
<213> ORGANISM: Artificial Sequence
<220> FEATURE:
<223> OTHER INFORMATION: Synthetic: ATI_1760_E01 w/ N leader + his tag

<400> SEQUENCE: 403

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Lys Tyr
            20                  25                  30

Arg Ile Thr Tyr Gly Glu Thr Gly Gly Asn Ser Pro Val Gln Glu Phe
        35                  40                  45

Thr Val Ala Gly Ala Asp Tyr Ala Thr Ile Ser Gly Leu Lys Pro Gly
    50                  55                  60

Val Asp Tyr Thr Ile Thr Val Tyr Ala Thr Tyr Gly Ala Ser Ile Ala
65                  70                  75                  80

Ser Tyr Ala Phe Ile Ser Ile Asn Tyr Arg Thr His His His His
                85                  90                  95
His

<210> SEQ ID NO 404
<211> LENGTH: 98
<212> TYPE: PRT
<213> ORGANISM: Artificial Sequence
<220> FEATURE:
<223> OTHER INFORMATION: Synthetic: ATI_1760_E01 w/ N leader and C tail

<400> SEQUENCE: 404

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Lys Tyr
            20                  25                  30

Arg Ile Thr Tyr Gly Glu Thr Gly Gly Asn Ser Pro Val Gln Glu Phe
        35                  40                  45

Thr Val Ala Gly Ala Asp Tyr Ala Thr Ile Ser Gly Leu Lys Pro Gly
    50                  55                  60

Val Asp Tyr Thr Ile Thr Val Tyr Ala Thr Tyr Gly Ala Ser Ile Ala
65                  70                  75                  80

Ser Tyr Ala Phe Ile Ser Ile Asn Tyr Arg Thr Glu Ile Asp Lys Pro
                85                  90                  95

Ser Gln

<210> SEQ ID NO 405
<211> LENGTH: 104
<212> TYPE: PRT
<213> ORGANISM: Artificial Sequence
<220> FEATURE:
<223> OTHER INFORMATION: Synthetic: ATI_1760_E01 w/ N leader and C
      tail + his tag

<400> SEQUENCE: 405

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Lys Tyr
            20                  25                  30

Arg Ile Thr Tyr Gly Glu Thr Gly Gly Asn Ser Pro Val Gln Glu Phe
        35                  40                  45

Thr Val Ala Gly Ala Asp Tyr Ala Thr Ile Ser Gly Leu Lys Pro Gly
    50                  55                  60

Val Asp Tyr Thr Ile Thr Val Tyr Ala Thr Tyr Gly Ala Ser Ile Ala
65                  70                  75                  80

Ser Tyr Ala Phe Ile Ser Ile Asn Tyr Arg Thr Glu Ile Asp Lys Pro
                85                  90                  95

Ser Gln His His His His His His
            100

<210> SEQ ID NO 406
<211> LENGTH: 93
<212> TYPE: PRT
<213> ORGANISM: Artificial Sequence
<220> FEATURE:
<223> OTHER INFORMATION: Synthetic: ATI_1760_E01 w/ N leader and
      modified C-terminus including PC

<400> SEQUENCE: 406

```
Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Lys Tyr
            20                  25                  30

Arg Ile Thr Tyr Gly Glu Thr Gly Gly Asn Ser Pro Val Gln Glu Phe
            35                  40                  45

Thr Val Ala Gly Ala Asp Tyr Ala Thr Ile Ser Gly Leu Lys Pro Gly
        50                  55                  60

Val Asp Tyr Thr Ile Thr Val Tyr Ala Thr Tyr Gly Ala Ser Ile Ala
65                  70                  75                  80

Ser Tyr Ala Phe Ile Ser Ile Asn Tyr Arg Thr Pro Cys
                85                  90
```

<210> SEQ ID NO 407
<211> LENGTH: 99
<212> TYPE: PRT
<213> ORGANISM: Artificial Sequence
<220> FEATURE:
<223> OTHER INFORMATION: Synthetic: ATI_1760_E01 w/ N leader and
    modified C-terminus including PC + his tag

<400> SEQUENCE: 407

```
Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ser Val Lys Tyr
            20                  25                  30

Arg Ile Thr Tyr Gly Glu Thr Gly Gly Asn Ser Pro Val Gln Glu Phe
            35                  40                  45

Thr Val Ala Gly Ala Asp Tyr Ala Thr Ile Ser Gly Leu Lys Pro Gly
        50                  55                  60

Val Asp Tyr Thr Ile Thr Val Tyr Ala Thr Tyr Gly Ala Ser Ile Ala
65                  70                  75                  80

Ser Tyr Ala Phe Ile Ser Ile Asn Tyr Arg Thr Pro Cys His His His
                85                  90                  95

His His His
```

<210> SEQ ID NO 408
<211> LENGTH: 105
<212> TYPE: PRT
<213> ORGANISM: Artificial Sequence
<220> FEATURE:
<223> OTHER INFORMATION: Synthetic: ATI_1760_E01 full length

<400> SEQUENCE: 408

```
Met Gly Val Ser Asp Val Pro Arg Asp Leu Glu Val Val Ala Ala Thr
1               5                   10                  15

Pro Thr Ser Leu Leu Ile Ser Trp Ile Ala Pro Tyr Tyr Ser Val Lys
            20                  25                  30

Tyr Arg Ile Thr Tyr Gly Glu Thr Gly Gly Asn Ser Pro Val Gln Glu
            35                  40                  45

Phe Thr Val Ala Gly Ala Asp Tyr Ala Thr Ile Ser Gly Leu Lys Pro
        50                  55                  60

Gly Val Asp Tyr Thr Ile Thr Val Tyr Ala Thr Tyr Gly Ala Ser Ile
65                  70                  75                  80

Ala Ser Tyr Ala Phe Ile Ser Ile Asn Tyr Arg Thr Glu Ile Asp Lys
                85                  90                  95

Pro Ser Gln His His His His His
            100                 105
```

<210> SEQ ID NO 409
<211> LENGTH: 82
<212> TYPE: PRT
<213> ORGANISM: Artificial Sequence
<220> FEATURE:
<223> OTHER INFORMATION: Synthetic: ATI_1760_F01 core

<400> SEQUENCE: 409

Glu Val Val Ala Ala Thr Pro Thr Ser Leu Leu Ile Ser Trp Ile Ala
1               5                   10                  15

Pro Tyr Tyr Ala Val Met Tyr Arg Ile Thr Tyr Gly Glu Thr Gly Gly
                20                  25                  30

Asn Ser Pro Val Gln Glu Phe Thr Val Pro Gly Gly Tyr Ala Thr
            35                  40                  45

Ile Ser Gly Leu Lys Pro Gly Val Asp Tyr Thr Ile Thr Val Tyr Ala
    50                  55                  60

Thr Gly Gly Ala Ser Ile Ala Ala Tyr Ala Phe Ile Ser Ile Asn Tyr
65                  70                  75                  80

Arg Thr

<210> SEQ ID NO 410
<211> LENGTH: 8
<212> TYPE: PRT
<213> ORGANISM: Artificial Sequence
<220> FEATURE:
<223> OTHER INFORMATION: Synthetic: ATI_1760_F01 BC loop

<400> SEQUENCE: 410

Ile Ala Pro Tyr Tyr Ala Val Met
1               5

<210> SEQ ID NO 411
<211> LENGTH: 5
<212> TYPE: PRT
<213> ORGANISM: Artificial Sequence
<220> FEATURE:
<223> OTHER INFORMATION: Synthetic: ATI_1760_F01 DE loop

<400> SEQUENCE: 411

Pro Gly Gly Gly Tyr
1               5

<210> SEQ ID NO 412
<211> LENGTH: 11
<212> TYPE: PRT
<213> ORGANISM: Artificial Sequence
<220> FEATURE:
<223> OTHER INFORMATION: Synthetic: ATI_1760_F01 FG loop

<400> SEQUENCE: 412

Thr Gly Gly Ala Ser Ile Ala Ala Tyr Ala Phe
1               5                   10

<210> SEQ ID NO 413
<211> LENGTH: 91
<212> TYPE: PRT
<213> ORGANISM: Artificial Sequence
<220> FEATURE:
<223> OTHER INFORMATION: Synthetic: ATI_1760_F01 w/ N leader

<400> SEQUENCE: 413

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ala Val Met Tyr
                20                  25                  30

Arg Ile Thr Tyr Gly Glu Thr Gly Gly Asn Ser Pro Val Gln Glu Phe
            35                  40                  45

Thr Val Pro Gly Gly Gly Tyr Ala Thr Ile Ser Gly Leu Lys Pro Gly
    50                  55                  60

Val Asp Tyr Thr Ile Thr Val Tyr Ala Thr Gly Gly Ala Ser Ile Ala
65                  70                  75                  80

Ala Tyr Ala Phe Ile Ser Ile Asn Tyr Arg Thr
                85                  90

<210> SEQ ID NO 414
<211> LENGTH: 97
<212> TYPE: PRT
<213> ORGANISM: Artificial Sequence
<220> FEATURE:
<223> OTHER INFORMATION: Synthetic: ATI_1760_F01 w/ N leader + his tag

<400> SEQUENCE: 414

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ala Val Met Tyr
                20                  25                  30

Arg Ile Thr Tyr Gly Glu Thr Gly Gly Asn Ser Pro Val Gln Glu Phe
            35                  40                  45

Thr Val Pro Gly Gly Gly Tyr Ala Thr Ile Ser Gly Leu Lys Pro Gly
    50                  55                  60

Val Asp Tyr Thr Ile Thr Val Tyr Ala Thr Gly Gly Ala Ser Ile Ala
65                  70                  75                  80

Ala Tyr Ala Phe Ile Ser Ile Asn Tyr Arg Thr His His His His His
                85                  90                  95

His

<210> SEQ ID NO 415
<211> LENGTH: 98
<212> TYPE: PRT
<213> ORGANISM: Artificial Sequence
<220> FEATURE:
<223> OTHER INFORMATION: Synthetic: ATI_1760_F01 w/ N leader and C tail

<400> SEQUENCE: 415

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ala Val Met Tyr
                20                  25                  30

Arg Ile Thr Tyr Gly Glu Thr Gly Gly Asn Ser Pro Val Gln Glu Phe
            35                  40                  45

Thr Val Pro Gly Gly Gly Tyr Ala Thr Ile Ser Gly Leu Lys Pro Gly
    50                  55                  60

Val Asp Tyr Thr Ile Thr Val Tyr Ala Thr Gly Gly Ala Ser Ile Ala
65                  70                  75                  80

Ala Tyr Ala Phe Ile Ser Ile Asn Tyr Arg Thr Glu Ile Asp Lys Pro
                85                  90                  95

Ser Gln

<210> SEQ ID NO 416
<211> LENGTH: 104

```
<212> TYPE: PRT
<213> ORGANISM: Artificial Sequence
<220> FEATURE:
<223> OTHER INFORMATION: Synthetic: ATI_1760_F01 w/ N leader and C
      tail + his tag

<400> SEQUENCE: 416
```

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ala Val Met Tyr
            20                  25                  30

Arg Ile Thr Tyr Gly Glu Thr Gly Gly Asn Ser Pro Val Gln Glu Phe
        35                  40                  45

Thr Val Pro Gly Gly Gly Tyr Ala Thr Ile Ser Gly Leu Lys Pro Gly
    50                  55                  60

Val Asp Tyr Thr Ile Thr Val Tyr Ala Thr Gly Gly Ala Ser Ile Ala
65                  70                  75                  80

Ala Tyr Ala Phe Ile Ser Ile Asn Tyr Arg Thr Glu Ile Asp Lys Pro
                85                  90                  95

Ser Gln His His His His His His
            100

```
<210> SEQ ID NO 417
<211> LENGTH: 93
<212> TYPE: PRT
<213> ORGANISM: Artificial Sequence
<220> FEATURE:
<223> OTHER INFORMATION: Synthetic: ATI_1760_F01 w/ N leader and
      modified C-terminus including PC

<400> SEQUENCE: 417
```

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ala Val Met Tyr
            20                  25                  30

Arg Ile Thr Tyr Gly Glu Thr Gly Gly Asn Ser Pro Val Gln Glu Phe
        35                  40                  45

Thr Val Pro Gly Gly Gly Tyr Ala Thr Ile Ser Gly Leu Lys Pro Gly
    50                  55                  60

Val Asp Tyr Thr Ile Thr Val Tyr Ala Thr Gly Gly Ala Ser Ile Ala
65                  70                  75                  80

Ala Tyr Ala Phe Ile Ser Ile Asn Tyr Arg Thr Pro Cys
                85                  90

```
<210> SEQ ID NO 418
<211> LENGTH: 99
<212> TYPE: PRT
<213> ORGANISM: Artificial Sequence
<220> FEATURE:
<223> OTHER INFORMATION: Synthetic: ATI_1760_F01 w/ N leader and
      modified C-terminus including PC + his tag

<400> SEQUENCE: 418
```

Gly Val Ser Asp Val Pro Arg Asp Leu Glu Val Val Ala Ala Thr Pro
1               5                   10                  15

Thr Ser Leu Leu Ile Ser Trp Ile Ala Pro Tyr Tyr Ala Val Met Tyr
            20                  25                  30

Arg Ile Thr Tyr Gly Glu Thr Gly Gly Asn Ser Pro Val Gln Glu Phe
        35                  40                  45

Thr Val Pro Gly Gly Gly Tyr Ala Thr Ile Ser Gly Leu Lys Pro Gly

```
                50                  55                  60
Val Asp Tyr Thr Ile Thr Val Tyr Ala Thr Gly Gly Ala Ser Ile Ala
 65                  70                  75                  80

Ala Tyr Ala Phe Ile Ser Ile Asn Tyr Arg Thr Pro Cys His His His
                     85                  90                  95

His His His

<210> SEQ ID NO 419
<211> LENGTH: 105
<212> TYPE: PRT
<213> ORGANISM: Artificial Sequence
<220> FEATURE:
<223> OTHER INFORMATION: Synthetic: ATI_1760_F01 full length

<400> SEQUENCE: 419

Met Gly Val Ser Asp Val Pro Arg Asp Leu Glu Val Val Ala Ala Thr
 1               5                  10                  15

Pro Thr Ser Leu Leu Ile Ser Trp Ile Ala Pro Tyr Tyr Ala Val Met
                20                  25                  30

Tyr Arg Ile Thr Tyr Gly Glu Thr Gly Gly Asn Ser Pro Val Gln Glu
             35                  40                  45

Phe Thr Val Pro Gly Gly Tyr Ala Thr Ile Ser Gly Leu Lys Pro
         50                  55                  60

Gly Val Asp Tyr Thr Ile Thr Val Tyr Ala Thr Gly Gly Ala Ser Ile
 65                  70                  75                  80

Ala Ala Tyr Ala Phe Ile Ser Ile Asn Tyr Arg Thr Glu Ile Asp Lys
                     85                  90                  95

Pro Ser Gln His His His His His His
            100                 105

<210> SEQ ID NO 420
<211> LENGTH: 79
<212> TYPE: PRT
<213> ORGANISM: Artificial Sequence
<220> FEATURE:
<223> OTHER INFORMATION: Synthetic: ATI_1494_D03 core

<400> SEQUENCE: 420

Glu Val Val Ala Ala Thr Pro Thr Ser Leu Leu Ile Ser Trp Ser Tyr
 1               5                  10                  15

Pro Ser Tyr His Leu Tyr Arg Ile Thr Tyr Gly Glu Thr Gly Gly Asn
                20                  25                  30

Ser Pro Val Gln Glu Phe Thr Val His Ile Asp Tyr Ala Thr Ile Ser
             35                  40                  45

Gly Leu Lys Pro Gly Val Asp Tyr Thr Ile Thr Val Tyr Ala Gln Ser
         50                  55                  60

Pro Pro Tyr Asp Ile Tyr Tyr Glu Ile Ser Ile Asn Tyr Arg Thr
 65                  70                  75

<210> SEQ ID NO 421
<211> LENGTH: 7
<212> TYPE: PRT
<213> ORGANISM: Artificial Sequence
<220> FEATURE:
<223> OTHER INFORMATION: Synthetic: ATI_1494_D03 BC loop

<400> SEQUENCE: 421

Ser Tyr Pro Ser Tyr His Leu
 1               5
```

<210> SEQ ID NO 422
<211> LENGTH: 4
<212> TYPE: PRT
<213> ORGANISM: Artificial Sequence
<220> FEATURE:
<223> OTHER INFORMATION: Synthetic: ATI_1494_D03 DE loop

<400> SEQUENCE: 422

His Ile Asp Tyr
1

<210> SEQ ID NO 423
<211> LENGTH: 10
<212> TYPE: PRT
<213> ORGANISM: Artificial Sequence
<220> FEATURE:
<223> OTHER INFORMATION: Synthetic: ATI_1494_D03 FG loop

<400> SEQUENCE: 423

Gln Ser Pro Pro Tyr Asp Ile Tyr Tyr Glu
1               5                   10

<210> SEQ ID NO 424
<211> LENGTH: 88
<212> TYPE: PRT
<213> ORGANISM: Artificial Sequence
<220> FEATURE:
<223> OTHER INFORMATION: Synthetic: ATI_1494_D03 w/ N leader

<400> SEQUENCE: 424

Gly Val Ser Asp Val Pro Arg Asp Leu Glu Val Val Ala Ala Thr Pro
1               5                   10                  15

Thr Ser Leu Leu Ile Ser Trp Ser Tyr Pro Ser Tyr His Leu Tyr Arg
            20                  25                  30

Ile Thr Tyr Gly Glu Thr Gly Gly Asn Ser Pro Val Gln Glu Phe Thr
        35                  40                  45

Val His Ile Asp Tyr Ala Thr Ile Ser Gly Leu Lys Pro Gly Val Asp
    50                  55                  60

Tyr Thr Ile Thr Val Tyr Ala Gln Ser Pro Pro Tyr Asp Ile Tyr Tyr
65                  70                  75                  80

Glu Ile Ser Ile Asn Tyr Arg Thr
                85

<210> SEQ ID NO 425
<211> LENGTH: 94
<212> TYPE: PRT
<213> ORGANISM: Artificial Sequence
<220> FEATURE:
<223> OTHER INFORMATION: Synthetic: ATI_1494_D03 w/ N leader + his tag

<400> SEQUENCE: 425

Gly Val Ser Asp Val Pro Arg Asp Leu Glu Val Val Ala Ala Thr Pro
1               5                   10                  15

Thr Ser Leu Leu Ile Ser Trp Ser Tyr Pro Ser Tyr His Leu Tyr Arg
            20                  25                  30

Ile Thr Tyr Gly Glu Thr Gly Gly Asn Ser Pro Val Gln Glu Phe Thr
        35                  40                  45

Val His Ile Asp Tyr Ala Thr Ile Ser Gly Leu Lys Pro Gly Val Asp
    50                  55                  60

Tyr Thr Ile Thr Val Tyr Ala Gln Ser Pro Pro Tyr Asp Ile Tyr Tyr
65                  70                  75                  80

```
Glu Ile Ser Ile Asn Tyr Arg Thr His His His His His
                85                  90
```

<210> SEQ ID NO 426
<211> LENGTH: 95
<212> TYPE: PRT
<213> ORGANISM: Artificial Sequence
<220> FEATURE:
<223> OTHER INFORMATION: Synthetic: ATI_1494_D03 w/ N leader and C tail

<400> SEQUENCE: 426

```
Gly Val Ser Asp Val Pro Arg Asp Leu Glu Val Val Ala Ala Thr Pro
1               5                   10                  15

Thr Ser Leu Leu Ile Ser Trp Ser Tyr Pro Ser Tyr His Leu Tyr Arg
            20                  25                  30

Ile Thr Tyr Gly Glu Thr Gly Gly Asn Ser Pro Val Gln Glu Phe Thr
        35                  40                  45

Val His Ile Asp Tyr Ala Thr Ile Ser Gly Leu Lys Pro Gly Val Asp
    50                  55                  60

Tyr Thr Ile Thr Val Tyr Ala Gln Ser Pro Pro Tyr Asp Ile Tyr Tyr
65                  70                  75                  80

Glu Ile Ser Ile Asn Tyr Arg Thr Glu Ile Asp Lys Pro Ser Gln
                85                  90                  95
```

<210> SEQ ID NO 427
<211> LENGTH: 101
<212> TYPE: PRT
<213> ORGANISM: Artificial Sequence
<220> FEATURE:
<223> OTHER INFORMATION: Synthetic: ATI_1494_D03 w/ N leader and C
      tail + his tag

<400> SEQUENCE: 427

```
Gly Val Ser Asp Val Pro Arg Asp Leu Glu Val Val Ala Ala Thr Pro
1               5                   10                  15

Thr Ser Leu Leu Ile Ser Trp Ser Tyr Pro Ser Tyr His Leu Tyr Arg
            20                  25                  30

Ile Thr Tyr Gly Glu Thr Gly Gly Asn Ser Pro Val Gln Glu Phe Thr
        35                  40                  45

Val His Ile Asp Tyr Ala Thr Ile Ser Gly Leu Lys Pro Gly Val Asp
    50                  55                  60

Tyr Thr Ile Thr Val Tyr Ala Gln Ser Pro Pro Tyr Asp Ile Tyr Tyr
65                  70                  75                  80

Glu Ile Ser Ile Asn Tyr Arg Thr Glu Ile Asp Lys Pro Ser Gln His
                85                  90                  95

His His His His His
            100
```

<210> SEQ ID NO 428
<211> LENGTH: 90
<212> TYPE: PRT
<213> ORGANISM: Artificial Sequence
<220> FEATURE:
<223> OTHER INFORMATION: Synthetic: ATI_1494_D03 w/ N leader and
      modified C-terminus including PC

<400> SEQUENCE: 428

```
Gly Val Ser Asp Val Pro Arg Asp Leu Glu Val Val Ala Ala Thr Pro
1               5                   10                  15

Thr Ser Leu Leu Ile Ser Trp Ser Tyr Pro Ser Tyr His Leu Tyr Arg
            20                  25                  30
```

Ile Thr Tyr Gly Glu Thr Gly Gly Asn Ser Pro Val Gln Glu Phe Thr
            35                  40                  45

Val His Ile Asp Tyr Ala Thr Ile Ser Gly Leu Lys Pro Gly Val Asp
    50                  55                  60

Tyr Thr Ile Thr Val Tyr Ala Gln Ser Pro Pro Tyr Asp Ile Tyr Tyr
65                  70                  75                  80

Glu Ile Ser Ile Asn Tyr Arg Thr Pro Cys
                85                  90

<210> SEQ ID NO 429
<211> LENGTH: 96
<212> TYPE: PRT
<213> ORGANISM: Artificial Sequence
<220> FEATURE:
<223> OTHER INFORMATION: Synthetic: ATI_1494_D03 w/ N leader and
      modified C-terminus including PC + his tag

<400> SEQUENCE: 429

Gly Val Ser Asp Val Pro Arg Asp Leu Glu Val Val Ala Ala Thr Pro
1               5                   10                  15

Thr Ser Leu Leu Ile Ser Trp Ser Tyr Pro Ser Tyr His Leu Tyr Arg
            20                  25                  30

Ile Thr Tyr Gly Glu Thr Gly Gly Asn Ser Pro Val Gln Glu Phe Thr
            35                  40                  45

Val His Ile Asp Tyr Ala Thr Ile Ser Gly Leu Lys Pro Gly Val Asp
    50                  55                  60

Tyr Thr Ile Thr Val Tyr Ala Gln Ser Pro Pro Tyr Asp Ile Tyr Tyr
65                  70                  75                  80

Glu Ile Ser Ile Asn Tyr Arg Thr Pro Cys His His His His His
                85                  90                  95

<210> SEQ ID NO 430
<211> LENGTH: 102
<212> TYPE: PRT
<213> ORGANISM: Artificial Sequence
<220> FEATURE:
<223> OTHER INFORMATION: Synthetic: ATI_1494_D03 full length

<400> SEQUENCE: 430

Met Gly Val Ser Asp Val Pro Arg Asp Leu Glu Val Val Ala Ala Thr
1               5                   10                  15

Pro Thr Ser Leu Leu Ile Ser Trp Ser Tyr Pro Ser Tyr His Leu Tyr
            20                  25                  30

Arg Ile Thr Tyr Gly Glu Thr Gly Gly Asn Ser Pro Val Gln Glu Phe
            35                  40                  45

Thr Val His Ile Asp Tyr Ala Thr Ile Ser Gly Leu Lys Pro Gly Val
    50                  55                  60

Asp Tyr Thr Ile Thr Val Tyr Ala Gln Ser Pro Pro Tyr Asp Ile Tyr
65                  70                  75                  80

Tyr Glu Ile Ser Ile Asn Tyr Arg Thr Glu Ile Asp Lys Pro Ser Gln
                85                  90                  95

His His His His His His
            100

<210> SEQ ID NO 431
<211> LENGTH: 79
<212> TYPE: PRT
<213> ORGANISM: Artificial Sequence
<220> FEATURE:

<223> OTHER INFORMATION: Synthetic: ATI_1494_D04 core

<400> SEQUENCE: 431

Glu Val Val Ala Ala Thr Pro Thr Ser Leu Leu Ile Ser Trp Met Glu
1               5                   10                  15

Ser Ser Ser Asn Ser Tyr Arg Ile Thr Tyr Gly Glu Thr Gly Gly Asn
            20                  25                  30

Ser Pro Val Gln Glu Phe Thr Val Pro Asp Gln Leu Ala Thr Ile Ser
        35                  40                  45

Gly Leu Lys Pro Gly Val Asp Tyr Thr Ile Thr Val Tyr Ala Leu Ala
    50                  55                  60

Asn Ala His Tyr Met Arg Val Gly Ile Ser Ile Asn Tyr Arg Thr
65                  70                  75

<210> SEQ ID NO 432
<211> LENGTH: 7
<212> TYPE: PRT
<213> ORGANISM: Artificial Sequence
<220> FEATURE:
<223> OTHER INFORMATION: Synthetic: ATI_1494_D04 BC loop

<400> SEQUENCE: 432

Met Glu Ser Ser Ser Asn Ser
1               5

<210> SEQ ID NO 433
<211> LENGTH: 4
<212> TYPE: PRT
<213> ORGANISM: Artificial Sequence
<220> FEATURE:
<223> OTHER INFORMATION: Synthetic: ATI_1494_D04 DE loop

<400> SEQUENCE: 433

Pro Asp Gln Leu
1

<210> SEQ ID NO 434
<211> LENGTH: 10
<212> TYPE: PRT
<213> ORGANISM: Artificial Sequence
<220> FEATURE:
<223> OTHER INFORMATION: Synthetic: ATI_1494_D04 FG loop

<400> SEQUENCE: 434

Leu Ala Asn Ala His Tyr Met Arg Val Gly
1               5                   10

<210> SEQ ID NO 435
<211> LENGTH: 88
<212> TYPE: PRT
<213> ORGANISM: Artificial Sequence
<220> FEATURE:
<223> OTHER INFORMATION: Synthetic: ATI_1494_D04 w/ N leader

<400> SEQUENCE: 435

Gly Val Ser Asp Val Pro Arg Asp Leu Glu Val Val Ala Ala Thr Pro
1               5                   10                  15

Thr Ser Leu Leu Ile Ser Trp Met Glu Ser Ser Ser Asn Ser Tyr Arg
            20                  25                  30

Ile Thr Tyr Gly Glu Thr Gly Gly Asn Ser Pro Val Gln Glu Phe Thr
        35                  40                  45

Val Pro Asp Gln Leu Ala Thr Ile Ser Gly Leu Lys Pro Gly Val Asp
    50                  55                  60

```
Tyr Thr Ile Thr Val Tyr Ala Leu Ala Asn Ala His Tyr Met Arg Val
 65                  70                  75                  80

Gly Ile Ser Ile Asn Tyr Arg Thr
                85

<210> SEQ ID NO 436
<211> LENGTH: 94
<212> TYPE: PRT
<213> ORGANISM: Artificial Sequence
<220> FEATURE:
<223> OTHER INFORMATION: Synthetic: ATI_1494_D04 w/ N leader + his tag

<400> SEQUENCE: 436

Gly Val Ser Asp Val Pro Arg Asp Leu Glu Val Val Ala Ala Thr Pro
1               5                   10                  15

Thr Ser Leu Leu Ile Ser Trp Met Glu Ser Ser Ser Asn Ser Tyr Arg
                20                  25                  30

Ile Thr Tyr Gly Glu Thr Gly Gly Asn Ser Pro Val Gln Glu Phe Thr
            35                  40                  45

Val Pro Asp Gln Leu Ala Thr Ile Ser Gly Leu Lys Pro Gly Val Asp
    50                  55                  60

Tyr Thr Ile Thr Val Tyr Ala Leu Ala Asn Ala His Tyr Met Arg Val
 65                  70                  75                  80

Gly Ile Ser Ile Asn Tyr Arg Thr His His His His His His
                85                  90

<210> SEQ ID NO 437
<211> LENGTH: 95
<212> TYPE: PRT
<213> ORGANISM: Artificial Sequence
<220> FEATURE:
<223> OTHER INFORMATION: Synthetic: ATI_1494_D04 w/ N leader and C tail

<400> SEQUENCE: 437

Gly Val Ser Asp Val Pro Arg Asp Leu Glu Val Val Ala Ala Thr Pro
1               5                   10                  15

Thr Ser Leu Leu Ile Ser Trp Met Glu Ser Ser Ser Asn Ser Tyr Arg
                20                  25                  30

Ile Thr Tyr Gly Glu Thr Gly Gly Asn Ser Pro Val Gln Glu Phe Thr
            35                  40                  45

Val Pro Asp Gln Leu Ala Thr Ile Ser Gly Leu Lys Pro Gly Val Asp
    50                  55                  60

Tyr Thr Ile Thr Val Tyr Ala Leu Ala Asn Ala His Tyr Met Arg Val
 65                  70                  75                  80

Gly Ile Ser Ile Asn Tyr Arg Thr Glu Ile Asp Lys Pro Ser Gln
                85                  90                  95

<210> SEQ ID NO 438
<211> LENGTH: 101
<212> TYPE: PRT
<213> ORGANISM: Artificial Sequence
<220> FEATURE:
<223> OTHER INFORMATION: Synthetic: ATI_1494_D04 w/ N leader and C
      tail + his tag

<400> SEQUENCE: 438

Gly Val Ser Asp Val Pro Arg Asp Leu Glu Val Val Ala Ala Thr Pro
1               5                   10                  15

Thr Ser Leu Leu Ile Ser Trp Met Glu Ser Ser Ser Asn Ser Tyr Arg
                20                  25                  30
```

```
Ile Thr Tyr Gly Glu Thr Gly Gly Asn Ser Pro Val Gln Glu Phe Thr
            35                  40                  45

Val Pro Asp Gln Leu Ala Thr Ile Ser Gly Leu Lys Pro Gly Val Asp
 50                  55                  60

Tyr Thr Ile Thr Val Tyr Ala Leu Ala Asn Ala His Tyr Met Arg Val
 65                  70                  75                  80

Gly Ile Ser Ile Asn Tyr Arg Thr Glu Ile Asp Lys Pro Ser Gln His
                85                  90                  95

His His His His His
            100
```

<210> SEQ ID NO 439
<211> LENGTH: 90
<212> TYPE: PRT
<213> ORGANISM: Artificial Sequence
<220> FEATURE:
<223> OTHER INFORMATION: Synthetic: ATI_1494_D04 w/ N leader and modified C-terminus including PC

<400> SEQUENCE: 439

```
Gly Val Ser Asp Val Pro Arg Asp Leu Glu Val Val Ala Ala Thr Pro
 1               5                  10                  15

Thr Ser Leu Leu Ile Ser Trp Met Glu Ser Ser Ser Asn Ser Tyr Arg
            20                  25                  30

Ile Thr Tyr Gly Glu Thr Gly Gly Asn Ser Pro Val Gln Glu Phe Thr
            35                  40                  45

Val Pro Asp Gln Leu Ala Thr Ile Ser Gly Leu Lys Pro Gly Val Asp
 50                  55                  60

Tyr Thr Ile Thr Val Tyr Ala Leu Ala Asn Ala His Tyr Met Arg Val
 65                  70                  75                  80

Gly Ile Ser Ile Asn Tyr Arg Thr Pro Cys
                85                  90
```

<210> SEQ ID NO 440
<211> LENGTH: 96
<212> TYPE: PRT
<213> ORGANISM: Artificial Sequence
<220> FEATURE:
<223> OTHER INFORMATION: Synthetic: ATI_1494_D04 w/ N leader and modified C-terminus including PC + his tag

<400> SEQUENCE: 440

```
Gly Val Ser Asp Val Pro Arg Asp Leu Glu Val Val Ala Ala Thr Pro
 1               5                  10                  15

Thr Ser Leu Leu Ile Ser Trp Met Glu Ser Ser Ser Asn Ser Tyr Arg
            20                  25                  30

Ile Thr Tyr Gly Glu Thr Gly Gly Asn Ser Pro Val Gln Glu Phe Thr
            35                  40                  45

Val Pro Asp Gln Leu Ala Thr Ile Ser Gly Leu Lys Pro Gly Val Asp
 50                  55                  60

Tyr Thr Ile Thr Val Tyr Ala Leu Ala Asn Ala His Tyr Met Arg Val
 65                  70                  75                  80

Gly Ile Ser Ile Asn Tyr Arg Thr Pro Cys His His His His His
                85                  90                  95
```

<210> SEQ ID NO 441
<211> LENGTH: 102
<212> TYPE: PRT
<213> ORGANISM: Artificial Sequence
<220> FEATURE:
<223> OTHER INFORMATION: Synthetic: ATI_1494_D04 full length

<400> SEQUENCE: 441

Met Gly Val Ser Asp Val Pro Arg Asp Leu Glu Val Val Ala Ala Thr
1               5                   10                  15

Pro Thr Ser Leu Leu Ile Ser Trp Met Glu Ser Ser Asn Ser Tyr
            20                  25                  30

Arg Ile Thr Tyr Gly Glu Thr Gly Gly Asn Ser Pro Val Gln Glu Phe
        35                  40                  45

Thr Val Pro Asp Gln Leu Ala Thr Ile Ser Gly Leu Lys Pro Gly Val
    50                  55                  60

Asp Tyr Thr Ile Thr Val Tyr Ala Leu Ala Asn Ala His Tyr Met Arg
65                  70                  75                  80

Val Gly Ile Ser Ile Asn Tyr Arg Thr Glu Ile Asp Lys Pro Ser Gln
                85                  90                  95

His His His His His His
            100

<210> SEQ ID NO 442
<211> LENGTH: 79
<212> TYPE: PRT
<213> ORGANISM: Artificial Sequence
<220> FEATURE:
<223> OTHER INFORMATION: Synthetic: ATI_1523_A08 core
<220> FEATURE:
<221> NAME/KEY: misc_feature
<222> LOCATION: (21)..(21)
<223> OTHER INFORMATION: Xaa can be any naturally occurring amino acid

<400> SEQUENCE: 442

Glu Val Val Ala Ala Thr Pro Thr Ser Leu Leu Ile Ser Trp Ile Ser
1               5                   10                  15

Val Gln Thr Tyr Xaa Tyr Arg Ile Thr Tyr Gly Glu Thr Gly Gly Asn
            20                  25                  30

Ser Pro Val Gln Glu Phe Thr Val Pro Asp Gln Ser Ala Thr Ile Ser
        35                  40                  45

Gly Leu Lys Pro Gly Val Asp Tyr Thr Ile Thr Val Tyr Ala Leu Glu
    50                  55                  60

Lys Ala His Tyr Tyr Arg Gln Asn Ile Ser Ile Asn Tyr Arg Thr
65                  70                  75

<210> SEQ ID NO 443
<211> LENGTH: 7
<212> TYPE: PRT
<213> ORGANISM: Artificial Sequence
<220> FEATURE:
<223> OTHER INFORMATION: Synthetic: ATI_1523_A08 BC loop
<220> FEATURE:
<221> NAME/KEY: misc_feature
<222> LOCATION: (7)..(7)
<223> OTHER INFORMATION: Xaa can be any naturally occurring amino acid

<400> SEQUENCE: 443

Ile Ser Val Gln Thr Tyr Xaa
1               5

<210> SEQ ID NO 444
<211> LENGTH: 4
<212> TYPE: PRT
<213> ORGANISM: Artificial Sequence
<220> FEATURE:
<223> OTHER INFORMATION: Synthetic: ATI_1523_A08 DE loop

```
<400> SEQUENCE: 444

Pro Asp Gln Ser
1

<210> SEQ ID NO 445
<211> LENGTH: 10
<212> TYPE: PRT
<213> ORGANISM: Artificial Sequence
<220> FEATURE:
<223> OTHER INFORMATION: Synthetic: ATI_1523_A08 FG loop

<400> SEQUENCE: 445

Leu Glu Lys Ala His Tyr Tyr Arg Gln Asn
1               5                   10

<210> SEQ ID NO 446
<211> LENGTH: 88
<212> TYPE: PRT
<213> ORGANISM: Artificial Sequence
<220> FEATURE:
<223> OTHER INFORMATION: Synthetic: ATI_1523_A08 w/ N leader
<220> FEATURE:
<221> NAME/KEY: misc_feature
<222> LOCATION: (30)..(30)
<223> OTHER INFORMATION: Xaa can be any naturally occurring amino acid

<400> SEQUENCE: 446

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr
                85

<210> SEQ ID NO 447
<211> LENGTH: 94
<212> TYPE: PRT
<213> ORGANISM: Artificial Sequence
<220> FEATURE:
<223> OTHER INFORMATION: Synthetic: ATI_1523_A08 w/ N leader + his tag
<220> FEATURE:
<221> NAME/KEY: misc_feature
<222> LOCATION: (30)..(30)
<223> OTHER INFORMATION: Xaa can be any naturally occurring amino acid

<400> SEQUENCE: 447

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80
```

Asn Ile Ser Ile Asn Tyr Arg Thr His His His His His
                85                  90

<210> SEQ ID NO 448
<211> LENGTH: 95
<212> TYPE: PRT
<213> ORGANISM: Artificial Sequence
<220> FEATURE:
<223> OTHER INFORMATION: Synthetic: ATI_1523_A08 w/ N leader and C tail
<220> FEATURE:
<221> NAME/KEY: misc_feature
<222> LOCATION: (30)..(30)
<223> OTHER INFORMATION: Xaa can be any naturally occurring amino acid

<400> SEQUENCE: 448

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Glu Ile Asp Lys Pro Ser Gln
                85                  90                  95

<210> SEQ ID NO 449
<211> LENGTH: 101
<212> TYPE: PRT
<213> ORGANISM: Artificial Sequence
<220> FEATURE:
<223> OTHER INFORMATION: Synthetic: ATI_1523_A08 w/ N leader and C
      tail + his tag
<220> FEATURE:
<221> NAME/KEY: misc_feature
<222> LOCATION: (30)..(30)
<223> OTHER INFORMATION: Xaa can be any naturally occurring amino acid

<400> SEQUENCE: 449

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Glu Ile Asp Lys Pro Ser Gln His
                85                  90                  95

His His His His His
            100

<210> SEQ ID NO 450
<211> LENGTH: 90
<212> TYPE: PRT
<213> ORGANISM: Artificial Sequence
<220> FEATURE:
<223> OTHER INFORMATION: Synthetic: ATI_1523_A08 w/ N leader and -continued

```
<220> FEATURE:
<221> NAME/KEY: misc_feature
<222> LOCATION: (30)..(30)
<223> OTHER INFORMATION: Xaa can be any naturally occurring amino acid

<400> SEQUENCE: 450

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Pro Cys
                85                  90

<210> SEQ ID NO 451
<211> LENGTH: 96
<212> TYPE: PRT
<213> ORGANISM: Artificial Sequence
<220> FEATURE:
<223> OTHER INFORMATION: Synthetic: ATI_1523_A08 w/ N leader and
      modified C-terminus including PC + his tag
<220> FEATURE:
<221> NAME/KEY: misc_feature
<222> LOCATION: (30)..(30)
<223> OTHER INFORMATION: Xaa can be any naturally occurring amino acid

<400> SEQUENCE: 451

Gly Val Ser Asp Val Pro Arg Asp Leu Glu Val Val Ala Ala Thr Pro
1               5                   10                  15

Thr Ser Leu Leu Ile Ser Trp Ile Ser Val Gln Thr Tyr Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Pro Cys His His His His His
                85                  90                  95

<210> SEQ ID NO 452
<211> LENGTH: 102
<212> TYPE: PRT
<213> ORGANISM: Artificial Sequence
<220> FEATURE:
<223> OTHER INFORMATION: Synthetic: ATI_1523_A08 full length
<220> FEATURE:
<221> NAME/KEY: misc_feature
<222> LOCATION: (31)..(31)
<223> OTHER INFORMATION: Xaa can be any naturally occurring amino acid

<400> SEQUENCE: 452

Met Gly Val Ser Asp Val Pro Arg Asp Leu Glu Val Val Ala Ala Thr
1               5                   10                  15

Pro Thr Ser Leu Leu Ile Ser Trp Ile Ser Val Gln Thr Tyr Xaa Tyr
            20                  25                  30
```

-continued

```
Arg Ile Thr Tyr Gly Glu Thr Gly Gly Asn Ser Pro Val Gln Glu Phe
            35                  40                  45

Thr Val Pro Asp Gln Ser Ala Thr Ile Ser Gly Leu Lys Pro Gly Val
 50                  55                  60

Asp Tyr Thr Ile Thr Val Tyr Ala Leu Glu Lys Ala His Tyr Tyr Arg
 65                  70                  75                  80

Gln Asn Ile Ser Ile Asn Tyr Arg Thr Glu Ile Asp Lys Pro Ser Gln
                 85                  90                  95

His His His His His His
            100

<210> SEQ ID NO 453
<211> LENGTH: 79
<212> TYPE: PRT
<213> ORGANISM: Artificial Sequence
<220> FEATURE:
<223> OTHER INFORMATION: Synthetic: ATI_1523_B10 core
<220> FEATURE:
<221> NAME/KEY: misc_feature
<222> LOCATION: (20)..(20)
<223> OTHER INFORMATION: Xaa can be any naturally occurring amino acid

<400> SEQUENCE: 453

Glu Val Val Ala Ala Thr Pro Thr Ser Leu Leu Ile Ser Trp Val Tyr
 1               5                  10                  15

His Tyr Asp Xaa Gln Tyr Arg Ile Thr Tyr Gly Glu Thr Gly Gly Asn
                 20                  25                  30

Ser Pro Val Gln Glu Phe Thr Val Pro Asp Gln Lys Ala Thr Ile Ser
            35                  40                  45

Gly Leu Lys Pro Gly Val Asp Tyr Thr Ile Thr Val Tyr Ala Leu Ser
 50                  55                  60

Glu Ala His His Lys Arg Asp Ser Ile Ser Ile Asn Tyr Arg Thr
 65                  70                  75

<210> SEQ ID NO 454
<211> LENGTH: 7
<212> TYPE: PRT
<213> ORGANISM: Artificial Sequence
<220> FEATURE:
<223> OTHER INFORMATION: Synthetic: ATI_1523_B10  BC loop
<220> FEATURE:
<221> NAME/KEY: misc_feature
<222> LOCATION: (6)..(6)
<223> OTHER INFORMATION: Xaa can be any naturally occurring amino acid

<400> SEQUENCE: 454

Val Tyr His Tyr Asp Xaa Gln
 1               5

<210> SEQ ID NO 455
<211> LENGTH: 4
<212> TYPE: PRT
<213> ORGANISM: Artificial Sequence
<220> FEATURE:
<223> OTHER INFORMATION: Synthetic: ATI_1523_B10  DE loop

<400> SEQUENCE: 455

Pro Asp Gln Lys
 1

<210> SEQ ID NO 456
<211> LENGTH: 10
<212> TYPE: PRT
<213> ORGANISM: Artificial Sequence
```

```
<220> FEATURE:
<223> OTHER INFORMATION: Synthetic: ATI_1523_B10  FG loop

<400> SEQUENCE: 456

Leu Ser Glu Ala His His Lys Arg Asp Ser
1               5                   10

<210> SEQ ID NO 457
<211> LENGTH: 88
<212> TYPE: PRT
<213> ORGANISM: Artificial Sequence
<220> FEATURE:
<223> OTHER INFORMATION: Synthetic: ATI_1523_B10 w/ N leader
<220> FEATURE:
<221> NAME/KEY: misc_feature
<222> LOCATION: (29)..(29)
<223> OTHER INFORMATION: Xaa can be any naturally occurring amino acid

<400> SEQUENCE: 457

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Xaa Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr
                85

<210> SEQ ID NO 458
<211> LENGTH: 94
<212> TYPE: PRT
<213> ORGANISM: Artificial Sequence
<220> FEATURE:
<223> OTHER INFORMATION: Synthetic: ATI_1523_B10 w/ N leader + his tag
<220> FEATURE:
<221> NAME/KEY: misc_feature
<222> LOCATION: (29)..(29)
<223> OTHER INFORMATION: Xaa can be any naturally occurring amino acid

<400> SEQUENCE: 458

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Xaa Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr His His His His His
                85                  90

<210> SEQ ID NO 459
<211> LENGTH: 95
<212> TYPE: PRT
<213> ORGANISM: Artificial Sequence
<220> FEATURE:
<223> OTHER INFORMATION: Synthetic: ATI_1523_B10 w/ N leader and C tail
```

```
<220> FEATURE:
<221> NAME/KEY: misc_feature
<222> LOCATION: (29)..(29)
<223> OTHER INFORMATION: Xaa can be any naturally occurring amino acid

<400> SEQUENCE: 459
```

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Xaa Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Glu Ile Asp Lys Pro Ser Gln
                85                  90                  95

```
<210> SEQ ID NO 460
<211> LENGTH: 101
<212> TYPE: PRT
<213> ORGANISM: Artificial Sequence
<220> FEATURE:
<223> OTHER INFORMATION: Synthetic: ATI_1523_B10 w/ N leader and C
      tail + his tag
<220> FEATURE:
<221> NAME/KEY: misc_feature
<222> LOCATION: (29)..(29)
<223> OTHER INFORMATION: Xaa can be any naturally occurring amino acid

<400> SEQUENCE: 460
```

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Xaa Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Glu Ile Asp Lys Pro Ser Gln His
                85                  90                  95

His His His His His
            100

```
<210> SEQ ID NO 461
<211> LENGTH: 90
<212> TYPE: PRT
<213> ORGANISM: Artificial Sequence
<220> FEATURE:
<223> OTHER INFORMATION: Synthetic: ATI_1523_B10 w/ N leader and
      modified C-terminus including PC
<220> FEATURE:
<221> NAME/KEY: misc_feature
<222> LOCATION: (29)..(29)
<223> OTHER INFORMATION: Xaa can be any naturally occurring amino acid

<400> SEQUENCE: 461
```

Gly Val Ser Asp Val Pro Arg Asp Leu Glu Val Val Ala Ala Thr Pro
1               5                   10                  15

```
Thr Ser Leu Leu Ile Ser Trp Val Tyr His Tyr Asp Xaa Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Pro Cys
                85                  90

<210> SEQ ID NO 462
<211> LENGTH: 96
<212> TYPE: PRT
<213> ORGANISM: Artificial Sequence
<220> FEATURE:
<223> OTHER INFORMATION: Synthetic: ATI_1523_B10 w/ N leader and
      modified C-terminus including PC + his tag
<220> FEATURE:
<221> NAME/KEY: misc_feature
<222> LOCATION: (29)..(29)
<223> OTHER INFORMATION: Xaa can be any naturally occurring amino acid

<400> SEQUENCE: 462

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Xaa Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Pro Cys His His His His His
                85                  90                  95

<210> SEQ ID NO 463
<211> LENGTH: 102
<212> TYPE: PRT
<213> ORGANISM: Artificial Sequence
<220> FEATURE:
<223> OTHER INFORMATION: Synthetic: ATI_1523_B10  full length
<220> FEATURE:
<221> NAME/KEY: misc_feature
<222> LOCATION: (30)..(30)
<223> OTHER INFORMATION: Xaa can be any naturally occurring amino acid

<400> SEQUENCE: 463

Met Gly Val Ser Asp Val Pro Arg Asp Leu Glu Val Val Ala Ala Thr
1               5                   10                  15

Pro Thr Ser Leu Leu Ile Ser Trp Val Tyr His Tyr Asp Xaa Gln Tyr
            20                  25                  30

Arg Ile Thr Tyr Gly Glu Thr Gly Gly Asn Ser Pro Val Gln Glu Phe
        35                  40                  45

Thr Val Pro Asp Gln Lys Ala Thr Ile Ser Gly Leu Lys Pro Gly Val
    50                  55                  60

Asp Tyr Thr Ile Thr Val Tyr Ala Leu Ser Glu Ala His His Lys Arg
65                  70                  75                  80

Asp Ser Ile Ser Ile Asn Tyr Arg Thr Glu Ile Asp Lys Pro Ser Gln
                85                  90                  95
```

His His His His His His
                    100

<210> SEQ ID NO 464
<211> LENGTH: 79
<212> TYPE: PRT
<213> ORGANISM: Artificial Sequence
<220> FEATURE:
<223> OTHER INFORMATION: Synthetic: ATI_1523_C07 core

<400> SEQUENCE: 464

Glu Val Val Ala Ala Thr Pro Thr Ser Leu Leu Ile Ser Trp Arg Met
1               5                   10                  15

His Thr Asp Pro Asp Tyr Arg Ile Thr Tyr Gly Glu Thr Gly Gly Asn
            20                  25                  30

Ser Pro Val Gln Glu Phe Thr Val Pro Asp Gln Glu Ala Thr Ile Ser
        35                  40                  45

Gly Leu Lys Pro Gly Val Asp Tyr Thr Ile Thr Val Tyr Ala Ile Gln
    50                  55                  60

Thr Ala His Tyr Tyr Arg Ile Asn Ile Ser Ile Asn Tyr Arg Thr
65                  70                  75

<210> SEQ ID NO 465
<211> LENGTH: 7
<212> TYPE: PRT
<213> ORGANISM: Artificial Sequence
<220> FEATURE:
<223> OTHER INFORMATION: Synthetic: ATI_1523_C07 BC loop

<400> SEQUENCE: 465

Arg Met His Thr Asp Pro Asp
1               5

<210> SEQ ID NO 466
<211> LENGTH: 4
<212> TYPE: PRT
<213> ORGANISM: Artificial Sequence
<220> FEATURE:
<223> OTHER INFORMATION: Synthetic: ATI_1523_C07 DE loop

<400> SEQUENCE: 466

Pro Asp Gln Glu
1

<210> SEQ ID NO 467
<211> LENGTH: 10
<212> TYPE: PRT
<213> ORGANISM: Artificial Sequence
<220> FEATURE:
<223> OTHER INFORMATION: Synthetic: ATI_1523_C07 FG loop

<400> SEQUENCE: 467

Ile Gln Thr Ala His Tyr Tyr Arg Ile Asn
1               5                   10

<210> SEQ ID NO 468
<211> LENGTH: 88
<212> TYPE: PRT
<213> ORGANISM: Artificial Sequence
<220> FEATURE:
<223> OTHER INFORMATION: Synthetic: ATI_1523_C07 w/ N leader

<400> SEQUENCE: 468

Gly Val Ser Asp Val Pro Arg Asp Leu Glu Val Val Ala Ala Thr Pro

```
1               5                   10                  15
Thr Ser Leu Leu Ile Ser Trp Arg Met His Thr Asp Pro Asp Tyr Arg
                20                  25                  30

Ile Thr Tyr Gly Glu Thr Gly Gly Asn Ser Pro Val Gln Glu Phe Thr
                35                  40                  45

Val Pro Asp Gln Glu Ala Thr Ile Ser Gly Leu Lys Pro Gly Val Asp
    50                  55                  60

Tyr Thr Ile Thr Val Tyr Ala Ile Gln Thr Ala His Tyr Tyr Arg Ile
65                  70                  75                  80

Asn Ile Ser Ile Asn Tyr Arg Thr
                85

<210> SEQ ID NO 469
<211> LENGTH: 94
<212> TYPE: PRT
<213> ORGANISM: Artificial Sequence
<220> FEATURE:
<223> OTHER INFORMATION: Synthetic: ATI_1523_C07 w/ N leader + his tag

<400> SEQUENCE: 469

Gly Val Ser Asp Val Pro Arg Asp Leu Glu Val Val Ala Ala Thr Pro
1               5                   10                  15

Thr Ser Leu Leu Ile Ser Trp Arg Met His Thr Asp Pro Asp Tyr Arg
                20                  25                  30

Ile Thr Tyr Gly Glu Thr Gly Gly Asn Ser Pro Val Gln Glu Phe Thr
                35                  40                  45

Val Pro Asp Gln Glu Ala Thr Ile Ser Gly Leu Lys Pro Gly Val Asp
    50                  55                  60

Tyr Thr Ile Thr Val Tyr Ala Ile Gln Thr Ala His Tyr Tyr Arg Ile
65                  70                  75                  80

Asn Ile Ser Ile Asn Tyr Arg Thr His His His His His
                85                  90

<210> SEQ ID NO 470
<211> LENGTH: 95
<212> TYPE: PRT
<213> ORGANISM: Artificial Sequence
<220> FEATURE:
<223> OTHER INFORMATION: Synthetic: ATI_1523_C07 w/ N leader and C tail

<400> SEQUENCE: 470

Gly Val Ser Asp Val Pro Arg Asp Leu Glu Val Val Ala Ala Thr Pro
1               5                   10                  15

Thr Ser Leu Leu Ile Ser Trp Arg Met His Thr Asp Pro Asp Tyr Arg
                20                  25                  30

Ile Thr Tyr Gly Glu Thr Gly Gly Asn Ser Pro Val Gln Glu Phe Thr
                35                  40                  45

Val Pro Asp Gln Glu Ala Thr Ile Ser Gly Leu Lys Pro Gly Val Asp
    50                  55                  60

Tyr Thr Ile Thr Val Tyr Ala Ile Gln Thr Ala His Tyr Tyr Arg Ile
65                  70                  75                  80

Asn Ile Ser Ile Asn Tyr Arg Thr Glu Ile Asp Lys Pro Ser Gln
                85                  90                  95

<210> SEQ ID NO 471
<211> LENGTH: 101
<212> TYPE: PRT
<213> ORGANISM: Artificial Sequence
<220> FEATURE:
```

<223> OTHER INFORMATION: Synthetic: ATI_1523_C07 w/ N leader and C
      tail + his tag

<400> SEQUENCE: 471

Gly Val Ser Asp Val Pro Arg Asp Leu Glu Val Val Ala Ala Thr Pro
1               5                   10                  15

Thr Ser Leu Leu Ile Ser Trp Arg Met His Thr Asp Pro Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Glu Ala Thr Ile Ser Gly Leu Lys Pro Gly Val Asp
    50                  55                  60

Tyr Thr Ile Thr Val Tyr Ala Ile Gln Thr Ala His Tyr Tyr Arg Ile
65                  70                  75                  80

Asn Ile Ser Ile Asn Tyr Arg Thr Glu Ile Asp Lys Pro Ser Gln His
                85                  90                  95

His His His His His
            100

<210> SEQ ID NO 472
<211> LENGTH: 90
<212> TYPE: PRT
<213> ORGANISM: Artificial Sequence
<220> FEATURE:
<223> OTHER INFORMATION: Synthetic: ATI_1523_C07 w/ N leader and
      modified C-terminus including PC

<400> SEQUENCE: 472

Gly Val Ser Asp Val Pro Arg Asp Leu Glu Val Val Ala Ala Thr Pro
1               5                   10                  15

Thr Ser Leu Leu Ile Ser Trp Arg Met His Thr Asp Pro Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Glu Ala Thr Ile Ser Gly Leu Lys Pro Gly Val Asp
    50                  55                  60

Tyr Thr Ile Thr Val Tyr Ala Ile Gln Thr Ala His Tyr Tyr Arg Ile
65                  70                  75                  80

Asn Ile Ser Ile Asn Tyr Arg Thr Pro Cys
                85                  90

<210> SEQ ID NO 473
<211> LENGTH: 96
<212> TYPE: PRT
<213> ORGANISM: Artificial Sequence
<220> FEATURE:
<223> OTHER INFORMATION: Synthetic: ATI_1523_C07 w/ N leader and
      modified C-terminus including PC + his tag

<400> SEQUENCE: 473

Gly Val Ser Asp Val Pro Arg Asp Leu Glu Val Val Ala Ala Thr Pro
1               5                   10                  15

Thr Ser Leu Leu Ile Ser Trp Arg Met His Thr Asp Pro Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Glu Ala Thr Ile Ser Gly Leu Lys Pro Gly Val Asp
    50                  55                  60

Tyr Thr Ile Thr Val Tyr Ala Ile Gln Thr Ala His Tyr Tyr Arg Ile

```
                65                  70                  75                  80
Asn Ile Ser Ile Asn Tyr Arg Thr Pro Cys His His His His His
                85                  90                  95
```

<210> SEQ ID NO 474
<211> LENGTH: 102
<212> TYPE: PRT
<213> ORGANISM: Artificial Sequence
<220> FEATURE:
<223> OTHER INFORMATION: Synthetic: ATI_1523_C07 full length

<400> SEQUENCE: 474

```
Met Gly Val Ser Asp Val Pro Arg Asp Leu Glu Val Val Ala Ala Thr
1               5                   10                  15

Pro Thr Ser Leu Leu Ile Ser Trp Arg Met His Thr Asp Pro Asp Tyr
                20                  25                  30

Arg Ile Thr Tyr Gly Glu Thr Gly Gly Asn Ser Pro Val Gln Glu Phe
                35                  40                  45

Thr Val Pro Asp Gln Glu Ala Thr Ile Ser Gly Leu Lys Pro Gly Val
            50                  55                  60

Asp Tyr Thr Ile Thr Val Tyr Ala Ile Gln Thr Ala His Tyr Tyr Arg
65                  70                  75                  80

Ile Asn Ile Ser Ile Asn Tyr Arg Thr Glu Ile Asp Lys Pro Ser Gln
                85                  90                  95

His His His His His His
            100
```

<210> SEQ ID NO 475
<211> LENGTH: 79
<212> TYPE: PRT
<213> ORGANISM: Artificial Sequence
<220> FEATURE:
<223> OTHER INFORMATION: Synthetic: ATI_1523_D07 core

<400> SEQUENCE: 475

```
Glu Val Val Ala Ala Thr Pro Thr Ser Leu Leu Ile Ser Trp Glu Asn
1               5                   10                  15

Leu Ala Ser Tyr Gln Tyr Arg Ile Thr Tyr Gly Glu Thr Gly Gly Asn
                20                  25                  30

Ser Pro Val Gln Glu Phe Thr Val Pro Asp Val Gln Ala Thr Ile Ser
            35                  40                  45

Gly Leu Lys Pro Gly Val Asp Tyr Thr Ile Thr Val Tyr Ala Leu Pro
        50                  55                  60

Tyr Ile His Met Lys Gln Arg Val Ile Ser Ile Asn Tyr Arg Thr
65                  70                  75
```

<210> SEQ ID NO 476
<211> LENGTH: 7
<212> TYPE: PRT
<213> ORGANISM: Artificial Sequence
<220> FEATURE:
<223> OTHER INFORMATION: Synthetic: ATI_1523_D07 BC loop

<400> SEQUENCE: 476

```
Glu Asn Leu Ala Ser Tyr Gln
1               5
```

<210> SEQ ID NO 477
<211> LENGTH: 4
<212> TYPE: PRT
<213> ORGANISM: Artificial Sequence

```
<220> FEATURE:
<223> OTHER INFORMATION: Synthetic: ATI_1523_D07 DE loop

<400> SEQUENCE: 477

Pro Asp Val Gln
1

<210> SEQ ID NO 478
<211> LENGTH: 10
<212> TYPE: PRT
<213> ORGANISM: Artificial Sequence
<220> FEATURE:
<223> OTHER INFORMATION: Synthetic: ATI_1523_D07 FG loop

<400> SEQUENCE: 478

Leu Pro Tyr Ile His Met Lys Gln Arg Val
1               5                   10

<210> SEQ ID NO 479
<211> LENGTH: 88
<212> TYPE: PRT
<213> ORGANISM: Artificial Sequence
<220> FEATURE:
<223> OTHER INFORMATION: Synthetic: ATI_1523_D07 w/ N leader

<400> SEQUENCE: 479

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
                20                  25                  30

Ile Thr Tyr Gly Glu Thr Gly Gly Asn Ser Pro Val Gln Glu Phe Thr
            35                  40                  45

Val Pro Asp Val Gln Ala Thr Ile Ser Gly Leu Lys Pro Gly Val Asp
        50                  55                  60

Tyr Thr Ile Thr Val Tyr Ala Leu Pro Tyr Ile His Met Lys Gln Arg
65                  70                  75                  80

Val Ile Ser Ile Asn Tyr Arg Thr
                85

<210> SEQ ID NO 480
<211> LENGTH: 94
<212> TYPE: PRT
<213> ORGANISM: Artificial Sequence
<220> FEATURE:
<223> OTHER INFORMATION: Synthetic: ATI_1523_D07 w/ N leader + his tag

<400> SEQUENCE: 480

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
                20                  25                  30

Ile Thr Tyr Gly Glu Thr Gly Gly Asn Ser Pro Val Gln Glu Phe Thr
            35                  40                  45

Val Pro Asp Val Gln Ala Thr Ile Ser Gly Leu Lys Pro Gly Val Asp
        50                  55                  60

Tyr Thr Ile Thr Val Tyr Ala Leu Pro Tyr Ile His Met Lys Gln Arg
65                  70                  75                  80

Val Ile Ser Ile Asn Tyr Arg Thr His His His His His His
                85                  90

<210> SEQ ID NO 481
```

<211> LENGTH: 95
<212> TYPE: PRT
<213> ORGANISM: Artificial Sequence
<220> FEATURE:
<223> OTHER INFORMATION: Synthetic: ATI_1523_D07 w/ N leader and C tail

<400> SEQUENCE: 481

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Gly Asn Ser Pro Val Gln Glu Phe Thr
        35                  40                  45

Val Pro Asp Val Gln Ala Thr Ile Ser Gly Leu Lys Pro Gly Val Asp
    50                  55                  60

Tyr Thr Ile Thr Val Tyr Ala Leu Pro Tyr Ile His Met Lys Gln Arg
65                  70                  75                  80

Val Ile Ser Ile Asn Tyr Arg Thr Glu Ile Asp Lys Pro Ser Gln
                85                  90                  95

<210> SEQ ID NO 482
<211> LENGTH: 101
<212> TYPE: PRT
<213> ORGANISM: Artificial Sequence
<220> FEATURE:
<223> OTHER INFORMATION: Synthetic: ATI_1523_D07 w/ N leader and C
      tail + his tag

<400> SEQUENCE: 482

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Gly Asn Ser Pro Val Gln Glu Phe Thr
        35                  40                  45

Val Pro Asp Val Gln Ala Thr Ile Ser Gly Leu Lys Pro Gly Val Asp
    50                  55                  60

Tyr Thr Ile Thr Val Tyr Ala Leu Pro Tyr Ile His Met Lys Gln Arg
65                  70                  75                  80

Val Ile Ser Ile Asn Tyr Arg Thr Glu Ile Asp Lys Pro Ser Gln His
                85                  90                  95

His His His His His
        100

<210> SEQ ID NO 483
<211> LENGTH: 90
<212> TYPE: PRT
<213> ORGANISM: Artificial Sequence
<220> FEATURE:
<223> OTHER INFORMATION: Synthetic: ATI_1523_D07 w/ N leader and
      modified C-terminus including PC

<400> SEQUENCE: 483

Gly Val Ser Asp Val Pro Arg Asp Leu Glu Val Val Ala Ala Thr Pro
1               5                   10                  15

Thr Ser Leu Leu Ile Ser Trp Glu Asn Leu Ala Ser Tyr Gln Tyr Arg
            20                  25                  30

Ile Thr Tyr Gly Glu Thr Gly Gly Asn Ser Pro Val Gln Glu Phe Thr
        35                  40                  45

Val Pro Asp Val Gln Ala Thr Ile Ser Gly Leu Lys Pro Gly Val Asp

```
                    50                  55                  60

Tyr Thr Ile Thr Val Tyr Ala Leu Pro Tyr Ile His Met Lys Gln Arg
 65                  70                  75                  80

Val Ile Ser Ile Asn Tyr Arg Thr Pro Cys
                 85                  90

<210> SEQ ID NO 484
<211> LENGTH: 96
<212> TYPE: PRT
<213> ORGANISM: Artificial Sequence
<220> FEATURE:
<223> OTHER INFORMATION: Synthetic: ATI_1523_D07 w/ N leader and
      modified C-terminus including PC + his tag

<400> SEQUENCE: 484

Gly Val Ser Asp Val Pro Arg Asp Leu Glu Val Val Ala Ala Thr Pro
  1               5                  10                  15

Thr Ser Leu Leu Ile Ser Trp Glu Asn Leu Ala Ser Tyr Gln Tyr Arg
                 20                  25                  30

Ile Thr Tyr Gly Glu Thr Gly Gly Asn Ser Pro Val Gln Glu Phe Thr
             35                  40                  45

Val Pro Asp Val Gln Ala Thr Ile Ser Gly Leu Lys Pro Gly Val Asp
         50                  55                  60

Tyr Thr Ile Thr Val Tyr Ala Leu Pro Tyr Ile His Met Lys Gln Arg
 65                  70                  75                  80

Val Ile Ser Ile Asn Tyr Arg Thr Pro Cys His His His His His His
                 85                  90                  95

<210> SEQ ID NO 485
<211> LENGTH: 102
<212> TYPE: PRT
<213> ORGANISM: Artificial Sequence
<220> FEATURE:
<223> OTHER INFORMATION: Synthetic: ATI_1523_D07  full length

<400> SEQUENCE: 485

Met Gly Val Ser Asp Val Pro Arg Asp Leu Glu Val Val Ala Ala Thr
  1               5                  10                  15

Pro Thr Ser Leu Leu Ile Ser Trp Glu Asn Leu Ala Ser Tyr Gln Tyr
                 20                  25                  30

Arg Ile Thr Tyr Gly Glu Thr Gly Gly Asn Ser Pro Val Gln Glu Phe
             35                  40                  45

Thr Val Pro Asp Val Gln Ala Thr Ile Ser Gly Leu Lys Pro Gly Val
         50                  55                  60

Asp Tyr Thr Ile Thr Val Tyr Ala Leu Pro Tyr Ile His Met Lys Gln
 65                  70                  75                  80

Arg Val Ile Ser Ile Asn Tyr Arg Thr Glu Ile Asp Lys Pro Ser Gln
                 85                  90                  95

His His His His His His
            100

<210> SEQ ID NO 486
<211> LENGTH: 79
<212> TYPE: PRT
<213> ORGANISM: Artificial Sequence
<220> FEATURE:
<223> OTHER INFORMATION: Synthetic: ATI_1523_D08 core

<400> SEQUENCE: 486

Glu Val Val Ala Ala Thr Pro Thr Ser Leu Leu Ile Ser Trp Met Arg
```

```
                1               5                  10                 15
Tyr Tyr Asp Ala Tyr Tyr Arg Ile Thr Tyr Gly Glu Thr Gly Gly Asn
                20                 25                 30

Ser Pro Val Gln Glu Phe Thr Val Pro Asp Gln Ser Ala Thr Ile Ser
            35                 40                 45

Gly Leu Lys Pro Gly Val Asp Tyr Thr Ile Thr Val Tyr Ala Leu Glu
        50                 55                 60

Lys Ala His Tyr Tyr Arg Gln Asn Ile Ser Ile Asn Tyr Arg Thr
65                  70                 75
```

<210> SEQ ID NO 487
<211> LENGTH: 7
<212> TYPE: PRT
<213> ORGANISM: Artificial Sequence
<220> FEATURE:
<223> OTHER INFORMATION: Synthetic: ATI_1523_D08 BC loop

<400> SEQUENCE: 487

```
Met Arg Tyr Tyr Asp Ala Tyr
1               5
```

<210> SEQ ID NO 488
<211> LENGTH: 4
<212> TYPE: PRT
<213> ORGANISM: Artificial Sequence
<220> FEATURE:
<223> OTHER INFORMATION: Synthetic: ATI_1523_D08 DE loop

<400> SEQUENCE: 488

```
Pro Asp Gln Ser
1
```

<210> SEQ ID NO 489
<211> LENGTH: 10
<212> TYPE: PRT
<213> ORGANISM: Artificial Sequence
<220> FEATURE:
<223> OTHER INFORMATION: Synthetic: ATI_1523_D08 FG loop

<400> SEQUENCE: 489

```
Leu Glu Lys Ala His Tyr Tyr Arg Gln Asn
1               5                  10
```

<210> SEQ ID NO 490
<211> LENGTH: 88
<212> TYPE: PRT
<213> ORGANISM: Artificial Sequence
<220> FEATURE:
<223> OTHER INFORMATION: Synthetic: ATI_1523_D08 w/ N leader

<400> SEQUENCE: 490

```
Gly Val Ser Asp Val Pro Arg Asp Leu Glu Val Val Ala Ala Thr Pro
1               5                  10                 15

Thr Ser Leu Leu Ile Ser Trp Met Arg Tyr Tyr Asp Ala Tyr Tyr Arg
            20                 25                 30

Ile Thr Tyr Gly Glu Thr Gly Gly Asn Ser Pro Val Gln Glu Phe Thr
        35                 40                 45

Val Pro Asp Gln Ser Ala Thr Ile Ser Gly Leu Lys Pro Gly Val Asp
    50                 55                 60

Tyr Thr Ile Thr Val Tyr Ala Leu Glu Lys Ala His Tyr Tyr Arg Gln
65                 70                 75                  80

Asn Ile Ser Ile Asn Tyr Arg Thr
```

<210> SEQ ID NO 491
<211> LENGTH: 94
<212> TYPE: PRT
<213> ORGANISM: Artificial Sequence
<220> FEATURE:
<223> OTHER INFORMATION: Synthetic: ATI_1523_D08 w/ N leader + his tag

<400> SEQUENCE: 491

Gly Val Ser Asp Val Pro Arg Asp Leu Glu Val Val Ala Ala Thr Pro
1               5                   10                  15

Thr Ser Leu Leu Ile Ser Trp Met Arg Tyr Tyr Asp Ala Tyr Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr His His His His His
                85                  90

<210> SEQ ID NO 492
<211> LENGTH: 95
<212> TYPE: PRT
<213> ORGANISM: Artificial Sequence
<220> FEATURE:
<223> OTHER INFORMATION: Synthetic: ATI_1523_D08 w/ N leader and C tail

<400> SEQUENCE: 492

Gly Val Ser Asp Val Pro Arg Asp Leu Glu Val Val Ala Ala Thr Pro
1               5                   10                  15

Thr Ser Leu Leu Ile Ser Trp Met Arg Tyr Tyr Asp Ala Tyr Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp
    50                  55                  60

Tyr Thr Ile Thr Val Tyr Ala Leu Glu Lys Ala His Tyr Tyr Arg Gln
65                  70                  75                  80

Asn Ile Ser Ile Asn Tyr Arg Thr Glu Ile Asp Lys Pro Ser Gln
                85                  90                  95

<210> SEQ ID NO 493
<211> LENGTH: 101
<212> TYPE: PRT
<213> ORGANISM: Artificial Sequence
<220> FEATURE:
<223> OTHER INFORMATION: Synthetic: ATI_1523_D08 w/ N leader and C
      tail + his tag

<400> SEQUENCE: 493

Gly Val Ser Asp Val Pro Arg Asp Leu Glu Val Val Ala Ala Thr Pro
1               5                   10                  15

Thr Ser Leu Leu Ile Ser Trp Met Arg Tyr Tyr Asp Ala Tyr Tyr Arg
            20                  25                  30

Ile Thr Tyr Gly Glu Thr Gly Gly Asn Ser Pro Val Gln Glu Phe Thr
        35                  40                  45

Val Pro Asp Gln Ser Ala Thr Ile Ser Gly Leu Lys Pro Gly Val Asp 50                  55                  60

Tyr Thr Ile Thr Val Tyr Ala Leu Glu Lys Ala His Tyr Tyr Arg Gln
 65                  70                  75                  80

Asn Ile Ser Ile Asn Tyr Arg Thr Glu Ile Asp Lys Pro Ser Gln His
                     85                  90                  95

His His His His His
            100

<210> SEQ ID NO 494
<211> LENGTH: 90
<212> TYPE: PRT
<213> ORGANISM: Artificial Sequence
<220> FEATURE:
<223> OTHER INFORMATION: Synthetic: ATI_1523_D08 w/ N leader and
      modified C-terminus including PC

<400> SEQUENCE: 494

Gly Val Ser Asp Val Pro Arg Asp Leu Glu Val Val Ala Ala Thr Pro
  1               5                  10                  15

Thr Ser Leu Leu Ile Ser Trp Met Arg Tyr Tyr Asp Ala Tyr Tyr Arg
                 20                  25                  30

Ile Thr Tyr Gly Glu Thr Gly Gly Asn Ser Pro Val Gln Glu Phe Thr
             35                  40                  45

Val Pro Asp Gln Ser Ala Thr Ile Ser Gly Leu Lys Pro Gly Val Asp
         50                  55                  60

Tyr Thr Ile Thr Val Tyr Ala Leu Glu Lys Ala His Tyr Tyr Arg Gln
 65                  70                  75                  80

Asn Ile Ser Ile Asn Tyr Arg Thr Pro Cys
                 85                  90

<210> SEQ ID NO 495
<211> LENGTH: 96
<212> TYPE: PRT
<213> ORGANISM: Artificial Sequence
<220> FEATURE:
<223> OTHER INFORMATION: Synthetic: ATI_1523_D08 w/ N leader and
      modified C-terminus including PC + his tag

<400> SEQUENCE: 495

Gly Val Ser Asp Val Pro Arg Asp Leu Glu Val Val Ala Ala Thr Pro
  1               5                  10                  15

Thr Ser Leu Leu Ile Ser Trp Met Arg Tyr Tyr Asp Ala Tyr Tyr Arg
                 20                  25                  30

Ile Thr Tyr Gly Glu Thr Gly Gly Asn Ser Pro Val Gln Glu Phe Thr
             35                  40                  45

Val Pro Asp Gln Ser Ala Thr Ile Ser Gly Leu Lys Pro Gly Val Asp
         50                  55                  60

Tyr Thr Ile Thr Val Tyr Ala Leu Glu Lys Ala His Tyr Tyr Arg Gln
 65                  70                  75                  80

Asn Ile Ser Ile Asn Tyr Arg Thr Pro Cys His His His His His
                 85                  90                  95

<210> SEQ ID NO 496
<211> LENGTH: 102
<212> TYPE: PRT
<213> ORGANISM: Artificial Sequence
<220> FEATURE:
<223> OTHER INFORMATION: Synthetic: ATI_1523_D08 full length

<400> SEQUENCE: 496

Met Gly Val Ser Asp Val Pro Arg Asp Leu Glu Val Val Ala Ala Thr
1               5                   10                  15

Pro Thr Ser Leu Leu Ile Ser Trp Met Arg Tyr Tyr Asp Ala Tyr Tyr
            20                  25                  30

Arg Ile Thr Tyr Gly Glu Thr Gly Gly Asn Ser Pro Val Gln Glu Phe
            35                  40                  45

Thr Val Pro Asp Gln Ser Ala Thr Ile Ser Gly Leu Lys Pro Gly Val
            50                  55                  60

Asp Tyr Thr Ile Thr Val Tyr Ala Leu Glu Lys Ala His Tyr Tyr Arg
65                  70                  75                  80

Gln Asn Ile Ser Ile Asn Tyr Arg Thr Glu Ile Asp Lys Pro Ser Gln
            85                  90                  95

His His His His His His
            100

<210> SEQ ID NO 497
<211> LENGTH: 79
<212> TYPE: PRT
<213> ORGANISM: Artificial Sequence
<220> FEATURE:
<223> OTHER INFORMATION: Synthetic: ATI_1523_E08 core

<400> SEQUENCE: 497

Glu Val Val Ala Ala Thr Pro Thr Ser Leu Leu Ile Ser Trp His His
1               5                   10                  15

Tyr Gln His Tyr Glu Tyr Arg Ile Thr Tyr Gly Glu Thr Gly Gly Asn
            20                  25                  30

Ser Pro Val Gln Glu Phe Thr Val Pro Asp Met Gly Ala Thr Ile Ser
            35                  40                  45

Gly Leu Lys Pro Gly Val Asp Tyr Thr Ile Thr Val Tyr Ala Leu Glu
            50                  55                  60

Glu Ala His Ser Asp Arg Ser Ser Ile Ser Ile Asn Tyr Arg Thr
65                  70                  75

<210> SEQ ID NO 498
<211> LENGTH: 7
<212> TYPE: PRT
<213> ORGANISM: Artificial Sequence
<220> FEATURE:
<223> OTHER INFORMATION: Synthetic: ATI_1523_E08 BC loop

<400> SEQUENCE: 498

His His Tyr Gln His Tyr Glu
1               5

<210> SEQ ID NO 499
<211> LENGTH: 4
<212> TYPE: PRT
<213> ORGANISM: Artificial Sequence
<220> FEATURE:
<223> OTHER INFORMATION: Synthetic: ATI_1523_E08 DE loop

<400> SEQUENCE: 499

Pro Asp Met Gly
1

<210> SEQ ID NO 500
<211> LENGTH: 10
<212> TYPE: PRT
<213> ORGANISM: Artificial Sequence
<220> FEATURE:
<223> OTHER INFORMATION: Synthetic: ATI_1523_E08 FG loop

```
<400> SEQUENCE: 500

Leu Glu Glu Ala His Ser Asp Arg Ser Ser
1               5                  10

<210> SEQ ID NO 501
<211> LENGTH: 88
<212> TYPE: PRT
<213> ORGANISM: Artificial Sequence
<220> FEATURE:
<223> OTHER INFORMATION: Synthetic: ATI_1523_E08 w/ N leader

<400> SEQUENCE: 501

Gly Val Ser Asp Val Pro Arg Asp Leu Glu Val Val Ala Ala Thr Pro
1               5                   10                  15

Thr Ser Leu Leu Ile Ser Trp His His Tyr Gln His Tyr Glu Tyr Arg
            20                  25                  30

Ile Thr Tyr Gly Glu Thr Gly Gly Asn Ser Pro Val Gln Glu Phe Thr
        35                  40                  45

Val Pro Asp Met Gly Ala Thr Ile Ser Gly Leu Lys Pro Gly Val Asp
    50                  55                  60

Tyr Thr Ile Thr Val Tyr Ala Leu Glu Glu Ala His Ser Asp Arg Ser
65                  70                  75                  80

Ser Ile Ser Ile Asn Tyr Arg Thr
                85

<210> SEQ ID NO 502
<211> LENGTH: 94
<212> TYPE: PRT
<213> ORGANISM: Artificial Sequence
<220> FEATURE:
<223> OTHER INFORMATION: Synthetic: ATI_1523_E08 w/ N leader + his tag

<400> SEQUENCE: 502

Gly Val Ser Asp Val Pro Arg Asp Leu Glu Val Val Ala Ala Thr Pro
1               5                   10                  15

Thr Ser Leu Leu Ile Ser Trp His His Tyr Gln His Tyr Glu Tyr Arg
            20                  25                  30

Ile Thr Tyr Gly Glu Thr Gly Gly Asn Ser Pro Val Gln Glu Phe Thr
        35                  40                  45

Val Pro Asp Met Gly Ala Thr Ile Ser Gly Leu Lys Pro Gly Val Asp
    50                  55                  60

Tyr Thr Ile Thr Val Tyr Ala Leu Glu Glu Ala His Ser Asp Arg Ser
65                  70                  75                  80

Ser Ile Ser Ile Asn Tyr Arg Thr His His His His His
                85                  90

<210> SEQ ID NO 503
<211> LENGTH: 95
<212> TYPE: PRT
<213> ORGANISM: Artificial Sequence
<220> FEATURE:
<223> OTHER INFORMATION: Synthetic: ATI_1523_E08 w/ N leader and C tail

<400> SEQUENCE: 503

Gly Val Ser Asp Val Pro Arg Asp Leu Glu Val Val Ala Ala Thr Pro
1               5                   10                  15

Thr Ser Leu Leu Ile Ser Trp His His Tyr Gln His Tyr Glu Tyr Arg
            20                  25                  30

Ile Thr Tyr Gly Glu Thr Gly Gly Asn Ser Pro Val Gln Glu Phe Thr
```

```
                35                  40                  45
Val Pro Asp Met Gly Ala Thr Ile Ser Gly Leu Lys Pro Gly Val Asp
 50                  55                  60

Tyr Thr Ile Thr Val Tyr Ala Leu Glu Glu Ala His Ser Asp Arg Ser
 65                  70                  75                  80

Ser Ile Ser Ile Asn Tyr Arg Thr Glu Ile Asp Lys Pro Ser Gln
                 85                  90                  95

<210> SEQ ID NO 504
<211> LENGTH: 101
<212> TYPE: PRT
<213> ORGANISM: Artificial Sequence
<220> FEATURE:
<223> OTHER INFORMATION: Synthetic: ATI_1523_E08 w/ N leader and C
      tail + his tag

<400> SEQUENCE: 504

Gly Val Ser Asp Val Pro Arg Asp Leu Glu Val Val Ala Ala Thr Pro
 1               5                  10                  15

Thr Ser Leu Leu Ile Ser Trp His His Tyr Gln His Tyr Glu Tyr Arg
                 20                  25                  30

Ile Thr Tyr Gly Glu Thr Gly Gly Asn Ser Pro Val Gln Glu Phe Thr
             35                  40                  45

Val Pro Asp Met Gly Ala Thr Ile Ser Gly Leu Lys Pro Gly Val Asp
 50                  55                  60

Tyr Thr Ile Thr Val Tyr Ala Leu Glu Glu Ala His Ser Asp Arg Ser
 65                  70                  75                  80

Ser Ile Ser Ile Asn Tyr Arg Thr Glu Ile Asp Lys Pro Ser Gln His
                 85                  90                  95

His His His His His
            100

<210> SEQ ID NO 505
<211> LENGTH: 90
<212> TYPE: PRT
<213> ORGANISM: Artificial Sequence
<220> FEATURE:
<223> OTHER INFORMATION: Synthetic: ATI_1523_E08 w/ N leader and
      modified C-terminus including PC

<400> SEQUENCE: 505

Gly Val Ser Asp Val Pro Arg Asp Leu Glu Val Val Ala Ala Thr Pro
 1               5                  10                  15

Thr Ser Leu Leu Ile Ser Trp His His Tyr Gln His Tyr Glu Tyr Arg
                 20                  25                  30

Ile Thr Tyr Gly Glu Thr Gly Gly Asn Ser Pro Val Gln Glu Phe Thr
             35                  40                  45

Val Pro Asp Met Gly Ala Thr Ile Ser Gly Leu Lys Pro Gly Val Asp
 50                  55                  60

Tyr Thr Ile Thr Val Tyr Ala Leu Glu Glu Ala His Ser Asp Arg Ser
 65                  70                  75                  80

Ser Ile Ser Ile Asn Tyr Arg Thr Pro Cys
                 85                  90

<210> SEQ ID NO 506
<211> LENGTH: 96
<212> TYPE: PRT
<213> ORGANISM: Artificial Sequence
<220> FEATURE:
<223> OTHER INFORMATION: Synthetic: ATI_1523_E08 w/ N leader and
``` modified C-terminus including PC + his tag

<400> SEQUENCE: 506

Gly Val Ser Asp Val Pro Arg Asp Leu Glu Val Ala Ala Thr Pro
1               5                   10                  15

Thr Ser Leu Leu Ile Ser Trp His His Tyr Gln His Tyr Glu Tyr Arg
            20                  25                  30

Ile Thr Tyr Gly Glu Thr Gly Gly Asn Ser Pro Val Gln Glu Phe Thr
                35                  40                  45

Val Pro Asp Met Gly Ala Thr Ile Ser Gly Leu Lys Pro Gly Val Asp
    50                  55                  60

Tyr Thr Ile Thr Val Tyr Ala Leu Glu Glu Ala His Ser Asp Arg Ser
65                  70                  75                  80

Ser Ile Ser Ile Asn Tyr Arg Thr Pro Cys His His His His His
                85                  90                  95

<210> SEQ ID NO 507
<211> LENGTH: 102
<212> TYPE: PRT
<213> ORGANISM: Artificial Sequence
<220> FEATURE:
<223> OTHER INFORMATION: Synthetic: ATI_1523_E08 full length

<400> SEQUENCE: 507

Met Gly Val Ser Asp Val Pro Arg Asp Leu Glu Val Ala Ala Thr
1               5                   10                  15

Pro Thr Ser Leu Leu Ile Ser Trp His His Tyr Gln His Tyr Glu Tyr
            20                  25                  30

Arg Ile Thr Tyr Gly Glu Thr Gly Gly Asn Ser Pro Val Gln Glu Phe
                35                  40                  45

Thr Val Pro Asp Met Gly Ala Thr Ile Ser Gly Leu Lys Pro Gly Val
    50                  55                  60

Asp Tyr Thr Ile Thr Val Tyr Ala Leu Glu Glu Ala His Ser Asp Arg
65                  70                  75                  80

Ser Ser Ile Ser Ile Asn Tyr Arg Thr Glu Ile Asp Lys Pro Ser Gln
                85                  90                  95

His His His His His His
            100

<210> SEQ ID NO 508
<211> LENGTH: 76
<212> TYPE: PRT
<213> ORGANISM: Artificial Sequence
<220> FEATURE:
<223> OTHER INFORMATION: Synthetic: ATI_1523_F01 core

<400> SEQUENCE: 508

Glu Val Val Ala Ala Thr Pro Thr Ser Leu Leu Ile Ser Trp Tyr Lys
1               5                   10                  15

Pro Ser Thr Ile Val Thr Tyr Arg Ile Thr Tyr Gly Glu Thr Gly Gly
            20                  25                  30

Asn Ser Pro Val Gln Glu Phe Thr Val Tyr Gly Tyr Asn Ala Thr Ile
                35                  40                  45

Ser Gly Leu Lys Pro Gly Val Asp Tyr Thr Ile Thr Val Tyr Ala Val
    50                  55                  60

His Gly Val Arg Phe Ile Ser Ile Asn Tyr Arg Thr
65                  70                  75

-continued

```
<210> SEQ ID NO 509
<211> LENGTH: 8
<212> TYPE: PRT
<213> ORGANISM: Artificial Sequence
<220> FEATURE:
<223> OTHER INFORMATION: Synthetic: ATI_1523_F01 BC loop

<400> SEQUENCE: 509

Tyr Lys Pro Ser Thr Ile Val Thr
1               5

<210> SEQ ID NO 510
<211> LENGTH: 4
<212> TYPE: PRT
<213> ORGANISM: Artificial Sequence
<220> FEATURE:
<223> OTHER INFORMATION: Synthetic: ATI_1523_F01 DE loop

<400> SEQUENCE: 510

Tyr Gly Tyr Asn
1

<210> SEQ ID NO 511
<211> LENGTH: 6
<212> TYPE: PRT
<213> ORGANISM: Artificial Sequence
<220> FEATURE:
<223> OTHER INFORMATION: Synthetic: ATI_1523_F01 FG loop

<400> SEQUENCE: 511

Val His Gly Val Arg Phe
1               5

<210> SEQ ID NO 512
<211> LENGTH: 85
<212> TYPE: PRT
<213> ORGANISM: Artificial Sequence
<220> FEATURE:
<223> OTHER INFORMATION: Synthetic: ATI_1523_F01 w/ N leader

<400> SEQUENCE: 512

Gly Val Ser Asp Val Pro Arg Asp Leu Glu Val Val Ala Ala Thr Pro
1               5                   10                  15

Thr Ser Leu Leu Ile Ser Trp Tyr Lys Pro Ser Thr Ile Val Thr Tyr
            20                  25                  30

Arg Ile Thr Tyr Gly Glu Thr Gly Gly Asn Ser Pro Val Gln Glu Phe
        35                  40                  45

Thr Val Tyr Gly Tyr Asn Ala Thr Ile Ser Gly Leu Lys Pro Gly Val
    50                  55                  60

Asp Tyr Thr Ile Thr Val Tyr Ala Val His Gly Val Arg Phe Ile Ser
65                  70                  75                  80

Ile Asn Tyr Arg Thr
                85

<210> SEQ ID NO 513
<211> LENGTH: 91
<212> TYPE: PRT
<213> ORGANISM: Artificial Sequence
<220> FEATURE:
<223> OTHER INFORMATION: Synthetic: ATI_1523_F01 w/ N leader + his tag

<400> SEQUENCE: 513

Gly Val Ser Asp Val Pro Arg Asp Leu Glu Val Val Ala Ala Thr Pro
1               5                   10                  15
```

```
Thr Ser Leu Leu Ile Ser Trp Tyr Lys Pro Ser Thr Ile Val Thr Tyr
            20                  25                  30

Arg Ile Thr Tyr Gly Glu Thr Gly Gly Asn Ser Pro Val Gln Glu Phe
        35                  40                  45

Thr Val Tyr Gly Tyr Asn Ala Thr Ile Ser Gly Leu Lys Pro Gly Val
    50                  55                  60

Asp Tyr Thr Ile Thr Val Tyr Ala Val His Gly Val Arg Phe Ile Ser
65                  70                  75                  80

Ile Asn Tyr Arg Thr His His His His His
                85                  90

<210> SEQ ID NO 514
<211> LENGTH: 92
<212> TYPE: PRT
<213> ORGANISM: Artificial Sequence
<220> FEATURE:
<223> OTHER INFORMATION: Synthetic: ATI_1523_F01 w/ N leader and C tail

<400> SEQUENCE: 514

Gly Val Ser Asp Val Pro Arg Asp Leu Glu Val Val Ala Ala Thr Pro
1               5                   10                  15

Thr Ser Leu Leu Ile Ser Trp Tyr Lys Pro Ser Thr Ile Val Thr Tyr
            20                  25                  30

Arg Ile Thr Tyr Gly Glu Thr Gly Gly Asn Ser Pro Val Gln Glu Phe
        35                  40                  45

Thr Val Tyr Gly Tyr Asn Ala Thr Ile Ser Gly Leu Lys Pro Gly Val
    50                  55                  60

Asp Tyr Thr Ile Thr Val Tyr Ala Val His Gly Val Arg Phe Ile Ser
65                  70                  75                  80

Ile Asn Tyr Arg Thr Glu Ile Asp Lys Pro Ser Gln
                85                  90

<210> SEQ ID NO 515
<211> LENGTH: 98
<212> TYPE: PRT
<213> ORGANISM: Artificial Sequence
<220> FEATURE:
<223> OTHER INFORMATION: Synthetic: ATI_1523_F01 w/ N leader and C
      tail + his tag

<400> SEQUENCE: 515

Gly Val Ser Asp Val Pro Arg Asp Leu Glu Val Val Ala Ala Thr Pro
1               5                   10                  15

Thr Ser Leu Leu Ile Ser Trp Tyr Lys Pro Ser Thr Ile Val Thr Tyr
            20                  25                  30

Arg Ile Thr Tyr Gly Glu Thr Gly Gly Asn Ser Pro Val Gln Glu Phe
        35                  40                  45

Thr Val Tyr Gly Tyr Asn Ala Thr Ile Ser Gly Leu Lys Pro Gly Val
    50                  55                  60

Asp Tyr Thr Ile Thr Val Tyr Ala Val His Gly Val Arg Phe Ile Ser
65                  70                  75                  80

Ile Asn Tyr Arg Thr Glu Ile Asp Lys Pro Ser Gln His His His His
                85                  90                  95

His His

<210> SEQ ID NO 516
<211> LENGTH: 87
<212> TYPE: PRT
<213> ORGANISM: Artificial Sequence
```

<220> FEATURE:
<223> OTHER INFORMATION: Synthetic: ATI_1523_F01 w/ N leader and
      modified C-terminus including PC

<400> SEQUENCE: 516

Gly Val Ser Asp Val Pro Arg Asp Leu Glu Val Val Ala Ala Thr Pro
1               5                   10                  15

Thr Ser Leu Leu Ile Ser Trp Tyr Lys Pro Ser Thr Ile Val Thr Tyr
            20                  25                  30

Arg Ile Thr Tyr Gly Glu Thr Gly Gly Asn Ser Pro Val Gln Glu Phe
        35                  40                  45

Thr Val Tyr Gly Tyr Asn Ala Thr Ile Ser Gly Leu Lys Pro Gly Val
    50                  55                  60

Asp Tyr Thr Ile Thr Val Tyr Ala Val His Gly Val Arg Phe Ile Ser
65                  70                  75                  80

Ile Asn Tyr Arg Thr Pro Cys
                85

<210> SEQ ID NO 517
<211> LENGTH: 93
<212> TYPE: PRT
<213> ORGANISM: Artificial Sequence
<220> FEATURE:
<223> OTHER INFORMATION: Synthetic: ATI_1523_F01 w/ N leader and
      modified C-terminus including PC + his tag

<400> SEQUENCE: 517

Gly Val Ser Asp Val Pro Arg Asp Leu Glu Val Val Ala Ala Thr Pro
1               5                   10                  15

Thr Ser Leu Leu Ile Ser Trp Tyr Lys Pro Ser Thr Ile Val Thr Tyr
            20                  25                  30

Arg Ile Thr Tyr Gly Glu Thr Gly Gly Asn Ser Pro Val Gln Glu Phe
        35                  40                  45

Thr Val Tyr Gly Tyr Asn Ala Thr Ile Ser Gly Leu Lys Pro Gly Val
    50                  55                  60

Asp Tyr Thr Ile Thr Val Tyr Ala Val His Gly Val Arg Phe Ile Ser
65                  70                  75                  80

Ile Asn Tyr Arg Thr Pro Cys His His His His His
                85                  90

<210> SEQ ID NO 518
<211> LENGTH: 99
<212> TYPE: PRT
<213> ORGANISM: Artificial Sequence
<220> FEATURE:
<223> OTHER INFORMATION: Synthetic: ATI_1523_F01 full length

<400> SEQUENCE: 518

Met Gly Val Ser Asp Val Pro Arg Asp Leu Glu Val Val Ala Ala Thr
1               5                   10                  15

Pro Thr Ser Leu Leu Ile Ser Trp Tyr Lys Pro Ser Thr Ile Val Thr
            20                  25                  30

Tyr Arg Ile Thr Tyr Gly Glu Thr Gly Gly Asn Ser Pro Val Gln Glu
        35                  40                  45

Phe Thr Val Tyr Gly Tyr Asn Ala Thr Ile Ser Gly Leu Lys Pro Gly
    50                  55                  60

Val Asp Tyr Thr Ile Thr Val Tyr Ala Val His Gly Val Arg Phe Ile
65                  70                  75                  80

Ser Ile Asn Tyr Arg Thr Glu Ile Asp Lys Pro Ser Gln His His His 85                  90                  95

His His His

<210> SEQ ID NO 519
<211> LENGTH: 78
<212> TYPE: PRT
<213> ORGANISM: Artificial Sequence
<220> FEATURE:
<223> OTHER INFORMATION: Synthetic: ATI_1523_F04 core

<400> SEQUENCE: 519

Glu Val Val Ala Ala Thr Pro Thr Ser Leu Leu Ile Ser Trp Gly Gly
1               5                   10                  15

Ser Leu Ser Pro Thr Phe Tyr Arg Ile Thr Tyr Gly Glu Thr Gly Gly
            20                  25                  30

Asn Ser Pro Val Gln Glu Phe Thr Val Thr Tyr Gln Gly Ala Thr Ile
        35                  40                  45

Ser Gly Leu Lys Pro Gly Val Asp Tyr Thr Ile Thr Val Tyr Ala Thr
    50                  55                  60

Glu Gly Ile Val Tyr Tyr Gln Ile Ser Ile Asn Tyr Arg Thr
65                  70                  75

<210> SEQ ID NO 520
<211> LENGTH: 8
<212> TYPE: PRT
<213> ORGANISM: Artificial Sequence
<220> FEATURE:
<223> OTHER INFORMATION: Synthetic: ATI_1523_F04 BC loop

<400> SEQUENCE: 520

Gly Gly Ser Leu Ser Pro Thr Phe
1               5

<210> SEQ ID NO 521
<211> LENGTH: 4
<212> TYPE: PRT
<213> ORGANISM: Artificial Sequence
<220> FEATURE:
<223> OTHER INFORMATION: Synthetic: ATI_1523_F04 DE loop

<400> SEQUENCE: 521

Thr Tyr Gln Gly
1

<210> SEQ ID NO 522
<211> LENGTH: 8
<212> TYPE: PRT
<213> ORGANISM: Artificial Sequence
<220> FEATURE:
<223> OTHER INFORMATION: Synthetic: ATI_1523_F04 FG loop

<400> SEQUENCE: 522

Thr Glu Gly Ile Val Tyr Tyr Gln
1               5

<210> SEQ ID NO 523
<211> LENGTH: 87
<212> TYPE: PRT
<213> ORGANISM: Artificial Sequence
<220> FEATURE:
<223> OTHER INFORMATION: Synthetic: ATI_1523_F04 w/ N leader

<400> SEQUENCE: 523

Gly Val Ser Asp Val Pro Arg Asp Leu Glu Val Val Ala Ala Thr Pro

```
            1               5                  10                  15
Thr Ser Leu Leu Ile Ser Trp Gly Gly Ser Leu Ser Pro Thr Phe Tyr
                    20                  25                  30

Arg Ile Thr Tyr Gly Glu Thr Gly Gly Asn Ser Pro Val Gln Glu Phe
                35                  40                  45

Thr Val Thr Tyr Gln Gly Ala Thr Ile Ser Gly Leu Lys Pro Gly Val
        50                  55                  60

Asp Tyr Thr Ile Thr Val Tyr Ala Thr Glu Gly Ile Val Tyr Tyr Gln
65                  70                  75                  80

Ile Ser Ile Asn Tyr Arg Thr
                85

<210> SEQ ID NO 524
<211> LENGTH: 93
<212> TYPE: PRT
<213> ORGANISM: Artificial Sequence
<220> FEATURE:
<223> OTHER INFORMATION: Synthetic: ATI_1523_F04 w/ N leader + his tag

<400> SEQUENCE: 524

Gly Val Ser Asp Val Pro Arg Asp Leu Glu Val Val Ala Ala Thr Pro
1               5                   10                  15

Thr Ser Leu Leu Ile Ser Trp Gly Gly Ser Leu Ser Pro Thr Phe Tyr
                    20                  25                  30

Arg Ile Thr Tyr Gly Glu Thr Gly Gly Asn Ser Pro Val Gln Glu Phe
                35                  40                  45

Thr Val Thr Tyr Gln Gly Ala Thr Ile Ser Gly Leu Lys Pro Gly Val
        50                  55                  60

Asp Tyr Thr Ile Thr Val Tyr Ala Thr Glu Gly Ile Val Tyr Tyr Gln
65                  70                  75                  80

Ile Ser Ile Asn Tyr Arg Thr His His His His His His
                85                  90

<210> SEQ ID NO 525
<211> LENGTH: 94
<212> TYPE: PRT
<213> ORGANISM: Artificial Sequence
<220> FEATURE:
<223> OTHER INFORMATION: Synthetic: ATI_1523_F04 w/ N leader and C tail

<400> SEQUENCE: 525

Gly Val Ser Asp Val Pro Arg Asp Leu Glu Val Val Ala Ala Thr Pro
1               5                   10                  15

Thr Ser Leu Leu Ile Ser Trp Gly Gly Ser Leu Ser Pro Thr Phe Tyr
                    20                  25                  30

Arg Ile Thr Tyr Gly Glu Thr Gly Gly Asn Ser Pro Val Gln Glu Phe
                35                  40                  45

Thr Val Thr Tyr Gln Gly Ala Thr Ile Ser Gly Leu Lys Pro Gly Val
        50                  55                  60

Asp Tyr Thr Ile Thr Val Tyr Ala Thr Glu Gly Ile Val Tyr Tyr Gln
65                  70                  75                  80

Ile Ser Ile Asn Tyr Arg Thr Glu Ile Asp Lys Pro Ser Gln
                85                  90

<210> SEQ ID NO 526
<211> LENGTH: 100
<212> TYPE: PRT
<213> ORGANISM: Artificial Sequence
<220> FEATURE:
```

<223> OTHER INFORMATION: Synthetic: ATI_1523_F04 w/ N leader and C
      tail + his tag

<400> SEQUENCE: 526

Gly Val Ser Asp Val Pro Arg Asp Leu Glu Val Val Ala Ala Thr Pro
1               5                   10                  15

Thr Ser Leu Leu Ile Ser Trp Gly Gly Ser Leu Ser Pro Thr Phe Tyr
            20                  25                  30

Arg Ile Thr Tyr Gly Glu Thr Gly Gly Asn Ser Pro Val Gln Glu Phe
        35                  40                  45

Thr Val Thr Tyr Gln Gly Ala Thr Ile Ser Gly Leu Lys Pro Gly Val
    50                  55                  60

Asp Tyr Thr Ile Thr Val Tyr Ala Thr Glu Gly Ile Val Tyr Tyr Gln
65                  70                  75                  80

Ile Ser Ile Asn Tyr Arg Thr Glu Ile Asp Lys Pro Ser Gln His His
                85                  90                  95

His His His His
        100

<210> SEQ ID NO 527
<211> LENGTH: 89
<212> TYPE: PRT
<213> ORGANISM: Artificial Sequence
<220> FEATURE:
<223> OTHER INFORMATION: Synthetic: ATI_1523_F04 w/ N leader and
      modified C-terminus including PC

<400> SEQUENCE: 527

Gly Val Ser Asp Val Pro Arg Asp Leu Glu Val Val Ala Ala Thr Pro
1               5                   10                  15

Thr Ser Leu Leu Ile Ser Trp Gly Gly Ser Leu Ser Pro Thr Phe Tyr
            20                  25                  30

Arg Ile Thr Tyr Gly Glu Thr Gly Gly Asn Ser Pro Val Gln Glu Phe
        35                  40                  45

Thr Val Thr Tyr Gln Gly Ala Thr Ile Ser Gly Leu Lys Pro Gly Val
    50                  55                  60

Asp Tyr Thr Ile Thr Val Tyr Ala Thr Glu Gly Ile Val Tyr Tyr Gln
65                  70                  75                  80

Ile Ser Ile Asn Tyr Arg Thr Pro Cys
                85

<210> SEQ ID NO 528
<211> LENGTH: 95
<212> TYPE: PRT
<213> ORGANISM: Artificial Sequence
<220> FEATURE:
<223> OTHER INFORMATION: Synthetic: ATI_1523_F04 w/ N leader and
      modified C-terminus including PC + his tag

<400> SEQUENCE: 528

Gly Val Ser Asp Val Pro Arg Asp Leu Glu Val Val Ala Ala Thr Pro
1               5                   10                  15

Thr Ser Leu Leu Ile Ser Trp Gly Gly Ser Leu Ser Pro Thr Phe Tyr
            20                  25                  30

Arg Ile Thr Tyr Gly Glu Thr Gly Gly Asn Ser Pro Val Gln Glu Phe
        35                  40                  45

Thr Val Thr Tyr Gln Gly Ala Thr Ile Ser Gly Leu Lys Pro Gly Val
    50                  55                  60

Asp Tyr Thr Ile Thr Val Tyr Ala Thr Glu Gly Ile Val Tyr Tyr Gln

```
                65                  70                  75                  80
Ile Ser Ile Asn Tyr Arg Thr Pro Cys His His His His His
                85                  90                  95

<210> SEQ ID NO 529
<211> LENGTH: 101
<212> TYPE: PRT
<213> ORGANISM: Artificial Sequence
<220> FEATURE:
<223> OTHER INFORMATION: Synthetic: ATI_1523_F04 full length

<400> SEQUENCE: 529

Met Gly Val Ser Asp Val Pro Arg Asp Leu Glu Val Val Ala Ala Thr
1               5                   10                  15

Pro Thr Ser Leu Leu Ile Ser Trp Gly Gly Ser Leu Ser Pro Thr Phe
            20                  25                  30

Tyr Arg Ile Thr Tyr Gly Glu Thr Gly Asn Ser Pro Val Gln Glu
        35                  40                  45

Phe Thr Val Thr Tyr Gln Gly Ala Thr Ile Ser Gly Leu Lys Pro Gly
    50                  55                  60

Val Asp Tyr Thr Ile Thr Val Tyr Ala Thr Glu Gly Ile Val Tyr Tyr
65                  70                  75                  80

Gln Ile Ser Ile Asn Tyr Arg Thr Glu Ile Asp Lys Pro Ser Gln His
                85                  90                  95

His His His His His
            100

<210> SEQ ID NO 530
<211> LENGTH: 79
<212> TYPE: PRT
<213> ORGANISM: Artificial Sequence
<220> FEATURE:
<223> OTHER INFORMATION: Synthetic: ATI_1523_F08 core

<400> SEQUENCE: 530

Glu Val Val Ala Ala Thr Pro Thr Ser Leu Leu Ile Ser Trp Val Tyr
1               5                   10                  15

His Tyr Asp Ala Gln Tyr Arg Ile Thr Tyr Gly Glu Thr Gly Gly Asn
            20                  25                  30

Ser Pro Val Gln Glu Phe Thr Val Pro Asp Gln Lys Ala Thr Ile Ser
        35                  40                  45

Gly Leu Lys Pro Gly Val Asp Tyr Thr Ile Thr Val Tyr Ala Leu Pro
    50                  55                  60

Arg Ala His Met Asp Arg Ser His Ile Ser Ile Asn Tyr Arg Thr
65                  70                  75

<210> SEQ ID NO 531
<211> LENGTH: 7
<212> TYPE: PRT
<213> ORGANISM: Artificial Sequence
<220> FEATURE:
<223> OTHER INFORMATION: Synthetic: ATI_1523_F08 BC loop

<400> SEQUENCE: 531

Val Tyr His Tyr Asp Ala Gln
1               5

<210> SEQ ID NO 532
<211> LENGTH: 4
<212> TYPE: PRT
<213> ORGANISM: Artificial Sequence
```

```
<220> FEATURE:
<223> OTHER INFORMATION: Synthetic: ATI_1523_F08 DE loop

<400> SEQUENCE: 532

Pro Asp Gln Lys
1

<210> SEQ ID NO 533
<211> LENGTH: 10
<212> TYPE: PRT
<213> ORGANISM: Artificial Sequence
<220> FEATURE:
<223> OTHER INFORMATION: Synthetic: ATI_1523_F08 FG loop

<400> SEQUENCE: 533

Leu Pro Arg Ala His Met Asp Arg Ser His
1               5                   10

<210> SEQ ID NO 534
<211> LENGTH: 88
<212> TYPE: PRT
<213> ORGANISM: Artificial Sequence
<220> FEATURE:
<223> OTHER INFORMATION: Synthetic: ATI_1523_F08 w/ N leader

<400> SEQUENCE: 534

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Pro Arg Ala His Met Asp Arg Ser
65                  70                  75                  80

His Ile Ser Ile Asn Tyr Arg Thr
                85

<210> SEQ ID NO 535
<211> LENGTH: 94
<212> TYPE: PRT
<213> ORGANISM: Artificial Sequence
<220> FEATURE:
<223> OTHER INFORMATION: Synthetic: ATI_1523_F08 w/ N leader + his tag

<400> SEQUENCE: 535

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Pro Arg Ala His Met Asp Arg Ser
65                  70                  75                  80

His Ile Ser Ile Asn Tyr Arg Thr His His His His His His
                85                  90

<210> SEQ ID NO 536
```

```
<211> LENGTH: 95
<212> TYPE: PRT
<213> ORGANISM: Artificial Sequence
<220> FEATURE:
<223> OTHER INFORMATION: Synthetic: ATI_1523_F08 w/ N leader and C tail

<400> SEQUENCE: 536

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Pro Arg Ala His Met Asp Arg Ser
65                  70                  75                  80

His Ile Ser Ile Asn Tyr Arg Thr Glu Ile Asp Lys Pro Ser Gln
                85                  90                  95

<210> SEQ ID NO 537
<211> LENGTH: 101
<212> TYPE: PRT
<213> ORGANISM: Artificial Sequence
<220> FEATURE:
<223> OTHER INFORMATION: Synthetic: ATI_1523_F08 w/ N leader and C
      tail + his tag

<400> SEQUENCE: 537

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Pro Arg Ala His Met Asp Arg Ser
65                  70                  75                  80

His Ile Ser Ile Asn Tyr Arg Thr Glu Ile Asp Lys Pro Ser Gln His
                85                  90                  95

His His His His His
        100

<210> SEQ ID NO 538
<211> LENGTH: 90
<212> TYPE: PRT
<213> ORGANISM: Artificial Sequence
<220> FEATURE:
<223> OTHER INFORMATION: Synthetic: ATI_1523_F08 w/ N leader and
      modified C-terminus including PC

<400> SEQUENCE: 538

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Gln Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
```

```
                    50                  55                  60

Tyr Thr Ile Thr Val Tyr Ala Leu Pro Arg Ala His Met Asp Arg Ser
 65                  70                  75                  80

His Ile Ser Ile Asn Tyr Arg Thr Pro Cys
                 85                  90

<210> SEQ ID NO 539
<211> LENGTH: 96
<212> TYPE: PRT
<213> ORGANISM: Artificial Sequence
<220> FEATURE:
<223> OTHER INFORMATION: Synthetic: ATI_1523_F08 w/ N leader and
      modified C-terminus including PC + his tag

<400> SEQUENCE: 539

Gly Val Ser Asp Val Pro Arg Asp Leu Glu Val Val Ala Ala Thr Pro
 1               5                  10                  15

Thr Ser Leu Leu Ile Ser Trp Val Tyr His Tyr Asp Ala Gln Tyr Arg
                 20                  25                  30

Ile Thr Tyr Gly Glu Thr Gly Gly Asn Ser Pro Val Gln Glu Phe Thr
                 35                  40                  45

Val Pro Asp Gln Lys Ala Thr Ile Ser Gly Leu Lys Pro Gly Val Asp
     50                  55                  60

Tyr Thr Ile Thr Val Tyr Ala Leu Pro Arg Ala His Met Asp Arg Ser
 65                  70                  75                  80

His Ile Ser Ile Asn Tyr Arg Thr Pro Cys His His His His His
                 85                  90                  95

<210> SEQ ID NO 540
<211> LENGTH: 102
<212> TYPE: PRT
<213> ORGANISM: Artificial Sequence
<220> FEATURE:
<223> OTHER INFORMATION: Synthetic: ATI_1523_F08 full length

<400> SEQUENCE: 540

Met Gly Val Ser Asp Val Pro Arg Asp Leu Glu Val Val Ala Ala Thr
 1               5                  10                  15

Pro Thr Ser Leu Leu Ile Ser Trp Val Tyr His Tyr Asp Ala Gln Tyr
                 20                  25                  30

Arg Ile Thr Tyr Gly Glu Thr Gly Gly Asn Ser Pro Val Gln Glu Phe
                 35                  40                  45

Thr Val Pro Asp Gln Lys Ala Thr Ile Ser Gly Leu Lys Pro Gly Val
     50                  55                  60

Asp Tyr Thr Ile Thr Val Tyr Ala Leu Pro Arg Ala His Met Asp Arg
 65                  70                  75                  80

Ser His Ile Ser Ile Asn Tyr Arg Thr Glu Ile Asp Lys Pro Ser Gln
                 85                  90                  95

His His His His His His
             100

<210> SEQ ID NO 541
<211> LENGTH: 79
<212> TYPE: PRT
<213> ORGANISM: Artificial Sequence
<220> FEATURE:
<223> OTHER INFORMATION: Synthetic: ATI_1523_G06 core

<400> SEQUENCE: 541

Glu Val Val Ala Ala Thr Pro Thr Ser Leu Leu Ile Ser Trp Arg Ile
```

```
               1               5                  10                  15
Lys Ser Tyr His Lys Tyr Arg Ile Thr Tyr Gly Glu Thr Gly Gly Asn
                    20                  25                  30

Ser Pro Val Gln Glu Phe Thr Val Arg Ser Tyr Ala Ala Thr Ile Ser
                    35                  40                  45

Gly Leu Lys Pro Gly Val Asp Tyr Thr Ile Thr Val Tyr Ala Ile Met
 50                  55                  60

Glu Glu Thr His Leu Ala Tyr Ala Ile Ser Ile Asn Tyr Arg Thr
 65                  70                  75
```

<210> SEQ ID NO 542
<211> LENGTH: 7
<212> TYPE: PRT
<213> ORGANISM: Artificial Sequence
<220> FEATURE:
<223> OTHER INFORMATION: Synthetic: ATI_1523_G06 BC loop

<400> SEQUENCE: 542

```
Arg Ile Lys Ser Tyr His Lys
 1               5
```

<210> SEQ ID NO 543
<211> LENGTH: 4
<212> TYPE: PRT
<213> ORGANISM: Artificial Sequence
<220> FEATURE:
<223> OTHER INFORMATION: Synthetic: ATI_1523_G06 DE loop

<400> SEQUENCE: 543

```
Arg Ser Tyr Ala
 1
```

<210> SEQ ID NO 544
<211> LENGTH: 10
<212> TYPE: PRT
<213> ORGANISM: Artificial Sequence
<220> FEATURE:
<223> OTHER INFORMATION: Synthetic: ATI_1523_G06 FG loop

<400> SEQUENCE: 544

```
Ile Met Glu Glu Thr His Leu Ala Tyr Ala
 1               5                  10
```

<210> SEQ ID NO 545
<211> LENGTH: 88
<212> TYPE: PRT
<213> ORGANISM: Artificial Sequence
<220> FEATURE:
<223> OTHER INFORMATION: Synthetic: ATI_1523_G06 w/ N leader

<400> SEQUENCE: 545

```
Gly Val Ser Asp Val Pro Arg Asp Leu Glu Val Val Ala Ala Thr Pro
 1               5                  10                  15

Thr Ser Leu Leu Ile Ser Trp Arg Ile Lys Ser Tyr His Lys Tyr Arg
                    20                  25                  30

Ile Thr Tyr Gly Glu Thr Gly Gly Asn Ser Pro Val Gln Glu Phe Thr
                    35                  40                  45

Val Arg Ser Tyr Ala Ala Thr Ile Ser Gly Leu Lys Pro Gly Val Asp
                    50                  55                  60

Tyr Thr Ile Thr Val Tyr Ala Ile Met Glu Glu Thr His Leu Ala Tyr
 65                  70                  75                  80

Ala Ile Ser Ile Asn Tyr Arg Thr
```

```
                85

<210> SEQ ID NO 546
<211> LENGTH: 94
<212> TYPE: PRT
<213> ORGANISM: Artificial Sequence
<220> FEATURE:
<223> OTHER INFORMATION: Synthetic: ATI_1523_G06 w/ N leader + his tag

<400> SEQUENCE: 546

Gly Val Ser Asp Val Pro Arg Asp Leu Glu Val Val Ala Ala Thr Pro
1               5                   10                  15

Thr Ser Leu Leu Ile Ser Trp Arg Ile Lys Ser Tyr His Lys Tyr Arg
            20                  25                  30

Ile Thr Tyr Gly Glu Thr Gly Gly Asn Ser Pro Val Gln Glu Phe Thr
        35                  40                  45

Val Arg Ser Tyr Ala Ala Thr Ile Ser Gly Leu Lys Pro Gly Val Asp
    50                  55                  60

Tyr Thr Ile Thr Val Tyr Ala Ile Met Glu Glu Thr His Leu Ala Tyr
65                  70                  75                  80

Ala Ile Ser Ile Asn Tyr Arg Thr His His His His His
                85                  90

<210> SEQ ID NO 547
<211> LENGTH: 95
<212> TYPE: PRT
<213> ORGANISM: Artificial Sequence
<220> FEATURE:
<223> OTHER INFORMATION: Synthetic: ATI_1523_G06 w/ N leader and C tail

<400> SEQUENCE: 547

Gly Val Ser Asp Val Pro Arg Asp Leu Glu Val Val Ala Ala Thr Pro
1               5                   10                  15

Thr Ser Leu Leu Ile Ser Trp Arg Ile Lys Ser Tyr His Lys Tyr Arg
            20                  25                  30

Ile Thr Tyr Gly Glu Thr Gly Gly Asn Ser Pro Val Gln Glu Phe Thr
        35                  40                  45

Val Arg Ser Tyr Ala Ala Thr Ile Ser Gly Leu Lys Pro Gly Val Asp
    50                  55                  60

Tyr Thr Ile Thr Val Tyr Ala Ile Met Glu Glu Thr His Leu Ala Tyr
65                  70                  75                  80

Ala Ile Ser Ile Asn Tyr Arg Thr Glu Ile Asp Lys Pro Ser Gln
                85                  90                  95

<210> SEQ ID NO 548
<211> LENGTH: 101
<212> TYPE: PRT
<213> ORGANISM: Artificial Sequence
<220> FEATURE:
<223> OTHER INFORMATION: Synthetic: ATI_1523_G06 w/ N leader and C
      tail + his tag

<400> SEQUENCE: 548

Gly Val Ser Asp Val Pro Arg Asp Leu Glu Val Val Ala Ala Thr Pro
1               5                   10                  15

Thr Ser Leu Leu Ile Ser Trp Arg Ile Lys Ser Tyr His Lys Tyr Arg
            20                  25                  30

Ile Thr Tyr Gly Glu Thr Gly Gly Asn Ser Pro Val Gln Glu Phe Thr
        35                  40                  45

Val Arg Ser Tyr Ala Ala Thr Ile Ser Gly Leu Lys Pro Gly Val Asp
```

```
                    50                  55                  60
Tyr Thr Ile Thr Val Tyr Ala Ile Met Glu Glu Thr His Leu Ala Tyr
 65                  70                  75                  80

Ala Ile Ser Ile Asn Tyr Arg Thr Glu Ile Asp Lys Pro Ser Gln His
                 85                  90                  95

His His His His His
            100
```

<210> SEQ ID NO 549
<211> LENGTH: 90
<212> TYPE: PRT
<213> ORGANISM: Artificial Sequence
<220> FEATURE:
<223> OTHER INFORMATION: Synthetic: ATI_1523_G06 w/ N leader and
      modified C-terminus including PC

<400> SEQUENCE: 549

```
Gly Val Ser Asp Val Pro Arg Asp Leu Glu Val Val Ala Ala Thr Pro
  1               5                  10                  15

Thr Ser Leu Leu Ile Ser Trp Arg Ile Lys Ser Tyr His Lys Tyr Arg
                 20                  25                  30

Ile Thr Tyr Gly Glu Thr Gly Gly Asn Ser Pro Val Gln Glu Phe Thr
             35                  40                  45

Val Arg Ser Tyr Ala Ala Thr Ile Ser Gly Leu Lys Pro Gly Val Asp
     50                  55                  60

Tyr Thr Ile Thr Val Tyr Ala Ile Met Glu Glu Thr His Leu Ala Tyr
 65                  70                  75                  80

Ala Ile Ser Ile Asn Tyr Arg Thr Pro Cys
                 85                  90
```

<210> SEQ ID NO 550
<211> LENGTH: 96
<212> TYPE: PRT
<213> ORGANISM: Artificial Sequence
<220> FEATURE:
<223> OTHER INFORMATION: Synthetic: ATI_1523_G06 w/ N leader and
      modified C-terminus including PC + his tag

<400> SEQUENCE: 550

```
Gly Val Ser Asp Val Pro Arg Asp Leu Glu Val Val Ala Ala Thr Pro
  1               5                  10                  15

Thr Ser Leu Leu Ile Ser Trp Arg Ile Lys Ser Tyr His Lys Tyr Arg
                 20                  25                  30

Ile Thr Tyr Gly Glu Thr Gly Gly Asn Ser Pro Val Gln Glu Phe Thr
             35                  40                  45

Val Arg Ser Tyr Ala Ala Thr Ile Ser Gly Leu Lys Pro Gly Val Asp
     50                  55                  60

Tyr Thr Ile Thr Val Tyr Ala Ile Met Glu Glu Thr His Leu Ala Tyr
 65                  70                  75                  80

Ala Ile Ser Ile Asn Tyr Arg Thr Pro Cys His His His His His
                 85                  90                  95
```

<210> SEQ ID NO 551
<211> LENGTH: 102
<212> TYPE: PRT
<213> ORGANISM: Artificial Sequence
<220> FEATURE:
<223> OTHER INFORMATION: Synthetic: ATI_1523_G06 full length

<400> SEQUENCE: 551

Met Gly Val Ser Asp Val Pro Arg Asp Leu Glu Val Val Ala Ala
1               5                   10                  15

Pro Thr Ser Leu Leu Ile Ser Trp Arg Ile Lys Ser Tyr His Lys Tyr
            20                  25                  30

Arg Ile Thr Tyr Gly Glu Thr Gly Gly Asn Ser Pro Val Gln Glu Phe
        35                  40                  45

Thr Val Arg Ser Tyr Ala Ala Thr Ile Ser Gly Leu Lys Pro Gly Val
    50                  55                  60

Asp Tyr Thr Ile Thr Val Tyr Ala Ile Met Glu Glu Thr His Leu Ala
65                  70                  75                  80

Tyr Ala Ile Ser Ile Asn Tyr Arg Thr Glu Ile Asp Lys Pro Ser Gln
                85                  90                  95

His His His His His His
            100

<210> SEQ ID NO 552
<211> LENGTH: 79
<212> TYPE: PRT
<213> ORGANISM: Artificial Sequence
<220> FEATURE:
<223> OTHER INFORMATION: Synthetic: ATI_1523_G07 core

<400> SEQUENCE: 552

Glu Val Val Ala Ala Thr Pro Thr Ser Leu Leu Ile Ser Trp Val Tyr
1               5                   10                  15

Pro Gln Ala Asp Asp Tyr Arg Ile Thr Tyr Gly Glu Thr Gly Gly Asn
            20                  25                  30

Ser Pro Val Gln Glu Phe Thr Val Pro Asp Gln Asn Ala Thr Ile Ser
        35                  40                  45

Gly Leu Lys Pro Gly Val Asp Tyr Thr Ile Thr Val Tyr Ala Leu Ala
    50                  55                  60

Glu Ala His Leu Val Arg Ile Tyr Ile Ser Ile Asn Tyr Arg Thr
65                  70                  75

<210> SEQ ID NO 553
<211> LENGTH: 7
<212> TYPE: PRT
<213> ORGANISM: Artificial Sequence
<220> FEATURE:
<223> OTHER INFORMATION: Synthetic: ATI_1523_G07 BC loop

<400> SEQUENCE: 553

Val Tyr Pro Gln Ala Asp Asp
1               5

<210> SEQ ID NO 554
<211> LENGTH: 4
<212> TYPE: PRT
<213> ORGANISM: Artificial Sequence
<220> FEATURE:
<223> OTHER INFORMATION: Synthetic: ATI_1523_G07 DE loop

<400> SEQUENCE: 554

Pro Asp Gln Asn
1

<210> SEQ ID NO 555
<211> LENGTH: 10
<212> TYPE: PRT
<213> ORGANISM: Artificial Sequence
<220> FEATURE:
<223> OTHER INFORMATION: Synthetic: ATI_1523_G07 FG loop -continued

```
<400> SEQUENCE: 555

Leu Ala Glu Ala His Leu Val Arg Ile Tyr
1               5                   10

<210> SEQ ID NO 556
<211> LENGTH: 88
<212> TYPE: PRT
<213> ORGANISM: Artificial Sequence
<220> FEATURE:
<223> OTHER INFORMATION: Synthetic: ATI_1523_G07 w/ N leader

<400> SEQUENCE: 556

Gly Val Ser Asp Val Pro Arg Asp Leu Glu Val Val Ala Ala Thr Pro
1               5                   10                  15

Thr Ser Leu Leu Ile Ser Trp Val Tyr Pro Gln Ala Asp Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Asn Ala Thr Ile Ser Gly Leu Lys Pro Gly Val Asp
    50                  55                  60

Tyr Thr Ile Thr Val Tyr Ala Leu Ala Glu Ala His Leu Val Arg Ile
65                  70                  75                  80

Tyr Ile Ser Ile Asn Tyr Arg Thr
                85

<210> SEQ ID NO 557
<211> LENGTH: 94
<212> TYPE: PRT
<213> ORGANISM: Artificial Sequence
<220> FEATURE:
<223> OTHER INFORMATION: Synthetic: ATI_1523_G07 w/ N leader + his tag

<400> SEQUENCE: 557

Gly Val Ser Asp Val Pro Arg Asp Leu Glu Val Val Ala Ala Thr Pro
1               5                   10                  15

Thr Ser Leu Leu Ile Ser Trp Val Tyr Pro Gln Ala Asp Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Asn Ala Thr Ile Ser Gly Leu Lys Pro Gly Val Asp
    50                  55                  60

Tyr Thr Ile Thr Val Tyr Ala Leu Ala Glu Ala His Leu Val Arg Ile
65                  70                  75                  80

Tyr Ile Ser Ile Asn Tyr Arg Thr His His His His His His
                85                  90

<210> SEQ ID NO 558
<211> LENGTH: 95
<212> TYPE: PRT
<213> ORGANISM: Artificial Sequence
<220> FEATURE:
<223> OTHER INFORMATION: Synthetic: ATI_1523_G07 w/ N leader and C tail

<400> SEQUENCE: 558

Gly Val Ser Asp Val Pro Arg Asp Leu Glu Val Val Ala Ala Thr Pro
1               5                   10                  15

Thr Ser Leu Leu Ile Ser Trp Val Tyr Pro Gln Ala Asp Asp Tyr Arg
            20                  25                  30

Ile Thr Tyr Gly Glu Thr Gly Gly Asn Ser Pro Val Gln Glu Phe Thr
```

```
                35                  40                  45

Val Pro Asp Gln Asn Ala Thr Ile Ser Gly Leu Lys Pro Gly Val Asp
 50                  55                  60

Tyr Thr Ile Thr Val Tyr Ala Leu Ala Glu Ala His Leu Val Arg Ile
 65                  70                  75                  80

Tyr Ile Ser Ile Asn Tyr Arg Thr Glu Ile Asp Lys Pro Ser Gln
                 85                  90                  95

<210> SEQ ID NO 559
<211> LENGTH: 101
<212> TYPE: PRT
<213> ORGANISM: Artificial Sequence
<220> FEATURE:
<223> OTHER INFORMATION: Synthetic: ATI_1523_G07 w/ N leader and C
      tail + his tag

<400> SEQUENCE: 559

Gly Val Ser Asp Val Pro Arg Asp Leu Glu Val Val Ala Ala Thr Pro
 1               5                  10                  15

Thr Ser Leu Leu Ile Ser Trp Val Tyr Pro Gln Ala Asp Asp Tyr Arg
                20                  25                  30

Ile Thr Tyr Gly Glu Thr Gly Gly Asn Ser Pro Val Gln Glu Phe Thr
             35                  40                  45

Val Pro Asp Gln Asn Ala Thr Ile Ser Gly Leu Lys Pro Gly Val Asp
 50                  55                  60

Tyr Thr Ile Thr Val Tyr Ala Leu Ala Glu Ala His Leu Val Arg Ile
 65                  70                  75                  80

Tyr Ile Ser Ile Asn Tyr Arg Thr Glu Ile Asp Lys Pro Ser Gln His
                 85                  90                  95

His His His His His
            100

<210> SEQ ID NO 560
<211> LENGTH: 90
<212> TYPE: PRT
<213> ORGANISM: Artificial Sequence
<220> FEATURE:
<223> OTHER INFORMATION: Synthetic: ATI_1523_G07 w/ N leader and
      modified C-terminus including PC

<400> SEQUENCE: 560

Gly Val Ser Asp Val Pro Arg Asp Leu Glu Val Val Ala Ala Thr Pro
 1               5                  10                  15

Thr Ser Leu Leu Ile Ser Trp Val Tyr Pro Gln Ala Asp Asp Tyr Arg
                20                  25                  30

Ile Thr Tyr Gly Glu Thr Gly Gly Asn Ser Pro Val Gln Glu Phe Thr
             35                  40                  45

Val Pro Asp Gln Asn Ala Thr Ile Ser Gly Leu Lys Pro Gly Val Asp
 50                  55                  60

Tyr Thr Ile Thr Val Tyr Ala Leu Ala Glu Ala His Leu Val Arg Ile
 65                  70                  75                  80

Tyr Ile Ser Ile Asn Tyr Arg Thr Pro Cys
                85                  90

<210> SEQ ID NO 561
<211> LENGTH: 96
<212> TYPE: PRT
<213> ORGANISM: Artificial Sequence
<220> FEATURE:
<223> OTHER INFORMATION: Synthetic: ATI_1523_G07 w/ N leader and
``` modified C-terminus including PC + his tag

<400> SEQUENCE: 561

Gly Val Ser Asp Val Pro Arg Asp Leu Glu Val Val Ala Ala Thr Pro
1               5                   10                  15

Thr Ser Leu Leu Ile Ser Trp Val Tyr Pro Gln Ala Asp Asp Tyr Arg
            20                  25                  30

Ile Thr Tyr Gly Glu Thr Gly Gly Asn Ser Pro Val Gln Glu Phe Thr
        35                  40                  45

Val Pro Asp Gln Asn Ala Thr Ile Ser Gly Leu Lys Pro Gly Val Asp
    50                  55                  60

Tyr Thr Ile Thr Val Tyr Ala Leu Ala Glu Ala His Leu Val Arg Ile
65                  70                  75                  80

Tyr Ile Ser Ile Asn Tyr Arg Thr Pro Cys His His His His His
                85                  90                  95

<210> SEQ ID NO 562
<211> LENGTH: 102
<212> TYPE: PRT
<213> ORGANISM: Artificial Sequence
<220> FEATURE:
<223> OTHER INFORMATION: Synthetic: ATI_1523_G07 full length

<400> SEQUENCE: 562

Met Gly Val Ser Asp Val Pro Arg Asp Leu Glu Val Val Ala Ala Thr
1               5                   10                  15

Pro Thr Ser Leu Leu Ile Ser Trp Val Tyr Pro Gln Ala Asp Asp Tyr
            20                  25                  30

Arg Ile Thr Tyr Gly Glu Thr Gly Gly Asn Ser Pro Val Gln Glu Phe
        35                  40                  45

Thr Val Pro Asp Gln Asn Ala Thr Ile Ser Gly Leu Lys Pro Gly Val
    50                  55                  60

Asp Tyr Thr Ile Thr Val Tyr Ala Leu Ala Glu Ala His Leu Val Arg
65                  70                  75                  80

Ile Tyr Ile Ser Ile Asn Tyr Arg Thr Glu Ile Asp Lys Pro Ser Gln
                85                  90                  95

His His His His His His
            100

<210> SEQ ID NO 563
<211> LENGTH: 79
<212> TYPE: PRT
<213> ORGANISM: Artificial Sequence
<220> FEATURE:
<223> OTHER INFORMATION: Synthetic: ATI_1523_H07 core
<220> FEATURE:
<221> NAME/KEY: misc_feature
<222> LOCATION: (21)..(21)
<223> OTHER INFORMATION: Xaa can be any naturally occurring amino acid

<400> SEQUENCE: 563

Glu Val Val Ala Ala Thr Pro Thr Ser Leu Leu Ile Ser Trp Val Tyr
1               5                   10                  15

His Tyr Asp Ala Xaa Tyr Arg Ile Thr Tyr Gly Glu Thr Gly Gly Asn
            20                  25                  30

Ser Pro Val Gln Glu Phe Thr Val Pro Asp Gln Lys Ala Thr Ile Ser
        35                  40                  45

Gly Leu Lys Pro Gly Val Asp Tyr Thr Ile Thr Val Tyr Ala Leu Ser
    50                  55                  60

Glu Ala His His Lys Arg Asp Ser Ile Ser Ile Asn Tyr Arg Thr
65                  70                  75

<210> SEQ ID NO 564
<211> LENGTH: 7
<212> TYPE: PRT
<213> ORGANISM: Artificial Sequence
<220> FEATURE:
<223> OTHER INFORMATION: Synthetic: ATI_1523_H07 BC loop
<220> FEATURE:
<221> NAME/KEY: misc_feature
<222> LOCATION: (7)..(7)
<223> OTHER INFORMATION: Xaa can be any naturally occurring amino acid

<400> SEQUENCE: 564

Val Tyr His Tyr Asp Ala Xaa
1               5

<210> SEQ ID NO 565
<211> LENGTH: 4
<212> TYPE: PRT
<213> ORGANISM: Artificial Sequence
<220> FEATURE:
<223> OTHER INFORMATION: Synthetic: ATI_1523_H07 DE loop

<400> SEQUENCE: 565

Pro Asp Gln Lys
1

<210> SEQ ID NO 566
<211> LENGTH: 10
<212> TYPE: PRT
<213> ORGANISM: Artificial Sequence
<220> FEATURE:
<223> OTHER INFORMATION: Synthetic: ATI_1523_H07 FG loop

<400> SEQUENCE: 566

Leu Ser Glu Ala His His Lys Arg Asp Ser
1               5                   10

<210> SEQ ID NO 567
<211> LENGTH: 88
<212> TYPE: PRT
<213> ORGANISM: Artificial Sequence
<220> FEATURE:
<223> OTHER INFORMATION: Synthetic: ATI_1523_H07 w/ N leader
<220> FEATURE:
<221> NAME/KEY: misc_feature
<222> LOCATION: (30)..(30)
<223> OTHER INFORMATION: Xaa can be any naturally occurring amino acid

<400> SEQUENCE: 567

Gly Val Ser Asp Val Pro Arg Asp Leu Glu Val Val Ala Ala Thr Pro
1 5 10 15

Thr Ser Leu Leu Ile Ser Trp Val Tyr His Tyr Asp Ala Xaa Tyr Arg
20 25 30

Ile Thr Tyr Gly Glu Thr Gly Gly Asn Ser Pro Val Gln Glu Phe Thr
35 40 45

Val Pro Asp Gln Lys Ala Thr Ile Ser Gly Leu Lys Pro Gly Val Asp
50 55 60

Tyr Thr Ile Thr Val Tyr Ala Leu Ser Glu Ala His His Lys Arg Asp
65 70 75 80

Ser Ile Ser Ile Asn Tyr Arg Thr
85

-continued

```
<210> SEQ ID NO 568
<211> LENGTH: 94
<212> TYPE: PRT
<213> ORGANISM: Artificial Sequence
<220> FEATURE:
<223> OTHER INFORMATION: Synthetic: ATI_1523_H07 w/ N leader + his tag
<220> FEATURE:
<221> NAME/KEY: misc_feature
<222> LOCATION: (30)..(30)
<223> OTHER INFORMATION: Xaa can be any naturally occurring amino acid

<400> SEQUENCE: 568

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr His His His His His
                85                  90

<210> SEQ ID NO 569
<211> LENGTH: 95
<212> TYPE: PRT
<213> ORGANISM: Artificial Sequence
<220> FEATURE:
<223> OTHER INFORMATION: Synthetic: ATI_1523_H07 w/ N leader and C tail
<220> FEATURE:
<221> NAME/KEY: misc_feature
<222> LOCATION: (30)..(30)
<223> OTHER INFORMATION: Xaa can be any naturally occurring amino acid

<400> SEQUENCE: 569

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Glu Ile Asp Lys Pro Ser Gln
                85                  90                  95

<210> SEQ ID NO 570
<211> LENGTH: 101
<212> TYPE: PRT
<213> ORGANISM: Artificial Sequence
<220> FEATURE:
<223> OTHER INFORMATION: Synthetic: ATI_1523_H07 w/ N leader and C
     tail + his tag
<220> FEATURE:
<221> NAME/KEY: misc_feature
<222> LOCATION: (30)..(30)
<223> OTHER INFORMATION: Xaa can be any naturally occurring amino acid

<400> SEQUENCE: 570

Gly Val Ser Asp Val Pro Arg Asp Leu Glu Val Val Ala Ala Thr Pro
```

```
                 1               5                  10                 15
Thr Ser Leu Leu Ile Ser Trp Val Tyr His Tyr Asp Ala Xaa Tyr Arg
            20                  25                 30

Ile Thr Tyr Gly Glu Thr Gly Gly Asn Ser Pro Val Gln Glu Phe Thr
            35                  40                 45

Val Pro Asp Gln Lys Ala Thr Ile Ser Gly Leu Lys Pro Gly Val Asp
    50                  55                 60

Tyr Thr Ile Thr Val Tyr Ala Leu Ser Glu Ala His His Lys Arg Asp
65                  70                 75                      80

Ser Ile Ser Ile Asn Tyr Arg Thr Glu Ile Asp Lys Pro Ser Gln His
                85                  90                 95

His His His His His
            100

<210> SEQ ID NO 571
<211> LENGTH: 90
<212> TYPE: PRT
<213> ORGANISM: Artificial Sequence
<220> FEATURE:
<223> OTHER INFORMATION: Synthetic: ATI_1523_H07 w/ N leader and
      modified C-terminus including PC
<220> FEATURE:
<221> NAME/KEY: misc_feature
<222> LOCATION: (30)..(30)
<223> OTHER INFORMATION: Xaa can be any naturally occurring amino acid

<400> SEQUENCE: 571

Gly Val Ser Asp Val Pro Arg Asp Leu Glu Val Val Ala Ala Thr Pro
1               5                  10                 15

Thr Ser Leu Leu Ile Ser Trp Val Tyr His Tyr Asp Ala Xaa Tyr Arg
            20                  25                 30

Ile Thr Tyr Gly Glu Thr Gly Gly Asn Ser Pro Val Gln Glu Phe Thr
            35                  40                 45

Val Pro Asp Gln Lys Ala Thr Ile Ser Gly Leu Lys Pro Gly Val Asp
    50                  55                 60

Tyr Thr Ile Thr Val Tyr Ala Leu Ser Glu Ala His His Lys Arg Asp
65                  70                 75                      80

Ser Ile Ser Ile Asn Tyr Arg Thr Pro Cys
                85                  90

<210> SEQ ID NO 572
<211> LENGTH: 96
<212> TYPE: PRT
<213> ORGANISM: Artificial Sequence
<220> FEATURE:
<223> OTHER INFORMATION: Synthetic: ATI_1523_H07 w/ N leader and
      modified C-terminus including PC + his tag
<220> FEATURE:
<221> NAME/KEY: misc_feature
<222> LOCATION: (30)..(30)
<223> OTHER INFORMATION: Xaa can be any naturally occurring amino acid

<400> SEQUENCE: 572

Gly Val Ser Asp Val Pro Arg Asp Leu Glu Val Val Ala Ala Thr Pro
1               5                  10                 15

Thr Ser Leu Leu Ile Ser Trp Val Tyr His Tyr Asp Ala Xaa Tyr Arg
            20                  25                 30

Ile Thr Tyr Gly Glu Thr Gly Gly Asn Ser Pro Val Gln Glu Phe Thr
            35                  40                 45

Val Pro Asp Gln Lys Ala Thr Ile Ser Gly Leu Lys Pro Gly Val Asp
    50                  55                 60
```

-continued

Tyr Thr Ile Thr Val Tyr Ala Leu Ser Glu Ala His His Lys Arg Asp
65                  70                  75                  80

Ser Ile Ser Ile Asn Tyr Arg Thr Pro Cys His His His His His
                85                  90                  95

<210> SEQ ID NO 573
<211> LENGTH: 101
<212> TYPE: PRT
<213> ORGANISM: Artificial Sequence
<220> FEATURE:
<223> OTHER INFORMATION: Synthetic: ATI_1523_H07 full length
<220> FEATURE:
<221> NAME/KEY: misc_feature
<222> LOCATION: (30)..(30)
<223> OTHER INFORMATION: Xaa can be any naturally occurring amino acid

<400> SEQUENCE: 573

Gly Val Ser Asp Val Pro Arg Asp Leu Glu Val Val Ala Ala Thr Pro
1               5                   10                  15

Thr Ser Leu Leu Ile Ser Trp Val Tyr His Tyr Asp Ala Xaa Tyr Arg
            20                  25                  30

Ile Thr Tyr Gly Glu Thr Gly Gly Asn Ser Pro Val Gln Glu Phe Thr
        35                  40                  45

Val Pro Asp Gln Lys Ala Thr Ile Ser Gly Leu Lys Pro Gly Val Asp
    50                  55                  60

Tyr Thr Ile Thr Val Tyr Ala Leu Ser Glu Ala His His Lys Arg Asp
65                  70                  75                  80

Ser Ile Ser Ile Asn Tyr Arg Thr Glu Ile Asp Lys Pro Ser Gln His
                85                  90                  95

His His His His His
            100

<210> SEQ ID NO 574
<211> LENGTH: 10
<212> TYPE: PRT
<213> ORGANISM: Artificial Sequence
<220> FEATURE:
<223> OTHER INFORMATION: Synthetic: N-terminal leader

<400> SEQUENCE: 574

Met Gly Val Ser Asp Val Pro Arg Asp Leu
1               5                   10

<210> SEQ ID NO 575
<211> LENGTH: 9
<212> TYPE: PRT
<213> ORGANISM: Artificial Sequence
<220> FEATURE:
<223> OTHER INFORMATION: Synthetic: N-terminal leader

<400> SEQUENCE: 575

Gly Val Ser Asp Val Pro Arg Asp Leu
1               5

<210> SEQ ID NO 576
<211> LENGTH: 9
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa may or may not be present; if one is present, Xaa is Met or Gly; if two are present, Xaa is Met-Gly

<400> SEQUENCE: 576

Xaa Xaa Ser Asp Val Pro Arg Asp Leu
1               5

<210> SEQ ID NO 577
<211> LENGTH: 8
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa may or may not be present; if one is
      present, Xaa is Met or Gly; if two are present, Xaa is Met-Gly

<400> SEQUENCE: 577

Xaa Xaa Asp Val Pro Arg Asp Leu
1               5

<210> SEQ ID NO 578
<211> LENGTH: 7
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa may or may not be present; if one is
      present, Xaa is Met or Gly; if two are present, Xaa is Met-Gly

<400> SEQUENCE: 578

Xaa Xaa Val Pro Arg Asp Leu
1               5

<210> SEQ ID NO 579
<211> LENGTH: 6
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa may or may not be present; if one is
      present, Xaa is Met or Gly; if two are present, Xaa is Met-Gly

<400> SEQUENCE: 579

Xaa Xaa Pro Arg Asp Leu
1               5

<210> SEQ ID NO 580
<211> LENGTH: 5
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa may or may not be present; if one is
      present, Xaa is Met or Gly; if two are present, Xaa is Met-Gly

<400> SEQUENCE: 580

Xaa Xaa Arg Asp Leu
1               5

```
<210> SEQ ID NO 581
<211> LENGTH: 4
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa may or may not be present; if one is
      present, Xaa is Met or Gly; if two are present, Xaa is Met-Gly

<400> SEQUENCE: 581

Xaa Xaa Asp Leu
1

<210> SEQ ID NO 582
<211> LENGTH: 6
<212> TYPE: PRT
<213> ORGANISM: Artificial Sequence
<220> FEATURE:
<223> OTHER INFORMATION: Synthetic: N-terminal leader

<400> SEQUENCE: 582

Met Ala Ser Thr Ser Gly
1               5

<210> SEQ ID NO 583
<211> LENGTH: 20
<212> TYPE: PRT
<213> ORGANISM: Artificial Sequence
<220> FEATURE:
<223> OTHER INFORMATION: Synthetic: N-terminal leader

<400> SEQUENCE: 583

Met Glu Thr Asp Thr Leu Leu Leu Trp Val Leu Leu Leu Trp Val Pro
1               5                   10                  15

Gly Ser Thr Gly
            20

<210> SEQ ID NO 584
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 584

Glu Ile Glu Lys
1

<210> SEQ ID NO 585
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 585

Glu Gly Ser Gly Cys
1               5

<210> SEQ ID NO 586
<211> LENGTH: 7
<212> TYPE: PRT
<213> ORGANISM: Artificial Sequence
<220> FEATURE:
```

<223> OTHER INFORMATION: Synthetic: C-terminal tail

<400> SEQUENCE: 586

Glu Ile Glu Lys Pro Cys Gln
1               5

<210> SEQ ID NO 587
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 587

Glu Ile Glu Lys Pro Ser Gln
1               5

<210> SEQ ID NO 588
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 588

Glu Ile Glu Lys Pro
1               5

<210> SEQ ID NO 589
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 589

Glu Ile Glu Lys Pro Ser
1               5

<210> SEQ ID NO 590
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 590

Glu Ile Glu Lys Pro Cys
1               5

<210> SEQ ID NO 591
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 591

Glu Ile Asp Lys
1

<210> SEQ ID NO 592
<211> LENGTH: 7
<212> TYPE: PRT
<213> ORGANISM: Artificial Sequence
<220> FEATURE:
<223> OTHER INFORMATION: Synthetic: C-terminal tail

```
<400> SEQUENCE: 592

Glu Ile Asp Lys Pro Cys Gln
1               5

<210> SEQ ID NO 593
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 593

Glu Ile Asp Lys Pro Ser Gln
1               5

<210> SEQ ID NO 594
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 594

Glu Ile Glu Pro Lys Ser Ser
1               5

<210> SEQ ID NO 595
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 595

Glu Ile Asp Lys Pro Cys
1               5

<210> SEQ ID NO 596
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 596

Glu Ile Asp Lys Pro
1               5

<210> SEQ ID NO 597
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 597

Glu Ile Asp Lys Pro Ser
1               5

<210> SEQ ID NO 598
<211> LENGTH: 9
<212> TYPE: PRT
<213> ORGANISM: Artificial Sequence
<220> FEATURE:
<223> OTHER INFORMATION: Synthetic: C-terminal tail
```

```
<400> SEQUENCE: 598

Glu Ile Asp Lys Pro Ser Gln Leu Glu
1               5

<210> SEQ ID NO 599
<211> LENGTH: 12
<212> TYPE: PRT
<213> ORGANISM: Artificial Sequence
<220> FEATURE:
<223> OTHER INFORMATION: Synthetic: C-terminal tail

<400> SEQUENCE: 599

Glu Ile Glu Asp Glu Asp Glu Asp Glu Asp Glu Asp
1               5                   10

<210> SEQ ID NO 600
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 600

Glu Gly Ser Gly Ser
1               5

<210> SEQ ID NO 601
<211> LENGTH: 9
<212> TYPE: PRT
<213> ORGANISM: Artificial Sequence
<220> FEATURE:
<223> OTHER INFORMATION: Synthetic: C-terminal tail

<400> SEQUENCE: 601

Glu Ile Asp Lys Pro Cys Gln Leu Glu
1               5

<210> SEQ ID NO 602
<211> LENGTH: 13
<212> TYPE: PRT
<213> ORGANISM: Artificial Sequence
<220> FEATURE:
<223> OTHER INFORMATION: Synthetic: C-terminal tail

<400> SEQUENCE: 602

Glu Ile Asp Lys Pro Ser Gln His His His His His
1               5                   10

<210> SEQ ID NO 603
<211> LENGTH: 10
<212> TYPE: PRT
<213> ORGANISM: Artificial Sequence
<220> FEATURE:
<223> OTHER INFORMATION: Synthetic: C-terminal tail

<400> SEQUENCE: 603

Gly Ser Gly Cys His His His His His His
1               5                   10

<210> SEQ ID NO 604
<211> LENGTH: 11
<212> TYPE: PRT
<213> ORGANISM: Artificial Sequence
<220> FEATURE:
<223> OTHER INFORMATION: Synthetic: C-terminal tail

<400> SEQUENCE: 604
```

```
Glu Gly Ser Gly Cys His His His His His
1               5                   10

<210> SEQ ID NO 605
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 605

Pro Ile Asp Lys
1

<210> SEQ ID NO 606
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 606

Pro Ile Glu Lys
1

<210> SEQ ID NO 607
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 607

Pro Ile Asp Lys Pro
1               5

<210> SEQ ID NO 608
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 608

Pro Ile Glu Lys Pro
1               5

<210> SEQ ID NO 609
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 609

Pro Ile Asp Lys Pro Ser
1               5

<210> SEQ ID NO 610
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 610
```

```
Pro Ile Glu Lys Pro Ser
1               5

<210> SEQ ID NO 611
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 611

Pro Ile Asp Lys Pro Cys
1               5

<210> SEQ ID NO 612
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 612

Pro Ile Glu Lys Pro Cys
1               5

<210> SEQ ID NO 613
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 613

Pro Ile Asp Lys Pro Ser Gln
1               5

<210> SEQ ID NO 614
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 614

Pro Ile Glu Lys Pro Ser Gln
1               5

<210> SEQ ID NO 615
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 615

Pro Ile Asp Lys Pro Cys Gln
1               5

<210> SEQ ID NO 616
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 616

Pro Ile Glu Lys Pro Cys Gln
```

-continued

```
1               5

<210> SEQ ID NO 617
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 617

Pro His His His His His His
1               5

<210> SEQ ID NO 618
<211> LENGTH: 8
<212> TYPE: PRT
<213> ORGANISM: Artificial Sequence
<220> FEATURE:
<223> OTHER INFORMATION: Synthetic: C-terminal tail

<400> SEQUENCE: 618

Pro Cys His His His His His His
1               5

<210> SEQ ID NO 619
<211> LENGTH: 6
<212> TYPE: PRT
<213> ORGANISM: Artificial Sequence
<220> FEATURE:
<223> OTHER INFORMATION: Synthetic: 6X-His tag

<400> SEQUENCE: 619

His His His His His His
1               5

<210> SEQ ID NO 620
<211> LENGTH: 227
<212> TYPE: PRT
<213> ORGANISM: Artificial Sequence
<220> FEATURE:
<223> OTHER INFORMATION: Synthetic: Human IgG1 Fc domain

<400> SEQUENCE: 620

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
```

```
            145                 150                 155                 160
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 621
<211> LENGTH: 16
<212> TYPE: PRT
<213> ORGANISM: Artificial Sequence
<220> FEATURE:
<223> OTHER INFORMATION: Synthetic: Core hinge region of Fc

<400> SEQUENCE: 621

Asp Lys Thr His Thr Cys Pro Pro Cys Pro Ala Pro Glu Leu Leu Gly
1               5                   10                  15

<210> SEQ ID NO 622
<211> LENGTH: 24
<212> TYPE: PRT
<213> ORGANISM: Artificial Sequence
<220> FEATURE:
<223> OTHER INFORMATION: Synthetic: Exemplary hinge sequence

<400> SEQUENCE: 622

Glu Pro Lys Ser Ser Asp Lys Thr His Thr Cys Pro Pro Cys Pro Ala
1               5                   10                  15

Pro Glu Leu Leu Gly Gly Pro Ser
            20

<210> SEQ ID NO 623
<211> LENGTH: 24
<212> TYPE: PRT
<213> ORGANISM: Artificial Sequence
<220> FEATURE:
<223> OTHER INFORMATION: Synthetic: Exemplary hinge sequence

<400> SEQUENCE: 623

Glu Pro Lys Ser Ser Asp Lys Thr His Thr Cys Pro Pro Cys Pro Ala
1               5                   10                  15

Pro Glu Leu Leu Gly Gly Ser Ser
            20

<210> SEQ ID NO 624
<211> LENGTH: 24
<212> TYPE: PRT
<213> ORGANISM: Artificial Sequence
<220> FEATURE:
<223> OTHER INFORMATION: Synthetic: Exemplary hinge sequence

<400> SEQUENCE: 624

Glu Pro Lys Ser Ser Gly Ser Thr His Thr Cys Pro Pro Cys Pro Ala
1               5                   10                  15

Pro Glu Leu Leu Gly Gly Ser Ser
            20
```

```
<210> SEQ ID NO 625
<211> LENGTH: 19
<212> TYPE: PRT
<213> ORGANISM: Artificial Sequence
<220> FEATURE:
<223> OTHER INFORMATION: Synthetic: Exemplary hinge sequence

<400> SEQUENCE: 625

Asp Lys Thr His Thr Cys Pro Pro Cys Pro Ala Pro Glu Leu Leu Gly
1               5                   10                  15

Gly Pro Ser

<210> SEQ ID NO 626
<211> LENGTH: 19
<212> TYPE: PRT
<213> ORGANISM: Artificial Sequence
<220> FEATURE:
<223> OTHER INFORMATION: Synthetic: Exemplary hinge sequence

<400> SEQUENCE: 626

Asp Lys Thr His Thr Cys Pro Pro Cys Pro Ala Pro Glu Leu Leu Gly
1               5                   10                  15

Gly Ser Ser

<210> SEQ ID NO 627
<211> LENGTH: 208
<212> TYPE: PRT
<213> ORGANISM: Artificial Sequence
<220> FEATURE:
<223> OTHER INFORMATION: Synthetic: Fc with CH2 and CH3 regions of IgG1
      for Adnectin-hinge-Fc construct

<400> SEQUENCE: 627

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205
```

<210> SEQ ID NO 628
<211> LENGTH: 206
<212> TYPE: PRT
<213> ORGANISM: Artificial Sequence
<220> FEATURE:
<223> OTHER INFORMATION: Synthetic: Fc with CH2 and CH3 regions of IgG1
      for Fc-hinge-Adnectin construct

<400> SEQUENCE: 628

Val Phe Leu Phe Pro Pro Lys Pro Lys Asp Thr Leu Met Ile Ser Arg
1               5                   10                  15

Thr Pro Glu Val Thr Cys Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro
        195                 200                 205

<210> SEQ ID NO 629
<211> LENGTH: 8
<212> TYPE: PRT
<213> ORGANISM: Artificial Sequence
<220> FEATURE:
<223> OTHER INFORMATION: Synthetic: Linker 1

<400> SEQUENCE: 629

Gly Ala Gly Gly Gly Gly Ser Gly
1               5

<210> SEQ ID NO 630
<211> LENGTH: 6
<212> TYPE: PRT
<213> ORGANISM: Artificial Sequence
<220> FEATURE:
<223> OTHER INFORMATION: Synthetic: Linker 2

<400> SEQUENCE: 630

Glu Pro Lys Ser Ser Asp
1               5

<210> SEQ ID NO 631
<211> LENGTH: 5

```
<212> TYPE: PRT
<213> ORGANISM: Artificial Sequence
<220> FEATURE:
<223> OTHER INFORMATION: Synthetic: Linker 3

<400> SEQUENCE: 631

Pro Val Gly Val Val
1               5

<210> SEQ ID NO 632
<211> LENGTH: 21
<212> TYPE: PRT
<213> ORGANISM: Artificial Sequence
<220> FEATURE:
<223> OTHER INFORMATION: Synthetic: Linker 4

<400> SEQUENCE: 632

Glu Ser Pro Lys Ala Gln Ala Ser Ser Val Pro Thr Ala Gln Pro Gln
1               5                   10                  15

Ala Glu Gly Leu Ala
            20

<210> SEQ ID NO 633
<211> LENGTH: 17
<212> TYPE: PRT
<213> ORGANISM: Artificial Sequence
<220> FEATURE:
<223> OTHER INFORMATION: Synthetic: Linker 5

<400> SEQUENCE: 633

Glu Leu Gln Leu Glu Glu Ser Ala Ala Glu Ala Gln Asp Gly Glu Leu
1               5                   10                  15

Asp

<210> SEQ ID NO 634
<211> LENGTH: 9
<212> TYPE: PRT
<213> ORGANISM: Artificial Sequence
<220> FEATURE:
<223> OTHER INFORMATION: Synthetic: Linker 6

<400> SEQUENCE: 634

Gly Gln Pro Asp Glu Pro Gly Gly Ser
1               5

<210> SEQ ID NO 635
<211> LENGTH: 13
<212> TYPE: PRT
<213> ORGANISM: Artificial Sequence
<220> FEATURE:
<223> OTHER INFORMATION: Synthetic: Linker 7

<400> SEQUENCE: 635

Gly Gly Ser Gly Ser Gly Ser Gly Ser Gly Ser Gly Ser
1               5                   10

<210> SEQ ID NO 636
<211> LENGTH: 17
<212> TYPE: PRT
<213> ORGANISM: Artificial Sequence
<220> FEATURE:
<223> OTHER INFORMATION: Synthetic: Linker 8

<400> SEQUENCE: 636

Glu Leu Gln Leu Glu Glu Ser Ala Ala Glu Ala Gln Glu Gly Glu Leu
1               5                   10                  15
```

Glu

<210> SEQ ID NO 637
<211> LENGTH: 5
<212> TYPE: PRT
<213> ORGANISM: Artificial Sequence
<220> FEATURE:
<223> OTHER INFORMATION: Synthetic: Linker 9

<400> SEQUENCE: 637

Gly Ser Gly Ser Gly
1               5

<210> SEQ ID NO 638
<211> LENGTH: 4
<212> TYPE: PRT
<213> ORGANISM: Artificial Sequence
<220> FEATURE:
<223> OTHER INFORMATION: Synthetic: Linker 10

<400> SEQUENCE: 638

Gly Ser Gly Cys
1

<210> SEQ ID NO 639
<211> LENGTH: 7
<212> TYPE: PRT
<213> ORGANISM: Artificial Sequence
<220> FEATURE:
<223> OTHER INFORMATION: Synthetic: Linker 11

<400> SEQUENCE: 639

Ala Gly Gly Gly Gly Ser Gly
1               5

<210> SEQ ID NO 640
<211> LENGTH: 4
<212> TYPE: PRT
<213> ORGANISM: Artificial Sequence
<220> FEATURE:
<223> OTHER INFORMATION: Synthetic: Linker 12

<400> SEQUENCE: 640

Gly Ser Gly Ser
1

<210> SEQ ID NO 641
<211> LENGTH: 8
<212> TYPE: PRT
<213> ORGANISM: Artificial Sequence
<220> FEATURE:
<223> OTHER INFORMATION: Synthetic: Linker 13

<400> SEQUENCE: 641

Gln Pro Asp Glu Pro Gly Gly Ser
1               5

<210> SEQ ID NO 642
<211> LENGTH: 6
<212> TYPE: PRT
<213> ORGANISM: Artificial Sequence
<220> FEATURE:
<223> OTHER INFORMATION: Synthetic: Linker 14

<400> SEQUENCE: 642

Gly Ser Gly Ser Gly Ser

```
1               5

<210> SEQ ID NO 643
<211> LENGTH: 6
<212> TYPE: PRT
<213> ORGANISM: Artificial Sequence
<220> FEATURE:
<223> OTHER INFORMATION: Synthetic: Linker 15

<400> SEQUENCE: 643

Thr Val Ala Ala Pro Ser
1               5

<210> SEQ ID NO 644
<211> LENGTH: 8
<212> TYPE: PRT
<213> ORGANISM: Artificial Sequence
<220> FEATURE:
<223> OTHER INFORMATION: Synthetic: Linker 16

<400> SEQUENCE: 644

Lys Ala Gly Gly Gly Gly Ser Gly
1               5

<210> SEQ ID NO 645
<211> LENGTH: 13
<212> TYPE: PRT
<213> ORGANISM: Artificial Sequence
<220> FEATURE:
<223> OTHER INFORMATION: Synthetic: Linker 17

<400> SEQUENCE: 645

Lys Gly Ser Gly Ser Gly Ser Gly Ser Gly Ser Gly Ser
1               5                   10

<210> SEQ ID NO 646
<211> LENGTH: 9
<212> TYPE: PRT
<213> ORGANISM: Artificial Sequence
<220> FEATURE:
<223> OTHER INFORMATION: Synthetic: Linker 18

<400> SEQUENCE: 646

Lys Gln Pro Asp Glu Pro Gly Gly Ser
1               5

<210> SEQ ID NO 647
<211> LENGTH: 18
<212> TYPE: PRT
<213> ORGANISM: Artificial Sequence
<220> FEATURE:
<223> OTHER INFORMATION: Synthetic: Linker 19

<400> SEQUENCE: 647

Lys Glu Leu Gln Leu Glu Glu Ser Ala Ala Glu Ala Gln Asp Gly Glu
1               5                   10                  15

Leu Asp

<210> SEQ ID NO 648
<211> LENGTH: 7
<212> TYPE: PRT
<213> ORGANISM: Artificial Sequence
<220> FEATURE:
<223> OTHER INFORMATION: Synthetic: Linker 20

<400> SEQUENCE: 648
```

```
Lys Thr Val Ala Ala Pro Ser
1               5

<210> SEQ ID NO 649
<211> LENGTH: 9
<212> TYPE: PRT
<213> ORGANISM: Artificial Sequence
<220> FEATURE:
<223> OTHER INFORMATION: Synthetic: Linker 21

<400> SEQUENCE: 649

Lys Ala Gly Gly Gly Gly Ser Gly Gly
1               5

<210> SEQ ID NO 650
<211> LENGTH: 14
<212> TYPE: PRT
<213> ORGANISM: Artificial Sequence
<220> FEATURE:
<223> OTHER INFORMATION: Synthetic: Linker 22

<400> SEQUENCE: 650

Lys Gly Ser Gly Ser Gly Ser Gly Ser Gly Ser Gly Ser Gly
1               5                   10

<210> SEQ ID NO 651
<211> LENGTH: 10
<212> TYPE: PRT
<213> ORGANISM: Artificial Sequence
<220> FEATURE:
<223> OTHER INFORMATION: Synthetic: Linker 23

<400> SEQUENCE: 651

Lys Gln Pro Asp Glu Pro Gly Gly Ser Gly
1               5                   10

<210> SEQ ID NO 652
<211> LENGTH: 19
<212> TYPE: PRT
<213> ORGANISM: Artificial Sequence
<220> FEATURE:
<223> OTHER INFORMATION: Synthetic: Linker 24

<400> SEQUENCE: 652

Lys Glu Leu Gln Leu Glu Glu Ser Ala Ala Glu Ala Gln Asp Gly Glu
1               5                   10                  15

Leu Asp Gly

<210> SEQ ID NO 653
<211> LENGTH: 8
<212> TYPE: PRT
<213> ORGANISM: Artificial Sequence
<220> FEATURE:
<223> OTHER INFORMATION: Synthetic: Linker 25

<400> SEQUENCE: 653

Lys Thr Val Ala Ala Pro Ser Gly
1               5

<210> SEQ ID NO 654
<211> LENGTH: 8
<212> TYPE: PRT
<213> ORGANISM: Artificial Sequence
<220> FEATURE:
<223> OTHER INFORMATION: Synthetic: Linker 26

<400> SEQUENCE: 654
```

```
Ala Gly Gly Gly Gly Ser Gly Gly
1               5
```

<210> SEQ ID NO 655
<211> LENGTH: 7
<212> TYPE: PRT
<213> ORGANISM: Artificial Sequence
<220> FEATURE:
<223> OTHER INFORMATION: Synthetic: Linker 27

<400> SEQUENCE: 655

```
Ala Gly Gly Gly Gly Ser Gly
1               5
```

<210> SEQ ID NO 656
<211> LENGTH: 13
<212> TYPE: PRT
<213> ORGANISM: Artificial Sequence
<220> FEATURE:
<223> OTHER INFORMATION: Synthetic: Linker 28

<400> SEQUENCE: 656

```
Gly Ser Gly Ser Gly Ser Gly Ser Gly Ser Gly Ser Gly
1               5                   10
```

<210> SEQ ID NO 657
<211> LENGTH: 9
<212> TYPE: PRT
<213> ORGANISM: Artificial Sequence
<220> FEATURE:
<223> OTHER INFORMATION: Synthetic: Linker 29

<400> SEQUENCE: 657

```
Gln Pro Asp Glu Pro Gly Gly Ser Gly
1               5
```

<210> SEQ ID NO 658
<211> LENGTH: 7
<212> TYPE: PRT
<213> ORGANISM: Artificial Sequence
<220> FEATURE:
<223> OTHER INFORMATION: Synthetic: Linker 30

<400> SEQUENCE: 658

```
Thr Val Ala Ala Pro Ser Gly
1               5
```

<210> SEQ ID NO 659
<211> LENGTH: 7
<212> TYPE: PRT
<213> ORGANISM: Artificial Sequence
<220> FEATURE:
<223> OTHER INFORMATION: Synthetic: Linker 31

<400> SEQUENCE: 659

```
Pro Ser Thr Ser Thr Ser Thr
1               5
```

<210> SEQ ID NO 660
<211> LENGTH: 7
<212> TYPE: PRT
<213> ORGANISM: Artificial Sequence
<220> FEATURE:
<223> OTHER INFORMATION: Synthetic: Linker 32

<400> SEQUENCE: 660

-continued

```
Glu Ile Asp Lys Pro Ser Gln
1               5

<210> SEQ ID NO 661
<211> LENGTH: 8
<212> TYPE: PRT
<213> ORGANISM: Artificial Sequence
<220> FEATURE:
<223> OTHER INFORMATION: Synthetic: Linker 33

<400> SEQUENCE: 661

Gly Ser Gly Ser Gly Ser Gly Ser
1               5

<210> SEQ ID NO 662
<211> LENGTH: 10
<212> TYPE: PRT
<213> ORGANISM: Artificial Sequence
<220> FEATURE:
<223> OTHER INFORMATION: Synthetic: Linker 34

<400> SEQUENCE: 662

Gly Ser Gly Ser Gly Ser Gly Ser Gly Ser
1               5                   10

<210> SEQ ID NO 663
<211> LENGTH: 12
<212> TYPE: PRT
<213> ORGANISM: Artificial Sequence
<220> FEATURE:
<223> OTHER INFORMATION: Synthetic: Linker 35

<400> SEQUENCE: 663

Gly Ser Gly Ser Gly Ser Gly Ser Gly Ser Gly Ser
1               5                   10

<210> SEQ ID NO 664
<211> LENGTH: 14
<212> TYPE: PRT
<213> ORGANISM: Artificial Sequence
<220> FEATURE:
<223> OTHER INFORMATION: Synthetic: Linker 36

<400> SEQUENCE: 664

Gly Ser Gly Ser Gly Ser Gly Ser Gly Ser Gly Ser Gly Ser
1               5                   10

<210> SEQ ID NO 665
<211> LENGTH: 13
<212> TYPE: PRT
<213> ORGANISM: Artificial Sequence
<220> FEATURE:
<223> OTHER INFORMATION: Synthetic: Linker 37

<400> SEQUENCE: 665

Gly Gly Ser Gly Ser Gly Ser Gly Ser Gly Ser Gly Ser
1               5                   10

<210> SEQ ID NO 666
<211> LENGTH: 16
<212> TYPE: PRT
<213> ORGANISM: Artificial Sequence
<220> FEATURE:
<223> OTHER INFORMATION: Synthetic: Linker 38

<400> SEQUENCE: 666

Gly Gly Ser Gly Ser Gly Ser Gly Ser Gly Ser Gly Ser Gly Ser Gly
```

-continued

```
1               5                   10                  15

<210> SEQ ID NO 667
<211> LENGTH: 15
<212> TYPE: PRT
<213> ORGANISM: Artificial Sequence
<220> FEATURE:
<223> OTHER INFORMATION: Synthetic: Linker 39

<400> SEQUENCE: 667

Gly Ser Glu Gly Ser Glu Gly Ser Glu Gly Ser Glu Gly Ser Glu
1               5                   10                  15

<210> SEQ ID NO 668
<211> LENGTH: 8
<212> TYPE: PRT
<213> ORGANISM: Artificial Sequence
<220> FEATURE:
<223> OTHER INFORMATION: Synthetic: Linker 40

<400> SEQUENCE: 668

Gly Gly Ser Glu Gly Gly Ser Glu
1               5

<210> SEQ ID NO 669
<211> LENGTH: 35
<212> TYPE: PRT
<213> ORGANISM: Artificial Sequence
<220> FEATURE:
<223> OTHER INFORMATION: Synthetic: Linker 41

<400> SEQUENCE: 669

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 670
<211> LENGTH: 25
<212> TYPE: PRT
<213> ORGANISM: Artificial Sequence
<220> FEATURE:
<223> OTHER INFORMATION: Synthetic: Linker 42

<400> SEQUENCE: 670

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 671
<211> LENGTH: 16
<212> TYPE: PRT
<213> ORGANISM: Artificial Sequence
<220> FEATURE:
<223> OTHER INFORMATION: Synthetic: Linker 43

<400> SEQUENCE: 671

Gly Gly Gly Gly Ser Gly Gly Gly Gly Ser Gly Gly Gly Gly Ser Gly
1               5                   10                  15

<210> SEQ ID NO 672
<211> LENGTH: 7
```

```
<212> TYPE: PRT
<213> ORGANISM: Artificial Sequence
<220> FEATURE:
<223> OTHER INFORMATION: Synthetic: Linker 44

<400> SEQUENCE: 672

Gly Pro Gly Pro Gly Pro Gly
1               5

<210> SEQ ID NO 673
<211> LENGTH: 11
<212> TYPE: PRT
<213> ORGANISM: Artificial Sequence
<220> FEATURE:
<223> OTHER INFORMATION: Synthetic: Linker 45

<400> SEQUENCE: 673

Gly Pro Gly Pro Gly Pro Gly Pro Gly Pro Gly
1               5                   10

<210> SEQ ID NO 674
<211> LENGTH: 6
<212> TYPE: PRT
<213> ORGANISM: Artificial Sequence
<220> FEATURE:
<223> OTHER INFORMATION: Synthetic: Linker 46

<400> SEQUENCE: 674

Pro Ala Pro Ala Pro Ala
1               5

<210> SEQ ID NO 675
<211> LENGTH: 12
<212> TYPE: PRT
<213> ORGANISM: Artificial Sequence
<220> FEATURE:
<223> OTHER INFORMATION: Synthetic: Linker 47

<400> SEQUENCE: 675

Pro Ala Pro Ala Pro Ala Pro Ala Pro Ala Pro Ala
1               5                   10

<210> SEQ ID NO 676
<211> LENGTH: 18
<212> TYPE: PRT
<213> ORGANISM: Artificial Sequence
<220> FEATURE:
<223> OTHER INFORMATION: Synthetic: Linker 48

<400> SEQUENCE: 676

Pro Ala Pro Ala Pro Ala Pro Ala Pro Ala Pro Ala Pro Ala Pro Ala
1               5                   10                  15

Pro Ala

<210> SEQ ID NO 677
<211> LENGTH: 20
<212> TYPE: PRT
<213> ORGANISM: Artificial Sequence
<220> FEATURE:
<223> OTHER INFORMATION: Synthetic: Linker 49

<400> SEQUENCE: 677

Gly Ser Gly Ser Gly Ser Gly Ser Gly Ser Gly Ser Gly Ser Gly Ser
1               5                   10                  15

Gly Ser Gly Ser
                20
```

<210> SEQ ID NO 678
<211> LENGTH: 20
<212> TYPE: PRT
<213> ORGANISM: Artificial Sequence
<220> FEATURE:
<223> OTHER INFORMATION: Synthetic: Linker 50

<400> SEQUENCE: 678

Gly Gly Gly Gly Ser Gly Gly Gly Ser Gly Gly Gly Gly Ser Gly
1               5                   10                  15

Gly Gly Gly Ser
            20

<210> SEQ ID NO 679
<211> LENGTH: 94
<212> TYPE: PRT
<213> ORGANISM: Artificial Sequence
<220> FEATURE:
<223> OTHER INFORMATION: Synthetic: ATI-968

<400> SEQUENCE: 679

Val Ser Asp Val Pro Arg Asp Leu Glu Val Val Ala Ala Thr Pro Thr
1               5                   10                  15

Ser Leu Leu Ile Ser Trp Ile Ala Pro Phe Tyr Asn Val Ile Tyr Tyr
                20                  25                  30

Arg Ile Thr Tyr Gly Glu Thr Gly Gly Asn Ser Pro Val Gln Glu Phe
            35                  40                  45

Thr Val Pro Gly Thr Gly Tyr Thr Ala Thr Ile Ser Gly Leu Lys Pro
        50                  55                  60

Gly Val Asp Tyr Thr Ile Thr Val Tyr Ala Val Thr Asp Gly Ala Ser
65                  70                  75                  80

Ile Ala Ser Tyr Ala Phe Pro Ile Ser Ile Asn Tyr Arg Thr
                85                  90

<210> SEQ ID NO 680
<211> LENGTH: 94
<212> TYPE: PRT
<213> ORGANISM: Artificial Sequence
<220> FEATURE:
<223> OTHER INFORMATION: Synthetic: ATI-964

<400> SEQUENCE: 680

Val Ser Asp Val Pro Arg Asp Leu Glu Val Val Ala Ala Thr Pro Thr
1               5                   10                  15

Ser Leu Leu Ile Ser Trp Ser Tyr Asp Gly Ser Ile Glu Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Asp Gln Lys Thr Ala Thr Ile Ser Gly Leu Lys Pro
        50                  55                  60

Gly Val Asp Tyr Thr Ile Thr Val Tyr Ala Val Arg Leu Glu Glu Ala
65                  70                  75                  80

His Tyr Tyr Arg Glu Ser Pro Ile Ser Ile Asn Tyr Arg Thr
                85                  90

<210> SEQ ID NO 681
<211> LENGTH: 92
<212> TYPE: PRT
<213> ORGANISM: Artificial Sequence
<220> FEATURE:

<223> OTHER INFORMATION: Synthetic: ATI-967

<400> SEQUENCE: 681

Val Ser Asp Val Pro Arg Asp Leu Glu Val Val Ala Ala Thr Pro Thr
1               5                   10                  15

Ser Leu Leu Ile Ser Trp Gln Gly Gln Leu Ser Pro Ser Phe Tyr Tyr
            20                  25                  30

Arg Ile Thr Tyr Gly Glu Thr Gly Gly Asn Ser Pro Val Gln Glu Phe
        35                  40                  45

Thr Val Pro Val Ala Ser Gly Thr Ala Thr Ile Ser Gly Leu Lys Pro
    50                  55                  60

Gly Val Asp Tyr Thr Ile Thr Val Tyr Ala Val Thr Ser His Gly Ile
65                  70                  75                  80

Tyr Phe Tyr Ala Pro Ile Ser Ile Asn Tyr Arg Thr
                85                  90

<210> SEQ ID NO 682
<211> LENGTH: 94
<212> TYPE: PRT
<213> ORGANISM: Artificial Sequence
<220> FEATURE:
<223> OTHER INFORMATION: Synthetic: A02

<400> SEQUENCE: 682

Val Ser Asp Val Pro Arg Asp Leu Glu Val Val Ala Ala Thr Pro Thr
1               5                   10                  15

Ser Leu Leu Ile Ser Trp Ser Tyr Asp Gly Pro Ile Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Asp Gln Lys Thr Ala Thr Ile Ser Gly Leu Lys Pro
    50                  55                  60

Gly Val Asp Tyr Thr Ile Thr Val Tyr Ala Val Arg Leu Glu Glu Ala
65                  70                  75                  80

His Tyr Asn Arg Glu Phe Pro Ile Ser Ile Asn Tyr Arg Thr
                85                  90

<210> SEQ ID NO 683
<211> LENGTH: 92
<212> TYPE: PRT
<213> ORGANISM: Artificial Sequence
<220> FEATURE:
<223> OTHER INFORMATION: Synthetic: E01

<400> SEQUENCE: 683

Val Ser Asp Val Pro Arg Asp Leu Glu Val Val Ala Ala Thr Pro Thr
1               5                   10                  15

Ser Leu Leu Ile Ser Trp Arg Ala Gln Leu Ser Pro Ser Phe Tyr Tyr
            20                  25                  30

Arg Ile Thr Tyr Gly Glu Thr Gly Gly Asn Ser Pro Val Gln Glu Phe
        35                  40                  45

Thr Val Pro Asn Asp Val Met Thr Ala Thr Ile Ser Gly Leu Lys Pro
    50                  55                  60

Gly Val Asp Tyr Thr Ile Thr Val Tyr Ala Val Thr Thr His Gly Val
65                  70                  75                  80

Tyr Phe Tyr Ser Pro Ile Ser Ile Asn Tyr Arg Thr
                85                  90

<210> SEQ ID NO 684
<211> LENGTH: 94
<212> TYPE: PRT
<213> ORGANISM: Artificial Sequence
<220> FEATURE:
<223> OTHER INFORMATION: Synthetic: ATI-965

<400> SEQUENCE: 684

Val Ser Asp Val Pro Arg Asp Leu Glu Val Val Ala Ala Thr Pro Thr
1               5                   10                  15

Ser Leu Leu Ile Ser Trp Thr Ala Tyr Asp Ser Val Asp Lys Tyr Tyr
            20                  25                  30

Arg Ile Thr Tyr Gly Glu Thr Gly Gly Asn Ser Pro Val Gln Glu Phe
        35                  40                  45

Thr Val Gly Pro Arg His His Thr Ala Thr Ile Ser Gly Leu Lys Pro
    50                  55                  60

Gly Val Asp Tyr Thr Ile Thr Val Tyr Ala Val Tyr His Thr Glu Pro
65                  70                  75                  80

Gly Tyr His Ala His Met Pro Ile Ser Ile Asn Tyr Arg Thr
                85                  90

<210> SEQ ID NO 685
<211> LENGTH: 90
<212> TYPE: PRT
<213> ORGANISM: Artificial Sequence
<220> FEATURE:
<223> OTHER INFORMATION: Synthetic: ATI-966

<400> SEQUENCE: 685

Val Ser Asp Val Pro Arg Asp Leu Glu Val Val Ala Ala Thr Pro Thr
1               5                   10                  15

Ser Leu Leu Ile Ser Trp His Arg Phe Ser Ser Ile Met Ala Tyr Tyr
            20                  25                  30

Arg Ile Thr Tyr Gly Glu Thr Gly Gly Asn Ser Pro Val Gln Glu Phe
        35                  40                  45

Thr Val Ala Gly Ser Val Asn Thr Ala Thr Ile Ser Gly Leu Lys Pro
    50                  55                  60

Gly Val Asp Tyr Thr Ile Thr Val Tyr Ala Val Thr Ile His Asn Val
65                  70                  75                  80

Ser Phe Pro Ile Ser Ile Asn Tyr Arg Thr
                85                  90

<210> SEQ ID NO 686
<211> LENGTH: 12
<212> TYPE: PRT
<213> ORGANISM: Artificial Sequence
<220> FEATURE:
<223> OTHER INFORMATION: Synthetic

<400> SEQUENCE: 686

Asn Tyr Arg Thr Pro Cys His His His His His
1               5                   10

<210> SEQ ID NO 687
<211> LENGTH: 6
<212> TYPE: PRT
<213> ORGANISM: Artificial Sequence
<220> FEATURE:
<223> OTHER INFORMATION: Synthetic

<400> SEQUENCE: 687

Asn Tyr Arg Thr Pro Cys
1               5

We claim:

1. A nucleic acid encoding a polypeptide comprising a modified fibronectin type III tenth domain ($^{10}$Fn3), wherein the $^{10}$Fn3 domain comprises AB, BC, CD, DE, EF, and FG loops and the polypeptide specifically binds to human Programmed Death Ligand-1 (PD-L1), and wherein the BC, DE, and FG loops of the modified $^{10}$Fn3 domain comprise the amino acid sequences set forth in:
  (1) SEQ ID NOs: 6, 7 and 8, respectively;
  (2) SEQ ID NOs: 21, 22 and 23, respectively;
  (3) SEQ ID NOs: 36, 37 and 38, respectively;
  (4) SEQ ID NOs: 51, 52 and 53, respectively;
  (5) SEQ ID NOs: 66, 67 and 68, respectively;
  (6) SEQ ID NOs: 81, 82 and 83, respectively;
  (7) SEQ ID NOs: 97, 98 and 99, respectively;
  (8) SEQ ID NOs: 113, 114 and 115, respectively;
  (9) SEQ ID NOs: 124, 125 and 126, respectively;
  (10) SEQ ID NOs: 135, 136 and 137, respectively;
  (11) SEQ ID NOs: 146, 147 and 148, respectively;
  (12) SEQ ID NOs: 157, 158 and 159, respectively;
  (13) SEQ ID NOs: 168, 169 and 170, respectively;
  (14) SEQ ID NOs: 179, 180 and 181, respectively;
  (15) SEQ ID NOs: 190, 191 and 192, respectively;
  (16) SEQ ID NOs: 201, 202 and 203, respectively;
  (17) SEQ ID NOs: 212, 213 and 214, respectively;
  (18) SEQ ID NOs: 223, 224 and 225, respectively;
  (19) SEQ ID NOs: 234, 235 and 236, respectively;
  (20) SEQ ID NOs: 245, 246 and 247, respectively;
  (21) SEQ ID NOs: 256, 257 and 258, respectively;
  (22) SEQ ID NOs: 267, 268 and 269, respectively;
  (23) SEQ ID NOs: 278, 279 and 280, respectively;
  (24) SEQ ID NOs: 289, 290 and 291, respectively;
  (25) SEQ ID NOs: 300, 301 and 302, respectively;
  (26) SEQ ID NOs: 311, 312 and 313, respectively;
  (27) SEQ ID NOs: 322, 323 and 324, respectively;
  (28) SEQ ID NOs: 333, 334 and 335, respectively;
  (29) SEQ ID NOs: 344, 345 and 346, respectively;
  (30) SEQ ID NOs: 355, 356 and 357, respectively;
  (31) SEQ ID NOs: 366, 367 and 368, respectively;
  (32) SEQ ID NOs: 377, 378 and 379, respectively;
  (33) SEQ ID NOs: 388, 389 and 390, respectively;
  (34) SEQ ID NOs: 399, 400 and 401, respectively;
  (35) SEQ ID NOs: 410, 411 and 412, respectively;
  (36) SEQ ID NOs: 421, 422 and 423, respectively;
  (37) SEQ ID NOs: 432, 433 and 434, respectively;
  (38) SEQ ID NOs: 443, 444 and 445, respectively;
  (39) SEQ ID NOs: 454, 455 and 456, respectively;
  (40) SEQ ID NOs: 465, 466 and 467, respectively;
  (41) SEQ ID NOs: 476, 477 and 478, respectively;
  (42) SEQ ID NOs: 487, 488 and 489, respectively;
  (43) SEQ ID NOs: 498, 499 and 500, respectively;
  (44) SEQ ID NOs: 509, 510 and 511, respectively;
  (45) SEQ ID NOs: 520, 521 and 522, respectively;
  (46) SEQ ID NOs: 531, 532 and 533, respectively;
  (47) SEQ ID NOs: 542, 543 and 544, respectively;
  (48) SEQ ID NOs: 553, 554 and 555, respectively; or
  (49) SEQ ID NOs: 564, 565 and 566, respectively.

2. The nucleic acid of claim 1, wherein the nucleic acid encodes a polypeptide comprising the amino acid sequence set forth in any one of SEQ ID NOs: 5, 20, 35, 50, 65, 80, 96, 112, 123, 134, 145, 156, 167, 178, 189, 200, 211, 222, 233, 244, 255, 266, 277, 288, 299, 310, 321, 332, 343, 354, 365, 376, 387, 398, 409, 420, 431, 442, 453, 464, 475, 486, 497, 508, 519, 530, 541, 552 and 563.

3. A vector comprising the nucleic acid of claim 1.

4. A cell comprising the nucleic acid of claim 1.

5. The nucleic acid of claim 1, wherein the nucleic acid encodes a polypeptide comprising a modified human $^{10}$Fn3 domain wherein the BC, DE and FG loops of the modified human $^{10}$Fn3 domain comprise the amino acid sequences set forth in:
  (a) SEQ ID NOs: 6, 7 and 8, respectively;
  (b) SEQ ID NOs: 21, 22 and 23, respectively;
  (c) SEQ ID NOs: 36, 37 and 38, respectively;
  (d) SEQ ID NOs: 51, 52 and 53, respectively;
  (e) SEQ ID NOs: 66, 67 and 68, respectively;
  (f) SEQ ID NOs: 81, 82 and 83, respectively; or
  (g) SEQ ID NOs: 97, 98 and 99, respectively.

6. The nucleic acid of claim 5, wherein the nucleic acid encodes a polypeptide comprising a modified human $^{10}$Fn3 domain comprising the amino acid sequence set forth in any one of SEQ ID NOs: 5, 20, 35, 65, 80 and 96.

7. The nucleic acid of claim 5, wherein the nucleic acid comprises the nucleotide sequence set forth in any of SEQ ID NOs: 16-19, 31-34, 46-49, 61-64, 76-79-92-95, and 108-111.

8. The nucleic acid of claim 1, wherein the nucleic acid encodes a polypeptide comprising a modified human $^{10}$Fn3 domain wherein the BC, DE and FG loops of the modified human $^{10}$Fn3 domain comprise the amino acid sequences set forth in SEQ ID NOs: 81, 82 and 83, respectively.

9. The nucleic acid of claim 8, wherein the nucleic acid encodes a polypeptide comprising the amino acid sequence set forth in SEQ ID NO: 80.

10. The nucleic acid of claim 8, wherein the nucleic acid encodes a polypeptide comprising the amino acid sequence set forth in SEQ ID NO: 84.

11. The nucleic acid of claim 8, wherein the nucleic acid encodes a polypeptide comprising the amino acid sequence set forth in SEQ ID NO: 88.

12. The nucleic acid of claim 8, wherein the nucleic acid comprises the nucleotide sequence set forth in any of SEQ ID NOs: 92-95.

13. The nucleic acid of claim 12, wherein the nucleic acid comprises the nucleotide sequence set forth in SEQ ID NO: 92.

14. The nucleic acid of claim 12, wherein the nucleic acid comprises the nucleotide sequence set forth in SEQ ID NO: 94.

15. The nucleic acid of claim 1, wherein the nucleic acid encodes a polypeptide comprising a modified human $^{10}$Fn3 domain wherein the BC, DE and FG loops of the modified human $^{10}$Fn3 domain comprise the amino acid sequences set forth in SEQ ID NOs: 97, 98 and 99, respectively.

16. The nucleic acid of claim 15, wherein the nucleic acid encodes a polypeptide comprising the amino acid sequence set forth in SEQ ID NO: 96.

17. The nucleic acid of claim 15, wherein the nucleic acid encodes a polypeptide comprising the amino acid sequence set forth in SEQ ID NO: 100.

18. The nucleic acid of claim 15, wherein the nucleic acid encodes a polypeptide comprising the amino acid sequence set forth in SEQ ID NO: 104.

19. The nucleic acid of claim 15, wherein the nucleic acid comprises the nucleotide sequence set forth in any one of SEQ ID NOs: 108-111.

20. The nucleic acid of claim 15, wherein the nucleic acid comprises the nucleotide sequence set forth in SEQ ID NO: 108.

21. The nucleic acid of claim 15, wherein the nucleic acid comprises the nucleotide sequence set forth in SEQ ID NO: 110.

\* \* \* \* \*

UNITED STATES PATENT AND TRADEMARK OFFICE
CERTIFICATE OF CORRECTION

PATENT NO. : 11,173,219 B2  
APPLICATION NO. : 16/520965  
DATED : November 16, 2021  
INVENTOR(S) : Paul E. Morin et al.

Page 1 of 1

It is certified that error appears in the above-identified patent and that said Letters Patent is hereby corrected as shown below:

In the Claims

At Column 552, Claim number 7, Line number 38, please delete "76-79-92-95" and insert -- 76-79, 92-95, --.

Signed and Sealed this
Twenty-fifth Day of July, 2023

Katherine Kelly Vidal
*Director of the United States Patent and Trademark Office*